US010040770B2

(12) United States Patent
Delgado et al.

(10) Patent No.: US 10,040,770 B2
(45) **Date of Patent: *Aug. 7, 2018**

(54) SUBSTITUTED DIAMINOCARBOXAMIDE AND DIAMINOCARBONITRILE PYRIMIDINES, COMPOSITIONS THEREOF, AND METHODS OF TREATMENT THEREWITH

(71) Applicant: SIGNAL PHARMACEUTICALS, LLC, San Diego, CA (US)

(72) Inventors: Mercedes Delgado, San Diego, CA (US); Jan Elsner, Solana Beach, CA (US); Paul Erdman, San Diego, CA (US); Robert Hilgraf, San Diego, CA (US); Laurie Ann LeBrun, San Diego, CA (US); Meg McCarrick, San Diego, CA (US); Mark A. Nagy, Encinitas, CA (US); Stephen Norris, San Diego, CA (US); David A. Paisner, Portland, OR (US); Yoshitaka Satoh, Poway, CA (US); Marianne Sloss, San Diego, CA (US); Jayashree Tikhe, San Diego, CA (US); Won Hyung Yoon, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/616,039

(22) Filed: Jun. 7, 2017

(65) Prior Publication Data

US 2017/0267647 A1 Sep. 21, 2017

Related U.S. Application Data

(63) Continuation of application No. 14/814,633, filed on Jul. 31, 2015, now Pat. No. 9,701,643, which is a continuation of application No. 13/451,574, filed on Apr. 20, 2012, now Pat. No. 9,139,534.

(60) Provisional application No. 61/555,339, filed on Nov. 3, 2011, provisional application No. 61/478,076, filed on Apr. 22, 2011.

(51) Int. Cl.

| | |
|---|---|
| *C07D 239/48* | (2006.01) |
| *A61K 31/505* | (2006.01) |
| *C07D 401/12* | (2006.01) |
| *C07D 409/12* | (2006.01) |
| *C07D 403/12* | (2006.01) |
| *C07D 401/04* | (2006.01) |
| *C07D 405/12* | (2006.01) |

(52) U.S. Cl.

CPC .......... *C07D 239/48* (2013.01); *A61K 31/505* (2013.01); *C07D 401/04* (2013.01); *C07D 401/12* (2013.01); *C07D 403/12* (2013.01); *C07D 405/12* (2013.01); *C07D 409/12* (2013.01)

(58) Field of Classification Search

CPC ............................ C07D 239/48; A61K 31/505

USPC .......................................... 544/323; 514/275

See application file for complete search history.

(56) References Cited

U.S. PATENT DOCUMENTS

| | | | |
|---|---|---|---|
| 3,845,055 | A | 10/1974 | Hoegerle et al. |
| 6,432,963 | B1 | 8/2002 | Hisamichi et al. |
| 7,517,886 | B2 | 4/2009 | Singh et al. |
| 7,524,849 | B2 | 4/2009 | Zhang et al. |
| 7,589,200 | B2 | 9/2009 | Singh et al. |

(Continued)

FOREIGN PATENT DOCUMENTS

| | | | |
|---|---|---|---|
| EP | 1 184 376 | A1 | 3/2002 |
| EP | 1 518 855 | A1 | 3/2005 |

(Continued)

OTHER PUBLICATIONS

Bogoyevitch et al., c-Jun N-terminal kinase (JNK) signaling: Recent advances and challenges, Biochimica et Biophysica Acta, 1804 (2010), pp. 463-475.

(Continued)

*Primary Examiner* — Deepak R Rao
(74) *Attorney, Agent, or Firm* — Jones Day

(57) ABSTRACT

Provided herein are Diaminopyrimidine Compounds having the following structures:

(I)

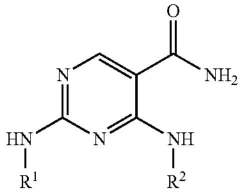

or (IB)

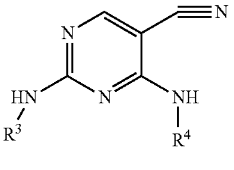

wherein $R^1$, $R^2$, $R^3$, and $R^4$ are as defined herein, compositions comprising an effective amount of a Diaminopyrimidine Compound, and methods for treating or preventing liver fibrotic disorders or a condition treatable or preventable by inhibition of a JNK pathway.

18 Claims, No Drawings

(56) References Cited

U.S. PATENT DOCUMENTS

| | | | | |
|---|---|---|---|---|
| 7,601,714 | B2 | 10/2009 | Barbosa et al. | |
| 7,718,653 | B2 | 5/2010 | Barlaam et al. | |
| 7,893,074 | B2 | 2/2011 | Garcia-Echeverria et al. | |
| 7,956,060 | B2 | 6/2011 | Arai et al. | |
| 8,012,959 | B2 | 9/2011 | Nagashima et al. | |
| 8,188,113 | B2 | 5/2012 | Flynn et al. | |
| 8,338,439 | B2 | 12/2012 | Sing et al. | |
| 8,519,129 | B2 | 8/2013 | Marsilje et al. | |
| 9,139,534 | B2 | 9/2015 | Bennett et al. | |
| 9,365,524 | B2 * | 6/2016 | Man | C07D 239/48 |
| 9,513,297 | B2 * | 12/2016 | Horan | G01N 33/6881 |
| 9,556,126 | B2 * | 1/2017 | Papa | C07D 239/48 |
| 9,701,643 | B2 * | 7/2017 | Bennett | C07D 239/48 |
| 9,796,685 | B2 * | 10/2017 | Boersen | C07D 239/48 |
| 9,814,713 | B2 * | 11/2017 | Man | A61K 31/505 |
| 2008/0139531 | A1 | 6/2008 | Yanni et al. | |
| 2009/0036440 | A1 | 2/2009 | Barlaam et al. | |
| 2011/0159019 | A1 | 1/2011 | Tanaka et al. | |
| 2011/0130415 | A1 | 6/2011 | Singh et al. | |

FOREIGN PATENT DOCUMENTS

| | | | |
|---|---|---|---|
| JP | 2006/124387 | A | 5/2006 |
| WO | WO 1999/31073 | A1 | 6/1993 |
| WO | WO 2000/012485 | | 3/2000 |
| WO | WO 2000/76980 | A1 | 12/2000 |
| WO | WO 2003/063794 | A2 | 8/2003 |
| WO | WO 2003/078404 | | 9/2003 |
| WO | WO 2003/082855 | A1 | 9/2003 |
| WO | WO 2004/014382 | A1 | 2/2004 |
| WO | WO 2004/054617 | A1 | 7/2004 |
| WO | WO 2004/002964 | A1 | 8/2004 |
| WO | WO 2004/065378 | A1 | 8/2004 |
| WO | WO 2004/067516 | | 8/2004 |
| WO | WO 2005/095382 | A1 | 10/2005 |
| WO | WO 2006/027377 | A1 | 3/2006 |
| WO | WO 2006/027378 | A1 | 3/2006 |
| WO | WO 2006/035069 | A1 | 4/2006 |
| WO | WO 2006/091737 | A1 | 8/2006 |
| WO | WO 2006/099231 | | 9/2006 |
| WO | WO 2007/032445 | A1 | 3/2007 |
| WO | WO 2008/009458 | A1 | 1/2008 |
| WO | WO 2008/034008 | A3 | 7/2008 |
| WO | WO 2008/129380 | A1 | 10/2008 |
| WO | WO 2009/012421 | A1 | 1/2009 |
| WO | WO 2009/131687 | A2 | 10/2009 |
| WO | WO 2009/132980 | A1 | 11/2009 |
| WO | WO 2009/136995 | A2 | 11/2009 |
| WO | WO 2009/143389 | A1 | 11/2009 |
| WO | WO 2009/145856 | A1 | 12/2009 |
| WO | WO 2009/158571 | A1 | 12/2009 |
| WO | WO 2010/024430 | | 3/2010 |
| WO | WO 2010/024430 | A1 | 3/2010 |
| WO | WO 2010/032875 | A2 | 3/2010 |
| WO | WO 2010/038081 | A2 | 4/2010 |
| WO | WO 2010/051223 | A1 | 5/2010 |
| WO | WO 2010/080864 | A1 | 7/2010 |
| WO | WO 2010/090875 | A1 | 8/2010 |
| WO | WO 2010/097248 | A1 | 9/2010 |
| WO | WO 2010/129802 | A1 | 11/2010 |
| WO | WO 2010/134533 | | 11/2010 |
| WO | WO 2010/134533 | A1 | 11/2010 |
| WO | WO 2010/144468 | A1 | 12/2010 |
| WO | WO 2001/000213 | A1 | 1/2011 |
| WO | WO 2011/016472 | A1 | 2/2011 |
| WO | WO 2011/065800 | A2 | 6/2011 |
| WO | WO 2011/090760 | A1 | 7/2011 |
| WO | WO 2012/012619 | A1 | 1/2012 |
| WO | WO 2012/044936 | A1 | 4/2012 |
| WO | WO 2012/045010 | A1 | 4/2012 |
| WO | WO 2012/045020 | A1 | 4/2012 |

OTHER PUBLICATIONS

Bosseray et al., PubMed Abstract (Pathol Bioi (Paris) 50(8):483-92), Oct. 2002.

Bundgaard, Design of Prodrugs, Chapter 1, p. 1, 1985.

Cohen 2001, "The role of protein phosphorylation in human health and disease. The Sir Hans Krebs Medal Lecture," Eur J Biochem., 268:5001-5010.

Cohen 2002, "Protein kinases—the major drug targets of the twenty-first century," Nat Rev Drug Discov., 1:309-315.

Das et al., 1996, "Activation of raf-1, MEK, and MAP kinase in prolactin responsive mammary cells," Breast Cancer Res. Treat., 40(2):141-149.

Davis 1994, "MAPKs: new JNK expands the group," Trends Biochem Sci., 19:470-473.

Douglas, Jr. Introduction to Viral Diseases, Cecil Textbook of Medicine, 20th Edition, vol. 2, pp. 1739-47, 1996.

Eferl et al., 2008, "Development of pulmonary fibrosis through a pathway involving the transcription factor Fra-2/AP-1," PNAS, 105(30):10525-10530.

Fanger et al., 1997, "MEKKs, GCKs, MLKs, PAKs, TAKs, and tpls: upstream regulators of the c-Jun aminoterminal kinases?" Curr Opin Genet Dev., 7:67-74.

Gaestel et al., 2007, "Protein kinases as small molecule inhibitor targets in inflammation," Curr Med Chem., 14:2214-2234.

Gemcitabine in Patients With Advanced Solid Tumors,' Cancer Investigation, 30:481-486.

Goff, PubMed Abstract (J Gene Med 3(6):517-28), Nov.-Dec. 2001.

Grimminger et al., 2010, "Targeting non-malignant disorders with tyrosine kinase inhibitors," Nat Rev Drug. Sisc., 9(12):956-970.

Hirabayashi et al., 2008, "A novel Syk family kinase inhibitor: design, synthesis, and structure-activity relationship of 1,2,4-triazolo[4,3-c]pyrimidine and 1,2,4-triazolo[1,5-c]pyrimidine derivatives," Bioorg Med Chem., 16:7347-7357.

Hirosumi et al., 2002, "A central role for JNK in obesity and insulin resistance," Nature, 420:333-336.

Hisamichi et al., 2005, "Corrigendum to Synthetic studies on novel Syk inhibitors. Part 1: Synthesis and structure-activity relationships of pyrimidine-5-carboxamide derivatives," Bioorg. Med. Chem., 13:6277-6279.

Hisamichi et al., 2005, "Synthetic studies on novel Syk inhibitors. Part 1: Synthesis and structure-activity relationships of pyrimidine-5-carboxamide derivatives," Bioorg. Med. Chem., 13:4936-4951.

Hu et al., 2000, "Prolonged activation of the mitogen-activated protein kinase pathway is required for macrophage-like differentiation of a human myeloid leukemic cell line," Cell Growth Differ., 11(4):191-200.

Hulikal, Deuterium Labeled Compounds in Drug Discovery Process, Abstract, 2010.

Ichijo 1999, "From receptors to stress-activated MAP kinases," Oncogene, 18:6087-6093.

Jones et al., 2012, Phase 1 Results From a Study of Romidepsin in Combination With Gemcitabine, Cancer Investigation, 30:481-486.

Kaneto et al., 2007, "Oxidative stress and the JNK pathway are involved in the development of type 1 and type 2 diabetes," Curr Mol Med., 7:674-686.

Katayama et al., 2008, "Identification of a key element for hydrogen-bonding patterns between protein kinases and their inhibitors," Proteins, 73:795-801.

Kluwe et al., 2010, "Modulation of hepatic fibrosis by c-Jun-N-terminal kinase inhibition," Gastroenterology 138:347-359.

Kodama et al., 2009, "c-Jun N-terminal kinase-1 from hematopoietic cells mediates progression from hepatic steatosis to steatohepatitis and fibrosis in mice," Gastroenterology, 137:1467-1477.e5.

Kyriakis JM., 2000. "MAP kinases and the regulation of nuclear receptors," Sci. STKE (48), pe1:1-4.

Liddle et al., 2011, "Discovery of GSK143, a highly potent, selective and orally efficacious spleen tyrosine kinase inhibitor," Bioorg Chem Chem Lett., 21:6188-6194.

Malhi et al., 2006, "Free fatty acids induce JNK-dependent hepatocyte lipoapoptosis," J Biol Chem., 281:12093-12101.

Malhi et al., 2008, "Molecular mechanisms of lipotoxicity in nonalcoholic fatty liver disease," Semin Liver Dis., 28(4):360-369.

(56) References Cited

OTHER PUBLICATIONS

Nagashima et al., 2007, "Synthesis and evaluation of 2-{[2-(4-hydroxyphenyl)-ethyl]amino}pyrimidine-5-carboxamide derivatives as novel STAT6 inhibitors," Bioorg Med Chem., 15:1044-1055.
Nagashima et al., 2008, "Identification of 4-benzylamino-2-[(4-morphalin-4-ylphenyl)amino]pyrimidine-5-carboxamide derivatives as potent and orally bioavailable STAT6 inhibitors," Biorg Med Chem., 16:6509-6521.
Nagashima et al., 2009, "Novel 7H-pyrrolo[2,3-d]pyrimidine derivatives as potent and orally active STAT6 inhibitors," Bioorg Med Chem., 17:6926-6936.
Ohga et al., 2008, "YM-341619 suppresses the differentiation of spleen T cells into Th2 cells in vitro, eosinophilia, and airway hyperresponsiveness in rat allergic models," Eur J Pharmacol., 590:409-416.
Papp et al., 2007, "Steady state kinetics of spleen tyrosine kinase investigated by a real time fluorescence assay," Biochemistry, 46;15103-15114.
Pimlott, Sally L., 2005, "Radiotracer development in psychiatry," *Nuclear medicine communications*, 26.3 (2005): 183-188.
Razonable et al., PubMed Abstract (Herpes 1 0(3):60-5), Dec. 2003.
Reilly et al., 2011, "PRT-060318, a novel Syk inhibitor, prevents heparin-induced thrombocytopenia and thrombosis in a transgenic mouse model," Blood, 117(7):2241-2246.
Sanam et al., 2009, "Discovery of potential ZAP-70 kinase inhibitors: pharmacophore design, database screening and docking studies," Eur J Med Chem., 44:4793-4800.
Sanchez-Tillo et al., 2007, "JNK1 Is required for the induction of Mkpl expression in macrophages during proliferation and lipopolysaccharide-dependent activation," J Biol Chem., 282(17):12566-73.
Schramek 2002, "Map kinases: from intracellular signals to physiology and disease," News Physiol. Sci., 17:62-67.
Schwabe et al., 2004, FASEB J. 18(6):720-722.
Segar et al., 1995, "The MAPK signaling cascade," FASEB J., 9:726-735.
Silverman, Prodrugs and Drug Delivery Systems, The Organic Chemistry of Drug Design and Drug action, Chapter 8, pp. 352-400, 1992.
Singh et al., 2009, "Differential effects of JNK1 and JNK2 inhibition on murine steatohepatitis and insulin resistance," Hepatology, 49(1):87-96.
Singh et al., 2009, Hepatology 49(1):87-96.
Singh et al., 2012, "Discovery and development of spleen tyrosine kinase (SYK) inhibitors," J Med Chem., 55:3614-1643.
Sridhar et al., 2000, "Protein kinases as therapeutic targets," Pharm Res., 17(11):1345-1353.
Uehara et al., 2004, Transplantation 78(3):324-332.
Vallerie et al., 2010, "The role of JNK proteins in metabolism," Sci Transl Med., 2(60):1-7.
Villasenor et al., 2009, "Structural insights for design of potent spleen tyrosine kinase inhibitors from crystallographic analysis of three inhibitor complexes," Chem Biol Drug Des., 73:466-470.
Virkamaki et al., 1999, "Protein-protein interaction in insulin signaling and the molecular mechanisms of insulin resistance," J Clin Invest., 103(7):931-943.
Whitmarsh et al., 1999, "Signal transduction by MAP kinases: regulation by phosphorylation-dependent switches," Sci. STKE (1),pel:1-3.
Tedesco et al., 2009, "Synthesis and biological activity of heteromyl 3-(1,1-dioxo-2H-(1,2,4)-benzothiadizin-3-yl)-4-hydroxy-2-(1H)-quinolinone derivatives as hepatitis C virus NSSB polymerase inhibitors," *Bioorganic & Medicinal Chemistry Letters*, 2009, 19.15: 4354-4358.
Ishida et al., 2008, "Novel and orally active 5-(1,3,4-oxadiazol-2-yl) pyrimidine derivatives as selective FLT3 inhibitors," Bioorganic & Medicinal Chemistry Letters, 2008, 18.20: 5472-5477.
Martin et al., 2008, "Structure-Based Design of Novel 2-Amino-6-phenyl-pyrimido [5',4':5,6] pyrimido [1,2-a] benzimidazol-5(6H)-ones as Potent and Orally Active Inhibitors of Lymphocyte Specific Kinase (Lck): Synthesis, SAR, and In Vivo AntiInflammatory Activity," Journal of Medicinal Chemistry, 2008, 51.6: 1637-1648.

* cited by examiner

SUBSTITUTED DIAMINOCARBOXAMIDE AND DIAMINOCARBONITRILE PYRIMIDINES, COMPOSITIONS THEREOF, AND METHODS OF TREATMENT THEREWITH

CROSS-REFERENCE TO RELATED APPLICATIONS

This application is a continuation of U.S. application Ser. No. 14/814,633, filed Jul. 31, 2015, currently allowed, which is a continuation of U.S. application Ser. No. 13/451,574, filed Apr. 20, 2012, issued as U.S. Pat. No. 9,139,534 on Sep. 22, 2015, which claims the benefit of U.S. Provisional Application No. 61/478,076, filed Apr. 22, 2011 and claims the benefit of U.S. Provisional Application No. 61/555,339, filed Nov. 3, 2011, the entire contents of each of which are incorporated herein by reference.

FIELD

Provided herein are certain diaminocarboxamide and diaminocarbonitrile pyrimidine compounds, compositions comprising an effective amount of such compounds, and methods for treating or preventing liver fibrotic disorders or a condition treatable or preventable by inhibition of a JNK pathway, comprising administering an effective amount of such diaminocarboxamide and diaminocarbonitrile pyrimidine compounds to a subject in need thereof.

BACKGROUND

The connection between abnormal protein phosphorylation and the cause or consequence of diseases has been known for over 20 years. Accordingly, protein kinases have become a very important group of drug targets. [See Cohen, *Nature,* 1:309-315 (2002), Gaestel et al. *Curr. Med. Chem.* 14: 2214-223 (2007); Grimminger et al. *Nat. Rev. Drug Disc.* 9(12):956-970 (2010)]. Various protein kinase inhibitors have been used clinically in the treatment of a wide variety of diseases, such as cancer and chronic inflammatory diseases, including rheumatoid arthritis and psoriasis. [See Cohen, *Eur. J. Biochem.,* 268:5001-5010 (2001); Protein Kinase Inhibitors for the Treatment of Disease: The Promise and the Problems, *Handbook of Experimental Pharmacology*, Springer Berlin Heidelberg, 167 (2005)].

JNK is a ubiquitously expressed serine/threonine kinase belonging, together with ERK (extracellular-regulated kinase) and p38, to the family of mitogen-activated protein kinases (MAPKs). [Kyriakis J M, *Sci. STKE* (48):pel (2000); Whitmarsh A J, et al. *Sci. STKE* (1):pel (1999); Schramek H, *News Physiol. Sci.* 17:62-7 (2002); Ichijo H, *Oncogene* 18(45):6087-93 (1999)]. MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates non-nuclear proteins, for example, IRS-1, and Bcl-2 family members. [Davis R J, *Trends Biochem. Sci.* 9(11):470-473 (1994); Seger R et al., *FASEB J.;* 9(9):726-35 (1995); Fanger G R et al., *Curr. Opin. Genet. Dev.;* 7(1):67-74 (1997)].

The mitogen activated protein (MAP) kinases participate in the transduction of signals to the nucleus of the cell in response to extracellular stimuli. Examples of MAP kinases from the ERK p38 and JNK isoforms include but are not limited to, mitogen-activated protein kinase 1 (ERK2), mitogen-activated protein kinase 8 (JNK1), mitogen-activated protein kinase 9 (MAPK9 or JNK2), mitogen-activated protein kinase 10 (MAPK10 or JNK3) and mitogen-activated protein kinase 14 (MAPK14 or p38alpha). MAP kinases are a family of proline-directed serine/threonine kinases that mediate signal transduction from extracellular receptors or heat shock, osmotic stress, reactive oxidant species (ROS) or UV radiation. [See Sridhar et al., *Pharmaceutical Research,* 17:11 1345-1353 (2000)]. MAP kinases are activated via the phosphorylation of theonine and tyrosine by upstream dual-specificity protein kinases, including MKK and MEKK kinases. Cell proliferation and differentiation have been shown to be under the regulatory control of multiple MAP kinase cascades. [See Sridhar et al., *Pharmaceutical Research,* 17:11 1345-1353 (2000)]. As such, the MAP kinase pathway plays critical roles in a number of disease states. For example, defects in activities of MAP kinases have been shown to lead to aberrant cell proliferation and carcinogenesis. [See Hu et al., *Cell Growth Differ.* 11:191-200 (2000); and Das et al., *Breast Cancer Res. Treat.* 40:141 (1996)]. Moreover, MAP kinase activity has also been implicated in insulin resistance associated with type-2 diabetes [See Virkamaki et al., *J. Clin. Invest.* 103:931-943 (1999)] and obesity. Changes in insulin resistance may have a direct impact on the metabolism of glucose and lipid in the liver contributing to the development of steatosis that may progress to liver fibrosis [Vallerie et al. *Science Translational Medicine* 2(60):1-7 (2010)].

Steatosis may develop in the presence of either saturated or unsaturated free fatty acids (FFA). FFA promote robust JNK activation in liver and excessive concentrations of FFA may lead to hepatocyte apoptosis. It has been reported that JNK2−/− mice are partially protected from steatosis and apoptosis by saturated FFA (e.g. stearic acid) but not by unsaturated FFA [Malhi et al. *J. Biol. Chem.* 281:12093-12101 (2006)]. JNK1−/− mice were not protected from FFA induced injury. The role of JNK1 and JNK2 has been studied in CDAA-fed mice that progressed from steatosis to steatohepatitis to hepatic fibrosis [Kodama et al., *Gastroenterology* 137:1467-1477 (2009)]. While both JNK1−/− and JNK2−/− mice developed steatosis, the JNK1−/− mice, but not JNK2−/− mice, were remarkably resistant to progression to hepatitis and fibrosis. Chimeric mice with JNK1−/− deletion restricted to bone marrow cells were similarly resistant to hepatitis and fibrosis implicating the activated Kupffer cell as a key trigger for disease progression beyond steatosis. Indeed, JNK1−/− macrophages do not express IL-1, IL-6, TNF and NO in response to LPS [Sanchez-Tillo et al., *J. Biol Chem.* 282(17):12566-73 (2007)], and Kupffer cells derived from JNK1−/− mice or from wild-type mice and treated with JNK inhibitor SP600125 display reduced TNF, IL-6, and IL-1 expression in response to LPS [Kodama et al., *Gastroenterology* 137:1467-1477 (2009)].

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators, and in particular JNK modulators.

Citation or identification of any reference in Section 2 of this application is not to be construed as an admission that the reference is prior art to the present application.

SUMMARY

Provided herein are compounds having the following formula (I):

(I)

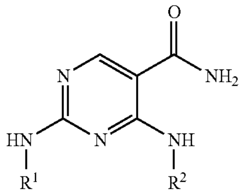

and pharmaceutically acceptable salts, tautomers, isotopologues, stereoisomers and prodrugs thereof, wherein $R^1$, and $R^2$ are as defined herein.

Provided herein are compounds having the following formula (IB):

(IB)

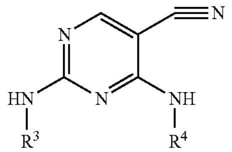

and pharmaceutically acceptable salts, tautomers, isotopologues, stereoisomers and prodrugs thereof, wherein $R^3$, and $R^4$ are as defined herein.

A compound of formula (I) or formula (IB) or a pharmaceutically acceptable salt, tautomer, isotopologue, stereoisomer or prodrug thereof (each being referred to herein as an "Diaminopyrimidine Compound") is useful for treating or preventing liver fibrotic disorders, or diabetes and/or metabolic syndrome leading to liver fibrotic disorders, as described herein. In another aspect, a Diaminopyrimidine Compound is useful for treating or preventing a condition treatable or preventable by inhibition of a JNK pathway, as described herein.

In one aspect, provided herein are Diaminopyrimidine Compounds as described in the instant disclosure, such as, for example, in Tables 1, 2 and 3.

In one aspect, provided herein are pharmaceutical compositions comprising an effective amount of a Diaminopyrimidine Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing liver fibrotic disorders, such as non-alcoholic steatohepatitis, steatosis, cirrhosis, primary sclerosing cholangitis, primary biliary cirrhosis, hepatitis, hepatocellular carcinoma, and liver fibrosis coincident with chronic or repeated alcohol ingestion, with infection, with liver transplant, or with drug induced liver injury, comprising administering to a subject in need thereof an effective amount of a Diaminopyrimidine Compound as described herein; and a pharmaceutically acceptable carrier, excipient or vehicle. In another aspect, provided herein are methods for treating or preventing diabetes or metabolic syndrome leading to liver fibrotic disorders, such as non-alcoholic steatohepatitis, steatosis, hepatitis, or cirrhosis, comprising administering to a subject in need thereof an effective amount of a Diaminopyrimidine Compound. Also provided herein are methods for treating or preventing a condition treatable or preventable by inhibition of a JNK pathway, comprising administering to a subject in need thereof an effective amount of a Diaminopyrimidine Compound as described herein; and a pharmaceutically acceptable carrier, excipient or vehicle.

In one aspect, provided herein are methods for inhibiting a kinase, for example JNK1, JNK2 or both, in a cell expressing said kinase, comprising contacting said cell with an effective amount of a Diaminopyrimidine Compound as described herein.

In another aspect provided herein are methods for preparing Diaminopyrimidine Compounds as described herein.

The present embodiments can be understood more fully by reference to the detailed description and examples, which are intended to exemplify non-limiting embodiments.

DETAILED DESCRIPTION

Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, $—CH{=}CH(CH_3)$, $—CH{=}C(CH_3)_2$, $—C(CH_3){=}CH_2$, $—C(CH_3){=}CH(CH_3)$, $—C(CH_2CH_3){=}CH_2$, $—C{\equiv}C(CH_3)$, $—C{\equiv}C(CH_2CH_3)$, $—CH_2C{\equiv}CH$, $—CH_2C{\equiv}C(CH_3)$ and $—CH_2C{\equiv}C(CH_7CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

A "cycloalkyl" group is a saturated, partially saturated, or unsaturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: $—NH_2$.

An "alkylamino" group is a radical of the formula: —NH-alkyl or $—N(alkyl)_2$, wherein each alkyl is independently as defined above.

A "carboxy" group is a radical of the formula: —C(O)OH.

An "aminocarbonyl" group is a radical of the formula: $—C(O)N(R^\#)_2$, $—C(O)NH(R^\#)$ or $—C(O)NH_2$, wherein each $R^\#$ is independently a substituted or unsubstituted alkyl, cycloalkyl, aryl, aralkyl, heterocyclyl or heterocyclyl group as defined herein.

An "acylamino" group is a radical of the formula: $—NHC(O)(R^\#)$ or $—N(alkyl)C(O)(R^\#)$, wherein each alkyl and $R^\#$ are independently as defined above.

A "sulfonylamino" group is a radical of the formula: $—NHSO_2(R^\#)$ or $—N(alkyl)SO_2(R^\#)$, wherein each alkyl and $R^\#$ are defined above.

A "urea" group is a radical of the formula: $—N(alkyl)C(O)N(R^\#)_2$, $—N(alkyl)C(O)NH(R^\#)$, $—N(alkyl)C(O)NH_2$, $—NHC(O)N(R^\#)_2$, $—NHC(O)NH(R^\#)$, or $—NH(CO)NHR^\#$, wherein each alkyl and $R^\#$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (═O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "Diaminopyrimidine Compound" refers to compounds of formula (I) and formula (IB) as well as to further embodiments provided herein. In one embodiment, a "Diaminopyrimidine Compound" is a compound set forth in Tables 1, 2 and 3. The term "Diaminopyrimidine Compound" includes pharmaceutically acceptable salts, tautomers, isotopologues, stereoisomers, and prodrugs of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences,* $18^{th}$ eds., Mack Publishing, Easton Pa. (1990) or *Remington: The Science and Practice of Pharmacy,* $19^{th}$ eds., Mack Publishing, Easton Pa. (1995).

As used herein and unless otherwise indicated, the term "prodrug" means a Diaminopyrimidine Compound that can hydrolyze, oxidize, or otherwise react under biological conditions (in vitro or in vivo) to provide an active compound, particularly a Diaminopyrimidine Compound or a compound of formula (I). Examples of prodrugs include, but are not limited to, derivatives and metabolites of a Diaminopyrimidine Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* $6^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a Diaminopyrimidine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Diaminopyrimidine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Diaminopyrimidine Compounds, as well as the use of mixtures of those forms, are encompassed by the embodiments disclosed herein. For example, mixtures comprising equal or unequal amounts of the enantiomers of a particular Diaminopyrimidine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Diaminopyrimidine Compounds can include E and Z isomers, or a mixture thereof, and cis and trans isomers or a mixture thereof. In certain embodiments, the Diaminopyrimidine Compounds are isolated as either the E or Z isomer. In other embodiments, the Diaminopyrimidine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

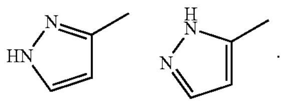

As readily understood by one skilled in the art, a wide variety of functional groups and other structures may exhibit tautomerism and all tautomers of compounds of formula (I) are within the scope of the present invention.

It should also be noted the Diaminopyrimidine Compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Diaminopyrimidine Compounds as described herein, whether radioactive or not, are intended to be encompassed within the scope of the embodiments provided herein. In some embodiments, there are provided isotopologues of the Diaminopyrimidine Compounds, for example, the isotopologues are deuterium, carbon-13, or nitrogen-15 enriched Diaminopyrimidine Compounds.

"JNK" means a protein or an isoform thereof expressed by a JNK1, JNK2, or JNK3 gene (Gupta, S., Barrett, T., Whitmarsh, A. J., Cavanagh, J., Sluss, H. K., Derijard, B. and Davis, R. J. *The EMBO J.* 15:2760-2770 (1996)).

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g. viral infection such as HCV), with liver transplant, or with drug induced liver injury (e.g. acetaminophen toxicity). In some embodiments, "treating" means an alleviation, in whole or in part, of a disorder, disease or condition, or symptoms associated with diabetes or metabolic syndrome leading to liver fibrotic disorders, such as non-alcoholic steatohepatitis, steatosis (i.e. fatty liver), hepatitis or cirrhosis, or a slowing, or halting of further progression or worsening of those symptoms. In one embodiment, the symptom is jaundice. In another embodiment, "treating" means and alleviation, in whole or in part, of a disorder, disease or condition, or symptoms associated with a condition, treatable or preventable by inhibition of a JNK pathway.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a liver fibrotic disorder, or diabetes or metabolic syndrome leading to liver fibrotic disorders, as described herein, or symptoms thereof. In another, the disorder is a condition, treatable or preventable by inhibition of a JNK pathway.

The term "effective amount" in connection with a Diaminopyrimidine Compound means an amount capable of treating or preventing a disorder, disease or condition, or symptoms thereof, disclosed herein.

The term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having liver fibrotic disorders or diabetes or metabolic syndrome leading to liver fibrotic disorders, or a condition, treatable or preventable by inhibition of a INK pathway, or a symptom thereof.

Diaminopyrimidine Compounds

Provided herein are compounds having the following formula (I):

(I)

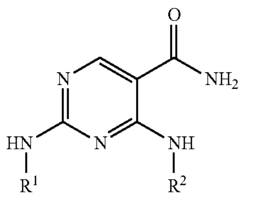

and pharmaceutically acceptable salts, tautomers, stereoisomers, enantiomers, isotopologues, and prodrugs thereof, wherein:

$R^1$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkylheterocyclyl, provided that $R^1$ is not 1-aminocyclohexyl; and $R^2$ is substituted or unsubstituted $C_{1-8}$ alkyl, substituted or unsubstituted saturated cycloalkyl, substituted or unsubstituted alkylcycloalkyl, or substituted or unsubstituted non-aromatic heterocyclyl.

In one embodiment, the compound of formula (I) is not:

2-(2-aminoethylamino)-4-(methylamino)pyrimidine-5-carboxamide

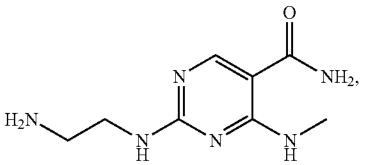

2-(2-aminopropylamino)-4-(cyclohexylamino)pyrimidine-5-carboxamide

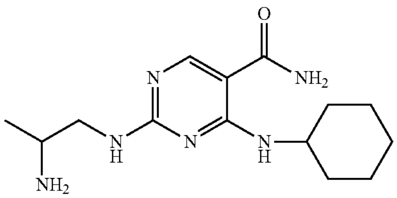

, 2-(2-amino-2-oxoethylamino)-4-(cyclohexylamino)pyrimidine-5-carboxamide

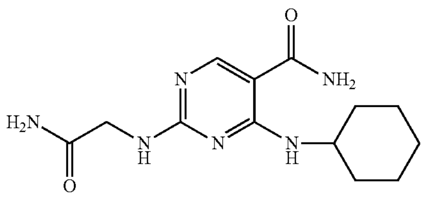

, 2-(2-aminoethylamino)-4-(cyclohexylamino)pyrimidine-5-carboxamide

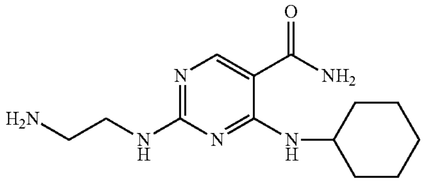

, (S)-2-(2-aminopropylamino)-4-(cyclobutylamino)pyrimidine-5-carboxamide

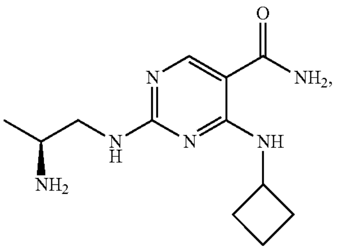 [SMILES: C[C@H](N)CNc1ncc(C(N)=O)c(NC2CCC2)n1]

(R)-2-(1-amino-3-methyl-1-oxobutan-2-ylamino)-4-(cyclobutylamino)-pyrimidine-5-carboxamide

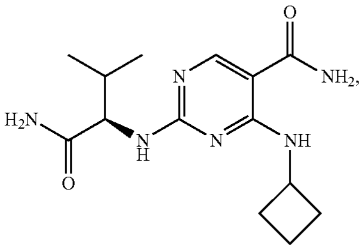 [SMILES: CC(C)[C@@H](Nc1ncc(C(N)=O)c(NC2CCC2)n1)C(N)=O]

4-(cyclopentylamino)-2-(methylamino)pyrimidine-5-carboxamide

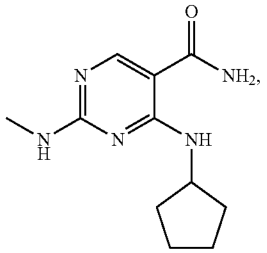 [SMILES: CNc1ncc(C(N)=O)c(NC2CCCC2)n1]

or 2-(1-acetylpiperidin-4-ylamino)-4-(cyclopropylamino)pyrimidine-5-carboxamide

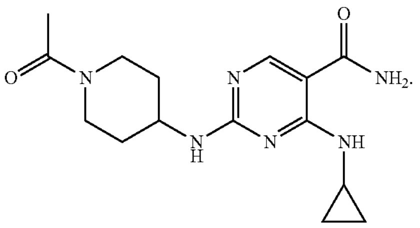 [SMILES: CC(=O)N1CCC(Nc2ncc(C(N)=O)c(NC3CC3)n2)CC1]

In one embodiment, $R^1$ is not

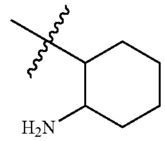

, for example,

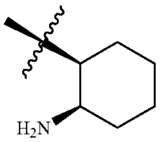

,

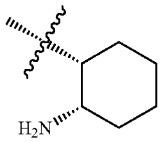

,

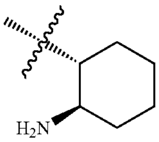

, or

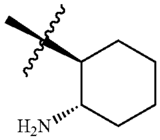

.

In some embodiments of compounds of formula (I), $R^1$ is a branched $C_{1-8}$ alkyl, for example, $R^1$ is isopropyl, sec-butyl, isobutyl, tert-butyl, isopentyl, 2-methylpentyl, or tert-pentyl. In others, $R^1$ is isopropyl, sec-butyl, isobutyl, tert-butyl, 2,3-dimethylbutyl, isopentyl, 2-methylpentyl, neopentyl, tert-pentyl, or 3-methylpentyl. In others, $R^1$ is a substituted or unsubstituted cycloalkyl, for example, cyclopropyl, cyclobutyl, cyclopentyl, cyclohexyl, cycloheptyl, cyclooctyl, bicyclo[1.1.1]pentyl, or bicyclo[2.2.2]octyl. In others, the cycloalkyl is cyclopropyl, cyclobutyl, cyclopentyl, cyclohexyl, cycloheptyl, cyclooctyl, bicyclo[1.1.1]pentyl, bicyclo[2.2.1]heptyl, or bicyclo[2.2.2]octyl. In some such embodiments, the cycloalkyl is substituted with one or more halogen, —($C_{1-4}$ alkyl), —$NR_2$, —($C_{0-3}$ alkyl)OR, —NRC(O)R', —C(O)R', —C(O)$NR_2$, —C(O)OR', or —$NRS(O)_2R'$, wherein each R is independently H, or $C_{1-4}$ alkyl, wherein the alkyl is optionally fluorinated, and each R' is independently $C_{1-4}$ alkyl, wherein the alkyl is optionally fluorinated. For example, the cycloalkyl is substituted with one or more methyl, ethyl, t-butyl, —F, —OH, —$OCH_3$, —$OCHF_2$, —$OCF_3$, —$OCH_2CH_3$, —$OCH_2CH_2F$, —$OCH_2CF_3$, —$CH_2OH$, —$CH_2OCH_3$, —$C(CH_3)_2OH$, —$NH_2$, —$NH(CH_3)$, —NHC(O)$CH_3$, —C(O)$NHCH_3$, —C(O)$N(CH_3)_2$, or —$NHSO_2CH_3$. In other embodiments, the cycloalkyl is substituted with one or more halogen, —$CF_3$, —($C_{1-4}$ alkyl), —($C_{1-6}$ cycloalkyl), —$NR_2$, —($C_{0-3}$ alkyl)OR, —($C_{0-3}$ alkyl)OR", —NRC(O)R', —C(O)R', —C(O)$NR_2$, —C(O)OR', or —$NRS(O)_2R'$, wherein each R is independently H, or $C_{1-4}$ alkyl, wherein the alkyl is optionally fluorinated, each R' is independently $C_{1-4}$ alkyl, wherein the alkyl is optionally fluorinated, and each R" is independently a $C_{1-6}$ cycloalkyl, wherein the cycloalkyl is optionally fluorinated. For example, the cycloalkyl is substituted with one or more methyl, ethyl, t-butyl, cyclopropyl, —$CF_3$, —F, —OH, —$OCH_3$, —$OCHF_2$, —$OCF_3$, —$OCH_2CH_3$, —$OCH_2CH_2F$, —$OCH_2CF_3$, —O(cyclopropyl), —$CH_2OH$, —$CH_2OCH_3$, —$C(CH_3)_2OH$, —$NH_2$, —$NH(CH_3)$, —NHC(O)$CH_3$, —C(O)$NHCH_3$, —C(O)N$(CH_3)_2$, or —$NHSO_2CH_3$. In some embodiments, $R^1$ is a substituted or unsubstituted non-aromatic heterocyclyl, for example, pyrrolidinyl, tetrahydropyranyl, 1,4-dioxaspiro[4.5]decanyl, or piperidyl. In others, the non-aromatic heterocyclyl is oxetanyl, pyrrolidinyl, tetrahydropyranyl, 1,4-dioxaspiro[4.5]decanyl, or piperidyl. In some such embodiments, the piperidyl is substituted with —C(O)R', or —C(O)OR', wherein R' is $C_{1-4}$ alkyl, wherein the alkyl is optionally fluorinated. In yet other embodiments, $R^1$ is a substituted or unsubstituted alkylcycloalkyl, for example, ($C_{1-3}$ alkyl)cyclopropyl, ($C_{1-3}$ alkyl)cyclobutyl, ($C_{1-3}$ alkyl)cyclopentyl, or ($C_{1-3}$ alkyl)cyclohexyl. In some such embodiments, $R^1$ is —($CH_2$)cyclopropyl, —($CH_2$)cyclobutyl, —($CH_2$)cyclopentyl, —($CH_2$)cyclohexyl, —CH($CH_3$)cyclopropyl, —CH($CH_3$)cyclobutyl, —CH($CH_3$)cyclopentyl, or —CH($CH_3$)cyclohexyl. In others, $R^1$ is —($CH_2$)cyclopropyl, —CH($CH_3$)cyclopropyl, —CH($CH_3$)cyclobutyl, —CH($CH_3$)cyclohexyl, or —$C(CH_3)_2$cyclopropyl. In still other embodiments, $R^1$ is a substituted or unsubstituted alkylheterocyclyl, for example, —($C_{1-4}$ alkyl)tetrahydrofuranyl, —($C_{1-4}$ alkyl)dioxolanyl, ($C_{1-4}$ alkyl)furanyl, ($C_{1-3}$ alkyl)thiophenyl, or —($C_{1-3}$ alkyl)pyridyl.

In some embodiments of compounds of formula (I), $R^1$ is selected from branched $C_{1-8}$ alkyl,

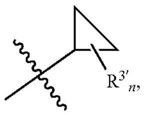

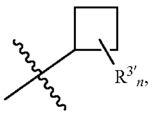

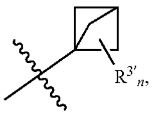

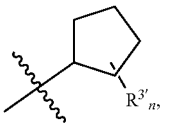

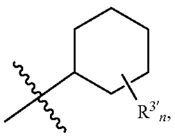

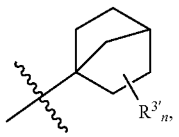

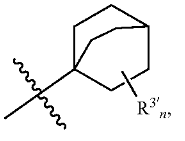

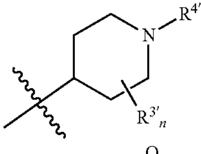

,

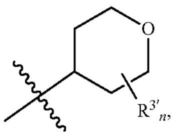

or

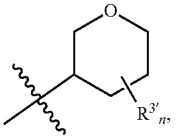

wherein $R^{3'}$ is halogen, —$CF_3$, —($C_{1-4}$ alkyl), —($C_{1-6}$ cycloalkyl), —$NR_2$, —($C_{0-3}$ alkyl)OR, —($C_{0-3}$ alkyl)OR", —NRC(O)R', —C(O)R', —C(O)$NR_2$, —C(O)OR', or —$NRS(O)_2R'$;

$R^{4'}$ is —C(O)R', or —C(O)OR';

each R is independently H, or $C_{1-4}$ alkyl, wherein the alkyl is optionally fluorinated;

each R' is independently $C_{1-4}$ alkyl, wherein the alkyl is optionally fluorinated;

each R" is independently a $C_{1-6}$ cycloalkyl wherein the cycloalkyl is optionally fluorinated; and n is 0-2.

In some such embodiments, $R^{3'}$ is methyl, ethyl, t-butyl, cyclopropyl, —$CF_3$, —F, —OH, —$OCH_3$, —$OCHF_2$, —$OCF_3$, —$OCH_2CH_3$, —$OCH_2CH_2F$, —$OCH_2CF_3$, —O(cyclopropyl), —$CH_2OH$, —$CH_2OCH_3$, —$C(CH_3)_2OH$, —$NH_2$, —$NH(CH_3)$, —NHC(O)$CH_3$, —C(O)$NHCH_3$, —C(O)$N(CH_3)_2$, or —$NHSO_2CH_3$.

In some embodiments, $R^2$ is a substituted or unsubstituted $C_{1-8}$ alkyl, for example, methyl, ethyl, n-propyl, isopropyl, n-butyl, sec-butyl, isobutyl, tert-butyl, tert-pentyl, isopentyl, or 2-methylpentyl. In other embodiments, $R^2$ is methyl, ethyl, n-propyl, isopropyl, n-butyl, sec-butyl, isobutyl, tert-butyl, 3-methylbutyl, 2,3-dimethylbutyl, 3,3-dimethylbutyl, 2,3,3-trimethylbutyl, tert-pentyl, isopentyl, 3-pentyl, 3-methylpentyl, 2-methylpentyl, or 2,4-dimethylpentyl. In some such embodiments, $R^2$ is substituted with one or more —($C_{1-4}$ alkyl), —($C_{0-3}$ alkyl)OR, —C(O)$NR_2$ or —NRCOR', wherein each R is independently H, or $C_{1-4}$ alkyl, wherein the alkyl is optionally fluorinated, and each R' is independently $C_{1-4}$ alkyl, wherein the alkyl is optionally fluorinated. For example, $R^2$ is substituted with one or more —OH, or —$CH_3$. In other embodiments, $R^2$ is substituted with one or more —OH, —$OCH_3$, or —$CH_3$. In some embodiments, $R^2$ is a substituted or unsubstituted cycloalkyl, for example, $R^2$ is cyclopropyl, cyclobutyl, cyclopentyl, cyclohexyl, cycloheptyl, or cyclooctyl. In some such embodiments, $R^2$ is substituted with one or more —($C_{1-4}$ alkyl), —($C_{0-3}$ alkyl)OR, —($C_{0-3}$ alkyl)C(O)$NR_2$, —$NR_2$, or —NRCOR', wherein each R is independently H, or $C_{1-4}$ alkyl, wherein the alkyl is optionally fluorinated, and each R' is independently $C_{1-4}$ alkyl, wherein the alkyl is optionally fluorinated. In other embodiments, $R^2$ is cyclopropyl, cyclobutyl, cyclopentyl, cyclohexyl, cycloheptyl, cyclooctyl, bicyclo[1.1.1]pentyl, bicyclo[2.1.1]hexyl, or bicyclo[2.2.1]heptyl. In some such embodiments, $R^2$ is substituted with one or more —$CF_3$, —($C_{1-4}$ alkyl), —($C_{1-6}$ cycloalkyl), —($C_{0-3}$ alkyl)OR, —($C_{0-3}$ alkyl)C(O)$NR_2$, —$NR_2$, or —NRCOR', wherein each R is independently H, or $C_{1-4}$ alkyl, wherein the alkyl is optionally fluorinated, each R' is independently $C_{1-4}$ alkyl, wherein the alkyl is optionally fluorinated, and wherein the cycloalkyl is optionally fluorinated. In some such embodiments, $R^2$ is substituted with one or more methyl, ethyl, isopropyl, —$CH_2OH$, —OH, —$OCH_3$, —$OCH_2CH_3$, —C(O)$NH_2$, —NHC(O)$CH_3$, or —NHC(O)$CH_2CH_3$. In others, $R^2$ is substituted with one or more methyl, ethyl, isopropyl, -cyclopropyl, —$CF_3$, —$CH_2OH$, —OH, —$OCH_3$, —$OCH_2CH_3$, —C(O)$NH_2$, —NHC(O)$CH_3$, or —NHC(O)$CH_2CH_3$. In some embodiments, $R^2$ is a substituted or unsubstituted alkylcycloalkyl, for example, a substituted or unsubstituted ($C_{1-3}$ alkyl)cyclopropyl, ($C_{1-3}$ alkyl)cyclobutyl, ($C_{1-3}$ alkyl)cyclopentyl, or ($C_{1-3}$ alkyl)cyclohexyl. For example, $R^2$ is —($CH_2$)cyclopropyl, —($CH_2$)cyclobutyl, —CH($CH_3$)cyclopropyl, —CH($CH_3$)cyclobutyl, —CH($CH_2CH_3$)cyclopropyl, —C$(CH_3)_2$cyclopropyl, or —$CH_2CH_2$cyclobutyl. In some embodiments, $R^2$ is a substituted or unsubstituted non-aromatic heterocyclyl, for example, tetrahydrofuranyl, tetrahydropyranyl, piperidyl, piperidinonyl or 1,4-dioxaspiro[4.5]decanyl. In others, $R^2$ is oxetanyl, tetrahydrofuranyl, tetrahydropyranyl, piperidyl, piperidinonyl or 1,4-dioxaspiro[4.5]decanyl. In some such embodiments, $R^2$ is substituted with one or more —($C_{1-4}$ alkyl), —($C_{0-3}$ alkyl)OR, or —C(O)R', wherein each R is independently H, or $C_{1-4}$ alkyl, wherein the alkyl is optionally fluorinated, and each R' is independently $C_{1-4}$ alkyl, wherein the alkyl is optionally fluorinated.

In some embodiments of compounds of formula (I), $R^2$ is a substituted or unsubstituted $C_{1-8}$ alkyl,

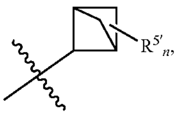 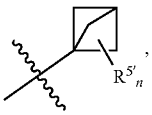, 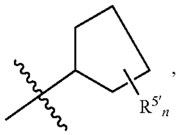,

-continued

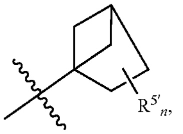 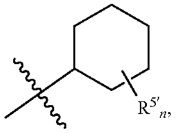 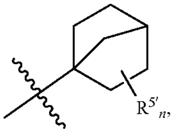

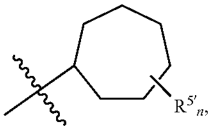 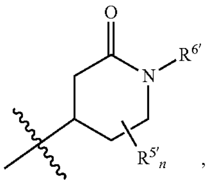,

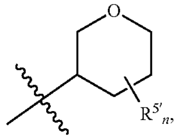 or 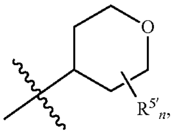

wherein $R^{5'}$ is —$CF_3$, —($C_{1-4}$ alkyl), —($C_{1-6}$ cycloalkyl), —($C_{0-3}$ alkyl)OR, —($C_{0-3}$ alkyl)C(O)$NR_2$, —$NR_2$, or —NRCOR', wherein the cycloalkyl is optionally fluorinated;

$R^6$ is H, or —C(O)R';

each R is independently H, or $C_{1-4}$ alkyl, wherein the alkyl is optionally fluorinated;

each R' is independently $C_{1-4}$ alkyl, wherein the alkyl is optionally fluorinated; and n is 0-2.

In some such embodiments, $R^{5'}$ is methyl, ethyl, isopropyl, -cyclopropyl, —$CF_3$, —$CH_2OH$, —OH, —$OCH_3$, —$OCH_2CH_3$, —C(O)$NH_2$, —NHC(O)$CH_3$, or —NHC(O)$CH_2CH_3$. In some embodiments, $R^{6'}$ is H or —C(O)$CH_3$, —C(O)$CH_2CH_3$, —C(O)CH$(CH_3)_2$, or —C(O)$CH_2CH(CH_3)_2$.

In some such embodiments of $R^2$, $R^1$ is a cycloalkyl, optionally substituted with one or more halogen, —$CF_3$, —($C_{1-4}$ alkyl), —($C_{1-6}$ cycloalkyl), —$NR_2$, —($C_{0-3}$ alkyl) OR, —($C_{0-3}$ alkyl)OR'', —NRC(O)R', —C(O)R', —C(O)$NR_2$, —C(O)OR', or —NRS$(O)_2$R', wherein each R is independently H, or $C_{1-4}$ alkyl, wherein the alkyl is optionally fluorinated, each R' is independently $C_{1-4}$ alkyl, wherein the alkyl is optionally fluorinated, and each R'' is independently a $C_{1-6}$ cycloalkyl., wherein the cycloalkyl is optionally fluorinated.

Further embodiments provided herein include combinations of one or more of the particular embodiments set forth above.

Representative compounds of formula (I) are set forth in Table 1.

In some embodiments, the compound is selected from Table 2.

Provided herein are compounds having the following formula (IB):

(IB)

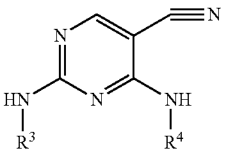

and pharmaceutically acceptable salts, tautomers, stereoisomers, enantiomers, isotopologues, and prodrugs thereof, wherein:

$R^3$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkyl-(non-aromatic heterocyclyl); and $R^4$ is substituted or unsubstituted $C_{1-8}$ alkyl, substituted or unsubstituted cycloalkyl, or substituted or unsubstituted non-aromatic heterocyclyl.

In one embodiment, the compound is not 4-(isopentylamino)-2-(3-(2-methylpiperidin-1-yl)propylamino)pyrimidine-5-carbonitrile

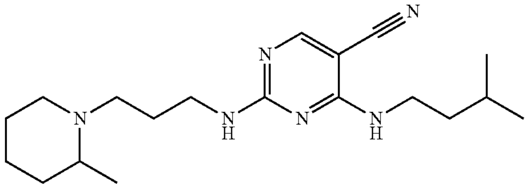

;

(2S,2'S)-dimethyl 2,2'-(5-cyanopyrimidine-2,4-diyl)bis(azanediyl)-bis(4-methylpentanoate)

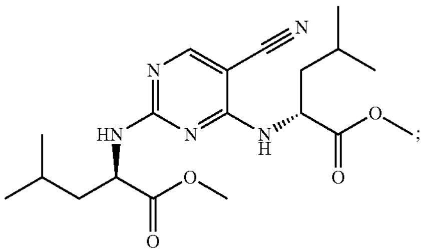 [SMILES: COC(=O)[C@@H](CC(C)C)Nc1ncc(C#N)c(N[C@H](CC(C)C)C(=O)OC)n1]

;

(2S,2'S)-diethyl 2,2'-(5-cyanopyrimidine-2,4-diyl)bis(azanediyl)-bis(3-methylbutanoate)

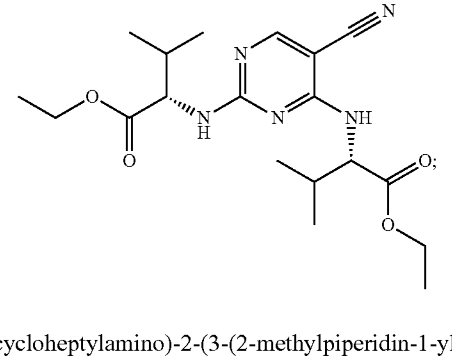

;

4-(cycloheptylamino)-2-(3-(2-methylpiperidin-1-yl)propylamino)-pyrimidine-5-carbonitrile

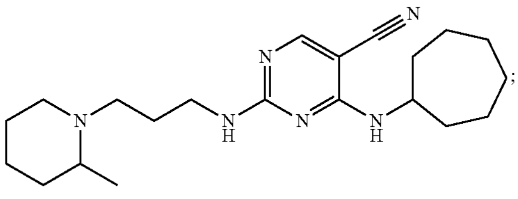 [SMILES: CC1CCCCN1CCCNc1ncc(C#N)c(NC2CCCCCC2)n1]

;

4-(4-methylcyclohexylamino)-2-(3-(2-methylpiperidin-1-yl)propylamino)-pyrimidine-5-carbonitrile

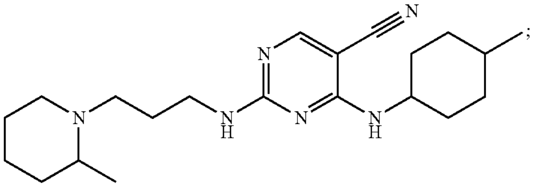 [SMILES: CC1CCC(Nc2nc(NCCCN3CCCCC3C)ncc2C#N)CC1]

;

or 2-(3-(diethylamino)propylamino)-4-(4-methylcyclohexylamino)pyrimidine-5-carbonitrile

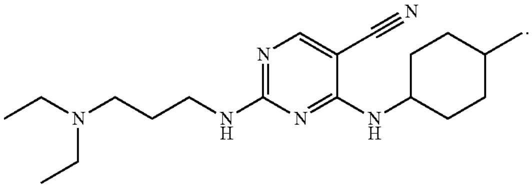 [SMILES: CCN(CC)CCCNc1ncc(C#N)c(NC2CCC(C)CC2)n1]

.

In one embodiment of compounds of formula (TB), $R^3$ is a branched $C_{1-8}$ alkyl, for example, $R^3$ is isopropyl, sec-butyl, isobutyl, tert-butyl, isopentyl, 2-methylpentyl, or tert-pentyl. In other embodiments, $R^3$ is isopropyl, sec-butyl, isobutyl, tert-butyl, 2,3-dimethylbutyl, isopentyl, 2-methylpentyl, neopentyl, tert-pentyl, or 3-methylpentyl. In some embodiments, $R^3$ is tert-butyl. In other embodiments, $R^3$ is a substituted or unsubstituted cycloalkyl, for example, cyclopropyl, cyclobutyl, cyclopentyl, cyclohexyl, cycloheptyl, cyclooctyl, bicyclo[1.1.1]pentyl, or bicyclo[2.2.2]octyl. In some such embodiments, $R^3$ is cyclopropyl, cyclobutyl, cyclopentyl, cyclohexyl, cycloheptyl, cyclooctyl, bicyclo[1.1.1]pentyl, bicyclo[2.2.1]heptyl, or bicyclo[2.2.2]octyl. In some embodiments, $R^3$ is cyclobutyl or cyclohexyl. In some embodiments, the cycloalkyl is substituted with one or more halogen, —$CF_3$, —($C_{1-4}$ alkyl), —($C_{1-6}$ cycloalkyl), —$NR_2$, —($C_{0-3}$ alkyl)OR, —($C_{0-3}$ alkyl)OR'', —NRC(O)R', —C(O)R', —($C_{0-3}$ alkyl)C(O)$NR_2$, —C(O)OR', or —NRS$(O)_2$R', wherein each R is independently H, or $C_{1-4}$ alkyl, wherein the alkyl is optionally fluorinated, and each R' is independently $C_{1-4}$ alkyl, wherein the alkyl is optionally fluorinated, and each R'' is independently a $C_{1-6}$ cycloalkyl, wherein the cycloalkyl is optionally fluorinated. For example, the cycloalkyl is substituted with one or more methyl, ethyl, t-butyl, cyclopropyl, —$CF_3$, —F, —OH, —$OCH_3$, —$OCHF_2$, —$OCF_3$, —$OCH_2CH_3$, —$OCH_2CH_2F$, —$OCH_2CF_3$, —O(cyclopropyl), —$CH_2OH$, —$CH_2OCH_3$, —$C(CH_3)_2OH$, —$NH_2$, —$NH(CH_3)$, —$NHC(O)CH_3$, —$C(CH_3)_2C(O)N(CH_3)_2$, —$C(O)NHCH_3$, —C(O)N$(CH_3)_2$, or —$NHSO_2CH_3$. In other embodiments, the cycloalkyl is substituted with one or more halogen, —($C_{1-4}$ alkyl), —$NR_2$, —($C_{0-3}$ alkyl)OR, —NRC(O)R', —C(O)R', —($C_{0-3}$ alkyl)C(O)$NR_2$, —C(O)OR', or —NRS$(O)_2$R', wherein each R is independently H, or $C_{1-4}$ alkyl, wherein the alkyl is optionally fluorinated, and each R' is independently $C_{1-4}$ alkyl, wherein the alkyl is optionally fluorinated. For example, the cycloalkyl is substituted with one or more methyl, ethyl, t-butyl, —F, —OH, —$OCH_3$, —$OCHF_2$, —$OCF_3$, —$OCH_2CH_3$, —$OCH_2CH_2F$, —$OCH_2CF_3$, —O(cyclopropyl), —$CH_2OH$, —$CH_2OCH_3$, —$C(CH_3)_2$OH, —$NH_2$, —$NH(CH_3)$, —$NHC(O)CH_3$, —$C(CH_3)_2$C (O)N($CH_3$)$_2$, —C(O)NH$CH_3$, —C(O)N($CH_3$)$_2$, or —NH$SO_2CH_3$. In some embodiments, the cycloalkyl is substituted with one or more methyl, —F, —OH, —$OCH_3$, —$OCH_2CH_3$, —$OCHF_2$, —$OCH_2CF_3$, —NH($CH_3$), —NHC(O)$CH_3$, —C(O)N($CH_3$)$_2$, or —C($CH_3$)$_2$C(O)N($CH_3$)$_2$. In yet other embodiments, $R^3$ is a substituted or unsubstituted non-aromatic heterocyclyl, for example, pyrrolidinyl, tetrahydrofuranyl, tetrahydropyranyl, 1,4-dioxaspiro[4.5]decanyl, or piperidyl. In some embodiments, the non-aromatic heterocyclyl is oxetanyl, tetrahydrofuranyl, tetrahydropyranyl, piperidyl, piperidinonyl or 1,4-dioxaspiro[4.5]decanyl. In some embodiments, $R^3$ is tetrahydropyranyl. In some embodiments, the piperidyl is substituted with —C(O)R', or —C(O)OR', wherein R' is $C_{1-4}$ alkyl, wherein the alkyl is optionally fluorinated. In some embodiments, $R^3$ is a substituted or unsubstituted alkylcycloalkyl, for example, ($C_{1-3}$ alkyl)cyclopropyl, ($C_{1-3}$ alkyl)cyclobutyl, ($C_{1-3}$ alkyl)cyclopentyl, or ($C_{1-3}$ alkyl)cyclohexyl. In some embodiments, $R^3$ is —($CH_2$)cyclopropyl, —($CH_2$)cyclobutyl, —($CH_2$)cyclopentyl, —($CH_2$)cyclohexyl, —CH($CH_3$)cyclopropyl, —CH($CH_3$)cyclobutyl, —CH($CH_3$)cyclopentyl, or —CH($CH_3$)cyclohexyl. In others, $R^3$ is —($CH_2$)cyclopropyl, —CH($CH_3$)cyclopropyl, —CH($CH_3$)cyclobutyl, —CH($CH_3$)cyclohexyl, or —C($CH_3$)$_2$cyclopropyl. In some embodiments, $R^3$ is a substituted or unsubstituted alkyl-(non-aromatic heterocyclyl), for example, —($C_{1-4}$ alkyl)tetrahydrofuranyl, or —($C_{1-4}$ alkyl)dioxolanyl.

In some embodiments of compounds of formula (TB), $R^3$ is selected from branched $C_{1-8}$ alkyl,

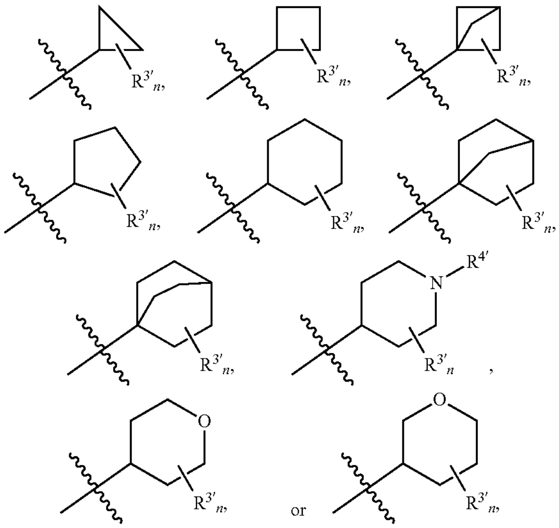

or wherein $R^{3'}$ is halogen, —$CF_3$, —($C_{1-4}$ alkyl), —($C_{1-6}$ cycloalkyl), —$NR_2$, —($C_{0-3}$ alkyl)OR, —($C_{0-3}$ alkyl)OR'', —NRC(O)R', —C(O)R', —C(O)$NR_2$, —C(O)OR', or —NRS(O)$_2$R';

$R^{4'}$ is —C(O)R', or —C(O)OR';

each R is independently H, or $C_{1-4}$ alkyl, wherein the alkyl is optionally fluorinated;

each R' is independently $C_{1-4}$ alkyl, wherein the alkyl is optionally fluorinated;

each R'' is independently a $C_{1-6}$ cycloalkyl, wherein the cycloalkyl is optionally fluorinated; and n is 0-2.

In some embodiments, $R^{3'}$ is methyl, ethyl, t-butyl, cyclopropyl —$CF_3$, —F, —OH, —$OCH_3$, —$OCHF_2$, —$OCF_3$, —$OCH_2CH_3$, —$OCH_2CH_2F$, —$OCH_2CF_3$, —O(cyclopropyl), —$CH_2OH$, —$CH_2OCH_3$, —C($CH_3$)$_2$OH, —$NH_2$, —NH($CH_3$), —NHC(O)$CH_3$, —C(O)NH$CH_3$, —C(O)N($CH_3$)$_2$, or —NH$SO_2CH_3$.

In some embodiments of compounds of formula (TB), $R^3$ is selected from branched $C_{1-8}$ alkyl,

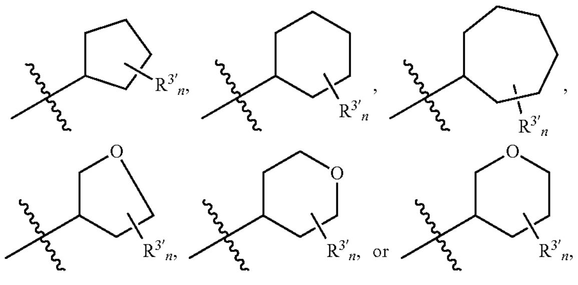

or wherein $R^{3'}$ is halogen, —($C_{1-4}$ alkyl), —$NR_2$, —($C_{0-3}$ alkyl)OR, —NRC(O)R', —C(O)R', —($C_{0-3}$ alkyl)C(O)$NR_2$, —C(O)OR', or —NRS(O)$_2$R';

each R is independently H, or $C_{1-4}$ alkyl, wherein the alkyl is optionally fluorinated, each R' is independently $C_{1-4}$ alkyl, wherein the alkyl is optionally fluorinated;

and n is 0-2.

In some such embodiments, $R^{3'}$ is methyl, ethyl, t-butyl, —F, —OH, —$OCH_3$, —$OCHF_2$, —$OCF_3$, —$OCH_2CH_3$, —$OCH_2CH_2F$, —$OCH_2CF_3$, —$CH_2OH$, —$CH_2OCH_3$, —C($CH_3$)$_2$OH, —$NH_2$, —NH($CH_3$), —NHC(O)$CH_3$, —C($CH_3$)$_2$C(O)N($CH_3$)$_2$, —C(O)NH$CH_3$, —C(O)N($CH_3$)$_2$, or —NH$SO_2CH_3$ In some embodiments of compounds of formula (TB), $R^4$ is a substituted or unsubstituted $C_{1-8}$ alkyl, for example, methyl, ethyl, n-propyl, isopropyl, n-butyl, sec-butyl, isobutyl, tert-butyl, isopentyl, 2-methylpentyl, or tert-pentyl. In some embodiments, $R^4$ is methyl, ethyl, n-propyl, isopropyl, n-butyl, sec-butyl, isobutyl, tert-butyl, 3-methylbutyl, 2,3-dimethylbutyl, 3,3-dimethylbutyl, 2,3,3-trimethylbutyl, tert-pentyl, isopentyl, 3-pentyl, 3-methylpentyl, 2-methylpentyl, or 2,4-dimethylpentyl. In some embodiments, $R^4$ is isopropyl, isobutyl, isopentyl, tert-butyl, or tert-pentyl. In some such embodiments, $R^4$ is substituted with one or more —($C_{1-4}$ alkyl), —($C_{0-3}$ alkyl)OR, —C(O)$NR_2$ or —NRCOR', wherein each R is independently H, or $C_{1-4}$ alkyl, wherein the alkyl is optionally fluorinated, and each R' is independently $C_{1-4}$ alkyl, wherein the alkyl is optionally fluorinated. For example, $R^4$ is substituted with one or more —OH, or —$CH_3$. In some other embodiments, $R^4$ is a substituted or unsubstituted cycloalkyl, for example, cyclopropyl, cyclobutyl, cyclopentyl, cyclohexyl, cycloheptyl, cyclooctyl, bicyclo[1.1.1]pentyl, bicyclo[2.1.1]hexyl, or bicyclo[2.2.1]heptyl. In some embodiments, $R^4$ is cyclobutyl, cyclopentyl, cyclohexyl, cycloheptyl, or bicyclo[1.1.1]pentyl. In some embodiments, $R^4$ is substituted with one or more halogen, —$CF_3$, —($C_{1-4}$ alkyl), —($C_{1-6}$ cycloalkyl), —($C_{0-3}$ alkyl)OR, —($C_{0-3}$ alkyl)C(O)$NR_2$, —$NR_2$, or —NRCOR', wherein each R is independently H, or $C_{1-4}$ alkyl, wherein the alkyl is optionally fluorinated, each R' is independently $C_{1-4}$ alkyl, wherein the alkyl is optionally fluorinated, and wherein the cycloalkyl is optionally fluorinated. For example, $R^4$ is substituted with one or more methyl, ethyl, isopropyl, -cyclopropyl, —$CF_3$, —$CH_2OH$, —OH, —$OCH_3$, —$OCH_2CH_3$, —$C(O)NH_2$, —NHC(O)$CH_3$, or —$NHC(O)CH_2CH_3$. In some embodiments, $R^4$ is substituted with one or more halogen, —($C_{1-4}$ alkyl), —($C_{0-3}$ alkyl)OR, —($C_{0-3}$ alkyl)C(O)$NR_2$, —$NR_2$, or —NRCOR', wherein each R is independently H, or $C_{1-4}$ alkyl, wherein the alkyl is optionally fluorinated, and each R' is independently $C_{1-4}$ alkyl, wherein the alkyl is optionally fluorinated. In some such embodiments, $R^4$ is substituted with one or more F, methyl, ethyl, isopropyl, —$CH_2OH$, —OH, —$OCH_3$, —$OCH_2CH_3$, —$OCHF_2$, —$OCH_2CF_3$, —$C(O)NH_2$, —C(O)$NHCH_3$, —C(O)$N(CH_3)_2$, —$CH_2C(O)NH_2$, —$CH_2C(O)NHCH_3$, —$CH_2C(O)N(CH_3)_2$, —$CH(CH_3)C(O)NH_2$, —$CH(CH_3)C(O)NHCH_3$, —$CH(CH_3)C(O)N(CH_3)_2$, —$C(CH_3)_2C(O)NH_2$, —$C(CH_3)_2C(O)NHCH_3$, —$C(CH_3)_2C(O)N(CH_3)_2$, —$NH(CH_3)$, —NHC(O)$CH_3$, or —$NHC(O)CH_2CH_3$. In some embodiments, $R^4$ is substituted with one or more methyl, ethyl, —F, —$CH_2OH$, or —OH. In some embodiments, $R^4$ is a substituted or unsubstituted non-aromatic heterocyclyl, for example, oxetanyl, tetrahydrofuranyl, tetrahydropyranyl, piperidyl, piperidinonyl or 1,4-dioxaspiro[4.5]decanyl. In some embodiments, $R^4$ is tetrahydrofuranyl or tetrahydropyranyl. In some such embodiments, $R^4$ is substituted with one or more —($C_{1-4}$ alkyl), —($C_{0-3}$ alkyl)OR, or —C(O)R', wherein each R is independently H, or $C_{1-4}$ alkyl, wherein the alkyl is optionally fluorinated, and each R' is independently $C_{1-4}$ alkyl, wherein the alkyl is optionally fluorinated.

In some embodiments of compounds of formula (IB), $R^4$ is a substituted or unsubstituted $C_{1-8}$ alkyl,

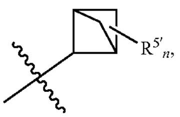
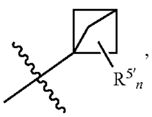
,
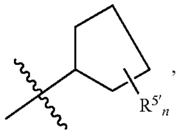
,

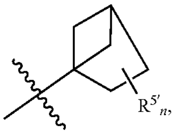
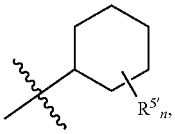
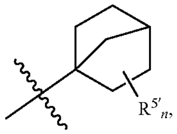

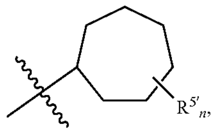
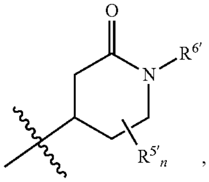
,

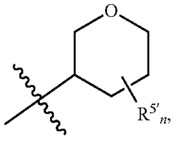
or
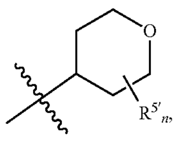

wherein $R^{5'}$ is —$CF_3$, —($C_{1-4}$ alkyl), —($C_{1-6}$ cycloalkyl), —($C_{0-3}$ alkyl)OR, —($C_{0-3}$ alkyl)C(O)$NR_2$, —$NR_2$, or —NRCOR', wherein the cycloalkyl is optionally fluorinated;

$R^{6'}$ is H, or —C(O)R';

each R is independently H, or $C_{1-4}$ alkyl, wherein the alkyl is optionally fluorinated;

each R' is independently $C_{1-4}$ alkyl, wherein the alkyl is optionally fluorinated; and n is 0-2.

In some such embodiments, $R^{5'}$ is methyl, ethyl, isopropyl, -cyclopropyl, —$CF_3$, —$CH_2OH$, —OH, —$OCH_3$, —$OCH_2CH_3$, —$C(O)NH_2$, —NHC(O)$CH_3$, or —NHC(O)$CH_2CH_3$. In some embodiments, $R^{6'}$ is H or —C(O)$CH_3$, —C(O)$CH_2CH_3$, —C(O)$CH(CH_3)_2$, or —C(O)$CH_2CH(CH_3)_2$.

In some embodiments of compounds of formula (IB), $R^4$ is a substituted or unsubstituted $C_{1-8}$ alkyl,

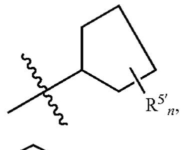
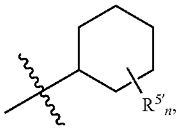

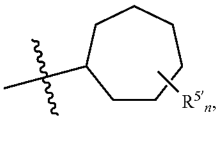
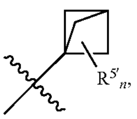
or
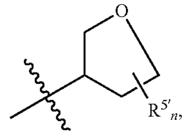

wherein $R^{5'}$ is halogen, —($C_{1-4}$ alkyl), —($C_{0-3}$ alkyl)OR, —($C_{0-3}$ alkyl)C(O)$NR_2$, —$NR_2$, or —NRCOR';

each R is independently H, or $C_{1-4}$ alkyl, wherein the alkyl is optionally fluorinated;

each R' is independently $C_{1-4}$ alkyl, wherein the alkyl is optionally fluorinated; and n is 0-2.

In some such embodiments, $R^{5'}$ is F, methyl, ethyl, isopropyl, —$CH_2OH$, —OH, —$OCH_3$, —$OCH_2CH_3$, —$OCHF_2$, —$OCH_2CF_3$, —$C(O)NH_2$, —C(O)$NHCH_3$, —C(O)$N(CH_3)_2$, —$CH_2C(O)NH_2$, —$CH_2C(O)NHCH_3$, —$CH_2C(O)N(CH_3)_2$, —$CH(CH_3)C(O)NH_2$, —$CH(CH_3)C(O)NHCH_3$, —$CH(CH_3)C(O)N(CH_3)_2$, —$C(CH_3)_2C(O)NH_2$, —$C(CH_3)_2C(O)NHCH_3$, —$C(CH_3)_2C(O)N(CH_3)_2$, —$NH(CH_3)$, —NHC(O)$CH_3$, or —$NHC(O)CH_2CH_3$. In some embodiments, $R^{5'}$ is F, —OH, —$OCH_3$, —$OCH_2CH_3$, —$OCHF_2$, —$OCH_2CF_3$, —$NH(CH_3)$, —NHC(O)$CH_3$, —C(O)$N(CH_3)_2$, —$C(CH_3)_2C(O)N(CH_3)_2$.

In some embodiments, wherein $R^4$ is a substituted or unsubstituted cycloalkyl, $R^3$ is a cycloalkyl, optionally substituted with one or more halogen, —$CF_3$, —($C_{1-4}$ alkyl), —($C_{1-6}$ cycloalkyl), —$NR_2$, —($C_{0-3}$ alkyl)OR, —($C_{0-3}$ alkyl)OR'', —NRC(O)R', —C(O)R', —C(O)$NR_2$, —C(O)OR', or —$NRS(O)_2R'$, wherein each R is independently H, or $C_{1-4}$ alkyl, wherein the alkyl is optionally fluorinated, each R' is independently $C_{1-4}$ alkyl, wherein the alkyl is optionally fluorinated and each R'' is independently a $C_{1-6}$ cycloalkyl, wherein the cycloalkyl is optionally fluorinated.

Further embodiments provided herein include combinations of one or more of the particular embodiments set forth above.

Representative compounds of formula (TB) are set forth in Table 3.

Diaminopyrimidine Compounds set forth in Table 1, Table 2, and Table 3 were tested in the JNK inhibitor assays described herein and were found to have activity as JNK inhibitors. In one embodiment, the Diaminopyrimidine Compound is a compound as described herein, wherein the compound at a concentration of 10 μM inhibits JNK1 by at least about 50% or more.

Methods for Making Diaminopyrimidine Compounds

The Diaminopyrimidine Compounds can be made using conventional organic syntheses and commercially available starting materials. By way of example and not limitation, Diaminopyrimidine Compounds of formula (I) can be prepared as outlined in Schemes 1-9 shown below as well as in the examples set forth herein. It should be noted that one skilled in the art would know how to modify the procedures set forth in the illustrative schemes and examples to arrive at the desired products.

Scheme 1

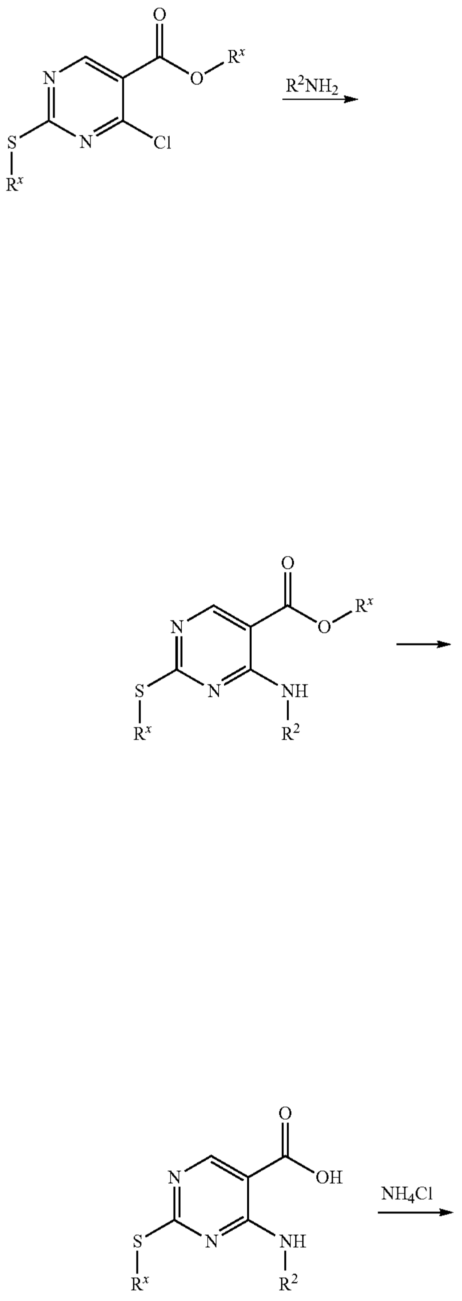

-continued

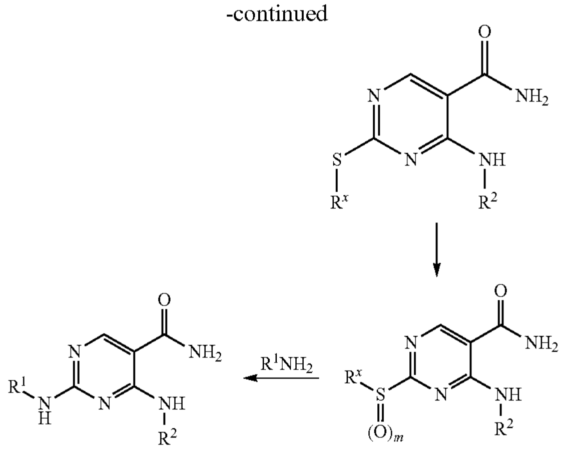

(I)

As shown in Scheme 1, compounds of formula (I), wherein $R^1$ and $R^2$ are as defined herein, can be prepared starting from an appropriately derivatized 4-chloro-2-alkylthiopyrimidine carboxylate ester (wherein each $R^x$ is independently a $C_{1-2}$ alkyl), by treatment with $R^2NH_2$ at elevated temperature (for example 60-80° C.) in an organic solvent (for example, ethanol, methanol, isopropanol, THF, NMP, DMF, DMSO, or dioxane), in the presence of a base (for example, DIEA, TEA, N-methylmorpholine, 1,8-diazabicyclo[5.4.0]undec-7-ene, cesium carbonate, sodium carbonate, sodium bicarbonate, potassium carbonate, or potassium phosphate). Hydrolysis of the ester is achieved by treatment with an aqueous base, such as for example aqueous sodium hydroxide, potassium hydroxide, or lithium hydroxide, in a cosolvent such as ethanol, methanol, isopropanol, THF, or dioxane. Amide formation is accomplished by reaction with $NH_4Cl$ in the presence of a coupling agent (such as, for example, HATU, CDI, HBTU, EDC optionally in combination with HOBt, or ethyl chloroformate), in an organic solvent, such as NMP, DMF, DMSO, dioxane, THF, DCM, or chloroform, in the presence of a base (such as DIEA, TEA, or potassium carbonate). Oxidation of the alkylthiol moiety is achieved by treatment in an organic solvent (such as, for example, acetone, DCM, NMP, DMF, or chloroform) with an oxidant such as mCPBA, oxone, hydrogen peroxide, or 3-phenyl-2-(phenylsulfonyl)-1,2-oxaziridine. The resulting mixture of sulfone (m=1) and sulfoxide (m=2) is treated at elevated temperature (for example, 80-100° C.) with $R^1NH_2$ in a solvent (such as, for example, dioxane, DMSO, NMP, DMF, THF, or water) in the presence of an organic base, such as DIEA, TEA, N-methylmorpholine, or 1,8-diazabicyclo[5.4.0]undec-7-ene, to afford the compounds of formula (I).

Scheme 2

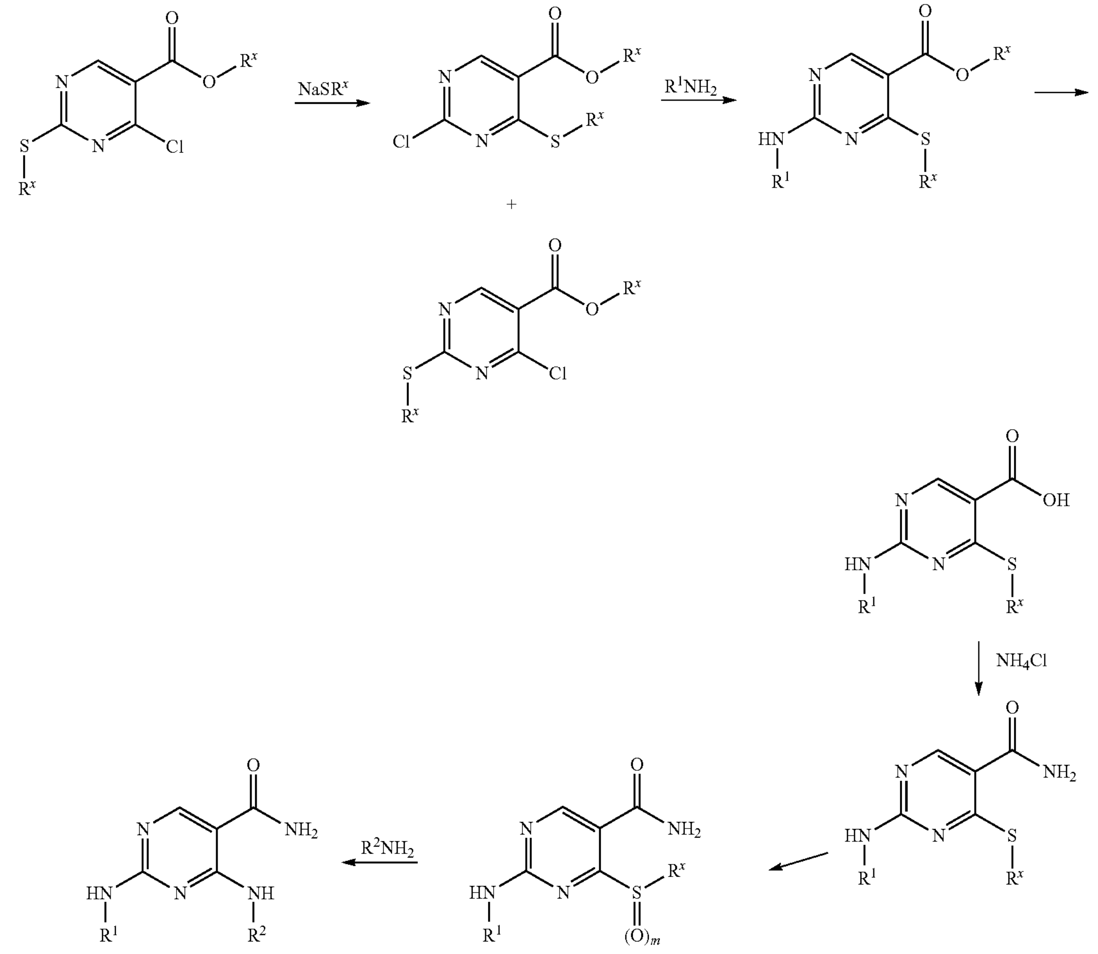

Alternatively, compounds of formula (I) can be prepared as shown in Scheme 2 (wherein R', $R^2$ and $R^x$ are as defined above). Treatment of a 2,4-dichloropyrimidine-5-carboxylate alkyl ester with NaSR$^x$ in an organic solvent (for example THF, DCM, or dioxane) in the presence of a catalyst (for example, triethylbenzylammonium chloride, tetrabutylammonium chloride, or tetrabutylammonium bromide), under cooling (for example, at −10° C.) affords a mixture of thioalkyl derivatives. Subsequent treatment with $R^1NH_2$ at elevated temperature (e.g. 80° C.) in an organic solvent (for example, dioxane, THF, NMP, DMF, DMSO, ethanol, methanol, or isopropanol), in the presence of a base (for example, DIEA, TEA, N-methylmorpholine, 1,8-diazabicyclo[5.4.0]undec-7-ene, cesium carbonate, sodium carbonate, sodium bicarbonate, potassium carbonate, or potassium phosphate) incorporates the $R^1$ sidechain. Hydrolysis of the alkyl ester, coupling with $NH_4Cl$ and oxidation as above, provides a mixture of sulfone (m=1) and sulfoxide (m=2) derivatives, which upon treatment with $R^2NH_2$ in a solvent (such as dioxane, NMP, DMF, DMSO, THF, or water), in the presence of an organic base (such as DIEA, TEA, 1,8-diazabicyclo[5.4.0]undec-7-ene, or N-methylmorpholine), at elevated temperature (e.g. 80-110° C.) provides the compounds of formula (I).

Scheme 3

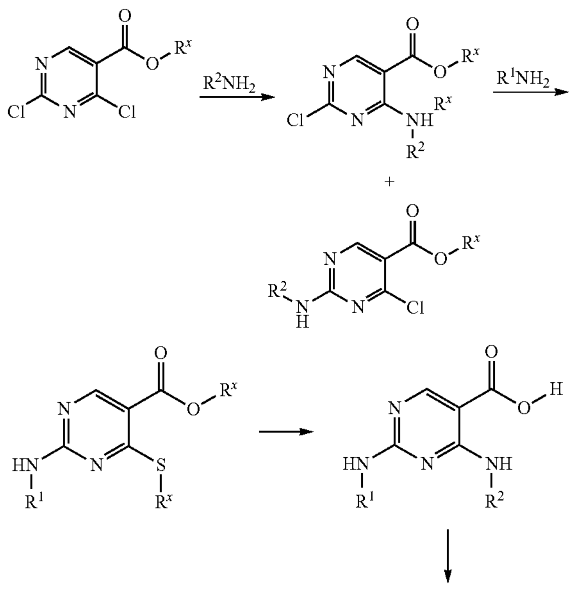

-continued

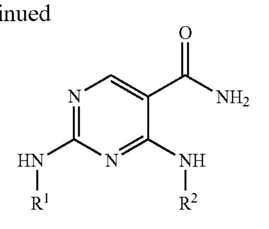

(I)

Compounds of formula (I) can also be prepared as shown in Scheme 3. Treatment of 2,4-dichloropyrimidine-5-carboxylate alkyl ester with $R^2NH_2$ in a solvent (for example, ethyl ether, THF, DCM, toluene, or methyl tert-butyl ether) in the presence of a base (for example, DIEA, TEA, 1,8-diazabicyclo[5.4.0]undec-7-ene, N-methylmorpholine, sodium bicarbonate, cesium carbonate, or potassium phosphate) at low temperature (for example, −70° C.) provides introduction of the $R^2$ sidechain. Separation of the mixture of regioisomers, and hydrogenation of the remaining chlorine in a sample allows for regiomeric assignment of the $R^2$ sidechain incorporation. The desired regioisomer compound is then further derivatized. Subsequent treatment with $R^1NH_2$ in an organic solvent (for example, THF, NMP, DMF, DMSO, dioxane, ethanol, methanol, or isopropanol) in the presence of a base (for example, DIEA, TEA, 1,8-diazabicyclo[5.4.0]undec-7-ene, N-methylmorpholine, sodium carbonate, sodium bicarbonate, cesium carbonate, or potassium phosphate) at elevated temperature (for example, 70° C.) provides introduction of the $R^1$ sidechain. Hydrolysis of the alkyl ester and coupling with $NH_4Cl$, as before, provides the compounds of formula (I).

Scheme 4

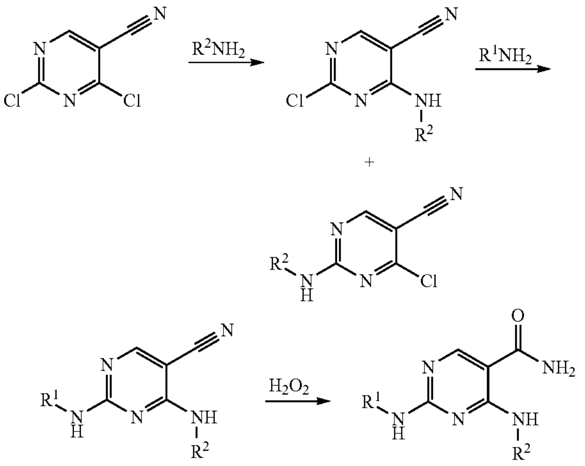

(I)

An alternative method to the synthesis of compounds of formula (I) is shown in Scheme 4. Treatment of 2,4-dichloropyrimidine-5-carbonitrile with $R^2NH_2$ in an organic solvent (for example, ethanol, methanol, isopropanol or THF) in the presence of a base (for example, DIEA, TEA, 1,8-diazabicyclo[5.4.0]undec-7-ene, N-methylmorpholine, sodium carbonate, sodium bicarbonate, cesium carbonate, or potassium phosphate) at low temperature (for example, −60° C.) provides introduction of the $R^2$ sidechain. As before, hydrogenation of the remaining chlorine allows for regioisomeric assignment of the $R^2$ incorporation. Subsequent treatment with $R^1NH_2$ in an organic solvent (for example, 1-butanol, THF, NMP, DMF, DMSO, dioxane, ethanol, methanol, or isopropanol) in the presence of a base (for example, cesium carbonate, potassium carbonate, sodium carbonate, sodium bicarbonate, potassium phosphate, 1,8-diazabicyclo[5.4.0]undec-7-ene, N-methylmorpholine, DIEA, or TEA) at elevated temperature (for example, 120° C.) provides introduction of the $R^1$ sidechain (providing in some instances when $R^1$═$R^3$ and $R^2$═$R^4$, compounds of formula (IB)). Conversion of the nitrile moiety with, for example, catalytic peroxide, in the presence of a strong aqueous base, such as sodium hydroxide or potassium hydroxide, in a solvent, such as, for example, DMSO, NMP, DMF, ethanol or methanol, provides the compounds of formula (T).

Scheme 5

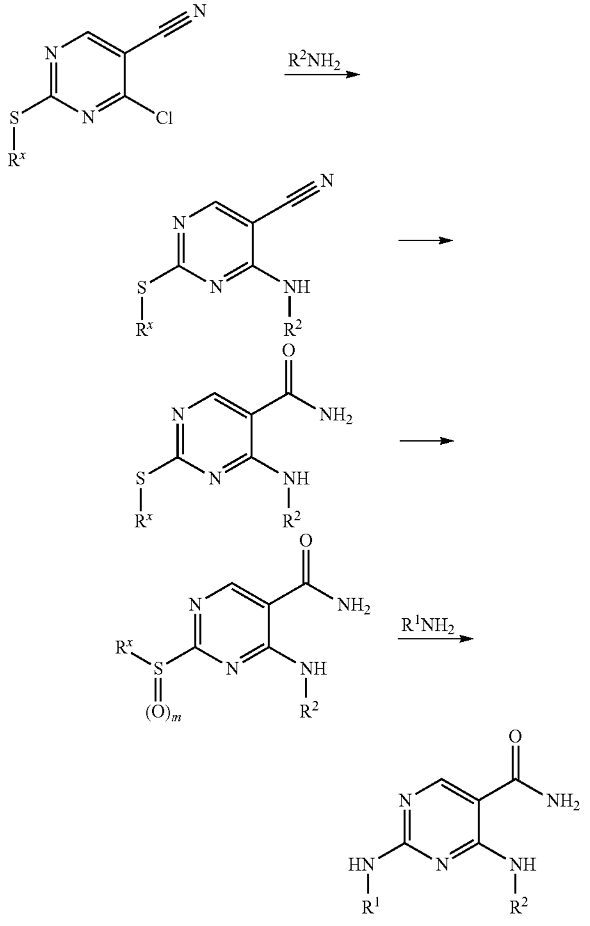

(I)

Yet another method for the synthesis of compounds of formula (I) is shown in Scheme 5. Treatment of 4-chloro-2-(alkylthio)pyrimidine-5-carbonitrile with $R^1NH_2$ in an organic solvent (for example, n-butanol, NMP, DMF, DMSO, dioxane, or ethanol) in the presence of a base (such as, for example, DIEA, TEA, N-methylmorpholine, 1,8-diazabicyclo[5.4.0]undec-7-ene, potassium carbonate, sodium carbonate, sodium bicarbonate, cesium carbonate, or potassium phosphate), at a temperature between 50° C. and 90° C.) introduces the $R^1$ sidechain. Conversion of the carbonitrile to the amide, for example by treatment with peroxide ($H_2O_2$), in a solvent (such as, for example, DMSO, NMP, DMF, ethanol, or methanol), in the presence of a base (such as sodium hydroxide or potassium hydroxide), and oxidation, (for example using mCPBA, oxone, hydrogen peroxide, or 3-phenyl-2-(phenylsulfonyl)-1,2-oxaziridine, in a solvent such as DCM, NMP, DMF, or DMA), provides the mixture of sulfone (m=1) and sulfoxide (m=2) as before, which can be treated with $R^2NH_2$ in a solvent such as (dioxane, DMSO, NMP, DMF, THF, or n-butanol) in the presence of a base (such as DIEA, TEA, 1,8-diazabicyclo [5.4.0]undec-7-ene, or N-methylmorpholine), optionally at elevated temperature (for example, between room temperature and 130° C.) to provide compounds of formula (I).

the sulfone/sulfoxide, and treatment with $R^2NH_2$ provides the compounds of formula (I). Alternatively, the alkylthio moiety is oxidized first, followed by introduction of the $R^2$ sidechain, (providing in some instances when $R^1$=$R^3$ and $R^2$=$R^4$ compounds of formula (IB)), and conversion to the amide moiety, provides compounds of formula (I).

Alternatively, Diaminopyrimidine Compounds of Formula (TB), wherein $R^3$ and $R^4$ are as defined herein, can be made as outlined in Schemes 7, 8 and 9 shown below, as well as in the examples set forth herein. It should be noted that one skilled in the art would know how to modify the Scheme 6

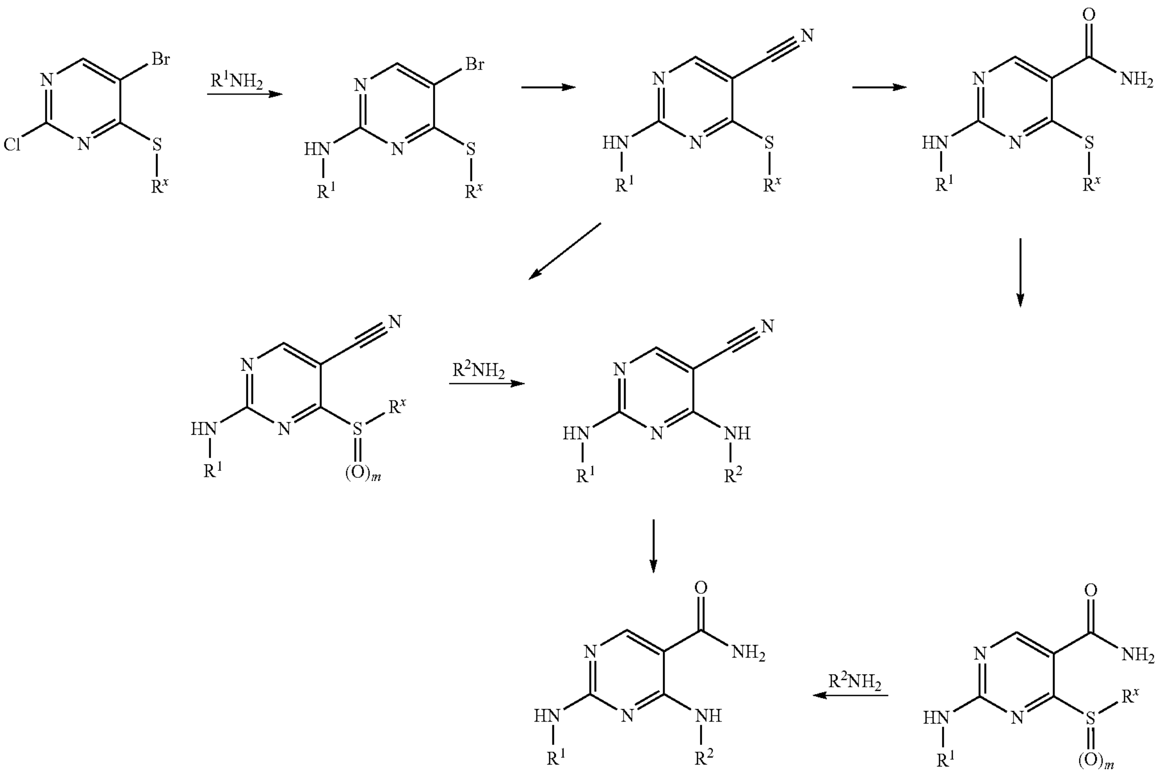

(I)

Compounds of formula (I) can also be obtained as shown in Scheme 6. Treatment of 5-bromo-2-chloro-4-(alkylthio) pyrimidine with $R^1NH_2$ in an organic solvent (for example, n-butanol, NMP, DMF, DMSO, dioxane, or ethanol) in the presence of a base (such as, for example, DIEA, TEA, N-methylmorpholine, 1,8-diazabicyclo-[5.4.0]undec-7-ene, potassium carbonate, sodium carbonate, sodium bicarbonate, cesium carbonate, or potassium phosphate), at a temperature between 80° C. and 100° C., introduces the $R^1$ sidechain. Introduction of the carbonitrile moiety is achieved by treatment with zinc and dicyanozinc in a solvent (such as DMF, DMSO, NMP, or DMA) in the presence of a catalyst such as Pd(O), at elevated temperature (for example, between 80° C.-100° C.). As before, conversion to the amide moiety by treatment with peroxide, followed by oxidation to procedures set forth in the illustrative schemes and examples to arrive at the Scheme 7

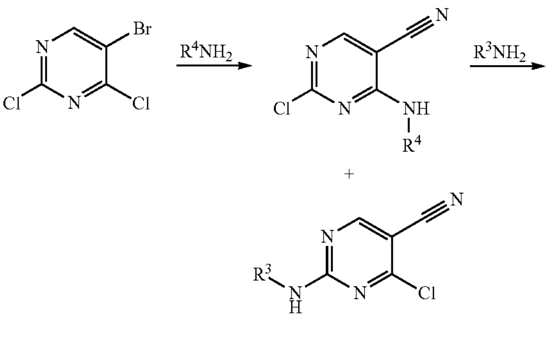

-continued

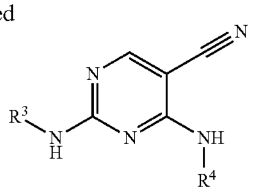

(1B)

As shown in Scheme 7, treatment of 2,4-dichloropyrimidine-5-carbonitrile with $R^4NH_2$ in an organic solvent (for example, ethanol, methanol, isopropanol or THF) in the presence of a base (for example, DIEA, TEA, 1,8-diazabicyclo[5.4.0]undec-7-ene, N-methylmorpholine, sodium carbonate, sodium bicarbonate, cesium carbonate, or potassium phosphate) provides introduction of the $R^4$ sidechain. Subsequent treatment with $R^3NH_2$ in an organic solvent (for example, 1-butanol, THF, NMP, DMF, DMSO, dioxane, ethanol, methanol, or isopropanol) in the presence of a base (for example, cesium carbonate, potassium carbonate, sodium carbonate, sodium bicarbonate, potassium phosphate, 1,8-diazabicyclo[5.4.0]undec-7-ene, N-methylmorpholine, DIEA, or TEA) at elevated temperature (for example, 50° C. to 90° C.) provides compounds of formula (TB).

Scheme 8

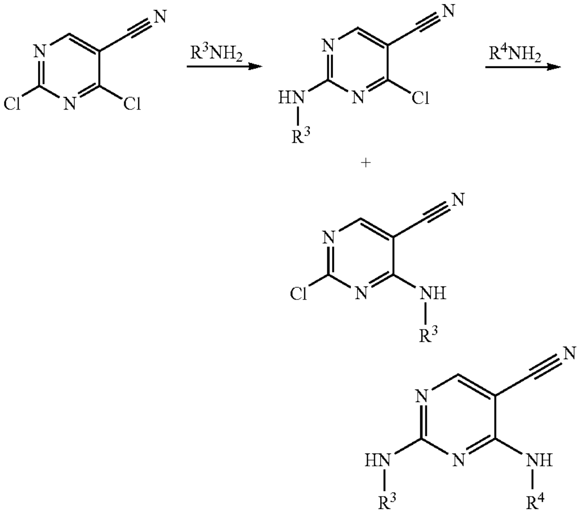

(1B)

Alternatively, the $R^3$ substituent is introduced first, followed by introduction of the $R^4$ substituent by essentially the same methods, as shown in Scheme 8. In some embodiments, coupling with $R^4NH_2$ is performed at a temperature between room temperature and 110° C.

Scheme 9

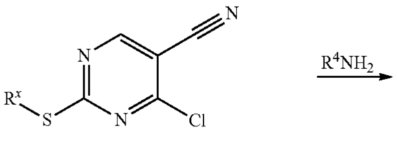

-continued

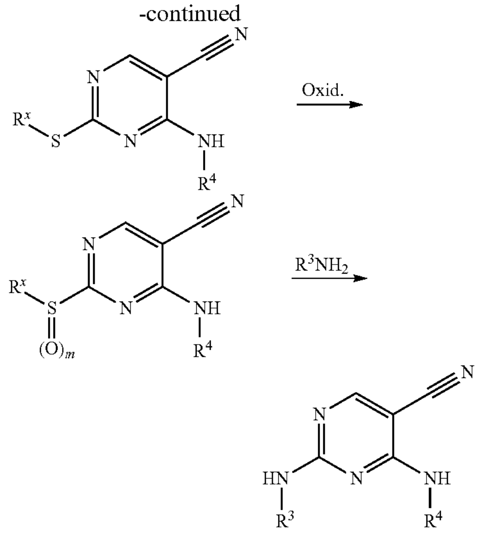

(IB)

In a third approach, compounds of formula (IB) can be prepared starting from an appropriately derivatized 4-chloro-2-alkylthiopyrimidine-carbonitrile (wherein each $R^x$ is independently a $C_{1-2}$ alkyl), by treatment with $R^4NH_2$ at elevated temperature (for example 50° C.-90° C.) in an organic solvent (for example, n-butanol, NMP, DMF, DMSO, or dioxane), in the presence of a base (for example, DIEA, TEA, N-methylmorpholine, 1,8-diazabicyclo[5.4.0]undec-7-ene, potassium carbonate, sodium carbonate, sodium bicarbonate, cesium carbonate or potassium phosphate). Oxidation of the alkylthiol moiety is achieved by treatment in an organic solvent (such as, for example, DCM, NMP, DMF, or DMA) with an oxidant such as mCPBA, oxone, hydrogen peroxide, or 3-phenyl-2-(phenylsulfonyl)-1,2-oxaziridine. The resulting mixture of sulfone (m=1) and sulfoxide (m=2) is treated at room temperature or elevated temperature (for example, 25° C.-110° C.) with $R^3NH_2$ in a solvent (such as, for example, dioxane, DMSO, NMP, DMF, THF, or n-butanol) in the presence of an organic base, such as DIEA, TEA, 1,8-diazabicyclo[5.4.0]undec-7-ene, N-methylmorpholine, to afford the compounds of formula (IB).

In one aspect, provided herein are methods for preparing a compound of formula (I):

(I)

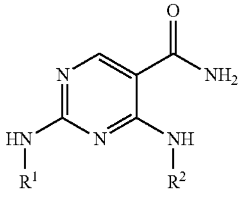

the methods comprising contacting a compound of formula (Ia)

(Ia)

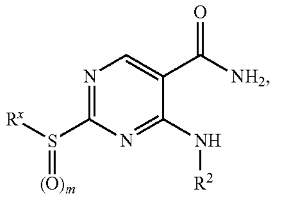

with $R^1NH_2$ in a solvent, in the presence of an organic base, wherein:

$R^1$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkylheterocyclyl, provided that $R^1$ is not 1-aminocyclohexyl;

$R^2$ is substituted or unsubstituted $C_{1-8}$ alkyl, substituted or unsubstituted saturated cycloalkyl, substituted or unsubstituted alkylcycloalkyl, substituted or unsubstituted non-aromatic heterocyclyl;

$R^x$ is a $C_{1-2}$ alkyl; and m is 1 or 2.

In one embodiment, the compound of formula (I) is not 2-(2-aminoethyl-amino)-4-(methylamino)pyrimidine-5-carboxamide; 2-(2-aminopropylamino)-4-(cyclohexylamino) pyrimidine-5-carboxamide; 2-(2-amino-2-oxoethylamino)-4-(cyclohexylamino)pyrimidine-5-carboxamide; 2-(2-aminoethylamino)-4-(cyclohexylamino)pyrimidine-5-carboxamide; (S)-2-(2-aminopropylamino)-4-(cyclobutylamino)pyrimidine-5-carboxamide; (R)-2-(1-amino-3-methyl-1-oxobutan-2-ylamino)-4-(cyclobutylamino)pyrimidine-5-carboxamide; 4-(cyclopentylamino)-2-(methylamino)pyrimidine-5-carboxamide; or 2-(1-acetylpiperidin-4-ylamino)-4-(cyclopropylamino)pyrimidine-5-carboxamide.

In one embodiment, the solvent is dioxane, DMSO, NMP, DMF, THF, or water. In another, the base is DIEA, TEA, 1,8-diazabicyclo[5.4.0]undec-7-ene, or N-methylmorpholine. In some embodiments, the contacting is performed at elevated temperature, for example, from about 80° C. to about 100° C.

In some embodiments, the methods further comprise preparing a compound of formula (Ia):

(Ia)

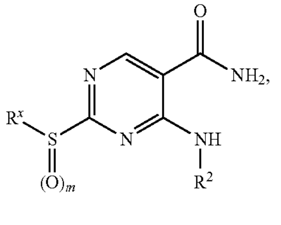

the methods comprising oxidizing a compound of formula (Ib)

(Ib)

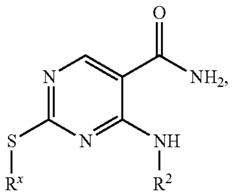

in a solvent by treatment with an oxidant selected from mCPBA, oxone, hydrogen peroxide, or 3-phenyl-2-(phenylsulfonyl)-1,2-oxaziridine.

In one embodiment, the solvent is acetone, DCM, NMP, DMF, or chloroform. In some embodiments, the method is performed at a temperature between about 0° C. to about 20° C.

In some embodiments, the methods further comprise preparing a compound of formula (Ib):

(Ib)

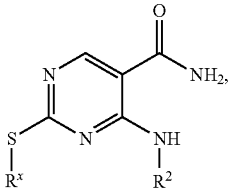

the methods comprising contacting a compound of formula (Ic)

(Ic)

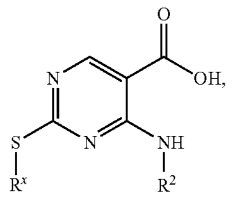

with $NH_4Cl$, in the presence of a coupling agent and a base, in a solvent.

In some embodiments, the solvent is NMP, DMF, DMSO, dioxane, THF, DCM, or chloroform. In others, the coupling agent is HATU, CDI, HBTU, EDC/HOBt, or ethyl chloroformate, and the base is DIEA, TEA, or potassium carbonate.

In some embodiments, the methods further comprise preparing a compound of formula (Ic)

(Ic)

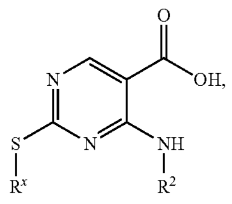

the methods comprising contacting a compound of formula (Id)

(Id)

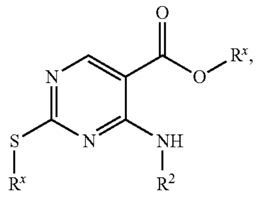

with an aqueous base, in a cosolvent.

In some embodiments, the aqueous base is aqueous sodium hydroxide, potassium hydroxide, or lithium hydroxide. In other embodiments, the cosolvent is ethanol, methanol, isopropanol, THF, or dioxane.

In some embodiments, the methods further comprise preparing a compound of formula (Id)

(Id)

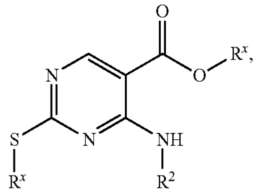

the methods comprising contacting a compound of formula (Ie)

(Ie)

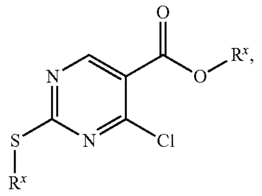

with $R^2NH_2$ in an organic solvent, in the presence of a base.

In some embodiments, the organic solvent is ethanol, methanol, isopropanol, THF, NMP, DMF, DMSO, or dioxane. In others, the base is DIEA, TEA, N-methylmorpholine, 1,8-diazabicyclo[5.4.0]undec-7-ene, cesium carbonate, sodium carbonate, sodium bicarbonate, potassium carbonate, or potassium phosphate. In some embodiments, the contacting is performed at elevated temperature, for example, from about 60° C. to about 80° C.

In some embodiments, the methods further comprise preparing a compound of formula (Ib)

(Ib)

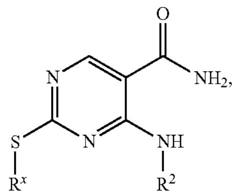

the methods comprising contacting a compound of formula (If)

(If)

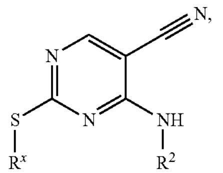

with peroxide, in the presence of a base, in a solvent.

In some embodiments, the solvent is DMSO, NMP, DMF, ethanol, or methanol. In others, the base is sodium hydroxide or potassium hydroxide.

In some embodiments, the methods further comprise preparing a compound of formula (If)

(If)

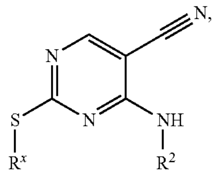

the methods comprising contacting a compound of formula (Ig)

(Ig)

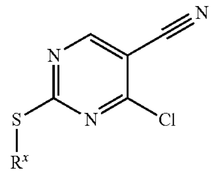

with $R^2NH_2$ in an organic solvent, in the presence of a base.

In some embodiments, the organic solvent is n-butanol, NMP, DMF, DMSO, dioxane, or ethanol. In others, the base is DIEA, TEA, N-methylmorpholine, 1,8-diazabicyclo[5.4.0]undec-7-ene, potassium carbonate, sodium carbonate, sodium bicarbonate, cesium carbonate, or potassium phosphate. In some embodiments, the contacting is performed at elevated temperature, for example, from about 50° C. to about 90° C.

Further provided are methods for preparing a compound of formula (I):

(I)

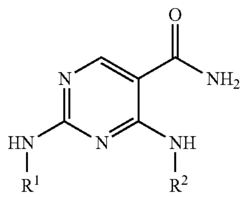

the methods comprising contacting a compound of formula (IIa)

(IIa)

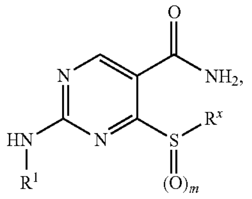

with $R^2NH_2$ in a solvent, in the presence of an organic base, wherein:

$R^1$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkylheterocyclyl, provided that $R^1$ is not 1-aminocyclohexyl;

$R^2$ is substituted or unsubstituted $C_{1-8}$ alkyl, substituted or unsubstituted saturated cycloalkyl, substituted or unsubstituted alkylcycloalkyl, substituted or unsubstituted non-aromatic heterocyclyl;

$R^x$ is a $C_{1-2}$ alkyl; and m is 1 or 2.

In one embodiment, the compound of formula (I) is not 2-(2-aminoethyl-amino)-4-(methylamino)pyrimidine-5-carboxamide; 2-(2-aminopropylamino)-4-(cyclohexylamino) pyrimidine-5-carboxamide; 2-(2-amino-2-oxoethylamino)-4-(cyclohexylamino)pyrimidine-5-carboxamide; 2-(2-aminoethylamino)-4-(cyclohexylamino)pyrimidine-5-carboxamide; (S)-2-(2-aminopropylamino)-4-(cyclobutylamino)pyrimidine-5-carboxamide; (R)-2-(1-amino-3-methyl-1-oxobutan-2-ylamino)-4-(cyclobutylamino)pyrimidine-5-carboxamide; 4-(cyclopentylamino)-2-(methylamino)pyrimidine-5-carboxamide; or 2-(1-acetylpiperidin-4-ylamino)-4-(cyclopropylamino)pyrimidine-5-carboxamide.

In one embodiment, the solvent is dioxane, DMSO, NMP, DMF, THF, or water. In another, the base is DIEA, TEA, 1,8-diazabicyclo[5.4.0]undec-7-ene, or N-methylmorpholine. In some embodiments, the contacting is performed at elevated temperature, for example, from about 80° C. to about 110° C.

In some embodiments, the methods further comprise preparing a compound of formula (IIa):

(IIa)

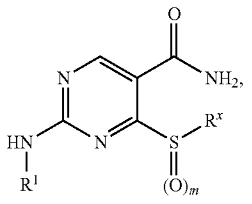

the methods comprising oxidizing a compound of formula (IIb)

(IIb)

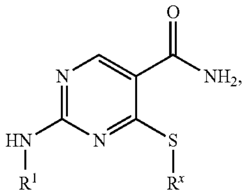

in a solvent by treatment with an oxidant selected from mCPBA, oxone, hydrogen peroxide, or 3-phenyl-2-(phenylsulfonyl)-1,2-oxaziridine.

In one embodiment, the solvent is acetone, DCM, NMP, DMF, or chloroform. In some embodiments, the oxidizing is performed at low temperature, for example, at about 0° C.

In some embodiments, the methods further comprise preparing a compound of formula (IIb):

(IIb)

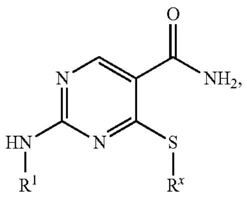

the methods comprising contacting a compound of formula (IIc)

(IIc)

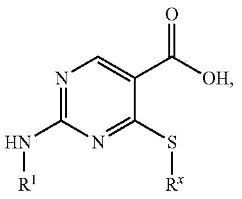

with $NH_4Cl$ in the presence of a coupling agent and a base, in a solvent.

In some embodiments, the solvent is NMP, DMF, DMSO, dioxane, THF, DCM, or chloroform. In others, the coupling agent is HATU, CDI, HBTU, EDC/HOBt, or ethyl chloroformate, and the base is DIEA, TEA, or potassium carbonate.

In some embodiments, the methods further comprise preparing a compound of formula (IIc)

(IIc)

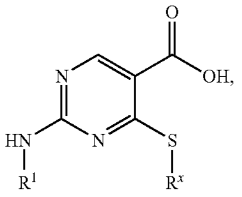

the methods comprising contacting a compound of formula (IId)

(IId)

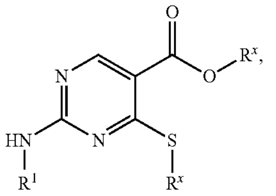

with an aqueous base, in a cosolvent.

In some embodiments, the aqueous base is aqueous sodium hydroxide, potassium hydroxide, or lithium hydroxide. In other embodiments, the cosolvent is ethanol, methanol, isopropanol, THF, or dioxane.

In some embodiments, the methods further comprise preparing a compound of formula (IId)

(IId)

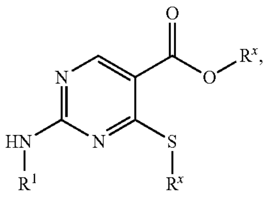

the methods comprising contacting a compound of formula (IIe)

(IIe)

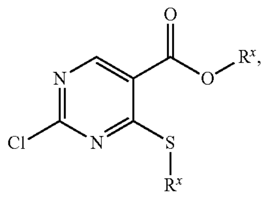

with $R^1NH_2$ in an organic solvent, in the presence of an organic base.

In one embodiment, the organic solvent is dioxane, THF, NMP, DMF, DMSO, ethanol, methanol, or isopropanol. In another, the base is DIEA, TEA, N-methylmorpholine, 1,8-diazabicyclo[5.4.0]undec-7-ene, cesium carbonate, sodium carbonate, sodium bicarbonate, potassium carbonate, or potassium phosphate. In some embodiments, the contacting is performed at elevated temperature, for example, from about 80° C. to about 100° C.

In some embodiments, the methods further comprise preparing a compound of formula (IIe)

(IIe)

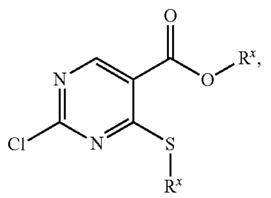

the methods comprising contacting a compound of formula (IIf)

(IIf)

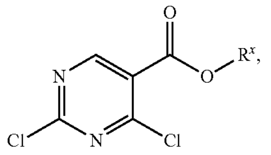

with $NaSR^x$ in an organic solvent in the presence of a catalyst.

In one embodiment, the solvent is THF, DCM, or dioxane. In one embodiment, the catalyst is triethylbenzyl ammonium chloride, tetrabutylammonium chloride, or tetrabutylammonium bromide. In some embodiments, the contacting is performed under cooling for example, about −10° C.

In some embodiments, the methods further comprise preparing a compound of formula (IIb):

(IIb)

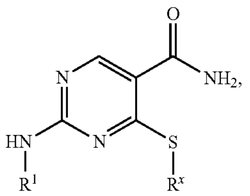

the methods comprising contacting a compound of formula (IIg)

(IIg)

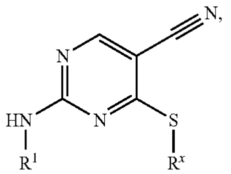

with peroxide, in the presence of a base, in a solvent.

In some embodiments, the solvent is DMSO, NMP, DMF, ethanol, or methanol. In others, the base is sodium hydroxide or potassium hydroxide.

In some embodiments, the methods further comprise preparing a compound of formula (IIg)

(IIg)

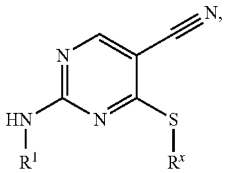

the methods comprising contacting a compound of formula (IIh)

(IIh)

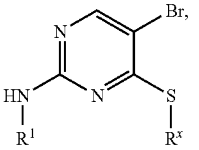

with zinc and dicyanozinc, in the presence of a catalyst, in a solvent.

In some embodiments, the catalyst is Pd(0). In some embodiments, the solvent is DMF, DMSO, NMP, or DMA. In others, the contacting is performed at elevated temperature, for example at a temperature between about 80° C. and about 100° C.

In some embodiments, the methods further comprise preparing a compound of formula (IIh)

(IIh)

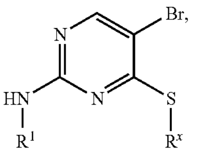

the methods comprising contacting a compound of formula (IIi)

(IIi)

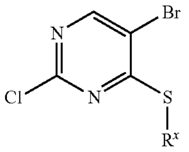

with $R^1NH_2$, in the presence of a base, in an organic solvent.

In some embodiments, the organic solvent is n-butanol, NMP, DMF, DMSO, dioxane, or ethanol. In others, the base is DIEA, TEA, N-methylmorpholine, 1,8-diazabicyclo-[5.4.0]undec-7-ene, potassium carbonate, sodium carbonate, sodium bicarbonate, cesium carbonate, or potassium phosphate. In some embodiments, the contacting is performed at elevated temperature, for example at a temperature between about 80° C. and about 100° C.

Also provided are methods for preparing a compound of formula (I):

(I)

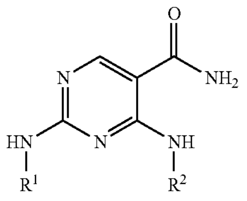

the methods comprising contacting a compound of formula (IIIa)

(IIIa)

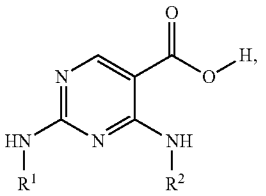

with $NH_4Cl$, in the presence of a coupling agent and a base, in a solvent, wherein:

$R^1$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkylheterocyclyl, provided that $R^1$ is not 1-aminocyclohexyl; and $R^2$ is substituted or unsubstituted $C_{1-8}$ alkyl, substituted or unsubstituted saturated cycloalkyl, substituted or unsubstituted alkylcycloalkyl, substituted or unsubstituted non-aromatic heterocyclyl.

In one embodiment, the compound of formula (I) is not 2-(2-aminoethyl-amino)-4-(methylamino)pyrimidine-5-carboxamide; 2-(2-aminopropylamino)-4-(cyclohexylamino) pyrimidine-5-carboxamide; 2-(2-amino-2-oxoethylamino)-4-(cyclohexylamino)pyrimidine-5-carboxamide; 2-(2-aminoethylamino)-4-(cyclohexylamino)pyrimidine-5-carboxamide; (S)-2-(2-aminopropylamino)-4-(cyclobutylamino)pyrimidine-5-carboxamide; (R)-2-(1-amino-3-methyl-1-oxobutan-2-ylamino)-4-(cyclobutylamino)pyrimidine-5-carboxamide; 4-(cyclopentylamino)-2-(methylamino)pyrimidine-5-carboxamide; or 2-(1-acetylpiperidin-4-ylamino)-4-(cyclopropylamino)pyrimidine-5-carboxamide.

In some embodiments, the solvent is NMP, DMF, DMSO, dioxane, THF, DCM, or chloroform. In others, the coupling agent is HATU, CDI, HBTU, EDC/HOBt, or ethyl chloroformate, and the base is DIEA, TEA, or potassium carbonate.

In some such embodiments, the methods further comprise preparing a compound of formula (Ma):

(IIIa)

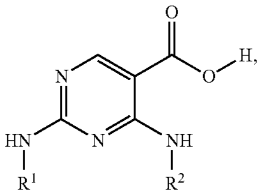

the methods comprising contacting a compound of formula (IIIb)

(IIIb)

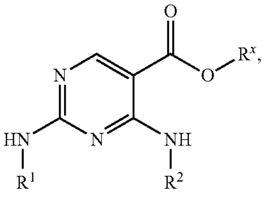

with an aqueous base, in a cosolvent, wherein $R^x$ is a $C_{1-2}$ alkyl.

In some embodiments the aqueous base is aqueous sodium hydroxide, potassium hydroxide, or lithium hydroxide. In other embodiments, the cosolvent is ethanol, methanol, isopropanol, THF, or dioxane.

In some embodiments, the method further comprise preparing a compound of formula (IIIb):

(IIIb)

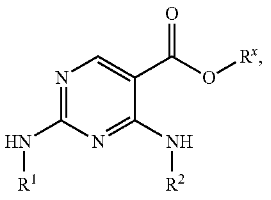

the method comprising contacting a compound of formula (IIIc)

(IIIc)

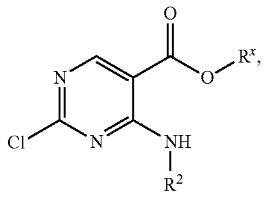

with $R^1NH_2$ in the presence of an organic base, in an organic solvent.

In some embodiments, the organic solvent is THF, NMP, DMF, DMSO, dioxane, ethanol, methanol, or isopropanol. In others the organic base is DIEA, TEA, 1,8-diazabicyclo [5.4.0]undec-7-ene, N-methylmorpholine, sodium carbonate, sodium bicarbonate, cesium carbonate, or potassium phosphate. In some embodiments, the contacting is performed at elevated temperature, for example, about 70° C.

In some embodiments, the methods further comprise preparing a compound of formula (IIIc)

(IIIc)

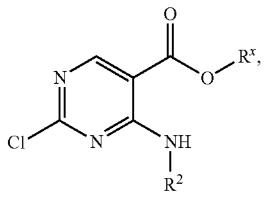

the methods comprising contacting a compound of formula (IIId)

(IIId)

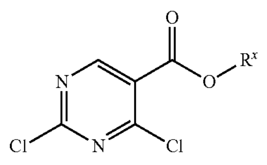

with $R^2NH_2$ in the presence of an organic base in a solvent.

In some embodiments, the solvent is ethyl ether, THF, DCM, toluene, or methyl tert-butyl ether. In others, the base is DIEA, TEA, 1,8-diazabicyclo[5.4.0]undec-7-ene, N-methylmorpholine, sodium bicarbonate, cesium carbonate, or potassium phosphate. In some embodiments the contacting is performed at low temperature, for example, about −70° C.

Also provided are methods for preparing a compound of formula (I):

(I)

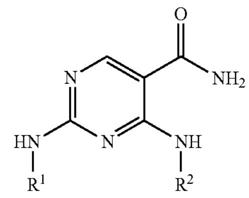

the methods comprising contacting a compound of formula (IVa)

(IVa)

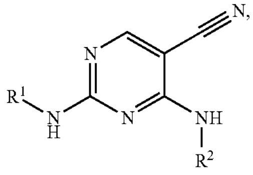

with catalytic peroxide, in the presence of a strong aqueous base, in a solvent, wherein:

$R^1$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkylheterocyclyl, provided that $R^1$ is not 1-aminocyclohexyl; and $R^2$ is substituted or unsubstituted $C_{1-8}$ alkyl, substituted or unsubstituted saturated cycloalkyl, substituted or unsubstituted alkylcycloalkyl, substituted or unsubstituted non-aromatic heterocyclyl.

In one embodiment, the compound of formula (I) is not 2-(2-aminoethyl-amino)-4-(methylamino)pyrimidine-5-carboxamide; 2-(2-aminopropylamino)-4-(cyclohexylamino) pyrimidine-5-carboxamide; 2-(2-amino-2-oxoethylamino)-4-(cyclohexylamino)pyrimidine-5-carboxamide; 2-(2-aminoethylamino)-4-(cyclohexylamino)pyrimidine-5-carboxamide; (S)-2-(2-aminopropylamino)-4-(cyclobutylamino)pyrimidine-5-carboxamide, (R)-2-(1-amino-3-methyl-1-oxobutan-2-ylamino)-4-(cyclobutylamino)pyrimidine-5-carboxamide; 4-(cyclopentylamino)-2-(methylamino)pyrimidine-5-carboxamide; or 2-(1-acetylpiperidin-4-ylamino)-4-(cyclopropylamino)pyrimidine-5-carboxamide.

In some embodiments, the solvent is DMSO, NMP, DMF, ethanol or methanol. In others, the strong aqueous base is such as sodium hydroxide or potassium hydroxide.

In some such embodiments, the methods further comprise preparing a compound of formula (IVa):

(IVa)

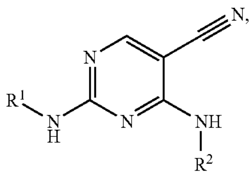

the methods comprising contacting a compound of formula (IVb)

(IVb)

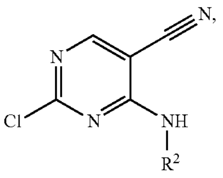

with $R^1NH_2$ in the presence of a base, in an organic solvent.

In some embodiments, the organic solvent is 1-butanol, THF, NMP, DMF, DMSO, dioxane, ethanol, methanol, or isopropanol. In others the base is cesium carbonate, potassium carbonate, sodium carbonate, sodium bicarbonate, potassium phosphate, 1,8-diazabicyclo[5.4.0]undec-7-ene, N-methylmorpholine, DIEA, or TEA. In some embodiments, the contacting is performed at elevated temperature, for example, about 120° C.

In some such embodiments, the methods further comprise preparing a compound of formula (IVb):

(IVb)

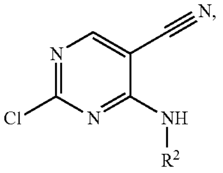

the methods comprising contacting a compound of formula (IVc)

(IVc)

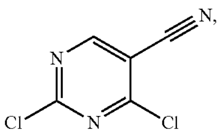

with $R^2NH_2$ in the presence of a base, in an organic solvent.

In some embodiments, the organic solvent is ethanol, methanol, isopropanol or THF. In others the base is DIEA, TEA, 1,8-diazabicyclo[5.4.0]undec-7-ene, N-methylmorpholine, sodium carbonate, sodium bicarbonate, cesium carbonate, or potassium phosphate. In some embodiments, the contacting is performed at low temperature, for example, about −60° C.

In some embodiments, the methods further comprise preparing a compound of formula (IVa):

(IVa)

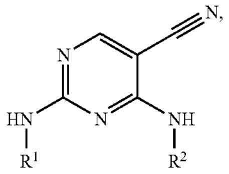

the methods comprising contacting a compound of formula (IVd)

(IVd)

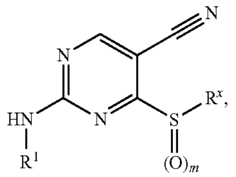

with $R^2NH_2$ in the presence of a base, in an organic solvent.

In some embodiments, the organic solvent is DCM, NMP, DMF, or DMA. In others, the base is DIEA, TEA, 1,8-diazabicyclo[5.4.0]undec-7-ene, or N-methylmorpholine. In some embodiments, the contacting is performed at a temperature between room temperature and about 130° C.

In some embodiments, the methods further comprise preparing a compound of formula (IVd):

(IVd)

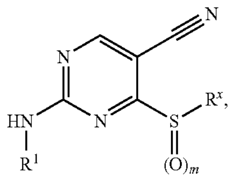

the methods comprising oxidizing a compound of formula (IIg)

(IIg)

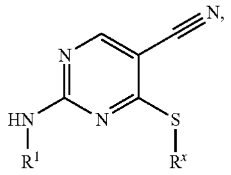

in a solvent by treatment with an oxidant selected from mCPBA, oxone, hydrogen peroxide, or 3-phenyl-2-(phenylsulfonyl)-1,2-oxaziridine.

In one embodiment, the solvent is DCM, NMP, DMF, or DMA. In some embodiments, the oxidizing is performed at a temperature from about 0° C. to about room temperature.

Also provided are methods for preparing a compound of formula (IB)

(IB)

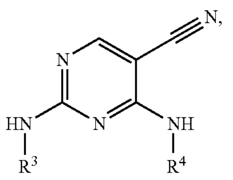

the methods comprising contacting a compound of formula (Va)

(Va)

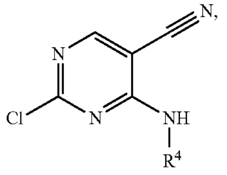

with $R^3NH_2$ in the presence of a base, in an organic solvent, wherein $R^3$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkyl-(non-aromatic heterocyclyl); and $R^4$ is substituted or unsubstituted $C_{1-8}$ alkyl, substituted or unsubstituted cycloalkyl, or substituted or unsubstituted non-aromatic heterocyclyl.

In one embodiment, the compound is not 4-(isopentylamino)-2-(3-(2-methylpiperidin-1-yl)propylamino)pyrimidine-5-carbonitrile; (2S,2'S)-dimethylcyanopyrimidine-2,4-diyl)bis(azanediyl)bis(4-methylpentanoate); (2S,2'S)-diethylcyanopyrimidine-2,4-diyl)bis(azanediyl)bis(3-methylbutanoate); 4-(cycloheptylamino)-2-(3-(2-methylpiperidin-1-yl)propylamino)pyrimidine-5-carbonitrile; 4-(4-methylcyclohexylamino)-2-(3-(2-methylpiperidin-1-yl)propylamino)pyrimidine-5-carbonitrile; or 2-(3-(diethylamino)propylamino)-4-(4-methylcyclohexylamino)-pyrimidine-5-carbonitrile.

In some embodiments, the organic solvent is 1-butanol, THF, NMP, DMF, DMSO, dioxane, ethanol, methanol, or isopropanol. In others the base is cesium carbonate, potassium carbonate, sodium carbonate, sodium bicarbonate, potassium phosphate, 1,8-diazabicyclo[5.4.0]undec-7-ene, N-methylmorpholine, DIEA, or TEA. In some embodiments, the contacting is performed at elevated temperature, for example, from about 50° C. to about 90° C.

In some such embodiments, the methods further comprise preparing a compound of formula (Va):

(Va)

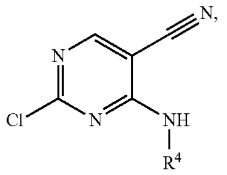

the methods comprising contacting a compound of formula (Vb)

(Vb)

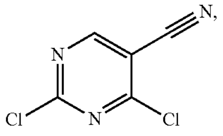

with $R^4NH_2$ in the presence of a base, in an organic solvent.

In some embodiments, the organic solvent is ethanol, methanol, isopropanol or THF. In others the base is DIEA, TEA, 1,8-diazabicyclo[5.4.0]undec-7-ene, N-methylmorpholine, sodium carbonate, sodium bicarbonate, cesium carbonate, or potassium phosphate. In some embodiments, the contacting is performed at low temperature, for example, from about −70° C. to about 20° C.

Also provided are methods for preparing a compound of formula (TB)

(IB)

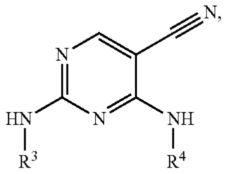

the methods comprising contacting a compound of formula (VIa)

(VIa)

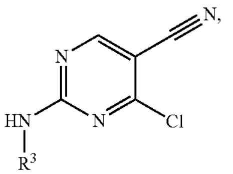

with $R^4NH_2$ in the presence of a base, in an organic solvent, wherein $R^3$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkyl-(non-aromatic heterocyclyl); and $R^4$ is substituted or unsubstituted $C_{1-8}$ alkyl, substituted or unsubstituted cycloalkyl, or substituted or unsubstituted non-aromatic heterocyclyl.

In one embodiment, the compound is not 4-(isopentylamino)-2-(3-(2-methylpiperidin-1-yl)propylamino)pyrimidine-5-carbonitrile; (2S,2'S)-dimethyl 2,2'-(5-cyanopyrimidine-2,4-diyl)bis(azanediyl)bis(4-methylpentanoate); (2S, 2'S)-diethyl 2,2'-(5-cyanopyrimidine-2,4-diyl)bis(azanediyl)bis(3-methylbutanoate); 4-(cycloheptylamino)-2-(3-(2-methylpiperidin-1-yl)propylamino)pyrimidine-5-carbonitrile; 4-(4-methylcyclohexylamino)-2-(3-(2-methylpiperidin-1-yl)propylamino)pyrimidine-5-carbonitrile; or 2-(3-(diethylamino)propylamino)-4-(4-methylcyclohexylamino)-pyrimidine-5-carbonitrile.

In some embodiments, the organic solvent is 1-butanol, NMP, DMF, DMSO, or dioxane. In others the base is cesium carbonate, potassium carbonate, sodium carbonate, sodium bicarbonate, potassium phosphate, 1,8-diazabicyclo[5.4.0]undec-7-ene, N-methylmorpholine, DIEA, or TEA. In some embodiments, the contacting is performed at elevated temperature, for example, from about 25° C. to about 110° C.

In some such embodiments, the methods further comprise preparing a compound of formula (VIa):

(VIa)

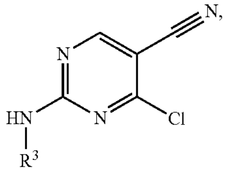

the methods comprising contacting a compound of formula (Vb)

(Vb)

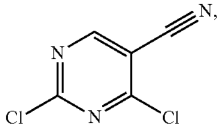

with $R^3NH_2$ in the presence of a base, in an organic solvent.

In some such embodiments, the organic solvent is ethanol, methanol, isopropanol or THF. In others the base is DIEA, TEA, 1,8-diazabicyclo[5.4.0]undec-7-ene, N-methylmorpholine, sodium carbonate, sodium bicarbonate, cesium carbonate, or potassium phosphate. In some embodiments, the contacting is performed at low temperature, for example, from about −70° C. to about 20° C.

Provided are methods for preparing a compound of formula (TB)

(IB)

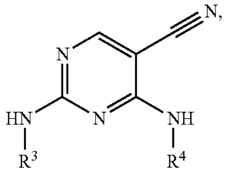

the methods comprising contacting a compound of formula (VIIa)

(VIIa)

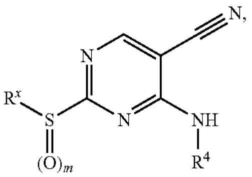

with $R^3NH_2$ in the presence of a base, in an organic solvent, wherein $R^3$ is substituted or unsubstituted $C_{1-8}$ alkyl, substituted or unsubstituted cycloalkyl, substituted or unsubstituted non-aromatic heterocyclyl, substituted or unsubstituted alkylcycloalkyl, or substituted or unsubstituted alkyl-(non-aromatic heterocyclyl);

$R^4$ is substituted or unsubstituted $C_{1-8}$ alkyl, substituted or unsubstituted cycloalkyl, or substituted or unsubstituted non-aromatic heterocyclyl;

$R^x$ is $C_{1-2}$ alkyl and m is 1 or 2.

In one embodiment, the compound is not 4-(isopentylamino)-2-(3-(2-methylpiperidin-1-yl)propylamino)pyrimidine-5-carbonitrile; (2S,2'S)-dimethyl 2,2'-(5-cyanopyrimidine-2,4-diyl)bis(azanediyl)bis(4-methylpentanoate); (2S,2'S)-diethyl 2,2'-(5-cyanopyrimidine-2,4-diyl)bis(azanediyl)bis(3-methylbutanoate); 4-(cycloheptylamino)-2-(3-(2-methylpiperidin-1-yl)propylamino)pyrimidine-5-carbonitrile; 4-(4-methylcyclohexylamino)-2-(3-(2-methylpiperidin-1-yl)propylamino)pyrimidine-5-carbonitrile; or 2-(3-(diethylamino)propylamino)-4-(4-methylcyclohexylamino)-pyrimidine-5-carbonitrile.

In one embodiment, the solvent is dioxane, DMSO, NMP, DMF, THF, or n-butanol. In another, the base is DIEA, TEA, 1,8-diazabicyclo[5.4.0]undec-7-ene, N-methylmorpholine. In some embodiments, the contacting is performed at elevated temperature, for example, from about 25° C. to about 110° C.

In some embodiments, the methods further comprise preparing a compound of formula (VIIa):

(VIIa)

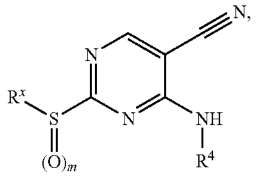

the methods comprising oxidizing a compound of formula (VIIb)

(VIIb)

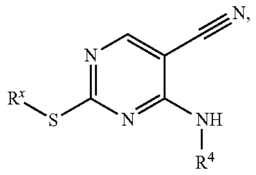

in a solvent by treatment with an oxidant selected from mCPBA, oxone, hydrogen peroxide, or 3-phenyl-2-(phenylsulfonyl)-1,2-oxaziridine.

In one embodiment, the solvent is DCM, NMP, DMF, or DMA. In some embodiments, the oxidizing is performed at low temperature, for example, about 0° C.

In some embodiments, the methods further comprise preparing a compound of formula (VIIb)

(VIIb)

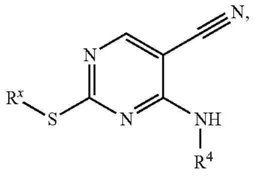

the methods comprising contacting a compound of formula (VIII)

(VIIc)

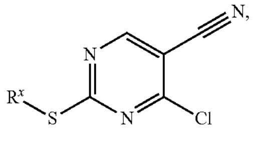

with $R^4NH_2$ in an organic solvent, in the presence of a base.

In one embodiment, the organic solvent is n-butanol, NMP, DMF, DMSO, or dioxane. In another, the base is DIEA, TEA, N-methylmorpholine, 1,8-diazabicyclo[5.4.0]undec-7-ene, potassium carbonate, sodium carbonate, sodium bicarbonate, cesium carbonate or potassium phosphate. In some embodiments, the contacting is performed at elevated temperature, for example, from about 50° C. to about 90° C.

Methods of Use

The Diaminopyrimidine Compounds have utility as pharmaceuticals to treat, prevent or improve conditions in animals or humans. Further, the Diaminopyrimidine Compounds are active against protein kinases, particularly JNK1 and/or JNK2. Accordingly, provided herein are many uses of the Diaminopyrimidine Compounds, including the treatment or prevention of those diseases set forth below. The methods provided herein comprise the administration of an effective amount of one or more Diaminopyrimidine Compound(s) to a subject in need thereof.

In one aspect provided herein are methods of inhibiting a kinase in a cell expressing said kinase, comprising contacting said cell with an effective amount of a Diaminopyrimidine Compound. In one embodiment the kinase is JNK1, JNK2, or mutants or isoforms thereof, or a combination thereof. For example, the Diaminopyrimidine Compound is a compound from Table 1, 2 or 3.

In another aspect provided herein are methods for treating or preventing liver fibrotic disorders, such as non-alcoholic steatohepatitis, steatosis (i.e. fatty liver), cirrhosis, primary sclerosing cholangitis, primary biliary cirrhosis, hepatitis, hepatocellular carcinoma, and liver fibrosis coincident with chronic or repeated alcohol ingestion (alcoholic hepatitis), with infection (e.g. viral infection such as HCV), with liver transplant, or with drug induced liver injury (e.g. acetaminophen toxicity), comprising administering to a subject in need thereof an effective amount of a Diaminopyrimidine Compound. In some such aspects, provided herein are methods for treating or preventing diabetes or metabolic syndrome leading to liver fibrotic disorders, such as non-alcoholic steatohepatitis, steatosis (i.e. fatty liver), cirrhosis, primary sclerosing cholangitis, primary biliary cirrhosis, and hepatitis, comprising administering to a subject in need thereof an effective amount of a Diaminopyrimidine Compound.

In another aspect provided herein are methods for treating or preventing one ore more disorders selected from interstitial pulmonary fibrosis, systemic sclerosis, scleroderma, chronic allograft nephropathy, antibody mediated rejection, or lupus, comprising administering to a subject in need thereof an effective amount of a Diaminopyrimidine Compound. In some such embodiments, the lupus is lupus erythematosus (such as discoid lupus erythematosus, or cutaneous lupus erythematosus) or systemic lupus.

In another aspect provided herein are methods for treating or preventing conditions treatable or preventable by inhibition of JNK1 and/or JNK2, the method comprising administering to a subject in need thereof an effective amount of a Diaminopyrimidine Compound. Examples of such conditions include rheumatoid arthritis; rheumatoid spondylitis; osteoarthritis; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

Pharmaceutical Compositions and Routes of Administration

The Diaminopyrimidine Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Diaminopyrimidine Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a Diaminopyrimidine Compound to be administered to a subject is rather widely variable and can be subject to the judgment of a health-care practitioner. In general, the Diaminopyrimidine Compounds can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Diaminopyrimidine Compound administered will depend on such factors as the solubility of the active component, the formulation used and the route of administration. In one embodiment, application of a topical concentration provides intracellular exposures or concentrations of about 0.01-10 μM.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Diaminopyrimidine Compound to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Diaminopyrimidine Compound to a subject in need thereof. In a particular embodiment, the methods disclosed herein comprise the administration of 400 mg/day, 600 mg/day or 800 mg/day of a Diaminopyrimidine Compound to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Diaminopyrimidine Compound.

In a particular embodiment, provided herein are unit dosage formulations comprising about 100 mg or 400 mg of a Diaminopyrimidine Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Diaminopyrimidine Compound.

A Diaminopyrimidine Compound can be administered once, twice, three, four or more times daily. In a particular embodiment, doses of 600 mg or less are administered as a once daily dose and doses of more than 600 mg are administered twice daily in an amount equal to one half of the total daily dose.

A Diaminopyrimidine Compound can be administered orally for reasons of convenience. In one embodiment, when administered orally, a Diaminopyrimidine Compound is administered with a meal and water. In another embodiment, the Diaminopyrimidine Compound is dispersed in water or juice (e.g., apple juice or orange juice) and administered orally as a suspension.

The Diaminopyrimidine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Diaminopyrimidine Compound without an additional carrier, excipient or vehicle.

In another embodiment, provided herein are compositions comprising an effective amount of a Diaminopyrimidine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Diaminopyrimidine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, aligns and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Diaminopyrimidine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Diaminopyrimidine Compound can be delayed or prolonged by proper formulation. For example, a slowly soluble pellet of the Diaminopyrimidine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Diaminopyrimidine Compound in oily or emulsified vehicles that allow it to disperse slowly in the serum.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| | |
|---|---|
| DCM | Dichloromethane |
| DEA | Diethylamine |
| DIEA | N,N-Diisopropylethylamine |
| DMA | N,N-Dimethylacetamide |
| DMF | N,N-Dimethylformamide |
| DMSO | Dimethylsulfoxide |
| EDC | Ethyl-(N',N'-dimethylamino)propylcarbodiimide hydrochloride |
| ESI | Electrospray ionization |
| HATU | O-(7-azabenzotriazol-1-yl)-N,N,N',N'-tetramethyluronium hexafluorophosphate |
| HOBt | 1-Hydroxybenzotriazole |
| HPLC | High performance liquid chromatography |
| HTRF | Homogeneous time resolved fluorescence |
| LCMS | Liquid chromatography mass spectrometry |
| mCPBA | Meta-chloroperoxybenzoic acid |
| MS | Mass spectrometry |
| NMP | N-methylpyrrolidone |
| NMR | Nuclear magnetic resonance |
| SFC | Supercritical fluid chromatography |
| TBTU | O-benzotriazol-1-yl-N,N,N',N'-tetramethyluronium tetrafluoroborate |

-continued

| | |
|---|---|
| TEA | Triethylamine |
| TFA | Trifluoracetic acid |
| THF | Tetrahydrofuran |
| TLC | Thin layer chromatography |

Compound Synthesis

Example 1: 4-((1R,3R)-3-Hydroxycyclohexylamino)-2-((1r,4R)-4-methoxycyclohexylamino)pyrimidine-5-carboxamide

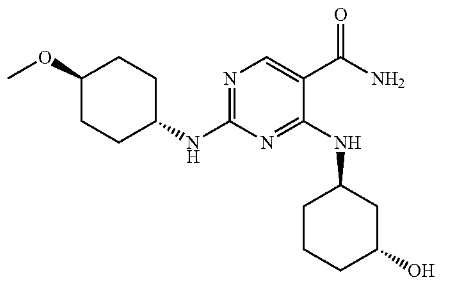 [SMILES: CO[C@H]1CC[C@H](Nc2ncc(C(N)=O)c(N[C@@H]3CCC[C@@H](O)C3)n2)CC1]

4-Chloro-2-((1r,4r)-4-methoxycyclohexylamino)pyrimidine-5-carbonitrile 2,4-Dichloro-pyrimidine-5-carbonitrile (1.2 g, 6.93 mmol) in anhydrous ethanol (10 mL) and (1r,4r)-4-methoxycyclohexanamine (893 mg, 6.93 mmol) in anhydrous ethanol (10 mL) were mixed at −60° C., then DIEA (1.34 g, 10.4 mmol) was added drop wise. The mixture was stirred at −60° C. for 1.5 h, then at room temperature overnight. Volatile fractions were removed and the residue was purified on silica gel (eluting with 9.1%-25% ethyl acetate in petroleum ether and 3.2%-4.7% methanol in DCM) to give the 2 isomers (identified as described below), namely 4-chloro-2-((1r,4r)-4-methoxycyclohexylamino)-pyrimidine-5-carbonitrile (560 mg, 2.10 mmol, yield 30%) as a white solid and 2-chloro-4-((1r,4r)-4-methoxycyclohexylamino)pyrimidine-5-carbonitrile (227 mg, 0.85 mmol, yield 12%) as a white solid. MS(ESI): m/z 266.9 $[M+1]^+$.

Identification of the two isomers was achieved by characterization of the dehalogenated intermediate. Dehalogenation for the two fractions was achieved as follows. 4-Chloro-2-((1r,4r)-4-methoxycyclohexylamino)pyrimidine-5-carbonitrile (50 mg, 0.18 mmol) and Raney nickel in a cosolvent of THF (10 mL) and aqueous ammonia (1 mL) was stirred at room temperature under a hydrogen balloon overnight. The mixture was filtered and the filtrate was concentrated and purified by reverse-phase preparatory HPLC (10% to 40% acetonitrile+0.005% ammonia solution) to give 5-(aminomethyl)-N-((1r,4r)-4-methoxycyclohexyl)pyrimidin-2-amine (25 mg, 0.10 mmol, yield 58%). $^1H$ NMR ($CDCl_3$ 300 MHz): δ ppm 8.23 (s, 2H), 4.96 (d, J=10.0 Hz, 1H), 3.85-3.73 (m, 1H), 3.69 (s, 2H), 3.34 (s, 3H), 3.22-3.11 (m, 1H), 2.15-2.04 (m, 4H), 1.44-1.34 (m, 4H); MS(ESI): m/z 236.9 $[M+1]^+$.

Similarly, 2-chloro-4-((1r,4r)-4-methoxycyclohexylamino)pyrimidine-5-carbonitrile (50 mg, 0.18 mmol) and Raney nickel in a cosolvent of THF (10 mL) and aqueous ammonia (1 mL) was stirred at room temperature under a hydrogen balloon overnight. The mixture was filtered and the filtrate was concentrated and purified by reverse-phase preparatory HPLC (10% to 40% acetonitrile+0.005% ammonia solution) to give 5-(aminomethyl)-N-((1r,4r)-4-methoxycyclohexyl)pyrimidin-4-amine (30 mg, 0.12 mmol, yield 66%). $^1$H NMR ($CDCl_3$ 300 MHz): δ ppm 8.46 (s, 1H), 7.84 (s, 1H), 7.25 (s, 1H), 4.00-3.93 (m, 1H), 3.79 (s, 2H), 3.34 (s, 3H), 3.23-3.14 (m, 1H), 2.14-2.02 (m, 4H), 1.48-1.22 (m, 4H); MS(ESI): m/z 236.9 $[M+1]^+$.

B. 4-((1R,3R)-3-Hydroxycyclohexylamino)-2-((1r,4R)-4-methoxy-cyclohexylamino)pyrimidine-5-carbonitrile A mixture of 4-chloro-2-((1r,4r)-4-methoxycyclohexylamino)pyrimidine-5-carbonitrile (236 mg, 0.88 mmol), (1R,3R)-3-aminocyclohexanol (151 mg, 1.32 mmol; prepared as described in *Tetrahedron: Asymmetry* 15:2051-2056 (2004)) and cesium carbonate (573 mg, 1.76 mmol) in anhydrous n-butanol (20 mL) was stirred at 120° C. under nitrogen for 3 h. The mixture was partitioned between water and DCM. The organic layers were combined, concentrated and purified on silica gel (eluting with 16%-50% ethyl acetate in petroleum ether and 3.2%-4.7% methanol in DCM) to give 4-((1R,3R)-3-hydroxycyclohexylamino)-2-((1r,4R)-4-methoxycyclohexylamino)-pyrimidine-5-carbonitrile (140 mg, 0.40 mmol, yield 46%) as a white solid. MS(ESI): m/z 346.0 $[M+1]^+$.

C. 4-((1R,3R)-3-Hydroxycyclohexylamino)-2-((1r,4R)-4-methoxy-cyclohexylamino)pyrimidine-5-carboxamide 4-((1R,3R)-3-Hydroxycyclohexylamino)-2-((1r,4R)-4-methoxycyclohexylamino)pyrimidine-5-carbonitrile (140 mg, 0.40 mmol) was dissolved in DMSO (10 mL) and ten drops of saturated aqueous sodium hydroxide solution and ten drops of aqueous hydrogen peroxide solution (30%) were added at room temperature. The reaction mixture was stirred at 50° C. for 6 h. The reaction mixture was partitioned between water and DCM-isopropanol (5:1). The organic layers were combined, concentrated and purified on silica gel (eluting with 50%-75% ethyl acetate in petroleum ether and 4.76%-9.1% methanol in DCM) to give 4-((1R,3R)-3-hydroxycyclohexylamino)-2-((1r,4R)-4-methoxycyclohexylamino)-pyrimidine-5-carboxamide (103 mg, 0.28 mmol, yield 70%) as a white solid. $^1$H NMR (DMSO-$d_6$ 400 MHz): δ ppm 9.00 (d, J=5.2 Hz, 1H), 8.33 (s, 1H), 7.54 (brs, 1H), 7.00 (s, 1H), 6.81 (s, 1H), 4.47 (s, 1H), 4.28 (s, 1H), 3.81 (s, 1H), 3.63 (s, 1H), 3.22 (s, 3H), 3.08 (s, 1H), 1.98-1.54 (m, 8H), 1.41-1.14 (m, 7H); MS(ESI): m/z 363.9 $[M+1]^+$.

Example 2: 4-((1S,3S)-3-Hydroxycyclohexylamino)-2-((1r,4S)-4-methoxycyclohexylamino)pyrimidine-5-carboxamide

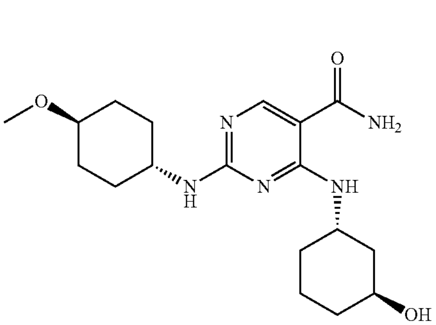 [SMILES: CO[C@H]1CC[C@H](Nc2ncc(C(N)=O)c(N[C@H]3CCC[C@H](O)C3)n2)CC1]

A. 4-((1S,3S)-3-Hydroxycyclohexylamino)-2-((1r,4S)-4-methoxy-cyclohexylamino)pyrimidine-5-carbonitrile A mixture of 4-chloro-2-((1r,4r)-4-methoxycyclohexylamino)pyrimidine-5-carbonitrile (236 mg, 0.88 mmol, synthesis described herein), (1S,3S)-3-aminocyclohexanol (209 mg, 1.33 mmol; prepared as described in *Tetrahedron: Asymmetry* 15: 2051-2056 (2004)) and cesium carbonate (573 mg, 1.76 mmol) in anhydrous n-butanol (20 mL) was stirred at 120° C. under nitrogen for 3 h. The mixture was partitioned between water and DCM. The organic layers were combined, concentrated and purified on silica gel (eluting with 16%-50% ethyl acetate in petroleum ether and 3.2%-4.7% methanol in DCM) to give 4-((1S,3S)-3-hydroxycyclohexylamino)-2-((1r,4S)-4-methoxycyclohexylamino)pyrimidine-5-carbonitrile (140 mg, 0.40 mmol, yield 46%) as a white solid. MS(ESI): m/z 346.1 $[M+1]^+$.

B. 4-((1S,3S)-3-Hydroxycyclohexylamino)-2-((1r,4S)-4-methoxy-cyclohexylamino)pyrimidine-5-carboxamide 4-((1S,3S)-3-Hydroxycyclohexylamino)-2-((1r,4S)-4-methoxycyclohexylamino)pyrimidine-5-carbonitrile (140 mg, 0.40 mmol) was dissolved in DMSO (10 mL) and ten drops of saturated aqueous sodium hydroxide solution and ten drops of aqueous hydrogen peroxide solution (30%) were added at room temperature. The reaction mixture was stirred at 50° C. for 6 h. The reaction mixture was partitioned between water and DCM-isopropanol (5:1). The organic layers were combined, concentrated and purified on silica gel (eluting with 50%-75% ethyl acetate in petroleum ether and 4.76%-9.1% methanol in DCM) to give 4-((1S,3S)-3-hydroxycyclohexylamino)-2-((1r,4S)-4-methoxycyclohexylamino)pyrimidine-5-carboxamide (102 mg, 0.28 mmol, yield 70%) as a white solid. $^1$H NMR (DMSO-$d_6$ 400 MHz): δ ppm 9.01 (d, J=6.0 Hz, 1H), 8.34 (s, 1H), 7.56 (brs, 1H), 7.02 (d, J=4.8 Hz, 1H), 6.82 (s, 1H), 4.48 (s, 1H), 4.29 (s, 1H), 3.81 (s, 1H), 3.64 (s, 1H), 3.23 (s, 3H), 3.08 (s, 1H), 2.01-1.55 (m, 8H), 1.41-1.15 (m, 7H); MS(ESI): m/z 363.9 $[M+1]^+$.

Example 3: 2-((1r,4S)-4-Ethoxycyclohexylamino)-4-((1S,2S)-2-hydroxycyclopentylamino)pyrimidine-5-carboxamide

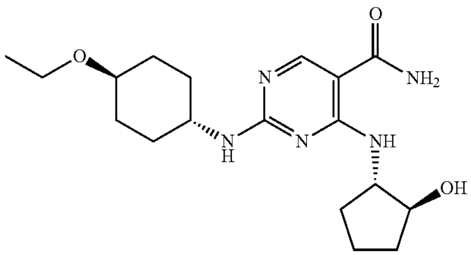 [SMILES: CCO[C@H]1CC[C@H](Nc2ncc(C(N)=O)c(N[C@H]3CCC[C@@H]3O)n2)CC1]

A. tert-Butyl (1r,4r)-4-hydroxycyclohexylcarbamate

To a suspension of (1r,4r)-4-aminocyclohexanol hydrochloride (25 g, 217 mmol) in dioxane (200 mL) was added a solution of sodium hydroxide (8.7 g, 217 mmol) in water (150 mL) at room temperature, followed by addition of di-tert-butyl-dicarbonate (47 g, 270 mmol). The resulting mixture was stirred at room temperature for 15 h. When the starting material was consumed, the volatiles were removed and the residue was diluted with water. The solid was collected by filtration and dried to give tert-butyl (1r,4r)-4-hydroxycyclohexyl-carbamate as a white solid (33 g, 0.15 mol, yield 92%). $^1$H NMR (DMSO-$d_6$, 300 MHz): δ ppm 6.65 (d, J=7.5 Hz, 1H), 4.48 (d, J=3.0 Hz, 1H), 3.14 (s, 1H), 1.77 (m, 4H), 1.37 (s, 9H), 1.14 (m, 4H).

B. tert-Butyl (1r,4r)-4-ethoxycyclohexylcarbamate

To a solution of tert-butyl (1r,4r)-4-hydroxycyclohexyl-carbamate (20 g, 93 mmol) in anhydrous THF (100 mL) was added sodium hydride (4 g, 100 mmol, 60% in mineral oil) in portions under nitrogen at 0° C. The mixture was warmed to room temperature and stirred for 30 min. A solution of iodoethane (16 g, 102 mmol) in anhydrous THF (50 mL) was added dropwise to the mixture at 0° C. and the resulting mixture was heated to 60° C. for 15 h. After being cooled to room temperature, the mixture was poured into ice-water (100 mL). The aqueous mixture was extracted with ethyl acetate (100 mL×3), and the organic phase was washed with brine, dried over sodium sulfate and filtered. The filtrate was concentrated in vacuo. The residue was purified on silica gel column (eluting with 5% to 30% ethyl acetate in petroleum ether) to give tert-butyl (1r,4r)-4-ethoxycyclohexylcarbamate (3.7 g, 15 mmol, yield 16%). $^1$H NMR (DMSO-$d_6$, 400 MHz): δ ppm 6.70 (d, J=7.6 Hz, 1H), 3.42 (q, J=7.2 Hz, 2H), 3.11-3.17 (m, 2H), 1.92 (m, 2H), 1.74 (m, 2H), 1.37 (s, 9H), 1.21 (m, 4H), 1.07 (t, J=7.2 Hz, 3H).

C. (1r,4r)-4-Ethoxycyclohexanamine hydrochloride

A solution of tert-butyl (1r,4r)-4-ethoxycyclohexylcarbamate (3.7 g, 15 mmol) in methanolic hydrochloride solution (2 M, 20 mL) was stirred at room temperature for 2 h. The reaction mixture was evaporated under reduced pressure to give (1r,4r)-4-ethoxycyclohexanamine hydrochloride (2.7 g, yield 100%).

D. (1S,2S)-2-Aminocyclopentanol hydrochloride

To a solution of (1S,2S)-2-(benzyloxy)cyclopentanamine (4.5 g, 22 mmol) and hydrochloric acid (0.5 mL) in methanol (100 mL) was added 10 wt. % palladium on activated carbon (500 mg). The mixture was stirred at room temperature under hydrogen atmosphere (40 psi) for 24 h. The catalyst was filtered off and the filtrate was concentrated under reduced pressure to give (1S,2S)-2-aminocyclopentanol hydrochloride as a white solid (2.14 g, 15 mmol, yield 93%).

E. Ethyl 4-((1S,2S)-2-hydroxycyclopentylamino)-2-(methylthio)-pyrimidine-5-carboxylate A mixture of ethyl 4-chloro-2-(methylthio)pyrimidine-5-carboxylate (1.4 g, 6.0 mmol), (1S,2S)-2-aminocyclopentanol hydrochloride (0.7 g, 6.9 mmol) and DIEA (1.0 g) in ethanol (20 mL) was heated at 60° C. for 15 h. After being cooled to room temperature, the reaction solution was concentrated and the residue was purified on silica gel column (eluting with 0~10% ethyl acetate in petroleum ether) to give ethyl 4-((1S,2S)-2-hydroxycyclopentylamino)-2-(methylthio)pyrimidine-5-carboxylate (1.3 g, 4.37 mmol, yield 73%) as a white solid. MS (ESI): m/z 298.5 [M+1]$^+$.

F. 4-((1S,2S)-2-Hydroxycyclopentylamino)-2-(methylthio)pyrimidine-5-carboxylic acid To a solution of ethyl 4-((1S,2S)-2-hydroxycyclopentylamino)-2-(methylthio)pyrimidine-5-carboxylate (1.3 g, 4.37 mmol) in ethanol (15 mL) was added aqueous sodium hydroxide solution (15 mL, 2 N), and the mixture was stirred for 1 h at room temperature. When the starting material was consumed, the reaction mixture was neutralized with saturated aqueous citric acid solution. The solids were collected by filtration and dried to give 4-((1S,2S)-2-hydroxycyclopentylamino)-2-(methylthio)pyrimidine-5-carboxylic acid (1.0 g, 3.7 mmol, yield 85%) as a white solid. MS (ESI): m/z 270.6 [M+1]$^+$.

G. 4-((1S,2S)-2-Hydroxycyclopentylamino)-2-(methylthio)pyrimidine-5-carboxamide

The mixture of 4-((1S,2S)-2-hydroxycyclopentylamino)-2-(methylthio)-pyrimidine-5-carboxylic acid (1.0 g, 3.7 mmol), ammonium chloride (0.989 g, 18.5 mmol), HATU (2.25 g, 5.92 mmol), DIEA (2.39 g, 18.5 mmol) and 1-HOBt (0.80 g, 5.92 mmol) in DMF (10 mL) was stirred at room temperature for 2 h. The reaction mixture was diluted with water (15 mL), and the aqueous mixture was extracted with ethyl acetate (20 mL×3). The combined organic layers were washed with brine, dried over sodium sulfate and filtered. The filtrate was evaporated in vacuo. The residue was purified on silica gel column (eluting with 30~50% ethyl acetate in petroleum ether) to give 4-((1S,2S)-2-hydroxycyclopentylamino)-2-(methylthio)pyramidine-5-carboxamide (800 mg, 2.98 mmol, yield 81%) as a white solid. MS (ESI): m/z 269.4 [M+1]$^+$.

H. 4-((1S,2S)-2-Hydroxycyclopentylamino)-2-(methylsulfonyl)-pyrimidine-5-carboxamide To a mixture of 4-((1S,2S)-2-hydroxycyclopentylamino)-2-(methylthio)pyrimidine-5-carboxamide (800 mg, 2.98 mmol) in acetone (10 mL) was added a solution of potassium peroxymonosulfate (4.66 g, 7.45 mmol) in water (10 mL), and the resulting mixture was stirred at room temperature for 2 h. When the starting material was consumed, the reaction mixture was partitioned between ethyl acetate (20 mL) and water (15 mL). The aqueous layer was extracted with ethyl acetate (20 mL×3). The combined organic layers were washed with brine, dried over sodium sulfate and filtered. The filtrate was evaporated in vacuo to give 4-((1S,2S)-2-hydroxycyclopentylamino)-2-(methylsulfonyl)pyrimidine-5-carboxamide (700 mg, 2.3 mmol, yield 78%) as a solid. MS (ESI): m/z 301.2 [M+1]$^+$.

I. 2-((1r,4S)-4-Ethoxycyclohexylamino)-4-((1S,2S)-2-hydroxy-cyclopentylamino)pyrimidine-5-carboxamide A solution of 4-((1S,2S)-2-hydroxycyclopentylamino)-2-(methylsulfonyl)pyrimidine-5-carboxamide (700 mg, 2.3 mmol), (1r,4r)-4-ethoxycyclohexanamine hydrochloride (668 mg, 4.66 mmol) and DIEA (600 mg, 4.66 mmol) in dioxane (10 mL) was heated at 80° C. for 15 h. After being cooled to room temperature, the reaction mixture was concentrated and the residue was dissolved in ethyl acetate (20 mL). The organic solution was washed with water and brine, dried over sodium sulfate and filtered. The filtrate was evaporated in vacuo. The residue was purified by a reverse-phase preparatory HPLC (40-75% acetonitrile+0.05% ammonium hydroxide in water, 7.5 min.) to give 2-((1r,4S)-4-ethoxycyclohexylamino)-4-((1S,2S)-2-hydroxycyclopentylamino)pyrimidine-5-carboxamide (320 mg, 0.88 mmol, yield 38%, m.p. 126.0~126.6° C.) as a solid. $^1$H NMR (DMSO-$d_6$, 400 MHz): δ ppm 9.02-8.93 (m, 1H), 8.32 (d, J=9.2 Hz, 1H), 7.60-7.51 (m, 1H), 7.04 (d, J=7.2 Hz, 1H), 6.88 (d, J=7.2 Hz, 1H), 4.82 (s, 1H), 3.99-3.89 (m, 3H), 3.42 (q, J=7.2 Hz, 2H), 3.15 (s, J=6.0 Hz, 1H), 2.10-2.06 (m, 1H), 1.97-1.77 (m, 5H), 1.66-1.60 (m, 2H), 1.46 (s, 1H), 1.28-1.18 (m, 5H), 1.06 (t, J=7.2 Hz, 3H); MS (ESI): m/z 364.3 $[M+1]^+$.

Example 4: 4-(((1R,3S)-3-Hydroxycyclohexylamino)-2-((1R,4R)-4-(methylcarbamoyl)cyclohexylamino)pyrimidine-5-carboxamide

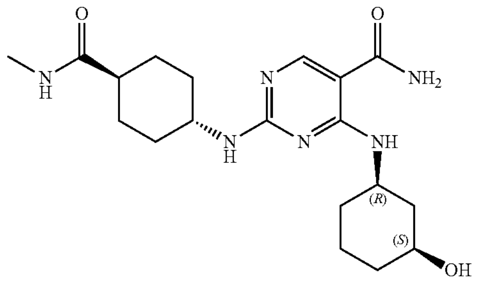

A. Ethyl 4-((1R,3S)-3-hydroxycyclohexylamino)-2-(methylthio)-pyrimidine-5-carboxylate Ethyl 4-chloro-2-(methylthio)pyrimidine-5-carboxylate (4.38 g, 18.82 mmol) and (1S,3R)-3-aminocyclohexanol (2.276 g, 19.76 mmol; prepared as described in *Tetrahedron: Asymmetry* 15:2051-2056 (2004)) were dissolved in ethanol (75 mL) before adding DIEA (4.93 ml, 28.2 mmol) and heating to 60° C. After 2 hrs, LCMS showed the desired product mass was the dominant peak formed. The reaction was removed from heat and concentrated. The crude material was purified on a 340G SNAP Biotage column (20-100% ethyl acetate in hexane) to give ethyl 4-((1R,3S)-3-hydroxy-cyclohexylamino)-2-(methylthio)pyrimidine-5-carboxylate (5 g, 16.06 mmol, 85% yield) as a white foam; MS (ESI) m/z 312.1 $[M+1]^+$ B. 4-((1R,3S)-3-Hydroxycyclohexylamino)-2-(methylthio)pyrimidine-5-carboxylic acid Ethyl 4-((1R,3S)-3-hydroxycyclohexylamino)-2-(methylthio)-pyrimidine-5-carboxylate (5 g, 16.06 mmol) was dissolved in ethanol (50 mL) before adding sodium hydroxide solution (2 M in water, 20 mL, 40.0 mmol) and stirring at room temperature. After 30 min, LCMS shows mostly desired product mass. The reaction mixture was neutralized by addition of saturated aqueous citric acid solution. The resulting precipitate was filtered and dried to give 4-((1R,3S)-3-hydroxycyclohexylamino)-2-(methylthio)pyrimidine-5-carboxylic acid (4.5 g, 15.88 mmol, 99% yield) as a white solid; $^1$H NMR (400 MHz, DMSO-$d_6$) δ ppm 13.21 (br. s., 1H), 8.44-8.54 (m, 2H), 4.74 (d, J=3.90 Hz, 1H), 3.97-4.12 (m, 1H), 3.56 (d, J=3.12 Hz, 1H), 2.46 (s, 3H), 2.05-2.16 (m, 1H), 1.84 (d, J=10.15 Hz, 1H), 1.65-1.80 (m, 2H), 1.11-1.36 (m, 4H); MS (ESI) m/z 284.1 [M+1]+

C. 4-((1R,3S)-3-Hydroxycyclohexylamino)-2-(methylthio)pyrimidine-5-carboxamide 4-((1R,3S)-3-Hydroxycyclohexylamino)-2-(methylthio) pyrimidine-5-carboxylic acid (4.5 g, 15.88 mmol) and HATU (9.06 g, 23.82 mmol) were dissolved in DMF (75 mL) and allowed to stir for 5 min at room temperature before adding ammonium chloride (4.25 g, 79 mmol) and DIEA (13.87 mL, 79 mmol). The reaction was allowed to stir at room temperature overnight. After LCMS showed the desired product mass as the dominant peak, the reaction was partitioned between water and ethyl acetate. The organic layer was washed once with brine before drying over sodium sulfate, filtering, and condensing. After drying, 4-((1R,3S)-3-hydroxycyclohexylamino)-2-(methylthio)-pyrimidine-5-carboxamide (4.19 g, 14.84 mmol, 93% yield) was obtained as an off-white solid; MS (ESI) m/z 283.2 [M+1]+

D. 4-((1R,3S)-3-Hydroxycyclohexylamino)-2-(methylsulfonyl)-pyrimidine-5-carboxamide 4-((1R,3S)-3-Hydroxycyclohexylamino)-2-(methylthio)-pyrimidine-5-carboxamide (302 mg, 1.070 mmol) was suspended in DCM (10 mL) and acetone (10 mL). mCPBA (479 mg, 2.139 mmol) was then added and the reaction was stirred at room temperature. After 90 min, LCMS showed the desired product mass as the dominant peak. The reaction was quenched by addition of 10 mL of 10% aqueous sodium thiosulfate solution. After stirring for 5 minutes, the reaction was partitioned between ethyl acetate and water. The organic layer was then washed with saturated sodium bicarbonate and brine. The combined aqueous layers were washed with ethyl acetate three times before combining the organic layers, drying over sodium sulfate, filtering, and condensing. After drying, 4-((1R,3S)-3-hydroxycyclohexylamino)-2-(methylsulfonyl)-pyrimidine-5-carboxamide (259 mg, 0.824 mmol, 77% yield) was obtained as a white solid; MS (ESI) m/z 315.2 [M+1]+

E. (1R,4R)-4-Amino-N-methylcyclohexanecarboxamide tert-Butyl (1R,4R)-4-(methylcarbamoyl)cyclohexylcarbamate (0.411 g, 1.603 mmol) was dissolved in DCM (5 mL), treated with TFA (5.56 mL, 72.1 mmol) and stirred at room temperature for 1 h. After that the solvent was reduced in vacuo, the residue dissolved in acetonitrile and loaded on a Phenomenex Strada-X-C solid phase extraction column and flushed with 300 mL of acetonitrile. The desired compound was released from the column using 2 M ammonia in methanol. The solution containing the desired compound was reduced in vacuo to afford (1R,4R)-4-amino-N-methylcyclohexanecarboxamide (0.230 g, 1.475 mmol, 92% yield); MS (ESI) m/z 157.0 $[M+1]^+$.

F. 4-((1R,3S)-3-Hydroxycyclohexylamino)-2-((1R,4R)-4-(methyl-carbamoyl)cyclohexylamino)pyrimidine-5-carboxamide 4-((1R,3S)-3-Hydroxy-cyclohexylamino)-2-(methylsulfonyl)pyrimidine-5-carboxamide (0.231 g, 0.736 mmol), (1R,4R)-4-amino-N-methylcyclohexanecarboxamide (0.230 g, 1.472 mmol), DIEA (0.514 mL, 2.94 mmol), and DMSO (4 mL) were combined and heated at 100° C. for 2 h. The solvent was evaporated under reduced pressure, the residue dissolved in a minimum amount of methanol, loaded on a silica gel column and purified (0-15% ammonia saturated methanol in DCM) to afford 4-((1R,3S)-3-hydroxycyclohexylamino)-2-((1R,4R)-4-(methylcarbamoyl)-cyclohexylamino)pyrimidine-5-carboxamide (0.106 g, 0.271 mmol, 36.9% yield) as a white powder; MS (ESI) m/z 391.2 $[M+1]^+$; $^1$H NMR (400 MHz, DMSO-$d_6$) δ ppm 9.10 (br. s., 1H), 8.33 (s, 1H), 7.68 (br. s., 1H), 6.92-7.29 (m, 3H), 4.67 (br. s., 1H), 3.87 (br. s., 1H), 3.41-3.71 (m, 2H), 2.55 (d, J=4.30 Hz, 3H), 1.66-2.16 (m, 9H), 1.00-1.47 (m, 8H).

Example 5: 4-((1R,3S)-3-Hydroxycyclohexylamino)-2-((1r,4R)-4-(methylamino)cyclohexylamino)pyrimidine-5-carboxamide hydrochloride

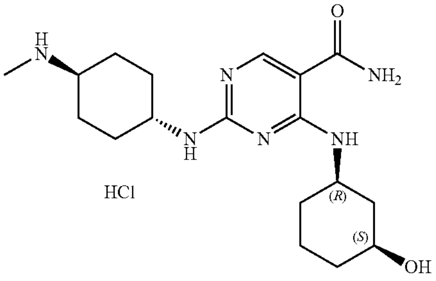

A. tert-Butyl (1R,4R)-4-(5-carbamoyl-4-((1R,3S)-3-hydroxycyclohexyl-amino)pyrimidin-2-ylamino) cyclohexyl(methyl)carbamate 4-((1R,3S)-3-Hydroxy-cyclohexylamino)-2-(methylsulfonyl)pyrimidine-5-carboxamide (0.397 g, 1.264 mmol; synthesis described herein), tert-butyl (1R,4R)-4-aminocyclohexyl-(methyl)carbamate (0.577 g, 2.53 mmol), DIEA (0.883 mL, 5.05 mmol), and DMSO (4 mL) were combined and heated at 100° C. for 2 h. The solvent was evaporated under reduced pressure, the residue dissolved in a minimum amount of methanol, loaded on a silica gel column and purified (0-15% ammonia saturated methanol in DCM) to afford tert-butyl (1R,4r)-4-(5-carbamoyl-4-((1R,3S)-3-hydroxycyclohexylamino)pyrimidin-2-ylamino)cyclohexyl-(methyl)carbamate (0.210 g, 0.455 mmol, 36% yield) as a white powder; MS (ESI) m/z 463.3 $[M+1]^+$.

B. 4-((1R,3S)-3-Hydroxycyclohexylamino)-2-((1R,4R)-4-(methyl-amino)cyclohexylamino)pyrimidine-5-carboxamide hydrochloride tert-Butyl (1R,4r)-4-(5-carbamoyl-4-((1R,3S)-3-hydroxycyclohexylamino)pyrimidin-2-ylamino)-cyclohexyl (methyl)carbamate (0.150 g, 0.324 mmol) was dissolved in DCM (2 mL) and TFA (2 mL, 26.9 mmol) was added drop wise. The solution was stirred at room temperature for 1 h and then concentrated under reduced pressure. The residue was purified via preparative HPLC (5-40% acetonitrile/water, 20 mL/min.) to afford the title compound as the corresponding TFA-salt. The fractions containing the desired compound were concentrated under reduced pressure, the residue dissolved in methanol and hydrogen chloride (4N in dioxane; 3 mL) was added. The resulting solution was concentrated under reduced pressure and this procedure was repeated twice to afford 4-((1R,3S)-3-hydroxy-cyclohexylamino)-2-((1r,4R)-4-(methylamino)cyclohexylamino) pyrimidine-5-carboxamide hydrochloride (0.063 g, 0.158 mmol, 48.7% yield). MS (ESI) m/z 363.5 $[M+1]^+$; $^1$H NMR (400 MHz, DMSO-$d_6$) δ ppm 9.94 (br. s., 1H), 8.83-9.01 (m, 1H), 8.38-8.49 (m, 2H), 8.15 (br. s., 1H), 7.64 (br. s., 1H), 3.96 (br. s., 1H), 3.69 (d, J=13.67 Hz, 2H), 3.49 (d, J=11.32 Hz, 3H), 2.97 (br. s., 1H), 2.52 (br. s., 2H), 1.69-2.17 (m, 7H), 1.09-1.53 (m, 8H).

Example 6: 2-(4,4-Difluorocyclohexylamino)-4-((1R,3S)-3-hydroxycyclohexylamino)pyrimidine-5-carboxamide

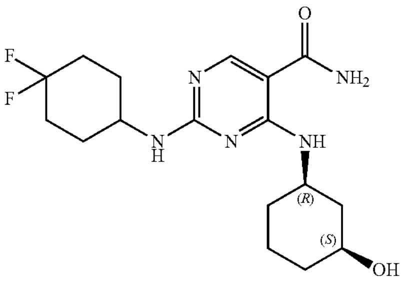

4-((1R,3S)-3-Hydroxycyclohexylamino)-2-(methylsulfonyl)pyrimidine-5-carboxamide (478 mg, 1.521 mmol; synthesis described herein), 4,4-difluorocyclohexanamine hydrochloride (522 mg, 3.04 mmol), DIEA (1.062 mL, 6.08 mmol), and DMSO (8 mL) were combined in a round bottom flask and heated at 100° C. for 1 h. The reaction was removed from heat and condensed in vacuo. The crude material was purified on a 100G SNAP Biotage column (2-12% ammonia saturated methanol in DCM). The peak fractions were combined and evaporated. After drying under high vacuum, 2-(4,4-difluorocyclohexylamino)-4-((1R,3S)-3-hydroxycyclohexylamino)pyrimidine-5-carboxamide (325 mg, 0.880 mmol, 58%) was obtained as a slightly yellow powder;

$^1$H NMR (400 MHz, DMSO-$d_6$) δ ppm 8.93 (d, J=7.42 Hz, 1H), 8.36 (s, 1H), 7.22 (br. s., 1H), 2.94-3.05 (m, 1H), 1.64-2.21 (m, 14H), 1.36-1.62 (m, 4H), 0.92-1.33 (m, 3H); MS (ESI) m/z 370.2 $[M+1]^+$.

Example 7: 4-((3S,5R)-5-Hydroxytetrahydro-2H-pyran-3-ylamino)-2-((1r,4S)-4-methoxycyclohexylamino)pyrimidine-5-carboxamide, 4-((3R,5S)-5-hydroxy-tetrahydro-2H-pyran-3-ylamino)-2-((1r,4R)-4-methoxycyclohexylamino)pyrimidine-5-carboxamide, 4-((3S,5S)-5-hydroxytetrahydro-2H-pyran-3-ylamino)-2-((1r,4S)-4-methoxycyclohexylamino)pyrimidine-5-carboxamide, 4-((3R,5R)-5-hydroxy-tetrahydro-2H-pyran-3-ylamino)-2-((1r,4R)-4-methoxycyclohexylamino)pyrimidine-5-carboxamide

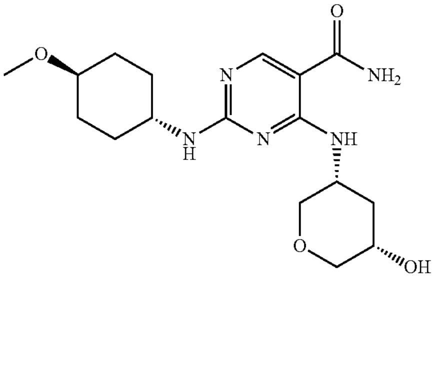

-continued

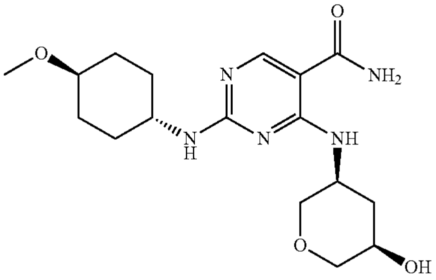

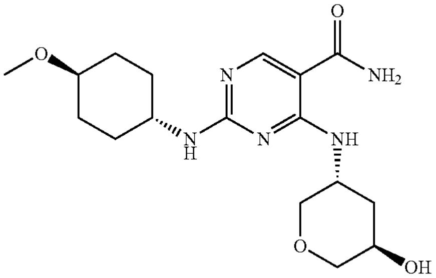

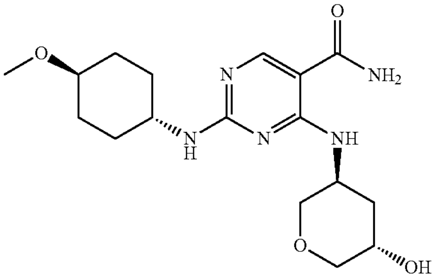

A. 6-Hydroxy-2H-pyran-3(6H)-one

Furan-2-ylmethanol (17.67 mL, 204 mmol) was dissolved in DCM (500 mL) and cooled to 0° C. before adding 3-chloroperoxybenzoic acid (68.5 g, 306 mmol) portion wise. The reaction was slowly allowed to warm to room temperature over 6 h, during which time solid m-chlorobenzoic acid precipitated from solution. The solution was cooled to −78° C. for 15 min and the solids were filtered off. The filtrate was condensed to give a yellow solid. The crude material was purified on a 340G SNAP Biotage column (20-100% ethyl acetate in hexane). The peak fractions were combined and evaporated to give 6-hydroxy-2H-pyran-3(6H)-one (15.8 g, 138 mmol, 67.9% yield) as a pale yellow oil; $^1$H NMR (400 MHz, $CDCl_3$) δ ppm 6.94-7.01 (m, 1H), 6.18 (d, J=10.93 Hz, 1H), 5.61-5.68 (m, 1H), 4.56 (s, 1H), 4.17 (s, 1H), 3.61 (br. s., 1H).

B. 6-(tert-Butyldimethylsilyloxy)-2H-pyran-3(6H)-one

6-Hydroxy-2H-pyran-3(6H)-one (9 g, 79 mmol) was dissolved in DCM (250 mL), placed under a nitrogen atmosphere, and cooled to −78° C. 2,6-Lutidine (13.78 mL, 118 mmol) was then added in one portion, followed by slow addition of t-butyldimethylsilyltrifluoromethanesulfonate (21.74 mL, 95 mmol). The reaction was allowed to slowly warm to 0° C. over 4 h. The reaction was quenched by addition of ~20 mL of water. The solution turned pale yellow upon quenching. After transferring to a separatory funnel, the organic phase was washed successively with 10% citric acid and brine. The organic layer was then dried over sodium sulfate, filtered and condensed to give a yellow oil. The crude material was purified on a 340G SNAP Biotage column (0-20% ethyl acetate in hexane) to give 6-(tert-butyldimethylsilyloxy)-2H-pyran-3(6H)-one (9.90 g, 43.4 mmol, 55.0% yield) as a yellow oil; $^1$H NMR (400 MHz, $CDCl_3$) δ ppm 6.87 (dd, J=10.54, 3.12 Hz, 1H), 6.08 (d, J=10.15 Hz, 1H), 5.53 (d, J=3.12 Hz, 1H), 4.51 (d, J=16.79 Hz, 1H), 4.08 (d, J=16.79 Hz, 1H), 0.92 (s, 9H), 0.17 (s, 6H).

C. 6-(tert-Butyldimethylsilyloxy)-3,6-dihydro-2H-pyran-3-ol

To a cooled (−20° C.) solution of 6-(tert-butyldimethylsilyloxy)-2H-pyran-3(6H)-one (9.9 g, 43.4 mmol) and cerium(III) chloride heptahydrate (16.15 g, 43.4 mmol) in methanol (173 mL) was added portion wise sodium borohydride (1.640 g, 43.4 mmol). Intense bubbling was observed upon addition. After the mixture was stirred for 30 min at −20° C., the reaction was quenched with acetone (~20 mL) and stirred at room temperature for 1 h. Most of the volatile solvents were then evaporated. Brine was added and the slurry was transferred to a separatory funnel. The mixture was extracted with DCM (thick emulsion formed) three times. The combined organic layers were dried over sodium sulfate, filtered and condensed to give crude 6-(tert-butyldimethylsilyloxy)-3,6-dihydro-2H-pyran-3-ol (5.6 g, 24.31 mmol, 56.1% yield) as a tan colored oil; $^1$H NMR (400 MHz, $CDCl_3$) δ ppm 5.95 (dd, J=10.15, 2.34 Hz, 1H), 5.75 (d, J=10.15 Hz, 1H), 5.25 (s, 1H), 4.15 (d, J=9.37 Hz, 1H), 3.72-3.82 (m, 2H), 1.74 (d, J=8.98 Hz, 1H), 0.86-0.95 (m, 9H), 0.13 (s, 6H).

D. 6-(tert-Butyldimethylsilyloxy)-3,6-dihydro-2H-pyran-3-yl acetate

To a solution of 6-(tert-butyldimethylsilyloxy)-3,6-dihydro-2H-pyran-3-ol (13.3 g, 57.7 mmol) and TEA (16.09 mL, 115 mmol) in DCM (200 mL) was added acetic anhydride (27.2 mL, 289 mmol), and the mixture was stirred at room temperature overnight. Methanol (~3 mL) was added and the mixture was stirred for 30 min at room temperature before adding water and transferring to a separatory funnel. The organic layer was washed with water and brine, dried over sodium sulfate, filtered and condensed. The crude material was purified on a 340G SNAP Biotage column (0-50% ethyl acetate in hexane) to give 6-(tert-butyldimethylsilyloxy)-3,6-dihydro-2H-pyran-3-yl acetate (13.6 g, 49.9 mmol, 86% yield) as a pale yellow oil; $^1$H NMR (400 MHz, $CDCl_3$) δ ppm 5.84-5.88 (m, 2H), 5.26-5.28 (m, 1H), 5.20-5.25 (m, 1H), 3.84 (dd, J=6.25, 1.95 Hz, 2H), 2.08 (s, 3H), 0.91 (s, 9H), 0.13 (d, J=1.17 Hz, 6H).

E. 3,6-Dihydro-2H-pyran-3-yl acetate 6-(tert-Butyldimethylsilyloxy)-3,6-dihydro-2H-pyran-3-yl acetate (13.6 g, 49.9 mmol) was dissolved in DCM (250 mL), placed under a nitrogen atmosphere, and cooled to −30° C. (dry ice/acetone, until temperature was reached). Triethylsilane (15.95 mL, 100 mmol) was then added slowly via syringe, followed by drop wise addition of boron trifluoride etherate (7.59 mL, 59.9 mmol). The reaction was kept under nitrogen and slowly allowed to warm. After 1 h, the reaction mixture was quenched by additions of saturated sodium bicarbonate. After transferring to a separatory funnel, the organic layer was washed with water and brine, dried over sodium sulfate, filtered and condensed. The crude material was purified on a 340G SNAP Biotage column (0-80% ethyl acetate in hexane). Evaporation of clean fractions gave 3,6-dihydro-2H-pyran-3-yl acetate (5.5 g, 38.7 mmol, 77% yield) as a colorless oil; $^1$H NMR (400 MHz, $CDCl_3$) δ ppm 5.09 (dtt, J=5.73, 2.21, 2.21, 1.17, 1.17 Hz, 1H), 4.19-4.28 (m, 1H), 4.04-4.15 (m, 1H), 3.89-3.98 (m, 1H), 3.76-3.84 (m, 1H), 2.10 (s, 3H).

F. 3,6-Dihydro-2H-pyran-3-ol

To a solution of 3,6-dihydro-2H-pyran-3-yl acetate (5.5 g, 38.7 mmol) in methanol (130 mL) was added 10 drops of 25% sodium methoxide in methanol. The solution was allowed to stir at room temperature. After 30 min, TLC (10% ethyl acetate in hexane; permanganate stain) shows ~1:1 ratio of starting material to product. An additional 10 drops of 25% sodium methoxide in methanol was added. After 30 min, TLC showed ~3:1 ratio of product to starting material. An additional 10 drops of 25% sodium methoxide in methanol were added. After 30 more min, TLC showed complete conversion to product. Amberlist 15 was added and stirring was continued for 15 min before filtering off. Evaporation of the solvent gave 3,6-dihydro-2H-pyran-3-ol (3.8 g, 38.0 mmol, 98% yield) as a colorless oil; $^1$H NMR (400 MHz, $CDCl_3$) δ ppm 5.90-6.02 (m, 2H), 4.19 (dt, J=2.83, 1.51 Hz, 1H), 4.15 (dt, J=2.83, 1.51 Hz, 1H), 4.09 (q, J=1.95 Hz, 1H), 4.05 (q, J=1.95 Hz, 1H), 3.96-4.00 (m, 1H), 1.92 (br. s., 1H).

G. 2H-Pyran-3(6H)-one 3,6-Dihydro-2H-pyran-3-ol (2.44 g, 24.37 mmol) was dissolved in DCM (100 mL) and cooled to 0° C. before slowly adding Dess-Martin periodinane (10.34 g, 24.37 mmol). The reaction was allowed to slowly warm to room temperature over 5 h. The reaction was then filtered through celite. After concentrating the filtrate, the crude material was purified on a 100G SNAP Biotage column (0-80% ethyl acetate in hexane) to give 2H-pyran-3(6H)-one (2.33 g, 23.75 mmol, 97% yield) as a colorless oil; $^1$H NMR (400 MHz, $CDCl_3$) δ ppm 7.07-7.17 (m, 1H), 6.15-6.25 (m, 1H), 4.39 (t, J=2.54 Hz, 2H), 4.19 (s, 2H).

H. Benzyl 5-oxotetrahydro-2H-pyran-3-ylcarbamate 2H-pyran-3(6H)-one (2.33 g, 23.75 mmol), benzyl carbamate (4.31 g, 28.5 mmol), and DCM (2.375 mL) were added to a small vial and stirred vigorously. To the thick syrup was added bismuth(III) nitrate pentahydrate (1.728 g, 3.56 mmol). The vial was capped and the reaction was stirred vigorously overnight. The reaction was diluted with DCM and filtered through a pad of celite. The filtrate was condensed and purified on a 100G SNAP Biotage column (10-100% ethyl acetate in hexane) to give benzyl 5-oxotetrahydro-2H-pyran-3-ylcarbamate (4.35 g, 17.45 mmol, 73.5% yield) as a pale yellow oil; $^1$H NMR (400 MHz, $CDCl_3$) δ ppm 7.28-7.41 (m, 5H), 5.20-5.28 (m, 1H), 5.05-5.15 (m, 2H), 4.24-4.35 (m, 1H), 4.01-4.06 (m, 1H), 3.89-3.95 (m, 1H), 3.80-3.87 (m, 1H), 2.73 (d, J=5.47 Hz, 1H), 2.64-2.71 (m, 1H).

I. Benzyl 5-hydroxytetrahydro-2H-pyran-3-ylcarbamate

Benzyl 5-oxotetrahydro-2H-pyran-3-ylcarbamate (4.35 g, 17.45 mmol) and cerium(III) chloride heptahydrate (6.50 g, 17.45 mmol) were dissolved in methanol (100 mL) before cooling to 0° C. Sodium borohydride (0.660 g, 17.45 mmol) was then added slowly. Intense bubbling was observed. The reaction was allowed to stir at 0° C. for 30 min before quenching by addition of acetone (~3 mL) and stirring at room temperature for 30 additional min. The reaction was then evaporated to dryness. The material was partitioned between DCM and water and the aqueous layer was washed with DCM (5×). The organic layers were combined, dried over sodium sulfate, filtered, and condensed to give impure benzyl 5-hydroxytetrahydro-2H-pyran-3-ylcarbamate (2.5 g, 9.95 mmol, 57.0% yield) as a white solid; $^1$H NMR (400 MHz, $CDCl_3$) δ ppm 7.28-7.39 (m, 5H), 5.90-6.06 (m, 1H), 5.10 (d, J=4.29 Hz, 2H), 3.59-3.97 (m, 6H), 1.77-2.06 (m, 3H); MS (ESI) m/z 252.1 $[M+1]^+$.

J. 5-Aminotetrahydro-2H-pyran-3-ol

Benzyl 5-hydroxytetrahydro-2H-pyran-3-ylcarbamate (2.5 g, 9.95 mmol) was dissolved in DCM (20 mL) and methanol (20.00 mL) before loading catalyst (10% palladium on carbon) and capping with a t-joint. The flask was evacuated and flushed with hydrogen (3×), maintaining a hydrogen atmosphere with a balloon. The reaction was allowed to stir at room temperature overnight. Once the material had all been converted to product (as determined by LCMS), the reaction was filtered through a pad of celite, washing thoroughly with DCM and methanol. The filtrate was condensed to give crude 5-aminotetrahydro-2H-pyran-3-ol (1.13 g, 9.65 mmol, 97% yield) as tan gum. $^1$H NMR (400 MHz, DMSO-$d_6$) δ ppm 4.28-4.66 (m, 2H), 3.66 (ddd, J=10.93, 3.90, 1.56 Hz, 2H), 3.44-3.55 (m, 1H), 2.89-3.01 (m, 2H), 2.81 (s, 1H), 2.01-2.13 (m, 1H), 1.22 (d, J=12.10 Hz, 1H).

K. Ethyl 2-((1r,4r)-4-methoxycyclohexylamino)-4-(methylthio)-pyrimidine-5-carboxylate (1r,4r)-4-Methoxycyclohexanamine (4.39 g, 34.0 mmol), ethyl 2-chloro-4-(methylthio)pyrimidine-5-carboxylate (3.95 g, 16.98 mmol), DIEA (5.93 mL, 34.0 mmol) and 1,4-dioxane (100 mL) were combined and heated at 80° C. overnight. The reaction was removed from heat and condensed. The crude material was purified on a Biotage (20-80% ethyl acetate in hexanes) to give ethyl 2-((1r,4r)-4-methoxycyclohexylamino)-4-(methylthio)pyrimidine-5-carboxylate (3.1 g, 9.53 mmol, 56% yield) as a pale yellow solid; $^1$H NMR (DMSO-$d_6$, 400 MHz) δ ppm 8.60 (s, 0.35H), 8.54 (s, 0.65H), 8.05 (d, J=7.4 Hz, 0.64H), 7.87 (d, J=8.2 Hz, 0.36H), 4.22 (q, J=7.0 Hz, 2H), 3.69-3.90 (m, 1H), 3.23 (s, 3H), 3.00-3.20 (m, 1H), 2.40 (s, 2H), 2.38 (s, 1H), 1.79-2.12 (m, 4H), 1.09-1.44 ppm (m, 7H); MS (ESI) m/z 326.3 $[M+1]^+$.

L. 2-((1r,4r)-4-Methoxycyclohexylamino)-4-(methylthio)pyrimidine-5-carboxylic acid Ethyl 2-((1r,4r)-4-methoxycyclohexylamino)-4-(methylthio)pyrimidine-5-carboxylate (3.1 g, 9.53 mmol) was dissolved in ethanol (60 mL) before adding aqueous sodium hydroxide solution (2 M, 23.81 mL, 47.62 mmol) and stirring at room temperature. After 30 min, LCMS showed mostly desired product mass. The reaction mixture was neutralized by addition of saturated aqueous citric acid solution. The resulting precipitate was filtered and dried to give 2-((1r,4r)-4-methoxycyclohexylamino)-4-(methylthio)-pyrimidine-5-carboxylic acid (2.76 g, 9.28 mmol, 97% yield) as a white solid; $^1$H NMR (DMSO-$d_6$, 400 MHz) δ ppm 12.59 (s, 1H), 8.57 (s, 0.38H), 8.50 (s, 0.62H), 7.94 (d, J=7.4 Hz, 0.62H), 7.77 (d, J=7.8 Hz, 0.38H), 3.70-3.90 (m, 1H), 3.23 (s, 3H), 3.02-3.18 (m, 1H), 2.37 (s, 2H), 2.36 (s., 1H), 1.83-2.09 (m, 4H), 1.11-1.46 ppm (m, 4H); MS (ESI) m/z 298.2 [M+1]$^+$ M. 2-((1r,4r)-4-Methoxycyclohexylamino)-4-(methylthio)pyrimidine-5-carboxamide 2-((1r,4r)-4-methoxycyclohexylamino)-4-(methylthio) pyrimidine-5-carboxylic acid (2.66 g, 8.94 mmol) and HATU (5.10 g, 13.42 mmol) were dissolved in DMF (35 mL) and allowed to stir for 5 minutes at room temperature before adding ammonium chloride (2.392 g, 44.7 mmol) and DIEA (7.81 mL, 44.7 mmol). The reaction was allowed to stir at room temperature for 30 min. LCMS shows the desired product mass as dominant and the reaction was partitioned between water and ethyl acetate. The organic layer was washed once with brine before drying over sodium sulfate, filtering, and condensing. After drying, 2-((1r,4r)-4-methoxycyclohexylamino)-4-(methylthio) pyrimidine-5-carboxamide (2.54 g, 8.57 mmol, 96% yield) was obtained as an white solid; $^1$H NMR (DMSO-$d_6$, 400 MHz) δ ppm 8.41 (s, 1H), 7.63 (d, J=7.0 Hz, 0.76H), 7.45 (d, J=7.0 Hz, 0.24H), 7.08 (br. s., 1H), 3.66-3.85 (m, 1H), 3.23 (s, 3H), 3.11 (br. s., 1H), 2.32 (s, 3H), 1.81-2.11 (m, 4H), 1.10-1.44 ppm (m, 4H); MS (ESI) m/z 283.2 [M+1]$^+$ N. 2-((1r,4r)-4-Methoxycyclohexylamino)-4-(methylsulfinyl)-pyrimidine-5-carboxamide 2-((1r,4r)-4-Methoxycyclohexylamino)-4-(methylthio) pyrimidine-5-carboxamide (3 g, 10.12 mmol) was dissolved in NMP (30 mL). At 0° C., mCPBA (2.268 g, 10.12 mmol) was then added portion wise and the reaction was stirred while elevating the reaction temperature to room temperature slowly. After 30 min, the reaction mixture was diluted with water (200 mL), stirred for 10 min and the resulting solid was removed by filtration. The filtrate was concentrated in vacuo to afford 2-((1r,4r)-4-methoxycyclohexylamino)-4-(methylsulfinyl)pyrimidine-5-carboxamide as a clear, slightly yellow solution in NMP (~25 mL). This crude product was used in the next step without further purification. MS (ESI) m/z 313.3 [M+1]$^+$.

O. 4-((3S,5R)-5-Hydroxytetrahydro-2H-pyran-3-ylamino)-2-((1r,4S)-4-methoxycyclohexylamino) pyrimidine-5-carboxamide, 4-((3R,5S)-5-hydroxy-tetrahydro-2H-pyran-3-ylamino)-2-((1r,4R)-4-methoxycyclohexylamino)pyrimidine-5-carboxamide, 4-((3S,5S)-5-hydroxytetrahydro-2H-pyran-3-ylamino)-2-((1r,4S)-4-methoxycyclohexylamino)pyrimidine-5-carboxamide, 4-((3R,5R)-5-hydroxy-tetrahydro-2H-pyran-3-ylamino)-2-((1r,4R)-4-methoxycyclohexylamino)pyrimidine-5-carboxamide To 2-((1r,4r)-4-methoxycyclohexylamino)-4-(methylsulfinyl)-pyrimidine-5-carboxamide (3.1 g, 9.92 mmol) in NMP (25 mL)) was added crude 5-aminotetrahydro-2H-pyran-3-ol (1.15 g, 9.82 mmol) as a solution in NMP (20 mL). To the suspension was added DIEA (8.57 mL, 49.1 mmol) and the reaction was heated to 100° C. overnight. Most of the NMP was removed by evaporation at 70° C., the residue was diluted with DCM and purified on a 340G SNAP Biotage column (0-15% methanol in DCM over 2000 mL). The product fractions were combined and concentrated to give 2.8 g (78%) of material that was ~85% pure. The material was dissolved in DCM and repurified on a 340G SNAP Biotage column (2-15% ammonia saturated methanol in dichloromethane). The product fractions were combined and concentrated to afford a mixture of four products (two diastereomers and their corresponding enantiomers; 1.95 g), >99% pure. The crude material was separated by chiral SFC using an AD-H column to afford 4 compounds labeled PEAK 1 to PEAK 4, with PEAK 1 being the first eluting compound and PEAK 4 being the latest eluting compound.

PEAK 1:

$^1$H NMR (400 MHz, DMSO-$d_6$) δ ppm 8.41 (s, 1H), 4.38 (br. s., 1H), 3.53-3.79 (m, 4H), 3.24 (s, 3H), 2.87-2.98 (m, 3H), 1.89-2.07 (m, 4H), 1.65-1.78 (m, 1H), 1.19-1.43 (m, 4H); MS (ESI) m/z 366.3 [M+1]$^+$.

PEAK 2:

$^1$H NMR (400 MHz, DMSO-$d_6$) δ ppm 8.86-9.01 (m, 1H), 8.35 (br. s., 1H), 6.91-7.18 (m, 1H), 4.91-4.99 (m, 1H), 3.49-4.13 (m, 4H), 3.23 (s, 3H), 2.85-3.15 (m, 3H), 1.79-2.28 (m, 5H), 1.08-1.41 (m, 5H), 1.04 (d, J=6.25 Hz, 1H); MS (ESI) m/z 366.3 [M+1]$^+$.

PEAK 3:

$^1$H NMR (400 MHz, DMSO-$d_6$) δ ppm 8.86-9.02 (m, 1H), 8.32-8.40 (m, 1H), 6.88-7.20 (m, 1H), 4.91-5.00 (m, 1H), 3.49-4.15 (m, 5H), 3.22 (s, 3H), 2.79-3.14 (m, 3H), 1.82 (s, 5H), 1.12 (t, J=7.22 Hz, 6H); MS (ESI) m/z 366.3 [M+1]$^+$.

PEAK 4:

$^1$H NMR (400 MHz, DMSO-$d_6$) δ ppm 8.99-9.24 (m, 1H), 8.36 (br. s., 1H), 6.79-7.20 (m, 2H), 4.72-4.94 (m, 1H), 4.17-4.46 (m, 1H), 3.43-3.77 (m, 4H), 3.23 (s, 4H), 3.03-3.13 (m, 1H), 2.73 (s, 1H), 1.98 (br. s., 6H), 1.03-1.35 (m, 5H); MS (ESI) m/z 366.3 [M+1]$^+$.

Example 8: 4-(3-Hydroxy-3-methylbutylamino)-2-((1r,4r)-4-methoxycyclohexylamino)pyrimidine-5-carboxamide

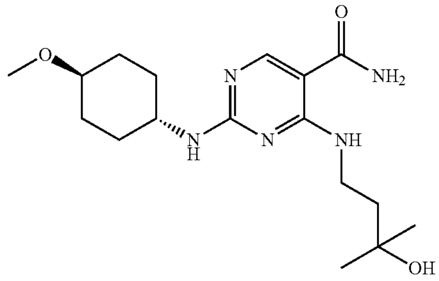 [SMILES: CO[C@H]1CC[C@H](Nc2ncc(C(N)=O)c(NCCC(C)(C)O)n2)CC1]

A. 2-((1r,4r)-4-Methoxycyclohexylamino)-4-(methylsulfinyl)-pyrimidine-5-carboxamide To a stirred colorless solution of 2-((1r,4r)-4-methoxycyclohexylamino)-4-(methylthio)pyrimidine-5-carboxamide (0.200 g, 0.675 mmol; synthesis described herein) in NMP (2 mL) was added mCPBA (0.151 g, 0.675 mmol) at 0° C. portion wise. The reaction mixture was then stirred at room temperature for 2 h until completion of the reaction as indicated by LCMS. The reaction mixture was diluted with water (20 mL) and filtered. The filtrate was concentrated to afford 2-((1r,4r)-4-methoxycyclohexylamino)-4-(methylsulfinyl)pyrimidine-5-carboxamide (0.211 g, 100% yield) as a white sticky solid which was used in the next step without further purification. MS (ESI) m/z 313.1 $[M+1]^+$.

B. 4-(3-Hydroxy-3-methylbutylamino)-2-((1r,4r)-4-methoxy-cyclo-hexylamino)pyrimidine-5-carboxamide To a solution of 2-((1r,4r)-4-methoxy-cyclohexylamino)-4-(methylsulfinyl)pyrimidine-5-carboxamide (0.211 g, 0.675 mmol) and DIEA (0.236 mL, 1.351 mmol) in NMP (2 mL) was added 4-amino-2-methylbutan-2-ol (0.105 g, 1.013 mmol) at room temperature. The reaction mixture was stirred for 2 h at 70° C. Upon completion of the reaction as indicated by LCMS and TLC the reaction mixture was concentrated and purified by silica gel chromatography (0%-15% ammonia saturated methanol in DCM). The product fractions were combined and concentrated to afford 4-(3-hydroxy-3-methylbutylamino)-2-((1r,4r)-4-methoxy-cyclohexylamino)-pyrimidine-5-carboxamide (0.143 g, 60.2% yield, 95.8% pure) as a pale yellow solid.

$^1H$ NMR (400 MHz, DMSO-$d_6$) δ ppm 8.81-9.03 (m, 1H), 8.32 (s, 1H), 6.75-7.06 (m, 2H), 4.28 (s, 1H), 3.63-3.77 (m, 1H), 3.39-3.52 (m, 2H), 3.22 (s, 3H), 3.02-3.11 (m, 1H), 1.81-2.06 (m, 4H), 1.57-1.67 (m, 2H), 1.21-1.34 (m, 2H), 1.16 (br. s., 1H), 1.13 (s, 8H). MS (ESI) m/z 352.4 $[M+1]^+$.

Example 9: 4-((1R,2S)-2-(Hydroxymethyl)cyclopentylamino)-2-((1r,4R)-4-methoxycyclohexylamino)pyrimidine-5-carboxamide, 4-((1S,2R)-2-(Hydroxymethyl)cyclopentylamino)-2-((1r,4S)-4-methoxycyclohexylamino)pyrimidine-5-carboxamide

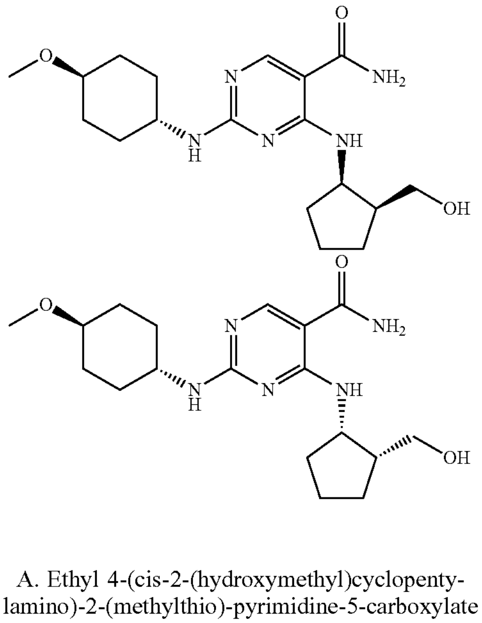

A. Ethyl 4-(cis-2-(hydroxymethyl)cyclopentylamino)-2-(methylthio)-pyrimidine-5-carboxylate To a stirred solution of ethyl 4-chloro-2-(methylthio)-pyrimidine-5-carboxylate (5.00 g, 21.49 mmol) and cis-(2-aminocyclopentyl)-methanol (2.60 g, 22.56 mmol) in ethanol (85 mL) was added DIEA (5.61 mL, 32.2 mmol) and heated to 60° C. for 2.5 h. Upon completion of reaction, as indicated by LCMS and TLC, the reaction was removed from heat and concentrated, then purified by silica gel chromatography (0-80% ethyl acetate/hexane). The desired product fractions were combined and concentrated to afford ethyl 4-(cis-2-(hydroxymethyl)cyclopentylamino)-2-(methylthio)pyrimidine-5-carboxylate (6.4 g, 96% yield) as a white solid. MS (ESI) m/z 312.4 $[M+1]^+$.

B. 4-(cis-2-(Hydroxymethyl)cyclopentylamino)-2-(methylthio)-pyrimidine-5-carboxylic acid To a stirred solution of the ethyl 4-(cis-2-(hydroxylmethyl)cyclopentylamino)-2-(methylthio)pyrimidine-5-carboxylate (6.4 g, 20.55 mmol) in ethanol (100 mL) was added aqueous sodium hydroxide solution (1 M, 51.4 mL, 51.4 mmol) at room temperature. The reaction mixture was stirred at room temperature for 2 h. Upon completion of reaction as indicated by LCMS and TLC, the reaction mixture was concentrated, diluted with water (100 mL), then neutralized while stirring with aqueous citric acid solution (2 M, 51.4 mL, 103 mmol). The resulting precipitate was filtered, washed with water (2×50 mL) and dried to afford 4-(cis-2-(hydroxymethyl)-cyclopentylamino)-2-(methylthio)pyrimidine-5-carboxylic acid (5.6 g, 96% yield) as a white solid. $^1H$ NMR (400 MHz, DMSO-$d_6$) δ ppm δ 13.17 (br. s., 1H), 8.71 (d, J=7.42 Hz, 1H), 8.50 (s, 1H), 4.49-4.60 (m, 2H), 3.40-3.46 (m, 1H), 3.32-3.39 (m, 2H), 2.47 (s, 3H), 2.22 (sxt, J=6.87 Hz, 1H), 1.95-2.04 (m, 1H), 1.78 (qd, J=4.49, 8.00 Hz, 1H), 1.66-1.72 (m, 1H), 1.49-1.61 (m, 2H). MS (ESI) m/z 284.3 $[M+1]^+$.

C. 4-(cis-2-(Hydroxymethyl)cyclopentylamino)-2-(methylthio)-pyrimidine-5-carboxamide A white suspension of the 4-(cis-2-(hydroxymethyl)-cyclopentylamino)-2-(methylthio)pyrimidine-5-carboxylic acid (5.6 g, 19.76 mmol) and HATU (11.27 g, 29.60 mmol) were dissolved in DMF (79 mL) and stirred for 5 min at room temperature before adding ammonium chloride (5.29 g, 99 mmol) and DIEA (17.26 mL, 99 mmol). The reaction mixture was stirred at room temperature for 1 h and then diluted with water (200 mL) and extracted with ethyl acetate (2×200 mL). The combined organic layers were washed with brine (100 mL), dried over sodium sulfate, filtered, and concentrated. The residual DMF was removed by suspending the white suspension in 200 mL water and 200 mL hexanes. The biphasic mixture was stirred vigorously for 30 min, filtered and washed with hexanes to afford 4-(cis-2-(hydroxyl-methyl)cyclopentylamino)-2-(methylthio)pyrimidine-5-carboxamide (4.50 g, 81% yield) as a white solid. MS (ESI) m/z 283.4 $[M+1]^+$.

D. 4-(cis-2-(Hydroxymethyl)cyclopentylamino)-2-(methylsulfonyl)-pyrimidine-5-carboxamide To a stirred suspension of the 4-(cis-2-(hydroxymethyl)-cyclopentylamino)-2-(methylthio)pyrimidine-5-carboxamide (3.5 g, 12.40 mmol) in DCM (62 mL) and acetone (62 mL) was added mCPBA (5.56 g, 24.79 mmol) and stirred at room temperature for 1.5 h. The crude reaction mixture was quenched by addition of 75 mL of 10% aqueous sodium thiosulfate solution, stirred for 5 min, before evaporating most of the volatile solvents. The material was partitioned between ethyl acetate (200 mL) and water (200 mL), and the combined organic layers were washed with saturated sodium bicarbonate solution and then brine. The combined aqueous layers were then washed with ethyl acetate (3×), the organic layers were combined, dried over sodium sulfate, filtered, and condensed. After drying under high vacuum, 4-(cis-2-(hydroxymethyl)cyclopentyl-amino)-2-(methylsulfonyl)pyrimidine-5-carboxamide (1.2 g, 3.82 mmol, 30.8% yield) was obtained as a white solid. MS (ESI) m/z 315.2 $[M+1]^+$.

E. 4-((1R,2S)-2-(Hydroxymethyl)cyclopentylamino)-2-((1r,4R)-4-methoxycyclohexylamino)pyrimidine-5-carboxamide, 4-((1S,2R)-2-(Hydroxymethyl)-cyclopentylamino)-2-((1r,4S)-4-methoxycyclohexylamino)pyrimidine-5-carboxamide To a stirred suspension of 4-(cis-2-(hydroxymethyl)cyclopentylamino)-2-(methyl-sulfonyl)pyrimidine-5-carboxamide (1.2 g, 3.82 mmol) and (1r,4r)-4-methoxycyclohexanamine hydrochloride (1.90 g, 11.46 mmol) in dioxane (40 mL) was added DIEA (4 mL, 22.92 mmol) and the resulting solution was stirred at 100° C. for 48 h. The crude reaction mixture was concentrated, and then purified by silica gel chromatography (0%-15% ammonia saturated methanol in DCM). The product fractions were impure and the desired product was precipitated and filtered from the combined fractions using DCM, methanol and water to afford the title compound as a mixture of two enantiomers (0.420 g, 30.3% yield) as a white solid. The crude material was separated by chiral SFC using an AD-H column to afford 2 compounds labeled PEAK 1 and PEAK 2, with PEAK 1 being the first eluting compound and PEAK 2 being the second eluting compound.

PEAK 1.

$^1$H NMR (400 MHz, DMSO-$d_6$) δ ppm 9.04-9.21 (m, 1H), 8.31-8.39 (m, 1H), 6.87-7.12 (m, 2H), 4.33-4.46 (m, 2H), 3.57-3.80 (m, 1H), 3.35-3.44 (m, 1H), 3.25-3.31 (m, 1H), 3.23 (s, 3H), 3.08 (t, J=8.20 Hz, 1H), 2.09-2.23 (m, 1H), 2.00 (d, J=11.71 Hz, 2H), 1.80-1.94 (m, 3H), 1.63-1.78 (m, 2H), 1.50-1.61 (m, 2H), 1.44 (br. s., 1H), 1.09-1.33 (m, 5H); MS (ESI) m/z 364.5 $[M+1]^+$.

PEAK 2.

$^1$H NMR (400 MHz, DMSO-$d_6$) δ ppm 9.03-9.18 (m, 1H), 8.34 (br. s., 1H), 6.87-7.11 (m, 2H), 4.32-4.48 (m, 2H), 3.58-3.77 (m, 1H), 3.35-3.45 (m, 1H), 3.28 (dd, J=7.03, 10.15 Hz, 1H), 3.22 (s, 3H), 3.03-3.13 (m, 1H), 2.09-2.25 (m, 1H), 2.00 (d, J=8.59 Hz, 2H), 1.81-1.95 (m, 3H), 1.63-1.77 (m, 2H), 1.51-1.60 (m, 2H), 1.37-1.47 (m, 1H), 1.09-1.33 (m, 5H); MS (ESI) m/z 364.5 $[M+1]^+$.

Example 10: 4-((1R,3R)-3-Hydroxy-3-methylcyclohexylamino)-2-((1r,4R)-4-methoxycyclohexylamino)pyrimidine-5-carboxamide, 4-((1R,3S)-3-Hydroxy-3-methylcyclohexylamino)-2-((1r,4R)-4-methoxycyclohexylamino)pyrimidine-5-carboxamide

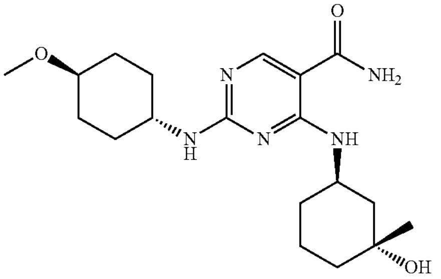

-continued

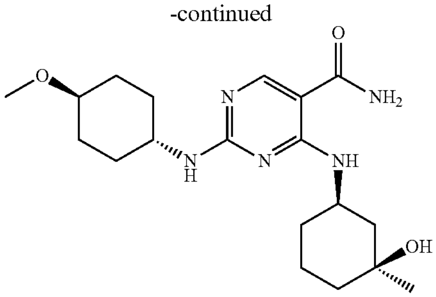

A. (1S,3R)-3-(Dibenzylamino)cyclohexanol

To a suspension of (1S,3R)-3-aminocyclohexanol (5 g, 43.4 mmol; prepared as described in *Tetrahedron: Asymmetry* 15: 2051-2056 (2004)) and sodium bicarbonate (12.03 g, 143 mmol) in ethanol (100 mL) was added (chloromethyl) benzene (15.01 mL, 130 mmol) at room temperature. The reaction mixture was heated at 75° C. overnight. Upon completion of reaction as indicated by LCMS and TLC the reaction mixture was filtered and the filtrate was concentrated. The residue was then dissolved in DCM (250 mL) and washed with aqueous sodium hydroxide solution (1 N, 2×100 mL) and brine (1×100 mL). The combined organic layers were dried over anhydrous magnesium sulfate, concentrated, and purified by silica gel chromatography (0%-80% ethyl acetate in hexanes) to yield (1S,3R)-3-(dibenzylamino)cyclohexanol (11.70 g, 91%) as a thick yellow oil. $^1$H NMR (400 MHz, DMSO-$d_6$) δ ppm 7.26-7.37 (m, 8H), 7.17-7.22 (m, 2H), 4.56 (d, J=4.30 Hz, 1H), 3.57 (s, 4H), 3.16-3.26 (m, 1H), 2.41 (tt, J=3.17, 11.86 Hz, 1H), 1.99-2.06 (m, 1H), 1.72 (d, J=8.20 Hz, 2H), 1.63-1.69 (m, 1H), 1.18-1.28 (m, 2H), 0.98 (t, 2H); MS (ESI) m/z 296.4 $[M+1]^+$.

B. (R)-3-(Dibenzylamino)cyclohexanone

Oxalyl chloride (2.70 mL, 30.9 mmol) was dissolved in dry DCM (150 mL) and cooled to −78° C. DMSO (4.78 mL, 67.3 mmol) in dry DCM (20 mL) was added dropwise to the reaction mixture and the reaction was stirred for 15 min at −78° C. Next, (1S,3R)-3-(dibenzylamino)cyclohexanol (8.287 g, 28.1 mmol) in dry DCM (100 mL) was added drop wise using an addition funnel and the reaction mixture was stirred at −78° C. for 15 min. TEA (19.55 mL, 140 mmol) was then added and the reaction was stirred at −78° C. for 1 h. The dry-ice bath was removed and the reaction mixture was allowed to warm to room temperature and stirred overnight. The reaction mixture was washed with brine (100 mL), the organic layer was separated, dried over magnesium sulfate and concentrated. Upon slow addition of diethyl ether to the residue the impurities precipitated, and were separated by filtration. Addition of diethyl ether to the filtrate yielded (R)-3-(dibenzylamino)cyclohexanone (6.05 g, 74%) as a white solid which was collected by filtration and dried. $^1$H NMR (400 MHz, DMSO-$d_6$) δ ppm 7.26-7.39 (m, 8H), 7.17-7.25 (m, 2H), 3.56-3.70 (m, 4H), 2.71-2.81 (m, 1H), 2.60-2.69 (m, 1H), 2.25-2.42 (m, 2H), 2.04-2.11 (m, 1H), 1.88-1.99 (m, 2H), 1.69-1.82 (m, 1H), 1.18-1.33 (m, 1H); MS (ESI) m/z 294.4 $[M+1]^+$.

C. (3R)-3-(Dibenzylamino)-1-methylcyclohexanol

To a clear colorless solution of (R)-3-(dibenzylamino) cyclohexanone (5.697 g, 19.42 mmol) in dry diethyl ether (300 mL) was added a solution of 3 M methylmagnesium bromide (8.09 mL, 24.27 mmol) dropwise slowly at 0° C. The reaction mixture was stirred at 0° C. for 15 min and the ice-bath was then removed. The reaction mixture was stirred at room temperature for 2 h. Upon completion of the reaction, as indicated by LCMS and TLC, the cloudy solution was slowly poured into a saturated aqueous solution of ammonium chloride (250 mL). The ether layer was separated, and the aqueous layer was re-extracted with ether (250 mL). The combined ether layers were dried over magnesium sulfate concentrated and purified by silica gel chromatography (0%-80% ethyl acetate in hexanes) to yield two diastereomeric isomers of (3R)-3-(dibenzylamino)-1-methylcyclohexanol (isomer 1 and isomer 2). Isomer 1 (2.704 g, 45%) was obtained as a white solid and isomer 2 (1.866 g, 31%) as a colorless oil, which still contained a small amount of impurities. Isomer 2 was used without further purification in the next step.

Isomer 1:

$^1$H NMR (400 MHz, DMSO-$d_6$) δ ppm 7.25-7.36 (m, 8H), 7.15-7.21 (m, 2H), 3.85 (s, 1H), 3.55 (s, 4H), 2.86 (tt, J=3.37, 12.06 Hz, 1H), 1.70-1.81 (m, 2H), 1.38-1.49 (m, 3H), 1.32 (t, J=12.30 Hz, 1H), 1.15-1.27 (m, 2H), 1.12 (s, 3H); MS (ESI) m/z 310.4 [M+1]$^+$.

Isomer 2:

MS (ESI) m/z 310.4 [M+1]$^+$.

D. (3R)-3-Amino-1-methylcyclohexanol

A solution of isomer 1 (2.704 g, 8.74 mmol) in ethanol (50 mL) was treated with palladium hydroxide on carbon and stirred under a balloon filled with hydrogen gas overnight. Upon completion of the reaction as indicated by LCMS and TLC the reaction mixture was filtered through a pad of celite and the filtrate was concentrated to yield one diastereomeric isomer of (3R)-3-amino-1-methylcyclohexanol (isomer 3, 0.856 g, 76%) as a thick yellow oil. Isomer 3: $^1$H NMR (400 MHz, DMSO-$d_6$) δ ppm 3.91 (br. s., 1H), 2.73-2.84 (m, 1H), 1.61-1.72 (m, 2H), 1.54 (tt, J=3.66, 13.13 Hz, 1H), 1.34-1.47 (m, 2H), 1.01-1.13 (m, 4H), 0.86-0.93 (m, 1H), 0.74-0.85 (m, 1H); MS (ESI) m/z 130.2 [M+1]$^+$.

The same procedure as described above using isomer 2 (1.823 g, 5.89 mmol) in ethanol (25 mL) was utilized to access another diastereomeric isomer of (3R)-3-amino-1-methylcyclohexanol (isomer 4, 0.162 g, 21%) containing a small amount of impurities. Isomer 4 was used without further purification in the next step.

E. 2-((1r,4r)-4-Methoxycyclohexylamino)-4-(methylsulfinyl)-pyrimidine-5-carboxamide To a stirred colorless solution of 2-((1r,4r)-4-methoxycyclohexylamino)-4-(methylthio)pyrimidine-5-carboxamide (0.250 g, 0.843 mmol; synthesis described herein) in NMP (2 mL) was added mCPBA (0.189 g, 0.843 mmol) at 0° C. portion wise. The reaction mixture was then stirred at room temperature for 2 h until completion of the reaction as indicated by LCMS. The reaction mixture was diluted with water (20 mL) and filtered. The filtrate was concentrated to afford 2-((1r,4r)-4-methoxycyclohexylamino)-4-(methylsulfinyl)pyrimidine-5-carboxamide (0.263 g, 100% yield) as a white sticky solid which was used in the next step without further purification. MS (ESI) m/z 313.1 [M+1]$^+$.

F. 4-((1R,3R)-3-Hydroxy-3-methylcyclohexylamino)-2-((1r,4R)-4-methoxycyclohexylamino) pyrimidine-5-carboxamide, 4-((1R,3S)-3-Hydroxy-3-methylcyclohexylamino)-2-((1r,4R)-4-methoxycyclohexylamino)pyrimidine-5-carboxamide To a solution of 2-((1r,4r)-4-methoxycyclohexylamino)-4-(methylsulfinyl)pyrimidine-5-carboxamide (0.263 g, 0.842 mmol) and DIEA (0.294 mL, 1.684 mmol) in NMP (3 mL) was added isomer 3 (0.163 g, 1.263 mmol) at room temperature. The reaction mixture was stirred for 2 h at 70° C. Upon completion of the reaction as indicated by LCMS and TLC the reaction mixture was concentrated and purified by silica gel chromatography (0%-20% ammonia saturated methanol in DCM). The product fractions were combined and concentrated to afford one diastereomeric isomer of 4-((1R)-3-hydroxy-3-methylcyclohexylamino)-2-((1r,4R)-4-methoxycyclo-hexylamino)pyrimidine-5-carboxamide (isomer 5, 0.265 g, 83% yield) as a white solid. Isomer 5: $^1$H NMR (400 MHz, DMSO-$d_6$) δ ppm 8.79 (d, J=7.42 Hz, 1H), 8.32 (s, 1H), 6.76-7.05 (m, 2H), 4.12-4.32 (m, 1H), 4.07 (s, 1H), 3.57-3.82 (m, 1H), 3.23 (s, 3H), 3.04-3.16 (m, 1H), 1.81-2.05 (m, 6H), 1.60-1.74 (m, 2H), 1.42-1.54 (m, 2H), 1.15-1.35 (m, 6H), 1.12 (s, 4H); MS (ESI) m/z 378.5 [M+1]$^+$.

The same procedure as described above using isomer 4 (0.163 g, 1.263 mmol), 2-((1r,4r)-4-methoxycyclohexylamino)-4-(methylsulfinyl)pyrimidine-5-carboxamide (0.263 g, 0.842 mmol) and DIEA (0.294 mL, 1.684 mmol) in NWP (3 mL) was utilized to access another diastereomeric isomer of 4-((1R)-3-hydroxy-3-methylcyclohexylamino)-2-((1r,4R)-4-methoxycyclohexylamino)pyrimidine-5-carboxamide (isomer 6, 0.043 g, 14% yield) as a white solid. Isomer 6: $^1$H NMR (400 MHz, DMSO-$d_6$) δ ppm 8.99 (d, J=4.69 Hz, 1H), 8.32 (s, 1H), 6.69-7.08 (m, 2H), 4.45 (s, 1H), 3.95-4.13 (m, 1H), 3.59-3.71 (m, 1H), 3.22 (s, 3H), 3.04-3.16 (m, 1H), 1.86-2.05 (m, 5H), 1.62-1.83 (m, 2H), 1.43-1.57 (m, 1H), 1.23-1.40 (m, 5H), 1.09-1.21 (m, 7H); MS (ESI) m/z 378.5 [M+1]$^+$.

The stereochemistry of the individual isomers could be determined after repeating the synthesis using (1S,3R)-3-amino-1-methylcyclohexanol (prepared as described herein), which provided isomer 6, namely 4-((1R,3S)-3-hydroxy-3-methylcyclohexylamino)-2-((1r,4R)-4-methoxycyclohexylamino)pyrimidine-5-carboxamide. Therefore, isomer 5 is 4-((1R,3R)-3-hydroxy-3-methylcyclohexylamino)-2-((1r,4R)-4-methoxycyclohexylamino)pyrimidine-5-carboxamide.

Example 11: 2-((1r,4R)-4-Acetamidocyclohexylamino)-4-((1R,3S)-3-hydroxycyclohexylamino)pyrimidine-5-carboxamide

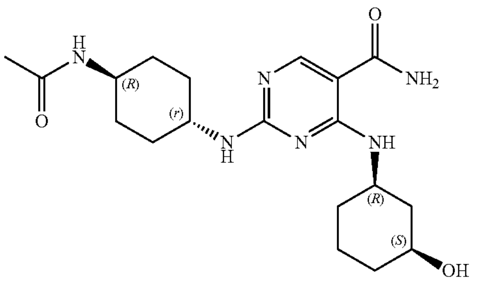

A. tert-Butyl (1r,4r)-4-acetamidocyclohexylcarbamate

To a stirring solution of tert-butyl (1r,4r)-4-aminocyclohexylcarbamate (1.0 g, 4.67 mmol) in ethyl acetate (30 mL) was added acetic anhydride (0.485 mL, 5.13 mmol) in one portion. The resulting mixture was allowed to stir overnight at room temperature. Additional acetic anhydride (0.162 mL, 1.71 mmol) was added to the mixture and the mixture was stirred for an additional hour at room temperature. The reaction mixture was then diluted with an additional 50 mL of ethyl acetate and was washed with 50 mL each of a saturated aqueous sodium bicarbonate solution and saturated aqueous sodium chloride solution. The aqueous layers were combined and extracted with 50 mL ethyl acetate. The combined ethyl acetate layers were dried over anhydrous magnesium sulfate, filtered, and concentrated to a afford tert-butyl (1r,4r)-4-acetamidocyclohexylcarbamate (1.04 g, 4.06 mmol, 87% yield) as a solid that was used without further purification. $^1$H NMR (400 MHz, DMSO-$d_6$) δ ppm 7.66-7.74 (m, 1H), 6.67-6.77 (m, 1H), 3.40 (d, J=7.42 Hz, 1H), 3.11-3.22 (m, 1H), 1.65-1.82 (m, 7H), 1.37 (s, 9H), 1.16 (d, J=8.20 Hz, 4H). MS (ESI) m/z 201.2 $[M-tBu]^+$.

B. N-((1r,4r)-4-Aminocyclohexyl)acetamide 2,2,2-trifluoroacetate

To a stirring solution of tert-butyl (1r,4r)-4-acetamidocyclohexylcarbamate (1.04 g, 4.06 mmol) in DCM (25 mL) was added TFA (25 mL) in one portion. The resulting mixture was allowed to stir at room temperature for 90 min. The reaction mixture was concentrated to dryness. The resulting oil was triturated with diethyl ether to afford solids that were filtered, rinsed with additional diethyl ether and then dried in vacuo to afford N-((1r,4r)-4-aminocyclohexyl) acetamide 2,2,2-trifluoroacetate (1.07 g, 3.96 mmol, 98% yield), which was used without further purification. $^1$H NMR (400 MHz, DMSO-$d_6$) δ ppm 7.82 (br. s., 3H), 3.42 (ddd, J=15.42, 7.61, 3.90 Hz, 1H), 2.89-3.04 (m, 1H), 1.87-1.95 (m, 2H), 1.78-1.85 (m, 2H), 1.77 (s, 3H), 1.29-1.42 (m, 2H), 1.11-1.25 (m, 2H). MS (ESI) m/z 157.0 $[M+1]^+$.

C. 2-((1r,4R)-4-acetamidocyclohexylamino)-4-((1R,3S)-3-hydroxycyclohexylamino)pyrimidine-5-carboxamide To a stirring solution of 4-((1R,3S)-3-hydroxycyclohexylamino)-2-(methylsulfonyl)pyrimidine-5-carboxamide (190 mg, 0.604 mmol; synthesis described herein) and N-((1r,4r)-4-aminocyclohexyl)-acetamide 2,2,2-trifluoroacetate (245 mg, 0.907 mmol) in DMSO (3 mL) was added DIEA (0.317 mL, 1.813 mmol). The resulting mixture was stirred at 100° C. overnight. The crude reaction mixture was concentrated and then purified by silica gel chromatography (0-15% methanol in DCM). The product fractions were combined and concentrated to afford 2-((1r,4R)-4-acetamidocyclohexylamino)-4-((1R,3S)-3-hydroxycyclohexylamino)pyrimidine-5-carboxamide (102 mg, 0.261 mmol, 43.2% yield) as a solid. $^1$H NMR (400 MHz, DMSO-$d_6$) δ ppm 8.29 (s, 1H), 7.69 (d, J=7.81 Hz, 1H), 4.60 (br. s., 1H), 3.36-3.62 (m, 2H), 2.00-2.17 (m, 1H), 1.60-1.97 (m, 10H), 0.93-1.35 (m, 10H). MS (ESI) m/z 391.2 $[M+1]^+$.

Example 12A: 4-((1R,3S)-3-Hydroxycycloheptylamino)-2-((1r,4R)-4-methoxycyclohexylamino)-pyrimidine-5-carboxamide, 4-((1R,3R)-3-Hydroxycycloheptylamino)-2-((1r,4R)-4-methoxycyclohexylamino)-pyrimidine-5-carboxamide, 4-((1S,3R)-3-Hydroxycycloheptylamino)-2-((1r,4S)-4-methoxycyclohexylamino)-pyrimidine-5-carboxamide, 4-((1S,3S)-3-Hydroxycycloheptylamino)-2-((1r,4S)-4-methoxycyclohexylamino)-pyrimidine-5-carboxamide

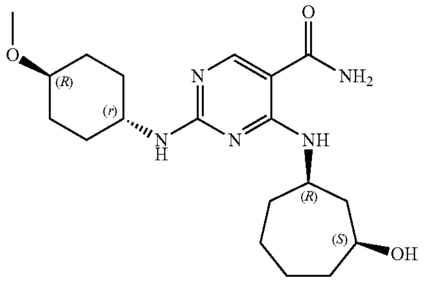

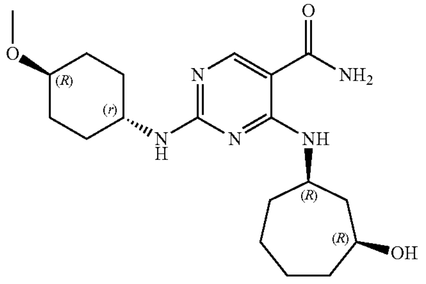

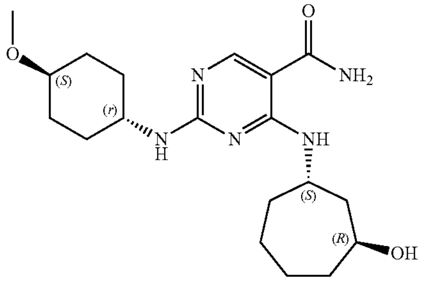

-continued

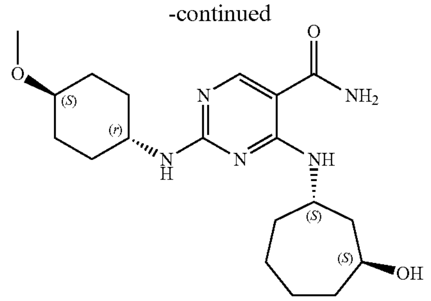

A. tert-Butyl 3-oxocycloheptylcarbamate

To a stirring mixture of cyclohept-2-enone (26.96 g, 245.0 mmol) and tert-butyl carbamate (28.7 g, 245 mmol) in DCM (245 mL) was added bismuth nitrate pentahydrate (22.79 g, 47.0 mmol). The resulting mixture was stirred at room temperature overnight. The reaction was diluted reaction with ethyl acetate (500 mL) and water (300 mL) and the biphasic mixture was filtered through a bed of Celite. The bed of Celite was washed well with ethyl acetate and water, and layers of the filtrate separated. The organic layer was concentrated to an oil that was purified by silica gel chromatography (0-40% ethyl acetate in hexanes). Product containing fractions were concentrated to afford the title compound (31.09 g, 137 mmol, 55.9% yield). $^1H$ NMR (400 MHz, DMSO-$d_6$) δ ppm 6.92 (d, J=7.03 Hz, 1H), 3.60 (d, J=8.59 Hz, 1H), 2.55-2.69 (m, 1H), 2.26-2.45 (m, 2H), 1.69-1.93 (m, 3H), 1.44-1.61 (m, 2H), 1.37 (d, J=5.08 Hz, 11H). MS (ESI) m/z 228.5 $[M+H]^+$.

B. tert-Butyl (1R,3S)-3-hydroxycycloheptylcarbamate, tert-butyl (1R,3R)-3-hydroxycycloheptylcarbamate, tert-butyl (1S,3S)-3-hydroxycycloheptylcarbamate, tert-butyl (1S,3R)-3-hydroxycycloheptylcarbamate To a solution of tert-butyl 3-oxocycloheptyl-carbamate (31.09 g, 137 mmol) in methanol (454 mL) was added sodium borohydride (15.52 g, 410 mmol) portion-wise over ~10 minutes with mixing. The resulting solution was stirred for 2 h at room temperature and then diluted with water (200 mL). The methanol was removed in-vacuo and the resulting aqueous mixture was diluted further with 500 mL ethyl acetate and 100 mL saturated aqueous sodium bicarbonate. The layers were separated and the aqueous layer back-extracted with 2×1000 mL ethyl acetate. The combined organic layers were dried over anhydrous magnesium sulfate, filtered and concentrated to an oil that was purified by silica gel chromatography (0-50% ethyl acetate in hexanes). Product containing fractions were concentrated to afford tert-butyl 3-hydroxycycloheptylcarbamate (21.1 g, 92 mmol, 67.3% yield). MS (ESI) m/z 230.3 $[M+H]^+$. The above two reactions were repeated starting with 9.52 g cyclohept-2-enone and yielding 9.27 g of tert-butyl 3-hydroxycycloheptylcarbamate. The two batches of tert-butyl 3-hydroxycycloheptylcarbamate were then combined. 29.2 g of the combined material was separated into the 4 constituent stereoisomers (two diastereomers and their corresponding enantiomers) by preparative chiral SFC utilizing multiple injections over a series of 3 separate columns. First column: ChiralPak IC-H, 250×30 mm I.D., isocratic 15% ethanol in $CO_2$, 38° C. Second column: ChiralCel OJ-H, 250×30 mm I.D., isocratic 10% isopropanol in $CO_2$, 38° C. Third column: ChiralPak AD-H, 250×50 mm I.D., isocratic 20% isopropanol in $CO_2$, 38° C. The separated isomers were characterized on an analytical scale Phenomenex Lux Amylose-2 column, 250×4.6 mm I.D., isocratic 15% ethanol in $CO_2$ (10 min run time) and labeled as Intermediate 1 to Intermediate 4.

Intermediate 1:

5.4 g (23.55 mmol, 18.5% yield from SFC purification). Retention time: 4.065 minutes.

Intermediate 2:

5.5 g (23.98 mmol, 18.8% yield from SFC purification). Retention time: 3.019 minutes.

Intermediate 3:

7.2 g (31.34 mmol, 24.6% yield from SFC purification). Retention time: 3.675 minutes.

Intermediate 4:

4.7 g (20.50 mmol, 16.1% yield from SFC purification). Retention time: 3.263 minutes.

C. (1S,3R)-3-Aminocycloheptanol, (1R,3R)-3-aminocycloheptanol, (1S,3S)-3-aminocycloheptanol, (1R,3S)-3-aminocycloheptanol 75 mg (0.327 mmol) of each of the materials corresponding to Intermediate 1 through Intermediate 4 from step B was separately dissolved in DCM (11.25 mL) and TFA (3.75 mL). Each reaction was allowed to stir overnight at ambient temperature. The solvent of each reaction was removed in vacuo and each was then dissolved in a mixture of 4N hydrochloric acid in dioxane (5 mL) and methanol (5 mL). Each reaction was mixed overnight at ambient temperature. Each of the 4 reaction mixtures (each containing an individual 3-aminocycloheptanol isomer) was concentrated under reduce pressure and used without further purification. MS (ESI) m/z 130.2 $[M+H]^+$ for each. The nomenclature of Intermediate 1 to Intermediate 4 was maintained for tracking purposes.

D. 4-((1R,3S)-3-Hydroxycycloheptylamino)-2-((1r,4R)-4-methoxycyclohexyl-amino)pyrimidine-5-carboxamide, 4-((1R,3R)-3-hydroxycycloheptylamino)-2-((1r,4R)-4-methoxycyclohexylamino)pyrimidine-5-carboxamide, 4-((1S,3R)-3-hydroxycycloheptylamino)-2-((1r,4R)-4-methoxycyclohexylamino) pyrimidine-5-carboxamide, 4-((1S,3S)-3-hydroxycycloheptylamino)-2-((1r,4R)-4-methoxycyclohexylamino)pyrimidine-5-carboxamide To each of the concentrates (Intermediate 1 to Intermediate 4) from step C was added 2-((1r,4r)-4-methoxycyclohexylamino)-4-(methylsulfonyl)pyrimidine-5-carboxamide (53.7 mg, 0.1635 mmol), NMP (2 mL), and DIEA (0.286 mL, 1.635 mmol). The resulting 4 mixtures were stirred at 80° C. overnight. The reaction solutions were condensed separately under reduced pressure and the products purified by reverse-phase preparative HPLC (5-80% acetonitrile+0.1% trifluoroacetic acid in water+0.1% trifluoroacetic acid, over 30 min). Fractions containing product were concentrated under reduced pressure. The resulting residues were separately redissolved in a methanol (5 mL), passed over an Varian StratoSpheres HCO3 resin SPE tube for TFA removal (0.9 mmol bicarbonate equiv.), and then concentrated under reduced pressure to afford the title compounds as Peak 1 to Peak 4. The separate isomers (Peak 1 to Peak 4) were characterized on an analytical scale ChiralPak AD-H column, 250×4.6 mm I.D., isocratic 40% methanol+0.1% diethylamine in $CO_2$ (10 minute run time).

PEAK 1:

10.3 mg (0.027 mmol); $^1$H NMR (400 MHz, DMSO-$d_6$) δ ppm 9.02 (d, J=6.64 Hz, 1H), 8.33 (s, 1H), 7.04 (d, J=7.42 Hz, 1H), 4.44 (br. s., 1H), 4.19 (br. s., 1H), 3.56-3.90 (m, 2H), 3.23 (s, 3H), 3.09 (br. s., 1H), 1.04-2.11 (m, 18H). MS (ESI) m/z 378.3 $[M+H]^+$. Retention time: 2.534 minutes.

PEAK 2:

30.0 mg (0.079 mmol); $^1$H NMR (400 MHz, DMSO-$d_6$) δ ppm 8.95 (d, J=6.25 Hz, 1H), 8.33 (s, 1H), 7.06 (d, J=7.03 Hz, 1H), 4.46 (d, J=3.12 Hz, 1H), 3.86-4.18 (m, 1H), 3.48-3.81 (m, 2H), 3.23 (s, 3H), 3.09 (br. s., 1H), 1.06-2.16 (m, 18H). MS (ESI) m/z 378.5 $[M+H]^+$. Retention time: 3.848 minutes.

PEAK 3:

22.0 mg (0.058 mmol); $^1$H NMR (400 MHz, DMSO-$d_6$) δ ppm 9.02 (d, J=7.03 Hz, 1H), 8.33 (s, 1H), 7.04 (d, J=7.03 Hz, 1H), 4.45 (d, J=3.12 Hz, 1H), 4.20 (br. s., 1H), 3.56-3.91 (m, 2H), 3.23 (s, 3H), 3.09 (br. s., 1H), 1.06-2.12 (m, 18H). MS (ESI) m/z 378.5 $[M+H]^+$. Retention time: 4.557 minutes.

PEAK 4:

22.5 mg (0.060 mmol); $^1$H NMR (400 MHz, DMSO-$d_6$) δ ppm 8.95 (d, J=6.64 Hz, 1H), 8.33 (s, 1H), 6.47-7.21 (m, 1H), 4.46 (d, J=3.12 Hz, 1H), 3.94 (br. s., 1H), 3.73 (br. s., 2H), 3.23 (s, 3H), 3.09 (br. s., 1H), 1.04-2.18 (m, 18H). MS (ESI) m/z 378.3 $[M+H]^+$. Retention time: 2.607 minutes.

From the chemical shift of the proton at ~4.2 ppm in Peak 1 and Peak 3 versus that of ~3.94 ppm in Peaks 2 and 4 and also of the proton at ~9.02 ppm in Peak 1 and Peak 3 versus that of ~8.95 ppm in Peaks 2 and 4 in the 1H NMR data given above, the following assignment was made: Peak 1 and Peak 3 are enantiomers. Peak 2 and Peak 4 are enantiomers.

Alternatively, a chiral synthetic route was used, described below.

Example 12B: 4-((1R,3S)-3-hydroxycycloheptylamino)-2-((1r,4R)-4-methoxycyclohexylamino)pyrimidine-5-carboxamide

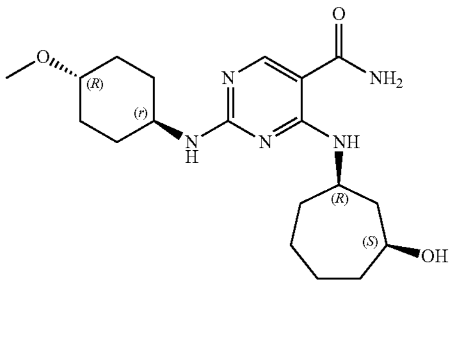

A. Cyclohept-2-enol

To a solution of cyclohept-2-enone (10 g, 91 mmol) and cerium(III) chloride heptahydrate (33.8 g, 91 mmol) in methanol (45.5 mL) was added sodium borohydride (3.43 g, 91 mmol) portion-wise over 10 minutes period with cooling in a water bath. The reaction mixture was then stirred for 2.5 hr at room temperature. The reaction was quenched by addition of water (45 mL) and then was extracted with pentane (4×100 mL). The combined organic extracts were dried over anhydrous magnesium sulfate, filtered, and concentrated under reduced pressure to afford the title compound (8.30 g, 74.0 mmol, 82% yield) as an oil that was used without further purification. $^1$H NMR (400 MHz, DMSO-$d_6$) δ ppm 5.49-5.71 (m, 2H), 4.66 (d, J=4.29 Hz, 1H), 4.05-4.20 (m, 1H), 1.07-2.14 (m, 8H).

B. Cyclohept-2-enyl methyl carbonate

To a solution of cyclohept-2-enol (8.3 g, 74.0 mmol) in DCM (227 ml) and pyridine (35.9 ml, 444 mmol), was added methyl chloroformate (14.24 ml, 185 mmol) with cooling in an ice bath at such a rate that T<10° C. Once addition was complete, the reaction was allowed to mix and warm to ambient temperature overnight. The reaction mixture was washed with 2×150 mL 1N aqueous hydrochloric acid. The combined washes were back-extracted with 100 mL DCM. The combined DCM layers were then washed with 150 mL of an aqueous saturated sodium bicarbonate solution, dried over anhydrous magnesium sulfate, filtered, and concentrated under reduced pressure to afford the title compound (11.95 g, 70.2 mmol, 95% yield) as an oil that was used without further purification. $^1$H NMR (400 MHz, DMSO-$d_6$) δ ppm 5.83 (dddd, J=11.81, 7.03, 5.17, 2.15 Hz, 1H), 5.65 (d, J=11.71 Hz, 1H), 5.17 (d, J=6.64 Hz, 1H), 4.71 (d, J=4.30 Hz, 1H), 3.69 (s, 2H), 1.99-2.23 (m, 2H), 1.79-1.94 (m, 2H), 1.56-1.72 (m, 3H), 1.34 (d, J=3.51 Hz, 1H).

C. (R)-2-(Cyclohept-2-enyl)isoindoline-1,3-dione

Phthalimide potassium salt (19.59 g, 106 mmol), allylpalladium chloride dimer (0.477 g, 1.322 mmol), (1S,2S)-(−)-1,2-diaminocyclohexane-N,N'-bis(2'-diphenylphosphinobenzoyl) (2.74 g, 3.97 mmol), tetrahexylammonium bromide (50.6 g, 116 mmol), and DCM (212 mL) were combined in a round-bottomed flask. The flask was flushed with nitrogen and then placed in a sonication bath for 10 minutes. Cyclohept-2-enyl methyl carbonate (9.00 g, 52.9 mmol) was then added to the flask in one portion and the resulting mixture was stirred under a nitrogen atmosphere at ambient temperature overnight. The reaction was quenched by addition of 50 mL water and was then extracted with 3×100 mL diethyl ether. The combined organic layers were dried over anhydrous magnesium sulfate, filtered, and concentrated to an oil that slowly solidified overnight. The solids were triturated with methanol (50 mL) and filtered to afford 7.6 g of crude product. The crude solid product was recrystallized from methanol and dried in vacuo to afford the title compound (6.70 g, 27.8 mmol, 52.5% yield) as a solid that was determined to have an % e.e. of 97.2 (the S isomer was analogously prepared as a standard using the (1R,2R)-(−)-1,2-diaminocyclohexane-N,N'-bis(2'-diphenylphosphinobenzoyl) ligand) by analytical chiral SFC chromatography (Phenomenex Lux Cellulose-4, 250×4.6 mm I.D., 5-50% isopropanol in $CO_2$, 13 minute gradient). $^1$H NMR (400 MHz, DMSO-$d_6$) δ ppm 7.41-8.22 (m, 4H), 5.62-5.97 (m, 2H), 4.77 (d, J=11.32 Hz, 1H), 2.01-2.29 (m, 3H), 1.87-2.00 (m, 1H), 1.62-1.78 (m, 2H), 1.45-1.61 (m, 1H), 1.17-1.32 (m, 1H). MS (ESI) m/z 242.3 $[M+1]^+$.

D. 2-((1R,2S,3S)-2-Bromo-3-hydroxycycloheptyl)isoindoline-1,3-dione

To a solution of (R)-2-(Cyclohept-2-enyl)isoindoline-1,3-dione (4.00 g, 16.58 mmol) in chloroform (40.0 ml) and ethanol (1.400 mL) was added N-bromosuccinimide (3.78 g, 21.22 mmol) as a solid over 5 minutes at room temperature.

After addition was complete, the reaction mixture was stirred at room temperature overnight under a nitrogen atmosphere. An additional portion of N-bromosuccinimide (1.9 g) and 1.4 mL of ethanol were then added and the mixture was allowed to continue to mix at room temperature overnight under a nitrogen atmosphere. A third portion of N-bromosuccinimide (1.0 g) and 1.4 mL additional ethanol were added to the mixture and it was again mixed at room temperature for a third night under a nitrogen atmosphere. The reaction mixture was then concentrated to dryness. The resulting residue was triturated with 25 mL fresh chloroform. The solids were filtered, rinsed with chloroform, and the filtrate concentrated under reduced pressure to dryness. THF (40 mL) and 1N hydrochloric acid (aq.) (10 mL) were added to the concentrated filtrate and the resulting mixture was stirred at room temperature for 90 minutes. The solution was concentrated under reduced pressure to remove THF. The concentrate was diluted with 125 mL ethyl acetate and 75 mL of a 1:1 mixture of water:saturated aqueous sodium bicarbonate. The layers were separated and the aqueous was back extracted with 75 mL ethyl acetate. The combined ethyl acetate layers were washed with brine, dried over anhydrous magnesium sulfate, filtered and concentrated under reduced pressure to afford an oil that was purified by silica gel chromatography (0-30% ethyl acetate in hexanes). Fractions containing the desired product were concentrated under reduced pressure to the title compound (3.9 g, 11.53 mmol, 69.6% yield) as a solid. $^1H$ NMR (400 MHz, DMSO-$d_6$) δ ppm 7.88 (d, J=7.42 Hz, 4H), 5.48 (d, J=5.47 Hz, 1H), 4.73 (dd, J=10.54, 6.25 Hz, 1H), 4.24-4.38 (m, 1H), 3.91-3.99 (m, 1H), 2.32 (br. s., 1H), 1.67-1.96 (m, 5H), 1.40-1.60 (m, 2H). MS (ESI) m/z 320.1 $[M-18]^+$. A COSY NMR experiment and the $^1H$ NMR data reported above were used to verify the bromohydrin regiochemistry. An NOE (via NOESY experiment) was observed between the protons on the amino group carbon and the hydroxyl group carbon. This verifies a cis relationship between these two functional groups (a trans relationship, lacking this spacial proximity, would not show such an effect).

E. 2-((1R,3S)-3-Hydroxycycloheptyl)isoindoline-1,3-dione

To a solution of 2-((1R,2S,3S)-2-bromo-3-hydroxycycloheptyl)isoindoline-1,3-dione (4.2 g, 12.42 mmol) in toluene (69 mL) and methanol (6.9 mL) was added tributyltin hydride (4.34 mL, 16.14 mmol) via syringe over 10 minutes under nitrogen followed by 2,2'-azobis(2-methylpropanenitrile) (0.204 g, 1.242 mmol) in one portion. The reaction was then heated to reflux overnight under a nitrogen atmosphere. The reaction mixture was concentrated to dryness under reduced pressure to afford a residue that was purified by silica gel chromatography (0-50% ethyl acetate in hexanes). Fractions containing the desired product were concentrated under reduced pressure to afford the title compound (2.6 g, 10.03 mmol, 81% yield) as a solid. $^1H$ NMR (400 MHz, DMSO-$d_6$) δ ppm 7.72-7.98 (m, 4H), 4.58 (d, J=4.29 Hz, 1H), 4.14 (br. s., 1H), 3.67 (dt, J=6.25, 3.90 Hz, 1H), 2.24-2.40 (m, 1H), 2.04-2.19 (m, 1H), 1.81-1.95 (m, 2H), 1.39-1.80 (m, 6H). MS (ESI) m/z 259.9 $[M+H]^+$.

E. (1S,3R)-3-Aminocycloheptanol 2-((1R,3S)-3-Hydroxycycloheptyl)-isoindoline-1,3-dione (1800 mg, 6.94 mmol) was dissolved in methanol (86.80 mL). Hydrazine monohydrate (0.354 mL, 7.29 mmol) was added to the solution and the resulting mixture was stirred overnight at reflux. An additional 0.2 eq (0.067 mL) of hydrazine was added and the mixture was refluxed for a second night. The reaction mixture was concentrated to a volume of a few milliliters and filtered. The solids were rinsed with 50 mL each of DCM and chloroform and the resulting filtrate concentrated under reduced pressure to afford the title compound (174 mg, 1.347 mmol, 19.40% yield) as an oil that was used without further purification. MS (ESI) m/z 130.2 $[M+H]^-$.

F. 4-((1R,3S)-3-Hydroxycycloheptylamino)-2-((1r,4R)-4-methoxycyclohexyl-amino)pyrimidine-5-carboxamide (1S,3R)-3-Aminocycloheptanol (87 mg, 0.672 mmol) and DIEA (0.235 mL, 1.344 mmol) were added to a solution of 2-((1r,4r)-4-methoxycyclohexyl-amino)-4-(methylsulfinyl)pyrimidine-5-carboxamide (105 mg, 0.336 mmol) in NMP (1 mL). The resulting mixture was heated to 80° C. for 4 h and then allowed to cool to ambient temperature overnight. The reaction mixture was condensed under reduced pressure and the residue purified by reverse-phase preparative HPLC (5-80% acetonitrile+0.1% TFA in water+0.1% TFA, over 30 min). Fractions containing product were concentrated under reduced pressure. The resulting residue was re-dissolved in a methanol (5 mL), passed over a Varian StratoSpheres HCO3 resin SPE tube for TFA removal (0.9 mmol bicarbonate equiv.), and then concentrated under reduced pressure. The residue was triturated with acetonitrile and concentrated under reduced pressure to afford the title compound (67 mg, 0.177 mmol, 52.8% yield) as a solid. $^1H$ NMR (400 MHz, DMSO-$d_6$) δ ppm 8.96 (d, J=5.86 Hz, 1H), 8.33 (s, 1H), 7.00-7.16 (m, 1H), 4.46 (d, J=3.90 Hz, 1H), 3.85-4.09 (m, 1H), 3.56-3.81 (m, 2H), 3.23 (s, 3H), 2.97-3.15 (m, 1H), 1.71-2.14 (m, 7H), 1.51 (d, J=10.15 Hz, 11H). MS (ESI) m/z 378.3 $[M+H]^+$.

Analytical chiral SFC using a ChiralPak AD-H column (250×4.6 mm I.D., isocratic 40% methanol+0.1% diethylamine in $CO_2$, 10 minute run time) was used to establish the relationship between the single isomer afforded in this chiral route with that of the previous preparation of all four stereoisomers. The material prepared in this chiral route was found to have an identical retention time (3.848 minutes) as Peak 2 in Example 12A thus:

PEAK 2=4-((1R,3S)-3-hydroxycycloheptylamino)-2-((1r,4R)-4-methoxycyclohexylamino)pyrimidine-5-carboxamide.

Based on $^1H$ NMR, Peak 2 and Peak 4 were found to be an enantiomeric pair in Example 12A, thus:

PEAK 4=4-((1S,3R)-3-hydroxycycloheptylamino)-2-((1r,4R)-4-methoxycyclohexylamino)pyrimidine-5-carboxamide.

In addition, it follows that Intermediate 2 used to make Peak 2 in Example 12A can then be assigned as tert-Butyl (1R,3S)-3-hydroxycycloheptylcarbamate and Intermediate 4 used to make Peak 4 in Example 12A can then be assigned as tert-Butyl (1S,3R)-3-hydroxycycloheptylcarbamate.

In order to identify the absolute stereochemistry of Intermediate 1 and Intermediate 3 (and thereby the absolute stereochemistry of Peak 1 and Peak 3) in Example 12A the following experiment was performed.

Mitsunobu Reaction of tert-butyl (1R,3R)-3-hydroxycycloheptyl-carbamate to afford tert-butyl (1R,3S)-3-hydroxycycloheptylcarbamate

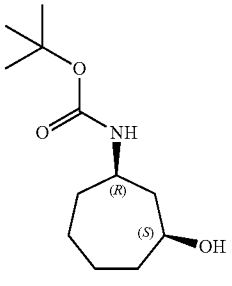

A. tert-Butyl (1R,3S)-3-hydroxycycloheptylcarbamate

Intermediate 3 from step B in Example 12A, was dissolved in THF (31.700 mL). The mixture was cooled to 0° C. in an ice bath under a nitrogen atmosphere and chloroacetic acid (261 mg, 2.76 mmol) followed by triphenylphosphine (723 mg, 2.76 mmol) were both added in one portion. A diethyl azodicarboxylate solution (0.437 mL, 2.76 mmol) was added drop-wise waiting until the disappearance of the yellow color before adding the next drop. Once addition was complete, the solution was stirred at 0° C. under a nitrogen atmosphere for 3 h. The reaction was concentrated under reduced pressure and the resulting oil purified by silica gel chromatography (0-40% ethyl acetate in hexanes). Pure product containing fractions were combined and concentrated under reduced pressure and then redissolved in methanol (16 mL). Sodium carbonate (186 mg, 1.755 mmol) was added to the solution and the resulting mixture was stirred at ambient temperature for 3 h. The reaction mixture was concentrated under reduced pressure to dryness. The residue was diluted with 50 mL of a 1:1 mixture of water:saturated aqueous sodium bicarbonate and 75 mL DCM. The layers were separated and the aqueous back extracted with 50 mL DCM. The combined DCM layers were dried over anhydrous magnesium sulfate, filtered, and concentrated under reduced pressure to afford a material that had an identical retention time by analytical SFC as Intermediate 2 from step B in Example 12A, or tert-butyl (1R,3S)-3-hydroxycycloheptylcarbamate (417 mg, 1.818 mmol, 72.5% yield) as a solid.

$^1H$ NMR (400 MHz, DMSO-$d_6$) δ ppm 6.63-6.87 (m, 1H), 4.44 (d, J=3.90 Hz, 1H), 3.47-3.71 (m, 1H), 0.99-1.98 (m, 19H). MS (ESI) m/z 260.1 $[M+1]^+$.

Intermediate 3 from step B in Example 12A is therefore assigned as tert-butyl (1R,3R)-3-hydroxycycloheptylcarbamate. Peak 3 from step D derived from Intermediate 3 in Example 12A is therefore assigned as 4-((1R,3R)-3-hydroxycycloheptylamino)-2-((1r,4R)-4-methoxycyclohexylamino)pyrimidine-5-carboxamide.

Because Peak 1 and Peak 3 are enantiomers by 1H NMR as described in Example 12A Peak 1 can be assigned as 4-((1S,3S)-3-Hydroxycycloheptylamino)-2-((1r,4S)-4-methoxycyclohexylamino)pyrimidine-5-carboxamide. It follows that Intermediate 1 from step B in Example 12A that was used to prepare Peak 1 in step D of Example 12A can be assigned as tert-butyl (1S,3S)-3-hydroxycycloheptylcarbamate.

Example 13: 4-((1R,3S)-3-Hydroxycyclohexylamino)-2-((1r,4R)-4-(2,2,2-trifluoroethoxy) cyclohexylamino)pyrimidine-5-carboxamide, 4-((1R,3S)-3-Hydroxycyclohexylamino)-2-((1s,4S)-4-(2,2,2-trifluoroethoxy)-cyclohexylamino)pyrimidine-5-carboxamide

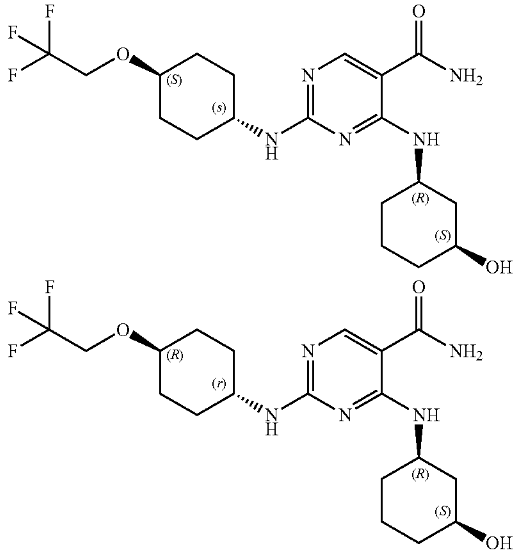

A. 4-((1R,3S)-3-Hydroxycyclohexylamino)-2-((1r,4R)-4-(2,2,2-trifluoro-ethoxy)cyclohexylamino)pyrimidine-5-carboxamide and 4-((1R,3S)-3-hydroxy-cyclo-hexylamino)-2-((1s,4S)-4-(2,2,2-trifluoroethoxy)cyclohexylamino)-pyrimidine-5-carboxamide To a stirring solution of 4-((1R,3S)-3-hydroxycyclohexylamino)-2-(methylsulfonyl)pyrimidine-5-carboxamide (440 mg, 1.400 mmol; synthesis described herein) and bis-4-(2,2,2-trifluoroethoxy)-cyclohexanamine trihydrochloride (529 mg, 2.099 mmol) in DMSO (6.964 mL) was added DIEA (0.978 mL, 5.60 mmol). The resulting mixture was allowed to stir overnight at 100° C. The crude reaction mixture was concentrated, purified by silica gel chromatography (0-10% methanol/dichloromethane), and then purified by reversed-phase silica gel chromatography (methanol/water with 0.1% formic acid modifier). The product containing fractions were neutralized and concentrated to afford 4-((1R,3S)-3-hydroxycyclohexylamino)-2-(4-(2,2,2-trifluoroethoxy)cyclohexyl-amino)pyrimidine-5-carboxamide (135 mg, 0.313 mmol, 22.36% yield) as a mixture of 2 stereoisomers. MS (ESI) m/z 432.2 $[M+H]^+$. This mixture was separated using chiral super-fluid chromatography (AD-H column) to afford 87.8 mg (0.203 mmol) of a single, faster eluting, stereoisomer (PEAK 1) and 24.2 mg (0.056 mmol) of a second single, slower eluting, stereoisomer (PEAK 2).

Subsequently the same reaction sequence was repeated using (1r,4r)-4-(2,2,2-trifluoroethoxy)cyclohexanamine, which was prepared as follows.

(1r,4r)-4-(Benzylamino)cyclohexanol

A mixture of (1r,4r)-4-amino-cyclohexanol (230 g, 2 mol), benzaldehyde (212 g, 2 mol) and 4 Å Molecular Sieves in methanol (2 L) was refluxed under a nitrogen atmosphere for 3 h. The mixture was cooled using an ice-water bath, and sodium borohydride (72 g, 2 mol) was carefully added in small portions. After the completion of the addition, the reaction was stirred at room temperature overnight. The solvent was evaporated, and the residue was partitioned between dichloromethane (2 L) and water (1 L). The dichloromethane layer was separated, washed with a saturated aqueous sodium chloride solution, and directly used in the next step.

Benzyl benzyl((1r,4r)-4-hydroxycyclohexyl)carbamate

To the dichloromethane solution of (1r,4r)-4-(benzylamino)cyclohexanol obtained in the previous step was added saturated aqueous sodium bicarbonate (1.5 L), and to this biphasic system was added benzyl chlorofomate (358.2 g, 2.1 mol) slowly at 0° C. After completion of addition, the reaction was stirred at room temperature for another 1 h. Then the organic phase was separated and evaporated. After concentration, the residue was purified by silica gel chromatography (0-30% ethyl acetate in hexanes) to give the title compound as a colorless liquid (400 g, 1.18 mol, 59% yield for two steps). Both steps were repeated, to afford a total of 800 g of benzyl benzyl((1r,4r)-4-hydroxycyclohexyl)carbamate.

Benzyl benzyl((1r,4r)-4-(2,2,2-trifluoroethoxy)cyclohexyl)carbamate

To a solution of benzyl benzyl((1r,4r)-4-hydroxycyclohexyl)carbamate (400 g, 1.18 mol) in chloroform (2 L) was added a 50% aqueous solution of fluoroboric acid (20 mL), and a stream of diazotrifluoroethane (freshly prepared by mixing trifluoroethaneamine hydrochloride (1.6 kg, 11.8 mol) and $NaNO_2$ (814 g, 11.8 mol) in water (3 L) and then bubbling it into the reaction solution above). The reaction was monitored by TLC, and after completion, a saturated aqueous solution of potassium carbonate (300 mL) was added. The chloroform layer was separated, concentrated under reduced pressure, and purified by column chromatography (0-10% ethyl acetate in hexanes) to afford benzyl benzyl ((1r,4r)-4-(2,2,2-trifluoroethoxy)cyclohexyl)carbamate (192 g, 0.456 mol, 38% yield). This reaction was repeated, and another batch of benzyl benzyl ((1r,4r)-4-(2,2,2-trifluoroethoxy)cyclohexyl)carbamate (185 g, 0.439 mol) was obtained.

(1r,4r)-4-(2,2,2-Trifluoroethoxy)cyclohexanamine

To a solution of benzyl benzyl((1r,4r)-4-(2,2,2-trifluoroethoxy)cyclohexyl)carbamate (377 g, 0.89 mol) in ethyl acetate (2 L) was added 20% palladium hydroxide on carbon (50 g), and the mixture was stirred under a 55 psi hydrogen atmosphere for 24 h at room temperature. The catalyst was removed by filtration, and the filtrate was concentrated under reduced pressure. The resulting residue was dissolved in 2N hydrochloric acid (1.5 L) and the solution was washed with methyl t-butyl ether (300 mL×5). Solid potassium carbonate was added to adjust the pH to above 10. The product was extracted into dichloromethane (500 mL×5). The combined organic phases were dried and concentrated under reduced pressure. The residue was purified by silica gel chromatography (10-30% methanol in dichloromethane) to afford (1r,4r)-4-(2,2,2-trifluoroethoxy)cyclohexanamine (115 g, 0.584 mol, 66% yield):

$^1$H NMR (400 MHz, DMSO-$d_6$) δ ppm 4.01 (q, J=8.8 Hz, 2H), 3.40-3.33 (m, 1H), 2.56-2.53 (m, 1H), 1.94-1.92 (m, 2H), 1.75-1.72 (m, 2H), 1.24-1.15 (m, 2H), 1.08-0.97 (m, 2H); MS (ESI) m/z 198.2 [M+1]+.

Using the intermediate above, it was shown that the material obtained as PEAK 1 corresponded to 4-((1R,3S)-3-hydroxycyclohexylamino)-2-((1r,4R)-4-(2,2,2-trifluoroethoxy)cyclohexylamino)pyrimidine-5-carboxamide, while the material obtained as PEAK 2 corresponded to 4-((1R,3S)-3-hydroxycyclohexylamino)-2-((1s,4S)-4-(2,2,2-trifluoroethoxy)cyclohexylamino)pyrimidine-5-carboxamide.

PEAK 1: 4-((1R,3S)-3-hydroxycyclohexylamino)-2-((1r,4R)-4-(2,2,2-trifluoroethoxy)cyclohexylamino)pyrimidine-5-carboxamide $^1$H NMR (400 MHz, DMSO-$d_6$) δ ppm 8.90 (d, J=6.25 Hz, 1H), 8.34 (s, 1H), 7.46-7.52 (m, 1H), 7.07-7.17 (m, 1H), 6.91 (dd, J=8.59, 2.73 Hz, 1H), 4.60-4.76 (m, 1H), 4.02 (q, J=9.63 Hz, 2H), 3.39-3.96 (m, 4H), 0.92-2.24 (m, 16H). $^{19}$F NMR (376 MHz, DMSO-$d_6$) δ ppm −76.47-72.01 (m, 3F). MS (ESI) m/z 432.0 $[M+H]^+$.

PEAK 2: 4-((1R,3S)-3-hydroxycyclohexylamino)-2-((1s,4S)-4-(2,2,2-trifluoroethoxy)cyclohexylamino)pyrimidine-5-carboxamide $^1$H NMR (400 MHz, DMSO-$d_6$) δ ppm 8.90 (d, J=6.64 Hz, 1H), 8.34 (br. s., 1H), 6.79-7.50 (m, 2H), 4.64 (br. s., 1H), 4.00-4.12 (m, 2H), 3.42 (d, J=4.69 Hz, 4H), 0.91-2.25 (m, 16H). $^{19}$F NMR (376 MHz, DMSO-$d_6$) δ ppm −73.63 (t, J=9.47 Hz, 3F). MS (ESI) m/z 432.0 $[M+H]^+$.

Example 14: 2-((1r,4R)-4-(Difluoromethoxy)cyclohexylamino)-4-((1R,3S)-3-hydroxycyclohexylamino)pyrimidine-5-carboxamide

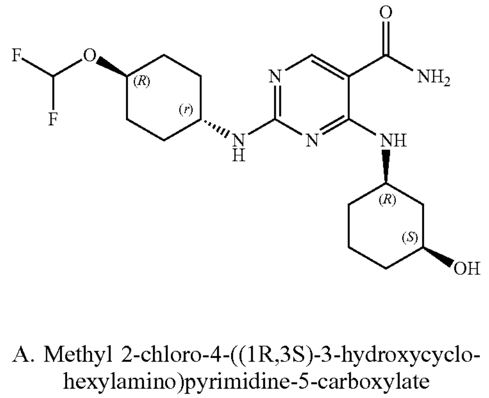

A. Methyl 2-chloro-4-((1R,3S)-3-hydroxycyclohexylamino)pyrimidine-5-carboxylate

To a stirring solution of methyl 2,4-dichloropyrimidine-5-carboxylate (4.00 g, 19.32 mmol) in THF (85 mL) was added DIEA (3.37 mL, 19.32 mmol). The resulting mixture was cooled to −78° C. in a dry ice/acetone bath. A solution of (1S,3R)-3-aminocyclohexanol (2.448 g, 21.25 mmol; prepared as described in *Tetrahedron: Asymmetry* 15:2051-2056 (2004)) in 40 mL THF was added at such a rate that the temperature remained at −78° C. The resulting mixture was stirred at −78° C. for 1 h. The reaction mixture was then concentrated to dryness and diluted with 200 mL ethyl acetate and 75 mL of a 1:1 mixture of water and an aqueous saturated sodium bicarbonate solution. The layers were separated and the aqueous layer back-extracted with 100 mL ethyl acetate. The combined ethyl acetate layers were washed with 50 mL of a saturated aqueous sodium chloride solution, dried over anhydrous magnesium sulfate, filtered and concentrated to an oil that solidified upon standing. The solid was triturated with diethyl ether (5 mL), filtered, rinsed with diethyl ether (5 mL) and dried in vacuo to afford methyl 2-chloro-4-((1R,3S)-3-hydroxycyclohexylamino)pyrimidine-5-carboxylate (3.7 g, 12.95 mmol, 67% yield) that was used without further purification. MS (ESI) m/z 286.0 $[M+1]^+$.

B. (1r,4r)-4-(Dibenzylamino)cyclohexanol trans-4-Aminocyclohexanol hydrochloride (25 g, 217 mmol) was suspended in acetonitrile (500 mL). Benzyl bromide (54.2 mL, 456 mmol) and potassium carbonate (120 g, 868 mmol) were added to the suspension and the resulting mixture was stirred vigorously overnight at room temperature. The reaction mixture was filtered through a plug of celite and the plug was washed thoroughly with acetonitrile. The filtrate was condensed to give a white solid. The crude solids were purified by silica gel chromatography (0-60% ethyl acetate in hexanes). Pure product containing fractions were combined and concentrated to afford (1r,4r)-4-(dibenzylamino)cyclohexanol (25 g, 85 mmol, 39.0% yield) as a white solid. $^1$H NMR (400 MHz, DMSO-$d_6$) δ ppm 7.26-7.36 (m, 8H), 7.16-7.22 (m, 2H), 4.43 (d, J=4.69 Hz, 1H), 3.55 (s, 4H), 3.27-3.33 (m, 1H), 2.28-2.40 (m, 1H), 1.69-1.88 (m, 4H), 1.40 (qd, J=12.56, 2.93 Hz, 2H), 0.89-1.05 (m, 2H); MS (ESI) m/z 296.3 $[M+1]^+$.

C. (1r,4r)-N,N-Dibenzyl-4-(difluoromethoxy)cyclohexanamine (1r,4r)-4-(Dibenzylamino)cyclohexanol (5 g, 16.93 mmol) and copper(I) iodide (0.645 g, 3.39 mmol) were dissolved in 170 mL acetonitrile and heated to 45° C. under a nitrogen atmosphere. To this mixture was added a solution of 2,2-difluoro-2-(fluorosulfonyl)acetic acid (3.50 mL, 33.9 mmol) in 30 mL acetontrile over 10 min. Once addition was complete, the mixture was stirred at 45° C. under nitrogen atmosphere for 1 h. An additional portion of 2,2-difluoro-2-(fluorosulfonyl)acetic acid (2.86 mL, 27.7 mmol) reagent in 30 mL acetonitirile was then added over 10 min. The reaction mixture was stirred for an additional 1 h at 45° C. under nitrogen atmosphere. Volatile components were then removed via evaporation and the residue was diluted with 175 mL ethyl acetate and 75 mL of a 1:1 mixture of water and saturated aqueous sodium bicarbonate. The resulting biphasic mixture containing solids was filtered through a sintered glass Buchner funnel. The filtrate layers were separated and the aqueous layer was extracted with 50 mL ethyl acetate. The combined ethyl acetate layers were washed with 50 mL of a 1:1 mixture of saturated sodium chloride and water, dried over anhydrous magnesium sulfate, filtered, and concentrated to an oil. The crude oil was purified by silica gel chromatography (0-30% ethyl acetate in hexanes). Product containing fractions were combined and concentrated to afford (1r,4r)-N,N-dibenzyl-4-(difluoromethoxy)cyclohexanamine (3.12 g, 9.03 mmol, 53.4% yield) as an oil that solidified to an off-white solid. $^1$H NMR (400 MHz, DMSO-$d_6$) δ ppm 7.26-7.38 (m, 8H), 7.17-7.23 (m, 2H), 6.66 (s, 1H), 3.97 (t, J=4.49 Hz, 1H), 3.57 (s, 4H), 2.36-2.47 (m, 1H), 1.98 (d, J=10.54 Hz, 2H), 1.83 (d, J=12.10 Hz, 2H), 1.49 (d, J=12.89 Hz, 2H), 1.22 (d, J=12.49 Hz, 2H). $^{19}$F NMR (376 MHz, DMSO-$d_6$) d ppm −79.28 (d, J=73.00 Hz, 2F). MS(ESI) m/z 346.1 $[M+1]^+$.

D. (1r,4r)-4-(Difluoromethoxy)cyclohexanamine (1r,4r)-N,N-Dibenzyl-4-(difluoromethoxy)cyclohexanamine (1.6 g, 4.63 mmol) was dissolved in ethanol (23 mL) in a Parr shaker flask and 20 wt % palladium hydroxide on carbon (0.650 g, 0.926 mmol) was added. The container was evacuated, placed on a Parr shaker apparatus, and shaken under a 50 psi hydrogen atmosphere overnight. The palladium hydroxide was removed by filtration through a pre-wetted (with ethanol) bed of celite. The filter cake was rinsed well with ethanol. The filtrate was concentrated to an oil that was dissolved in 100 mL ethyl acetate, dried over anhydrous magnesium sulfate, filtered, and concentrated to an oil that solidified, yielding (1r,4r)-4-(difluoromethoxy)cyclohexanamine (0.621 g, 3.76 mmol, 81% yield). $^1$H NMR (400 MHz, DMSO-$d_6$) δ ppm 6.46-6.93 (m, 1H), 3.96 (s, 1H), 2.52-2.59 (m, 1H), 1.84-1.95 (m, 2H), 1.68-1.79 (m, 2H), 1.29-1.43 (m, 2H), 1.01-1.14 (m, 2H). $^{19}$F NMR (376 MHz, DMSO-$d_6$) δ ppm −78.93 (d, J=91.00 Hz, 2F). MS(ESI) m/z 166.2 $[M+1]^+$.

E. Methyl 2-((1r,4R)-4-(difluoromethoxy)cyclohexylamino)-4-((1R,3S)-3 hydroxycyclohexylamino)pyrimidine-5-carboxylate To a stirring mixture of methyl 2-chloro-4-((1R,3S)-3-hydroxycyclohexylamino)pyrimidine-5-carboxylate (300 mg, 1.050 mmol) and (1r,4r)-4-(difluoromethoxy)cyclohexanamine (260 mg, 1.575 mmol) in DMSO (5 mL) was added DIEA (0.550 mL, 3.15 mmol). The resulting mixture was stirred at 70° C. for 1 h. The crude reaction mixture was concentrated and then purified by silica gel chromatography (0-60% ethyl acetate in hexanes). The product containing fractions were combined and concentrated to afford methyl 2-((1r,4R)-4-(difluoro-methoxy)cyclohexylamino)-4-(1R,3S)-3-hydroxycyclohexylamino)pyrimidine-5-carboxylate (165 mg, 0.398 mmol, 37.9% yield). $^1$H NMR (400 MHz, DMSO-$d_6$) δ ppm 8.37-8.49 (m, 1H), 8.06 (d, J=7.42 Hz, 1H), 7.22-7.55 (m, 1H), 6.49-6.94 (m, 1H), 4.67-4.76 (m, 1H), 3.75-4.10 (m, 2H), 3.72 (s, 3H), 3.43-3.69 (m, 2H), 1.63-2.24 (m, 8H), 1.08-1.54 (m, 8H). MS(ESI) m/z 415.5 $[M+1]^+$.

F. 2-((1r,4R)-4-(Difluoromethoxy)cyclohexylamino)-4-((1R,3S)-3 hydroxycyclohexylamino) pyrimidine-5-carboxylic acid To a stirring solution of methyl 2-((1r,4R)-4-(difluoromethoxy)cyclohexylamino)-4-((1R,3S)-3-hydroxycyclohexylamino)-pyrimidine-5-carboxylate (170 mg, 0.410 mmol) in methanol (10 mL) was added an aqueous solution of sodium hydroxide (1 M, 3.075 mL, 3.075 mmol) in one portion. The resulting mixture was allowed to stir at 50° C. for 2 days. The reaction mixture was concentrated to remove methanol, was diluted with additional water (10 mL), and an aqueous solution of citric acid (2 M, 4.10 mL, 8.20 mmol) was slowly added. The resulting precipitate was stirred at room temperature for 30 min, filtered, and the solids then washed well with water. The solids were dried in vacuo to afford 2-((1r,4R)-4-(difluoromethoxy)cyclohexylamino)-4-((1R,3S)-3-hydroxycyclohexylamino)pyrimidine-5-carboxylic acid (117 mg, 0.292 mmol, 71.2% yield) as a solid that was used without further purification. MS (ESI) m/z 401.5 $[M+1]^+$.

G. 2-((1r,4R)-4-(Difluoromethoxy)cyclohexylamino)-4-((1R,3S)-3-hydroxycyclohexylamino) pyrimidine-5-carboxamide To a stirring suspension of 2-((1r,4R)-4-(difluoromethoxy)cyclohexylamino)-4-((1R,3S)-3-hydroxycyclohexylamino)-pyrimidine-5-carboxylic acid (117 mg, 0.292 mmol) and HATU (167 mg, 0.438 mmol) in DMF (2 mL) was added ammonium chloride (78 mg, 1.461 mmol) and DIEA (0.255 mL, 1.461 mmol). The resulting mixture was stirred at room temperature overnight. The crude reaction mixture was concentrated to remove the volatile components and then purified by silica gel chromatography (10-90% ethyl acetate (containing 10% ammonia saturated methanol) in hexanes). The product fractions were combined and concentrated to afford 2-((1r,4R)-4-(difluoromethoxy)cyclohexylamino)-4-((1R,3 S)-3-hydroxycyclohexyl-amino)pyrimidine-5-carboxamide (35.3 mg, 0.088 mmol, 30.2% yield) as a solid.

$^1$H NMR (400 MHz, DMSO-$d_6$) δ ppm 8.90 (d, J=6.64 Hz, 1H), 8.34 (br. s., 1H), 6.50-7.14 (m, 2H), 4.64 (br. s., 1H), 3.42-4.11 (m, 4H), 0.87-2.23 (m, 16H). $^{19}$F NMR (376 MHz, DMSO-$d_6$) δ ppm −78.98 (d, J=110.82 Hz, 2F). MS (ESI) m/z 400.5 [M+1]$^+$.

Example 15: 4-((1R,3S)-3-Methoxycyclohexylamino)-2-((1r,4R)-4-methoxycyclohexylamino) pyrimidine-5-carboxamide

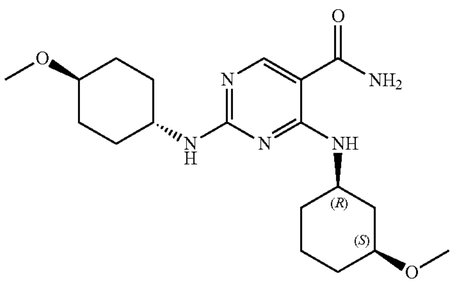

A. tert-Butyl (1R,3S)-3-hydroxycyclohexylcarbamate

To a stirring solution of (1S,3R)-3-aminocyclohexanol (1.0 g, 8.68 mmol; prepared as described in *Tetrahedron: Asymmetry* 15:2051-2056 (2004)) in dioxane (8.04 mL) was added di-tert-butyl-dicarbonate (2.369 g, 10.85 mmol). The resulting mixture was stirred at room temperature for 18 h. The reaction was concentrated, sodium chloride (0.507 g, 8.68 mmol) was added, and the resulting solution was diluted with water (20 mL) and hexanes (20 mL). The suspension was stirred vigorously for 20 min, then filtered and the solids were rinsed with hexanes and dried under vacuum to afford tert-butyl (1R,3S)-3-hydroxycyclohexylcarbamate (1.7836 g, 8.28 mmol, 95% yield) as an off-white solid.

$^1$H NMR (400 MHz, DMSO-$d_6$) δ ppm 6.74 (d, J=8.20 Hz, 1H), 4.58 (d, J=4.29 Hz, 1H), 3.35-3.43 (m, 1H), 3.11-3.27 (m, 1H), 1.90 (d, J=11.32 Hz, 1H), 1.68-1.78 (m, 1H), 1.63 (d, J=3.12 Hz, 2H), 1.37 (s, 9H), 0.87-1.23 (m, 4H); MS (ESI) m/z 216.3 [M+1]$^+$.

B. tert-Butyl (1R,3S)-3-methoxycyclohexylcarbamate

To a solution of tert-butyl (1R,3S)-3-hydroxycyclohexylcarbamate (1.78 g, 8.27 mmol) in anhydrous THF (8 mL) was added sodium hydride (0.230 g, 9.09 mmol) in portions under nitrogen at 0° C. The mixture was warmed to room temperature and stirred for 30 min. A solution of iodomethane (0.824 mL, 13.23 mmol) in anhydrous THF (4 mL) was added drop wise to the mixture at 0° C. and the resulting mixture was stirred at room temperature for 20 h. The crude mixture was quenched with water (50 mL) and extracted with ethyl acetate (3×50 mL). The combined organic layers were washed with brine, dried over sodium sulfate and filtered. The filtrate was concentrated in vacuo, and then purified by silica gel chromatography (0-50% ethyl acetate in hexanes). The product fractions were combined and concentrated to afford tert-butyl (1R,3S)-3-methoxycyclohexylcarbamate (1.0686 g, 4.66 mmol, 56.4% yield) as a white solid; MS (ESI) m/z 230.5 [M+1]$^+$.

C. (1R,3S)-3-Methoxycyclohexanamine trifluoroacetate

To a solution of tert-butyl (1R,3S)-3-methoxycyclohexylcarbamate (1.0686 g, 4.66 mmol) in anhydrous DCM (18.64 mL) was added TFA (3.59 mL, 46.6 mmol) and the resulting solution was stirred at room temperature for 1 h. After that, the solvents were removed in vacuo, and the resulting residue was triturated with ethyl ether (2×50 mL) to afford (1R,3S)-3-methoxycyclohexanamine trifluoroacetate (1.133 g, 4.66 mmol, 100% yield) as a white solid. The crude product was used without further purification in the next step.

D. Ethyl 4-((1R,3S)-3-methoxycyclohexylamino)-2-(methylthio)-pyrimidine-5-carboxylate To a stirring solution of ethyl 4-chloro-2-(methylthio)-pyrimidine-5-carboxylate (1.084 g, 4.66 mmol) and (1R, 3S)-3-methoxycyclohexanamine trifluoroacetate (1.133 g, 4.66 mmol) in ethanol (18.63 mL) was added DIEA (2.434 mL, 13.97 mmol). The reaction mixture was heated to 60° C. for 17 h. The reaction was removed from heat, cooled to room temperature and concentrated. The crude material was purified by silica gel chromatography (0-25% ethyl acetate in hexanes) to afford ethyl 4-((1R,3S)-3-methoxycyclohexylamino)-2-(methylthio)pyrimidine-5-carboxylate (1.4284 g, 4.39 mmol, 94% yield) as a clear oil. MS (ESI) m/z 326.2 [M+1]$^+$.

E. 4-((1R,3S)-3-Methoxycyclohexylamino)-2-(methylthio)pyrimidine-5-carboxylic acid To a stirring solution of ethyl 4-((1R,3S)-3-methoxycyclohexylamino)-2-(methylthio)pyrimidine-5-carboxylate (1.4284 g, 4.39 mmol) in ethanol (12.54 mL) was added aqueous sodium hydroxide solution (1 N, 8.78 mL, 8.78 mmol) and the mixture was stirred for 2 h. The reaction was concentrated, diluted with water (50 mL), and then neutralized while stirring with aqueous citric acid solution (2 M, 5.49 mL, 10.97 mmol). The precipitate was filtered, then washed with water (2×50 mL) and dried to afford 4-((1R,3S)-3-methoxycyclohexylamino)-2-(methylthio)pyrimidine-5-carboxylic acid (1.1679 g, 3.93 mmol, 89% yield) as a white solid. $^1$H NMR (400 MHz, DMSO-$d_6$) δ ppm 13.22 (s, 1H), 8.65 (d, J=7.03 Hz, 1H), 8.51 (s, 1H), 4.07-4.24 (m, 1H), 3.29-3.33 (m, 1H), 3.26 (s, 3H), 2.46 (s, 3H), 2.15 (d, J=12.10 Hz, 1H), 1.63-1.88 (m, 3H), 1.21-1.48 (m, 4H); MS (ESI) m/z 298.1 [M+1]$^+$.

F. 4-((1R,3S)-3-Methoxycyclohexylamino)-2-(methylthio)pyrimidine-5-carboxamide 4-((1R,3S)-3-Methoxycyclohexylamino)-2-(methylthio)pyrimidine-5-carboxylic acid (1.1662 g, 3.92 mmol) and HATU (2.237 g, 5.88 mmol) were stirred in DMF (7.84 mL) for 5 min at room temperature, then ammonium chloride (1.049 g, 19.61 mmol) and DIEA (3.42 mL, 19.61 mmol) were added while stirring. The reaction was allowed to stir at room temperature for 1 h. The reaction mixture was poured into water (100 mL) and extracted with ethyl acetate (3×50 mL). The combined organic layers were washed with water (50 mL), brine (25 mL), dried over sodium sulfate, filtered, and concentrated. The residual DMF was removed by suspending the oily residue in 100 mL water and 100 mL hexanes. The biphasic suspension was stirred vigorously for 30 min, filtered and washed with hexanes to afford 4-((1R,3S)-3-methoxycyclohexylamino)-2-(methylthio)pyrimidine-5-carboxamide (1.1081 g, 3.74 mmol, 95% yield) as an off-white solid. MS (ESI) m/z 397.2 [M+1]$^+$.

G. 4-((1R,3S)-3-Methoxycyclohexylamino)-2-(methylsulfonyl)-pyrimidine-5-carboxamide To a solution of 4-((1R,3S)-3-methoxycyclohexylamino)-2-(methylthio)pyrimidine-5-carboxamide (1.1081 g, 3.74 mmol) in DCM (18.69 mL) and acetone (18.69 mL) at room temperature was added mCPBA (1.676 g, 7.48 mmol) in five batches over 2 min and stirred at room temperature for 16 h. To the crude reaction mixture was added 10% aqueous sodium thiosulfate solution (35 mL) and the mixture was stirred for 5 min before evaporation of the volatile solvents. The material was partitioned between ethyl acetate and water, and the organic layer was then washed with saturated aqueous sodium bicarbonate solution and then brine. The combined aqueous layers were then washed with ethyl acetate (3×), organic layers were combined, dried over sodium sulfate, filtered, and condensed. After drying under high vacuum, 4-((1R,3S)-3-methoxy-cyclohexylamino)-2-(methylsulfonyl)pyrimidine-5-carboxamide (0.9887 g, 3.01 mmol, 81% yield) was obtained as a white solid. MS (ESI) m/z 329.3 [M+1]$^+$.

H. 4-((1R,3S)-3-Methoxycyclohexylamino)-2-((1r,4R)-4-methoxycyclohexylamino)pyrimidine-5-carboxamide To a stirring solution of 4-((1R,3S)-3-methoxycyclohexylamino)-2-(methylsulfonyl)pyrimidine-5-carboxamide (0.3 g, 0.914 mmol) and (1r,4r)-4-methoxycyclohexanamine (0.236 g, 1.827 mmol) in DMSO (0.914 mL) was added DIEA (0.637 mL, 3.65 mmol) and the reaction mixture was stirred at 100° C. for 17 h. The crude reaction mixture was concentrated and then purified by silica gel chromatography (0-10% methanol in ethyl acetate). The product fractions were combined and concentrated to afford 4-((1R,3S)-3-methoxycyclohexylamino)-2-((1r,4R)-4-methoxycyclohexylamino)-pyrimidine-5-carboxamide (0.155 g, 0.411 mmol, 44.9% yield) as a white solid. $^1$H NMR (400 MHz, DMSO-$d_6$) δ ppm 8.95 (d, J=7.42 Hz, 1H), 8.34 (s, 1H), 7.01-7.17 (m, 1H), 6.76-6.88 (m, 1H), 3.51-4.07 (m, 2H), 2.97-3.29 (m, 8H), 1.63-2.42 (m, 8H), 0.98-1.39 (m, 9H); MS (ESI) m/z 378.4 [M+1]$^+$.

Example 16: 2-((1r,4R)-4-Hydroxy-4-methylcyclohexylamino)-4-((1R,3S)-3-hydroxycyclohexylamino)pyrimidine-5-carboxamide

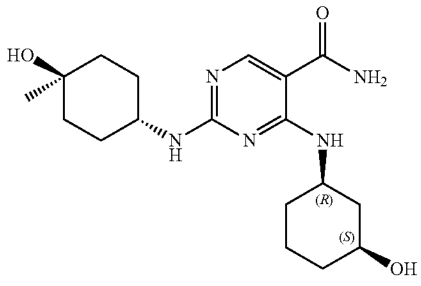

A. (1r,4r)-4-Amino-1-methylcyclohexanol hydrochloride

A solution of (1r,4r)-4-(dibenzylamino)-1-methylcyclohexanol (15.3 g, 49.4 mmol; prepared as described in PCT Int. Appl. publication WO2010/027500) in methanol (137 mL) and ethyl acetate (137 mL) in a 500 mL Parr vessel was degassed by bubbling nitrogen through the solution for 5 min. To the solution was added palladium hydroxide on carbon (6.94 g, 4.94 mmol) and the vessel was placed on a Parr shaker for 6 days at 3 atm hydrogen. The vessel was removed from the Parr shaker and then the suspension was filtered through celite. The filtrate was concentrated, the residue was dissolved in 50 mL methanol, acidified with aqueous hydrochloric acid solution (6 M, 9.06 mL, 54.4 mmol) and concentrated to afford (1r,4r)-4-amino-1-methylcyclohexanol hydrochloride (8.31 g, 50.2 mmol, 101% yield) as an off-white solid, which was used without further purification in the next step.

B. tert-Butyl (1r,4r)-4-hydroxy-4-methylcyclohexylcarbamate

To a stirring solution of (1r,4r)-4-amino-1-methylcyclohexanol hydrochloride (8.31 g, 50.2 mmol) in an aqueous sodium hydroxide solution (1 N, 100 mL, 100 mmol) was added di-tert-butyl-dicarbonate (13.68 g, 62.7 mmol) and the reaction mixture was stirred at room temperature for 2 h. The reaction was concentrated and then purified by silica gel chromatography (0-100% ethyl acetate in hexanes). The product fractions were combined and concentrated. The material contained ~50% desired product as shown by LCMS, so the material was repurified twice on silica gel, using 0-50% ethyl acetate in hexanes as the mobile phase. The product fractions were combined and concentrated to afford tert-butyl (1r,4r)-4-hydroxy-4-methylcyclohexylcarbamate (2.2 g, 9.59 mmol, 19.13% yield) as a white solid. MS (ESI) m/z 230.5 [M+1]$^+$.

C. (1r,4r)-4-Amino-1-methylcyclohexanol trifluoroacetate

To a stirring solution of tert-butyl (1r,4r)-4-hydroxy-4-methylcyclohexylcarbamate (2.04 g, 8.90 mmol) in DCM (44 mL) was added TFA (13.71 mL, 178 mmol) and the solution was stirred at room temperature for 22 h. The reaction was concentrated, the residue was triturated twice with ethyl ether to afford (1r,4r)-4-amino-1-methylcyclohexanol trifluoroacetate (2.106 g, 8.66 mmol, 97% yield) as a white solid. $^1$H NMR (400 MHz, DMSO-$d_6$) δ ppm 7.73 (br. s., 3H), 4.39 (br. s., 1H), 3.05 (d, J=3.51 Hz, 1H), 1.27-1.97 (m, 8H), 1.11 (s, 3H); MS (ESI) m/z 130.2 [M+1]$^+$.

D. 2-((1r,4R)-4-Hydroxy-4-methylcyclohexylamino)-4-((1R,3S)-3-hydroxycyclohexylamino)pyrimidine-5-carboxamide To a stirring solution of 4-((1R,3S)-3-hydroxycyclohexylamino)-2-(methylsulfonyl)pyrimidine-5-carboxamide (0.432 g, 1.374 mmol; synthesis described herein) and (1r,4r)-4-amino-1-methylcyclo-hexanol trifluoroacetate (0.435 g, 1.786 mmol) in dioxane (2.75 mL) was added DIEA (0.718 mL, 4.12 mmol) and the resulting solution was stirred at 110° C. for 23 h. The crude reaction mixture was concentrated and the residue was purified by HPLC (20-100% methanol in water). The product fractions were combined, concentrated and the residue was triturated with acetonitrile. The resulting precipitate was collected to afford 2-((1r,4R)-4-hydroxy-4-methylcyclohexylamino)-4-((1R,3S)-3-hydroxycyclohexyl-amino)pyrimidine-5-carboxamide (0.0483 g, 0.133 mmol, 9.67% yield) as an off white solid. $^1$H NMR (400 MHz, DMSO-$d_6$) δ ppm 8.91 (d, J=6.64 Hz, 1H), 8.34 (br. s., 1H), 6.56-7.26 (m, 1H), 3.39-4.78 (m, 4H), 2.54 (s, 3H), 0.66-2.25 (m, 19H); MS (ESI) m/z 364.5 [M+1]$^+$ Example 17: 4-((1S,3S,4S)-3-Hydroxy-4-methylcyclohexylamino)-2-((1r,4S)-4-methoxy-cyclohexylamino)pyrimidine-5-carboxamide; 4-((1R,3R,4R)-3-Hydroxy-4-methylcyclohexylamino)-2-((1r,4R)-4-methoxy-cyclohexylamino)pyrimidine-5-carboxamide; 4-((1S,3R,4R)-3-Hydroxy-4-methylcyclohexylamino)-2-((1r,4S)-4-methoxy-cyclohexylamino)pyrimidine-5-carboxamide; 4-((1R,3S,4S)-3-Hydroxy-4-methylcyclohexylamino)-2-((1r,4R)-4-methoxy-cyclohexylamino)pyrimidine-5-carboxamide

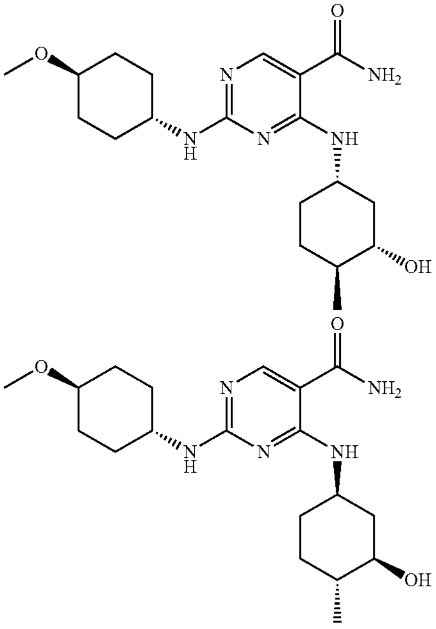

-continued

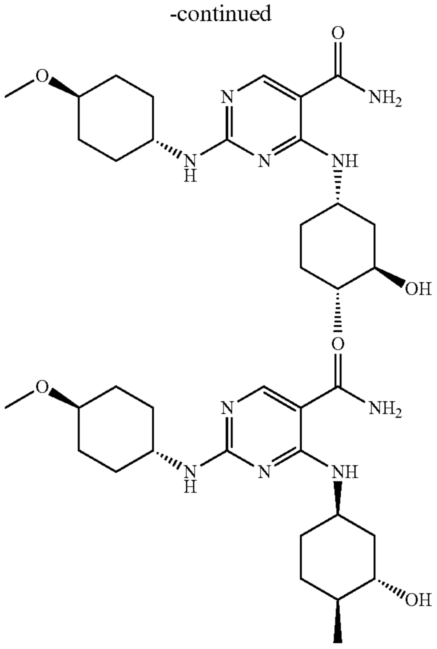

A. 2-((1s,4s)-4-Hydroxy-4-methylcyclohexyl)isoindoline-1,3-dione

To a stirring solution of (1s,4s)-4-amino-1-methylcyclohexanol (10 g, 77 mmol; prepared as described in PCT Int. Appl. publication WO2010/027500) and potassium carbonate (18.72 g, 135 mmol) in water (155 mL) at 0° C. was added N-carbethoxyphthalimide (18.66 g, 85 mmol) and the solution was stirred for 2 h at room temperature. The fine suspension was filtered, resuspended in 100 mL water, and refiltered to afford 2-((1s,4s)-4-hydroxy-4-methylcyclohexyl)isoindoline-1,3-dione (11.413 g, 44.0 mmol, 56.9% yield) as a white powder. $^1$H NMR (400 MHz, DMSO-$d_6$) δ ppm 7.79-7.88 (m, 4H), 4.11 (s, 1H), 3.94 (s, 1H), 2.51-2.56 (m, 1H), 2.44-2.49 (m, 1H), 1.56-1.70 (m, 2H), 1.33-1.47 (m, 4H), 1.13 (s, 3H); MS (ESI) m/z 260.5 [M+1]$^+$.

B. 2-(4-Methylcyclohex-3-enyl)isoindoline-1,3-dione 2-((1s,4s)-4-Hydroxy-4-methylcyclohexyl)isoindoline-1,3-dione (4.6568 g, 17.96 mmol) and potassium hydrogen sulfate (4.89 g, 35.9 mmol) were combined and heated to 140° C. for 20 min. No reaction was observed, so water (11.22 mL) and sulfuric acid (7.66 mL, 144 mmol) were added and the reaction mixture was heated to 100° C. for 2 h. The crude suspension was cooled to room temperature and poured into 200 mL crushed ice/water, stirred vigorously for 30 min, then filtered to afford the crude product as a white solid. The white solid was purified by silica gel chromatography (0-10% ethyl acetate in hexanes), and the product fractions were combined and concentrated to afford 2-(4-methylcyclohex-3-enyl)isoindoline-1,3-dione (3.33 g, 13.80 mmol, 77% yield) as a white solid. MS (ESI) m/z 242.0 [M+1]$^+$.

C. 4-Methylcyclohex-3-enamine

To a stirring suspension of 2-(4-methylcyclohex-3-enyl)isoindoline-1,3-dione (5.24 g, 21.72 mmol) in methanol (163 mL) and DCM (54.3 mL) was added hydrazine hydrate (3.69 mL, 76 mmol) and the reaction was stirred for 15 h. To the crude suspension was added 400 mL water, and the mixture was stirred for 10 min, then extracted with DCM (4×400 mL). The combined organic layers were dried over sodium sulfate then concentrated to afford 4-methylcyclohex-3-enamine (2.415 g, 21.72 mmol, 100% yield) as a light yellow oil. MS (ESI) m/z 112.2 [M+1]+.

D. tert-Butyl 4-methylcyclohex-3-enylcarbamate

To a stirring solution of 4-methylcyclohex-3-enamine (2.415 g, 21.72 mmol) and TEA (3.33 mL, 23.89 mmol) in DCM (43.4 mL) at 0° C. was added di-tert-butyl-dicarbonate (7.11 g, 32.6 mmol). The resulting mixture was stirred for 3 days at room temperature. The crude reaction mixture was concentrated then purified by silica gel chromatography (0-10% ethyl acetate in hexanes). The product fractions were combined and concentrated to afford tert-butyl 4-methylcyclohex-3-enylcarbamate (1.65 g, 7.81 mmol, 36.0% yield) as a white solid.
$^1$H NMR (400 MHz, DMSO-$d_6$) δ ppm 6.72 (d, J=7.42 Hz, 1H), 5.26 (br. s., 1H), 3.35-3.49 (m, 1H), 1.66-2.22 (m, 5H), 1.60 (s, 3H), 1.38 (s, 10H); MS (ESI) m/z 212.4 [M+1]−.

E. tert-Butyl 3-hydroxy-4-methylcyclohexylcarbamate

To a stirring solution of tert-butyl 4-methylcyclohex-3-enylcarbamate (1.5844 g, 7.50 mmol) in THF (94 mL) at 0° C. was added 1M borane THF complex (33.7 mL, 33.7 mmol). The solution was stirred at 0° C. for 1 h and then at room temperature for 2 h. The reaction was quenched very slowly with water (40.5 mL, 2249 mmol), diluted with ethanol (39.8 mL, 682 mmol) and basified with aqueous sodium hydroxide solution (5 N, 37.5 mL, 187 mmol). To the stirring biphasic mixture was slowly added hydrogen peroxide (38.3 mL, 375 mmol) and the resulting mixture was heated to 45° C. for 20 h. The crude reaction was quenched with saturated aqueous sodium sulfite solution (70 mL) and extracted with ethyl acetate (3×100 mL). The combined organic layers were washed with brine, dried over sodium sulfate, filtered and concentrated. The crude product was purified by silica gel chromatography (0-100% ethyl acetate in hexanes). The product fractions were combined and concentrated to afford a mixture of four isomers of tert-butyl 3-hydroxy-4-methylcyclohexylcarbamate (trans relationship between 3-hydroxy and 4-methyl moieties) (0.9608 g, 4.19 mmol, 55.9% yield) as a white solid. $^1$H NMR (400 MHz, DMSO-$d_6$) δ ppm 6.60-6.85 (m, 1H), 4.29-4.58 (m, 1H), 3.35-3.80 (m, 1H), 2.81-3.28 (m, 1H), 1.20-1.96 (m, 14H), 0.79-1.14 (m, 5H); MS (ESI) m/z 230.5 [M+1]−.

F. 5-Amino-(trans)-2-methylcyclohexanol hydrochloride

To vigorously stirring methanol (10.47 mL) at 0° C. was added acetyl chloride (0.893 mL, 12.57 mmol). The solution was stirred for 30 min, then tert-butyl 3-hydroxy-4-methylcyclohexyl-carbamate (0.9608 g, 4.19 mmol) was added and stirring was continued for 22 h at room temperature. The crude reaction mixture was concentrated, and the residue was triturated with ethyl ether (2×50 mL) to afford 5-amino-(trans)-2-methylcyclohexanol hydrochloride (0.694 g, 4.19 mmol, 100% yield) as a white solid. MS (ESI) m/z 112.2 [M+1]−.

G. 2-(trans-4-Methoxycyclohexylamino)-4-(methylsulfinyl)pyrimidine-5-carboxamide To a solution of 2-((1r,4r)-4-methoxycyclohexylamino)-4-(methylthio)-pyrimidine-5-carboxamide (1.24 g, 4.18 mmol; synthesis described herein) in NMP (12.30 mL) at 0° C. was added mCPBA (0.938 g, 4.18 mmol) portion wise and the reaction mixture was stirred for 1 h, while allowing to reach room temperature slowly. The reaction mixture was diluted with water (120 mL), stirred for 10 min and the resulting solids were removed by filtration. The filtrate was concentrated in vacuo at less than 30° C. to afford 2-((1r,4r)-4-methoxycyclohexylamino)-4-(methylsulfinyl)pyrimidine-5-carboxamide (1.307 g, 4.18 mmol, 100% yield) as a white suspension in NMP (~10 mL). This crude suspension was used in the next step without further purification. MS (ESI) m/z 313.5 [M+1]+.

H. 4-((1S,3S,4S)-3-Hydroxy-4-methylcyclohexylamino)-2-((1r,4S)-4-methoxycyclohexylamino)pyrimidine-5-carboxamide, 4-((1R,3R,4R)-3-hydroxy-4-methylcyclohexylamino)-2-((1r,4R)-4-methoxycyclohexylamino)pyrimidine-5-carboxamide, 4-((1S,3R,4R)-3-hydroxy-4-methylcyclohexylamino)-2-((1r,4S)-4-methoxycyclohexylamino)pyrimidine-5-carboxamide, 4-((1R,3S,4S)-3-hydroxy-4-methylcyclohexylamino)-2-((1r,4R)-4-methoxycyclohexylamino)pyrimidine-5-carboxamide To the crude reaction mixture of (2-((1r,4r)-4-methoxycyclohexylamino)-4-(methylsulfinyl)pyrimidine-5-carboxamide (1.31 g, 4.19 mmol) in NMP (10 mL) was added crude 5-amino-(trans)-2-methylcyclohexanol hydrochloride (0.695 g, 4.19 mmol) as a solution in NMP (15.00 mL). To the suspension was added DIEA (3.65 mL, 20.97 mmol) and the reaction was heated to 100° C. for 46 h. The NMP was removed by evaporation at 70° C., the residue was diluted with DCM and purified by silica gel chromatography (0-15% methanol in DCM). The product fractions were combined, concentrated, and then repurified by silica gel chromatography (0-10% methanol in DCM). The product fractions were combined and concentrated to afford a mixture of four products (two diastereomers and their corresponding enantiomers (1.665 g). NMR of mixture: $^1$H NMR (400 MHz, DMSO-$d_6$) δ ppm 8.35 (d, J=5.45 Hz, 1H), 4.50-4.71 (m, 1H), 4.34 (br. s., 1H), 3.53-3.69 (m, 1H), 3.23 (s, 3H), 3.03-3.19 (m, 2H), 1.77-2.09 (m, 5H), 1.65 (br. s., 1H), 1.07-1.39 (m, 13H), 0.94 (d, J=6.49 Hz, 3H); MS (ESI) m/z 378.0 [M+1]+ The crude material was separated by chiral SFC using an AD-H column to afford 4 compounds labeled PEAK 1 to PEAK 4, with PEAK 1 being the first eluting compound and PEAK 4 being the latest eluting compound. Stereochemistry of Peaks 1 through 4 was determined by methods known to one of skill in the art.

PEAK 1: 4-((1S,3S,4S)-3-Hydroxy-4-methylcyclohexylamino)-2-((1r,4S)-4-methoxycyclohexylamino)pyrimidine-5-carboxamide 0.3482 g, 0.922 mmol, 22% yield. $^1$H NMR (400 MHz, DMSO-$d_6$) δ ppm 8.88 (d, J=6.64 Hz, 1H), 8.34 (br. s., 1H), 7.07 (d, J=7.03 Hz, 1H), 4.58 (d, J=5.08 Hz, 1H), 4.10 (q, J=5.08 Hz, 1H), 3.51-3.92 (m, 1H), 3.44 (dd, J=7.03, 5.08 Hz, 1H), 3.23 (s, 3H), 3.17 (d, J=5.47 Hz, 3H), 3.09 (br. s., 1H), 2.98 (br. s., 1H), 2.55 (d, J=7.03 Hz, 1H), 1.77-2.23 (m, 5H), 1.66 (d, J=12.49 Hz, 1H), 1.04-1.35 (m, 6H), 0.94 (d, J=5.86 Hz, 3H).

PEAK 2: 4-((1R,3R,4R)-3-hydroxy-4-methylcyclohexylamino)-2-((1r,4R)-4-methoxycyclohexylamino) pyrimidine-5-carboxamide 0.4146 g, 1.098 mmol, 26.2% yield. $^1$H NMR (400 MHz, DMSO-$d_6$) δ ppm 8.88 (d, J=6.25 Hz, 1H), 8.34 (br. s., 1H), 7.07 (d, J=7.03 Hz, 1H), 4.57 (br. s., 1H), 4.11 (br. s., 1H), 3.50-3.67 (m, 1H), 3.23 (s, 2H), 3.17 (br. s., 2H), 3.03-3.13 (m, 1H), 2.94-3.02 (m, 1H), 2.89 (q, J=7.16 Hz, 4H), 1.60-2.22 (m, 4H), 0.87-1.37 (m, 13H).

PEAK 3: 4-((1S,3R,4R)-3-hydroxy-4-methylcyclohexylamino)-2-((1r,4R)-4-methoxycyclohexylamino) pyrimidine-5-carboxamide 0.3145 g, 0.833 mmol, 19.9% yield. $^1$H NMR (400 MHz, DMSO-$d_6$) δ ppm 9.25 (d, J=7.42 Hz, 1H), 8.35 (br. s., 1H), 7.05 (d, J=6.64 Hz, 1H), 6.76-6.92 (m, 1H), 4.53 (d, J=3.90 Hz, 1H), 4.32 (br. s., 1H), 4.03-4.17 (m, 1H), 3.52-3.84 (m, 1H), 3.40-3.50 (m, 1H), 3.13-3.26 (m, 4H), 3.00-3.12 (m, 1H), 1.77-2.12 (m, 5H), 1.10-1.69 (m, 9H), 0.94 (d, J=6.64 Hz, 3H).

PEAK 4: 4-((1R,3S,4S)-3-hydroxy-4-methylcyclohexylamino)-2-((1r,4R)-4-methoxycyclohexylamino) pyrimidine-5-carboxamide 0.4715 g, 1.249 mmol, 29.8% yield. $^1$H NMR (400 MHz, DMSO-$d_6$) δ ppm 9.46-9.75 (m, 1H), 8.35 (s, 1H), 4.57 (br. s., 1H), 4.35 (br. s., 1H), 3.60-3.79 (m, 1H), 3.23 (s, 4H), 3.00-3.15 (m, 1H), 2.87-2.99 (m, 1H), 1.75-2.06 (m, 5H), 1.06-1.73 (m, 11H), 0.94 (d, J=6.25 Hz, 3H).

Example 18: 4-((1R,3S)-3-Hydroxycyclohexylamino)-2-((1r,4R)-4-methoxycyclohexylamino) pyrimidine-5-carboxamide

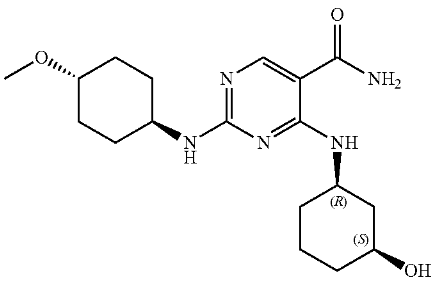

A. 2-Cyclohex-2-enyl-isoindole-1,3-dione

To a solution of 3-bromo-cyclohexene (500 g, 3.12 mmol) in DMF (2000 mL) was added potassium phtalimide (580 g, 3.12 mmol), and the reaction mixture was stirred at room temperature for 30 h. The reaction mixture was diluted with water (1000 mL), extracted with ethyl acetate (3 times), and the combined organic layers were concentrated to give 2-cyclohex-2-enyl-isoindole-1,3-dione (520 g, 2.30 mol) as a gray solid.

B. 2-(2-Bromo-3-hydroxy-cyclohexyl)-isoindole-1,3-dione

2-Cyclohex-2-enyl-isoindole-1,3-dione (520 g, 2.30 mol) and N-bromosuccinimide (416 g, 2.35 mol) were mixed in a cosolvent of chloroform (3000 mL) and ethanol (120 mL) and stirred at room temperature for 16 h. When HPLC showed the starting material was consumed, the reaction mixture was concentrated to give the residue, which was diluted with hydrochloride solution (450 mL, 2.0 mol) and THF (2000 mL), and the reaction mixture was stirred at room temperature for 2 h. The reaction mixture was concentrated to give the crude product. The crude product was washed with ethanol (2 times) to give 2-(2-bromo-3-hydroxy-cyclohexyl)-isoindole-1,3-dione (400 g, 1.23 mol) as a white solid. $^1$H NMR ($CD_3OD$, 400 MHz): δ ppm 7.87 (m, 4H), 4.70 (m, 1H), 4.33 (m, 1H),3.70 (m, 1H), 2.15 (m, 2H),1.88 (m, 2H), 1.53 (m, 2H).

C. 2-(3-Hydroxy-cyclohexyl)-isoindole-1,3-dione

Tri-n-butyltin hydride (430 g, 1.48 mol) was added to a stirred solution of 2-(2-bromo-3-hydroxy-cyclohexyl)-isoindole-1,3-dione (400 g, 1.23 mol) and 2,2'-azobis(2-methylpropionitrile) (20 g) in toluene (4000 mL) and methanol (400 mL) and the reaction mixture was stirred at 80° C. for 64 h. The reaction mixture was concentrated to give the crude product. The crude product was washed with petroleum ether and ethyl acetate (1:1) to give 2-(3-hydroxy-cyclohexyl)-isoindole-1,3-dione (240 g, 0.98 mol) as a white solid. $^1$H NMR ($CD_3OD$, 400 MHz): δ ppm 7.82 (m, 4H), 4.16 (m, 1H), 3.63 (m, 1H), 2.13 (m, 2H), 1.98 (d, 2H), 1.89 (m, 1H),1.68 (t, 1H), 1.46 (m, 1H),1.31 (m, 1H).

D. (1S,3R)-2-(3-Hydroxy-cyclohexyl)-isoindole-1,3-dione and (1R,3S) acetic acid 3-(1,3-dioxo-1,3-dihydro-isoindol-2-yl)-cyclohexyl ester A solution of 2-(3-hydroxy-cyclohexyl)-isoindole-1,3-dione (240 g, 0.98 mol) and Lipase B (87 g) in THF (3000 mL) was stirred at room temperature under nitrogen for 1-2 h. Then acetic acid vinyl ester (252 g, 2.88 mol) was added to the solution, and the reaction mixture was stirred at rt for 3~5 h. Then the reaction mixture was filtered, and the filtrate was concentrated to give crude product. The crude product was purified on silica gel (eluting with petroleum ether/ethyl acetate=10:1) to give (1S,3R)-2-(3-hydroxy-cyclohexyl)-isoindole-1,3-dione ($R_f$=0.6, petroleum ether/ethyl acetate=3/1, 90 g, 0.37 mol, yield: 39%) as a white solid. $^1$H NMR ($CD_3OD$, 400 MHz): δ ppm 7.82 (m, 4H), 4.16 (m, 1H), 3.63 (m, 1H), 2.13 (m, 2H), 1.98 (m, 2H), 1.89 (m, 1H), 1.68 (m, 1H), 1.46 (m, 1H), 1.31 (m, 1H).

(1R,3S) Acetic acid 3-(1,3-dioxo-1,3-dihydro-isoindol-2-yl)-cyclohexyl ester ($R_f$=0.2, petroleum ether/ethyl acetate=3/1, 110 g, 0.38 mol, yield: 39%) as a white solid. $^1$H NMR ($CD_3OD$, 400 MHz): δ ppm 7.83 (m, 4H), 4.78 (m, 1H), 4.23 (m, 1H), 2.33 (m, 2H), 2.13 (m, 2H), 2.07 (m, 5H), 1.95 (m, 1H), 1.74 (m, 1H), 1.46 (m, 1H).

E. (1S,3R)-3-Amino-cyclohexanol

To a solution of (1S,3R)-2-(3-hydroxy-cyclohexyl)-isoindole-1,3-dione (90 g, 0.37 mol) in ethanol (1500 mL) was added hydrazine (90 g, 1.8 mol), and the reaction solution was stirred at 100° C. for 3 h. The reaction solution was filtered, and the filtrate was concentrated to give (1S,3R)-3-amino-cyclohexanol (25 g, 0.21 mmol) as a yellow solid. $^1$H NMR ($CD_3OD$, 400 MHz) δ ppm 3.54 (m, 1H), 2.65 (m, 1H), 2.12 (m, 1H), 1.92 (m, 1H), 1.89 (m, 2H), 1.32 (m, 1H), 1.06 (m, 2H).

F. Ethyl 4-((1R,3S)-3-hydroxycyclohexylamino)-2-(methylthio)-pyrimidine-5-carboxylate To a stirring solution of ethyl 4-chloro-2-(methylthio)-pyrimidine-5-carboxylate (4.38 g, 18.82 mmol) and (1S,3R)-3-aminocyclohexanol (2.276 g, 19.76 mmol) in ethanol (75 ml) was added DIEA (4.93 ml, 28.2 mmol). The reaction mixture was heated to 60° C. for 2 h, was removed from heat and concentrated, then purified by silica gel chromatography (20-100% ethyl acetate/hexane). The desired product fractions were combined and concentrated to afford ethyl 4-((1R,3S)-3-hydroxycyclohexylamino)-2-(methylthio)pyrimidine-5-carboxylate (5 g, 16.06 mmol, 85% yield) as a white foam. MS (ESI) m/z 312.1 $[M+1]^+$.

G. 4-((1R,3S)-3-hydroxycyclohexylamino)-2-(methylthio)pyrimidine-5-carboxylic acid To a stirring solution of ethyl 4-((1R,3S)-3-hydroxycyclohexyl-amino)-2-(methylthio)pyrimidine-5-carboxylate (5 g, 16.06 mmol) in ethanol (50 ml) was added 2M sodium hydroxide (20 ml, 40.0 mmol). Stirring was continued at room temperature for 1 h. The reaction mixture was neutralized by addition of saturated citric acid. The resulting precipitate was filtered and dried to afford 4-((1R,3S)-3-hydroxycyclohexyl-amino)-2-(methylthio)pyrimidine-5-carboxylic acid (4.5 g, 15.88 mmol, 99% yield) as a white solid. $^1$H NMR (400 MHz, DMSO-$d_6$) δ ppm 13.21 (br. s., 1H), 8.44-8.54 (m, 2H), 4.74 (d, J=3.90 Hz, 1H), 3.97-4.12 (m, 1H), 3.56 (d, J=3.12 Hz, 1H), 2.46 (s, 3H), 2.05-2.16 (m, 1H), 1.84 (d, J=10.15 Hz, 1H), 1.65-1.80 (m, 2H), 1.11-1.36 (m, 4H). MS (ESI) m/z 284.1 $[M+1]^+$.

H. 4-((1R,3S)-3-Hydroxycyclohexylamino)-2-(methylthio)pyrimidine-5-carboxamide 4-((1R,3S)-3-hydroxycyclohexylamino)-2-(methylthio) pyrimidine-5-carboxylic acid (4.5 g, 15.88 mmol) and HATU (9.06 g, 23.82 mmol) were dissolved in DMF (75 ml) and allowed to stir for 5 min at room temperature before adding ammonium chloride (4.25 g, 79 mmol) and DIEA (13.87 ml, 79 mmol). The reaction turned yellow upon addition of the base. The reaction was allowed to stir at room temperature for 1 h then partitioned between water and ethyl acetate. The organic layer was washed once with brine before drying over sodium sulfate, filtering, and concentrating to afford 4-((1R,3S)-3-hydroxycyclohexylamino)-2-(methylthio)pyrimidine-5-carboxamide (4.19 g, 14.84 mmol, 93% yield) as an off-white solid. MS (ESI) m/z 283.2 $[M+1]^+$.

I. 4-((1R,3S)-3-Hydroxycyclohexylamino)-2-(methylsulfonyl)-pyrimidine-5-carboxamide To a stirring suspension of 4-((1R,3S)-3-hydroxycyclohexylamino)-2-(methylthio)pyrimidine-5-carboxamide (302 mg, 1.070 mmol) in DCM (10 ml) and acetone (10 ml) was added 3-chloroperoxybenzoic acid (479 mg, 2.139 mmol). The reaction was stirred at room temperature for 1.5 h. The crude reaction mixture was quenched by addition of 10 mL of 10% sodium thiosulfate solution, stirred for 5 minutes, then partitioned between ethyl acetate and water. The organic layer was washed with saturated sodium bicarbonate and brine. The combined aqueous layers were extracted with ethyl acetate (3×50 mL). The combined organic layers were dried over sodium sulfate, filtered, and concentrated to afford 4-((1R,3S)-3-hydroxycyclohexyl-amino)-2-(methylsulfonyl)pyrimidine-5-carboxamide (259 mg, 0.824 mmol, 77% yield) as a white solid. MS (ESI) m/z 315.2 $[M+1]^+$.

J. 4-((1R,3S)-3-Hydroxycyclohexylamino)-2-((1r,4R)-4-methoxycyclo-hexylamino)pyrimidine-5-carboxamide To a stirring solution of 4-((1R,3S)-3-hydroxy-cyclohexylamino)-2-(methylsulfonyl)pyrimidine-5-carboxamide (0.178 g, 0.566 mmol) and (1r,4r)-4-methoxycyclohexanamine (0.146 g, 1.132 mmol) in DMSO (1.132 ml) was added DIEA (0.395 ml, 2.265 mmol). The reaction mixture was stirred at 100° C. for 17 h. The crude reaction mixture was concentrated and purified by silica gel chromatography (0-15% methanol/ethyl acetate). The product fractions were combined and concentrated to afford 4-((1R,3S)-3-hydroxycyclohexylamino)-2-((1r,4R)-4-methoxycyclohexylamino)-pyrimidine-5-carboxamide (0.08 g, 0.220 mmol, 38.9% yield) as a light tan solid.

$^1$H NMR ($CD_3OD$, 400 MHz): δ ppm 8.29 (s, 1H), 3.99-4.04 (m, 1H), 3.76 (m, 1H), 3.50-3.63 (m, 1H), 3.37 (s, 3H), 3.24 (m, 1H), 3.23 (m, 1H), 1.92-2.12 (m, 6H), 1.83-1.87 (m, 1H), 1.19-1.41 (m, 8H). MS (ESI) m/z 364.6 $[M+1]^+$.

Example 19: 4-((1R,3S)-3-Hydroxycycloheptylamino)-2-((1r,4R)-4-methoxycyclohexylamino) pyrimidine-5-carbonitrile

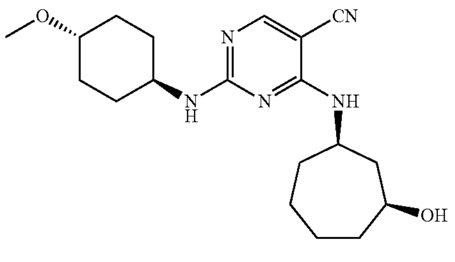 [SMILES: CO[C@H]1CC[C@H](Nc2ncc(C#N)c(N[C@@H]3CCCC[C@H](O)C3)n2)CC1]

A. 4-Chloro-2-((1R,4R)-4-methoxycyclohexylamino)-pyrimidine-5-carbonitrile (1r,4r)-4-Methoxycyclohexanamine (6.37 g, 49.3 mmol), 2,4-dichloropyrimidine-5-carbonitrile (6 g, 34.5 mmol) and DIEA (9.03 mL, 51.7 mmol) were mixed in THF (180 mL) at −10° C. (salt ice bath) and stirred at the same temperature for 5 h. The reaction mixture was stirred further overnight while the temperature went up to room temperature slowly. Analysis of the reaction mixture by LC/MS showed formation of the products with the ratio of about 3:7. The reaction mixture was concentrated under reduced pressure, diluted with water (100 mL) and extracted with ethyl acetate (2×). The combined organic layers were washed with water and brine and dried over magnesium sulfate. The drying agent was removed by filtration and the solution was concentrated. The resulting crude mixture was purified by flash chromatography (0-20% ethyl acetate in hexanes) to give 4-chloro-2-((1R,4R)-4-methoxycyclohexylamino)pyrimidine-5-carbonitrile (5.79 g, 21.71 mmol, 62.9% yield; $^1$H NMR (DMSO-$d_6$, 400 MHz): δ ppm 8.74 (d, J=8.2 Hz, 1H), 8.60-8.72 (m, 1H), 3.58-3.80 (m, 1H), 3.18 (d, J=2.0 Hz, 3H), 2.97-3.12 (m, 1H), 1.96 (d, J=10.9 Hz, 2H), 1.83 (d, J=10.5 Hz, 2H), 1.21-1.39 (m, 2H), 1.06-1.22 (m, 2H); MS (ES) m/z 267.2 [M+1]$^+$) as a white solid and 2-chloro-4-((1R,4R)-4-methoxycyclohexylamino)pyrimidine-5-carbonitrile (2.5 g, 9.37 mmol, 27.2% yield; $^1$H NMR (DMSO-$d_6$, 400 MHz): δ ppm 8.50 (s, 1H), 8.31 (d, J=7.8 Hz, 1H), 3.90 (dtd, J=11.6, 7.6, 4.1 Hz, 1H), 3.19 (s, 3H), 2.98-3.10 (m, 1H), 1.98 (d, J=10.5 Hz, 2H), 1.77 (d, J=11.3 Hz, 2H), 1.36-1.54 (m, 2H), 1.05-1.22 (m, 2H). MS (ES) m/z 267.1 [M+1]$^+$) as a white solid.

The regiochemistry of the separated isomers was confirmed in the following experiments:

4-Chloro-2-((1R,4R)-4-methoxycyclohexylamino)pyrimidine-5-carbonitrile (50 mg, 0.187 mmol), diacetoxypalladium (42.1 mg, 0.187 mmol) and ammonium formate (59.1 mg, 0.937 mmol) in methanol (1 mL) was stirred at 70° C. for 2 h. The reaction mixture was cooled down to room temperature and was filtered through a pad of celite. The resulting solution was concentrated and subjected to flash chromatography (0-15% methanol in DCM) to give 2-((1R,4R)-4-methoxycyclohexyl-amino)pyrimidine-5-carbonitrile as a white solid. $^1$H NMR (DMSO-$d_6$, 400 MHz; measured at room temperature): δ ppm 8.66 (d, J=2.7 Hz, 1H), 8.59 (d, J=3.1 Hz, 1H), 8.22 (d, J=8.2 Hz, 1H), 3.62-3.77 (m, 1H), 3.18 (s, 3H), 2.99-3.12 (m, 1H), 1.90-2.02 (m, 2H), 1.84 (d, J=10.5 Hz, 2H), 1.21-1.37 (m, 2H), 1.06-1.21 (m, 2H).

$^1$H NMR (DMSO-$d_6$, 400 MHz; measured at 80° C.): δ ppm 8.57 (br. s., 1H), 7.91 (d, J=7.0 Hz, 1H), 3.68-3.85 (m, 1H), 3.05-3.16 (m, 1H), 3.02 (s, 3H), 1.92-2.05 (m, 2H), 1.87 (d, J=10.2 Hz, 2H), 1.26-1.41 (m, 2H), 1.11-1.26 (m, 2H).

The same method described above was applied to 2-chloro-4-((1R,4R)-4-methoxycyclohexylamino)pyrimidine-5-carbonitrile to give 4-((1R,4R)-4-methoxy-cyclohexylamino)pyrimidine-5-carbonitrile as a white solid. $^1$H NMR (DMSO-$d_6$, 400 MHz; measured at room temperature): δ ppm 8.56 (d, J=15.2 Hz, 1H), 7.74-7.91 (m, 1H), 3.86-4.11 (m, 2H), 3.19 (s, 3H), 3.12 (d, J=5.1 Hz, 1H), 1.92-2.04 (m, 2H), 1.78 (d, J=10.5 Hz, 2H), 1.35-1.52 (m, 2H), 1.05-1.18 (m, 2H). $^1$H NMR (DMSO-$d_6$, 400 MHz; measured at 80° C.): δ ppm 8.53 (d, J=28.1 Hz, 1H), 7.47 (br. s., 1H), 3.93-4.08 (m, 1H), 3.16 (d, J=5.5 Hz, 1H), 1.91-2.07 (m, 2H), 1.84 (d, J=10.5 Hz, 2H), 1.37-1.54 (m, 2H), 1.10-1.21 (m, 2H).

B. (1S,3R)-3-Aminocycloheptanol hydrochloride

To vigorously stirring methanol (60 mL) at 0° C. was added acetyl chloride (5.11 mL, 72.0 mmol) and the resulting mixture was allowed to stir for 30 min. tert-Butyl (1R,3S)-3-hydroxy-cycloheptylcarbamate (5500 mg, 23.98 mmol; synthesis described herein) was added and the resulting mixture was then stirred overnight at room temperature. The reaction mixture was concentrated under reduced pressure to an oil that was triturated with ethyl ether (100 mL) overnight. The solids were filtered, rinsed with diethyl ether, and dried under reduced pressure for a few hours to afford (1S,3R)-3-aminocycloheptanol hydrochloride (3780 mg, 22.82 mmol, 95% yield) as a white solid. $^1$H NMR (400 MHz, DMSO-$d_6$) δ ppm 7.85 (br. s., 3H), 4.69 (d, J=7.42 Hz, 1H), 3.64 (t, J=8.79 Hz, 1H), 3.07-3.21 (m, 1H), 2.05 (d, J=12.89 Hz, 1H), 1.69-1.94 (m, 2H), 1.28-1.68 (m, 7H). MS (ESI) m/z 130.1 [M+1]$^+$.

C. 4-((1R,3S)-3-Hydroxycycloheptylamino)-2-((1r,4R)-4-methoxycyclohexylamino)pyrimidine-5-carbonitrile To a stirring solution of 4-chloro-2-((1r,4r)-4-methoxycyclohexylamino)pyrimidine-5-carbonitrile (200 mg, 0.750 mmol) and (1S,3R)-3-aminocycloheptanol hydrochloride (186 mg, 1.125 mmol) in DMF (4 mL) was added DIEA (0.458 mL, 2.62 mmol). The resulting mixture was stirred at 70° C. for 4 h and then allowed to cool to ambient temperature overnight. DMF was removed under reduced pressure and the remaining residue was purified using silica gel chromatography (0-50% ethyl acetate+10% 7 N ammonia in methanol in hexanes) to afford 4-((1R,3S)-3-hydroxycycloheptylamino)-2-((1r,4R)-4-methoxycyclohexylamino)pyrimidine-5-carbonitrile (210 mg, 0.584 mmol, 78% yield). $^1$H NMR (400 MHz, DMSO-$d_6$) δ ppm 8.07-8.23 (m, 1H), 7.06-7.61 (m, 2H), 4.49-4.63 (m, 1H), 4.00-4.27 (m, 1H), 3.55-3.82 (m, 2H), 3.23 (s, 3H), 3.00-3.16 (m, 1H), 1.07-2.08 (m, 18H). MS (ESI) m/z 360.5 [M+1]$^+$.

Example 20: 2-((1r,4R)-4-Ethoxycyclohexylamino)-4-((1R,3S)-3-hydroxy-3-methylcyclohexylamino)pyrimidine-5-carbonitrile

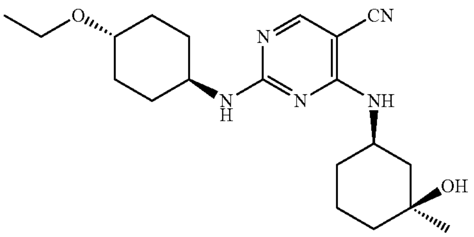 [SMILES: CCO[C@H]1CC[C@H](Nc2ncc(C#N)c(N[C@@H]3CCC[C@](C)(O)C3)n2)CC1]

A. (1r, 4r)-4-(Tritylamino)cyclohexanol

To a cooled (0° C.) solution of (1r, 4r)-4-aminocyclohexanol (10 g, 87 mmol) in DCM (250 mL) and TEA (11.2 g, 112 mmol) was added trityl chloride (24.2 g, 87 mmol). The resulting mixture was stirred at room temperature overnight. Saturated aqueous sodium bicarbonate solution was added to quench the reaction and the aqueous layer was extracted with ethyl acetate. The combined extracts were washed with brine, dried over anhydrous sodium sulfate. Filtration and concentration under vacuum gave crude product, which was purified by silica gel column chromatography (50% ethyl acetate in DCM) to afford the title compound (24.8 g, 70 mmol, 80% yield) as a white solid. MS (ESI) m/z 243.2 [M−4-aminocyclohexanol]$^+$.

B. (1r,4r)-4-Ethoxy-N-tritylcyclohexanamine

To a cooled (0° C.) solution of (1r,4r)-4-(tritylamino)cyclohexanol (15.0 g, 42 mmol) in DMF (100 mL) was added sodium hydride (3.4 g, 84 mmol, 60% in mineral oil) and ethyl iodide (7.2 g, 46 mmol) at 0° C. The resulting mixture was stirred at room temperature overnight under nitrogen atmosphere. Saturated aqueous ammonia chloride solution was added to quench the reaction and the aqueous layer was extracted with ethyl acetate. The combined extracts were washed with brine and dried over anhydrous sodium sulfate. Filtration and concentration under vacuum gave crude product, which was purified by silica gel column chromatography (5% ethyl acetate in petroleum ether) to afford the title compound (11.9 g, 31 mmol, 79% yield) as a white solid. $^{1}$H NMR (400 MHz, $CDCl_3$) δ ppm 7.56-7.54 (m, 6H), 7.27-7.20 (m, 6H), 7.18-7.14 (m, 3H), 3.42-3.38 (q, 2H), 3.09-3.04 (m, 1H), 2.25-2.21 (m, 1H), 1.80-1.78 (m, 2H), 1.38 (s, 1H), 1.27-1.25 (m, 2H), 1.10 (t, J=7.2 Hz, 3H), 1.01-0.88 (m, 4H); MS (ESI) m/z 243.2 [M−4-ethoxycyclohexanamine]$^+$.

C. (1r,4r)-4-Ethoxycyclohexanamine

To a cooled (0° C.) solution of (1r, 4r)-4-ethoxy-N-tritylcyclohexanamine (13.1 g, 34 mmol) in DCM (10 mL) was added trifluoroacetic acid (18 mL) at 0° C. The resulting mixture was dark red. Triethylsilane (5 mL) was added until the resulting mixture was colourless. The reaction was stirred at 0° C. for additional 15 minutes. After removal of all volatiles in vacuo, the residue was further dried under high vacuum for 2 h to give the crude product as a white solid. The crude product was dissolved in ethyl acetate and aqueous hydrochloride solution (150 mL, 0.25 mol/L). The organic layer was removed and the aqueous layer was washed with ethyl acetate twice. Concentration of the aqueous layer under high vacuum gave the crude hydrochloride salt of the desired amine (6.1 g, 34 mmol, 100% yield) as a white solid, which was used for the next step without further purification. MS (ESI) m/z 144.0 [M+H]$^-$.

D. 4-Chloro-2-((1r,4r)-4-ethoxycyclohexylamino) pyrimidine-5-carbonitrile

To a cooled (−60° C.) solution of (1r,4r)-4-ethoxycyclohexanamine (6.82 g, 37.9 mmol) and 2,4-dichloropyrimidine-5-carbonitrile (6 g, 34.5 mmol) in THF (115 mL) was added DIEA (15.02 mL, 86 mmol) dropwise. The resulting mixture was stirred at −60° C. for 1 h and then allowed to warm to room temperature overnight. The resulting mixture was concentrated and the residue was purified by silica gel column chromatography (14% ethyl acetate in petroleum ether). The product fractions were combined and concentrated to afford 2-chloro-4-((1r,4r)-4-ethoxycyclohexylamino)-pyrimidine-5-carbonitrile (3.33 g, 11.86 mmol, 34.4% yield) and 4-chloro-2-((1r,4r)-4-ethoxycyclohexylamino)pyrimidine-5-carbonitrile (5.5 g, 19.59 mmol, 56.8% yield;

$^{1}$H NMR (400 MHz, DMSO-$d_6$) δ ppm 8.62-8.87 (m, 2H), 3.61-3.86 (m, 1H), 3.44 (dd, J=7.03, 2.34 Hz, 2H), 3.12-3.26 (m, 1H), 1.75-2.15 (m, 4H), 1.13-1.44 (m, 4H), 1.08 (td, J=6.93, 1.76 Hz, 3H); MS (ESI) m/z 281.1 [M+1]$^+$) as white solids. The regiochemistry of the major isomer was confirmed by comparison with the proton spectra of 4-chloro-2-((1r,4r)-4-methoxycyclohexylamino)pyrimidine-5-carbonitrile (synthesis described herein).

E. (1S,3R)-3-(Dibenzylamino)cyclohexanol

To a suspension of (1S,3R)-3-aminocyclohexanol (5 g, 43.4 mmol; prepared as described in Tetrahedron: Asymmetry 15 (2004) 2051-2056) and sodium bicarbonate (12.03 g, 143 mmol) in ethanol (100 mL) was added (chloromethyl) benzene (15.01 mL, 130 mmol) at room temperature. The reaction mixture was heated at 75° C. overnight. Upon completion of the reaction as indicated by LCMS and TLC the reaction mixture was filtered and the filtrate concentrated. The residue was then dissolved in DCM (250 mL) and washed with aqueous sodium hydroxide solution (1N, 2×100 mL) and brine (2×100 mL). The combined organic layers were dried over anhydrous magnesium sulfate, concentrated, and purified by silica gel chromatography (0%-80% ethyl acetate in hexanes) to yield (1S,3R)-3-(dibenzylamino)cyclohexanol (11.70 g, 91%) as a thick yellow oil. $^{1}$H NMR (400 MHz, DMSO-$d_6$) δ ppm 7.26-7.37 (m, 8H), 7.17-7.22 (m, 2H), 4.56 (d, J=4.30 Hz, 1H), 3.57 (s, 4H), 3.16-3.26 (m, 1H), 2.41 (tt, J=3.17, 11.86 Hz, 1H), 1.99-2.06 (m, 1H), 1.72 (d, J=8.20 Hz, 2H), 1.63-1.69 (m, 1H), 1.18-1.28 (m, 2H), 0.98 (t, 2H); MS (ESI) m/z 296.4 [M+1]$^+$.

F. (R)-3-(Dibenzylamino)cyclohexanone

Oxalyl chloride (3.81 mL, 43.6 mmol) was dissolved in dry DCM (150 mL) and cooled to −78° C. DMSO (6.75 mL, 95.0 mmol) in dry DCM (20 mL) was added dropwise to the reaction mixture and the reaction was stirred for 15 minutes at −78° C. Next, (1S,3R)-3-(dibenzylamino)-cyclohexanol (11.7 g, 39.6 mmol) in dry DCM (100 mL) was added dropwise using an addition funnel and the reaction was stirred at −78° C. for 15 minutes. TEA (27.6 mL, 198 mmol) was then added and the reaction was stirred at −78° C. for 1 h. The dry-ice bath was removed and the reaction mixture was allowed to warm to room temperature and stir overnight. The reaction mixture was washed with brine (5×500 mL), the organic layer was separated, dried over magnesium sulfate and concentrated to yield (R)-3-(dibenzylamino) cyclohexanone (10.2 g, 88%) as a tan solid. $^{1}$H NMR (400 MHz, DMSO-$d_6$) δ ppm 7.26-7.39 (m, 8H), 7.17-7.25 (m, 2H), 3.56-3.70 (m, 4H), 2.71-2.81 (m, 1H), 2.60-2.69 (m, 1H), 2.25-2.42 (m, 2H), 2.04-2.11 (m, 1H), 1.88-1.99 (m, 2H), 1.69-1.82 (m, 1H), 1.18-1.33 (m, 1H); MS (ESI) m/z 294.4 [M+1]$^+$.

G. (3R,5R)—N,N-Dibenzyl-1-oxaspiro[2.5]octan-5-amine and (3S,5R)—N,N-dibenzyl-1-oxaspiro[2.5] octan-5-amine To a yellow solution of (R)-3-(dibenzylamino)cyclohexanone (10.2 g, 34.8 mmol) and trimethylsulfonium iodide (14.90 g, 73.0 mmol) in dry DMSO (260 mL) was added sodium tert-butoxide (6.68 g, 69.5 mmol) portion wise at room temperature under a nitrogen atmosphere. The reaction mixture was stirred at room temperature overnight under nitrogen. Upon completion of the reaction as indicated by LCMS and TLC the reaction was quenched with 1 L of water and extracted with ethyl acetate (2×800 mL). The organic phase was dried over sodium sulfate, concentrated and dried to yield a mixture of (3R,5R)—N,N-dibenzyl-1-oxaspiro[2.5]octan-5-amine and (3S,5R)—N,N-dibenzyl-1-oxaspiro[2.5]octan-5-amine (10.6 g, 99%) as a yellow solid. The mixture was used as is in the next step without further purification. MS (ESI) m/z 308.4 [M+1]$^+$.

H. (1R,3R)-3-(Dibenzylamino)-1-methylcyclohexanol and (1S,3R)-3-(dibenzylamino)-1-methylcyclohexanol To a mixture of solid lithium aluminum hydride (95% LAH, 3.47 g, 87 mmol) in THF (230 mL) was added very slowly a clear pale yellow solution of the above described mixture of (3R,5R)—N,N-dibenzyl-1-oxaspiro[2.5]octan-5-amine and (3S,5R)—N,N-dibenzyl-1-oxaspiro[2.5]octan-5- amine (10.69 g, 34.8 mmol) in THF (230 mL) at 0° C. under nitrogen. The reaction mixture was brought to room temperature and then heated at 65° C. overnight under nitrogen. Upon completion of the reaction as indicated by LCMS and TLC the reaction mixture was transferred to a round-bottom flask and then diluted with THF (100 mL), cooled to 0° C. and while stirring a saturated solution of aqueous sodium sulfate was added drop wise until the reaction stopped bubbling. The mixture was stirred overnight at room temperature and then was filtered through Celite in a coarse fritted funnel into a round-bottom flask. The filter cake was washed thoroughly with THF and the colorless filtrate was concentrated under reduced pressure. The resulting crude mixture was purified by silica gel chromatography (0%-60% ethyl acetate in hexanes) to yield the faster eluting isomer (1R,3R)-3-(dibenzylamino)-1-methylcyclohexanol (5.5 g, 50%; $^1$H NMR (400 MHz, DMSO-$d_6$) δ ppm 7.25-7.36 (m, 8H), 7.15-7.21 (m, 2H), 3.85 (s, 1H), 3.55 (s, 4H), 2.86 (tt, J=3.37, 12.06 Hz, 1H), 1.70-1.81 (m, 2H), 1.38-1.49 (m, 3H), 1.32 (t, J=12.30 Hz, 1H), 1.15-1.27 (m, 2H), 1.12 (s, 3H); MS (ESI) m/z 310.4 [M+1]$^+$) as a white solid, and then the slower eluting isomer (1S,3R)-3-(dibenzylamino)-1-methylcyclohexanol (5.1 g, 47%; $^1$H NMR (400 MHz, DMSO-$d_6$) δ □ppm 7.26-7.36 (m, 8H), 7.16-7.23 (m, 2H), 4.38 (s, 1H), 3.49-3.63 (m, 4H), 2.46 (d, J=8.98 Hz, 1H), 1.67-1.80 (m, 2H), 1.59 (d, J=9.76 Hz, 1H), 1.33-1.47 (m, 2H), 1.17-1.30 (m, 2H), 0.98-1.13 (m, 1H), 0.89 (s, 3H); MS (ESI) m/z 310.4 [M+1]$^+$) as a thick yellow oil. A COSY NMR experiment and the $^1$H NMR data reported above were used to verify the regiochemistry of the amino alcohols. For the slower eluting isomer an NOE (via NOESY experiment) was observed between the protons on the amino group cyclohexyl-carbon and the methyl group carbon. This verifies a cis relationship between these two functional groups (a trans relationship, lacking this spacial proximity, would not show such an effect), which in turn confirms this isomer to be (1S,3R)-3-(dibenzylamino)-1-methylcyclohexanol.

I. (1S,3R)-3-Amino-1-methylcyclohexanol

A solution of (1S,3R)-3-(dibenzylamino)-1-methylcyclohexanol (5.0 g, 16.16 mmol) in ethanol (150 mL) was treated with palladium hydroxide on carbon and stirred under a balloon filled with hydrogen gas overnight. Upon completion of the reaction as indicated by LCMS the reaction mixture was filtered through a pad of celite and the filtrate concentrated to yield (1R,3R)-3-amino-1-methylcyclohexanol (1.3 g, 62%) as a thick yellow oil. $^1$H NMR (400 MHz, DMSO-$d_6$) δ ppm 2.87 (br. s., 1H), 1.64-1.74 (m, 1H), 1.47-1.59 (m, 2H), 1.21-1.40 (m, 4H), 1.11-1.20 (m, 1H), 1.02 (s, 3H); MS (ESI) m/z 130.2 [M+1]$^+$.

J. 2-((1r,4R)-4-Ethoxycyclohexylamino)-4-((1R,3S)-3-hydroxy-3-methylcyclohexylamino)pyrimidine-5-carbonitrile 4-Chloro-2-((1r,4r)-4-ethoxycyclohexylamino)pyrimidine-5-carbonitrile (350 mg, 1.247 mmol), (1S,3R)-3-amino-1-methylcyclohexanol (242 mg, 1.870 mmol), and DIEA (0.327 mL, 1.870 mmol) were dissolved in DMF (3.5 mL) in a screw-capped vial. The reaction mixture was stirred at 70° C. for 4 h. After completion of the reaction as indicated by LCMS and TLC the reaction mixture was condensed and the resulting residue was purified by silica gel chromatography using a gradient of 0-100% ethyl acetate in hexanes. The desired product fractions were combined and concentrated to give 2-((1r,4R)-4-ethoxycyclohexylamino)-4-((1R,3S)-3-hydroxy-3-methylcyclohexylamino)pyrimidine-5-carbonitrile (0.356 g, 76% yield, 98.0% pure) as a white solid. $^1$H NMR (400 MHz, DMSO-$d_6$) δ ppm 8.09-8.24 (m, 1H), 7.28-7.63 (m, 2H), 4.71-4.90 (m, 1H), 4.21 (d, J=3.51 Hz, 1H), 3.57-3.78 (m, 1H), 3.43 (q, J=7.03 Hz, 2H), 3.11-3.23 (m, 1H), 1.78-2.02 (m, 4H), 1.48-1.74 (m, 5H), 1.16-1.47 (m, 6H), 1.11-1.16 (m, 4H), 1.08 (t, 3H); MS (ESI) m/z 374.5 [M+1]$^+$.

Example 21: 2-((1r,4R)-4-Ethoxycyclohexylamino)-4-((1R,3S)-3-hydroxycyclohexylamino)pyrimidine-5-carbonitrile

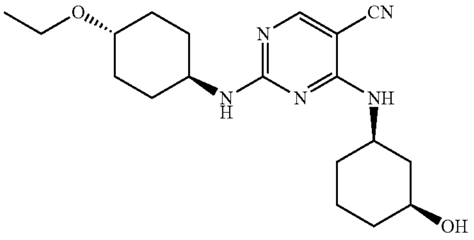 [SMILES: CCO[C@H]1CC[C@H](Nc2ncc(C#N)c(N[C@@H]3CCC[C@H](O)C3)n2)CC1]

A. 2-Chloro-4-((1R,3S)-3-hydroxycyclohexylamino)pyrimidine-5-carbonitrile and 4-chloro-2-((1R,3S)-3-hydroxycyclohexylamino)pyrimidine-5-carbonitrile 2,4-Dichloropyrimidine-5-carbonitrile (900 mg, 5.17 mmol) in anhydrous ethanol (5 mL) and (1R,3S)-3-aminocyclohexanol (624 mg, 5.43 mmol; prepared as described in Tetrahedron: Asymmetry 15 (2004) 2051-2056) in anhydrous ethanol (5 mL) were mixed at −60° C. and then DIEA (1.0 g, 7.75 mmol) was added dropwise. The mixture was stirred at −60° C. for 1 h and then at room temperature overnight. Volatile fractions were removed and the residue was purified on silica gel (eluting with 9.1%-33% ethyl acetate in petroleum ether) to give 4-chloro-2-((1R,3S)-3-hydroxycyclohexylamino)-pyrimidine-5-carbonitrile (600 mg, 2.38 mmol, yield 46%) as a white solid and 2-chloro-4-((1R,3S)-3-hydroxycyclohexylamino)pyrimidine-5-carbonitrile (270 mg, 1.07 mmol, yield 20%; $^1$H NMR (400 MHz, DMSO-$d_6$) δ ppm 8.55 (s, 1H), 8.46 (d, J=7.81 Hz, 1H), 4.83 (d, J=3.90 Hz, 1H), 3.95-4.11 (m, 1H), 3.45-3.61 (m, 1H), 1.93 (d, J=11.71 Hz, 1H), 1.60-1.84 (m, 3H), 1.03-1.50 (m, 4H); MS (ESI) m/z 253.2 [M+1]$^+$) as a white solid. The regiochemistry of the minor regioisomer was confirmed in step B below.

B. (1S,3R)-3-(5-(Aminomethyl)pyrimidin-4-ylamino)cyclohexanol

To a mixture of 2-chloro-4-((1R,3S)-3-hydroxycyclohexyl-amino)pyrimidine-5-carbonitrile (70 mg, 0.277 mmol) and ammonium hydroxide (500 μl, 12.84 mmol) in ethanol (4 mL) was added Raney nickel (16.26 mg, 0.277 mmol). The resulting mixture was evacuated and then stirred under a balloon of hydrogen at atmospheric pressure and ambient temperature overnight. Ethanol was removed in vacuo and the remaining residue was purified using reverse-phased preparative HPLC (5-80% acetonitrile+0.1% TFA in water+0.1% TFA, over 30 min). Fractions containing product were concentrated under reduced pressure. The resulting residue was redissolved in methanol (5 mL), passed over a Varian StratoSpheres HCO3 resin SPE tube for TFA removal (0.9 mmol bicarbonate equiv.), and then concentrated under reduced pressure to afford the title compound as an oil that was used for NMR purposes only. The regiochemistry was confirmed by the presence of two distinct aromatic peaks in the $^1$H NMR spectrum and the observation of an NOE signal between the C5 methylene hydrogens and only one of these aromatic peaks in the NOESY spectrum. $^1$H NMR (400 MHz, DMSO-$d_6$) δ ppm 8.32 (s, 1H), 7.92 (s, 1H), 7.32 (d, J=7.48 Hz, 1H), 4.67 (d, J=3.87 Hz, 1H), 3.88-4.01 (m, 1H), 3.59 (s, 2H), 3.49 (d, J=3.61 Hz, 1H), 2.06-2.16 (m, 1H), 1.99 (br. s., 2H), 1.81 (t, J=13.28 Hz, 2H), 1.69 (dt, J=13.35, 3.51 Hz, 1H), 1.01-1.35 (m, 4H). MS (ESI) m/z 223.5 $[M+1]^+$.

C. 2-((1r,4R)-4-Ethoxycyclohexylamino)-4-((1R,3S)-3-hydroxycyclohexylamino)pyrimidine-5-carbonitrile A mixture of 2-chloro-4-((1R,3S)-3-hydroxycyclohexylamino)pyrimidine-5-carbonitrile (270 mg, 1.07 mmol), (1r,4r)-4-ethoxycyclohexanamine hydrochloride (289 mg, 1.60 mmol; synthesis described herein) and cesium carbonate (698 mg, 2.14 mmol) in anhydrous n-butanol (10 mL) was stirred at 80° C. for 1 day and then at 120° C. for 5 h. The mixture was extracted between water and DCM. The organic layer was combined, concentrated and purified on silica gel (eluting with 9.1%-33% ethyl acetate in petroleum ether) to give 2-((1r,4R)-4-ethoxycyclohexyl-amino)-4-((1R,3S)-3-hydroxycyclohexylamino)pyrimidine-5-carbonitrile (202 mg, 0.56 mmol, yield 52%) as a white powder. $^1$H NMR (400 MHz, DMSO-$d_6$): δ ppm 8.11 (s, 1H), 7.10 (s, 1H), 6.95 (s, 1H), 4.51 (d, J=3.6, 1H), 4.05 (s, 1H), 3.67 (s, 1H), 3.58-3.55 (m, 1H), 3.47 (q, J=6.8, 2H), 3.24-3.19 (m, 1H), 2.00-1.90 (m, 5H), 1.73 (s, 3H), 1.47-1.25 (m, 8H), 1.10 (t, J=7.2, 3H); MS(ESI): m/z 359.9 $[M+1]^+$.

Example 22: 2-(Cyclohexylamino)-4-((1R,3S)-3-hydroxycyclohexylamino)-pyrimidine-5-carbonitrile

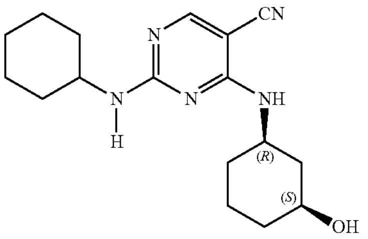

A. 2-(Cyclohexylamino)-4-((1R,3S)-3-hydroxycyclohexyl-amino)pyrimidine-5-carbonitrile A solution of cyclohexanamine (0.181 mL, 1.583 mmol) in DMSO (5 mL), 2-chloro-4-((1R,3S)-3-hydroxycyclohexylamino)-pyrimidine-5-carbonitrile (0.200 g, 0.791 mmol; synthesis described herein) and DIEA (0.276 mL, 1.583 mmol) was heated at 70° C. overnight. After completion of reaction as indicated by LCMS and TLC the reaction mixture was allowed to cool to room temperature and concentrated. The resulting crude was purified by silica gel chromatography using a gradient of 0%-70% ethyl acetate (containing 10% ammonia saturated methanol) in hexanes. The desired product fractions were combined and concentrated to yield 2-(cyclohexylamino)-4-((1R,3S)-3-hydroxycyclohexylamino)-pyrimidine-5-carbonitrile (0.220 g, 88% yield, 98.1% pure) as a pale yellow solid.

$^1$H NMR (400 MHz, DMSO-$d_6$) δ 8.08-8.21 (m, 1H), 7.08-7.56 (m, 2H), 4.74 (d, J=3.90 Hz, 1H), 3.93-4.13 (m, 1H), 3.44-3.77 (m, 2H), 1.83-2.02 (m, 2H), 1.65-1.82 (m, 6H), 1.58 (d, J=14.84 Hz, 1H), 1.32-1.45 (m, 2H), 1.08-1.30 (m, 7H); MS (ESI) m/z 316.4 $[M+1]^+$.

Example 23: 4-((1R,3S)-3-Hydroxycycloheptylamino)-2-((1R,4R)-4-(2,2,2-trifluoroethoxy)cyclohexylamino)pyrimidine-5-carbonitrile

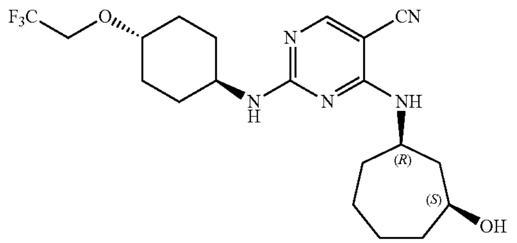

A. 4-((1R,3S)-3-Hydroxycycloheptylamino)-2-(methylthio)pyrimidine-5-carbonitrile To a stirring solution of 4-chloro-2-(methylthio)pyrimidine-5-carbonitrile (0.4 g, 2.155 mmol) and (1S,3R)-3-aminocycloheptanol hydrochloride (0.428 g, 2.59 mmol; synthesis described herein) in DMF (3 mL) was added DIEA (1.126 mL, 6.46 mmol) and stirred at 60° C. for 1 h. LCMS shows the reaction to be completed. The reaction mixture was cooled to room temperature, and poured into water (50 mL). The suspension was stirred for five minutes, then filtered to afford 4-((1R,3S)-3-hydroxycycloheptylamino)-2-(methylthio)pyrimidine-5-carbonitrile (0.404 g, 1.451 mmol, 67.4% yield) as an off-white solid; $^1$H NMR (DMSO-$d_6$, 400 MHz): δ ppm 8.39 (s, 1H), 8.00 (d, J=7.4 Hz, 1H), 4.63 (d, J=3.9 Hz, 1H), 4.21 (br. s., 1H), 3.74 (td, J=8.5, 4.1 Hz, 1H), 2.47 (s, 3H), 1.66-1.97 (m, 5H), 1.35-1.66 ppm (m, 5H); MS (ESI) m/z 138.1 $[M+1]^+$.

B. 4-((1R,3S)-3-Hydroxycycloheptylamino)-2-((1r,4r)-4-(2,2,2-trifluoroethoxy)cyclohexylamino)pyrimidine-5-carbonitrile 4-((1R,3S)-3-Hydroxycycloheptylamino)-2-(methylthio)pyrimidine-5-carbonitrile (381 mg, 1.369 mmol) was dissolved in NMP (7 mL). At 0° C., mCPBA (675 mg, 3.01 mmol) was then added portionwise and the reaction was stirred at room temp for 90 min. To the reaction mixture was added (1r,4r)-4-(2,2,2-trifluoroethoxy)cyclohexanamine (0.405 g, 2.054 mmol) (prepared as described herein) and DIEA (0.956 mL, 5.48 mmol) and stirred for 5 min at room temp. The reaction mixture was further stirred at 80° C. for 30 min after which LCMS showed the completion of the reaction. The reaction mixture was cooled down to room temperature and diluted with water (30 mL). The mixture was let standing at room temperature for 4 h during which the desired product precipitated out. The product was filtered and the collected solid was washed with water then hexanes and dried under vacuum to give 4-((1R,3S)-3-hydroxycycloheptylamino)-2-((1R,4R)-4-(2,2,2-trifluoroethoxy)-cyclohexylamino)pyrimidine-5-carbonitrile (0.444 g, 1.039 mmol, 76% yield) as a tan solid; $^1$H NMR (DMSO-$d_6$, 400 MHz): δ ppm 8.08-8.22 (m, 1H), 7.06-7.59 (m, 2H), 4.51-4.60 (m, 1H), 4.01-4.24 (m, 1H), 3.54-3.78 (m, 2H), 3.44 (q, J=7.0 Hz, 2H), 3.11-3.24 (m, 1H), 1.88-2.05 (m, 4H), 1.12-1.88 (m, 14H), 1.08 ppm (t, J=7.0 Hz, 3H); MS (ESI) m/z 374.2 $[M+1]^+$.

Example 24: 4-((1R,3S)-3-Hydroxycycloheptylamino)-2-((1r,4R)-4-hydroxycyclohexylamino)pyrimidine-5-carbonitrile

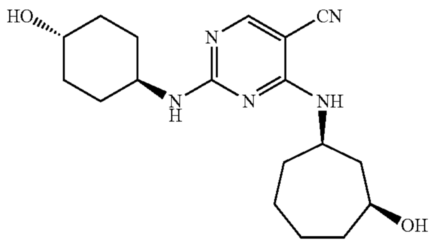 [SMILES: N#Cc1cnc(N[C@H]2CC[C@H](O)CC2)nc1N[C@@H]1CCCC[C@H](O)C1]

A. 4-((1R,3S)-3-Hydroxycycloheptylamino)-2-(methylsulfonyl)-pyrimidine-5-carbonitrile 4-((1R,3S)-3-Hydroxycycloheptylamino)-2-(methylthio) pyrimidine-5-carbonitrile (457 mg, 1.642 mmol; synthesis described herein) was dissolved in NMP (10 mL). At 0° C., mCPBA (736 mg, 3.28 mmol) was then added portionwise and the reaction was stirred for 2 h at room temperature. LCMS indicated consumption of the starting material and formation of sulfone intermediate. This reaction was carried onto the next step without further purification. MS (ESI) m/z 311.1 $[M+1]^+$.

B. 4-((1R,3S)-3-Hydroxycycloheptylamino)-2-((1r,4R)-4-hydroxycyclohexylamino)pyrimidine-5-carbonitrile To the reaction mixture of the previous step was added (1r,4r)-4-aminocyclohexanol hydrochloride (0.374 g, 2.465 mmol) and DIEA (1.435 mL, 8.22 mmol). The reaction mixture was stirred at 80° C. for 1 h and then the reaction mixture was cooled to room temperature. The solvent was evaporated under reduced pressure and the resulting residue was purified by flash chromatography (0-10% ammonia saturated methanol in DCM) to afford 4-((1R,3S)-3-hydroxycycloheptylamino)-2-((1r,4R)-4-hydroxycyclohexylamino)pyrimidine-5-carbonitrile (0.250 g, 0.724 mmol, 44.0% yield) as a tan solid. $^1$H NMR (400 MHz, DMSO-$d_6$) δ 8.07-8.21 (m, 1H), 7.05-7.55 (m, 2H), 4.52-4.59 (m, 2H), 4.02-4.25 (m, 1H), 3.51-3.79 (m, 2H), 3.35-3.42 (m, 1H), 1.75-1.97 (m, 8H), 1.39-1.70 (m, 6H), 1.14-1.31 (m, 4H); MS (ESI) m/z 346.1 $[M+1]^+$.

Example 25: 2-(4-Hydroxybicyclo[2.2.2]octan-1-ylamino)-4-(isopropylamino)pyrimidine-5-carboxamide

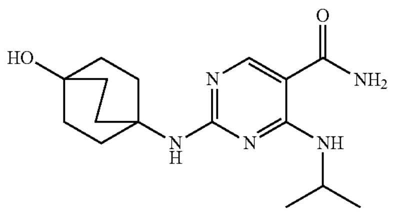 [SMILES: CC(C)Nc1nc(NC23CCC(O)(CC2)CC3)ncc1C(N)=O]

A. Dimethyl cyclohexane-1,4-dicarboxylate

To a stirred solution of cyclohexane-1,4-dicarboxylic acid (100 g, 0.58 mol) in anhydrous methanol (800 mL) was added sulfurous dichloride (208 g, 1.75 mol) at 0° C. The reaction mixture was stirred at room temperature overnight. The solution was then concentrated and the residue was poured into water. The mixture was extracted with ethyl acetate (3×200 mL). The combined organic layers were washed with brine, dried over anhydrous sodium sulfate and filtered. Concentration under reduced pressure afforded dimethyl cyclohexane-1,4-dicarboxylate (105 g, 0.53 mol, 90.5% yield), which was used in the next step without further purification.

B. Dimethyl 1-(2-chloroethyl)cyclohexane-1,4-dicarboxylate

To a solution of diisopropylamine (88 mL, 0.62 mol) in anhydrous THF (500 mL) was added n-butyl lithium (240 mL, 0.6 mol, 2.5 M solution in hexane) over 20 minutes at −78° C. The mixture was stirred at 0° C. under nitrogen for 30 min. To a mixture of dimethyl cyclohexane-1,4-dicarboxylate (100 g, 0.5 mol) and hexamethylphosphoramide (360 mL, 2 mol) in anhydrous THF (800 mL) was added lithium diisopropylamine (freshly prepared above) over 30 min at −40° C. After stirring for 1 h at this temperature, 1-bromo-2-chloroethane (42 mL, 0.5 mol) was added over 1 h. The mixture was stirred for 3 h at −78° C., then warmed to room temperature and stirred overnight. To the reaction mixture was added aqueous hydrochloric acid (3 N, 420 mL) and the mixture was stirred for 10 min. The solvent was removed by evaporation under reduced pressure. The aqueous layer was extracted with ethyl acetate (3×200 mL), and the combined extracts were washed with brine (2×300 mL) and dried over sodium sulfate. Concentration under reduced pressure afforded dimethyl 1-(2-chloroethyl)cyclohexane-1,4-dicarboxylate (116 g, 88% yield), which was used in the next step without further purification. $^1$H NMR (400 MHz, $CDCl_3$) δ ppm 3.72 (s, 3H), 3.65 (s, 3H), 3.46-3.42 (m, 2H), 2.33-2.21 (m, 3H), 2.05-1.85 (m, 4H), 1.58-1.42 (m, 2H), 1.25-1.15 (m, 2H).

C. Dimethyl bicyclo[2.2.2]octane-1,4-dicarboxylate

To a solution of diisopropylamine (77 mL, 0.54 mol) in anhydrous THF (500 mL) was added n-butyl lithium (210 mL, 0.53 mol, 2.5 M solution in hexane) over 20 min at −78° C. Then the mixture was stirred at 0° C. under nitrogen for 30 min. To a mixture of dimethyl 1-(2-chloroethyl)cyclohexane-1,4-dicarboxylate (116 g, 0.44 mol) and hexamethylphosphoramide (317 ml, 1.7 mol) in anhydrous THF (800 mL) was added lithium diisopropylamine (freshly prepared above) over 30 min at −40° C. The mixture was stirred for 2 h at −78° C. and then stirred overnight allowing warming to room temperature. To the reaction mixture was added saturated aqueous ammonium chloride (200 mL) and the mixture was stirred for 10 min. The solvent was removed by evaporation under reduced pressure. The aqueous layer was extracted with ethyl acetate (3×200 mL). The combined extracts were washed with brine (2×300 mL) and dried over sodium sulfate. Concentration under reduced pressure gave crude product, which was purified by silica gel column chromatography (10% ethyl acetate in petroleum ether) to afford the title compound (58 g, 0.25 mol, 50% yield in two steps). $^1$H NMR (400 MHz, $CDCl_3$) δ ppm 3.65 (s, 6H), 1.81 (s, 12H).

D. 4-(Methoxycarbonyl)bicyclo[2.2.2]octane-1-carboxylic acid

A solution of dimethyl bicyclo[2.2.2]octane-1,4-dicarboxylate (58.0 g, 0.25 mol) in methanol (600 mL) was heated under reflux. To this solution was added a solution of potassium hydroxide (9.8 g, 0.175 mol) in methanol (100 mL) and water (12 mL) over 30 minutes. The reaction mixture was refluxed for 24 h. The solvent was then removed and the residue was diluted with water. The aqueous solution was extracted with ethyl acetate (2×200 mL) to recover starting material (22.0 g), and the aqueous layer was acidified to pH 3 by addition of hydrochloric acid. A precipitate was formed and extracted with ethyl acetate (3×300 mL). The combined extracted were washed with brine, dried over sodium sulfate and concentrated to give the titled product (30.0 g, 0.14 mol, 55% yield). $^1$H NMR (400 MHz, $CDCl_3$) δ ppm 3.65 (s, 3H), 1.81 (s. 12H); MS (ESI) m/z 211.3 [M−H]$^-$.

E. Methyl 4-bromobicyclo[2.2.2]octane-1-carboxylate

To a suspension of 4-(methoxycarbonyl) bicyclo[2.2.2]octane-1-carboxylic acid (11.0 g, 51.8 mmol) in acetone (80 mL) was added 1 M aqueous sodium hydroxide solution (51.8 mL, 51.8 mmol). Then a solution of silver nitrate (8.8 g, 51.9 mol) in water (10 mL) was added. The formed precipitate was collected by filtration, washed with water, acetone and diethyl ether and dried in vacuo at 115° C. for 4 h. The obtained (4-(methoxycarbonyl)-bicyclo[2.2.2]octane-1-carbonyloxy)silver (15.3 g, 47.9 mmol) was suspended in hexane (125 mL), then bromine (7.7 g, 48.1 mmol) was added to the reaction mixture over 30 minutes at room temperature. After the addition was complete, the reaction mixture was stirred at room temperature for another 30 minutes. The reaction mixture was filtered to remove the solid, and the filter cake was washed with hexane (4×150 mL). The combined organic filtrates were washed with saturated sodium bicarbonate (2×150 mL) and brine (200 mL), and then dried over magnesium sulfate. Concentration under vacuum gave crude product, which was purified by silica gel column chromatography (5% ethyl acetate in petroleum ether) to afford the title compound (4.2 g, 0.17 mol, 33% yield in two steps). $^1$H NMR (400 MHz, $CDCl_3$) δ ppm 3.64 (s, 3H), 2.27-2.20 (m, 6H), 1.98-1.94 (m. 6H).

F. 4-Hydroxybicyclo[2.2.2]octane-1-carboxylic acid

Methyl 4-bromobicyclo [2.2.2]octane-1-carboxylate (17.0 g, 69.0 mol) was refluxed in aqueous sodium hydroxide solution (1500 mL, 1%) for 24 h. After cooling, the reaction solution was acidified with hydrochloric acid (6 N, 100 mL) and extracted with diethyl ether (6×500 mL). The combined ether layers were dried over magnesium sulfate and concentrated to afford the title compound (10.4 g, 61.1 mmol, 89% yield), which was used in the next step without further purification. MS (ESI) m/z 169.2 [M−H]$^-$.

G. Benzyl 4-hydroxybicyclo[2.2.2]octan-1-ylcarbamate

To a solution of 4-hydroxybicyclo[2.2.2]octane-1-carboxylic acid (10.4 g, 61.1 mmol) in dioxane (150 mL) was added DIEA (11.8 g, 91.5 mmol), diphenyl phosphoryl azide (25 g, 91.5 mmol) and benzyl alcohol (131 g, 1.22 mol). The mixture was stirred at 80° C. overnight. Then the reaction was concentrated under reduce pressure to remove dioxane and benzyl alcohol (100° C., 2 mm Hg). The residue was purified by silica gel column chromatography (5% methanol in DCM) to give the title product (15.4 g, 54 mmol, yield 91%). $^1$H NMR (400 MHz, $CDCl_3$) δ ppm 7.35-7.30 (m, 5H), 5.03 (s. 2H), 4.55 (br s, 1H), 2.01-1.95 (m, 6H), 1.77-1.72 (m, 6H); MS (ESI) m/z 276.3 [M+H]$^+$.

H. 4-Aminobicyclo[2.2.2]octan-1-ol hydrochloride

To a solution of benzyl 4-hydroxybicyclo[2.2.2]octan-1-ylcarbamate (14.8 g, 53 mmol) in methanol (200 mL) was added palladium on charcoal (0.5 g, 10%). The reaction mixture was stirred at 50° C. under hydrogen atmosphere (50 Psi) overnight and filtered through celite. The filtrate was concentrated and the residue was added to hydrochloric acid in methanol (10%, 50 mL). The mixture was stirred for 2 h at room temperature. Then the mixture was concentrated again and THF (20 mL) was added. The mixture was stirred at room temperature for 1 h and the precipitate was collected and dried to give the title product (6.7 g, 36 mmol, 70% yield). $^1$H NMR (DMSO-$d_6$) δ 8.00 (s, 3H), 4.48 (br s, 1H), 1.76-1.80 (m, 6H), 1.58-1.61 (m, 6H). MS (ESI) m/z 142.1 [M+1]$^+$.

I. Ethyl 4-(isopropylamino)-2-(methylthio)pyrimidine-5-carboxylate

A mixture of ethyl 4-chloro-2-(methylthio)pyrimidine-5-carboxylate (10 g, 43.0 mmol), propan-2-amine (4.21 mL, 49.4 mmol) and DIEA (9.76 mL, 55.9 mmol) in ethanol (140 mL) was heated at 60° C. overnight. After cooling to room temperature, the solvent was concentrated under reduced pressure and water was added. The aqueous phase was extracted three times with ethyl acetate and the combined organic phases were dried over magnesium sulfate, filtered and evaporated to give ethyl 4-(isopropylamino)-2-(methylthio)pyrimidine-5-carboxylate (10.10 g, 39.5 mmol, 92% yield) as a colorless oil. MS (ESI) m/z 256.1 [M+1]$^+$.

J. 4-(Isopropylamino)-2-(methylthio)pyrimidine-5-carboxylic acid

In a round-bottomed flask ethyl 4-(isopropylamino)-2-(methylthio)pyrimidine-5-carboxylate (10.97 g, 43.0 mmol) was dissolved in ethanol (150 mL) followed by the addition of aqueous sodium hydroxide solution (1M, 129 ml, 129 mmol). The resulting mixture was stirred overnight at room temperature and then the solvent was evaporated under reduced pressure. Aqueous citric acid solution (2M, 129 ml, 258 mmol) was slowly added and the resulting mixture was stirred for 0.5 h at room temperature. The suspension was filtered and the solids were washed twice with water (2×50 mL) and then dried in the vacuum oven at 45° C. overnight to afford 4-(isopropylamino)-2-(methylthio)pyrimidine-5-carboxylic acid (8.38 g, 36.9 mmol, 86% yield); MS (ESI) m/z 228.4 $[M+1]^+$.

K. 4-(Isopropylamino)-2-(methylthio)pyrimidine-5-carboxamide 4-(Isopropylamino)-2-(methylthio)pyrimidine-5-carboxylic acid (8.38 g, 36.9 mmol) and HATU (21.03 g, 55.3 mmol) were combined in a 250 mL round-bottomed flask followed by the addition of DMF (92 mL). After that ammonia hydrochloride (9.86 g, 184 mmol) and DIEA (32 mL, 184 mmol) were added and the mixture was stirred at room temperature overnight. The solvent was concentrated under reduced pressure and water (150 mL) was added. The resulting suspension was filtered, washed with water and dried under high vacuum overnight to afford 4-(isopropylamino)-2-(methylthio)pyrimidine-5-carboxamide (8 g, 35.4 mmol, 96% yield); MS (ESI) m/z 227.4 $[M+1]^+$.

L. 4-(Isopropylamino)-2-(methylsulfinyl)pyrimidine-5-carboxamide and 4-(Isopropylamino)-2-(methylsulfonyl)pyrimidine-5-carboxamide To a solution of 4-(isopropylamino)-2-(methylthio)pyrimidine-5-carboxamide (641 mg, 2.8 mmol) in NMP (6 mL) was added mCPBA (852 mg, 4.2 mmol, 85% purity) at 0° C. The reaction was stirred for 1 h at room temperature. Then water (25 mL) was added, which dissolved the suspension for a short time only to form another thick precipitate, which was filtered off. The resulting filtrate was concentrated under reduced pressure to afford the title mixture in NMP, which was used in the next step without further purification. MS (ESI) m/z 243.3, 259.2 $[M+1]^+$.

M. 2-(4-Hydroxybicyclo[2.2.2]octan-1-ylamino)-4-(isopropylamino)-pyrimidine-5-carboxamide To the solution of 4-(isopropylamino)-2-(methylsulfinyl)-pyrimidine-5-carboxamide and 4-(isopropylamino)-2-(methylsulfonyl)pyrimidine-5-carboxamide in NMP (from previous step, 2.8 mmol), 4-aminobicyclo[2.2.2]octan-1-ol hydrochloride (500 mg, 2.8 mmol), DIEA (1.1 g, 8.4 mmol) were added and heated at 100° C. for 3 d. The resulting mixture was concentrated under reduced pressure and the residue was purified by preparative thin layer chromatography to afford the final product (74.1 mg, 8.2% yield). $^1H$ NMR (DMSO-$d_6$) δ ppm 8.88 (br s, 1H), 8.31 (s, 1H), 7.5-6.5 (br s, 2H), 5.76 (s, 1H), 4.25 (s, 1H), 4.11 (brs, 1H), 2.05-1.97 (m, 6H), 1.61-1.54 (m, 6H), 1.24-1.12 (m, 6H); MS (ESI) m/z 320.2 $[M+H]^+$; Purity=96.5% at 214 nm, Purity=97.7% at 254 nm.

Example 26: 4-(tert-Butylamino)-2-((1r,4r)-4-hydroxycyclohexylamino)pyrimidine-5-carboxamide

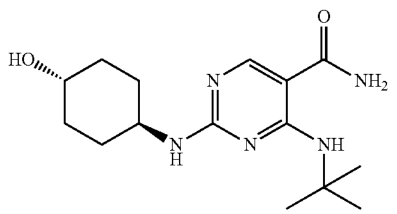 [SMILES: CC(C)(C)Nc1nc(N[C@H]2CC[C@H](O)CC2)ncc1C(N)=O]

A. Ethyl 4-(tert-butylamino)-2-(methylthio)pyrimidine-5-carboxylate

A mixture of ethyl 4-chloro-2-(methylthio)pyrimidine-5-carboxylate (3 g, 12.89 mmol), 2-methylpropan-2-amine (1.565 mL, 14.83 mmol) and DIEA (2.93 mL, 16.76 mmol) in ethanol (20 mL) was heated at 60° C. overnight. After cooling to room temperature, the solvent was concentrated under reduced pressure and water was added. The aqueous phase was extracted three times with ethyl acetate and the combined organic phases were dried over anhydrous magnesium sulfate, filtered and evaporated to give ethyl 4-(tert-butylamino)-2-(methylthio)pyrimidine-5-carboxylate (3.20 g, 11.86 mmol, 92% yield) as a colorless oil. MS (ESI) m/z 269.5 $[M+1]^+$.

B. 4-(tert-Butylamino)-2-(methylthio)pyrimidine-5-carboxylic acid

In a round-bottomed flask ethyl 4-(tert-butylamino)-2-(methylthio)pyrimidine-5-carboxylate (3.2 g, 11.88 mmol) was dissolved in ethanol (40 mL) followed by the addition of 1M aqueous sodium hydroxide solution (35.6 mL, 35.6 mmol). The resulting mixture was stirred overnight at room temperature and then the solvent was evaporated under reduced pressure. After that 2M aqueous citric acid solution (35.6 mL, 71.3 mmol) was slowly added and the resulting mixture was stirred for 0.5 h at room temperature. The suspension was filtered and the solids were washed twice with water (2×50 mL) and then dried in a vacuum oven at 45° C. overnight to afford 4-(tert-butylamino)-2-(methylthio)pyrimidine-5-carboxylic acid (2.83 g, 11.73 mmol, 99% yield). MS (ESI) m/z 242.3 [M+1]+.

C. 4-(tert-Butylamino)-2-(methylthio)pyrimidine-5-carboxamide 4-(tert-Butylamino)-2-(methylthio)pyrimidine-5-carboxylic acid (2.83 g, 11.73 mmol) and 2-(3H-[1,2,3]triazolo[4,5-b]pyridin-3-yl)-1,1,3,3-tetramethylisouronium hexafluoro-phosphate(V) (6.69 g, 17.59 mmol) were combined in a 250 mL round-bottomed flask followed by the addition of DMF (29 mL). After that ammonia hydrochloride (3.14 g, 58.6 mmol) and DIEA (10.21 mL, 58.6 mmol) were added and the mixture was stirred at room temperature overnight. The solvent was concentrated under reduced pressure and water (150 mL) was added. The resulting suspension was filtered, washed with water and dried under high vacuum overnight to afford 4-(tert-butylamino)-2-(methylthio)-pyrimidine-5-carboxamide (2.54 g, 10.57 mmol, 90% yield). MS (ESI) m/z 241.2 [M+1]+.

D. 4-(tert-Butylamino)-2-(methylsulfonyl)pyrimidine-5-carboxamide

To a stirring solution of 4-(tert-butylamino)-2-(methylthio)pyrimidine-5-carboxamide (0.6 g, 2.497 mmol) in NMP (5 mL) was added mCPBA (0.839 g, 3.74 mmol) at 0° C. and stirring was continued at room temperature for 1 h. LCMS showed complete conversion to desired product. The reaction mixture was carried on to next reaction without further purification. MS (ESI) m/z 273.2 $[M+1]^+$.

E. 4-(tert-Butylamino)-2-((1 r,4r)-4-hydroxycyclohexylamino)-pyrimidine-5-carboxamide To the solution of 4-(tert-butylamino)-2-(methylsulfonyl)-pyrimidine-5-carboxamide from the previous step was added DIEA (2.181 mL, 12.49 mmol) and (1r,4r)-4-aminocyclohexanol hydrochloride (0.568 g, 3.75 mmol), and the reaction was stirred at 90° C. for 16 h. The solvent was evaporated under reduced pressure and the resulting residue was purified using reverse-phased preparative HPLC (0-50% acetonitrile+0.1% TFA in water+0.1% TFA, over 30 min). Fractions containing product were concentrated under reduced pressure. The resulting residue was redissolved in a methanol (5 mL), passed over an Varian StratoSpheres HCO3 resin SPE tube for TFA removal (0.9 mmol bicarbonate equiv.), and then concentrated under reduced pressure to afford 4-(tert-butylamino)-2-((1r,4r)-4-hydroxycyclohexylamino)pyrimidine-5-carboxamide (0.350 g, 1.139 mmol, 45.6% yield). $^1$H NMR (DMSO-$d_6$, 400 MHz) δ ppm 0.82-0.88 (m, 1H) 1.14-1.30 (m, 5H) 1.42 (s, 9H) 1.85 (d, J=4.30 Hz, 4H) 3.38 (br. s, 1H) 3.59 (d, J=7.42 Hz, 1H) 4.54 (s, 1H) 7.02 (d, J=7.81 Hz, 1H) 8.32 (s, 1H) 9.18 (s, 1H); MS(ESI): m/z 308.1 $[M+1]^+$.

Example 27: 4-((1R,3R,4R)-3-Hydroxy-4-methylcyclohexylamino)-2-(isopropylamino)pyrimidine-5-carboxamide

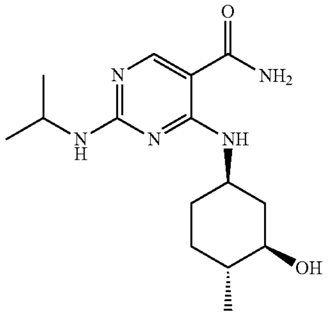 [SMILES: CC(C)Nc1ncc(C(N)=O)c(N[C@@H]2CC[C@@H](C)[C@H](O)C2)n1]

A. 4-((1R,3R,4R)-3-Hydroxy-4-methylcyclohexylamino)-2-(methylthio)pyrimidine-5-carbonitrile To a stirring solution of 4-chloro-2-(methylthio)-pyrimidine-5-carbonitrile (310 mg, 1.670 mmol) and (1R,2R,5R)-5-amino-2-methylcyclo-hexanol hydrochloride (304 mg, 1.837 mmol; synthesis described herein) in DMF (2.4 mL) was added DIEA (0.873 mL, 5.01 mmol). The resulting mixture was stirred at 60° C. for 2 h. LCMS showed the reaction to be complete. The solvent was evaporated under reduced pressure and the residue diluted with 150 mL ethyl acetate and 50 mL water. The layers were separated and the aqueous phase was extracted with 75 mL ethyl acetate. The combined ethyl acetate layers were washed with brine (2×50 mL), dried over anhydrous magnesium sulfate, filtered and concentrated to an oil that solidified upon standing to afford 4-((1R,3R,4R)-3-hydroxy-4-methylcyclohexylamino)-2-(methylthio)pyrimidine-5-carbonitrile (418 mg, 1.503 mmol, 90% yield). MS (ESI) m/z 279.3 $[M+1]^+$.

B. 4-((1R,3R,4R)-3-Hydroxy-4-methylcyclohexylamino)-2-(methylsulfonyl)pyrimidine-5-carbonitrile To a solution of 4-((1R,3R,4R)-3-hydroxy-4-methylcyclohexylamino)-2-(methylthio)pyrimidine-5-carbonitrile (400 mg, 1.437 mmol) in NMP (5 mL) at 0° C. was added mCPBA (805 mg, 3.59 mmol) and the reaction was stirred for 3 h at room temperature. The resulting solution was used directly in the next step without further purification. MS (ESI) m/z 311.4 $[M+1]^+$ C. 4-((1R,3R,4R)-3-Hydroxy-4-methylcyclohexylamino)-2-(isopropylamino)pyrimidine-5-carbonitrile To the solution of 4-((1R,3R,4R)-3-hydroxy-4-methylcyclohexylamino)-2-(methylsulfonyl)pyrimidine-5-carbonitrile (446 mg, 1.437 mmol) from the previous step was added propan-2-amine (0.367 mL, 4.31 mmol) and DIEA (1.004 mL, 5.75 mmol). The reaction was stirred at 80° C. for 4 h and then allowed to cool to ambient temperature. The solvent was evaporated under reduced pressure and the residue was purified by silica gel chromatography (0-90% ethyl acetate in hexanes) to afford 4-((1R,3R,4R)-3-hydroxy-4-methylcyclohexylamino)-2-(isopropylamino)pyrimidine-5-carbonitrile (381 mg, 1.317 mmol, 92% yield). MS (ESI) m/z 290.2 $[M+1]^+$ D. 4-((1R,3R,4R)-3-Hydroxy-4-methylcyclohexylamino)-2-(isopropylamino)pyrimidine-5-carboxamide 4-((1R,3R,4R)-3-Hydroxy-4-methyl-cyclohexylamino)-2-(isopropylamino)pyrimidine-5-carbonitrile (0.38 g, 1.313 mmol) was dissolved in DMSO (5 mL). To this solution was added a 50% aqueous sodium hydroxide solution (0.103 ml, 1.970 mmol) and a 30% aqueous hydrogen peroxide solution (0.101 ml, 0.985 mmol) at room temperature. Then the reaction mixture was stirred at 50° C. for 1 h. After that, the reaction mixture was poured into ice water (15 mL) and the resulting mixture was stirred for 1 h. The resulting precipitate was filtered and washed with water to afford 4-((1R,3R,4R)-3-hydroxy-4-methylcyclohexylamino)-2-(isopropylamino)pyrimidine-5-carboxamide (0.210 g, 0.683 mmol, 52% yield). $^1$H NMR (DMSO-$d_6$, 400 MHz) δ ppm 0.94 (d, J=6.40 Hz, 4H) 1.12 (d, J=5.91 Hz, 9H) 1.65 (dd, J=13.29, 2.95 Hz, 1H) 1.92 (br. s., 1H) 2.15 (br. s., 1H) 2.97 (br. s., 1H) 3.81-4.14 (m, 2H) 4.55 (d, J=5.41 Hz, 1H) 6.70-7.02 (m, 1H) 8.34 (br. s., 1H) 8.92 (br. s., 1H); MS (ESI) m/z 308.0 $[M+1]^+$.

Example 28: 2-(Bicyclo[1.1.1]pentan-1-ylamino)-4-((1R,3R,4R)-3-hydroxy-4-methylcyclohexylamino)pyrimidine-5-carboxamide

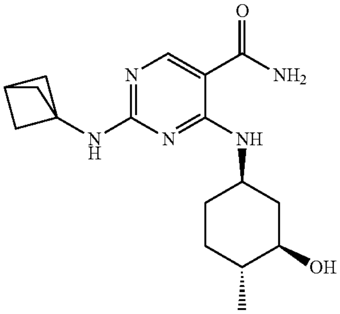 [SMILES: C[C@@H]1CC[C@@H](Nc2nc(NC34CC(C3)C4)ncc2C(N)=O)C[C@H]1O]

A. 2-(Bicyclo[1.1.1]pentan-1-ylamino)-4-((1R,3R,4R)-3-hydroxy-4-methylcyclohexylamino)pyrimidine-5-carbonitrile To a solution of 4-((1R,3R,4R)-3-hydroxy-4-methylcyclohexylamino)-2-(methylsulfonyl)pyrimidine-5-carbonitrile (446 mg, 1.437 mmol; synthesis described herein) in NMP (5 mL) was added bicyclo[1.1.1]pentan-1-amine hydrochloride (258 mg, 2.155 mmol; prepared according to *Org. Lett.*, 13(17): 4746-4748 (2011)) and DIEA (1.255 mL, 7.18 mmol). The reaction was stirred at 80° C. for 4 h and then allowed to cool to ambient temperature. The solvent was evaporated under reduced pressure and the residue was purified by flash chromatography (0-90% ethyl acetate in hexanes) to afford 2-(bicyclo[1.1.1]pentan-1-ylamino)-4-((1R,3R,4R)-3-hydroxy-4-methylcyclohexylamino)pyrimidine-5-carbonitrile (381 mg, 1.216 mmol, 85% yield). MS(ESI): m/z 314.0 $[M+1]^+$.

B. 2-(Bicyclo[1.1.1]pentan-1-ylamino)-4-((1R,3R,4R)-3-hydroxy-4-methylcyclohexylamino)pyrimidine-5-carboxamide 2-(Bicyclo[1.1.1]pentan-1-ylamino)-4-((1R,3R,4R)-3-hydroxy-4-methylcyclohexylamino)pyrimidine-5-carbonitrile (0.38 g, 1.213 mmol) was dissolved in DMSO (26.9 mL) and to this solution was added a 50% aqueous sodium hydroxide solution (0.097 ml, 1.213 mmol) and a 30% aqueous hydrogen peroxide solution 0.137 mL, 1.213 mmol) at room temperature. Then the reaction mixture was stirred at 50° C. for 1 h. The reaction was cooled to room temperature and it was poured into 50 mL of ice water. The white precipitate was collected on filter paper and was washed twice with water. The precipitate was dried to give 2-(bicyclo[1.1.1]pentan-1-ylamino)-4-((1R,3R,4R)-3-hydroxy-4-methylcyclohexylamino)-pyrimidine-5-carboxamide (0.269 g, 0.812 mmol, 67% yield). $^1$H NMR (DMSO-$d_6$, 400 MHz): δ ppm 0.94 (d, J=6.25 Hz, 3H) 1.10-1.26 (m, 3H) 1.68 (d, J=10.54 Hz, 1H) 1.92 (d, J=10.93 Hz, 1H) 2.06 (s, 6H) 2.17 (d, J=9.76 Hz, 1H) 2.46 (s, 1H) 2.98 (br. s., 1H) 3.82-3.95 (m, 1H) 4.63 (br. s., 1H) 7.16 (br. s., 1H) 7.77 (br. s., 1H) 8.11 (br. s., 1H) 8.33 (s, 1H) 9.24 (br. s., 1H); MS(ESI): m/z 332.3 $[M+1]^+$.

Example 29: 4-((2-Cyclopropylpropan-2-yl)amino)-2-(((1r,4r)-4-hydroxycyclohexyl)amino)pyrimidine-5-carboxamide

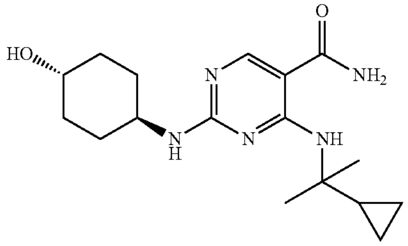 [SMILES: CC(C)(Nc1nc(N[C@H]2CC[C@H](O)CC2)ncc1C(N)=O)C1CC1]

A. 4-((2-Cyclopropylpropan-2-yl)amino)-2-(methylthio)pyrimidine-5-carbonitrile

To a solution of 4-chloro-2-(methylthio)pyrimidine-5-carbonitrile (750 mg, 4.0 mmol) in DMF (8 mL) was added 2-cyclopropylpropan-2-amine (400 mg, 4.0 mmol) and DIEA (1560 mg, 12.0 mmol). The resulting mixture was stirred at 60° C. for 2 h. Water was added and the mixture was extracted with ethyl acetate. The combined organic layers were washed with brine, dried over anhydrous sodium sulfate and filtered. The filtrate was concentrated to give the crude product, which was purified by silica gel column chromatography (0-30% ethyl acetate in petroleum ether) to afford the title compound (665 mg, 2.68 mmol, 66% yield) as a white solid. MS (ESI) m/z=249.2 $[M+H]^+$.

B. 4-((2-Cyclopropylpropan-2-yl)amino)-2-(methylthio)pyrimidine-5-carboxamide

To a stirring solution of 4-((2-cyclopropylpropan-2-yl)amino)-2-(methylthio)pyrimidine-5-carbonitrile (665 mg, 2.68 mmol) in DMSO (4 mL) was added aqueous hydrogen peroxide solution (0.162 mL, 30%) and aqueous sodium hydroxide (2.2 mL, 6 mol/L) solution. The resulting mixture was stirred at 50° C. for 12 min, and then water was added. The desired product was filtered and dried in vacuo to give the crude product (392 mg, 1.47 mmol, 55% yield) as a white solid. MS (ESI) m/z 267.3 [M+H]

C. 4-((2-Cyclopropylpropan-2-yl)amino)-2-(methylsulfinyl)pyrimidine-5-carboxamide and 4-((2-cyclopropylpropan-2-yl)amino)-2-(methylsulfonyl)pyrimidine-5-carboxamide To a cooled (0° C.) solution of 4-((2-cyclopropylpropan-2-yl)amino)-2-(methylthio)pyrimidine-5-carboxamide (390 mg, 1.46 mmol) in THF (6 mL) was added mCPBA (447 mg, 2.2 mmol) portion-wise. The reaction mixture was stirred for 0.5 h at 0° C. The mixture was concentrated under vacuum and purified by silica gel column chromatography (2.5%-10% DCM in methanol) to give a mixture of 4-((2-cyclopropylpropan-2-yl)amino)-2-(methylsulfinyl)pyrimidine-5-carboxamide and 4-((2-cyclopropylpropan-2-yl)amino)-2-(methylsulfonyl)pyrimidine-5-carboxamide (382 mg, 1.32 mmol, 90% yield). MS (ESI) m/z 299.1 $[M+H]^+$ and 283.1 $[M+H]^+$.

D. 4-((2-Cyclopropylpropan-2-yl)amino)-2-(((1r,4r)-4-hydroxycyclohexyl)-amino)pyrimidine-5-carboxamide A mixture of 4-((2-cyclopropylpropan-2-yl)amino)-2-(methylsulfinyl)pyrimidine-5-carboxamide, 4-((2-cyclopropylpropan-2-yl)amino)-2-(methylsulfonyl)pyrimidine-5-carboxamide (191 mg, 0.66 mmol), (1r,4r)-4-aminocyclohexanol (114 mg, 0.99 mmol), DIEA (256 g, 1.98 mmol) and NMP (5 mL) were combined and heated at 100° C. overnight. The resulting mixture was concentrated and the residue was purified by HPLC (5-95% acetonitrile in water) to afford the title compound (129.5 mg, 0.39 mmol, 59% yield).

$^1$H NMR (400 MHz, $CDCl_3$): δ ppm 8.96 (s, 1H), 8.09 (s, 1H), 5.38 (s, 2H), 4.98-4.96 (m, 1H), 3.79-3.77 (m, 1H), 3.69-3.67 (m, 1H), 2.14-2.11 (d, J=11.6 Hz, 2H), 2.04-2.01 (m, 2H), 1.48-1.41 (m, 4H), 1.38 (s, 6H), 1.32-1.22 (m, 2H), 0.48-0.39 (m, 4H); MS (ESI) m/z 334.3 $[M+H]^+$.

Example 30: 4-Cyclobutylamino-2-(((1r,4r)-4-methoxycyclohexyl)amino)pyrimidine-5-carboxamide

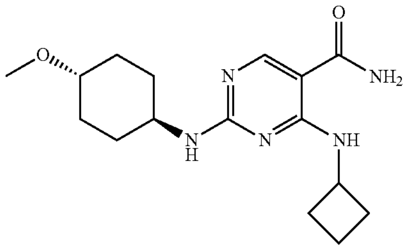 [SMILES: CO[C@H]1CC[C@H](Nc2ncc(C(N)=O)c(NC3CCC3)n2)CC1]

A. 4-(Cyclobutylamino)-2-(methylthio)pyrimidine-5-carbonitrile

To a stirring solution of 4-chloro-2-(methylthio)pyrimidine-5-carbonitrile (2 g, 10.8 mmol) in DMF (10 mL) was added DIEA (4.2 g, 32.4 mmol) and cyclobutanamine (2.3 g, 32.4 mmol) at 0° C. The resulting mixture was stirred at 60° C. for 2 h. The reaction mixture was poured into saturated sodium chloride, and extracted with ethyl acetate three times. The combined organic layers were dried over anhydrous sodium sulfate, filtered and concentrated to afford the crude product. The crude product was purified via silica gel column chromatography (10% ethyl acetate in petroleum ether) to get the desired product as a white solid (1.7 g, 7.7 mmol, 71% yield). MS (ESI) m/z=221.2[M+H]$^+$.

B. 4-(Cyclobutylamino)-2-(methylsulfinyl)pyrimidine-5-carbonitrile and 4-(cyclobutylamino)-2-(methylsulfonyl)pyrimidine-5-carbonitrile 4-(Cyclobutylamino)-2-(methylthio)pyrimidine-5-carbonitrile (1.7 g, 7.7 mmol) was dissolved in DCM (30 mL) and cooled to 0° C. To this mixture, mCPBA (4.6 g, 23 mmol) was added portionwise and the reaction was stirred for 1 h. The resulting mixture was poured into a saturated aqueous sodium bicarbonate solution. The aqueous layer was extracted three times with DCM. The combined organic layers were dried over anhydrous sodium sulfate, filtered and concentrated to afford a mixture of 4-(cyclobutylamino)-2-(methylsulfinyl)pyrimidine-5-carbonitrile and 4-(cyclobutylamino)-2-(methyl-sulfonyl)pyrimidine-5-carbonitrile as a yellow thick oil (1.6 g crude), which was used in the next step without further purification. MS (ESI) m/z=237.2/253.2 [M+H]$^+$.

C. 4-(Cyclobutylamino)-2-(((1r,4r)-4-methoxycyclohexyl)amino)pyrimidine-5-carbonitrile To the mixture of 4-(cyclobutylamino)-2-(methylsulfinyl) pyrimidine-5-carbonitrile and 4-(cyclobutylamino)-2-(methylsulfonyl)pyrimidine-5-carbonitrile (1.6 g, crude) from the previous step was added (1r,4r)-4-methoxycyclohexanamine (0.96 g, 7.4 mmol), 1,4-dioxane (100 mL) and DIEA (4.3 g, 33.4 mmol). The resulting mixture was stirred at 100° C. overnight. After removal of all volatile solvents under reduced pressure, the residue was purified by silica gel column chromatography (33.3% ethyl acetate in petroleum ether) to provide the desired product as a white solid (1.3 g, 57% yield). MS (ESI) m/z=302.1 [M+H]$^+$.

D. 4-(Cyclobutylamino)-2-(((1r,4r)-4-methoxycyclohexyl)amino)pyrimidine-5-carboxamide To the mixture of 4-(cyclobutylamino)-2-(((1r,4r)-4-methoxycyclohexyl)-amino)pyrimidine-5-carbonitrile (700 mg, 2.3 mmol) in DMSO (8 mL) was added aqueous hydrogen peroxide solution (1.3 g, 30%, 11.5 mmol), and then aqueous sodium hydroxide solution (2 mL, 6 mol/L, 11.5 mmol). The mixture was stirred at 50° C. for 0.5 h, then water (30 mL) was added to the reaction mixture, the product was collected and dried to give the desired compound (400 mg, 1.25 mmol, 54% yield). $^1$H NMR (400 MHz, $CDCl_3$) δ ppm 8.76 (s, 1H), 8.11 (s, 1H), 5.46 (s, 2H), 5.01 (s, 1H), 4.51-4.45 (m, 1H), 3.83-3.81 (m, 1H), 3.36 (s, 3H), 3.21-3.16 (m, 1H), 2.40-2.33 (m, 2H), 2.15-1.96 (m, 6H), 1.78 (s, 2H), 1.43-1.20 (m, 4H); MS (ESI) m/z=319.9 [M+H]$^+$).

Example 31: 4-(Cyclobutylamino)-2-(((1r,4r)-4-hydroxycyclohexyl)amino)-pyrimidine-5-carboxamide

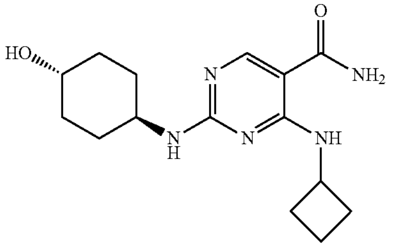 [SMILES: NC(=O)c1cnc(N[C@H]2CC[C@H](O)CC2)nc1NC1CCC1]

A. 4-(Cyclobutylamino)-2-(methylsulfinyl)pyrimidine-5-carbonitrile and 4-(cyclobutylamino)-2-(methylsulfonyl)pyrimidine-5-carbonitrile 4-(Cyclobutylamino)-2-(methylthio)pyrimidine-5-carbonitrile (889 mg, 4.04 mmol; synthesis described herein) was dissolved in DCM (20 mL) and cooled to 0° C. To this mixture, mCPBA (2.1 g, 12.1 mmol) was added portionwise and the reaction was stirred for 1 h. The resulting mixture was poured into a saturated aqueous sodium bicarbonate solution. The aqueous layer was extracted three times with DCM. The combined organic layers were dried over anhydrous sodium sulfate, filtered and concentrated to afford a mixture of 4-(cyclobutylamino)-2-(methylsulfinyl)pyrimidine-5-carbonitrile and 4-(cyclobutylamino)-2-(methylsulfonyl)pyrimidine-5-carbonitrile as a yellow thick oil (893 mg crude), which was used in the next step without further purification. MS (ESI) m/z=237.2/253.2 [M+H]$^+$.

B. 4-(Cyclobutylamino)-2-(((1r,4r)-4-hydroxycyclohexyl)amino)pyrimidine-5-carbonitrile To the mixture of 4-(cyclobutylamino)-2-(methylsulfinyl) pyrimidine-5-carbonitrile and 4-(cyclobutylamino)-2-(methylsulfonyl)pyrimidine-5-carbonitrile (424 mg, about 1.93 mmol) from the previous step was added (1r,4r)-4-aminocyclohexanol (244 mg, 2.12 mmol), 1,4-dioxane (50 mL) and DIEA (1.2 g, 9.65 mmol). The resulting mixture was stirred at 100° C. overnight. After removal of all volatile solvents under reduced pressure, the residue was purified by silica gel column chromatography (50% ethyl acetate in petroleum ether) to get the desired product as a white solid (305 mg, 1.06 mmol, 55.4% yield). MS (ESI) m/z=288.2 $[M+H]^+$.

C. 4-(Cyclobutylamino)-2-(((1r,4r)-4-hydroxycyclohexyl)amino)pyrimidine-5-carboxamide To a solution of 4-(cyclobutylamino)-2-(((1r,4r)-4-hydroxycyclohexyl)-amino)pyrimidine-5-carbonitrile (305 mg, 1.06 mmol) in DMSO (6 mL) was added aqueous hydrogen peroxide solution (600.1 mg, 30%, 5.3 mmol), and then aqueous sodium hydroxide solution (1 mL, 6 mol/L, 5.3 mmol). The mixture was stirred at 50° C. for 0.5 h, and then water was added and the mixture was extracted with ethyl acetate. The combined organic layers were washed with brine, dried over anhydrous sodium sulfate and filtered. Concentration under reduced pressure gave the crude product, which was purified by silica gel column chromatography (0-10% methanol in DCM) to afford the title compound (248.2 mg, 0.81 mmol, 76.6% yield). $^1H$ NMR (400 MHz, $CDCl_3$) δ ppm 8.74 (s, 1H), 8.12 (s, 1H), 5.46 (brs, 2H), 5.07-4.96 (m, 1H), 4.53-4.43 (m, 1H), 3.80-3.79 (m, 1H), 3.70-3.65 (m, 1H), 2.40-2.34 (m, 2H), 2.15-1.97 (m, 6H), 1.91-1.88 (s, 2H), 1.55-1.19 (m, 4H); MS (ESI) m/z=306.0 $[M+H]^+$.

Example 32: 2-(tert-Butylamino)-4-((1R,3R,4R)-3-hydroxy-4-methylcyclohexylamino)-pyrimidine-5-carboxamide

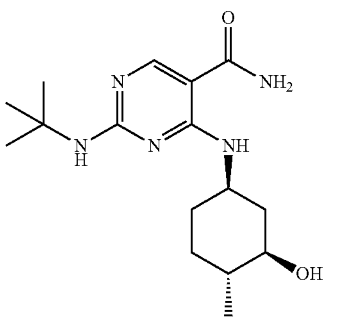 [SMILES: C[C@@H]1CC[C@@H](Nc2nc(NC(C)(C)C)ncc2C(N)=O)C[C@H]1O]

A. (R)-tert-Butyl 4-methylcyclohex-3-enylcarbamate and (S)-tert-butyl 4-methylcyclohex-3-enylcarbamate To a stirring solution of a mixture of (R)-4-methylcyclohex-3-enamine and (S)-4-methylcyclohex-3-enamine (40.2973 g, 359 mmol; prepared as described in *J. Org. Chem.* 1992, 57, 3454-3462) in ethyl ether (498 mL) at 0° C. was added a solution of di-tert-butyl-dicarbonate (81 g, 362 mmol) in ethyl ether (100 mL) dropwise over 30 min. The reaction was stirred at 0° C. for 1 h, allowed to slowly reach room temperature over 4 h, and then stirred at room temperature for 16 h. The reaction mixture was concentrated under reduced pressure to afford the crude residue. The crude residue was triturated with hexanes (500 mL), stirred for 5 min at 0° C., then filtered and washed with hexanes (50 mL) to afford a first crop of product (~55 g). The filtrate was concentrated under reduced pressure, triturated with hexanes and the precipitate was filtered to afford a second crop of product (~15 g). This was repeated to afford a third crop of product (4.25 g). The three crops were combined to afford a mixture of (R)-tert-butyl 4-methylcyclohex-3-enylcarbamate and (S)-tert-butyl 4-methylcyclohex-3-enylcarbamate (74.25 g, 351 mmol, 98% yield) as a white solid. $^1H$ NMR (400 MHz, DMSO-$d_6$) δ ppm 6.72 (d, J=7.42 Hz, 1H), 5.26 (br. s., 1H), 3.35-3.47 (m, 1H), 1.93 (br. s., 5H), 1.60 (s, 3H), 1.32-1.44 (m, 10H).

B. tert-Butyl (1R,3R,4R)-3-hydroxy-4-methylcyclohexylcarbamate, tert-butyl (1R,3S,4S)-3-hydroxy-4-methylcyclohexylcarbamate, tert-butyl (1S,3R,4R)-3-hydroxy-4-methylcyclohexylcarbamate, tert-butyl (1S,3S,4S)-3-hydroxy-4-methylcyclohexylcarbamate To a stirring solution of a mixture of (R)-tert-butyl 4-methylcyclohex-3-enylcarbamate and (S)-tert-butyl 4-methylcyclohex-3-enylcarbamate (13 g, 61.6 mmol) in THF (780 mL) at 0° C. was added 1 M borane THF complex (277 mL, 277 mmol). The solution was stirred at 0° C., allowed to reach room temperature over 1 h, and then stirred at room temperature for 20 h. The reaction was quenched very slowly with water (330 mL), diluted with ethanol (326 mL) and basified with 5 N aqueous sodium hydroxide (308 mL, 1.54 mol). To the stirring biphasic mixture was slowly added 30% hydrogen peroxide (316 mL, 3.08 mol) and the resulting mixture was heated to 45° C. for 20 h. The crude reaction was quenched with saturated aqueous sodium sulfite (573 mL) and extracted with ethyl acetate (4×1 L). The combined organic layers were washed with brine, dried over sodium sulfate, filtered, and concentrated under reduced pressure to give the crude product. The above reaction was repeated 5 times (using 3×13 g and 2×11 g starting material). The combined crude products from all 6 reactions were purified by silica gel chromatography (0-100% ethyl acetate in hexanes). The product containing fractions were combined and concentrated under reduced pressure to afford a mixture of tert-butyl (1R,3R,4R)-3-hydroxy-4-methylcyclohexylcarbamate, tert-butyl (1R,3S,4S)-3-hydroxy-4-methylcyclohexyl-carbamate, tert-butyl (1S,3R,4R)-3-hydroxy-4-methylcyclohexylcarbamate, and tert-butyl (1S,3S,4S)-3-hydroxy-4-methylcyclohexylcarbamate (55 g, 242 mmol, 72% yield) as a solid. The 4 constituent stereoisomers were separated by preparative chiral SFC utilizing multiple injections over a series of 3 separate columns. First column: ChiralPak AD-H, 250×50 mm I.D., isocratic 35% methanol in $CO_2$. Second column: ChiralPak AD-H, 250×50 mm I.D., isocratic 25% methanol in $CO_2$. Third column: ChiralPak AD-H, 250×50 mm I.D., isocratic 15% ethanol in $CO_2$. The separated isomers were characterized on an analytical scale ChiralPak AD-3 column, 150×4.6 mm I.D., 5-40% methanol (with 0.05% diethylamine) in $CO_2$ (15 min run time) and labeled as Intermediate 1 to Intermediate 4.

Intermediate 1:

2.0 g (8.72 mmol, 3.6% yield from SFC purification). Retention time: 4.77 min. MS (ESI) m/z 252.1 $[M+23]^+$.

Intermediate 2:

1.5 g (6.54 mmol, 2.7% yield from SFC purification). Retention time: 5.08 min. MS (ESI) m/z 252.1 $[M+23]^+$.

Intermediate 3:

16.0 g (69.78 mmol, 29.1% yield from SFC purification). Retention time: 5.48 min. $^1H$ NMR (400 MHz, DMSO-$d_6$) δ ppm 6.64-6.86 (m, 1H), 4.43-4.60 (m, 1H), 3.10-3.29 (m, 1H), 2.81-2.96 (m, 1H), 1.84-2.01 (m, 1H), 1.49-1.72 (m, 2H), 1.37 (s, 9H), 0.98-1.14 (m, 3H), 0.76-0.96 (m, 4H). MS (ESI) m/z 252.1 $[M+23]^+$.

Intermediate 4:

18.5 g (80.68 mmol, 33.6% yield from SFC purification). Retention time: 7.79 min. MS (ESI) m/z 252.1 $[M+23]^+$.

A small molecule X-ray crystal structure was solved for Intermediate 3 and the structure was demonstrated to be tert-butyl (1R,3R,4R)-3-hydroxy-4-methylcyclohexylcarbamate. The X-ray structure was solved as follows. Single crystal X-ray diffraction studies were carried out on a Bruker Kappa APEX CCD diffractometer equipped with Cu $K_\alpha$ radiation (λ=1.5478). Crystals of the subject compound were grown by vapor diffusion of hexanes into a hexanes/THF solution. A 0.21×0.05×0.03 mm colorless needle was mounted on a Cryoloop with Paratone oil. Data were collected in a nitrogen gas stream at 120(2) K using ϕ and $\overline{\omega}$ scans. Crystal-to-detector distance was 60 mm using variable exposure time (2 s-20 s) depending on θ with a scan width of 1.0°. Data collection was 97.0% complete to 68.00° in θ. A total of 9000 reflections were collected covering the indices, −33<=h<=32, −31<=k<=30, −6<=1<=5. 2554 reflections were found to be symmetry independent, with a $R_{int}$ of 0.0602. Indexing and unit cell refinement indicated a rhombohedral, hexagonal lattice. The space group was found to be R3. The data were integrated using the Bruker SAINT software program and scaled using the SADABS software program. Solution by direct methods (SHELXS) produced a complete phasing model consistent with the structure of tert-butyl (1R,3R,4R)-3-hydroxy-4-methylcyclohexylcarbamate.

All non-hydrogen atoms were refined anisotropically by full-matrix least-squares (SHELXL-97). All hydrogen atoms were placed using a riding model. Their positions were constrained relative to their parent atom using the appropriate HFIX command in SHELXL-97.

C. (1R,2R,5R)-5-Amino-2-methylcyclohexanol hydrochloride

To vigorously stirring methanol (149 mL) at 0° C. was added acetyl chloride (15.87 mL, 223 mmol) and the resulting mixture stirred for 10 min. To this solution was added tert-butyl (1R,3R,4R)-3-hydroxy-4-methylcyclohexylcarbamate (17.08 g, 74.5 mmol) and the mixture was stirred for 22 h at room temperature. The crude reaction was concentrated and then triturated with ethyl ether (2×300 mL) to afford (1R,2R,5R)-5-amino-2-methylcyclohexanol hydrochloride (12.2 g, 73.6 mmol, 99% yield) as a white solid.

$^1$H NMR (400 MHz, DMSO-$d_6$) δ ppm 8.02 (br. s., 3H), 4.77 (d, J=5.86 Hz, 1H), 2.85-3.10 (m, 2H), 2.03-2.21 (m, 1H), 1.83 (d, J=11.71 Hz, 1H), 1.65 (dd, J=13.47, 3.32 Hz, 1H), 1.24 (q, J=11.58 Hz, 2H), 1.12 (dd, J=6.05, 3.32 Hz, 1H), 0.82-1.03 (m, 4H).

D. 5-Bromo-N-tert-butyl-4-(methylthio)pyrimidin-2-amine

To 5-bromo-2-chloro-4-(methylthio)pyrimidine (3 g, 12.53 mmol) in dioxane (12.53 mL) was added 2-methylpropan-2-amine (7.93 mL, 75 mmol). The mixture was stirred at 100° C. overnight in a sealed vessel. The solvent was removed under reduced pressure and the residue was dissolved in 100 mL ethyl acetate and washed with 50 mL of a 1M aqueous solution of sodium hydrogen phosphate. The aqueous layer was back-extracted with 50 mL ethyl acetate. The combined organic layers were dried over anhydrous magnesium sulfate, filtered and concentrated to give 5-bromo-N-tert-butyl-4-(methylthio)pyrimidin-2-amine (3.4 g, 12.31 mmol, 98% yield) as a solid. $^1$H NMR (400 MHz, DMSO-$d_6$) δ ppm 8.61-8.72 (m, 1H), 8.08 (s, 1H), 6.95-7.17 (m, 1H), 2.48 (s, 2H), 1.38 (s, 9H). MS (ESI) m/z 276.0 $[M+1]^+$ and 278.2 $[M+1]^+$.

E. 2-(tert-Butylamino)-4-(methylthio)pyrimidine-5-carbonitrile

5-Bromo-N-tert-butyl-4-(methylthio)pyrimidin-2-amine (3400 mg, 12.31 mmol), zinc dust (201 mg, 3.08 mmol), zinc cyanide (940 mg, 8.00 mmol), 1,1'-bis-(diphenylphosphino)-ferrocene (552 mg, 0.985 mmol), tris(dibenzylideneacetone)dipalladium(O) (564 mg, 0.616 mmol), and DMF (20.5 mL) were combined and heated at 90° C. overnight under nitrogen. The reaction mixture was diluted with 125 mL ethyl acetate and 50 mL of water and then filtered through a pad of Celite. The layers of filtrate were separated and the aqueous layer was extracted with 75 mL ethyl acetate. The combined ethyl acetate layers were washed with 2×50 mL brine, dried over anhydrous magnesium sulfate, filtered and concentrated to an oil under reduced pressure. The crude oil was purified by silica gel chromatography (0-30% ethyl acetate/hexane) to afford 2-(tert-butylamino)-4-(methylthio)pyrimidine-5-carbonitrile (2.26 g, 10.17 mmol, 83% yield). $^1$H NMR (400 MHz, DMSO-$d_6$) δ ppm 8.37-8.51 (m, 1H), 7.85-8.10 (m, 1H), 2.53-2.62 (m, 3H), 1.41 (s, 9H). MS (ESI) m/z 223.1 $[M+1]^+$.

F. 2-(tert-Butylamino)-4-(methylthio)pyrimidine-5-carboxamide

To a stirring solution of 2-(tert-butylamino)-4-(methylthio)pyrimidine-5-carbonitrile (0.6 g, 2.70 mmol) in DMSO (7 mL) was added 6M aqueous sodium hydroxide solution (2.249 mL, 13.49 mmol) and 30% aqueous hydrogen peroxide (1.530 mL, 13.49 mmol) solution at 0° C. Then the mixture was stirred at 50° C. for 15 min. The reaction mixture was poured into water (40 mL) and extracted with ethyl acetate (3×50 mL). The combined organic layers were washed with brine, dried over anhydrous sodium sulfate and filtered. Concentration of the filtrate under reduced pressure gave the crude product, which was purified by silica gel column chromatography (5% methanol in DCM) to afford 2-(tert-butylamino)-4-(methylthio)pyrimidine-5-carboxamide (0.462 g, 1.922 mmol, 71.2% yield) as a white solid. MS (ESI) m/z 241.0 $[M+1]^+$.

G. 2-(tert-Butylamino)-4-(methylsulfinyl)pyrimidine-5-carboxamide

To a stirring solution of 2-(tert-butylamino)-4-(methylthio)pyrimidine-5-carboxamide (0.1 g, 0.416 mmol) in chloroform (12 mL) was added portion-wise 3-phenyl-2-(phenylsulfonyl)-1,2-oxaziridine (0.130 g, 0.499 mmol). The resulting pale yellow solution was stirred at ambient temperature overnight. The reaction solution was concentrated under reduced pressure to give the crude product as a white solid. Ethyl acetate (1 mL) was added and the slurry was stirred at room temp for 1 h. The solids were filtered, washed with ethyl acetate, and dried under vacuum to afford 2-(tert-butylamino)-4-(methylsulfinyl)pyrimidine-5-carboxamide (0.092 g, 0.359 mmol, 86% yield). MS (ESI) m/z 257.3 $[M+1]^+$.

H. 2-(tert-Butylamino)-4-((1R,3R,4R)-3-hydroxy-4-methylcyclohexyl-amino)pyrimidine-5-carboxamide To a stirring suspension of 2-(tert-butylamino)-4-(methylsulfinyl)pyrimidine-5-carboxamide (0.092 g, 0.359 mmol)

and (1R,2R,5R)-5-amino-2-methylcyclohexanol hydrochloride (0.065 g, 0.395 mmol) in DMF (2 mL) was added N-ethyl-N-isopropylpropan-2-amine (0.157 mL, 0.897 mmol) and the reaction was heated to 90° C. overnight. The crude reaction mixture was concentrated under reduced pressure and then ice-cold water (20 mL) was added to the residue. The resulting mixture was vigorously stirred for 1 h and then the product was filtered, washed with water and dried under vacuum to afford 2-(tert-butylamino)-4-((1R,3R,4R)-3-hydroxy-4-methylcyclohexylamino)pyrimidine-5-carboxamide (0.074 g, 0.230 mmol, 64.1% yield).

$^1$H NMR (400 MHz, DMSO-$d_6$) δ ppm 8.94 (br. s., 1H), 8.34 (s, 1H), 6.69 (br. s., 1H), 4.59 (d, J=5.47 Hz, 1H), 3.87 (br. s., 1H), 2.92-3.01 (m, 1H), 2.14 (d, J=10.15 Hz, 1H), 1.91 (d, J=11.71 Hz, 1H), 1.67 (dd, J=13.28, 3.12 Hz, 1H), 1.07-1.24 (m, 3H), 0.91-0.99 (m, 4H). MS (ESI) m/z 322.3 $[M+1]^+$.

Example 33: 2-(Cyclopropylamino)-4-((1R,3R,4R)-3-hydroxy-4-methylcyclohexylamino)pyrimidine-5-carboxamide

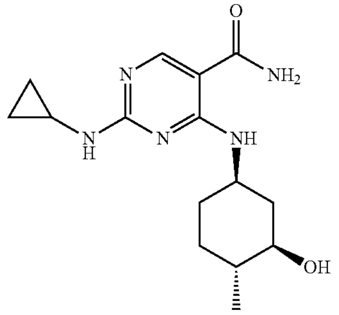 [SMILES: C[C@@H]1CC[C@@H](Nc2nc(NC3CC3)ncc2C(N)=O)C[C@H]1O]

A. 2-(Cyclopropylamino)-4-((1R,3R,4R)-3-hydroxy-4-methylcyclo-hexylamino)pyrimidine-5-carbonitrile To a solution of 4-((1R,3R,4R)-3-hydroxy-4-methylcyclohexylamino)-2-(methylsulfonyl)pyrimidine-5-carbonitrile (362 mg, 1.166 mmol; synthesis described herein) in NMP (5.832 mL), was added cyclopropanamine (0.485 mL, 7.00 mmol). The reaction was stirred at 80° C. for 5 h in a sealed vessel and then allowed to cool to ambient temperature overnight. The reaction mixture was concentrated under reduced pressure to an oil that was purified by silica gel chromatography (0-60% ethyl acetate/hexane) to afford 2-(cyclopropylamino)-4-((1R,3R,4R)-3-hydroxy-4-methylcyclohexylamino)pyrimidine-5-carbonitrile (265 mg, 0.922 mmol, 79% yield) as a solid. $^1$H NMR (400 MHz, DMSO-$d_6$) δ ppm 6.99-8.32 (m, 3H), 4.54 (d, J=5.08 Hz, 1H), 3.85-4.13 (m, 1H), 2.80-3.03 (m, 1H), 2.58-2.75 (m, 1H), 1.50-2.08 (m, 3H), 1.03-1.42 (m, 3H), 0.88 (d, J=6.25 Hz, 4H), 0.29-0.68 (m, 4H). MS (ESI) m/z 288.1 $[M+1]^+$.

B. 2-(Cyclopropylamino)-4-((1R,3R,4R)-3-hydroxy-4-methylcyclo-hexylamino)pyrimidine-5-carboxamide 2-(Cyclopropylamino)-4-((1R,3R,4R)-3-hydroxy-4-methylcyclohexylamino)pyrimidine-5-carbonitrile (265 mg, 0.922 mmol) was dissolved in DMSO (9.222 mL). To the solution was added 10 drops of 50% aqueous sodium hydroxide followed by 10 drops of 30% aqueous hydrogen peroxide at room temperature. The resulting reaction mixture was stirred at 50° C. for 2 h and was then added slowly to 60 mL of ice water. The resulting precipitate was stirred for 30 min, filtered, and washed with water. The solids were dried in a vacuum oven overnight at 45° C. to afford 2-(cyclopropylamino)-4-((1R,3R,4R)-3-hydroxy-4-methylcyclohexyl-amino)pyrimidine-5-carboxamide (229 mg, 0.750 mmol, 81% yield). $^1$H NMR (400 MHz, DMSO-$d_6$) δ ppm 8.73-8.95 (m, 1H), 8.18-8.42 (m, 1H), 7.17-7.37 (m, 1H), 4.39-4.62 (m, 1H), 3.75-3.99 (m, 1H), 2.81-3.06 (m, 1H), 2.53-2.74 (m, 1H), 2.09-2.34 (m, 1H), 1.82-2.05 (m, 1H), 1.50-1.69 (m, 1H), 0.99-1.24 (m, 3H), 0.81-0.98 (m, 4H), 0.50-0.67 (m, 2H), 0.26-0.47 (m, 2H). MS (ESI) m/z 306.3 $[M+1]^+$.

Example 34: 2-(tert-Butylamino)-4-((1R,3R)-3-hydroxy-4,4-dimethylcyclohexylamino)pyrimidine-5-carboxamide

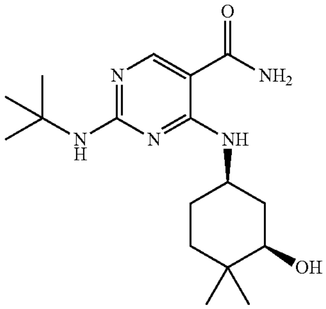 [SMILES: CC(C)(C)Nc1ncc(C(N)=O)c(N[C@@H]2CCC(C)(C)[C@H](O)C2)n1]

A. 4,4-Dimethylcyclohex-2-enol

Sodium borohydride (5.03 g, 133 mmol) was added portion-wise to a stirred solution of 4,4-dimethylcyclohex-2-enone (15.0 g, 121 mmol) in methanol (403 mL) in a water bath. Once addition was complete, the solution was allowed to stir under a nitrogen atmosphere at room temperature for 3 h. The reaction mixture was diluted with water (150 mL) and the majority of the methanol was removed under reduced pressure. The aqueous layer was extracted with ethyl acetate (2×200 mL). The combine ethyl acetate extracts were dried over anhydrous magnesium sulfate, filtered, and concentrated to an oil under reduced pressure to afford 4,4-dimethylcyclohex-2-enol (13.4 g, 106 mmol, 88% yield). $^1$H NMR (400 MHz, DMSO-$d_6$) δ ppm 5.41-5.57 (m, 1H), 5.24-5.42 (m, 1H), 4.61 (d, J=5.47 Hz, 1H), 3.82-3.99 (m, 1H), 1.65-1.83 (m, 1H), 1.21-1.59 (m, 3H), 0.93 (d, J=15.23 Hz, 6H).

B. 2-(4,4-Dimethylcyclohex-2-enyl)isoindoline-1,3-dione

Resin supported triphenylphosphine (32.7 g, 106 mmol), isoindoline-1,3-dione (17.19 g, 117 mmol), and 4,4-dimethylcyclohex-2-enol (13.4 g, 106 mmol) were combined and THF (197 mL) was added. The mixture was stirred and cooled to 0° C., then diisopropyl azodicarboxylate (21.09 mL, 107 mmol) was added drop-wise over 2 min. The reaction was stirred and allowed to warm slowly to ambient temperature overnight. The reaction mixture was filtered and then concentrated to a yellow solid under reduced pressure. Ethyl acetate (200 mL) was added and the resulting solids were filtered off again. The ethyl acetate filtrate was washed with water (100 mL), the aqueous layer extracted with ethyl acetate (100 mL), the combined organic layers were dried over anhydrous magnesium sulfate, filtered, and concentrated to an oil that was purified by silica gel chromatography (0-20% ethyl acetate/hexane) to afford 2-(4,4-dimethylcyclohex-2-enyl)isoindoline-1,3-dione (11.59 g, 45.4 mmol, 42.8% yield) as an oil. $^1$H NMR (400 MHz, DMSO-$d_6$) δ ppm 7.84 (s, 4H), 5.51-5.62 (m, 1H), 5.43 (d, J=10.15 Hz, 1H), 4.59-4.74 (m, 1H), 2.14-2.30 (m, 1H), 1.67-1.81 (m, 1H), 1.44-1.68 (m, 2H), 1.09 (s, 3H), 1.01 (s, 3H); MS (ESI) m/z 256.2 $[M+1]^+$.

C. Mixture of 2-((1R,2S,3S)-2-bromo-3-hydroxy-4,4-dimethylcyclohexyl)isoindoline-1,3-dione, 2-((1S,2R,3R)-2-bromo-3-hydroxy-4,4-dimethylcyclohexyl)isoindoline-1,3-dione, 2-((1R,2R,3R)-3-bromo-2-hydroxy-4,4-dimethylcyclohexyl)isoindoline-1,3-dione, 2-((1S,2S,3S)-3-bromo-2-hydroxy-4,4-dimethylcyclohexyl)isoindoline-1,3-dione To a solution of 2-(4,4-dimethylcyclohex-2-enyl)isoindoline-1,3-dione (11.59 g, 45.4 mmol) in chloroform (110 mL) and ethanol (3.83 mL) was added N-bromosuccinimide (10.34 g, 58.1 mmol) as a solid over a few min at ambient temperature. After addition was complete, the reaction mixture was stirred at ambient temperature overnight under nitrogen. The reaction mixture was washed with 1 M aqueous solution of sodium thiosulfate (100 mL). The aqueous layer was extracted with chloroform (100 mL) and the combined organic layers were dried over anhydrous magnesium sulfate, filtered and concentrated to an oil. To this oil was added 150 mL THF (150 mL) and a 1N aqueous solution of hydrochloric acid (30 mL). The resulting mixture was stirred at ambient temperature for 2 h. The THF was removed under reduced pressure and the remaining aqueous layer was diluted with ethyl acetate (150 mL) and 75 mL of a 1:1 water:saturated aqueous sodium bicarbonate solution mixture. The layers were separated and the aqueous was back-extracted aqueous with ethyl acetate (75 mL). The combined ethyl acetate layers were washed with brine (50 mL), dried over anhydrous magnesium sulfate, filtered and concentrated to an oil that was purified by silica gel chromatography (0-25% ethyl acetate/hexane) to afford a mixture of 2-((1R,2S,3S)-2-bromo-3-hydroxy-4,4-dimethylcyclohexyl)isoindoline-1,3-dione, 2-((1S,2R,3R)-2-bromo-3-hydroxy-4,4-dimethylcyclohexyl)isoindoline-1,3-dione, 2-((1R,2R,3R)-3-bromo-2-hydroxy-4,4-dimethylcyclohexyl)isoindoline-1,3-dione, and 2-((1S,2S,3S)-3-bromo-2-hydroxy-4,4-dimethylcyclohexyl)isoindoline-1,3-dione (11.4 g, 32.4 mmol, 71.3% yield). MS (ESI) m/z 374.5 $[M+1]^+$ and 376.5 $[M+1]^+$.

D. Mixture 2-((1R,3R)-3-hydroxy-4,4-dimethylcyclohexyl)isoindoline-1,3-dione and 2-((1S,3S)-3-hydroxy-4,4-dimethylcyclohexyl)isoindoline-1,3-dione A mixture of 2-((1R,2S,3 S)-2-bromo-3-hydroxy-4,4-dimethylcyclohexyl)isoindoline-1,3-dione, 2-((1S,2R,3R)-2-bromo-3-hydroxy-4,4-dimethylcyclohexyl)isoindoline-1,3-dione, 2-((1R,2R,3R)-3-bromo-2-hydroxy-4,4-dimethylcyclohexyl)isoindoline-1,3-dione, and 2-((1S,2S,3S)-3-bromo-2-hydroxy-4,4-dimethylcyclohexyl)isoindoline-1,3-dione (5.7 g, 16.18 mmol) was dissolved in toluene (90 mL) and methanol (9 mL). To the solution was added tributyltin hydride (5.66 mL, 21.04 mmol) over 10 min via syringe under nitrogen, followed by azobisisobutyronitrile (0.266 g, 1.618 mmol) in one portion. The mixture was allowed to stir at reflux under a nitrogen atmosphere overnight. The reaction mixture was concentrated under reduced pressure to afford a residue that was purified by silica gel chromatography (0-50% ethyl acetate/hexane) yielding a mixture of 2-((1R,3R)-3-hydroxy-4,4-dimethylcyclohexyl)isoindoline-1,3-dione and 2-((1S,3S)-3-hydroxy-4,4-dimethylcyclohexyl)isoindoline-1,3-dione (0.9 g, 3.29 mmol, 20.35% yield). $^1$H NMR (400 MHz, DMSO-$d_6$) δ ppm 7.82 (s, 4H), 4.51-4.80 (m, 1H), 3.80-4.03 (m, 2H), 2.84-3.11 (m, 1H), 1.49-1.67 (m, 3H), 1.37-1.47 (m, 1H), 1.22-1.35 (m, 1H), 1.13 (s, 3H), 0.80-0.93 (m, 3H). MS (ESI) m/z 274.0 $[M+1]^+$. The regiochemistry of the product mixture was verified by small molecule X-ray crystal diffraction. The X-ray structure was solved as follows. The single crystal X-ray diffraction studies were carried out on a Bruker Kappa APEX-II CCD diffractometer equipped with Mo $K_\alpha$ radiation (λ=0.71073 Å). Crystals were grown by vapor diffusion of pentane into a DCM solution. A 0.25×0.20×0.05 mm colorless plate was mounted on a Cryoloop with Paratone oil. Data were collected in a nitrogen gas stream at 90(2) K using ϕ and $\overline{\omega}$ scans. Crystal-to-detector distance was 60 mm and exposure time was 20 seconds per frame using a scan width of 0.5°. Data collection was 100% complete to 25.00° in θ. A total of 10827 reflections were collected covering the indices, −21<=h<=12, −7<=k<=8, −28<=1<=29. 2892 reflections were found to be symmetry independent, with a $R_{int}$ of 0.0821. Indexing and unit cell refinement indicated a primitive, orthorhombic lattice. The space group was found to be Pbcn. The data were integrated using the Bruker SAINT software program and scaled using the SADABS software program. Solution by direct methods (SHELXS) produced a complete phasing model consistent with the proposed structure of a mixture of the enantiomeric pair 2-((1R,3R)-3-hydroxy-4,4-dimethylcyclohexyl)isoindoline-1,3-dione and 2-((1S,3S)-3-hydroxy-4,4-dimethylcyclohexyl)isoindoline-1,3-dione.

All non-hydrogen atoms were refined anisotropically by full-matrix least-squares (SHELXL-97). All hydrogen atoms were placed using a riding model. Their positions were constrained relative to their parent atom using the appropriate HFIX command in SHELXL-97.

E. Mixture of (1R,5R)-5-amino-2,2-dimethylcyclohexanol hydrochloride and (1S,5S)-5-amino-2,2-dimethylcyclohexanol hydrochloride To a mixture of 2-((1R,3R)-3-hydroxy-4,4-dimethylcyclohexyl)isoindoline-1,3-dione and 2-((1S,3S)-3-hydroxy-4,4-dimethylcyclohexyl)isoindoline-1,3-dione (1.1 g, 4.02 mmol) in ethanol (50 mL) was added hydrazine hydrate (0.195 mL, 4.02 mmol). The resulting solution was allowed to stir at reflux overnight under a nitrogen atmosphere. The reaction was cooled to ambient temperature and then the pH was adjusted to <2 via addition of concentrated aqueous hydrochloric acid. The precipitate was filtered off, rinsed with ethanol, and then the resulting filtrate was concentrated to 20 mL under reduced pressure. An equal volume of water was added and this mixture was stirred at ambient temperature for 15 min. The solids were filtered off, rinsed with water, and the filtrate was concentrated under reduced pressure to give a solid that was dried in a vacuum oven for a few hours to afford a mixture of (1R,5R)-5-amino-2,2-dimethylcyclohexanol hydrochloride and (1S,5S)-5-amino-2,2-dimethylcyclohexanol hydrochloride (835 mg, 4.65 mmol, 115% yield) that was used without further purification. $^1H$ NMR (400 MHz, DMSO-$d_6$) δ ppm 7.87-8.21 (m, 3H), 2.98-3.23 (m, 1H), 2.75-3.02 (m, 1H), 1.49-1.92 (m, 2H), 1.26-1.47 (m, 3H), 0.96-1.16 (m, 1H), 0.48-0.93 (m, 6H)

F. 2-(tert-Butylamino)-4-((1R,3R)-3-hydroxy-4,4-dimethylcyclohexyl-amino)pyrimidine-5-carboxamide and 2-(tert-butylamino)-4-((1S,3S)-3-hydroxy-4,4-dimethylcyclohexylamino)pyrimidine-5-carboxamide To a stirring suspension of 2-(tert-butylamino)-4-(methylsulfinyl)pyrimidine-5-carboxamide (375 mg, 1.46 mmol) and a mixture of (1R,5R)-5-amino-2,2-dimethylcyclohexanol hydrochloride and (1S,5S)-5-amino-2,2-dimethylcyclohexanol hydrochloride (342 mg, 1.902 mmol) in DMF (4.877 mL) was added DIEA (0.767 mL, 4.39 mmol) and the reaction was heated to 90° C. overnight. The crude reaction mixture was concentrated under reduced pressure and then purified using reverse-phased semi-preparative HPLC (5-80% acetonitrile+0.1% TFA in water+0.1% TFA, over 30 min). Fractions containing product were concentrated under reduced pressure and redissolved in a mixture of ethyl acetate (125 mL) and saturated aqueous sodium bicarbonate solution (50 mL). The layers were separated and the aqueous layer was extracted with ethyl acetate (75 mL). The combined ethyl acetate layers were dried over anhydrous magnesium sulfate, filtered and concentrated under reduced pressure. The resulting residue was redissolved in a methanol (5 mL), passed over an Varian StratoSpheres HCO3 resin SPE tube for TFA removal (0.9 mmol bicarbonate equivalent), and then concentrated under reduced pressure to afford an oil that was triturated with diethyl ether and reconcentrated to give solids. The solids were dried for a few hours in a vacuum oven at 45° C. to afford a mixture of 2-(tert-butylamino)-4-((1R,3R)-3-hydroxy-4,4-dimethylcyclohexylamino)pyrimidine-5-carboxamide and 2-(tert-butylamino)-4-((1 S,3 S)-3-hydroxy-4,4-dimethylcyclohexylamino)pyrimidine-5-carboxamide (373 mg, 1.112 mmol, 76% yield).

G. SFC Separation of a mixture of 2-(tert-butylamino)-4-((1R,3R)-3-hydroxy-4,4-dimethylcyclohexylamino)pyrimidine-5-carboxamide and 2-(tert-butylamino)-4-((1S,3S)-3-hydroxy-4,4-dimethylcyclohexylamino)pyrimidine-5-carboxamide A mixture of the enantiomers 2-(tert-butylamino)-4-((1R,3R)-3-hydroxy-4,4-dimethylcyclohexylamino)pyrimidine-5-carboxamide and 2-(tert-butylamino)-4-((1S,3S)-3-hydroxy-4,4-dimethylcyclohexylamino)pyrimidine-5-carboxamide (373 mg) was separated by preparative chiral SFC utilizing a ChiralPak AD-H, 250×30 mm I.D. column with an isocratic 32% ethanol+0.1% ammonium hydroxide in $CO_2$ gradient at 50 mL/min flow rate. The faster eluting isomer was denoted as peak 1 and 155 mg (0.462 mmol) was obtained. The slower eluting isomer was denoted as peak 2 and 170.0 mg (0.502 mmol) was obtained. Peak 1: $^1H$ NMR (400 MHz, DMSO-$d_6$) δ ppm 8.82-9.11 (m, 1H), 8.34 (s, 1H), 6.50-6.82 (m, 1H), 4.40-4.72 (m, 1H), 3.72-4.01 (m, 1H), 3.01-3.25 (m, 1H), 1.83-1.99 (m, 1H), 1.65-1.81 (m, 1H), 1.37 (s, 13H), 0.89-0.95 (m, 3H), 0.72-0.88 (m, 3H). MS (ESI) m/z 336.2 $[M+1]^+$. Peak 2: $^1H$ NMR (400 MHz, DMSO-$d_6$) δ 8.95 (s, 1H), 8.34 (s, 1H), 6.68 (s, 1H), 4.52 (d, J=4.9 Hz, 1H), 3.86 (s, 1H), 3.15 (dt, J=11.3, 4.6 Hz, 1H), 1.90 (d, J=11.9 Hz, 1H), 1.72 (s, 1H), 1.40 (s, 1H), 1.36 (s, 9H), 1.34-1.05 (m, 3H), 0.91 (s, 3H), 0.82 (s, 3H). MS (ESI) m/z 336.2 $[M+1]^-$. By SAR potency comparison with similar compounds of known absolute stereochemistry provided herein, Peak 1 was assigned as 2-(tert-butylamino)-4-((1S,3S)-3-hydroxy-4,4-dimethylcyclohexylamino)pyrimidine-5-carboxamide. Peak 2 was assigned as 2-(tert-butylamino)-4-((1R,3R)-3-hydroxy-4,4-dimethylcyclohexylamino)-pyrimidine-5-carboxamide.

Example 35: 2-((1r,4r)-4-Hydroxycyclohexylamino)-4-(isopropylamino)pyrimidine-5-carboxamide

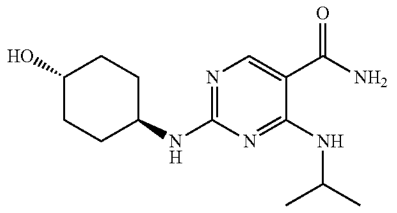 [SMILES: CC(C)Nc1nc(N[C@H]2CC[C@H](O)CC2)ncc1C(N)=O]

A. Ethyl 4-(isopropylamino)-2-(methylthio)pyrimidine-5-carboxylate

Ethyl 4-chloro-2-(methylthio)pyrimidine-5-carboxylate (900 g, 3.87 mol) ethanol (12 L), DIEA (876 mL, 5.05 mol), and isopropylamine (379 mL, 4.45 mol) were combined and mixed at ambient temperature for 4 h. An additional amount of isopropylamine (50 mL, 0.59 mol) was added and the mixture was stirred overnight at ambient temperature. The reaction was concentrated under reduced pressure and the crude product was diluted with water (2 L). The aqueous layer was extracted with chloroform (2×3 L). The combined organic layers were dried over anhydrous magnesium sulfate, filtered, and concentrated under reduced pressure to afford ethyl 4-(isopropylamino)-2-(methylthio)pyrimidine-5-carboxylate (1042 g, 4.08 mol, >100% yield, contaminated with trace DIEA) as a pale brown oil that was used without further purification. MS (ESI) m/z 256.4 $[M+1]^+$.

B. 4-(Isopropylamino)-2-(methylthio)pyrimidine-5-carboxylic acid

Ethyl 4-(isopropylamino)-2-(methylthio)pyrimidine-5-carboxylate (1042 g, 4.08 mol, >100%, contaminated with trace DIEA) was dissolved in ethanol (10 L) and to the resulting solution was added a 2M aqueous sodium hydroxide solution (3.87 L, 7.74 mol). The resulting mixture was stirred overnight at ambient temperature and then concentrated under reduced pressure. The resulting residue was diluted with 2 L of water and then washed with methyl t-butyl ether (2×1.2 L). The pH of the aqueous layer was adjusted to pH 4.2-4.5 with a 2N aqueous hydrochloric acid solution. The resulting solids were collected by filtration, washed with water (2 L) and hexanes (2 L) and then dried overnight in a vacuum oven at 45° C. to afford 4-(isopropylamino)-2-(methylthio)pyrimidine-5-carboxylic acid (848 g, 96.5% yield over 2 steps) as an off-white solid. MS (ESI) m/z 228.1 $[M+1]^+$.

C. 4-(Isopropylamino)-2-(methylthio)pyrimidine-5-carboxamide

To a solution of 4-(isopropylamino)-2-(methylthio)pyrimidine-5-carboxylic acid (180 g, 0.792 mol) and HOBt (123 g, 0.911 mol) in anhydrous THF (6.9 L) was added drop-wise a mixture of EDC (174.6 g, 0.911 mol) in acetonitrile (3.7 L) at ambient temperature. The mixture was stirred for 1 h at ambient temperature and then an aqueous ammonium hydroxide solution (989 mL, 28-30% concentrated, 10 eq) was added drop-wise over 30 min. The resulting mixture was heated to gentle reflux for 3 h and then concentrated under reduced pressure. The remaining residue was diluted with a saturated aqueous sodium bicarbonate solution (5 L) and then extracted twice with ethyl acetate (9 L and 2 L respectively). The combined organic layers were washed with a saturated aqueous sodium bicarbonate solution (4 L), water (4 L), dried over anhydrous sodium sulfate, filtered and concentrated under reduced pressure to afford 4-(isopropylamino)-2-(methylthio)-pyrimidine-5-carboxamide (171.2 g, 95.5% yield) as a solid. MS (ESI) m/z 227.4 $[M+1]^+$.

D. 4-(Isopropylamino)-2-(methylsulfinyl)pyrimidine-5-carboxamide

To a stirring solution of 4-(isopropylamino)-2-(methylthio)pyrimidine-5-carboxamide (170 g, 0.751 mol) in chloroform (22 L) was added portion-wise 3-phenyl-2-(phenylsulfonyl)-1,2-oxaziridine (235.6 g, 0.902 mol) and the resulting solution was stirred at ambient temperature overnight. An additional amount of 3-phenyl-2-(phenylsulfonyl)-1,2-oxaziridine (19.6 g, 0.075 mol) was added and the mixture was then stirred overnight at ambient temperature. The reaction solution was concentrated under reduced pressure to give the crude product as a white solid. The solids were triturated with ethyl acetate (1.5 L) at ambient temperature for 1 h, filtered, washed with ethyl acetate (250 mL), and dried in a vacuum oven overnight at 45° C. to afford 4-(isopropylamino)-2-(methylsulfinyl)pyrimidine-5-carboxamide (167.7 g, 92% yield) as white solid. MS (ESI) m/z 243.2 $[M+1]^+$.

E. 2-((1r,4r)-4-Hydroxycyclohexylamino)-4-(isopropylamino)-pyrimidine-5-carboxamide A mixture of (1r,4r)-4-aminocyclohexanol (262.4 g, 2.278 mol) and anhydrous DMF (79 mL) was heated to 100° C. To this mixture was added portion-wise 4-(isopropylamino)-2-(methylsulfinyl)pyrimidine-5-carboxamide (157.7 g, 0.651 mol). The resulting mixture was allowed to stir a under nitrogen atmosphere at 110° C. overnight. The reaction mixture was concentrated under reduced pressure to remove DMF. To the remaining residue was added water (2 L) and the mixture was extracted with ethyl acetate (3×2 L). The combined organic extracts were washed with water (2×2 L), dried over anhydrous sodium sulfate, filtered, and concentrated under reduced pressure until the remaining volume reached to 500 mL. The resulting material was filtered and washed with ethyl acetate (800 mL). The product was dried at 45° C. in a vacuum oven overnight. The product was triturated with water (2.1 L) for 4.5 h at 50° C., filtered and then dried at 45° C. in a vacuum oven overnight to afford 2-((1r,4r)-4-hydroxycyclohexylamino)-4-(isopropylamino) pyrimidine-5-carboxamide (134 g, 70% yield); $^1$H NMR (499 MHz, DMSO-$d_6$) δ ppm 8.71-9.01 (m, 1H), 8.33 (br. s., 1H), 7.42-7.70 (m, 1H), 6.67-7.12 (m, 2H), 4.51 (d, J=3.94 Hz, 1H), 3.98-4.25 (m, 1H), 3.51-3.77 (m, 1H), 3.34-3.41 (m, 1H), 1.82 (br. s., 4H), 1.06-1.33 (m, 10H). MS (ESI) m/z 294.1 $[M+1]^+$.

Example 36: (1R,4r)-4-(5-Cyano-4-((1R,3S)-3-hydroxy-3-methylcyclohexylamino)-pyrimidin-2-ylamino)-N,N-dimethylcyclohexanecarboxamide

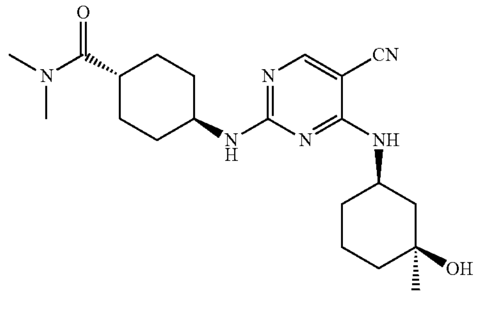 [SMILES: CN(C)C(=O)[C@H]1CC[C@H](Nc2ncc(C#N)c(N[C@@H]3CCC[C@](C)(O)C3)n2)CC1]

A. tert-Butyl (1r,4r)-4-(dimethylcarbamoyl)cyclohexylcarbamate

A mixture of (1r,4r)-4-(tert-butoxycarbonylamino)cyclohexanecarboxylic acid (7.5 g, 30.8 mmol), EDC (20.09 g, 105 mmol), HOBt (16.05 g, 105 mmol) in NMP (60 mL) was stirred at room temperature for 2 h. A solution of dimethylamine (46.2 mL, 92 mmol) (2.0 M in THF) was added and the reaction mixture was stirred for 2 days. Water and ethyl acetate were added and the phases separated. The organic phase was washed twice with saturated aqueous potassium carbonate solution, followed by 1M aqueous hydrogen chloride solution and brine. The organic phase was dried over anhydrous magnesium sulfate, filtered, and the solvent was evaporated to give the desired product (5.8 g, 19.3 mmol, 96% yield). MS (ESI) m/z 271.4 $[M+1]^+$.

B. (1r,4r)-4-Amino-N,N-dimethylcyclohexanecarboxamide hydrochloride tert-Butyl (1r,4r)-4-(dimethylcarbamoyl)cyclohexylcarbamate (8.27 g, 30.6 mmol) was dissolved in dioxane (110 mL) and hydrochloric acid (38.5 mL, 1267 mmol) was added. The reaction mixture was stirred at room temperature for 4 h, toluene was added and the solvent evaporated to give the product (6.0 g, 29.0 mmol, 95% yield). $^1$H NMR (400 MHz, DMSO-$d_6$) δ ppm 8.22 (br. S., 3H), 3.01 (s, 3H), 2.86-2.98 (m, 1H), 2.79 (s, 3H), 1.93-2.04 (m, 2H), 1.72 (d, J=7.81 Hz, 2H), 1.31-1.48 (m, 4H). MS (ESI) m/z 171.4 $[M+1]^+$ C. (1r,4r)-4-(5-Bromo-4-(methylthio)pyrimidin-2-ylamino)-N,N-dimethylcyclohexanecarboxamide To a stirring suspension of 5-bromo-2-chloro-4-(methylthio)pyrimidine (1.5 g, 6.26 mmol) in ethanol (7.5 mL) was added (1r,4r)-4-amino-N,N-dimethylcyclohexanecarboxamide hydrochloride (1.618 g, 7.83 mmol) and DIEA (3.28 mL, 18.79 mmol). The resulting mixture was stirred at 80° C. overnight. The ethanol was removed under reduced pressure and the remaining residue was purified using silica gel chromatography (0-90% ethyl acetate in hexanes) to afford (1r,4r)-4-(5-bromo-4-(methylthio)pyrimidin-2-ylamino)-N,N-dimethylcyclohexanecarboxamide (1085 mg, 2.91 mmol, 46.4% yield). MS (ESI) m/z 373.0 $[M+1]^+$, 375.2 $[M+1]^+$.

D. (1r,4r)-4-(5-Cyano-4-(methylthio)pyrimidin-2-ylamino)-N,N-dimethylcyclohexanecarboxamide (1r,4r)-4-(5-Bromo-4-(methylthio)pyrimidin-2-ylamino)-N,N-dimethylcyclohexanecarboxamide (500 mg, 1.339 mmol), zinc dust (21.90 mg, 0.335 mmol), zinc cyanide (102 mg, 0.871 mmol), 1,1'-bis-(diphenylphosphino)-ferrocene (60.0 mg, 0.107 mmol), tris(dibenzylideneacetone)dipalladium(O) (61.3 mg, 0.067 mmol), and N,N-dimethylacetamide (2.178 mL) were combined and the resulting mixture was mixed and heated at 90° C. overnight. The reaction mixture was diluted with ethyl acetate (125 mL) and water (50 mL) and filtered through a pad of Celite. The filtrate layers were separated and the aqueous layer was extracted with ethyl acetate (75 mL). The combined ethyl acetate layers were washed with brine (50 mL), dried over anhydrous magnesium sulfate, filtered, and concentrated to an oil under reduced pressure. The oil was purified using silica gel chromatography (0-10% methanol in DCM) to afford (1r,4r)-4-(5-cyano-4-(methylthio)pyrimidin-2-ylamino)-N,N-dimethylcyclohexanecarboxamide (400 mg, 1.252 mmol, 93% yield) as a solid. MS (ESI) m/z 320.2 $[M+1]^+$.

E. (1r,4r)-4-(5-Cyano-4-(methylsulfonyl)pyrimidin-2-ylamino)-N,N-dimethylcyclohexanecarboxamide To a solution of (1r,4r)-4-(5-cyano-4-(methylthio)-pyrimidin-2-ylamino)-N,N-dimethylcyclohexanecarboxamide (400 mg, 1.252 mmol) in NMP (6.261 mL) at 0° C. was added mCPBA (702 mg, 3.13 mmol). The reaction was stirred for 1 h at 0° C. and then at ambient temperature overnight. The solution was then used directly in the next step without further purification assuming a theoretical yield of (1r,4r)-4-(5-cyano-4-(methylsulfonyl)pyrimidin-2-ylamino)-N,N-dimethylcyclohexanecarboxamide (440 mg, 1.25 mmol, 100% yield). MS (ESI) m/z 352.3 $[M+1]^+$.

F. (1R,4r)-4-(5-Cyano-4-((1R,3S)-3-hydroxy-3-methylcyclohexylamino)-pyrimidin-2-ylamino)-N,N-dimethylcyclohexanecarboxamide To a solution of (1r,4r)-4-(5-cyano-4-(methylsulfonyl) pyrimidin-2-ylamino)-N,N-dimethylcyclohexanecarboxamide (440 mg, 1.252 mmol) in NMP (6.261 mL) was added (1S,3R)-3-amino-1-methylcyclohexanol hydrochloride (259 mg, 1.565 mmol) and DIEA (1.312 mL, 7.51 mmol). The reaction was stirred at 80° C. for 4 h and then allowed to cool to ambient temperature overnight The crude reaction mixture was concentrated under reduced pressure and purified using reverse-phased semi-preparative HPLC (5-60% acetonitrile+0.1% TFA in water+0.1% TFA, over 30 min). Fractions containing product were concentrated under reduced pressure. The resulting residue was redissolved in a methanol (5 mL), passed over Varian StratoSpheres HCO3 resin SPE tubes for TFA removal (0.9 mmol bicarbonate equivalent per tube), concentrated under reduced pressure, and dried overnight in a vacuum oven at 45° C. to afford (1R,4r)-4-(5-cyano-4-((1R,3S)-3-hydroxy-3-methylcyclohexylamino)pyrimidin-2-ylamino)-N,N-dimethyl-cyclohexanecarboxamide (138 mg, 0.345 mmol, 27.5% yield). $^1$H NMR (400 MHz, DMSO-$d_6$) δ ppm 8.11 (s, 1H), 7.58 (d, J=7.81 Hz, 2H), 4.70-5.01 (m, 1H), 4.12-4.42 (m, 2H), 3.52-3.79 (m, 1H), 3.00 (s, 3H), 2.79 (s, 3H), 1.21-2.07 (m, 16H), 1.03-1.20 (m, 3H). MS (ESI) m/z 401.5 $[M+1]^+$.

Example 37: 2-((1r,4r)-4-Hydroxycyclohexylamino)-4-(tert-pentylamino)pyrimidine-5-carboxamide

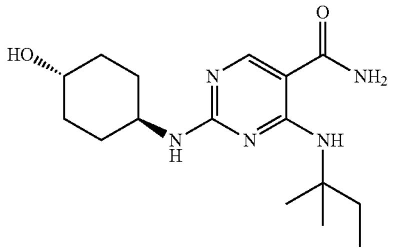 [SMILES: CCC(C)(C)Nc1nc(N[C@H]2CC[C@H](O)CC2)ncc1C(N)=O]

A. 2-(Methylthio)-4-(tert-pentylamino)pyrimidine-5-carbonitrile

4-Chloro-2-(methylthio)pyrimidine-5-carbonitrile (500 mg, 2.69 mmol) was dissolved in DMF (5 mL), 2-methylbutan-2-amine (0.378 mL, 3.24 mmol) and DIEA (1.411 mL, 8.08 mmol) were added and the reaction was heated at 70° C. overnight. LCMS showed the desired product mass as the dominant peak and no starting material remaining. The reaction was removed from heat and partitioned between ethyl acetate and water. The organic layer was washed once with brine before drying over magnesium sulfate, filtering, and condensing. The crude material was purified by silica gel chromatography (0-80% ethyl acetate in hexane over 1650 mL; 40 mL/min). Product fractions were combined, evaporated, and dried under high vacuum to afford 2-(methylthio)-4-(tert-pentylamino)pyrimidine-5-carbonitrile (359 mg, 1.519 mmol, 56.4% yield) as a white solid; MS (ESI) m/z 236.9 $[M+1]^+$ B. 2-(Methylsulfonyl)-4-(tert-pentylamino)pyrimidine-5-carbonitrile 2-(Methylthio)-4-(tert-pentylamino)pyrimidine-5-carbonitrile (350 mg, 1.481 mmol) was dissolved in NMP (5 mL), and cooled to 0° C. before adding mCPBA (664 mg, 2.96 mmol) portion-wise. The reaction was kept at 0° C. and allowed to slowly warm to room temperature. After 2 h, LCMS showed the desired product as the dominant peak and no starting material present. The crude reaction mixture was used directly in the next step assuming theoretical yield of the sulfone; MS (ESI) m/z 269.2 $[M+1]^+$ C. 2-((1r,4r)-4-Hydroxycyclohexylamino)-4-(tert-pentylamino)pyrimidine-5-carbonitrile To the crude reaction mixture from the previous step was added (1r,4r)-4-aminocyclohexanol hydrochloride (269 mg, 1.775 mmol) and DIEA (1.034 mL, 5.92 mmol). The reaction was then heated at 70° C. overnight. LCMS showed the desired product as the dominant peak and no starting material remaining. The reaction was removed from heat, and then partitioned between ethyl acetate and water. The organic layer was washed once with brine before drying over magnesium sulfate, filtering, and concentrating under reduced pressure. The material was purified by semi-preparative HPLC (5-80% acetonitrile+0.1% TFA in water+0.1% TFA). The product fractions were combined and concentrated under reduced pressure to a volume <5 mL.

The material was then neutralized with saturated sodium bicarbonate and extracted with ethyl acetate (2×). The combined organic layers were dried over magnesium sulfate, filtered, and concentrated under reduced pressure. The resulting solid was dissolved in methanol and washed through a StratoSpheres SPE PL-HCO3 MP-Resin column, eluting with methanol. Evaporation of the solvent under reduced pressure gave 2-((1r,4r)-4-hydroxycyclohexylamino)-4-(tert-pentylamino)pyrimidine-5-carbonitrile (200 mg, 0.659 mmol, 45% yield) as a white solid; $^1$H NMR (400 MHz, DMSO-$d_6$) δ ppm 8.07-8.24 (m, 1H), 7.24-7.63 (m, 1H), 5.67-5.95 (m, 1H), 4.56 (d, J=4.69 Hz, 1H), 3.35-3.60 (m, 2H), 1.74-1.96 (m, 6H), 1.09-1.43 (m, 10H), 0.72-0.86 (m, 3H); MS (ESI) m/z 304.1 $[M+1]^+$ D. 2-((1r,4r)-4-Hydroxycyclohexylamino)-4-(tert-pentylamino)pyrimidine-5-carboxamide 2-((1r,4r)-4-Hydroxycyclohexylamino)-4-(tert-pentylamino)pyrimidine-5-carbonitrile (141 mg, 0.465 mmol) was dissolved in DMSO (3 mL) and 10 drops of 50% aqueous sodium hydroxide and 10 drops of 30% aqueous hydrogen peroxide were added at room temperature. The reaction was then heated at 50° C. After 30 min, LCMS showed the desired product as the dominant peak and no starting material remaining. The reaction was removed from heat and slowly added to ~50 mL of ice water. The resulting material was allowed to mix for 3 h before filtering and drying under high vacuum at 60° C. overnight. 2-((1r,4r)-4-hydroxycyclohexylamino)-4-(tert-pentylamino)pyrimidine-5-carboxamide (125 mg, 0.389 mmol, 84% yield) was obtained; $^1$H NMR (400 MHz, DMSO-$d_6$) δ ppm 9.14 (s, 1H), 8.31 (s, 1H), 7.00 (d, J=7.81 Hz, 1H), 4.53 (d, J=4.29 Hz, 1H), 3.38 (d, J=3.51 Hz, 2H), 1.74-1.92 (m, 6H), 1.36 (s, 7H), 1.13-1.31 (m, 4H), 0.80 (t, J=7.42 Hz, 3H); MS (ESI) m/z 322.0 $[M+1]^+$.

Example 38: 4-(Bicyclo[1.1.1]pentan-1-ylamino)-2-((1R,4R)-4-hydroxycyclohexylamino)pyrimidine-5-carboxamide

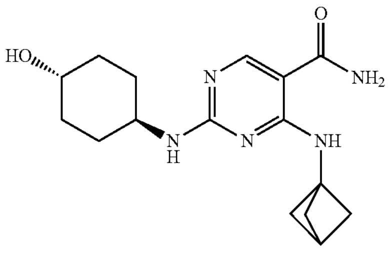 [SMILES: NC(=O)c1cnc(N[C@H]2CC[C@H](O)CC2)nc1NC12CC(C1)C2]

A. Ethyl 4-(bicyclo[1.1.1]pentan-1-ylamino)-2-(methylthio)pyrimidine-5-carboxylate A mixture of ethyl 4-chloro-2-(methylthio)pyrimidine-5-carboxylate (200 g, 0.86 mol), bicyclo[1.1.1]pentan-1-amine hydrochloride (171 g, 1.11 mol; prepared according to *Org. Lett.,* 13(17): 4746-4748 (2011)) and DIEA (278 g, 2.15 mol) in ethanol (2.4 L) was stirred overnight at room temperature. After completion of the reaction, the solvents were concentrated under reduced pressure to give the crude product, which was diluted with water (1 L). The aqueous layer was extracted with chloroform (2×1 L) and the combined organic layers were washed with brine and dried over anhydrous sodium sulfate. Evaporation of the solvents afforded the desired compound (231 g, 0.83 mol, 96% yield) as a pale brown oil which was contaminated with trace amounts of DIEA. This product was used in the next reaction without further purification; $^1$H NMR (400 MHz, $CDCl_3$) δ ppm 8.61 (s, 2H), 4.30 (q, J=7.2 Hz, 2H), 2.54 (s, 3H), 2.51 (s, 1H), 2.20 (s, 6H), 1.35 (t, J=7.2 Hz, 3H).

B. 4-(Bicyclo[1.1.1]pentan-1-ylamino)-2-(methylthio)pyrimidine-5-carboxylic acid Ethyl 4-(bicyclo[1.1.1]pentan-1-ylamino)-2-(methylthio)pyrimidine-5-carboxylate (120 g, 0.43 mol) was dissolved in ethanol (1.5 L) followed by the addition of an aqueous sodium hydroxide solution (530 mL, 1.06 mol, 2M) and the resulting mixture was stirred overnight at room temperature. After that the solvent was evaporated under reduced pressure (<42° C. bath temperature). The mixture was diluted with 500 mL of water and washed with tert-butyl methyl ether (2×500 mL). The aqueous layer was treated with aqueous hydrochloric acid solution (2N) to pH 4.2-4.5. The resulting solids were collected by filtration followed by washing with water (500 mL) and hexanes (500 mL). The wet cake was dried under reduced pressure overnight at 45° C. to afford the desired compound (108 g, 0.43 mol, 100% yield) as an off-white solid (116 mg, 0.365 mmol, 54.7% yield); $^1$H NMR (400 MHz, $CD_3OD$) δ ppm 8.52 (s, 1H), 2.55 (s, 3H), 2.52 (s, 1H), 2.24 (s, 6H)

C. 4-(Bicyclo[1.1.1]pentan-1-ylamino)-2-(methylthio)pyrimidine-5-carboxamide

To a stirring solution of 4-(bicyclo[1.1.1]pentan-1-ylamino)-2-(methylthio)pyrimidine-5-carboxylic acid (108 g, 0.43 mol) and HOBt (67 g, 0.49 mol) in anhydrous THF (4 L) was added drop-wise a mixture of EDC (94 g, 0.49 mol) in acetonitrile (2 L) at room temperature. After the reaction mixture was stirred for 1 hr at room temperature, aqueous ammonium hydroxide (600 mL, 28-30% concentrated, 10 eq) was added drop-wise over 30 min and then the mixture was heated to gentle reflux for 3 h (60±5° C.). After that all solvents were removed under reduced pressure, the residual paste/solid was diluted with saturated aqueous sodium bicarbonate solution (2 L) and the resulting suspension was filtered to afford the desired compound (100 g, 0.4 mol, 93% yield) as an off-white fluffy solid; MS(ESI): m/z 251.1 $[M+1]^+$.

D. 4-(Bicyclo[1.1.1]pentan-1-ylamino)-2-(methylsulfinyl)pyrimidine-5-carboxamide To a stirring solution of 4-(bicyclo[1.1.1]pentan-1-ylamino)-2-(methylthio)pyrimidine-5-carboxamide (76 g, 0.304 mol) in chloroform (7 L) was added 3-phenyl-2-(phenylsulfonyl)-1,2-oxaziridine (143 g, 0.547 mol, 1.8 equiv.) and the resulting pale yellow solution was stirred at ambient temperature overnight. The reaction solution was concentrated under reduced pressure to give the crude product as a white solid, which was diluted with ethyl acetate (1.5 L) and the slurry was stirred at room temperature for 1 h. The resulting suspension was filtered, washed with ethyl acetate, and dried under vacuum to afford the desired compound (73 g, 0.274 mol, 90% yield) as a white solid; MS(ESI): m/z 267.0 $[M+1]^+$.

E. 4-(Bicyclo[1.1.1]pentan-1-ylamino)-2-((1r,4r)-4-hydroxycyclohexyl-amino)pyrimidine-5-carboxamide A mixture of (1r,4r)-4-aminocyclohexanol (151.4 g, 1.314 mol) and anhydrous DMF (500 mL) was heated at ~100° C. To this mixture was added portion-wise 4-(bicyclo[1.1.1]pentan-1-ylamino)-2-(methylsulfinyl)pyrimidine-5-carboxamide (100 g, 0.376 mole) under nitrogen atmosphere and the reaction mixture was stirred at 110° C. overnight. The reaction mixture was cooled to ~45° C. and DMF was removed under reduced pressure followed by addition of water (500 mL) and ethyl acetate (500 mL). The resulting white slurry was filtered and washed with ethyl acetate (50 mL). The solid was dried at 55° C. under vacuum for 48 hrs to afford 100 g of the crude product. In order to get rid of traces of organic solvent the crude product was suspended in water (1 L) and stirred for 4.5 h keeping the internal temperature at 50±1° C. The slurry was filtered at 45-50° C. and rinsed with water (50 mL). The wet cake was dried under vacuum at 45-50° C. for 48 h to afford the desired compound (92 g, 0.289 mol, 77% yield);

$^1$H NMR ($CD_3OD$, 400 MHz): δ ppm 8.26 (s, 1H), 3.79 (m, 1H), 3.56-3.58 (m, 1H), 2.47 (s, 1H), 2.18 (s, 6H), 1.98-2.06 (m, 4H), 1.32-1.39 (m, 4H); MS(ESI): m/z 318.1 $[M+1]^+$.

Example 39: 2-((1r,4r)-4-Hydroxycyclohexylamino)-4-(1-methylcyclopropylamino)pyrimidine-5-carboxamide

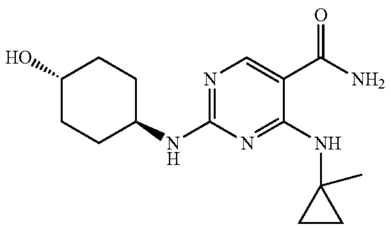 [SMILES: CC1(Nc2nc(N[C@H]3CC[C@H](O)CC3)ncc2C(N)=O)CC1]

A. (1r,4r)-4-(5-Bromo-4-(methylthio)pyrimidin-2-ylamino)-cyclohexanol

A 3-L, 3-neck, round-bottom flask was equipped with a J-KEM temperature controller, a mechanical stirrer, and a nitrogen inlet. The flask was charged with 5-bromo-2-chloro-4-(methylthio)pyrimidine (100 g, 417.5 mmol), (1r,4r)-4-aminocyclohexanol (76.4 g, 663.4 mmol), and ethanol (1 L). DIEA (109 mL, 626.3 mmol) was added, and the mixture was heated to reflux overnight. TLC (1:1 hexanes/ethyl acetate) analysis after 20 h indicated complete reaction. The reaction was allowed to cool to room temperature. Water (300 mL) was added, and a precipitate gradually formed. The solid was filtered and washed with water to give 111.7 g of a white solid. The filtrate was extracted with ethyl acetate (3×300 mL). The combined organic layers were dried over sodium sulfate, filtered, and concentrated to a semi-solid. The semi-solid was slurried in 1:1 hexanes/ethyl acetate and filtered to give an additional 12.1 g of a white solid. The two batches were combined to give 123.8 g (93%) of (1r,4r)-4-(5-bromo-4-(methylthio)pyrimidin-2-ylamino) cyclohexanol as a white solid. MS (ESI) m/z 318, 320 $[M+1]^+$.

B. 2-((1r,4r)-4-Hydroxycyclohexylamino)-4-(methylthio)pyrimidine-5-carbonitrile

A 2-L, 3-neck, round-bottom flask was equipped with a J-KEM temperature controller, a mechanical stirrer, and a nitrogen inlet. The flask was charged under nitrogen with (1r,4r)-4-(5-bromo-4-(methylthio)pyrimidin-2-ylamino)cyclohexanol (123.8 g, 389 mmol), zinc cyanide (29.2 g, 249 mmol), zinc dust (6.36 g, 97 mmol), and N,N-dimethylacetamide (478 mL). Tris(dibenzylideneacetone)dipalladium (O) (17.8 g, 0.05 equiv) and 1,1'-bis-(diphenylphosphino)-ferrocene (17.25 g, 0.08 equiv) were added, and the mixture was purged with nitrogen. The reaction was heated to 100° C. overnight. TLC (2:1 ethyl acetate/hexanes) analysis after 17 h indicated complete reaction. The reaction was allowed to cool to room temperature and diluted with ethyl acetate (2 L). The mixture was filtered through a short Celite-pad, and the pad was washed with ethyl acetate (3×400 mL). The combined organic layers were washed with water (1 L) and brine (400 mL), dried over sodium sulfate, and filtered. The filtrate was concentrated to remove most of the solvent, and a beige precipitate formed. The solids were filtered and washed with ethyl acetate (2×50 mL) to give 55 g (54%) of 2-((1r,4r)-4-hydroxycyclohexyl-amino)-4-(methylthio)pyrimidine-5-carbonitrile as a beige solid. MS (ESI) m/z 265 $[M+1]^+$.

C. 2-((1r,4r)-4-Hydroxycyclohexylamino)-4-(methylsulfinyl)-pyrimidine-5-carbonitrile and 2-((1r,4r)-4-hydroxycyclohexylamino)-4-(methylsulfonyl)pyrimidine-5-carbonitrile To a stirred colorless solution of 2-((1r,4r)-4-hydroxycyclohexylamino)-4-(methylthio)pyrimidine-5-carbonitrile (0.700 g, 2.65 mmol) in NMP (10 mL) was added mCPBA (1.306 g, 5.83 mmol) at 0° C. The reaction mixture was then stirred at room temperature for 2 h until completion of the reaction as indicated by LCMS. The reaction mixture was carried on to the next step without further purification. MS (ESI) m/z 281.4 $[M+1]^+$ and 297.2 $[M+1]^+$.

D. 2-((1r,4r)-4-Hydroxycyclohexylamino)-4-(1-methylcyclopropyl-amino)pyrimidine-5-carbonitrile To the reaction mixture of 2-((1r,4r)-4-hydroxycyclohexylamino)-4-(methylsulfinyl)pyrimidine-5-carbonitrile and 2-((1r,4r)-4-hydroxycyclohexylamino)-4-(methylsulfonyl)pyrimidine-5-carbonitrile from the previous step was added DIEA (2.78 mL, 15.89 mmol) and 1-methylcyclopropanamine hydrochloride (0.627 g, 5.83 mmol). The reaction was stirred at 90° C. for 16 h. Upon completion of reaction as indicated by LCMS and TLC the reaction mixture was concentrated and purified by silica gel chromatography using a gradient of 0%-80% ethyl acetate in hexanes. The product fractions were combined and concentrated to afford 2-((1s,4s)-4-hydroxycyclohexylamino)-4-(1-methylcyclopropylamino)pyrimidine-5-carbonitrile (0.147 g, 19% yield) as a pale yellow solid. MS (ESI) m/z 288.2 $[M+1]^+$.

E. 2-((1r,4r)-4-Hydroxycyclohexylamino)-4-(1-methylcyclopropyl-amino)pyrimidine-5-carboxamide 2-((1r,4r)-4-Hydroxycyclohexylamino)-4-(1-methylcyclopropylamino)pyrimidine-5-carbonitrile (0.225 g, 0.783 mmol) was dissolved in DMSO (15 ml). Sodium hydroxide (50% wt, 175 μL, 0.78 3 mmol) and 30% hydrogen peroxide (175 μL, 1.543 mmol) were added to the reaction mixture at room temperature. The reaction mixture was stirred at 50° C. for 1 h. Upon completion of the reaction, as indicated by LCMS and TLC, the reaction mixture was cooled to room temperature and was poured into 300 mL of ice water. The aqueous layer was extracted with 20% isopropanol in chloroform (×3) and the combined organic layers were dried over anhydrous magnesium sulfate and concentrated. The crude mixture was purified by reverse phase silica gel chromatography using a gradient of 0%-90% methanol in water. The product fractions were combined and concentrated to afford 2-((1r,4r)-4-hydroxycyclohexylamino)-4-(1-methylcyclopropylamino)pyrimidine-5-carboxamide (0.181 g, 76% yield); $^1$H NMR (400 MHz, DMSO-$d_6$) δ ppm 9.10 (s, 1H), 8.33 (s, 1H), 7.06 (d, J=7.42 Hz, 1H), 4.53 (d, J=4.30 Hz, 1H), 3.59-3.70 (m, 1H), 3.35-3.46 (m, 1H), 1.96 (d, J=9.76 Hz, 1H), 1.85 (d, J=9.76 Hz, 2H), 1.40 (s, 3H), 1.20-1.34 (m, 4H), 0.81-0.89 (m, 1H), 0.58-0.71 (m, 4H); MS (ESI) m/z 306.4 [M+1]$^+$ Example 40: 4-((R)-1-Cyclopropylethylamino)-2-((1r,4R)-4-hydroxycyclohexylamino)pyrimidine-5-carboxamide

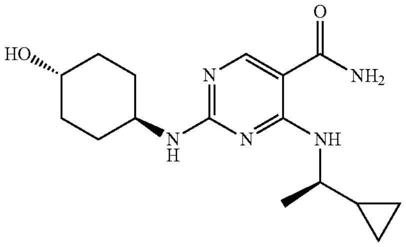 [SMILES: C[C@@H](Nc1nc(N[C@H]2CC[C@H](O)CC2)ncc1C(N)=O)C1CC1]

A. 2-((1r,4r)-4-Hydroxycyclohexylamino)-4-(methylthio)pyrimidine-5-carboxamide

A 2-L, 3-neck, round-bottom flask was equipped with a J-KEM temperature controller, a mechanical stirrer, and a nitrogen inlet. The flask was charged with 2-((1r,4r)-4-hydroxycyclohexylamino)-4-(methylthio)pyrimidine-5-carbonitrile (54 g, 204.3 mmol; synthesis described herein) and DMSO (270 mL), and the solution was cooled to 0° C. Sodium hydroxide solution (170 mL, 1021 mmol, 6 M in water) and hydrogen peroxide solution (99 mL, 1021 mmol, 35% in water) were slowly added to the reaction mixture. An exotherm to 30° C. was observed. The reaction was heated to 50° C. for 15 min. TLC (10% methanol/ethyl acetate) analysis indicated complete reaction. The mixture was cooled to 10° C., diluted with water (800 mL), and stirred for 10 min. The mixture was filtered to give 18 g of a crude solid. To recover more product, the filtrate was extracted with ethyl acetate (18×250 mL). The combined organic layers were washed with brine (75 mL), dried over sodium sulfate, filtered, and concentrated to give 33 g of a crude solid. The crude solids were combined and purified on silica gel eluting with 0-15% methanol/ethyl acetate to give 26 g of an off-white solid. The solid was slurried in acetonitrile and filtered to give 19.5 g (33%) of 2-((1r,4r)-4-hydroxycyclohexylamino)-4-(methylthio)pyrimidine-5-carboxamide as an off-white solid; MS (ESI) m/z 283.3 [M+1]$^+$ B. 2-((1r,4r)-4-Hydroxycyclohexylamino)-4-(methylsulfinyl)pyrimidine-5-carboxamide and 2-((1r,4r)-4-hydroxycyclohexylamino)-4-(methylsulfonyl)pyrimidine-5-carboxamide To a stirred yellow solution of 2-((1r,4r)-4-hydroxycyclohexylamino)-4-(methylthio)pyrimidine-5-carboxamide (0.400 g, 1.42 mmol) in NMP (5 mL) was added mCPBA (0.635 g, 2.83 mmol) at 0° C. The reaction mixture was then stirred at room temperature for 1.5 h until completion of the reaction as indicated by LCMS. The reaction mixture was carried on to next step without further purification. MS (ESI) m/z 298.0 [M+1]$^+$ and 315.1 [M+1]$^+$ C. 4-((R)-1-Cyclopropylethylamino)-2-((1r,4R)-4-hydroxycyclohexylamino)-pyrimidine-5-carboxamide To the reaction mixture of 2-((1r,4r)-4-hydroxycyclohexylamino)-4-(methylsulfinyl)pyrimidine-5-carboxamide and 2-((1r,4r)-4-hydroxycyclohexylamino)-4-(methylsulfonyl)pyrimidine-5-carboxamide from the previous reaction was added DIEA (1.56 mL, 8.95 mmol) and (R)-1-cyclopropylethanamine (0.254 g, 2.98 mmol). The reaction was stirred at 90° C. for 16 h. Upon completion of reaction, as indicated by LCMS and TLC, the reaction mixture was concentrated and purified by revere phase silica gel chromatography using a gradient of 0%-90% methanol in water. The desired fractions were purified again by silica gel chromatography using a gradient of 0%-15% methanol saturated with ammonia in DCM, followed by reverse-phased semi-preparative HPLC (0-50% acetonitrile+0.1% TFA in water+0.1% TFA, over 30 min). Fractions containing product were concentrated under reduced pressure. The resulting residue was redissolved in methanol (5 mL), passed over Varian StratoSpheres HCO3 resin SPE tubes for TFA removal (0.9 mmol bicarbonate equivalent per tube), and then concentrated under reduced pressure to afford 4-((R)-1-cyclopropylethylamino)-2-((1r,4R)-4-hydroxycyclohexylamino)pyrimidine-5-carboxamide (0.104 g, 22% yield);

$^1$H NMR (400 MHz, DMSO-$d_6$) δ ppm 8.87-9.10 (m, 1H), 8.32 (br. s., 1H), 6.68-7.02 (m, 1H), 4.51 (d, J=3.94 Hz, 1H), 3.52-3.72 (m, 2H), 3.36 (br. s., 1H), 1.82 (br. s., 4H), 1.12-1.32 (m, 8H), 0.95 (d, J=6.89 Hz, 1H), 0.25-0.50 (m, 3H), 0.10-0.23 (m, 1H); MS (ESI) m/z 320.1 [M+1]$^+$.

Example 41: 4-((1R,3R,4R)-3-Hydroxy-4-methylcyclohexylamino)-2-(1-methylcyclopropylamino)pyrimidine-5-carboxamide

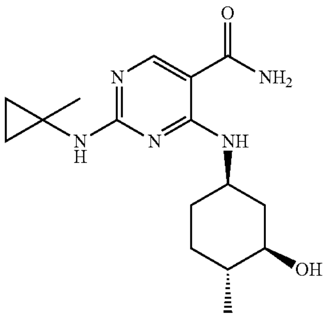 [SMILES: C[C@@H]1CC[C@@H](Nc2nc(NC3(C)CC3)ncc2C(N)=O)C[C@H]1O]

A. 5-Bromo-N-(1-methylcyclopropyl)-4-(methylthio)pyrimidin-2-amine

To a stirring suspension of 5-bromo-2-chloro-4-(methylthio)pyrimidine (1.0 g, 4.18 mmol) in ethanol (6.0 mL) was added 1-methylcyclopropanamine hydrochloride (0.674 g, 6.26 mmol) and DIEA (2.188 mL, 12.53 mmol). The mixture was stirred at 90° C. for 16 h. Upon completion of the reaction as indicated by LCMS and TLC the reaction mixture was concentrated and purified by silica gel chromatography using a gradient of 0%-20% ethyl acetate in hexanes. The product fractions were combined and concentrated to afford 5-bromo-N-(1-methylcyclopropyl)-4-(methylthio)pyrimidin-2-amine (0.665 g, 58% yield) as a white solid. MS (ESI) m/z 276.2 $[M+1]^+$.

B. 2-(1-Methylcyclopropylamino)-4-(methylthio) pyrimidine-5-carbonitrile

A black suspension of 5-bromo-N-(1-methylcyclopropyl)-4-(methylthio)pyrimidin-2-amine (0.665 g, 2.425 mmol), zinc (0.040 g, 0.606 mmol), zinc cyanide (0.185 g, 1.577 mmol), 1,1'-bis-(diphenylphosphino)-ferrocene (0.109 g, 0.194 mmol), tris(dibenzylideneacetone)dipalladium(O) (0.111 g, 0.121 mmol), and N, N'-dimethylacetamide (6 mL) was flushed with nitrogen and heated at 90° C. for 16 h. Upon completion of reaction, as indicated by LCMS and TLC, the reaction mixture was diluted with 125 mL ethyl acetate and 50 mL of water and filtered through a pad of Celite. The layers of the filtrate were separated and the aqueous layer was extracted with 75 mL of ethyl acetate. The combined ethyl acetate layers was washed with 2×50 mL brine, dried over anhydrous magnesium sulfate, filtered and concentrated to an oil. The crude oil was purified by silica gel chromatography using a gradient of 0%-30% ethyl acetate in hexanes. The product fractions were combined and concentrated to afford 2-(1-methylcyclopropylamino)-4-(methylthio)pyrimidine-5-carbonitrile (0.449 g, 84% yield) as a pale yellow solid. MS (ESI) m/z 221.2 $[M+1]^+$.

C. 2-(1-Methylcyclopropylamino)-4-(methylsulfonyl)pyrimidine-5-carbonitrile

To a stirred colorless solution of 2-(1-methylcyclopropylamino)-4-(methylthio)-pyrimidine-5-carbonitrile (0.449 g, 2.04 mmol) in NMP (6 mL) was added mCPBA (1.142 g, 5.10 mmol) at 0° C. The reaction mixture was then stirred at room temperature for 1 h until completion of the reaction as indicated by LCMS. The reaction mixture was carried on to next step without further purification. MS (ESI) m/z 253.3 $[M+1]^+$.

D. 4-((3R,4R)-3-Hydroxy-4-methylcyclohexylamino)-2-(1-methylcyclopropyl-amino)pyrimidine-5-carbonitrile To the reaction mixture of 2-(1-methylcyclopropylamino)-4-(methylsulfonyl)pyrimidine-5-carbonitrile from the previous step was added DIEA (2.14 mL, 12.22 mmol) and (1R,2R,5R)-5-amino-2-methylcyclohexanol hydrochloride (0.371 g, 2.241 mmol; synthesis described herein). The reaction was stirred at 90° C. for 16 h. Upon completion of reaction, as indicated by LCMS and TLC, the reaction mixture was concentrated and purified by silica gel chromatography using a gradient of 0%-60% ethyl acetate in hexanes. The product fractions were combined and concentrated to afford 4-((3R,4R)-3-hydroxy-4-methylcyclohexylamino)-2-(1-methylcyclopropylamino)pyrimidine-5-carbonitrile (0.185 g, 30% yield) as a pale yellow solid. MS (ESI) m/z 302.1 $[M+1]^+$ E. 4-((1R,3R,4R)-3-Hydroxy-4-methylcyclohexylamino)-2-(1-methylcyclopropylamino)pyrimidine-5-carboxamide 4-((3R,4R)-3-Hydroxy-4-methylcyclohexylamino)-2-(1-methylcyclopropylamino)pyrimidine-5-carbonitrile (0.181 g, 0.601 mmol) was dissolved in DMSO (6 mL). Ten drops of 50% aqueous sodium hydroxide (0.047 mL, 0.901 mmol) and ten drops of 30% aqueous hydrogen peroxide were added at room temperature. The reaction mixture was stirred at 50° C. for 1 h. Upon completion of reaction, as indicated by LCMS and TLC, the reaction mixture was cooled to room temperature and was poured into 300 mL of the ice water. The aqueous layer was extracted with 20% iPrOH/chloroform (×3) and the combined organic layers were dried over anhydrous magnesium sulfate and concentrated. The crude mixture was purified by reverse-phased semi-preparative HPLC (0-50% acetonitrile+0.1% TFA in water+0.1% TFA, over 30 min). Fractions containing product were concentrated under reduced pressure. The resulting residue was redissolved in methanol (5 mL), passed over Varian StratoSpheres HCO3 resin SPE tubes for TFA removal (0.9 mmol bicarbonate equiv. per tube), and then concentrated under reduced pressure to afford 4-((1R,3R,4R)-3-hydroxy-4-methylcyclohexylamino)-2-(1-methylcyclopropylamino) pyrimidine-5-carboxamide (0.069 g, 36% yield); $^1H$ NMR (400 MHz, DMSO-$d_6$) δ ppm 8.79-8.92 (m, 1H), 8.28-8.39 (m, 1H), 7.32-7.48 (m, 1H), 4.56 (s, 1H), 3.83-3.97 (m, 1H), 2.89-3.08 (m, 1H), 2.18-2.31 (m, 1H), 1.97-2.08 (m, 1H), 1.61-1.74 (m, 1H), 1.35 (s, 4H), 1.05-1.26 (m, 1H), 0.94 (d, J=6.64 Hz, 5H), 0.66 (s, 3H), 0.54 (br. s., 3H); MS (ESI) m/z 320.2 $[M+1]^+$.

Example 42: 4-(tert-Butylamino)-2-((1r,4r)-4-cyclopropoxycyclohexylamino)-pyrimidine-5-carboxamide

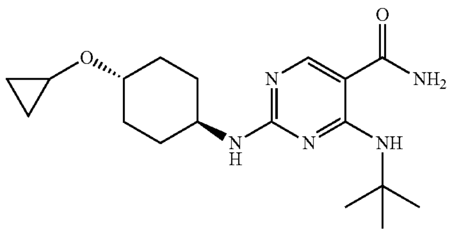 [SMILES: CC(C)(C)Nc1nc(N[C@H]2CC[C@H](OC3CC3)CC2)ncc1C(N)=O]

A. 2-((1r,4r)-4-Hydroxycyclohexyl)isoindoline-1,3-dione

To a stirring solution of isobenzofuran-1, 3-dione (90 g, 0.6 mol) and (1r,4r)-4-aminocyclohexanol (70 g, 0.6 mol) in toluene (250 mL) and DMF (250 mL) was stirred at 130° C. overnight. The reaction was cooled to room temperature, water was added and the product was filtered, washed with water and dried under vacuum to give the desired product as a white solid, which was used for the next step without further purification (119 g, 0.48 mol, yield: 81%). $^1H$ NMR (400 MHz, $CDCl_3$) δ ppm 7.84-7.79 (m, 2H), 7.72-7.68 (m, 2H), 4.18-4.10 (m, 1H), 3.80-3.73 (m, 1H), 2.40-2.29 (qd, J1=3.4 Hz, J2=130 Hz, 2H), 2.12-2.09 (dd, J=6.2 Hz, 2H), 1.78-1.74 (dd, J=6.6 Hz, 2H), 1.49-1.39 (qd, J1=3.3 Hz, J2=125 Hz, 2H).

B. 2-((1r,4r)-4-(Vinyloxy)cyclohexyl)isoindoline-1,3-dione

Palladium acetate (11 g, 0.048 mol) in ethoxyethene (500 mL) was stirred at 0° C. for 15 min, followed by the addition of a solution of 2-((1r,4r)-4-hydroxycyclohexyl)isoindoline-1,3-dione (118 g, 0.48 mol) in ethoxyethene (1000 mL). The mixture was stirred at 60° C. for 3 days. After that the mixture was cooled to room temperature, filtered and washed with ethyl acetate. The resulting filtrate was concentrated to give the crude product, which was purified by silica gel column chromatography (16.7%-25% ethyl acetate in petroleum ether) to afford the title compound as a white solid (80 g, 0.29 mol, yield: 61%). $^1$H NMR (400 MHz, $CDCl_3$) δ ppm 7.84-7.80 (m, 2H), 7.72-7.68 (m, 1H), 6.37-6.32 (dd, J=6.4 Hz, 1H), 4.34-4.30 (dd, J=1.2 Hz, 1H), 4.20-4.12 (m, 1H),4.04-4.02 (dd, J=2.0 Hz, 1H), 3.89-3.81 (m, 1H), 2.40-2.29 (qd, J1=3.4 Hz, J2=130.6 Hz, 2H), 2.21-2.17 (dd, J=64 Hz, 2H), 1.82-1.78 (dd, J=64 Hz, 2H), 1.53-1.43 (qd, J1=33 Hz, J2=126.6 Hz, 2H).

C. 2-((1r,4r)-4-Cyclopropoxycyclohexyl)isoindoline-1,3-dione

To a stirred mixture of diethyl ether (100 mL) and potassium hydroxide (2.5 N, 50 mL) was added 1-nitrosourea (38 g, 0.37 mol) at 0° C. After 15 min, the ether phase was collected and carefully added to the mixture of 2-((1r,4r)-4-(vinyloxy)cyclohexyl)isoindoline-1,3-dione (10 g, 36.9 mmol) and palladium acetate (826 mg, 3.69 mmol) in diethyl ether (100 mL) and DCM (100 mL). The resulting solution was stirred at 0° C. for 0.5 h. The procedure of generation and addition of the ethereal solution of diazomethane was then repeated three times. After the reaction was completed, the solid in the reaction mixture was filtered off, the filtrate was collected and concentrated to give the crude product which was purified by silica gel column chromatography (25% ethyl acetate in petroleum ether, then 33% ethyl acetate in petroleum ether) to give 2-((1r,4r)-4-cyclopropoxycyclohexyl)isoindoline-1,3-dione (9.3 g, 32.6 mmol, yield: 88%). $^1$H NMR (400 MHz, $CDCl_3$) δ ppm 7.84-7.79 (m, 2H), 7.72-7.67 (m, 1H), 4.18-4.09 (m, 1H), 3.56-3.48 (m, 1H),3.37-3.33 (m, 1H),2.38-2.27 (qd, J1=3.6 Hz, J2=130.6 Hz, 2H),2.21-2.18 (dd, J=6.4 Hz, 1H), 1.79-1.76 (dd, J=6.4 Hz, 2H), 1.50-1.33 (qd, J1=35 Hz, J2=126 Hz, 2H), 0.60-0.56 (m, 2H), 0.50-0.46 (m, 2H).

D. (1r,4r)-4-Cyclopropoxycyclohexanamine

A mixture of 2-((1r,4r)-4-cyclopropoxycyclohexyl)isoindoline-1,3-dione (30 g, 0.10 mol) and hydrazine hydrate (18.9 g, 0.31 mol) in methanol (600 mL) was heated at 80° C. for 2 h. The reaction was cooled to room temperature and filtered. The filtrate was collected and concentrated to give the crude product which was purified by silica gel column chromatography (3.33% methanol in DCM) to afford (1r,4r)-4-cyclopropoxycyclohexanamine as a yellow oil (10 g, 64.5 mmol, yield: 61%). $^1$H NMR (400 MHz, $CDCl_3$) δ ppm 3.40-3.28 (m, 2H), 2.72-2.65 (m, 1H), 2.06-2.03 (dd, J=3.8 Hz, 2H), 1.88-1.85 (dd, J=6.2 Hz, 2H), 1.34-1.24 (qd, J1=28 Hz, J2=123.3 Hz, 2H), 1.19-1.09 (qd, J1=28 Hz, J2=123.3 Hz, 2H), 0.56-0.51 (m, 2H), 0.49-0.44 (m, 2H); MS(ESI) m/z=156.1 $[M+1]^+$.

E. 4-(tert-Butylamino)-2-(methylsulfonyl)pyrimidine-5-carboxamide

To a stirred solution of 4-(tert-butylamino)-2-(methylthio)pyrimidine-5-carboxamide (0.500 g, 2.081 mmol; synthesis described herein) in NMP (6 mL) was added mCPBA (0.933 g, 4.16 mmol) at 0° C. The reaction mixture was stirred at room temperature for 1 h until completion of the reaction as indicated by LCMS. The reaction mixture was carried on to the next step without further purification. MS (ESI) m/z 273.2 $[M+1]^+$.

F. 4-(tert-Butylamino)-2-((1 r,4r)-4-cyclopropoxycyclohexylamino)-pyrimidine-5-carboxamide To the reaction mixture of 4-(tert-butylamino)-2-(methylsulfonyl)-pyrimidine-5-carboxamide from the previous step was added DIEA (1.5 mL, 8.33 mmol) and (1r,4r)-4-cyclopropoxycyclohexanamine (0.485 g, 3.12 mmol). The reaction was stirred at 90° C. for 16 h. Upon completion of the reaction, as indicated by LCMS and TLC, the reaction mixture was slowly added to ~70 mL of ice water. This product was filtered, washed with water, followed by a minimum amount of ethanol and diethyl ether and then dried to give the title compound 4-(tert-butylamino)-2-((1r,4r)-4-cyclopropoxycyclohexylamino)pyrimidine-5-carboxamide (0.214 g, 30% yield); $^1$H NMR (400 MHz, DMSO-$d_6$) δ 9.18 (s, 1H), 8.32 (s, 1H), 7.02-7.08 (m, 1H), 3.57-3.67 (m, 1H), 3.30 (t, J=2.93 Hz, 1H), 1.99-2.09 (m, 2H), 1.85-1.94 (m, 2H), 1.41 (s, 11H), 1.28 (br. s., 5H), 0.37-0.46 (m, 4H); MS (ESI) m/z 348.3 $[M+1]^+$.

Example 43: 4-((1R,3S)-3-Hydroxycyclohexylamino)-2-((1r,4R)-4-hydroxycyclohexylamino)pyrimidine-5-carbonitrile

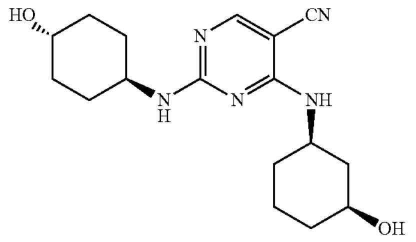 [SMILES: N#Cc1cnc(N[C@H]2CC[C@H](O)CC2)nc1N[C@@H]1CCC[C@H](O)C1]

A. 4-((1R,3S)-3-Hydroxycyclohexylamino)-2-((1r,4R)-4-hydroxycyclohexylamino)pyrimidine-5-carbonitrile 2-Chloro-4-((1R,3S)-3-hydroxycyclohexylamino)pyrimidine-5-carbonitrile (240 mg, 0.950 mmol; synthesis described herein), (1R,4R)-4-aminocyclohexanol hydrochloride (216 mg, 1.425 mmol), and cesium carbonate (619 mg, 1.899 mmol) were suspended in 1,4-dioxane (10 mL) and heated at 80° C. for 3 h. LCMS showed the desired product mass as the dominant peak and no starting material was remaining. The reaction mixture was concentrated and purified by silica gel column chromatography (10-100% ethyl acetate in hexanes, then 0-15% methanol in DCM) to give the title compound (159 mg, 0.480 mmol, 50.5% yield); $^1$H NMR (DMSO-$d_6$, 400 MHz) δ ppm 8.06-8.24 (m, 1H), 7.09-7.57 (m, 2H), 4.74 (d, J=4.3 Hz, 1H), 4.48-4.63

(m, 1H), 3.89-4.16 (m, 1H), 3.34-3.74 (m, 3H), 1.53-2.09 (m, 8H), 0.99-1.51 ppm (m, 8H); MS (ESI) m/z 332.1 [M+1]$^+$.

Example 44: 4-((1R,3S)-3-Hydroxycyclohexylamino)-2-((1r,4R)-4-(2,2,2-trifluoroethoxy)cyclohexylamino)pyrimidine-5-carbonitrile

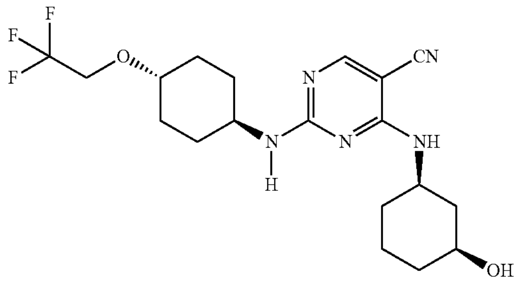 [SMILES: N#Cc1cnc(N[C@H]2CC[C@H](OCC(F)(F)F)CC2)nc1N[C@@H]1CCC[C@H](O)C1]

A. 4-((1R,3S)-3-Hydroxycyclohexylamino)-2-((1r,4R)-4-(2,2,2-trifluoroethoxy)cyclohexylamino)pyrimidine-5-carbonitrile To a stirring solution of 2-chloro-4-((1R,3S)-3-hydroxycyclohexylamino)pyrimidine-5-carbonitrile (113 mg, 0.447 mmol; synthesis described herein) and (1r,4r)-4-(2,2,2-trifluoroethoxy)cyclo-hexanamine (150 mg, 0.761 mmol; synthesis described herein) in DMSO (6.0 mL) was added DIEA (0.156 mL, 0.895 mmol). The resulting mixture was stirred at ambient temperature for 3 d. DMSO was removed under reduced pressure and the remaining residue was purified using silica gel chromatography (0-40% ethyl acetate+10% 7 N ammonia in methanol in hexanes) to afford the title compound (156 mg, 0.378 mmol, 84.6% yield). $^1$H NMR (400 MHz, DMSO-$d_6$) δ ppm 8.03-8.29 (m, 1H), 7.10-7.62 (m, 2H), 4.74 (d, J=3.90 Hz, 1H), 4.05 (q, J=9.37 Hz, 3H), 3.36-3.82 (m, 3H), 1.55-2.13 (m, 8H), 1.00-1.50 (m, 8H). $^{19}$F NMR (376 MHz, DMSO-$d_6$) δ ppm −73.64 (t, J=9.19 Hz, 3F). MS (ESI) m/z 414.2 [M+1]$^+$.

Example 45: 2-((1r,4R)-4-(Difluoromethoxy)cyclohexylamino)-4-((1R,3S)-3-hydroxycyclohexylamino)pyrimidine-5-carbonitrile

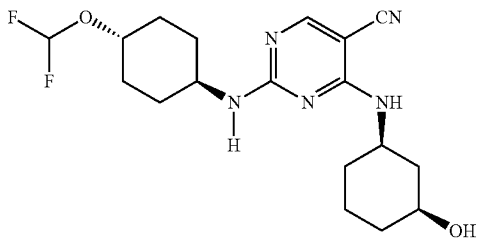 [SMILES: N#Cc1cnc(N[C@H]2CC[C@H](OC(F)F)CC2)nc1N[C@@H]1CCC[C@H](O)C1]

A. 2-((1r,4R)-4-(Difluoromethoxy)cyclohexylamino)-4-((1R,3S)-3-hydroxycyclo-hexylamino)pyrimidine-5-carbonitrile To a stirring solution of 2-chloro-4-((1R,3S)-3-hydroxycyclohexylamino)pyrimidine-5-carbonitrile (100 mg, 0.396 mmol; synthesis described herein) and (1r,4r)-4-(difluoromethoxy)cyclohexanamine (131 mg, 0.791 mmol; synthesis described herein) in DMSO (4.0 mL) was added DIEA (0.138 mL, 0.791 mmol). The resulting mixture was stirred at ambient temperature overnight. DMSO was removed under reduced pressure and the remaining residue was purified using silica gel chromatography (5-40% ethyl acetate+10% ammonia saturated methanol in hexanes) to afford the title compound (130 mg, 0.340 mmol, 86.0% yield).

$^1$H NMR (400 MHz, DMSO-$d_6$) δ ppm 8.08-8.25 (m, 1H), 7.12-7.62 (m, 2H), 6.47-6.94 (m, 1H), 4.74 (d, J=4.29 Hz, 1H), 3.88-4.18 (m, 2H), 3.41-3.85 (m, 2H), 1.01-2.11 (m, 16H). $^{19}$F NMR (376 MHz, DMSO-$d_6$) δ ppm −79.21-78.76 (m, 2F). MS (ESI) m/z 382.3 [M+1]$^+$.

Example 46: 4-(tert-Butylamino)-2-(4-hydroxybicyclo[2.2.1]heptan-1-ylamino)pyrimidine-5-carboxamide

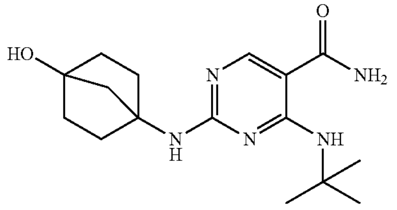 [SMILES: CC(C)(C)Nc1nc(NC23CCC(O)(CC2)C3)ncc1C(N)=O]

A. Cyclopentane-1,3-dicarboxylic acid

A 22-L, 3-neck, round bottom flask was equipped with a mechanical stirrer, a J-KEM temperature controller, and a nitrogen inlet. The flask was charged with norbornene (200 g, 2.123 mol), ethyl acetate (1.95 L), and acetonitrile (1.95 L). The reaction mixture was cooled to 5° C. using an acetone/dry ice bath. Ruthenium trichloride (9.69 g, 46.72 mmol) was added in one portion followed by the slow addition of a suspension of sodium periodate (1.816 kg, 8.707 mol) in water (2.925 L) over 30 min. The reaction slowly began to exotherm and was monitored to keep the temperature between 10° C. and 15° C. After 90 min the reaction mixture suddenly thickened to the point where stirring was difficult and exothermed rapidly up to 39° C. (a large amount of dry ice was added to the cooling bath to control the exotherm). The reaction mixture was allowed to cool to 20° C., the dry ice/acetone bath was removed, and the mixture was stirred at room temperature overnight. The solids were removed by filtration through a pad of celite and the filtrate was concentrated to a solid which was triturated with hexane (2 L), filtered, and rinsed with hexane (2×500 mL) to yield 195 g (58%) of cyclopentane-1,3-dicarboxylic acid.

$^1$H NMR (500 Hz, DMSO-$d_6$) δ ppm 12.07 (s, 2H), 2.66-2.73 (m, 2H), 2.06-2.12 (m, 1H), 1.85-1.89 (m, 1H), 1.72-1.85 (m, 4H).

B. Dimethyl cyclopentane-1,3-dicarboxylate

A 5-L, 3-neck, round bottom flask was equipped with a mechanical stirrer, a J-KEM temperature controller, and a reflux condenser. The flask was charged with cyclopentane-1,3-dicarboxylic acid (357 g, 2.262 mol) and methanol (1.75 L). The solution was cooled to 7° C. using an ice/water bath.

Concentrated sulfuric acid (70 mL) was added dropwise over 30 min resulting in an exotherm up to 12° C. The reaction mixture was heated to reflux and stirred for 16 h when TLC analysis (10% methanol/ethyl acetate) indicated that the reaction was complete. The reaction mixture was concentrated, redissolved in methyl tert-butyl ether, and washed with saturated aqueous sodium bicarbonate (2×150 mL) and brine (2×150 mL). The organic layer was dried over sodium sulfate, filtered, and concentrated. The resulting clear oil was dissolved in hexane (2 L) and treated with a 2 N aqueous sodium hydroxide solution (950 mL) until the pH ~10. The layers were separated and the aqueous layer was extracted with hexane (4×1 L). The organic layers were combined, dried over sodium sulfate, filtered, and concentrated to provide 360 g (100%) of dimethyl cyclopentane-1,3-dicarboxylate as a clear oil. $^1H$ NMR (500 Hz, $CDCl_3$) δ ppm 3.67 (s, 6H), 2.75-2.83 (m, 2H), 2.20-2.26 (m, 1H), 2.05-2.12 (m, 1H), 1.90-2.0 (m, 4H).

C. Dimethyl bicyclo[2.2.1]heptane-1,4-dicarboxylate

A 22-L, 3-neck, round bottom flask was equipped with a J-KEM temperature controller, a mechanical stirrer, a nitrogen inlet, and an addition funnel. The flask was flushed with nitrogen then charged with anhydrous THF (5 L) and diisopropylamine (731 mL, 5.219 mol). The solution was cooled to −20° C. using a dry ice/acetone bath. The stirring mixture was slowly treated with 1.6 M n-butyllithium in hexanes (3.02 L, 4.833 mol) via cannula over 1 h maintaining the temperature between −20° C. and −27° C. The reaction mixture was cooled to −40° C. and hexamethylphosphoramide (2.7 L, 16.317 mol) was slowly added via addition funnel over 40 min. The reaction mixture was cooled to −73° C. and dimethyl cyclopentane-1,3-dicarboxylate (360 g, 1.933 mol) dissolved in anhydrous THF (2 L) was slowly added via addition funnel over 2 h. The reaction mixture was warmed to −10° C. and stirred at that temperature for 30 min, then cooled to −70° C. and treated with 1-bromo-2-chloroethane (267 mL, 3.209 mol) via addition funnel over 4 h. The reaction mixture was allowed to slowly warm to room temperature over 12 h and then was quenched with saturated aqueous ammonium chloride (2 L) over 90 min. The reaction mixture was diluted with hexane (2 L), the layers were separated, and the aqueous layer was further extracted with hexane (3×2 L). The combined organic layers were washed with brine (2×1 L), dried over sodium sulfate, filtered, and concentrated to a brown oil. The crude product was purified by silica gel purification (0-10% ethyl acetate/hexane). The product containing fractions were concentrated to near dryness and diluted with hexanes. The resulting crystalline solids were filtered and washed with hexane (200 mL) providing pure product as a clear crystalline solid. Additional batches of product were obtained from the filtrate in a similar manner. All product batches were combined to provide 208 g (51%) of dimethyl bicyclo[2.2.1]heptane-1,4-dicarboxylate as a clear crystalline solid. $^1H$ NMR (500 Hz, $CDCl_3$) δ ppm 3.68 (s, 6H), 2.03 (d, J=6.4 Hz, 4H), 1.90 (s, 2H), 1.67 (d, J=7.0, 4H).

D. 4-(Methoxycarbonyl)bicyclo[2.2.1]heptane-1-carboxylic acid

A 12-L, 3-neck, round bottom flask was equipped with a mechanical stirrer, a J-KEM temperature controller, and a 250 mL addition funnel. The flask was charged with dimethyl bicyclo[2.2.1]heptane-1,4-dicarboxylate (208 g, 980 mmol) and THF (6.7 L). The resulting solution was cooled to 15° C. using an ice/water bath. Sodium hydroxide pellets (39.2 g, 980 mmol) were dissolved in methanol (400 mL) and slowly added to the stirring solution over 30 min. After the addition was complete, white solids began to precipitate. The reaction mixture was stirred at room temp for 16 h when TLC analysis (100% ethyl acetate) indicated about 90% conversion. The reaction mixture was concentrated to dryness, slurried in hexane (2 L), filtered, and washed with hexane (2×400 mL). The resulting sodium carboxylate salt was transferred to a 3-L, 3-neck, round bottom flask equipped with a mechanical stirrer, dissolved in water (1 L), and slowly treated with 2 N aqueous hydrochloric acid (430 mL) at 10° C. until pH ~4. The thick suspension was diluted with ethyl acetate (1 L) and transferred to a separatory funnel. The layers were separated and the aqueous layer was further extracted with ethyl acetate (2×500 mL), washed with brine (200 mL), dried over sodium sulfate, and concentrated to provide 170 g (87%) of 4-(methoxycarbonyl)bicyclo[2.2.1]heptane-1-carboxylic acid.

$^1H$ NMR (500 Hz, DMSO-$d_6$) δ ppm 12.21 (s, 1H), 3.60 (s, 3H), 1.91 (d, J=6.7 Hz, 4H), 1.75 (s, 2H), 1.56-1.62 (m, 4H).

E. 4-(Benzyloxycarbonylamino)bicyclo[2.2.1]heptane-1-carboxylic acid

A 2-L, 3-neck, round bottom flask was equipped with a mechanical stirrer, a J-KEM temperature controller, a reflux condenser, and a nitrogen inlet. The flask was charged with 4-(methoxycarbonyl)bicyclo[2.2.1]heptane-1-carboxylic acid (100 g, 0.504 mol) and anhydrous toluene (500 mL). The flask was cooled to 10° C. and DIEA (175 mL, 1.008 mol) was slowly added over 5 min resulting in a mild exotherm up to 14° C. Diphenylphosphonic azide (130 mL, 0.605 mol) was slowly added to the reaction mixture. The mixture was heated to about 60° C. when off-gassing began. The reaction quickly generated a large amount of gas and exothermed to reflux. The reaction was stirred at reflux (110° C.) for 2 h, then cooled to 50° C. and slowly treated with benzyl alcohol (104 mL, 1.008 mol) over 5 min. The reaction was heated again to 110° C. and stirred for 40 h. The reaction mixture was concentrated to an oil in vacuo, dissolved in ethyl acetate (2 L), washed with brine (500 mL), and the brine layer was extracted with ethyl acetate (2×400 mL). The combined organics were dried over sodium sulfate, filtered, and concentrated to a crude oil which was transferred to a 5-L, 3-neck, round bottom flask equipped with a mechanical stirrer, a J-KEM temperature controller, and a nitrogen inlet. The flask was charged with methanol (2 L). The mixture was cooled to 10° C. and treated with 2N sodium hydroxide (500 mL) over 5 min resulting in an exotherm to 16° C. The reaction was stirred at 60° C. for 20 h when TLC analysis (20% methanol/ethyl acetate) indicated a complete reaction. The reaction was cooled to room temperature and methanol was removed in vacuo. With cooling, the reaction mixture was acidified using 2 N hydrochloric acid (480 mL) to pH 2-3. The aqueous mixture was extracted using ethyl acetate (2 L, then 500 mL). The combined organic layers were washed with brine (400 mL), dried over sodium sulfate, and concentrated to provide the crude product as a brown oil. The crude product was purified by silica gel chromatography (20-100% ethyl acetate/hexane) providing 132 g (91%) of 4-(benzyloxycarbonylamino)-bicyclo[2.2.1]heptane-1-carboxylic acid. $^1H$ NMR (500 Hz, DMSO-$d_6$) δ ppm 12.12 (s, 1H), 7.56 (s, 1H), 7.34-7.38 (m, 4H), 7.28-7.32 (m, 1H), 4.98 (s, 2H), 1.80-1.93 (m, 4H), 1.79 (s, 2H), 1.64 (t, J=9.1 Hz, 2H), 1.57 (t, J=8.8 Hz, 2H).

F. 4-Aminobicyclo[2.2.1]heptane-1-carboxylic acid

A 2-L Parr bottle was charged with 4-(benzyloxycarbonylamino)bicyclo[2.2.1]heptane-1-carboxylic acid (105 g, 363 mmol), methanol (500 mL), 0.8 N hydrochloric acid (500 mL), and 10% palladium on carbon (38.6 g, 18.15 mmol, 50% wet with water). The reaction mixture was reacted on a Parr shaker under 30 gpsi hydrogen for 10 h when TLC analysis (10% methanol/ethyl acetate) indicated a complete reaction. The catalyst was removed by filtration through a short plug of celite and the plug was washed thoroughly with water (4×100 mL). The filtrate was concentrated to provide 4-aminobicyclo[2.2.1]heptane-1-carboxylic acid (56.3 g, 100%) as a wet white solid which was used in the next step without any further purification; MS (ESI) m/z 156.2 $[M+1]^+$ G. 4-Hydroxybicyclo[2.2.1]heptane-1-carboxylic acid A 2-L, 3-neck, round bottom flask was equipped with a mechanical stirrer, a reflux condenser, a J-KEM temperature controller, and a nitrogen inlet. The flask was charged with 4-aminobicyclo[2.2.1]heptane-1-carboxylic acid (56.3 g, 363 mmol) and 10% aqueous acetic acid (340 mL). The reaction mixture was cooled to 10° C. and was slowly treated over 45 min with sodium nitrite (75.0 g, 1.088 mol) in water (125 mL) via addition funnel. A significant amount of gas evolution was observed and the reaction mixture was stirred at 65° C. overnight. The reaction was cooled to 5° C. and slowly treated over 30 min with potassium hydroxide (183 g, 3.265 mol) in methanol (400 mL) via addition funnel. The reaction was stirred at 65° C. for 5 h when TLC analysis (10% methanol/ethyl acetate) indicated a complete reaction. The reaction mixture was concentrated to remove methanol and the remaining aqueous mixture was extracted with ethyl acetate (2×400 mL). The aqueous layer was acidified to pH 3 using concentrated hydrochloric acid (210 mL) while cooling in ice/water bath. The resulting solids (impurities) were filtered and washed with water (2×30 mL). The filtrate was extracted with ethyl acetate (10×400 mL), dried over sodium sulfate, and concentrated to dryness to provide 53 g (94%) of 4-hydroxybicyclo[2.2.1]heptane-1-carboxylic acid; MS (ESI) m/z 155.2 $[M-1]^-$ H. Benzyl 4-hydroxybicyclo[2.2.1]heptan-1-ylcarbamate A 3-L, 3-neck, round bottom flask was equipped with a mechanical stirrer, a J-KEM temperature controller, a nitrogen inlet, and a 125 mL addition funnel. The flask was flushed with nitrogen and charged with 4-hydroxybicyclo[2.2.1]heptane-1-carboxylic acid (53 g, 339 mmol) and anhydrous toluene (350 mL). The reaction mixture was cooled to 10° C. and treated with benzyl alcohol (175 mL, 1.695 mol). The reaction mixture was then slowly treated with DIEA (118 mL, 678 mmol) and diphenylphosphonic azide (87.7 mL, 407 mmol). The reaction mixture was slowly heated up to 50° C. when off-gassing began. The heating mantle was removed and the reaction mixture slowly exothermed up to 75° C. while off-gassing considerably. The reaction was heated to 110° C. and stirred for 20 h when TLC analysis (10% methanol/ethyl acetate) indicated a complete reaction. The reaction mixture was concentrated to remove solvent and partitioned between ethyl acetate (1.2 L) and brine (700 mL). The organic layer was dried over sodium sulfate, concentrated, and purified by silica gel chromatography (20-60% ethyl acetate/hexane) providing 61 g (69%) of benzyl 4-hydroxybicyclo[2.2.1]heptan-1-ylcarbamate; MS (ESI) m/z 260.1 $[M-1]^-$ I. 4-Aminobicyclo[2.2.1]heptan-1-ol hydrochloride A 2-L Parr bottle was charged with benzyl 4-hydroxybicyclo[2.2.1]heptan-1-ylcarbamate (61 g, 233 mmol), methanol (400 mL), and water (200 mL). The Parr bottle was flushed with nitrogen and charged with 10% palladium on carbon (25 g, 11.65 mmol, 50% wet with water). The reaction was run under 30 gpsi hydrogen on a parr shaker for 3 h when TLC analysis (15% methanol/DCM with 2% ammonium hydroxide) indicated a complete reaction. The reaction was filtered through a celite plug and concentrated to remove methanol. The resulting aqueous mixture was treated with 2 N hydrochloric acid (115 mL) until it reached pH 1-2. The aqueous mixture was extracted using ethyl acetate (5×400 mL) to remove an impurity. The aqueous mixture was concentrated to dryness and dried in a vacuum oven at 40° C. overnight to provide 36.91 g (97%) of 4-aminobicyclo[2.2.1]heptan-1-ol hydrochloride; MS (ESI) m/z 128.1 $[M+1]^+$ J. 4-(tert-Butylamino)-2-(4-hydroxybicyclo [2.2.1]heptan-1-ylamino)-pyrimidine-5-carboxamide 4-(tert-Butylamino)-2-(methylsulfonyl)pyrimidine-5-carboxamide (0.165 g, 0.606 mmol; synthesis described herein), 4-aminobicyclo[2.2.1]heptan-1-ol hydrochloride (0.105 g, 0.644 mmol) and DIEA (0.337 mL, 1.931 mmol) were mixed in DMF (8 mL) and heated at 90° C. overnight. The solvent was evaporated and the residue was purified by silica gel column chromatography (0-10% methanol in ethyl acetate) to give the desired product. (41 mg, 0.127 mmol, 21%). $^1$H NMR (400 MHz, DMSO-$d_6$) δ ppm 9.43 (br. s., 0H) 8.32 (s, 1H) 7.07 (br. s., 1H) 4.88 (br. s., 1H) 1.94-2.14 (m, 2H) 1.61-1.87 (m, 6H) 1.49-1.60 (m, 2H) 1.42 (s, 9H). MS (ESI) m/z 320.0 $[M+1]^+$ Example 47: 2-((1r,4r)-4-Hydroxycyclohexylamino)-4-(3-methylbicyclo[1.1.1]pentan-1-ylamino)pyrimidine-5-carboxamide

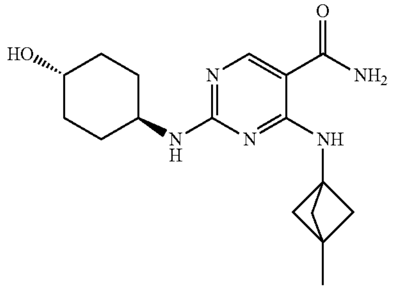 [SMILES: CC12CC(Nc3nc(N[C@H]4CC[C@H](O)CC4)ncc3C(N)=O)(C1)C2]

A. 3-Methylbicyclo[1.1.1]pentane-1-carboxylic acid

To a solution of 1-iodo-3-methylbicyclo[1.1.1]pentane (1.62 g, 7.79 mmol; prepared according to *Eur. J. Org.*

*Chem.* 1137-1155 (2000)) in diethyl ether (26 mL), a solution of tert-butyllithium (9.16 mL, 15.57 mmol, 1.7 M in pentane) was added over a period of 40 min at −78° C. After stirring the reaction mixture for 1 h at this temperature, carbon dioxide gas was bubbled through the reaction mixture for 5 min and then the mixture was allowed to warm to room temperature. The reaction mixture was extracted twice with a 5% aqueous sodium bicarbonate solution. The combined aqueous phases were acidified to pH 2-3 with concentrated hydrochloric acid at 0° C., saturated with sodium chloride, and extracted with diethyl ether. The combined organic phases were dried and, after evaporation of the solvent under reduced pressure, purified by column chromatography (0-20% ethyl acetate in hexanes) to afford 3-methylbicyclo[1.1.1]pentane-1-carboxylic acid (0.5 g, 3.96 mmol, 50.9% yield); $^1$H NMR (400 MHz, DMSO-$d_6$) δ ppm 12.21 (s, 1H), 1.82 (s, 6H), 1.14 (s, 3H).

B. tert-Butyl 3-methylbicyclo[1.1.1]pentan-1-ylcarbamate

Diphenylphosphonic azide (0.340 mL, 1.577 mmol) was added dropwise to a solution of 3-methylbicyclo[1.1.1]pentane-1-carboxylic acid (0.199 g, 1.577 mmol) and TEA (0.220 mL, 1.577 mmol) in dry tert-butanol (6 mL). The solution was stirred at room temperature for 4 h and then heated to reflux for 24 h. The solvent was evaporated under reduced pressure and the residue was extracted three times with tert-butyl methyl ether. The combined organic phase was washed with saturated aqueous sodium bicarconate solution and dried over anhydrous magnesium sulfate. After filtration and evaporation of the solvent under reduced pressure the residue was purified by column chromatography (0-5% ethyl acetate in hexanes) to afford tert-butyl 3-methylbicyclo[1.1.1]pentan-1-ylcarbamate (0.111 g, 0.563 mmol, 35.7% yield); $^1$H NMR (400 MHz, DMSO-$d_6$) δ ppm 1.74 (s, 6H), 1.36 (s, 9H), 1.17 (s, 3H).

C. 3-Methylbicyclo[1.1.1]pentan-1-amine hydrochloride

To a solution of tert-butyl 3-methylbicyclo[1.1.1]pentan-1-ylcarbamate (0.1 g, 0.507 mmol) in ethyl acetate (10 mL) was added hydrochloric acid (0.760 mL, 3.04 mmol, 4M in dioxane) at room temperature. The reaction was stirred at room temperature for 16 h. The reaction mixture was concentrated, the resulting solids were washed with diethyl ether and the resulting suspension filtered to give 3-methylbicyclo[1.1.1]pentan-1-amine hydrochloride (0.04 g, 0.299 mmol, 59.1% yield). $^1$H NMR (400 MHz, DMSO-$d_6$) δ ppm 8.59 (br. s., 3H), 1.84 (s, 6H), 1.22 (s, 3H).

D. 2-((1r,4r)-4-Hydroxycyclohexylamino)-4-(3-methylbicyclo[1.1.1]pentan-1-ylamino)pyrimidine-5-carboxamide To a stirring suspension of 2-((1r,4r)-4-hydroxycyclohexylamino)-4-(methylsulfinyl)pyrimidine-5-carboxamide (0.25 g, 0.838 mmol; synthesis described herein) and 3-methylbicyclo-[1.1.1]pentan-1-amine hydrochloride (0.123 g, 0.922 mmol) in DMF (3 mL) was added DIEA (0.366 mL, 2.095 mmol) and the reaction was heated to 80° C. overnight. The crude reaction mixture was concentrated under reduced pressure and then ice-cold water (20 mL) was added to the residue. The resulting mixture was vigorously stirred for 1 h and then the formed precipitate was filtered, washed with water and dried under vacuum to afford 2-((1r,4r)-4-hydroxycyclohexylamino)-4-(3-methylbicyclo[1.1.1]pentan-1-ylamino)pyrimidine-5-carboxamide (0.222 g, 0.670 mmol, 80% yield). $^1$H NMR (400 MHz, DMSO-$d_6$) δ ppm 1.15-1.31 (m, 7H), 1.81-1.93 (m, 4H), 1.98 (s, 6H), 3.35-3.44 (m, 1H), 3.54-3.63 (m, 1H), 4.56 (d, J=4.29 Hz, 1H), 7.12 (d, J=7.81 Hz, 1H), 8.35 (s, 1H), 9.35 (s, 1H); MS (ESI) m/z 332.4 $[M+1]^+$.

Example 48: 4-((1R,3S)-3-Hydroxycyclohexylamino)-2-(4-methyltetrahydro-2H-pyran-4-ylamino)pyrimidine-5-carboxamide

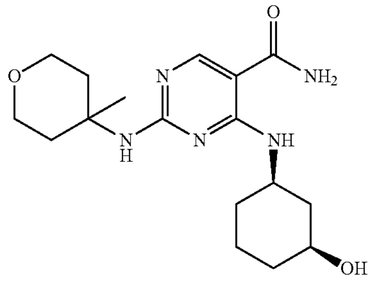 [SMILES: CC1(Nc2ncc(C(N)=O)c(N[C@@H]3CCC[C@H](O)C3)n2)CCOCC1]

A. 4-((1R,3S)-3-Hydroxycyclohexylamino)-2-(4-methyltetrahydro-2H-pyran-4-ylamino)pyrimidine-5-carboxamide 4-((1R,3S)-3-Hydroxycyclohexylamino)-2-(methylsulfonyl)pyrimidine-5-carboxamide (0.740 g, 2.354 mmol; synthesis described herein), 4-methyltetrahydro-2H-pyran-4-amine hydrochloride (0.892 g, 5.88 mmol), DIEA (1.645 mL, 9.42 mmol) and NMP (20 mL) were combined and heated for 1 h at 180° C. in a microwave. The solvent was concentrated under reduced pressure and the residue was purified by column chromatography (0-10% methanol in DCM) to afford 4-((1R,3S)-3-hydroxycyclohexylamino)-2-(4-methyltetrahydro-2H-pyran-4-ylamino)pyrimidine-5-carboxamide (88 mg, 0.252 mmol, 10.70% yield). $^1$H NMR (400 MHz, DMSO-$d_6$) δ ppm 8.96 (br. s., 1H), 8.35 (s, 1H), 6.76 (br. s., 1H), 4.65 (d, J=4.69 Hz, 1H), 3.56 (dd, J=3.32, 6.83 Hz, 4H), 3.40-3.47 (m, 1H), 2.20-2.29 (m, 2H), 2.10 (d, J=10.93 Hz, 1H), 1.76-1.89 (m, 2H), 1.66-1.73 (m, 1H), 1.50-1.59 (m, 2H), 1.39 (s, 3H), 1.16-1.26 (m, 1H), 1.03-1.12 (m, 3H). MS (ESI) m/z 350.4 $[M+1]^+$.

Example 49: 4-((1R,3S)-3-Hydroxycyclohexylamino)-2-((1r,4r)-4-[($^2H_3$)methyloxy]-cyclohexylamino) pyrimidine-5-carboxamide

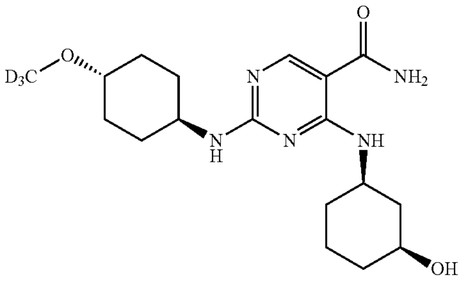 [SMILES: [2H]C([2H])([2H])O[C@H]1CC[C@H](Nc2ncc(C(N)=O)c(N[C@@H]3CCC[C@H](O)C3)n2)CC1]

A. (1r,4r)-4-[($^2H_3$)methyloxy]-N-tritylcyclohexanamine

To a solution of (1r,4r)-4-(tritylamino)cyclohexanol (2.34 g, 6.55 mmol) in dry THF (15 mL) was added sodium hydride (524 mg, 13.1 mmol, 60% in mineral oil) at 0° C. After the resulting mixture was stirred for 30 minutes at 0° C. under nitrogen atmosphere, a solution of iodo($^2H_3$)methane (1.0 g, 6.89 mmol) in THF (5 mL) was added dropwise at 0° C. The resulting mixture was stirred at room temperature overnight under nitrogen atmosphere, then poured into ice water and extracted with ethyl acetate. The combined organic layers were washed with brine, dried over anhydrous sodium sulfate and filtered. The filtrate was evaporated under vacuum to give crude product, which was purified by silica gel column chromatography (5% ethyl acetate in petroleum ether) to afford the title compound (2.0 g, 5.35 mmol, 83% yield) as a white solid. MS (ESI) m/z 375.0 $[M+1]^+$.

B. (1r,4r)-4-[($^2H_3$)Methyloxy]cyclohexanamine

To a cooled (0° C.) solution of (1r,4r)-4-[($^2H_3$)methyloxy]-N-tritylcyclohexanamine (2.0 g, 5.35 mmol) in DCM (10 mL) was added TFA (3 mL) at 0° C. The resulting mixture was dark red. Triethylsilane (0.4 mL) was added until the resulting mixture was changed to colourless. The reaction was stirred at 0° C. for additional 15 min. After removal of all volatile solvents in vacuo, the residue was further dried under high vacuum for 2 h to give the crude product as a white solid. The crude product was dissolved in ethyl acetate and aqueous hydrochloride solution (20 mL, 0.25 mol/L) was added. The organic layer was removed and the inorganic layer was washed with ethyl acetate twice. Aqueous ammonia solution (2 mL) was added to the inorganic layer and the mixture was stirred for 15 min. Concentration in vacuo gave the crude product as a white solid (706 mg, 5.35 mmol, 100% yield). MS (ESI) m/z 133.0 [M+1]

C. 4-((1R,3S)-3-Hydroxycyclohexylamino)-2-((1r,4r)-4-[($^2H_3$)methyloxy]cyclohexanamino)pyrimidine-5-carboxamide A mixture of 4-((1R,3S)-3-hydroxycyclohexylamino)-2-(methylsulfonyl)pyrimidine-5-carboxamide (160 mg, 0.5 mmol; synthesis described herein), (1r,4r)-4-[($^2H_3$)methyloxy]-cyclohexanamine (132 mg, 1.0 mmol), DIEA (194 mg, 1.5 mmol) and NMP (1 mL) were combined and heated at 80° C. overnight. The solvent was evaporated under reduced pressure and the residue was purified by column chromatography (0-15% methanol in DCM) to give the desired product as a white powder (120 mg, 0.33 mmol, 63% yield).

$^1$H NMR (400 MHz, $CD_3OD$) δ ppm 8.17 (s, 1H), 3.93-3.87 (m, 1H), 3.64 (s, 1H), 3.50 (d, J=6.0 Hz, 1H), 3.13 (s, 1H), 2.22 (s, 1H), 2.06-1.72 (m, 7H), 1.29-0.99 (m, 8H); MS (ESI) m/z 367.3 $[M+1]^+$.

Example 50: 4-(tert-Butylamino)-2-((1s,4s)-4-hydroxy-4-methylcyclohexylamino)pyrimidine-5-carboxamide

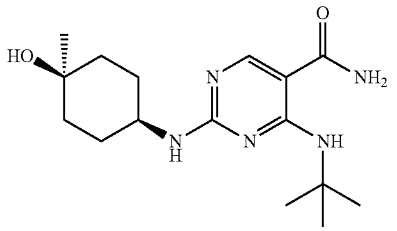 [SMILES: CC(C)(C)Nc1nc(N[C@H]2CC[C@@](C)(O)CC2)ncc1C(N)=O]

A. 4-(tert-Butylamino)-2-((1s,4s)-4-hydroxy-4-methylcyclohexyl-amino)pyrimidine-5-carboxamide 4-(tert-Butylamino)-2-(methylsulfonyl)pyrimidine-5-carboxamide (0.110 g, 0.404 mmol; synthesis described herein), (1s,4s)-4-amino-1-methylcyclohexanol (0.055 g, 0.429 mmol; prepared according to PCT Int. Appl. publication No. WO 2010027500) and DIEA (0.225 mL, 1.287 mmol) were mixed in DMF (5 mL) and heated at 90° C. overnight. The solvent was evaporated and the residue was purified by silica gel column chromatography (0-10% methanol in ethyl acetate) to give the desired product. (37 mg, 0.115 mmol, 27%). $^1$H NMR (400 MHz, DMSO-$d_6$) δ ppm 9.08-9.23 (m, 1H) 8.25-8.37 (m, 1H) 6.89-7.06 (m, 1H) 3.97-4.04 (m, 1H) 3.46-3.62 (m, 1H) 1.48-1.71 (m, 6H) 1.40 (s, 9H) 1.19-1.36 (m, 2H) 1.10 (s, 4H). MS (ESI) m/z 322.4 $[M+1]^+$ Example 51: 4-((1R,3R)-3-Hydroxy-4,4-dimethylcyclohexylamino)-2-(1-methylcyclopropylamino)pyrimidine-5-carboxamide

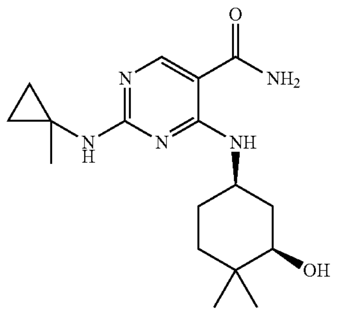 [SMILES: CC1(Nc2ncc(C(N)=O)c(N[C@@H]3CCC(C)(C)[C@H](O)C3)n2)CC1]

A. 2-(1-Methylcyclopropylamino)-4-(methylthio)pyrimidine-5-carboxamide

To a stirring solution of 2-(1-methylcyclopropylamino)-4-(methylthio)pyrimidine-5-carbonitrile (0.653 g, 2.96 mmol, synthesis described herein) in DMSO (8 mL) was added 6N aqueous sodium hydroxide (2.470 mL, 14.82 mmol) solution and 30% aqueous hydrogen peroxide solution (1.873 mL, 16.52 mmol) at 0° C. Then the mixture was stirred at 50° C. and for 20 minutes and was then diluted with 100 mL ethyl acetate and 30 mL water. The layers were separated and the aqueous layer was back extracted with 50 mL ethyl acetate. The combined ethyl acetate layers were dried over anhydrous magnesium sulfate, filtered and concentrated to solids that were dried in a vacuum oven at 45° C. to afford 2-(1-methylcyclopropylamino)-4-(methylthio) pyrimidine-5-carboxamide (305 mg, 1.280 mmol, 43.2% yield). $^1H$ NMR (400 MHz, DMSO-$d_6$) δ ppm 8.31-8.54 (m, 1H), 7.80-8.07 (m, 1H), 6.97-7.77 (m, 1H), 2.39 (br. s., 3H), 1.37 (s, 3H), 0.52-0.79 (m, 4H). MS (ESI) m/z 239.0 $[M+1]^+$.

B. 2-(1-Methylcyclopropylamino)-4-(methylsulfinyl)pyrimidine-5-carboxamide

To a stirring solution of 2-(1-methylcyclopropylamino)-4-(methylthio)-pyrimidine-5-carboxamide (305 mg, 1.280 mmol) in chloroform (25.6 mL) was added portionwise 3-phenyl-2-(phenylsulfonyl)-1,2-oxaziridine (502 mg, 1.920 mmol). The resulting pale yellow solution was stirred at ambient temperature overnight. The reaction solution was concentrated under reduced pressure to give crude product as a white solid. Ethyl acetate (10 mL) was added and the slurry was stirred at room temperature for 1 h, filtered, washed with ethyl acetate, and dried in a vacuum oven for a few hours to afford 2-(1-methylcyclopropylamino)-4-(methylsulfinyl)pyrimidine-5-carboxamide (242 mg, 0.952 mmol, 74.4% yield). $^1H$ NMR (400 MHz, DMSO-$d_6$) δ ppm 8.35-8.90 (m, 2H), 7.88-8.14 (m, 1H), 7.28-7.59 (m, 1H), 2.74 (s, 3H), 1.32-1.46 (m, 3H), 0.68-0.84 (m, 2H), 0.50-0.70 (m, 2H). MS (ESI) m/z 255.0 $[M+1]^-$.

C. 4-((1R,3R)-3-Hydroxy-4,4-dimethylcyclohexylamino)-2-(1-methylcyclopropylamino)pyrimidine-5-carboxamide To a stirring suspension of 2-(1-methylcyclopropylamino)-4-(methylsulfinyl)pyrimidine-5-carboxamide (242 mg, 0.952 mmol) and a mixture of (1R,5R)-5-amino-2,2-dimethylcyclohexanol hydrochloride and (1S,5S)-5-amino-2,2-dimethylcyclohexanol hydrochloride (222 mg, 1.237 mmol, synthesis described herein) in DMF (4.543 mL) was added DIEA (0.499 mL, 2.85 mmol) and the reaction was heated to 90° C. overnight. The crude reaction mixture was poured into 50 mL of ice water. The resulting solids were slurried for ~1 h, filtered, rinsed with water and dried for a few hours in a vacuum oven at 45° C. to afford a mixture of 4-((1R,3R)-3-hydroxy-4,4-dimethylcyclohexylamino)-2-(1-methylcyclopropylamino)-pyrimidine-5-carboxamide and 4-((1R,3R)-3-hydroxy-4,4-dimethylcyclohexylamino)-2-(1-methylcyclopropylamino)pyrimidine-5-carboxamide (169 mg, 0.507 mmol, 53.3% yield). This material was separated by preparative chiral SFC utilizing a ChiralPak AD-H, 250×30 mm I.D. column with an isocratic 40% ethanol+0.1% ammonium hydroxide in $CO_2$ gradient at 60 mL/min flow rate and at 38° C. The faster eluting isomer was denoted as peak 1 and 49 mg (0.147 mmol) was obtained. The slower eluting isomer was denoted as peak 2 and 51 mg (0.153 mmol) was obtained. Peak 1: $^1H$ NMR (400 MHz, DMSO-$d_6$) δ ppm 8.71-9.02 (m, 1H), 8.21-8.43 (m, 1H), 7.03-7.54 (m, 1H), 4.44-4.58 (m, 1H), 3.81-3.99 (m, 1H), 3.07-3.25 (m, 1H), 1.74-2.08 (m, 1H), 1.35 (s, 8H), 0.87-0.97 (m, 3H), 0.77-0.86 (m, 3H), 0.62-0.70 (m, 2H), 0.47-0.59 (m, 2H). MS (ESI) m/z 334.2 $[M+1]^+$. Peak 2: $^1H$ NMR (400 MHz, DMSO-$d_6$) δ ppm 8.72-9.00 (m, 1H), 8.18-8.46 (m, 1H), 7.12-7.60 (m, 1H), 4.38-4.61 (m, 1H), 3.76-3.98 (m, 1H), 3.04-3.26 (m, 1H), 1.75-2.10 (m, 1H), 1.35 (s, 8H), 0.92 (s, 3H), 0.82 (s, 3H), 0.61-0.72 (m, 2H), 0.47-0.60 (m, 2H). MS (ESI) m/z 334.2 $[M+1]^+$. By SAR potency comparison with similar compounds of known absolute stereochemistry, Peak 1 was assigned as 4-((1S,3S)-3-Hydroxy-4,4-dimethylcyclohexylamino)-2-(1-methyl-cyclopropylamino)pyrimidine-5-carboxamide. Peak 2 was assigned as 4-((1R,3R)-3-Hydroxy-4,4-dimethylcyclohexylamino)-2-(1-methylcyclopropylamino)pyrimidine-5-carboxamide.

Example 52: 4-(Bicyclo[1.1.1]pentan-2-ylamino)-2-((1r,4r)-4-hydroxycyclohexylamino)pyrimidine-5-carboxamide

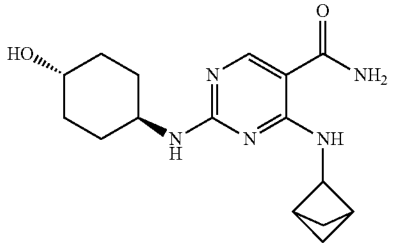 [SMILES: NC(=O)c1cnc(N[C@H]2CC[C@H](O)CC2)nc1NC1C2CC1C2]

A. 2-Phenylbicyclo[1.1.1]pentan-2-ol

A stirring solution of cyclobutyl(phenyl)methanone (3.0 g, 18.8 mmol) in 800 ml of benzene was irradiated with a 1000 W mercury arc lamp for 48 h at room temperature in a nitrogen atmosphere. The solution was concentrated and the residue (3.1 g) was purified by column chromatography (10%-25% ethyl acetate in petrolium ether) to give the desired product as a white solid (0.9 g, 5.6 mmol, yield: 30%). $^1H$ NMR (300 MHz, $CDCl_3$) δ ppm 7.41-7.28 (m, 5H), 3.04 (s, 2H), 2.82 (dd, J1=10.2 Hz, J2=2.4 Hz, 1H), 2.09 (s, 1H), 1.78 (d, J=2.4 Hz, 1H), 1.50 (d, J=3.3 Hz, 1H), 1.33 (dd, J1=9.9, J2=3.3 Hz, 1H).

B. 2-Phenylbicyclo[1.1.1]pentan-2-yl acetate

To a stirring solution of 2.7 g (16.8 mmol) of 2-phenyl-bicyclo[1.1.1]pentan-2-ol in pyridine (15 mL) at 0° C. was added dropwise acetyl chloride (1.5 mL, 21.0 mmol) in a nitrogen atmosphere. The reaction mixture was stirred for 0.5 h at 0° C. and for 1 h at room temperature. The solution was poured onto ice and extracted with 50 mL of diethyl ether twice. The combined diethyl ether solution was washed with saturated aqueous sodium bicarbonate solution and with saturated aqueous copper sulfate solution. After drying over anhydrous magnesium sulfate, the solution was concentrated and the crude product was purified by column chromatography (0-5% ethyl acetate in petrolium ether) to give the desired product (2.7 g, 13.4 mmol, yield: 80%). $^1H$ NMR (400 MHz, $CDCl_3$) δ ppm 7.47-7.26 (m, 5H), 3.31 (s, 2H), 2.43 (dd, J1=10.4 Hz, J2=2.8 Hz, 1H), 1.95 (s, 3H), 1.80 (d, J=2.8 Hz, 1H), 1.66 (d, J=3.2 Hz, 1H), 1.49 (dd, J1=10.4, J2=3.2 Hz, 1H).

C. 2-Phenylbicyclo[1.1.1]pentane

A solution of 2-phenyl-bicyclo[1.1.1]pentan-2-yl acetate (2.7 g, 13.4 mol) in 50 mL of anhydrous ether was placed in a three-necked flask. The flask was cooled to −78° C., and 150 mL of liquid ammonia was added. To the stirring mixture was added sodium (0.62 g, 27.0 mmol) in small pieces over a period of 10 minutes. Stirring was continued until the blue color was discharged. The reaction was quenched by the addition of saturated aqueous ammonia chloride solution (5 mL), and the solvent was allowed to evaporate overnight. Pentane (40 mL) was added to the residue, and the solution was washed with 30 mL saturated aqueous sodium chloride solution, dried over anhydrous magnesium sulfate, and then concentrated. The crude product was purified by column chromatography (100% pentane) to give the desired compound as a colorless liquid (1.8 g, 12.5 mmol, yield: 93%).

$^1$H NMR (300 MHz, $CDCl_3$) δ ppm 7.40-7.21 (m, 5H), 3.48 (d, J=6.9 Hz, 1H), 2.81 (s, 2H), 2.20 (dd, J1=9.9 Hz, J2=2.7 Hz, 1H), 2.00 (d, J=2.1 Hz, 1H), 1.94-1.85 (m, 2H).

D. Bicyclo[1.1.1]pentane-2-carboxylic acid

A mixture of 2-phenylbicyclo[1.1.1]pentane (2.8 g, 19.4 mmol), ruthenium(IV) oxide (0.1 g, 0.75 mmol), sodium periodate (41.5 g, 194 mmol), water (155 mL), perchloromethane (110 mL), and acetonitrile (110 mL) was stirred for 4 d. DCM (200 mL) was added to the mixture, and the solids were removed by filtration. The mother liquid was alkalized with aqueous sodium hydroxide solution (1 M), and the organic solvent was removed by reduced pressure. The residue inorganic layer was extracted with diethyl ether (100 mL×2) and the water phase was acidified with aqueous hydrochloric acid (2 M) to pH <3, then extracted with diethyl ether (100 mL×5). The organic layers were combined and concentrated to give the crude acid as a yellow liquid. Then the crude product was purified by column chromatography (10% ethyl acetate in petrolium ether) to give 400 mg (3.57 mmol, yield: 18%) of the desired product. $^1$H NMR (300 MHz, $CDCl_3$) δ ppm 2.97 (d, J=7.5 Hz, 1H), 2.82 (s, 2H), 2.49 (dd, J1=7.2 Hz, J2=3.3 Hz, 1H), 1.92 (dd, J1=7.2 Hz, J2=3.3 Hz, 1H), 1.79-1.76 (m, 2H).

E. Bicyclo[1.1.1]pentan-2-amine hydrochloride

To a stirring solution of bicyclo[1.1.1]pentane-2-carboxylic acid (1.0 g, 8.9 mmol) in anhydrous toluene (25 mL) and 2-methylpropan-2-ol (5 mL) was added DIEA (2.3 g, 17.8 mmol) and diphenyl phosphorazidate (2.9 g, 10.7 mmol). The mixture was heated at 90° C. for 16 h under nitrogen atmosphere. Then the reaction mixture was concentrated and the residue was purified by column chromatography (10% ethyl acetate in petrolium ether) to give crude tert-butyl bicyclo[1.1.1]pentan-2-ylcarbamate. The crude product was dissolved in 15 mL hydrochloric acid solution (1 M in methanol) and the solution was stirred at room temperature for 16 h. The solution was concentrated and the residue was suspended in 50 mL of diethyl ether. The mixture was stirred for 15 min and the precipitates were collected and dried to give the title compound (350 mg, yield: 33%). $^1$H NMR (DMSO-$d_6$) δ ppm 8.58 (brs, 3H), 3.35 (s, 1H), 2.62 (s, 2H), 2.60-2.57 (m, 1H), 1.90 (t, J=5.0 Hz, 1H), 1.79 (d, J=2.4 Hz, 1H), 1.50 (dd, J1=10.0 Hz, J1=2.8 Hz, 1H).

F. 4-(Bicyclo[1.1.1]pentan-2-ylamino)-2-((1r,4r)-4-hydroxycyclohexylamino)pyrimidine-5-carboxamide A mixture of 2-((1r,4r)-4-hydroxycyclohexylamino)-4-(methylsulfonyl)pyrimidine-5-carboxamide (300 mg, 0.95 mmol; synthesis described herein), bicyclo[1.1.1]pentan-2-amine hydrochloride (220 mg, 1.84 mmol) and DIEA (300 mg, 2.33 mmol) in NMP (3 mL) was heated at 100° C. for 16 h. The resulting mixture was purified by preparatory high performance liquid chromatography twice (5-80% acetonitrile in water) to give the crude product (105 mg), which was recrystallized from chloroform to give the desired compound (85.2 mg, 0.27 mmol, yield: 28%). $^1$H NMR (400 MHz, $CD_3OD$) δ ppm: 8.33 (s, 1H), 4.19 (d, J=6.8 Hz, 1H), 3.77-3.74 (m, 1H), 3.60-3.57 (m, 1H), 2.67 (s, 2H), 2.54 (dd, J1=9.6 Hz, J2=3.2 Hz, 1H), 2.07-1.88 (m, 6H), 1.66 (d, J=9.6 Hz, 1H), 1.39-1.34 (m, 4H); MS (ESI) m/z 318.1 $[M+H]^+$.

Example 53: 2-((S)-sec-Butylamino)-4-(((1R,3R,4R)-3-hydroxy-4-methylcyclohexyl)amino)pyrimidine-5-carboxamide

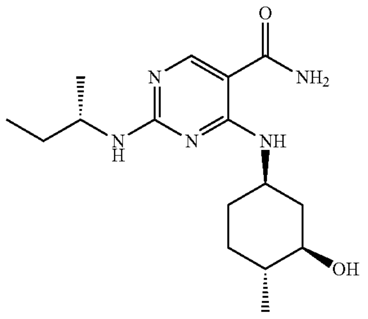 [SMILES: CC[C@H](C)Nc1ncc(C(N)=O)c(N[C@@H]2CC[C@@H](C)[C@H](O)C2)n1]

A. 4-((1R,3R,4R)-3-Hydroxy-4-methylcyclohexylamino)-2-(methylthio)pyrimidine-5-carboxamide 4-((1R,3R,4R)-3-Hydroxy-4-methylcyclohexylamino)-2-(methylthio)pyrimidine-5-carbonitrile (0.335 g, 1.203 mmol; synthesis described herein) was dissolved in DMSO (3 mL). Then aqueous sodium hydroxide solution (1.003 mL, 6 M, 6.02 mmol) and aqueous hydrogen peroxide solution (0.682 mL, 6.02 mmol, 30%) were added at room temperature. Then the reaction mixture was stirred at 50° C. for 2 h. The reaction was cooled to room temperature and it was poured into 100 mL of ice water. The white precipitate was collected and was washed twice with water. The solid was dried to give 4-((1R,3R,4R)-3-hydroxy-4-methyl-cyclohexylamino)-2-(methylthio)pyrimidine-5-carboxamide (0.260 g, 0.877 mmol, 72.9% yield); MS (ESI) m/z 297.7 $[M+1]^+$.

B. 4-((1R,3R,4R)-3-Hydroxy-4-methylcyclohexylamino)-2-(methylsulfonyl)pyrimidine-5-carboxamide 4-((1R,3R,4R)-3-Hydroxy-4-methylcyclohexylamino)-2-(methylthio)pyrimidine-5-carboxamide (315 mg, 1.063 mmol) was dissolved in NMP (4 mL) and cooled to 0° C. before adding mCPBA (476 mg, 2.126 mmol) portionwise. After 1 h, 75 mL of ice-cold water was added directly to the reaction mixture and the slurry was allowed to stir for 2 h before filtering off the white precipitate. The filtrate was then condensed under reduced pressure to remove water. The NMP solution was used directly in the next step assuming quantitative conversion to the desired product; MS (ESI) m/z 329.4 $[M+1]^+$.

C. 2-((S)-sec-Butylamino)-4-(((1R,3R,4R)-3-hydroxy-4-methylcyclohexyl)amino)pyrimidine-5-carboxamide To a stirring suspension of 4-((1R,3R,4R)-3-hydroxy-4-methylcyclohexylamino)-2-(methylsulfonyl)pyrimidine-5- carboxamide (0.2 g, 0.609 mmol) in DMF (3 mL) was added (S)-(+)-sec-butylamine (0.305 mL, 3.05 mmol) and the reaction was heated to 90° C. overnight. The crude reaction mixture was concentrated under reduced pressure and then purified using reverse-phased semi-preparative HPLC (5-75% methanol+0.1% formic acid in water+0.1% formic acid, over 26 min). Fractions containing product were concentrated under reduced pressure and the resulting residue was redissolved in methanol (5 mL), passed over a Varian StratoSpheres HCO3 resin SPE tube for formic acid removal (0.9 mmol bicarbonate equiv.), and then concentrated under reduced pressure to afford 2-((S)-sec-butylamino)-4-(((1R,3R,4R)-3-hydroxy-4-methylcyclohexyl)amino)pyrimidine-5-carboxamide (0.129 g, 0.402 mmol, 66% yield). $^1$H NMR (400 MHz, DMSO-$d_6$) δ ppm 0.80-1.24 (m, 15H) 1.35-1.45 (m, 1H) 1.54 (br. s., 1H) 1.66 (d, J=12.89 Hz, 1H) 1.92 (br. s., 1H) 2.14 (br. s., 1H) 2.97 (br. s., 1H) 3.71-3.99 (m, 1H) 4.55 (d, J=5.86 Hz, 1H) 6.96 (br. s., 1H) 8.34 (s, 1H) 8.90 (br. s., 1H); MS (ESI) m/z 322.5 $[M+1]^+$.

Example 54: 2-((1r,4r)-4-Hydroxycyclohexylamino)-4-(1-methylcyclobutylamino)pyrimidine-5-carboxamide

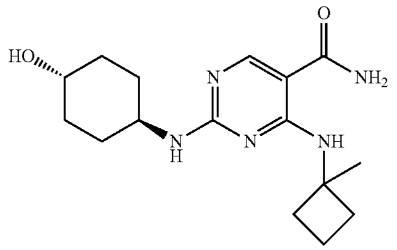 [SMILES: CC1(Nc2nc(N[C@H]3CC[C@H](O)CC3)ncc2C(N)=O)CCC1]

A. 2-((1r,4r)-4-Hydroxycyclohexylamino)-4-(1-methylcyclobutyl-amino)pyrimidine-5-carboxamide To a mixture of 2-((1r,4r)-4-hydroxycyclohexyl-amino)-4-(methylsulfinyl)pyrimidine-5-carboxamide and 2-((1r,4r)-4-hydroxycyclohexyl-amino)-4-(methylsulfonyl)pyrimidine-5-carboxamide (1.414 mmol total; synthesis described herein) in NMP (18 mL) was added 1-methylcyclobutanamine hydrochloride (0.189 g, 1.556 mmol) and DIEA (0.988 mL, 5.66 mmol). The resulting solution was heated at 100° C. overnight. Ethyl acetate and water were added to the reaction mixture and the resulting layers were separated. The ethyl acetate layer was dried over anhydrous magnesium sulfate, filtered, and concentrated under reduced pressure to an oil that was purified by silica gel chromatography (0-20% methanol in DCM) to afford 2-((1r,4r)-4-hydroxycyclohexylamino)-4-(1-methylcyclobutylamino)pyrimidine-5-carboxamide (0.193 g, 0.604 mmol, 42.7% yield). $^1$H NMR (400 MHz, DMSO-$d_6$) δ ppm 9.13 (s, 1H) 8.33 (s, 1H) 7.57 (br. s., 1H) 7.01 (d, J=7.81 Hz, 2H) 4.53 (d, J=4.69 Hz, 1H) 3.58 (br. s., 1H) 2.32 (d, J=10.54 Hz, 2H) 1.94-2.11 (m, 2H) 1.84 (d, J=5.08 Hz, 6H) 1.52 (s, 3H) 1.05-1.36 (m, 4H). MS (ESI) m/z 320.1 $[M+1]^+$.

Example 55: 4-(Bicyclo[2.1.1]hexan-1-ylamino)-2-(((1r,4r)-4-hydroxycyclohexyl)amino)pyrimidine-5-carboxamide

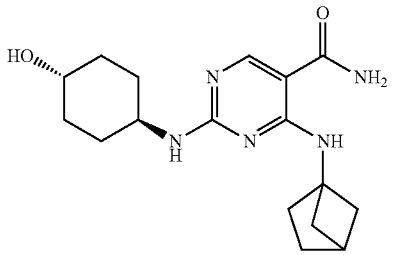 [SMILES: NC(=O)c1cnc(N[C@H]2CC[C@H](O)CC2)nc1NC12CCC(C1)C2]

A. 2-Methylbicyclo[2.2.1]heptan-2-ol

To a solution of bicyclo[2.2.1]heptan-2-one (25 g, 0.23 mol) in diethyl ether (250 mL) was added a solution of methylmagnesium bromide in THF (3 mol/L, 90 mL, 0.27 mol) over 1 h at 0° C. The reaction mixture was stirred for an additional 30 min as it was warmed to room temperature. Then the reaction was quenched with 40 mL saturated aqueous ammonium chloride solution. The resulting mixture was extracted with diethyl ether (3×80 mL). The organic layers were combined and concentrated to give the desired product (26 g, 0.205 mol, yield: 90%). $^1$H NMR (400 MHz, $CDCl_3$) δ ppm 2.20 (s, 1H), 2.01 (s, 1H), 1.94 (s, 1H), 1.61-1.49 (m, 3H), 1.34-1.20 (m, 7H).

B. 1-Methylbicyclo[2.2.1]heptan-2-ol

To a solution of 2-methyl-bicyclo[2.2.1]heptan-2-ol (26 g, 0.20 mol) in acetic acid (50 g, 0.83 mol) was added 1 mL sulfuric acid. The mixture was refluxed for 3 h and then concentrated under reduced pressure. The residue was poured into 100 mL water. The resulting mixture was extracted with ethyl acetate (3×50 mL) and the combined extracts were washed with saturated aqueous sodium bicarbonate solution (100 mL), brine (100 mL) and then dried over anhydrous sodium sulfate. Removal of the solvent gave 1-methyl-bicyclo[2.2.1]heptan-2-yl acetate (31 g, 0.173 mol, yield: 89%) as a colorless oil, which was used without further purification.

A mixture of 1-methylbicyclo[2.2.1]heptan-2-yl acetate (31 g, 0.17 mol) and aqueous sodium hydroxide solution (5%, 250 mL) was refluxed for 2 h. After being cooled to room temperature, the reaction mixture was extracted with diethyl ether (3×100 mL) and the combined organic layers were dried over magnesium sulfate and concentrated to afford the desired compound (21 g, 0.167 mol, yield: 82%), which was used in the next step without further purification. $^1$H NMR (400 MHz, $CDCl_3$) δ ppm 3.47-3.46 (m, 1H), 2.16-2.14 (m, 1H), 1.81-1.75 (m, 1H), 1.57-1.52 (m, 1H), 1.43-1.30 (m, 3H), 1.15 (brs, 3H), 1.01-0.97 (m, 2H).

C. Methylenebicyclo[2.2.1]heptan-1-yl trifluoromethanesulfonate

To a solution of oxalyl dichloride (31.75 g, 0.25 mol) in DCM (300 mL) was added at −78° C. in consecutive order DMSO (19.5 g, 0.25 mol), a solution of 1-methylbicyclo[2.2.1]heptan-2-ol (21 g, 0.167 mol) in DCM (50 mL) and then triethylamine (50 g, 0.5 mol). The mixture was stirred at room temperature overnight and then poured into 200 mL water. The resulting mixture was extracted with DCM (2×100 mL). The combined extracts were washed with saturated aqueous sodium bicarbonate solution (50 mL), brine (50 mL) and dried over anhydrous sodium sulfate. Concentration under reduced pressure gave crude methyl-bicyclo[2.2.1]heptan-2-one, which was purified by silica gel column chromatography (10% ethyl acetate in petroleum ether) to afford 12.4 g (0.10 mol, yield: 60%) of this compound.

To a solution of methylbicyclo[2.2.1]heptan-2-one (26 g, 0.209 mol) and 2,6-di-tert-butyl-4-methyl-pyridine (64 g, 0.315 mol) in DCM (300 mL) was added dropwise trifluoromethanesulfonic anhydride (88 g, 0.315 mol) in DCM (50 mL) at 0° C. The reaction mixture was stirred at room temperature for 24 h. The mixture was poured into water, and extracted with DCM (2×100 mL). The combined extracts were washed with a 10% hydrochloric acid solution (3×100 mL), saturated aqueous sodium bicarbonate solution (50 mL), brine (50 mL) and dried over sodium sulfate. Concentration under reduced pressure gave the crude product, which was purified by silica gel column chromatography (100% n-pentane) to give the desired product (7.6 g, 0.03 mol, 14%).

$^1$H NMR (400 MHz, $CDCl_3$): δ ppm 5.15 (brs, 1H), 4.89 (brs, 1H), 2.51-2.39 (m, 2H), 2.26-2.17 (m, 2H), 2.12-2.05 (m, 2H), 1.99-1.85 (m, 2H), 1.53-1.50 (m, 1H).

D. 2-Oxobicyclo[2.2.1]heptan-1-yl trifluoromethanesulfonate

A solution of methylenebicyclo[2.2.1]heptan-1-yl trifluoromethanesulfonate (7.6 g, 0.03 mol) in methanol (100 mL) was cooled to −40° C. and an ozone stream was passed through the reaction mixture. When the color of the mixture turned to blue, the ozone was eliminated by passing a stream of argon through the solution for 10 min. Dimethyl sulfide (5 mL) was added to the mixture and the reaction mixture was allowed to warm to room temperature. The resulting mixture was poured into water and extracted with DCM (2×40 mL). The combined extracts were washed with brine (100 mL) and dried over anhydrous sodium sulfate. The solution was concentrated under reduced pressure to give the crude product, which was purified by silica gel column chromatography (10% ethyl acetate in petroleum ether) to give the desired product (4.6 g, 18.1 mmol, yield: 60%) as a yellowish oil. $^1$H NMR (400 MHz, $CDCl_3$) δ ppm 2.73 (brs, 1H), 2.44-2.34 (m, 2H), 2.26-2.13 (m, 4H), 2.06-2.02 (m, 1H), 1.70-1.66 (m, 1H).

E. Bicyclo[2.1.1]hexane-1-carboxylic acid

A mixture of 2-oxobicyclo[2.2.1]heptan-1-yl trifluoromethanesulfonate (4.6 g, 18.1 mmol) in 600 mL ethanol/water (60% w/w) and TEA (3.7 g, 36.2 mmol) was heated at 130° C. for 100 h. The mixture was concentrated under reduced pressure and the residue was poured into aqueous hydrochloric acid solution (1 mol/L, 150 mL) and extracted with diethyl ether (3×100 mL). The combined extracts were washed with brine (100 mL) and dried over anhydrous sodium sulfate. The solution was concentrated under reduced pressure to give the crude product which was purified by silica gel column chromatography (10% ethyl acetate in petroleum ether) to give the desired product (1.00 g, 8.09 mmol, yield: 45%).

$^1$H NMR (400 MHz, $CDCl_3$) δ ppm 2.47-2.45 (m, 1H), 1.94-1.90 (m, 4H),1.79-1.74 (m, 2H), 1.37-1.35 (m, 2H).

F. Benzyl bicyclo[2.1.1]hexan-1-ylcarbamate

To a solution of bicyclo[2.1.1]hexane-1-carboxylic acid (1.0 g, 8.09 mmol) in dioxane (20 mL) was added DIEA (2.5 g, 12.4 mmol), diphenylphosphorylazide (3.1 g, 11.2 mmol) and phenylmethanol (1.5 g, 14.2 mmol). The mixture was stirred at 80° C. overnight under nitrogen atmosphere and concentrated under reduce pressure. The residue was purified by silica gel column chromatography (10% ethyl acetate in petroleum ether) to give the desired product (1.2 g, 5.2 mmol, yield: 65%). MS (ESI) m/z=231.2[M+H]$^+$.

G. Bicyclo[2.1.1]hexan-1-amine hydrochloride

To a solution of benzyl bicyclo[2.1.1]hexan-1-ylcarbamate (1.2 g, 5.2 mmol) in methanol (30 mL) was added palladium on charcoal (10%, 0.1 g). The reaction mixture was stirred at 50° C. under hydrogen atmosphere (50 Psi) overnight and filtered through celite. To the filtrate was added a hydrochloric acid solution (10% in methanol, 20 mL). The mixture was concentrated and the residue was suspended in THF (20 mL). The mixture was stirred at room temperature for 1 h. The precipitate was collected and dried to give the desired product (550 mg, 4.13 mmol, yield: 79%). $^1$H NMR (400 MHz, DMSO-$d_6$) δ ppm 8.73 (br. s, 3H), 2.4 (br. s, 1H), 1.71-1.69 (m, 6H), 1.32-1.31 (m, 2H). MS (ESI) m/z=98.2 [M+H]$^+$.

H. 4-(Bicyclo[2.1.1]hexan-1-ylamino)-2-(methylthio)pyrimidine-5-carbonitrile

To a stirred solution of 4-chloro-2-(methylthio)pyrimidine-5-carbonitrile (427 mg, 2.3 mmol) in 1,4-dioxane (10 mL) was added DIEA (890 mg, 6.9 mmol) and bicyclo[2.1.1]hexan-1-amine hydrochloride (320 mg, 2.4 mmol). The resulting mixture was stirred at 60° C. for 2 h. The reaction mixture was poured into a saturated brine solution and then extracted with ethyl acetate (20 mL) three times. The combined organic layers were dried over anhydrous sodium sulfate, filtered and concentrated to afford the crude product, which was purified by silica gel column chromatography (15% ethyl acetate in petroleum ether) to give the desired product (502 mg, 2.0 mmol, 89% yield). MS (ESI) m/z=247.2 [M+1]$^+$ I. 4-(Bicyclo[2.1.1]hexan-1-ylamino)-2-(methylthio)pyrimidine-5-carboxamide To a solution of 4-(bicyclo[2.1.1]hexan-1-ylamino)-2-(methylthio)pyrimidine-5-carbonitrile (502.0 mg, 2.0 mmol) in DMSO (5 mL) was added aqueous hydrogen peroxide solution (1.2 g, 30%, 10.2 mmol) and aqueous sodium hydroxide solution (1.7 mL, 6 mol/L, 10.2 mmol) at 0° C. The mixture was stirred at 50° C. for 15 min and then quenched by the addition of water (30 mL). The solid formed was collected and dried under vacuum to give the desired product (500 mg, 1.9 mmol, 93% yield). MS (ESI) m/z=265.3 [M+1]$^+$.

J. 4-(Bicyclo[2.1.1]hexan-1-ylamino)-2-(methylsulfinyl)pyrimidine-5-carboxamide and 4-(bicyclo[2.1.1]hexan-1-ylamino)-2-(methylsulfonyl)pyrimidine-5-carboxamide To a solution of 4-(bicyclo[2.1.1]hexan-1-ylamino)-2-(methylthio)-pyrimidine-5-carboxamide (500 mg, 1.9 mmol) in THF (10 mL) at 0° C. was added mCPBA (490 mg, 2.8 mmol) portion-wise. After 1 h, the reaction mixture was concentrated. The resulting crude material was purified by silica gel column chromatography (5-10% methanol in DCM) to give 510 mg of the desired mixture. MS (ESI) m/z=281.3, 297.3 $[M+1]^+$.

K. 4-(Bicyclo[2.1.1]hexan-1-ylamino)-2-(((1r,4r)-4-hydroxycyclo-hexyl)amino)pyrimidine-5-carboxamide To the mixture of 4-(bicyclo[2.1.1]hexan-1-ylamino)-2-(methylsulfinyl)pyrimidine-5-carboxamide and 4-(bicyclo[2.1.1]hexan-1-ylamino)-2-(methylsulfonyl)pyrimidine-5-carboxamide (200 mg, about 0.71 mmol) and (1r,4r)-4-aminocyclohexanol (123.3 mg, 1.02 mmol) in NMP (10 mL) was added DIEA (183.0 mg, 1.42 mmol). The resulting mixture was stirred at 100° C. overnight. The reaction mixture was purified by preparative HPLC to give the desired product (187.3 mg, 0.56 mmol, 72% yield). $^1$H NMR (400 MHz, $CD_3OD$) δ ppm 8.29 (s, 1H), 3.77 (m, 1H), 3.60 (m, 1H), 2.43 (s, 1H), 2.07-1.93 (m, 8H), 1.79-1.77 (m, 2H), 1.60 (s, 2H), 1.41-1.35 (m, 4H). MS (ESI) m/z=332.2 $[M+H]^+$.

Example 56: 4-(1-Ethylcyclopentylamino)-2-((1r,4r)-4-hydroxycyclohexylamino)pyrimidine-5-carboxamide

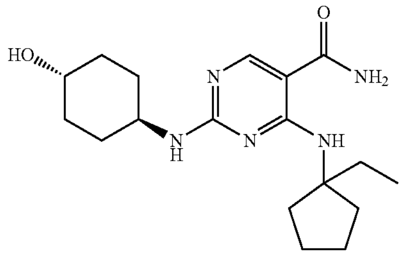 [SMILES: CCC1(Nc2nc(N[C@H]3CC[C@H](O)CC3)ncc2C(N)=O)CCCC1]

A. Ethyl cyclopent-3-enecarboxylate

To a stirred solution of cyclopent-3-enecarboxylic acid (10 g, 89.3 mmol) in anhydrous ethanol (30 mL) was added sulfurous dichloride (15.9 g, 134 mmol) at 0° C. The reaction mixture was stirred at room temperature overnight and then concentrated. The residue was poured into water. The resulting mixture was extracted with ethyl acetate (3×100 mL). The combined organic layers were washed with brine, dried over anhydrous sodium sulfate and filtered. The filtrate was concentrated and the residue was purified by silica gel column chromatography (2.5% ethyl acetate in petroleum ether) to give the desired product (6.7 g, 47.9 mmol, yield=54%) as a yellow oil which was used in the next step without further purification. $^1$H NMR (400 MHz, $CDCl_3$) δ ppm 5.66 (s, 2H), 4.18-4.10 (m, 2H), 3.16-3.05 (m, 1H), 2.66 (s, 2H), 2.63 (s, 2H), 1.29-1.24 (t, J=9.4, 3H).

B. Ethyl 1-ethylcyclopent-3-enecarboxylate

To a solution of diisopropylamine (10 mL, 72 mmol) in anhydrous THF (50 mL) was added n-butyl lithium (29 mL, 72 mmol, 2.5 M solution in hexane) over 20 min at −78° C. The mixture was stirred at 0° C. under nitrogen for 1 h. The freshly prepared lithium diisopropylamide was added to a mixture of ethyl cyclopent-3-enecarboxylate (6.7 g, 47.9 mmol) in anhydrous THF (50 mL) over 20 minutes at −78° C. After another 1 hour at this temperature, iodoethane (11.2 g, 72 mmol) was added over 20 min. Then the mixture was stirred at room temperature for 2 h and quenched with saturated aqueous ammonium chloride solution. The aqueous layer was extracted with ether (3×100 mL). The combined organic layers were washed with diluted hydrochloric acid (1 N), then washed with brine, dried over anhydrous sodium sulfate and filtered. Concentration gave the titled compound (7 g crude) which was used in the next step without further purification.

$^1$H NMR (400 MHz, $CDCl_3$) δ ppm 5.60 (s, 2H), 4.21-4.12 (m, 2H), 2.92-2.84 (m, 2H), 2.31-2.25 (m, 2H), 1.75-1.67 (m, 2H), 1.29-1.24 (m, 3H), 0.88-0.82 (m, 3H).

C. 1-Ethylcyclopent-3-enecarboxylic acid

A solution of ethyl 1-ethylcyclopent-3-enecarboxylate (3.5 g, 20.8 mmol) and aqueous sodium hydroxide solution (20.8 mL, 2 mol/L) in methanol (30 mL) was stirred at 80° C. for 2 h and then concentrated. The residue was poured into water, and extracted with ether (3×100 mL). The water layer was acidified with 4 mol/L aqueous hydrochloric acid solution to pH <3, and extracted with ethyl acetate (3×100 mL). The combined organic layers were washed with brine, dried over anhydrous sodium sulfate and filtered. Concentration under reduced pressure gave the crude product, which was purified by silica gel column chromatography (5% ethyl acetate in petroleum ether) to afford the title compound (1.9 g, 13.6 mmol, 65.5% yield). $^1$H NMR (400 MHz, $CDCl_3$) δ ppm 5.61 (s, 2H), 2.91 (d, J=14.8, 2H), 2.32 (d, J=14.4, 2H), 1.78-1.72 (m, 2H), 0.92-0.88 (t, J=7.4, 3H).

D. Benzyl (1-ethylcyclopent-3-en-1-yl)carbamate

To a solution of 1-ethylcyclopent-3-enecarboxylic acid (1.9 g, 13.6 mmol) in dioxane (30 mL) was added DIEA (5.3 g, 41 mmol), diphenyl phosphoryl azide (4.5 g, 16.3 mmol) and benzylalcohol (2.2 g, 20.4 mmol). The mixture was stirred at 80° C. overnight and then concentrated under reduced pressure. The residue was purified by silica gel column chromatography (2.5% ethyl acetate in petroleum ether) to give the title product. (1.3 g, 5.3 mmol, yield: 39%). MS (ESI) m/z=246.2 $[M+1]^+$.

E. 1-Ethylcyclopentanamine hydrochloride

To a solution of benzyl (1-ethylcyclopent-3-en-1-yl)carbamate (1.3 g, 5.3 mmol) in methanol (20 mL) was added palladium on charcoal (130 mg, 10%). The reaction mixture was stirred at 50° C. under hydrogen atmosphere overnight. A solution of hydrochloric acid (20 mL, 1 mol/L in methanol) was added to the reaction and the reaction mixture was filtered through celite. The filtrate was concentrated under reduced pressure to give the crude product (900 mg), which was used for the next step without further purification. MS (ESI) m/z=114.2 $[M+H]^+$ F. 4-(1-Ethylcyclopentylamino)-2-(methylthio)pyrimidine-5-carbonitrile To a stirring solution of 4-chloro-2-(methylthio)pyrimidine-5-carbonitrile (984 mg, 5.3 mmol) in DMSO (10 mL) was added DIEA (2.1 g, 15.9 mmol) and 1-ethylcyclopentanamine hydrochloride (900 mg crude). The resulting mixture was stirred at 60° C. for 2 h. The reaction mixture was poured into water and extracted with ethyl acetate. The combined organic layers were dried over anhydrous sodium sulfate, filtered and concentrated to afford the crude product. The crude product was purified by silica gel column chromatography (5% ethyl acetate in petroleum ether) to get the desired product as a yellow oil (830 mg, 3.2 mmol, 53.5% yield). MS (ESI) m/z=263.2 $[M+H]^+$.

G. 4-(1-Ethylcyclopentylamino)-2-(methylthio)pyrimidine-5-carboxamide

To a stirred solution of 4-(1-ethylcyclopentylamino)-2-(methylthio)-pyrimidine-5-carbonitrile (830 mg, 3.2 mmol) in DMSO (10 mL) was added aqueous hydrogen peroxide (1.8 g, 30%, 16 mmol), and aqueous sodium hydroxide solution (2.7 mL, 6 mol/L, 16 mmol) at 0° C. The mixture was stirred at 50° C. for 15 min and diluted with water. The mixture was extracted with ethyl acetate (3×100 mL). The combined organic layers were washed with brine, dried over anhydrous sodium sulfate and filtered. Concentration under reduced pressure gave the crude product, which was purified by silica gel column chromatography (5% methanol in DCM) to afford the desired product as a white solid (800 mg, 2.9 mmol, 90% yield). MS (ESI) m/z=281.2 [M+1]

H. 4-(1-Ethylcyclopentylamino)-2-(methylsulfonyl)pyrimidine-5-carboxamide

At 0° C., mCPBA (873 mg, 4.3 mmol) was added portion-wise to a solution of 4-(1-ethylcyclopentylamino)-2-(methylthio)pyrimidine-5-carboxamide (800 mg, 2.9 mmol) in THF (30 mL). After 1 h, the reaction mixture was concentrated and the resulting crude was purified by silica gel column chromatography (5% methanol in DCM) to afford the desired product (800 mg, 2.56 mmol, 90% yield). MS (ESI) m/z=313.2 $[M+1]^+$.

I. 4-(1-Ethylcyclopentylamino)-2-((1r,4r)-4-hydroxycyclohexylamino)-pyrimidine-5-carboxamide To a mixture of 4-(1-ethylcyclopentylamino)-2-(methylsulfonyl)pyrimidine-5-carboxamide (200 mg, 0.64 mmol) and (1r,4r)-4-amino-cyclohexanol (115 mg, 1 mmol) in NMP (10 mL) was added DIEA (255 mg, 1.98 mmol). The resulting mixture was stirred at 100° C. overnight. The reaction mixture was purified by preparative HPLC to give the desired product (117.0 mg, 0.34 mmol, yield 51%).

$^1H$ NMR (400 MHz, $CD_3OD$) δ ppm 8.17 (s, 1H), 3.66 (s, 1H), 3.46 (s, 1H), 2.06-2.04 (m, 2H), 1.98-1.89 (m, 6H), 1.66-1.58 (m, 6H), 1.26-1.24 (m, 4H), 1.77-0.73 (t, J=7.2 Hz, 3H); MS (ESI) m/z=348.2 $[M+1]^+$.

Example 57: 4-(((1R,3S)-3-Hydroxycyclohexyl)amino)-2-((4-methoxybicyclo[2.2.2]octan-1-yl)amino)pyrimidine-5-carboxamide

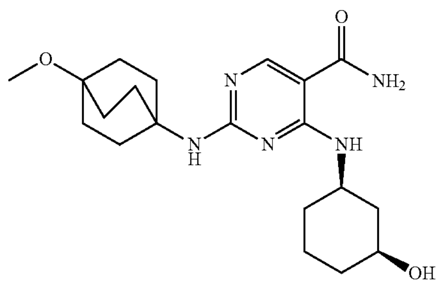 [SMILES: COC12CCC(Nc3ncc(C(N)=O)c(N[C@@H]4CCC[C@H](O)C4)n3)(CC1)CC2]

A. Dimethyl 1-(2-chloroethyl)cyclohexane-1,4-dicarboxylate

To a stirring solution of cyclohexane-1,4-dicarboxylic acid (100 g, 0.58 mol) in anhydrous methanol (800 mL) was added sulfurous dichloride (208 g, 1.75 mol) at 0° C. The reaction mixture was stirred at room temperature overnight and then concentrated under reduced pressure. The residue was poured into water. The resulting mixture was extracted with ethyl acetate (200 mL×3). The combined organic layers were washed with brine, dried over anhydrous sodium sulfate and filtered. Concentration gave crude dimethyl cyclohexane-1,4-dicarboxylate (105 g, 0.53 mol, yield 90.5%) which was used without further purification.

To a solution of diisopropylamine (88 mL, 0.62 mol) in anhydrous THF (500 mL) was added n-butyl lithium (240 mL, 0.6 mol, 2.5 M solution in hexane) over 20 min at −78° C. The mixture was stirred at 0° C. under nitrogen for 30 min.

To the above described mixture of crude dimethyl cyclohexane-1,4-dicarboxylate (100 g, 0.5 mol) and hexamethylphosphoramide (360 mL, 2 mol) in anhydrous THF (800 mL) was added the freshly prepared lithium diisopropylamide solution (preparation described above) over 30 min at −40° C. After stirring for 1 h at this temperature, 1-bromo-2-chloroethane (42 mL, 0.5 mol) was added over 1. The mixture was stirred for 3 h at −78° C. and then stirred overnight at room temperature. The reaction was quenched by the addition of aqueous hydrochloric acid solution (3 N, 420 mL). The solvent was removed under reduced pressure. The aqueous layer was extracted with ethyl acetate (200 mL×3). The combined extracts were washed with brine (2×300 mL) and dried over sodium sulfate. Concentration gave the title compound (116 g, yield 88%) which was used in the next step without further purification; $^1H$ NMR (400 MHz, $CDCl_3$) δ ppm 3.72 (s, 3H), 3.65 (s. 3H), 3.46-3.42 (m, 2H), 2.33-2.21 (m, 3H), 2.05-1.85 (m, 4H), 1.58-1.42 (m, 2H), 1.25-1.15 (m, 2H).

B. Dimethyl bicyclo[2.2.2]octane-1,4-dicarboxylate

To a solution of diisopropylamine (77 mL, 0.54 mol) in anhydrous THF (500 mL) was added n-butyl lithium (210 mL, 0.53 mol, 2.5 M solution in hexane) over 20 min at −78° C. The mixture was stirred at 0° C. under nitrogen for 30 min.

To a mixture of dimethyl 1-(2-chloroethyl)cyclohexane-1,4-dicarboxylate (116 g, 0.44 mol) and hexamethylphosphoramide (317 mL, 1.7 mol) in anhydrous THF (800 mL) was added freshly prepared lithium diisopropylamide (preparation described above) over 30 min at −40° C. The mixture was stirred for 2 h at −78° C. and then stirred overnight allowing warming to room temperature. To the reaction mixture was added saturated aqueous ammonium chloride solution (200 mL) and the mixture was stirred for 10 min. The volatile solvents were removed by evaporation under reduced pressure. The aqueous layer was extracted with ethyl acetate (3×200 mL) and the combined extracts were washed with brine (300 mL×2) and dried over sodium sulfate. Concentration under reduced pressure gave crude product, which was purified by silica gel column chromatography (10% ethyl acetate in petroleum ether) to afford the title compound (58.0 g, 0.25 mol, yield 50% over two steps). $^1H$ NMR (400 MHz, $CDCl_3$): δ ppm 3.65 (s, 6H), 1.81 (s. 12H).

C. 4-(Methoxycarbonyl)bicyclo[2.2.2]octane-1-carboxylic acid

A solution of dimethyl bicyclo[2.2.2]octane-1,4-dicarboxylate (58.0 g, 0.25 mol) in methanol (600 mL) was heated to reflux and then a solution of potassium hydroxide (9.8 g, 0.175 mol) in methanol (100 mL) and water (12 mL) was added over 30 min. The reaction mixture was refluxed for 24 h and concentrated. The residue was diluted with water and extracted with ethyl acetate (200 mL×2) to recover some starting material (22.0 g). The resulting aqueous layer was acidified to pH=3 by addition of hydrochloric acid and extracted with ethyl acetate (300 mL×3). The combined organic layers were washed with brine, dried over sodium sulfate and concentrated to give the titled product (30.0 g, 0.14 mol, yield 55%). $^{1}$H NMR (400 MHz, $CDCl_3$) δ ppm 3.65 (s, 3H), 1.81 (s. 12H); MS (ESI) m/z=211.3 $[M-H]^-$.

D. Methyl 4-bromobicyclo[2.2.2]octane-1-carboxylate

To a suspension of 4-(methoxycarbonyl)bicyclo[2.2.2]octane-1-carboxylic acid (11.0 g, 51.8 mmol) in acetone (80 mL) was added aqueous sodium hydroxide solution (1 M, 51.8 mL, 51.8 mmol) and a solution of silver nitrate (8.8 g, 51.9 mol) in water (10 mL). The precipitate formed was collected by filtration, washed with water, acetone and diethyl ether and dried in vacuo at 115° C. for 4 h. The obtained ((4-(methoxycarbonyl)-bicyclo[2.2.2]octane-1-carbonyl)oxy)silver (15.3 g, 47.9 mmol) was suspended in hexane (125 mL), followed by addition of bromine (7.7 g, 48.1 mmol) over 30 min at room temperature. After the addition was completed, the reaction mixture was stirred at room temperature for another 30 min. The reaction mixture was filtered to remove the solid, and the filter cake was washed with hexane (150 mL×4). The combined organic filtrates were washed with saturated aqueous sodium bicarbonate solution (150 mL×2) and brine (200 mL), then dried over magnesium sulfate. Concentration under reduced pressure gave the crude product, which was purified by silica gel column chromatography (5% ethyl acetate in petroleum ether) to afford the title compound (4.2 g, 0.17 mol, 33% yield over two steps). $^{1}$H NMR (400 MHz, $CDCl_3$): δ ppm 3.64 (s, 3H), 2.27-2.20 (m, 6H), 1.98-1.94 (m. 6H).

E. 4-Hydroxybicyclo[2.2.2]octane-1-carboxylic acid

Methyl 4-bromobicyclo [2.2.2]octane-1-carboxylate (17.0 g, 69.0 mmol) was refluxed in 1.5 L of 1% aqueous sodium hydroxide solution for 24 h. After cooling down, the reaction solution was acidified with hydrochloric acid (6N, 100 mL) and extracted with diethyl ether (6×500 mL). The combined organic layers were dried over magnesium sulfate and concentrated to afford the titled compound (10.4 g, 61.1 mmol, yield: 89%), which was used in the next step without further purification; MS (ESI) m/z=169.2 $[M-H]^-$.

F. Methyl 4-hydroxybicyclo[2.2.2]octane-1-carboxylate

To a solution of 4-hydroxybicyclo[2.2.2]octane-1-carboxylic acid (14 g, 82.4 mmol) in methanol (300 mL) was added concentrated sulfuric acid (1 mL). The mixture was refluxed for 10 h and then concentrated. The reside was dissolved in water (100 mL) and the mixture was extracted with ethyl acetate (200 mL×2). The combined organic phases were washed with saturated aqueous sodium hydrogen carbonate solution (100 mL), brine (100 mL) and dried over sodium sulfate. Concentration gave the title compound (14.5 g, yield 96%).

$^{1}$H NMR (400 MHz, $CDCl_3$) δ ppm 3.64 (s, 3H), 1.96-1.89 (m, 6H), 1.69-1.64 (m. 6H).

G. Methyl 4-methoxybicyclo[2.2.2]octane-1-carboxylate

To a solution of methyl 4-hydroxybicyclo[2.2.2]octane-1-carboxylate (8.9 g, 48 mmol) in anhydrous THF (150 mL) at −78° C. was added n-butyl lithium (23 mL, 57.5 mmol, 2.5 M solution in hexane) over 30 min, followed by the slow addition of iodomethane (14 g, 98 mmol). The mixture was stirred at 60° C. for 3 h and quenched by addition of saturated aqueous ammonium chloride solution (50 mL). The resulting solution was concentrated and the residue was extracted with ethyl acetate (150 mL×2). The organic layers were combined and washed with brine, dried over magnesium sulfate and then concentrated. The residue was purified by silica gel column chromatography (10% ethyl acetate in petroleum ether) to give the title product (6.5 g, 67%). $^{1}$H NMR (400 MHz, $CDCl_3$) δ ppm 3.64 (s, 3H), 3.18 (s, 3H), 1.95-1.89 (m, 6H), 1.70-1.65 (m. 6H).

H. 4-Methoxybicyclo[2.2.2]octane-1-carboxylic acid

Methyl 4-methoxybicyclo[2.2.2]octane-1-carboxylate (6.5 g, 33 mmol) was refluxed in aqueous sodium hydroxide solution (5%, 150 mL) for 2 h. After cooling down, the reaction solution was acidified with hydrochloric acid solution (6 N, 50 mL) and extracted with ethyl acetate (100 mL×2). The combined organic layers were dried over magnesium sulfate and concentrated to afford the title compound (5.9 g, 32 mmol, yield 97%) which was used in the next step without further purification. MS (ESI) m/z=183.2 $[M-H]^-$.

I. Benzyl (4-methoxybicyclo[2.2.2]octan-1-yl)carbamate

To a solution of 4-methoxybicyclo[2.2.2]octane-1-carboxylic acid (5.9 g, 32 mmol) in dioxane (80 mL) was added DIEA (8.3 g, 64.2 mmol), diphenyl phosphoryl azide (13.2 g, 48 mmol) and phenylmethanol (17.3 g, 160 mmol). The mixture was stirred at 80° C. overnight and then concentrated under reduce pressure. The residue was purified by silica gel column chromatography (5% methanol in DCM) to give the desired product. (9 g, 31 mmol, yield 96%). MS (ESI) m/z=290.2 $[M+H]^+$.

J. 4-Methoxybicyclo[2.2.2]octan-1-amine hydrochloride

To a solution of benzyl (4-methoxybicyclo[2.2.2]octan-1-yl)carbamate (9 g, 31 mmol) in methanol (150 mL) was added palladium on charcoal (0.5 g, 10%). The reaction mixture was stirred at 50° C. under hydrogen atmosphere (50 psi) overnight and then filtered through celite. The filtrate was concentrated under reduced pressure. The residue was dissolved in hydrochloric acid solution (10% in methanol, 50 mL) and stirred for 2 h at room temperature. The mixture was concentrated and the resulting residue was suspended in THF (20 mL). The mixture was stirred at room temperature for 1 h and the precipitate was collected and dried to give the desired product (3.8 g, 20 mmol, yield:

68%). $^1$H NMR (400 MHz, DMS-$d_6$) δ ppm 8.14 (brs, 3H), 3.04 (s, 3H), 1.83-1.80 (m, 6H), 1.68-1.64 (m, 6H); MS (ESI) m/z=156.1[M+1]$^+$.

K. 4-((1R,3S)-3-Hydroxycyclohexylamino)-2-(4-methoxy-bicyclo[2.2.2]octan-1-ylamino)pyrimidine-5-carboxamide To a solution of 4-((1R,3S)-3-hydroxycyclohexylamino)-2-(methylsulfonyl)pyrimidine-5-carboxamide (1.2 g, 3.8 mmol; synthesis described herein) and 4-methoxybicyclo[2.2.2]octan-1-amine hydrochloride (600 mg, 3.1 mmol) in NMP (12 mL) was added DIEA (1.03 g, 8 mmol). The resulting mixture was stirred at 130° C. under microwave irradiation for 3 h. The resulting mixture was purified by reverse phase column chromatography to give the desired product (230 mg, 0.6 mmol, 15.5% yield). $^1$H NMR (400 MHz, $CDCl_3$) δ ppm 8.70 (brs, 1H), 8.08 (s, 1H), 5.40 (brs, 2H), 5.01 (br. s, 1H), 3.99-3.96 (m, 1H), 3.75-3.70 (m, 1H), 3.19 (s, 3H), 2.37-2.34 (m, 1H), 2.15-2.11 (m, 6H), 1.99-1.97 (m, 2H), 1.90-1.86 (m, 1H), 1.80-1.76 (m, 6H), 1.38-1.22 (m, 4H). MS (ESI) m/z=390.2[M+1]$^+$.

Example 58: 2-((1r,4r)-4-Hydroxycyclohexylamino)-4-(3-(trifluoromethyl)bicyclo[1.1.1]pentan-1-ylamino)pyrimidine-5-carboxamide

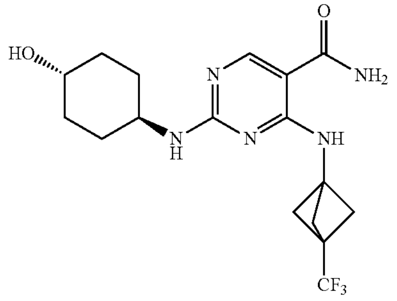 [SMILES: NC(=O)c1cnc(N[C@H]2CC[C@H](O)CC2)nc1NC12CC(C(F)(F)F)(C1)C2]

A. 2-((1r,4r)-4-Hydroxycyclohexylamino)-4-(3-(trifluoromethyl)-bicyclo[1.1.1]pentan-1-ylamino)pyrimidine-5-carboxamide To a 5 mL NMP solution of (2-((1r,4r)-4-hydroxycyclohexylamino)-4-(methylsulfonyl)pyrimidine-5-carboxamide (445 mg, 1.416 mmol)) was added 3-(trifluoromethyl)bicyclo[1.1.1]pentan-1-amine hydrochloride (266 mg, 1.416 mmol) and DIEA (0.494 mL, 2.83 mmol). The reaction was then heated at 90° C. overnight. LCMS showed the desired product mass as the dominant peak. The crude reaction was purified directly on a semi-prep HPLC (method: 5-80% acetonitrile+0.1% TFA in water+0.1% TFA). Product fractions were combined and evaporated under reduced pressure to a volume <5 mL. The material was then neutralized with saturated sodium bicarbonate and extracted with ethyl acetate (2×). The combined organic layers were dried over magnesium sulfate, filtered, and concentrated. The resulting solid was dissolved in methanol and washed through a StratoSpheres SPE PL-HCO3 MP-Resin column, eluting with methanol. Evaporation of solvent under reduced pressure gave 2-((1r,4r)-4-hydroxycyclohexylamino)-4-(3-(trifluoromethyl)bicyclo[1.1.1]pentan-1-ylamino)pyrimidine-5-carboxamide. The material was purified by silica gel chromatography (0-10% methanol in DCM over 1650 mL; 40 mL/min). Product fractions were combined and evaporated to dryness to afford 2-((1r,4r)-4-hydroxycyclohexylamino)-4-(3-(trifluoromethyl)bicyclo[1.1.1]pentan-1-ylamino)pyrimidine-5-carboxamide (135 mg, 0.35 mmol, 24.8% yield); $^1$H NMR (400 MHz, DMSO-$d_6$) δ ppm 9.54 (s, 1H), 8.41 (s, 1H), 7.57-7.86 (m, 1H), 7.26-7.32 (m, 1H), 6.91-7.17 (m, 1H), 4.60 (d, J=4.29 Hz, 1H), 3.49-3.73 (m, 1H), 3.35-3.46 (m, 1H), 2.38 (s, 6H), 1.86 (d, J=11.32 Hz, 4H), 1.26 (br. s., 4H); MS (ESI) m/z 386.0 [M+1]$^+$.

Example 59: 4-(tert-Butylamino)-2-(((1R,3S)-3-hydroxycyclohexyl)amino)pyrimidine-5-carboxamide

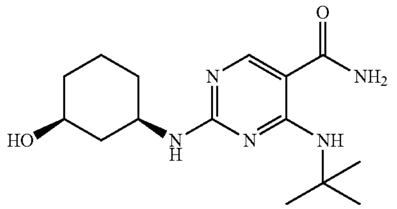 [SMILES: CC(C)(C)Nc1nc(N[C@@H]2CCC[C@H](O)C2)ncc1C(N)=O]

A. 4-(Tert-butylamino)-2-(((1R,3S)-3-hydroxycyclohexyl)-amino)pyrimidine-5-carboxamide To a mixture of 4-(tert-butylamino)-2-(methylsulfonyl)pyrimidine-5-carboxamide (250 mg, 0.918 mmol; synthesis described herein) and (1S,3R)-3-aminocyclohexanol (138 mg, 1.2 mmol; prepared as described in *Tetrahedron: Asymmetry* 15:2051-2056 (2004)) in NMP (10 mL) was added DIEA (374 mg, 2.9 mmol). The resulting mixture was stirred at 100° C. overnight. The reaction mixture was purified by preparative HPLC to give the desired product (212.2 mg, 0.69 mmol, yield 75%). $^1$H NMR (400 MHz, $CDCl_3$) δ ppm 8.86 (brs, 1H), 8.12 (s, 1H), 5.53 (brs, 3H), 3.93-3.91 (m, 1H), 3.88-3.82 (m, 1H), 2.27-2.25 (m, 1H), 1.92-1.85 (m, 3H), 1.47 (s, 9H), 1.42-1.25 (m, 4H); MS (ESI) m/z=308.2 [M+1]$^+$.

Example 60: 4-(Bicyclo[1.1.1]pentan-1-ylamino)-2-((tetrahydro-2H-pyran-4-yl)amino)pyrimidine-5-carboxamide

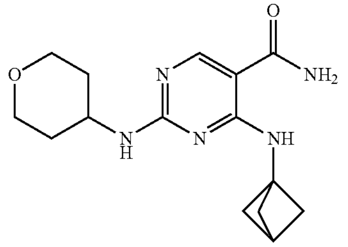 [SMILES: NC(=O)c1cnc(NC2CCOCC2)nc1NC12CC(C1)C2]

A. 4-(Bicyclo[1.1.1]pentan-1-ylamino)-2-(methylthio)pyrimidine-5-carbonitrile

To a stirred solution of 4-chloro-2-(methylthio)pyrimidine-5-carbonitrile (3.0 g, 16 mmol) in DMSO (20 mL) was added DIEA (6.2 g, 48 mmol) and bicyclo[1.1.1]pentan-1-amine hydrochloride (1.9 g, 16 mmol; prepared according to *Org. Lett.,* 13(17): 4746-4748 (2011)). The resulting mixture was stirred at 60° C. for 2 h and then poured into water. The mixture was extracted with ethyl acetate and the combined organic layers were dried over anhydrous sodium sulfate, filtered and concentrated to afford the crude product, which was purified by silica gel column chromatography (10% ethyl acetate in petroleum ether) to give the desired product (3.5 g, 14.9 mmol, 93% yield). MS (ESI) m/z=233.2 $[M+1]^+$.

B. 4-(Bicyclo[1.1.1]pentan-1-ylamino)-2-(methylthio)pyrimidine-5-carboxamide

To a solution of 4-(bicyclo[1.1.1]pentan-1-ylamino)-2-(methylthio)-pyrimidine-5-carbonitrile (3.45 g, 14.9 mmol) in DMSO (15 mL) was added aqueous hydrogen peroxide solution (8.4 g, 30%, 74.5 mmol) and aqueous sodium hydroxide solution (12.4 mL, 6 mol/L, 74.5 mmol) at 0° C. The mixture was stirred at 50° C. for 15 min and then quenched by the addition of water (30 mL). The solid formed was collected and dried under vacuum to give the desired product (3.5 g, 14.0 mmol, 94% yield). MS (ESI) m/z=251.2 $[M+1]^+$.

C. 4-(Bicyclo[1.1.1]pentan-1-ylamino)-2-(methylsulfinyl)pyrimidine-5-carboxamide and 4-(bicyclo[1.1.1]pentan-1-ylamino)-2-(methylsulfonyl)pyrimidine-5-carboxamide mCPBA (4.3 g, 21 mmol) was added portion-wise to a solution of 4-(bicyclo[1.1.1]pentan-1-ylamino)-2-(methylthio)pyrimidine-5-carboxamide (3.5 g, 14 mmol) in THF (40 mL) at 0° C. The reaction was monitored by thin layer chromatography. After 1 h, the reaction mixture was concentrated. The resulting crude product was purified by silica gel column chromatography (5% methanol in DCM) to afford 3.1 g of the titled mixture. MS (ESI) m/z=267.2 $[M+1]^+$/283.2 $[M+1]^+$.

D. 4-(Bicyclo[1.1.1]pentan-1-ylamino)-2-((tetrahydro-2H-pyran-4-yl)amino)pyrimidine-5-carboxamide To a mixture of 4-(bicyclo[1.1.1]pentan-1-ylamino)-2-(methylsulfinyl)pyrimidine-5-carboxamide, 4-(bicyclo[1.1.1]pentan-1-ylamino)-2-(methylsulfonyl)pyrimidine-5-carboxamide (300 mg) and tetrahydro-2H-pyran-4-amine hydrochloride (181.5 mg, 1.32 mmol) in NMP (10 mL) was added DIEA (426 mg, 3.3 mmol). The resulting mixture was stirred at 100° C. overnight. Then the reaction mixture was purified by preparative HPLC to give the desired product (221.3 mg, 0.73 mmol, yield 67%) as a yellow powder. $^1H$ NMR (400 MHz, $CD_3OD$) δ ppm 8.19 (s, 1H), 3.95-3.88 (m, 3H), 3.44-3.38 (m, 2H), 2.40 (s, 1H), 2.09 (s, 6H), 1.88-1.85 (m, 2H), 1.55-1.45 (m, 2H); MS (ESI) m/z=304.2 $[M+1]^+$.

Example 61: 4-(Bicyclo[1.1.1]pentan-1-ylamino)-2-(((1R,3S)-3-hydroxycyclohexyl)amino)pyrimidine-5-carboxamide

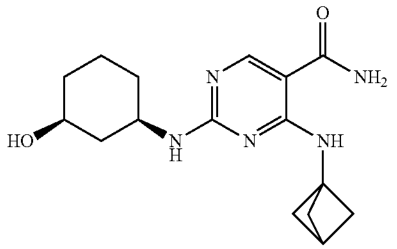 [SMILES: NC(=O)c1cnc(N[C@@H]2CCC[C@H](O)C2)nc1NC12CC(C1)C2]

A. 4-(bicyclo[1.1.1]pentan-1-ylamino)-2-(methylsulfinyl)pyrimidine-5-carboxamide and 4-(bicyclo[1.1.1]pentan-1-ylamino)-2-(methylsulfonyl)pyrimidine-5-carboxamide 3-Chlorobenzoperoxoic acid (4.27 g, 21 mmol) was added portion-wise to a solution of 4-(bicyclo[1.1.1]pentan-1-ylamino)-2-(methylthio)pyrimidine-5-carboxamide (3.50 mg, 14 mmol, synthesis described herein) in THF (40 mL) at 0° C. The resulting solution was mixed at 0° C. for 1 h and then concentrated under reduced pressure to an oil that was purified by silica gel column chromatography (5% methanol in DCM) to afford 310 mg of a mixture of 4-(bicyclo[1.1.1]pentan-1-ylamino)-2-(methylsulfinyl)pyrimidine-5-carboxamide and 4-(bicyclo[1.1.1]pentan-1-ylamino)-2-(methylsulfonyl)pyrimidine-5-carboxamide as a yellow solid. MS (ESI) m/z=267.2 $[M+1]^+$/283.2 $[M+1]^+$.

B. 4-(Bicyclo[1.1.1]pentan-1-ylamino)-2-(((1R,3S)-3-hydroxycyclo-hexyl)amino)pyrimidine-5-carboxamide To a mixture of 4-(bicyclo[1.1.1]pentan-1-ylamino)-2-(methylsulfinyl)pyrimidine-5-carboxamide and 4-(bicyclo[1.1.1]pentan-1-ylamino)-2-(methylsulfonyl)pyrimidine-5-carboxamide (300 mg) and (1S,3R)-3-aminocyclohexanol (152 mg, 1.32 mmol; prepared as described in *Tetrahedron: Asymmetry* 15:2051-2056 (2004)) in NMP (10 mL) was added DIEA (426 mg, 3.3 mmol). The resulting mixture was stirred at 100° C. overnight. The reaction mixture was purified by preparative HPLC to give the desired product (230.2 mg, 0.73 mmol, yield 66%).

$^1H$ NMR (400 MHz, $CD_3OD$) δ ppm 8.29 (s, 1H), 3.91-3.89 (m, 1H), 3.69-3.62 (m, 1H), 2.50 (s, 1H), 2.29-2.25 (m, 1H), 2.20 (s, 6H), 1.97-1.83 (m, 3H), 1.41-1.21 (m, 4H); MS (ESI) m/z=318.2 $[M+1]^+$.

Example 62: 2-(Bicyclo[1.1.1]pentan-1-ylamino)-4-((1R,3R)-3-hydroxy-4,4-dimethylcyclohexylamino)pyrimidine-5-carboxamide

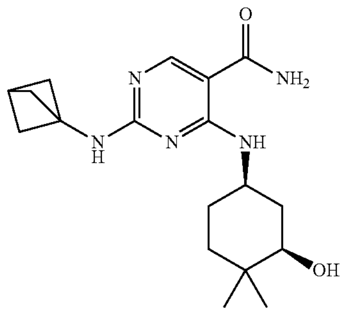 [SMILES: CC1(C)CC[C@@H](Nc2nc(NC34CC(C3)C4)ncc2C(N)=O)C[C@H]1O]

A. N-(Bicyclo[1.1.1]pentan-1-yl)-5-bromo-4-(methylthio)pyrimidin-2-amine

To a stirring solution of 5-bromo-2-chloro-4-(methylthio)pyrimidine (1.0 g, 4.18 mmol) in NMP (10.0 mL) was added bicyclo[1.1.1]pentan-1-amine hydrochloride (749 mg, 6.26 mmol, prepared according to *Org. Lett.,* 13(17): 4746-4748 (2011)) and DIEA (2.19 mL, 12.53 mmol). The mixture was stirred at 100° C. for 16 h and then the solvent was removed under reduced pressure. The residue was diluted in 100 mL ethyl acetate and 50 mL 1M aqueous solution of sodium hydrogen phosphate. The layers were separated and the aqueous layer was extracted with 50 mL ethyl acetate. The combined organic layers were dried over anhydrous magnesium sulfate, filtered and concentrated under reduced pressure to afford N-(bicyclo[1.1.1]pentan-1-yl)-5-bromo-4-(methylthio)pyrimidin-2-amine (1250 mg, 4.37 mmol, 105% yield) as a solid that was used without further purification. MS (ESI) m/z 286.0 $[M+1]^+$ and 288.0 $[M+H]^+$.

B. 2-(Bicyclo[1.1.1]pentan-1-ylamino)-4-(methylthio)pyrimidine-5-carbonitrile

N-(Bicyclo[1.1.1]pentan-1-yl)-5-bromo-4-(methylthio)pyrimidin-2-amine (1250 mg, 4.37 mmol), zinc dust (71.4 mg, 1.092 mmol), zinc cyanide (333 mg, 2.84 mmol), 1,1'-bis-(diphenylphosphino)-ferrocene (196 mg, 0.349 mmol), tris(dibenzylideneacetone)dipalladium(O) (200 mg, 0.218 mmol), and DMA (8.35 mL) were combined and heated overnight at 90° C. under a nitrogen atmosphere. The reaction mixture was diluted with 125 mL ethyl acetate and 50 mL water and filtered through a pad of Celite. The layers of the filtrate were separated and the aqueous layer was extracted with 75 mL ethyl acetate. The combined ethyl acetate layers were washed with 2×50 mL brine, dried over anhydrous magnesium sulfate, filtered and concentrated to an oil. The crude oil was purified by silica gel chromatography (0%-30% ethyl acetate in hexanes). The product containing fractions were combined and concentrated to afford 2-(bicyclo[1.1.1]pentan-1-ylamino)-4-(methylthio)pyrimidine-5-carbonitrile (566 mg, 2.436 mmol, 55.8% yield) as a solid. $^1H$ NMR (400 MHz, DMSO-$d_6$) δ ppm 8.81-9.08 (m, 1H), 8.31-8.57 (m, 1H), 2.55-2.63 (m, 3H), 2.11 (s, 7H). MS (ESI) m/z 233.3 $[M+1]^+$.

C. 2-(Bicyclo[1.1.1]pentan-1-ylamino)-4-(methylthio)pyrimidine-5-carboxamide

To a stirring solution of 2-(bicyclo[1.1.1]pentan-1-ylamino)-4-(methylthio)pyrimidine-5-carbonitrile (566 mg, 2.436 mmol) in DMSO (7 mL) was added 6 M aqueous sodium hydroxide solution (2.030 mL, 12.18 mmol) and 30% aqueous hydrogen peroxide solution (1.381 mL, 12.18 mmol) at 0° C. The mixture was then stirred at 50° C. for 30 min and then was poured into ice water (50 mL). The solids that formed were stirred in an ice bath for 30 min, filtered, washed with water, and then dried in a vacuum oven overnight at 45° C. to afford 2-(bicyclo[1.1.1]pentan-1-ylamino)-4-(methylthio)pyrimidine-5-carboxamide (410 mg, 1.638 mmol, 67.2% yield). $^1H$ NMR (400 MHz, DMSO-$d_6$) δ ppm 8.41 (s, 1H), 7.03-8.34 (m, 2H), 2.43-2.48 (m, 1H), 2.35 (br. s., 3H), 2.09 (s, 6H). MS (ESI) m/z 251.3 $[M+1]^+$.

D. 2-(Bicyclo[1.1.1]pentan-1-ylamino)-4-(methylsulfinyl)pyrimidine-5-carboxamide To a stirring solution of 2-(bicyclo[1.1.1]pentan-1-ylamino)-4-(methylthio)pyrimidine-5-carboxamide (410 mg, 1.638 mmol) in chloroform (39.0 mL) was added portionwise, 3-phenyl-2-(phenylsulfonyl)-1,2-oxaziridine (514 mg, 1.965 mmol). The resulting pale yellow solution was stirred at ambient temperature for two nights under nitrogen. The reaction mixture was concentrated under reduced pressure to give the crude product as a white solid. Ethyl acetate (15 mL) was added to these solids and the slurry was stirred at room temp for 1 h, filtered, washed with ethyl acetate, and dried in a vacuum oven for a few hours to afford 2-(bicyclo[1.1.1]pentan-1-ylamino)-4-(methylsulfinyl)pyrimidine-5-carboxamide (397 mg, 1.491 mmol, 91% yield) as white solid. $^1H$ NMR (400 MHz, DMSO-$d_6$) δ ppm 8.67-9.14 (m, 2H), 7.93-8.11 (m, 1H), 7.41-7.54 (m, 1H), 2.68-2.79 (m, 3H), 2.43-2.48 (m, 1H), 2.02-2.21 (m, 6H). MS (ESI) m/z 267.0 $[M+1]^+$.

E. 2-(Bicyclo[1.1.1]pentan-1-ylamino)-4-((1R,3R)-3-hydroxy-4,4-dimethylcyclohexylamino)pyrimidine-5-carboxamide To a stirring suspension of 2-(bicyclo[1.1.1]pentan-1-ylamino)-4-(methylsulfinyl)pyrimidine-5-carboxamide (397 mg, 1.491 mmol) and a mixture of (1R,5R)-5-amino-2,2-dimethylcyclohexanol hydrochloride and (1S,5S)-5-amino-2,2-dimethylcyclohexanol hydrochloride (348 mg, 1.938 mmol, synthesis described herein) in DMF (4.88 mL) was added DIEA (0.78 mL, 4.47 mmol) and the reaction was heated to 90° C. overnight. The crude reaction mixture was poured into 60 mL of ice water. The resulting solids were slurried for ~1 h, filtered, rinsed with water and dried for a few hours in a vacuum oven at 45° C. to afford a mixture of 2-(bicyclo[1.1.1]pentan-1-ylamino)-4-((1R,3R)-3-hydroxy-4,4-dimethyl-cyclohexylamino)pyrimidine-5-carboxamide and 2-(bicyclo[1.1.1]pentan-1-ylamino)-4-((1S,3S)-3-hydroxy-4,4-dimethylcyclohexylamino)pyrimidine-5-carboxamide (481 mg, 1.392 mmol, 93% yield). This material was separated by preparative chiral SFC utilizing a ChiralPak AD-H, 250×30 mm I.D. column with an isocratic 40% ethanol+0.1% ammonium hydroxide in $CO_2$ gradient at 120 mL/min flow rate and at 38° C. The faster eluting isomer was denoted as peak 1 and 132 mg (0.382 mmol) was obtained. The slower eluting isomer was denoted as peak 2 and 120 mg (0.349 mmol) was obtained.

Peak 1: $^1H$ NMR (400 MHz, DMSO-$d_6$) δ ppm 8.85-9.12 (m, 1H), 8.14-8.44 (m, 1H), 7.63-7.90 (m, 1H), 4.47-4.63 (m, 1H), 3.76-3.96 (m, 1H), 3.08-3.23 (m, 1H), 2.43 (s, 1H), 2.04 (s, 6H), 1.87-1.99 (m, 1H), 1.66-1.83 (m, 1H), 1.04-1.47 (m, 4H), 0.92 (s, 3H), 0.82 (s, 3H) MS (ESI) m/z 346.3 $[M+1]^+$.

Peak 2: $^1H$ NMR (400 MHz, DMSO-$d_6$) δ ppm 8.88-9.07 (m, 1H), 8.25-8.45 (m, 1H), 7.57-7.90 (m, 1H), 4.46-4.59 (m, 1H), 3.78-3.96 (m, 1H), 3.09-3.22 (m, 1H), 2.35-2.47 (m, 1H), 2.04 (s, 6H), 1.87-1.99 (m, 1H), 1.66-1.80 (m, 1H), 1.37-1.48 (m, 1H), 1.12-1.34 (m, 3H), 0.88-0.94 (m, 3H), 0.71-0.86 (m, 3H). MS (ESI) m/z 346.3 $[M+1]^+$. By SAR potency comparison with similar compounds of known absolute stereochemistry described herein, Peak 1 was assigned as 2-(bicyclo[1.1.1]pentan-1-ylamino)-4-((1S,3S)-3-hydroxy-4,4-dimethylcyclohexylamino)pyrimidine-5-carboxamide. Peak 2 was assigned as 2-(bicyclo[1.1.1]pentan-1-ylamino)-4-((1R,3R)-3-hydroxy-4,4-dimethylcyclohexylamino)pyrimidine-5-carboxamide.

Assays

Biochemical Assays

A. Time Resolved Fluorescence Assays

JNK1 Assay.

A 384-well time resolved fluorescence assay was used to monitor JNK1 activity. The JNK1 assay was run in the following assay buffer: 50 mM HEPES, 10 mM $MgCl_2$, 1 mM EGTA, 2 mM DTT, and 0.01% Tween 20. To initiate the reaction 100 nM of ULight™-labeled 4EBP1 peptide (Perkin-Elmer) and 5 μM of ATP were mixed with 500 pM of JNK1 (Carna Biosciences), for a total assay volume of 20 μL in each well. The assay was incubated at room temperature for 1 h and terminated using a mixture of 30 mM EDTA and 4 nM Eu-anti-4EBP1, by adding 20 μL of stop solution to each well. Plates were read on a Perkin-Elmer Envision Reader.

JNK2 Assay.

A 384-well time resolved fluorescence assay was used to monitor JNK2 activity. The JNK2 assay was run in the following assay buffer: 50 mM HEPES, 10 mM $MgCl_2$, 1 mM EGTA, 2 mM DTT, and 0.01% Tween 20. To initiate the reaction 100 nM of ULight™-labeled 4EBP1 peptide (Perkin-Elmer) and 5 μM of ATP were mixed with 500 pM of JNK2 (Carna Biosciences), for a total assay volume of 20 μL in each well. The assay was incubated at room temperature for 1 h and terminated using a mixture of 30 mM EDTA and 4 nM Eu-anti-4EBP1, by adding 20 μL of stop solution to each well. Plates were read on a Perkin-Elmer Envision Reader.

B. Z'-LYTE® Cascade Assays

JNK1 Assay.

The JNK1 Z'-LYTE Cascade kinase assay was run in the following buffer: 50 mM HEPES at pH 7.5, 0.01% BRIJ-35, 10 mM $MgCl_2$, 1 mM EGTA, and 1 mM DTT. A 10 μL kinase reaction mixture was prepared containing 1.81-7.25 ng JNK1, 25 ng inactive MAPKAPK2, 100 μM ATP, and 2 μM Ser/Thr 04 peptide. The assay was incubated at room temperature for 1 h. Next, 5 μL of a 1:512 dilution of Development Reagent A (Invitrogen, PV3295) was added to the reaction mixture and incubated at room temperature for an additional hour. The data was then read on a fluorescence plate reader and analyzed.

JNK2 Assay.

The JNK2 Z'-LYTE® Cascade kinase assay was run in the following buffer: 50 mM HEPES pH 7.5, 0.01% BRIJ-35, 10 mM $MgCl_2$, 1 mM EGTA, 2 mM DTT. A 10 μL kinase reaction mixture was prepared containing 0.38-1.5 ng JNK2, 100 ng inactive MAPKAPK2, 100 μM ATP, and 2 μM Ser/Thr 04 peptide. The assay was incubated at room temperature for 1 h. Next, 5 μL of a 1:512 dilution of Development Reagent A (Invitrogen, PV3295) was added to the reaction mixture and incubated at room temperature for an additional hour. The data was then read on a fluorescence plate reader and analyzed.

C. Radioactive Assays

JNK1 Assay.

The radioactive JNK kinase assay was carried out in a 96-well plate format at a final volume of 100 μL. The final assay concentration was 6.6 μM ATP (3-fold ATP Km), 2.64 to 5 μg/mL JNK1, and 100 μg/mL cJUN. JNK1 was diluted in the following dilution buffer (20 mM HEPES pH 7.6, 0.1 mM EDTA, 2.5 mM $MgCl_2$, 0.004% (w/v) Triton X100, 2 μg/ml Leupeptin, 20 mM B-glycerol phosphate, 0.1 mM $Na_3VO_4$ dithiothreitol) and then pre-mixed with cJun diluted in the substrate solution buffer (20 mM HEPES pH 7.6, 50 mM NaCl, 0.1 mM EDTA, 2.5 mM $MgCl_2$, 0.05% (w/v) Triton X100). The JNK1/cJun mix (85 μl) was added to the inhibitor (5 μl) diluted in 100% DMSO to give a final DMSO assay concentration of 5% (v/v). The enzyme, substrate and inhibitor mixture was allowed to equilibrate at room temperature for 15 minutes. The reaction was started by the addition of 104, of 10× ATP in kinase buffer (130 mM $MgCl_2$, 6 mM dithiothreitol, 150 mM para-nitrophenyl phosphate, 100 μCi/ml γ-[$^{33}P$]-ATP). Reactions were allowed to proceed for 60 minutes before precipitation of protein via trichloroacetic acid (7.2% TCA final). After a 30 minute incubation with TCA, reaction products were collected onto glass microfilter 96-well plates (Millipore MAHF CIH60) using a Packard Filtermate. The precipitate was washed with Phosphate Buffered Saline and the amount of phosphate incorporated into cJun was quantified by scintillation counting using a Packard Topcount-NXT. All assays were conducted under conditions where phosphate incorporation was linear with respect to time and enzyme concentration. The $IC_{50}$ values were calculated as the concentration of the inhibitor at which the c-Jun phosphorylation was reduced to 50% of the control value.

JNK2 Assay.

The assay was carried out in a 96-well plate format at a final volume of 100 μL. The final assay concentrations were 6.6 μM ATP (3-fold ATP Km), 0.2 to 0.53 μg/mL JNK2, and 100 μg/mL cJUN. JNK2 was diluted in the following dilution buffer (20 mM HEPES pH 7.6, 0.1 mM EDTA, 2.5 mM $MgCl_2$, 0.004% (w/v) Triton X100, 2 μg/ml Leupeptin, 20 mM B-glycerol phosphate, 0.1 mM $Na_3VO_4$ dithiothreitol) and then pre-mixed with cJun diluted in the substrate solution buffer (20 mM HEPES pH 7.6, 50 mM NaCl, 0.1 mM EDTA, 2.5 mM $MgCl_2$, 0.05% (w/v) Triton X100). The JNK2/cJun mix (85 μl) was added to the inhibitor (5 μl) diluted in 100% DMSO to give a final DMSO assay concentration of 5% (v/v). The enzyme, substrate and inhibitor mixture was allowed to equilibrate at room temperature for 15 minutes. The reaction was started by the addition of 104, of 10×ATP in kinase buffer (130 mM $MgCl_2$, 6 mM dithiothreitol, 150 mM para-nitrophenyl phosphate, 100 μCi/ml γ-[$^{33}P$]-ATP). Reactions were allowed to proceed for 60 minutes before precipitation of protein via trichloroacetic acid (7.2% TCA final). After a 30 minute incubation with TCA, reaction products are collected onto glass microfilter 96-well plates (Millipore MAHF CIH60) using a Packard Filtermate. The precipitate was washed with Phosphate Buffered Saline and the amount of phosphate incorporated into cJun was quantified by scintillation counting using a Packard Topcount-NXT. All assays were conducted under conditions where phosphate incorporation was linear with respect to time and enzyme concentration. The $IC_{50}$ values were calculated as the concentration of the inhibitor at which the c-Jun phosphorylation was reduced to 50% of the control value.

Cell Assays

RAW264.7 Phospho-cJun Whole Cell Assay.

RAW264.7 cells were purchased from the American Tissue Culture Collection and maintained in growth media consisting of 90% high glucose Dulbecco's Modified Eagle Medium (Invitrogen), 10% fetal bovine serum (Hyclone), and 2 mM L-glutamine (Invitrogen). All cells were cultured at 37° C. in 95% air and 5% $CO_2$. Cells were plated at a density of $1.0\times10^5$ cells per well in a 96-well plate in 120 μL of growth media. Diaminopyrimidine Compound stock (30 mM) was diluted serially in DMSO, further diluted in growth media, and was added to each well as a 10× concentrated solution in a volume of 15 μL, mixed, and allowed to incubate with cells. The compound vehicle (DMSO) was maintained at a final concentration of 0.2% in all wells. After 30 minutes, the cells were activated with lipopolysaccharide (ALEXIS Biochemicals) at a final concentration of 25 ng/mL. Lipopolysaccharide was added as a 10× concentrated solution in growth media and added in a volume of 15 μL per well. Cell plates were cultured for 1 h, after which the cell media was removed. The level of c-Jun protein which was phosphorylated at serine 63 was measured according to the manufacturer's instructions for the Whole Cell Lysate Kit-Phospho-c-Jun (Ser 63) Assay (Meso Scale Discovery) with the exception that the concentration of NaCl in the lysis buffer was increased to a final concentration of 350 mM. The $IC_{50}$ values were calculated as the concentration of Diaminopyrimidine Compound at which the level of phosphorylated c-Jun protein was reduced to 50% of the signal window. Certain compounds of Table 1, 2 and 3 have an $IC_{50}$ value ranging from 0.01-30 μM in this assay.

Jurkat T-Cell IL-2 Production Assay.

Jurkat T cells (clone E6-1) are purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells are cultured at 37° C. in 95% air and 5% $CO_2$. Cells are plated at a density of $1\times10^5$ cells per well in 120 μL of media in a 96-well plate. Diaminopyrimidine Compound stock (20 mM) is diluted in growth media and added to each well as a 10× concentrated solution in a volume of 15 μL, mixed, and allowed to pre-incubate with cells for 30 min. The compound vehicle (dimethylsulfoxide) is maintained at a final concentration of 0.2% in all samples. After 30 min the cells are activated with PMA (phorbol myristate acetate; final concentration 50 ng/mL) and PHA (phytohemagglutinin; final concentration 1 μg/mL). PMA and PHA are added as a 10× concentrated solution made up in growth media and added in a volume of 15 μL per well. Cell plates are cultured for 6 h. Cells are pelleted by centrifugation and the media removed and stored at −20° C. Media aliquots are analyzed according the manufacturers instructions for the Human IL-2 Tissue Culture Kit (Meso Scale Discovery). The $IC_{50}$ values are calculated as the concentration of the Diaminopyrimidine Compound at which the IL-2 production was reduced to 50% of the signal window. Certain compounds from Table 1, 2 and 3 have an $IC_{50}$ value ranging from 0.01-10 μM in this assay.

Animal Models

Rat or Mouse In Vivo LPS-Induced TNF-α Production and pcJun Assay.

Male CD rats or C57Bl/6 mice procured from Charles River Laboratories, at 7 weeks of age or 20 g weight respectively, were allowed to acclimate for one week prior to use. In the rat, the lateral tail vein was cannulated percutaneously with a 22-gage over-the-needle catheter under brief isoflurane anesthesia and 20 μg LPS (*E. Coli* 055:BS) and catheters were flushed with 2.5 mL/kg of normal injectable saline. In the mouse, 1 mg/kg LPS (*E. Coli* 055:BS) in saline was administered intraperitoneally in a volume of 200 μl. The animals were administered the Diaminopyrimidine Compound by oral gavage 15 to 180 min prior to injection of LPS. Blood was collected via cardiac puncture 90 minutes or 2 h after LPS challenge for rats and mice respectively, and the liver and epididymal fat was isolated for pcJun analysis using the Mesoscale Discovery Platform. The plasma was prepared using lithium heparin separation tubes and frozen at −80° C. until analyzed. The TNF-α levels were determined using a rat or mouse specific TNF-α ELISA kit (Mesoscale Discovery). The liver and epididymal fat were homogenized and sonicated in Mesoscale lysis buffer, the protein content was determined (BCA protein determination kit) and the pcJun levels were measured (Mesoscale Discovery). The $ED_{50}$ values were calculated as the dose of the Diaminopyrimidine Compound at which the TNF-α or pcJun levels were reduced to 50% of the control value. Certain compounds from Table 1, 2 and 3 were shown, or will be shown, to have an $ED_{50}$ value ranging from 30-100 mg/kg in this assay.

Choline Deficient Amino Acid Supplement Induced Non-Alcoholic Steatohepatitis (NASH) Model in the Rat.

Male Wistar rats obtained from Charles River Laboratories at 7 weeks of age are allowed to acclimate for one week prior to use. Rats are fed Choline Deficient L Amino Acid Supplemented (CDAA) diet (Dyets Inc) for up to 12 weeks. Rats are administered Diaminopyrimidine Compound by oral gavage once or twice daily starting at the time of introduction to the diet for between 2 and 12 weeks. At the termination of the study blood is collected via cardiac puncture and the liver and epididymal fat isolated. The liver tissue is processed for histology and the amount of steatosis or fibrosis is quantitated following H&E (hematoxylin and eosin) or picro Sirius red staining. The liver function is assessed by analysis of liver enzymes, for example, ALT and AST in plasma or serum. In addition, levels of phospho-cJun in the liver were quantitated by IHC, as described by Ma F. et. al. *Lab Invest.;* 89(4):470-84 (2009). The $ED_{50}$ values are calculated as the dose of Diaminopyrimidine Compound at which the fibrosis, steatosis, liver enzyme, and/or p-cJun levels are reduced to 50% of the control value. Certain compounds from Table 1, 2 and 3 have, or will be shown to have, an $ED_{50}$ value ranging from 10-100 mg/kg in this assay.

Bile Duct Ligation Model of Fibrosis.

Male BALB/c mice (22-24 g) were obtained from Charles River Laboratories, and were allowed to acclimate for one week prior to surgery. A ketamine (80-100 mg/kg)/xylazine (8 mg/kg) anesthetic delivered IP was used for the bile duct ligation surgical procedure. An abdominal incision provided access to the bile duct which was ligated with two 6.0 silk sutures placed rostral to the bile duct connection with the intestines. 3-0 vicryl suture was used to close the abdominal wall, and skin. Following surgery, mice were administered 1 mL of lactated ringers solution sub cutaneous daily as well as wet food for the duration of the study. Test compounds were administered by oral gavage starting the day after surgery. Studies were terminated 14 days post bile duct ligation. Blood was collected via cardiac puncture and serum was isolated for clinical chemistry analysis of liver function (ALT, AST, and bilirubin). Liver tissue was collected and processed histologically, stained with H&E (hematoxylin and eosin) or Picro Sirius red, and used to assess the amount of inflammation, periportal hyperplasia, necrosis and fibrosis induced by the bile duct ligation surgical procedure. In addition, levels of phospho-cJun in the liver were quantitated by IHC, as described by Ma F. et. al. *Lab Invest.;* 89(4):470-84 (2009). Certain compounds from Table 1, 2 and 3 show, or will show, statistically significant inhibition of inflammation, periportal hyperplasia, necrosis, fibrosis, and/or phosphor-cJun levels at dose levels of 10-300 mg/kg QD or BID.

Carbon Tetrachloride Model of Fibrosis.

Male C57Bl/6 mice obtained from Harlan weighing 22-24 g at arrival were allowed to acclimate for one week prior to use. Fibrosis was established via intraperitoneal injection of $CCl_4$ (0.75 mL/kg) in mineral oil (15% v/v $CCl_4$ in mineral oil) 3 times a week. The animals were administered the Diaminopyrimidine Compound by oral gavage 1 h prior to the initial $CCl_4$ injection and then daily or twice daily through the end of the study, 28 days later. At the termination of the study blood was collected via cardiac puncture and the liver was isolated. The liver tissue was processed for histology and the amount of steatosis or fibrosis was quantitated following H&E (hematoxylin and eosin) or picro Sirius red staining. The liver function was assessed by analysis of liver enzymes, for example, ALT and AST in plasma or serum. In addition, levels of phospho-cJun in the liver were quantitated by IHC, as described by Ma F. et. al. *Lab Invest.;* 89(4):470-84 (2009). Certain compounds from Table 1, 2 and 3 show, or will show, statistically significant inhibition of inflammation, periportal hyperplasia, necrosis, fibrosis, and/or phosphor-cJun levels at dose levels of 10-300 mg/kg QD or BID.

Skin Bleomycin Model:

Male or female DBA/2 mice are obtained from Harlan weighing 22-24 g at arrival and are allowed to acclimate for one week prior to use. Skin fibrosis is induced by intradermal injections of bleomycin (0.5 mg/mL in a total volume of 100 μL) every other day for 6 weeks in defined areas of the upper back. The animals are administered the Diaminopyrimidine Compound by oral gavage 1 h prior to the initial bleomycin injection and then daily or twice daily through the end of the study, 3 or 6 weeks later. At the termination of the study blood is collected via cardiac puncture and the skin is isolated. The skin is processed for histology and the dermal thickness is quantitated following H&E (hematoxylin and eosin) staining. Certain compounds from Table 1, 2 and 3 will show statistically significant inhibition of skin thickness at dose levels of 10-300 mg/kg QD or BID.

Lung Bleomycin model: Male C57Bl/6 mice are obtained from Charles River Laboratories and animals are allowed to acclimate for at least 5 days. Animals are kept on a 12-hours light/dark cycle and are approximately 8 weeks old at the beginning of the study. Mice are lightly anesthetized with isoflurane and the tracheae exposed. On Day 0, bleomycin (30 μL; 0.05 U) is injected into the trachea. Following injection of bleomycin, the wound is closed using wound clips and the animal is allowed to recover. Prednisolone (positive control, dosed intraperitoneally), vehicle (dosed orally), or Diaminopyrimidine Compound (dosed orally) is administered 30 min to 2 hours prior to bleomycin administration (prophylactic model) or 4 days after bleomycin (therapeutic model). Dosing with vehicle or Diaminopyrimidine Compound is carried out twice daily throughout all studies, dosing with prednisolone is carried out once daily. Mice are monitored daily for adverse effects from test article administration, including effect on body weight. Mice are euthanized on Day 13. Bronchoalveolar lavage is performed using 1 mL phosphate buffered saline (PBS) and total WBC counts are assessed. Results are expressed as total cells retrieved. Macrophages, eosinophils, neutrophils, and lymphocytes are quantified in BALF samples. Lung lobes are processed for histology using H&E (hematoxylin and eosin), Trichrome or TUNEL staining. Trichrome sections are scored for fibrosis severity as described previously (Ashcroft et al. *J. Clin. Pathol.* 41:467-470 (1988)). Certain compounds from Table 1, 2 and 3 will show statistically significant inhibition of lung fibrosis at dose levels of 10-300 mg/kg QD or BID.

Lupus Model:

Female NZB/NZW F1 mice are obtained from Jackson Laboratories between 4-12 weeks of age at arrival and are allowed to acclimate for one week prior to use and to develop spontaneous SLE-like disease. The animals are administered the Diaminopyrimidine Compound by oral gavage at the initiation of the study and then daily or twice daily through the end of the study up to 6 months later. Blood is collected throughout the study and serum isolated to measure occurrence of dsDNA via a standard ELISA method and proteinurea is measured in the urine. Certain compounds from Table 1, 2 and 3 will show statistically significant inhibition of proteinurea or dsDNA at dose levels of 10-300 mg/kg QD or BID.

UUO Model of Kidney Fibrosis:

Male CD-IGS rats are obtained from Charles River Laboratories at a body weight of approximately 150-160 g and are allowed to acclimate for one week prior to initiation of the study. Rats are anesthetized using ketamine/xylazine and the surgical area is sterilized with 70% ethanol and betadine. The ureter is exposed after a midline incision is made and ligated twice using 5.0 silk suture placed 1 cm apart and cut between the ligations. The incision is closed using 3.0 silk suture and the animal is allowed to recover. The animals are administered the Diaminopyrimidine Compound by oral gavage 1 h prior to the ureter ligation and then daily or twice daily through the end of the study 7 days later. At the termination of the study blood is collected via cardiac puncture and the kidney isolated. The kidney is processed for histology and the morphology and amount of fibrosis is quantitated following H&E (hematoxylin and eosin), picro sinus red or alpha-smooth muscle actin staining. Certain compounds from Table 1, 2 and 3 will show statistically significant inhibition of fibrosis or alpha-smooth muscle actin staining at dose levels of 10-300 mg/kg QD or BID.

Activity Tables

Each of the compounds in Tables 1, 2 and 3 was tested in one or more of the JNK1 biochemical assays and was found to have activity therein, with all of the compounds having an $IC_{50}$ below 10 μM in the assay, with some compounds having an $IC_{50}$ below 200 nM (activity level D), some an $IC_{50}$ between 200 nM and 800 nM (activity level C), some an $IC_{50}$ between 800 nM and 1 μM (activity level B), and others having an $IC_{50}$ between 1 μM and 10 μM (activity level A).

TABLE 1

| Cmpd. A- | Structure | NAME | MH+ | Act. Level |
|---|---|---|---|---|
| 1 | 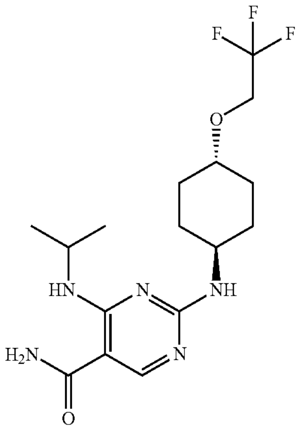 [SMILES: CC(C)Nc1nc(N[C@H]2CC[C@H](OCC(F)(F)F)CC2)ncc1C(N)=O] | 4-(isopropylamino)-2-((1r,4r)-4-(2,2,2-trifluoroethoxy) cyclohexylamino) pyrimidine-5-carboxamide | 376.3 | D |
| 2 | 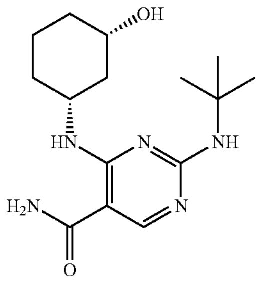 [SMILES: CC(C)(C)Nc1ncc(C(N)=O)c(N[C@@H]2CCC[C@H](O)C2)n1] | 2-(tert-butylamino)-4-((1R,3S)-3-hydroxycyclohexylamino) pyrimidine-5-carboxamide | 308.4 | D |
| 3 | 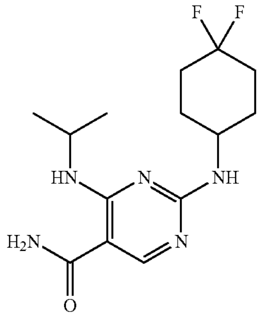 [SMILES: CC(C)Nc1nc(NC2CCC(F)(F)CC2)ncc1C(N)=O] | 2-(4,4-difluorocyclohexylamino)-4-(isopropylamino)pyrimidine-5-carboxamide | 314.2 | D |
| 4 | 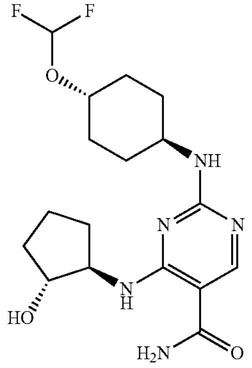 [SMILES: NC(=O)c1cnc(N[C@H]2CC[C@H](OC(F)F)CC2)nc1N[C@@H]1CCC[C@H]1O] | 2-((1r,4R)-4-(difluoromethoxy) cyclohexylamino)-4-((1R,2R)-2-hydroxycyclopentylamino) pyrimidine-5-carboxamide | 386.4 | D |

TABLE 1-continued

| Cmpd. A- | Structure | NAME | MH+ | Act. Level |
|---|---|---|---|---|
| 5 | 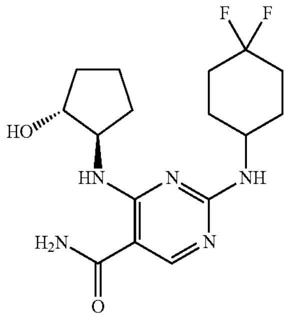 [SMILES: NC(=O)c1cnc(NC2CCC(F)(F)CC2)nc1N[C@@H]1CCC[C@H]1O] | 2-(4,4-difluorocyclohexylamino)-4-((1R,2R)-2-hydroxycyclopentylamino) pyrimidine-5-carboxamide | 356.3 | D |
| 6 | 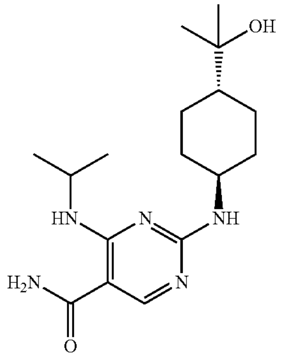 [SMILES: CC(C)Nc1nc(N[C@H]2CC[C@H](C(C)(C)O)CC2)ncc1C(N)=O] | 2-((1r,4r)-4-(2-hydroxypropan-2-yl)cyclohexylamino)-4-(isopropylamino)pyrimidine-5-carboxamide | 336.2 | D |
| 7 | 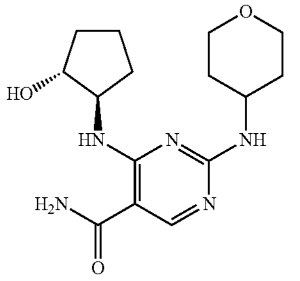 [SMILES: NC(=O)c1cnc(NC2CCOCC2)nc1N[C@@H]1CCC[C@H]1O] | 4-((1R,2R)-2-hydroxycyclopentylamino)-2-(tetrahydro-2H-pyran-4-ylamino)pyrimidine-5-carboxamide | 322.1 | D |
| 8 | 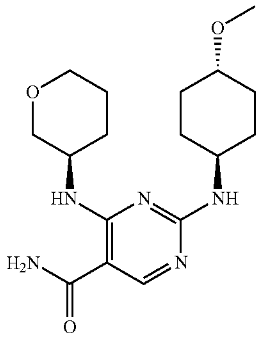 [SMILES: CO[C@H]1CC[C@H](Nc2ncc(C(N)=O)c(N[C@@H]3CCCOC3)n2)CC1] | 2-((1r,4R)-4-methoxycyclohexylamino)-4-((R)-tetrahydro-2H-pyran-3-ylamino)pyrimidine-5-carboxamide | 349.4 | D |

TABLE 1-continued
| Cmpd. A- | Structure | NAME | MH⁺ | Act. Level |
|---|---|---|---|---|
| 9 | 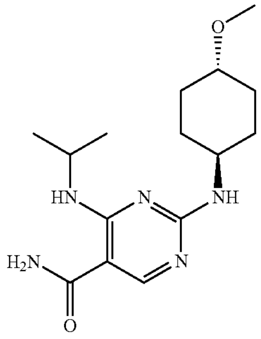 [SMILES: CO[C@H]1CC[C@H](Nc2ncc(C(N)=O)c(NC(C)C)n2)CC1] | 4-(isopropylamino)-2-((1r,4r)-4-methoxycyclohexylamino) pyrimidine-5-carboxamide | 308.3 | D |
| 10 | 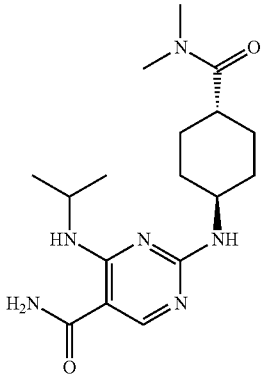 [SMILES: CC(C)Nc1nc(N[C@H]2CC[C@H](C(=O)N(C)C)CC2)ncc1C(N)=O] | 2-((1r,4r)-4-(dimethylcarbamoyl) cyclohexylamino)-4-(isopropylamino) pyrimidine-5-carboxamide | 349.3 | D |
| 11 | 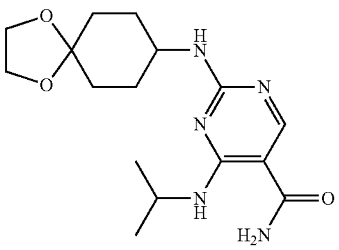 [SMILES: CC(C)Nc1nc(NC2CCC3(CC2)OCCO3)ncc1C(N)=O] | 2-(1,4-dioxaspiro[4.5]decan-8-ylamino)-4-(isopropylamino)pyrimidine-5-carboxamide | 336.2 | C |
| 12 | 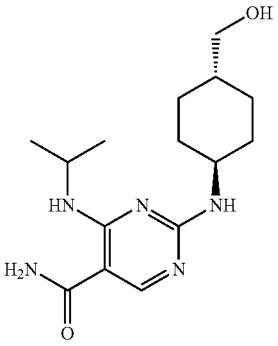 [SMILES: CC(C)Nc1nc(N[C@H]2CC[C@H](CO)CC2)ncc1C(N)=O] | 2-((1r,4r)-4-(hydroxymethyl) cyclohexylamino)-4-(isopropylamino)pyrimidine-5-carboxamide | 308.3 | D |

TABLE 1-continued

| Cmpd. A- | Structure | NAME | MH⁺ | Act. Level |
|---|---|---|---|---|
| 13 | Possible isomers:<br>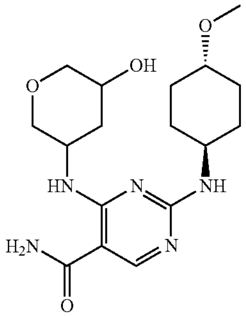<br>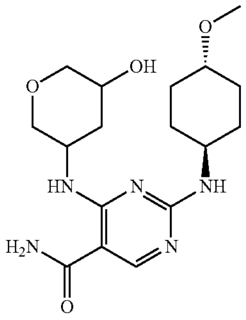<br>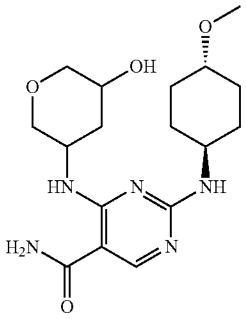<br>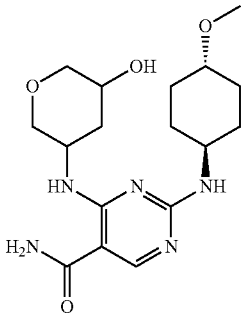 | Peak 4<br>Peak 3<br>Peak 2<br>Peak 1<br>One of:<br>4-(5-hydroxytetrahydro-2H-pyran-3-ylamino)-2-((1r,4r)-4-methoxycyclohexylamino) pyrimidine-5-carboxamide<br>4-(5-hydroxytetrahydro-2H-pyran-3-ylamino)-2-((1r,4r)-4-methoxycyclohexylamino) pyrimidine-5-carboxamide<br>4-(5-hydroxytetrahydro-2H-pyran-3-ylamino)-2-((1r,4r)-4-methoxycyclohexylamino) pyrimidine-5-carboxamide<br>4-(5-hydroxytetrahydro-2H-pyran-3-ylamino)-2-((1r,4r)-4-methoxycyclohexylamino) pyrimidine-5-carboxamide | 366.3<br>366.3<br>366.3<br>366.3 | D<br>D<br>D<br>D |

TABLE 1-continued

| Cmpd. A- | Structure | NAME | MH+ | Act. Level |
|---|---|---|---|---|
| 17 | 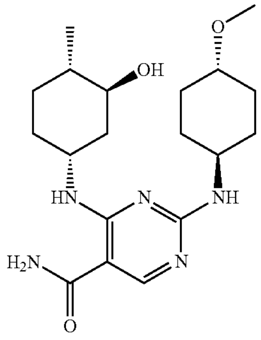 [SMILES: CO[C@H]1CC[C@H](Nc2ncc(C(N)=O)c(N[C@@H]3CC[C@H](C)[C@@H](O)C3)n2)CC1] | 4-((1R,3S,4S)-3-hydroxy-4-methylcyclohexylamino)-2-((1r,4R)-4-methoxycyclohexylamino) pyrimidine-5-carboxamide | 378 | D |
| 18 | 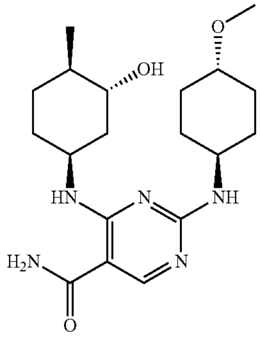 [SMILES: CO[C@H]1CC[C@H](Nc2ncc(C(N)=O)c(N[C@H]3CC[C@@H](C)[C@H](O)C3)n2)CC1] | 4-((1S,3R,4R)-3-hydroxy-4-methylcyclohexylamino)-2-((1r,4S)-4-methoxycyclohexylamino) pyrimidine-5-carboxamide | 378 | C |
| 19 | 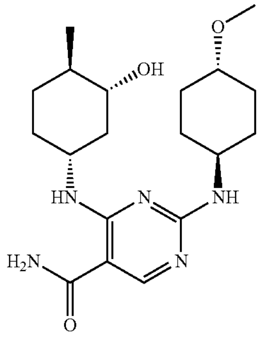 [SMILES: CO[C@H]1CC[C@H](Nc2ncc(C(N)=O)c(N[C@@H]3CC[C@@H](C)[C@H](O)C3)n2)CC1] | 4-((1R,3R,4R)-3-hydroxy-4-methylcyclohexylamino)-2-((1r,4R)-4-methoxycyclohexylamino) pyrimidine-5-carboxamide | 378 | D |
| 20 | 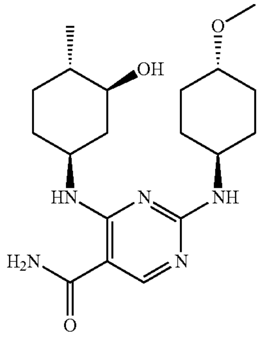 [SMILES: CO[C@H]1CC[C@H](Nc2ncc(C(N)=O)c(N[C@H]3CC[C@H](C)[C@@H](O)C3)n2)CC1] | 4-((1S,3S,4S)-3-hydroxy-4-methylcyclohexylamino)-2-((1r,4S)-4-methoxycyclohexylamino) pyrimidine-5-carboxamide | 378 | D |

TABLE 1-continued

| Cmpd. A- | Structure | NAME | MH+ | Act. Level |
|---|---|---|---|---|
| 21 | 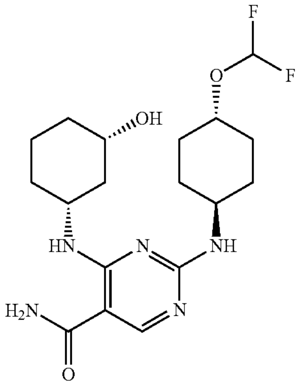 [SMILES: NC(=O)c1cnc(N[C@H]2CC[C@H](OC(F)F)CC2)nc1N[C@@H]1CCC[C@H](O)C1] | 2-((1r,4R)-4-(difluoromethoxy) cyclohexylamino)-4-((1R,3S)-3-hydroxycyclohexylamino) pyrimidine-5-carboxamide | 400.5 | D |
| 22 | 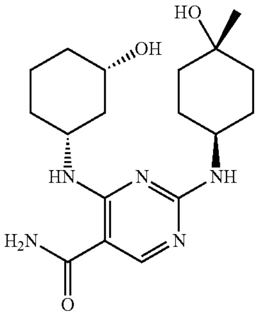 [SMILES: C[C@]1(O)CC[C@H](Nc2ncc(C(N)=O)c(N[C@@H]3CCC[C@H](O)C3)n2)CC1] | 2-((1r,4R)-4-hydroxy-4-methylcyclohexylamino)-4-((1R,3S)-3-hydroxycyclohexylamino) pyrimidine-5-carboxamide | 364.5 | D |
| 23 | 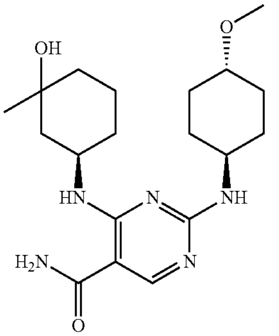 | 4-((1R,3R)-3-hydroxy-3-methylcyclohexylamino)-2-((1r,4R)-4-methoxycyclohexylamino) pyrimidine-5-carboxamide | 378.5 | D |
| 24 | 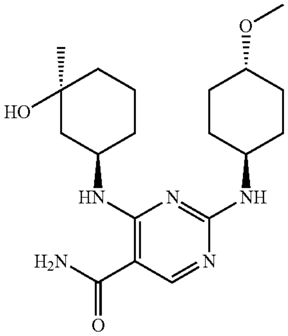 [SMILES: CO[C@H]1CC[C@H](Nc2ncc(C(N)=O)c(N[C@@H]3CCC[C@](C)(O)C3)n2)CC1] | 4-((1R,3S)-3-hydroxy-3-methylcyclohexylamino)-2-((1r,4R)-4-methoxycyclohexylamino) pyrimidine-5-carboxamide | 378.5 | D |

TABLE 1-continued

| Cmpd. A- | Structure | NAME | MH+ | Act. Level |
|---|---|---|---|---|
| 25 | 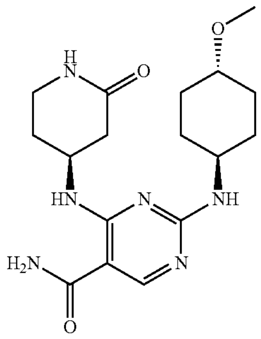 [SMILES: CO[C@H]1CC[C@H](Nc2ncc(C(N)=O)c(N[C@H]3CCNC(=O)C3)n2)CC1] | 2-((1r,4S)-4-methoxycyclohexylamino)-4-((S)-2-oxopiperidin-4-ylamino)pyrimidine-5-carboxamide | 363.2 | D |
| 26 | 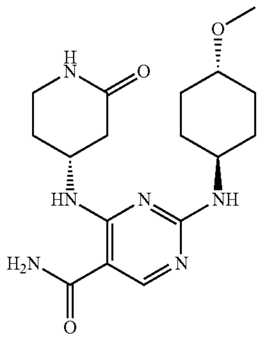 [SMILES: CO[C@H]1CC[C@H](Nc2ncc(C(N)=O)c(N[C@@H]3CCNC(=O)C3)n2)CC1] | 2-((1r,4R)-4-methoxycyclohexylamino)-4-((R)-2-oxopiperidin-4-ylamino)pyrimidine-5-carboxamide | 363.2 | C |
| 27 | 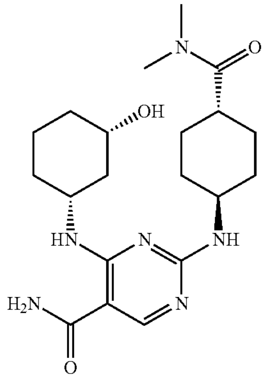 [SMILES: CN(C)C(=O)[C@H]1CC[C@H](Nc2ncc(C(N)=O)c(N[C@@H]3CCC[C@H](O)C3)n2)CC1] | 2-((1r,4R)-4-(dimethylcarbamoyl) cyclohexylamino)-4-((1R,3S)-3-hydroxycyclohexylamino) pyrimidine-5-carboxamide | 405 | D |
| 28 | 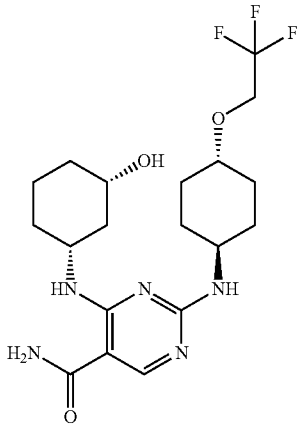 [SMILES: NC(=O)c1cnc(N[C@H]2CC[C@H](OCC(F)(F)F)CC2)nc1N[C@@H]1CCC[C@H](O)C1] | 4-((1R,3S)-3-hydroxycyclohexylamino)-2-((1r,4R)-4-(2,2,2-trifluoroethoxy) cyclohexylamino) pyrimidine-5-carboxamid | 432 | D |

TABLE 1-continued

| Cmpd. A- | Structure | NAME | MH+ | Act. Level |
|---|---|---|---|---|
| 29 | 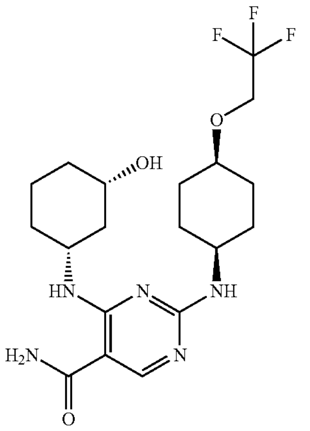 [SMILES: NC(=O)c1cnc(N[C@H]2CC[C@@H](OCC(F)(F)F)CC2)nc1N[C@@H]1CCC[C@H](O)C1] | 4-((1R,3S)-3-hydroxycyclohexylamino)-2-((1s,4S)-4-(2,2,2-trifluoroethoxy) cyclohexylamino) pyrimidine-5-carboxamid | 432 | D |
| 30 | 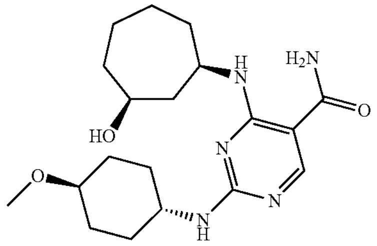 [SMILES: CO[C@H]1CC[C@H](Nc2ncc(C(N)=O)c(N[C@@H]3CCCC[C@H](O)C3)n2)CC1] | 4-((1R,3S)-3-hydroxycycloheptylamino)-2-((1r,4R)-4-methoxycyclohexylamino) pyrimidine-5-carboxamide | 378.3 | D |
| 31 | 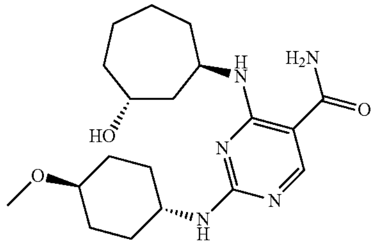 [SMILES: CO[C@H]1CC[C@H](Nc2ncc(C(N)=O)c(N[C@@H]3CCCC[C@@H](O)C3)n2)CC1] | 4-((1R,3R)-3-hydroxycycloheptylamino)-2-((1r,4R)-4-methoxycyclohexylamino) pyrimidine-5-carboxamide | 378.3 | D |
| 32 | 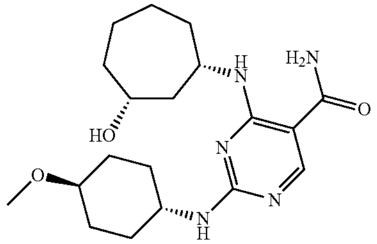 [SMILES: CO[C@H]1CC[C@H](Nc2ncc(C(N)=O)c(N[C@H]3CCCC[C@@H](O)C3)n2)CC1] | 4-((1S,3R)-3-hydroxycycloheptylamino)-2-((1r,4S)-4-methoxycyclohexylamino) pyrimidine-5-carboxamide | 378.3 | D |
| 33 | 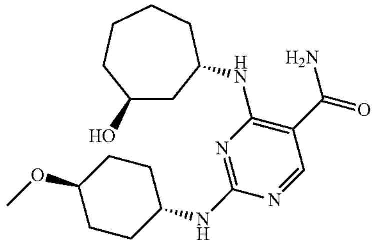 [SMILES: CO[C@H]1CC[C@H](Nc2ncc(C(N)=O)c(N[C@H]3CCCC[C@H](O)C3)n2)CC1] | 4-((1S,3S)-3-hydroxycycloheptylamino)-2-((1r,4S)-4-methoxycyclohexylamino) pyrimidine-5-carboxamide | 378.3 | D |

TABLE 1-continued

| Cmpd. A- | Structure | NAME | MH+ | Act. Level |
|---|---|---|---|---|
| 34 | 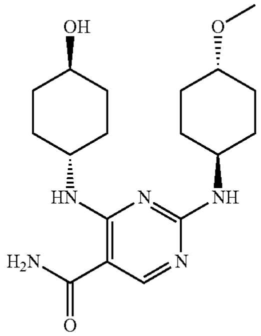 [SMILES: CO[C@H]1CC[C@H](Nc2ncc(C(N)=O)c(N[C@H]3CC[C@H](O)CC3)n2)CC1] | 4-((1r,4r)-4-hydroxycyclohexylamino)-2-((1r,4r)-4-methoxycyclohexylamino) pyrimidine-5-carboxamide | 364.2 | D |
| 35 | 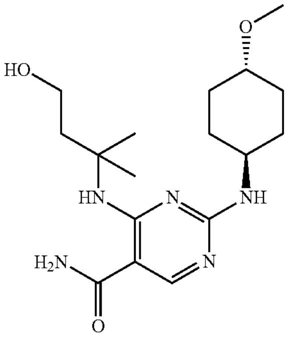 [SMILES: CO[C@H]1CC[C@H](Nc2ncc(C(N)=O)c(NC(C)(C)CCO)n2)CC1] | 4-(4-hydroxy-2-methylbutan-2-ylamino)-2-((1r,4r)-4-methoxycyclohexylamino) pyrimidine-5-carboxamide | 352.2 | D |
| 36 | 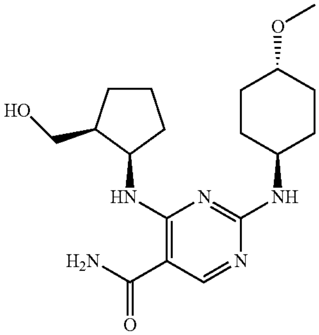 [SMILES: CO[C@H]1CC[C@H](Nc2ncc(C(N)=O)c(N[C@@H]3CCC[C@@H]3CO)n2)CC1] | 4-((1R,2S)-2-(hydroxymethyl) cyclopentylamino)-2-((1r,4R)-4-methoxycyclohexylamino) pyrimidine-5-carboxamide | 364.5 | D |
| 37 | 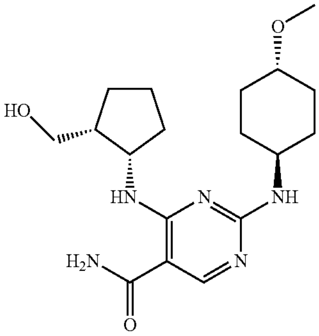 [SMILES: CO[C@H]1CC[C@H](Nc2ncc(C(N)=O)c(N[C@H]3CCC[C@H]3CO)n2)CC1] | 4-((1S,2R)-2-(hydroxymethyl) cyclopentylamino)-2-((1r,4S)-4-methoxycyclohexylamino) pyrimidine-5-carboxamide | 364.5 | C |

TABLE 1-continued

| Cmpd. A- | Structure | NAME | MH+ | Act. Level |
|---|---|---|---|---|
| 38 | 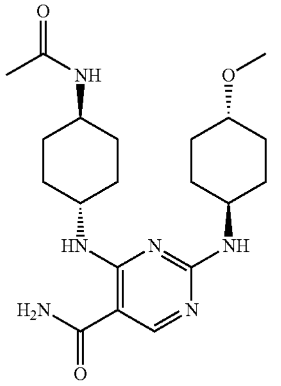 [SMILES: CO[C@H]1CC[C@H](Nc2ncc(C(N)=O)c(N[C@H]3CC[C@H](NC(C)=O)CC3)n2)CC1] | 4-((1r,4r)-4-acetamidocyclohexylamino)-2-((1r,4r)-4-methoxycyclohexylamino) pyrimidine-5-carboxamide | 405.2 | D |
| 39 | 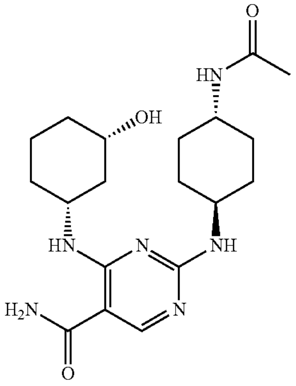 [SMILES: CC(=O)N[C@H]1CC[C@H](Nc2ncc(C(N)=O)c(N[C@@H]3CCC[C@H](O)C3)n2)CC1] | 2-((1r,4R)-4-acetamidocyclohexylamino)-4-((1R,3S)-3-hydroxycyclohexylamino) pyrimidine-5-carboxamide | 391.2 | D |
| 40 | 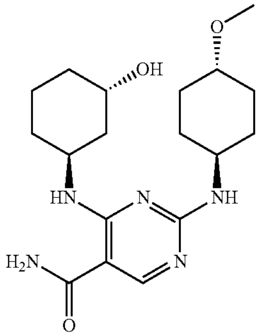 [SMILES: CO[C@H]1CC[C@H](Nc2ncc(C(N)=O)c(N[C@H]3CCC[C@H](O)C3)n2)CC1] | 4-((1S,3S)-3-hydroxycyclohexylamino)-2-((1r,4S)-4-methoxycyclohexylamino) pyrimidine-5-carboxamide | 363.9 | D |
| 41 | 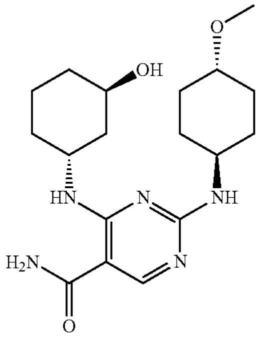 [SMILES: CO[C@H]1CC[C@H](Nc2ncc(C(N)=O)c(N[C@@H]3CCC[C@@H](O)C3)n2)CC1] | 4-((1R,3R)-3-hydroxycyclohexylamino)-2-((1r,4R)-4-methoxycyclohexylamino) pyrimidine-5-carboxamide | 363.9 | D |

TABLE 1-continued

| Cmpd. A- | Structure | NAME | MH+ | Act. Level |
|---|---|---|---|---|
| 42 | 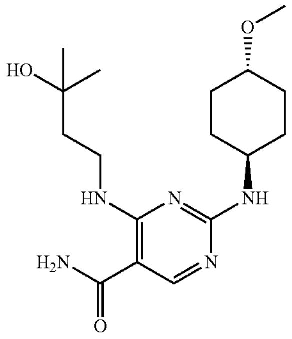 [SMILES: CO[C@H]1CC[C@H](Nc2ncc(C(N)=O)c(NCCC(C)(C)O)n2)CC1] | 4-(3-hydroxy-3-methylbutylamino)-2-((1r,4r)-4-methoxycyclohexylamino) pyrimidine-5-carboxamide | 352.4 | D |
| 43 | 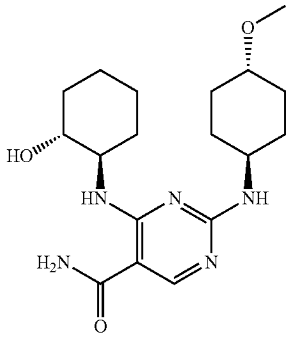 [SMILES: CO[C@H]1CC[C@H](Nc2ncc(C(N)=O)c(N[C@@H]3CCCC[C@H]3O)n2)CC1] | 4-((1R,2R)-2-hydroxycyclohexylamino)-2-((1r,4R)-4-methoxycyclohexylamino) pyrimidine-5-carboxamide | 364.2 | D |
| 44 | 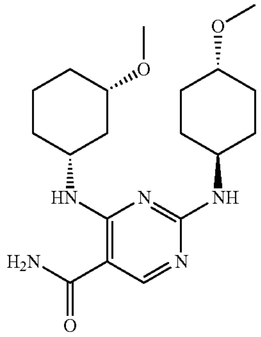 [SMILES: CO[C@H]1CCC[C@@H](Nc2nc(N[C@H]3CC[C@H](OC)CC3)ncc2C(N)=O)C1] | 4-((1R,3S)-3-methoxycyclohexylamino)-2-((1r,4R)-4-methoxycyclohexylamino) pyrimidine-5-carboxamide | 378.4 | D |
| 45 | 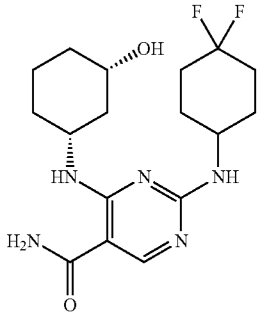 [SMILES: NC(=O)c1cnc(NC2CCC(F)(F)CC2)nc1N[C@@H]1CCC[C@H](O)C1] | 2-(4,4-difluorocyclohexylamino)-4-((1R,3S)-3-hydroxycyclohexylamino) pyrimidine-5-carboxamide | 370.2 | D |

TABLE 1-continued

| Cmpd. A- | Structure | NAME | MH⁺ | Act. Level |
|---|---|---|---|---|
| 46 | 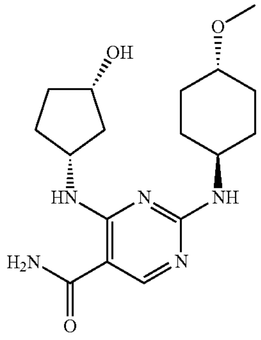 [SMILES: CO[C@H]1CC[C@H](Nc2ncc(C(N)=O)c(N[C@@H]3CC[C@H](O)C3)n2)CC1] | 4-((1R,3S)-3-hydroxycyclopentylamino)-2-((1r,4R)-4-methoxycyclohexylamino) pyrimidine-5-carboxamide | 350.1 | D |
| 47 | 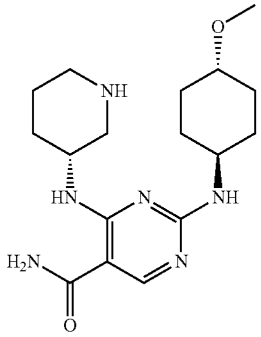 [SMILES: CO[C@H]1CC[C@H](Nc2ncc(C(N)=O)c(N[C@@H]3CCCNC3)n2)CC1] | 2-((1r,4R)-4-methoxycyclohexylamino)-4-((R)-piperidin-3-ylamino)pyrimidine-5-carboxamide | 349.2 | D |
| 48 | 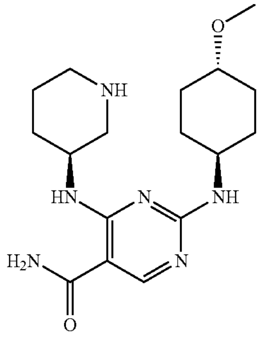 [SMILES: CO[C@H]1CC[C@H](Nc2ncc(C(N)=O)c(N[C@H]3CCCNC3)n2)CC1] | 2-((1r,4S)-4-methoxycyclohexylamino)-4-((S)-piperidin-3-ylamino)pyrimidine-5-carboxamide | 349.4 | B |
| 49 | 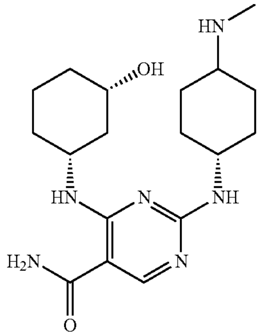 | 4-((1R,3S)-3-hydroxycyclohexylamino)-2-((1r,4R)-4-(methylamino) cyclohexylamino) pyrimidine-5-carboxamide | 363.5 | D |

TABLE 1-continued

| Cmpd. A- | Structure | NAME | MH+ | Act. Level |
|---|---|---|---|---|
| 50 | 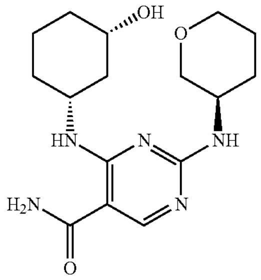 [SMILES: NC(=O)c1cnc(N[C@@H]2CCCOC2)nc1N[C@@H]1CCC[C@H](O)C1] | 4-((1R,3S)-3-hydroxycyclohexylamino)-2-((R)-tetrahydro-2H-pyran-3-ylamino)pyrimidine-5-carboxamide | 336.2 | D |
| 51 | 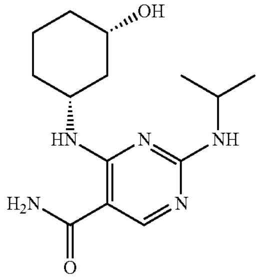 [SMILES: CC(C)Nc1ncc(C(N)=O)c(N[C@@H]2CCC[C@H](O)C2)n1] | 4-((1R,3S)-3-hydroxycyclohexylamino)-2-(isopropylamino)pyrimidine-5-carboxamide | 294.2 | D |
| 52 | 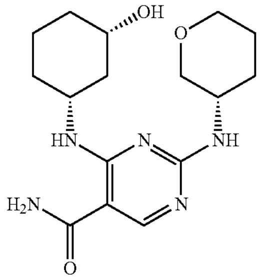 [SMILES: NC(=O)c1cnc(N[C@H]2CCCOC2)nc1N[C@@H]1CCC[C@H](O)C1] | 4-((1R,3S)-3-hydroxycyclohexylamino)-2-((S)-tetrahydro-2H-pyran-3-ylamino)pyrimidine-5-carboxamide | 336.2 | D |
| 53 | 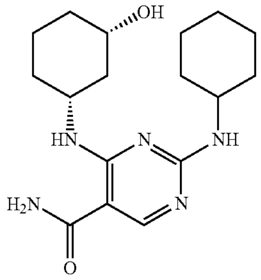 [SMILES: NC(=O)c1cnc(NC2CCCCC2)nc1N[C@@H]1CCC[C@H](O)C1] | 2-(cyclohexylamino)-4-((1R,3S)-3-hydroxycyclohexylamino) pyrimidine-5-carboxamide | 334.2 | D |
| 54 | 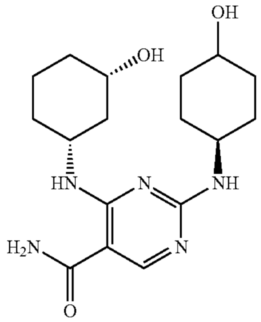 | 4-((1R,3S)-3-hydroxycyclohexylamino)-2-((1r,4R)-4-hydroxycyclohexylamino) pyrimidine-5-carboxamide | 350.3 | D |

TABLE 1-continued

| Cmpd. A- | Structure | NAME | MH+ | Act. Level |
|---|---|---|---|---|
| 55 | 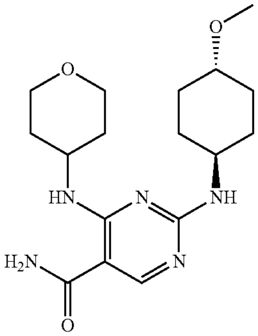 [SMILES: CO[C@H]1CC[C@H](Nc2ncc(C(N)=O)c(NC3CCOCC3)n2)CC1] | 2-((1r,4r)-4-methoxycyclohexylamino)-4-(tetrahydro-2H-pyran-4-ylamino)pyrimidine-5-carboxamide | 350.1 | C |
| 56 | 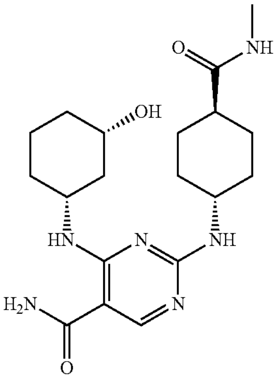 [SMILES: CNC(=O)[C@H]1CC[C@H](Nc2ncc(C(N)=O)c(N[C@@H]3CCC[C@H](O)C3)n2)CC1] | 4-((1R,3S)-3-hydroxycyclohexylamino)-2-((1r,4R)-4-(methylcarbamoyl)cyclohexylamino)pyrimidine-5-carboxamide | 391.2 | D |
| 57 | 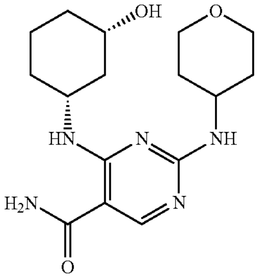 [SMILES: NC(=O)c1cnc(NC2CCOCC2)nc1N[C@@H]1CCC[C@H](O)C1] | 4-((1R,3S)-3-hydroxycyclohexylamino)-2-(tetrahydro-2H-pyran-4-ylamino)pyrimidine-5-carboxamide | 336.2 | D |
| 58 | 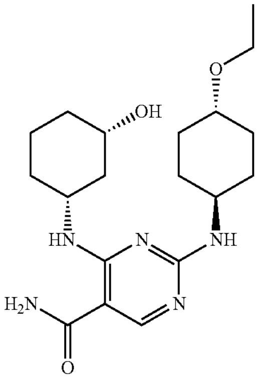 [SMILES: CCO[C@H]1CC[C@H](Nc2ncc(C(N)=O)c(N[C@@H]3CCC[C@H](O)C3)n2)CC1] | 2-((1r,4R)-4-ethoxycyclohexylamino)-4-((1R,3S)-3-hydroxycyclohexylamino)pyrimidine-5-carboxamide | 377.9 | D |

TABLE 1-continued

| Cmpd. A- | Structure | NAME | MH+ | Act. Level |
|---|---|---|---|---|
| 59 | 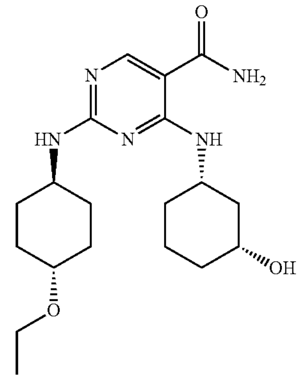 [SMILES: CCO[C@H]1CC[C@H](Nc2ncc(C(N)=O)c(N[C@H]3CCC[C@@H](O)C3)n2)CC1] | 2-((1r,4S)-4-ethoxycyclohexylamino)-4-((1S,3R)-3-hydroxycyclohexylamino)pyrimidine-5-carboxamide | 377.9 | D |
| 60 | 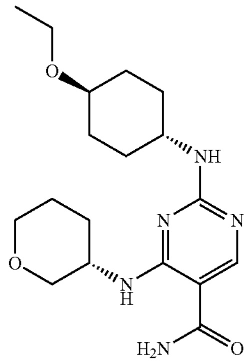 [SMILES: CCO[C@H]1CC[C@H](Nc2ncc(C(N)=O)c(N[C@H]3CCCOC3)n2)CC1] | 2-((1r,4S)-4-ethoxycyclohexylamino)-4-((S)-tetrahydro-2H-pyran-3-ylamino)pyrimidine-5-carboxamide | 364.3 | D |
| 61 | 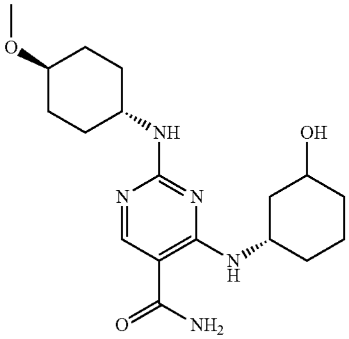 [SMILES: CO[C@H]1CC[C@H](Nc2ncc(C(N)=O)c(N[C@H]3CCCC(O)C3)n2)CC1] | 4-((1S,3R)-3-hydroxycyclohexylamino)-2-((1r,4S)-4-methoxycyclohexylamino)pyrimidine-5-carboxamide | 364.3 | D |
| 62 | 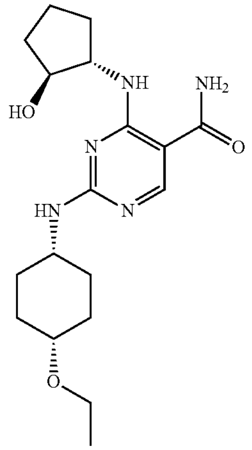 [SMILES: CCO[C@H]1CC[C@@H](Nc2ncc(C(N)=O)c(N[C@H]3CCC[C@@H]3O)n2)CC1] | 2-((1s,4R)-4-ethoxycyclohexylamino)-4-((1S,2S)-2-hydroxycyclopentylamino)pyrimidine-5-carboxamide | 364.3 | B |

TABLE 1-continued

| Cmpd. A- | Structure | NAME | MH+ | Act. Level |
|---|---|---|---|---|
| 63 | 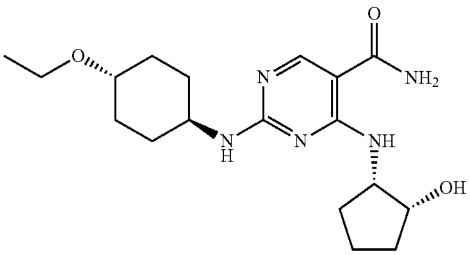 [SMILES: CCO[C@H]1CC[C@H](Nc2ncc(C(N)=O)c(N[C@H]3CCC[C@H]3O)n2)CC1] | 2-((1r,4S)-4-ethoxycyclohexylamino)-4-((1S,2R)-2-hydroxycyclopentylamino) pyrimidine-5-carboxamide | 364.3 | C |
| 64 | 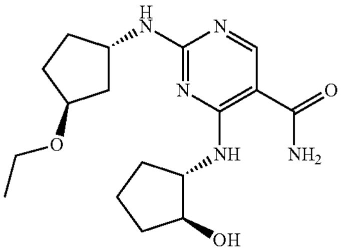 [SMILES: CCO[C@H]1CC[C@H](Nc2ncc(C(N)=O)c(N[C@H]3CCC[C@@H]3O)n2)C1] | 2-((1S,3S)-3-ethoxycyclohexylamino)-4-((1S,2S)-2-hydroxycyclopentylamino) pyrimidine-5-carboxamide | 350.3 | C |
| 65 | 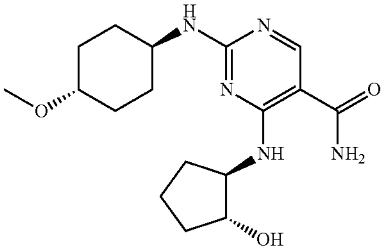 [SMILES: CO[C@H]1CC[C@H](Nc2ncc(C(N)=O)c(N[C@@H]3CCC[C@H]3O)n2)CC1] | 4-((1R,2R)-2-hydroxycyclopentylamino)-2-((1r,4R)-4-methoxycyclohexylamino) pyrimidine-5-carboxamide | 350.3 | D |
| 66 | 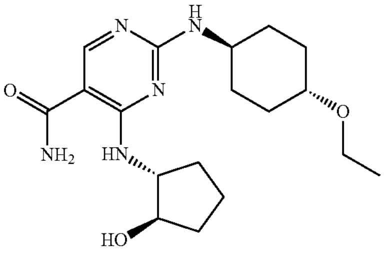 [SMILES: CCO[C@H]1CC[C@H](Nc2ncc(C(N)=O)c(N[C@@H]3CCC[C@H]3O)n2)CC1] | 2-((1r,4R)-4-ethoxycyclohexylamino)-4-((1R,2R)-2-hydroxycyclopentylamino) pyrimidine-5-carboxamide | 364.3 | D |
| 67 | 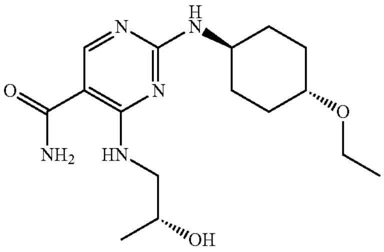 [SMILES: CCO[C@H]1CC[C@H](Nc2ncc(C(N)=O)c(NC[C@@H](C)O)n2)CC1] | 2-((1r,4R)-4-ethoxycyclohexylamino)-4-((R)-2-hydroxypropylamino) pyrimidine-5-carboxamide | 338.3 | D |
| 68 | 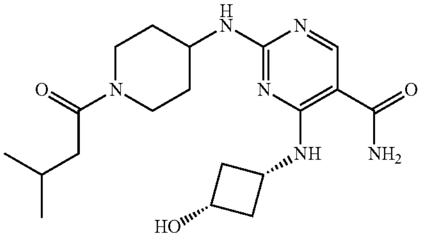 [SMILES: CC(C)CC(=O)N1CCC(Nc2ncc(C(N)=O)c(N[C@H]3C[C@@H](O)C3)n2)CC1] | 4-((1s,3s)-3-hydroxycyclobutylamino)-2-(1-(3-methylbutanoyl)piperidin-4-ylamino)pyrimidine-5-carboxamide | 391.3 | D |

TABLE 1-continued

| Cmpd. A- | Structure | NAME | $MH^+$ | Act. Level |
|---|---|---|---|---|
| 69 | 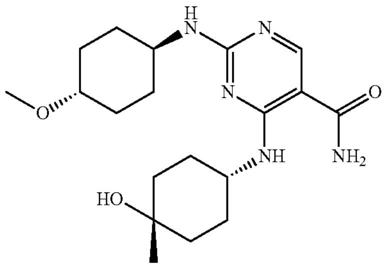 [SMILES: CO[C@H]1CC[C@H](Nc2ncc(C(N)=O)c(N[C@H]3CC[C@@](C)(O)CC3)n2)CC1] | 4-((1s,4s)-4-hydroxy-4-methylcyclohexylamino)-2-((1r,4r)-4-methoxycyclohexylamino) pyrimidine-5-carboxamide | 378.3 | D |
| 70 | 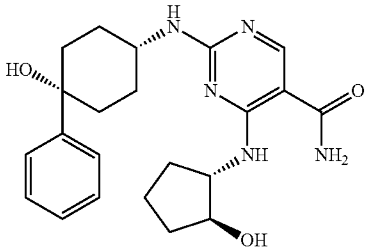 [SMILES: NC(=O)c1cnc(N[C@H]2CC[C@](O)(c3ccccc3)CC2)nc1N[C@H]1CCC[C@@H]1O] | 2-((1s,4R)-4-hydroxy-4-phenylcyclohexylamino)-4-((1S,2S)-2-hydroxycyclopentylamino) pyrimidine-5-carboxamide | 412.3 | C |
| 71 | 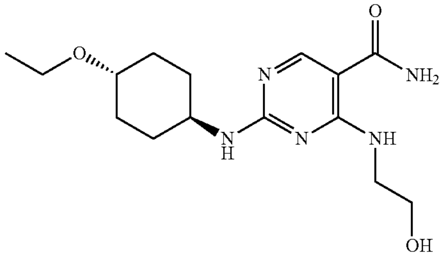 [SMILES: CCO[C@H]1CC[C@H](Nc2ncc(C(N)=O)c(NCCO)n2)CC1] | 2-((1r,4r)-4-ethoxycyclohexylamino)-4-(2-hydroxyethylamino) pyrimidine-5-carboxamide | 324.2 | D |
| 72 | 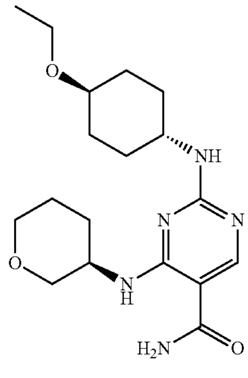 [SMILES: CCO[C@H]1CC[C@H](Nc2ncc(C(N)=O)c(N[C@@H]3CCCOC3)n2)CC1] | 2-((1r,4R)-4-ethoxycyclohexylamino)-4-((R)-tetrahydro-2H-pyran-3-ylamino)pyrimidine-5-carboxamide | 364.3 | D |
| 73 | 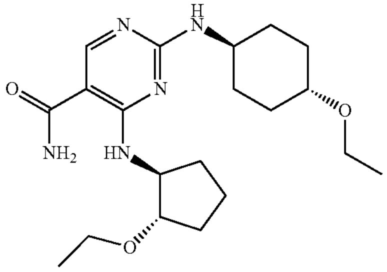 [SMILES: CCO[C@H]1CCC[C@@H]1Nc1nc(N[C@H]2CC[C@H](OCC)CC2)ncc1C(N)=O] | 2-((1r,4S)-4-ethoxycyclohexylamino)-4-((1S,2S)-2-ethoxycyclopentylamino) pyrimidine-5-carboxamide | 392.4 | D |

TABLE 1-continued

| Cmpd. A- | Structure | NAME | MH+ | Act. Level |
|---|---|---|---|---|
| 74 | 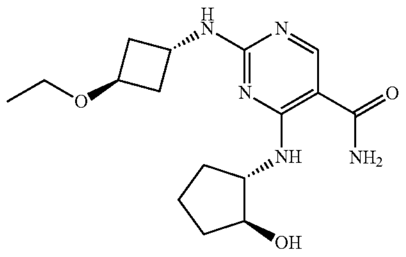 [SMILES: CCO[C@H]1C[C@H](Nc2ncc(C(N)=O)c(N[C@H]3CCC[C@@H]3O)n2)C1] | 2-((1r,3S)-3-ethoxycyclobutylamino)-4-((1S,2S)-2-hydroxycyclopentylamino) pyrimidine-5-carboxamide | 336.3 | C |
| 75 | 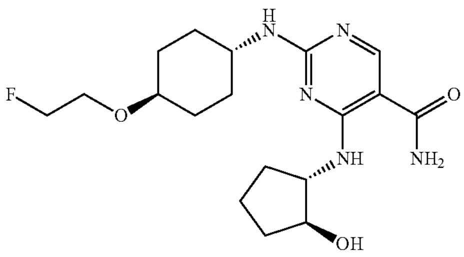 [SMILES: NC(=O)c1cnc(N[C@H]2CC[C@H](OCCF)CC2)nc1N[C@H]1CCC[C@@H]1O] | 2-((1r,4S)-4-(2-fluoroethoxy)cyclohexylamino)-4-((1S,2S)-2-hydroxycyclopentylamino) pyrimidine-5-carboxamide | 382.3 | D |
| 76 | 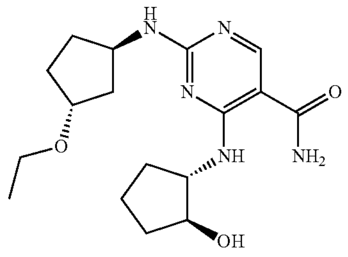 [SMILES: CCO[C@@H]1CC[C@@H](Nc2ncc(C(N)=O)c(N[C@H]3CCC[C@@H]3O)n2)C1] | 2-((1R,3R)-3-ethoxycyclopentylamino)-4-((1S,2S)-2-hydroxycyclopentylamino) pyrimidine-5-carboxamide | 350.3 | C |
| 77 | 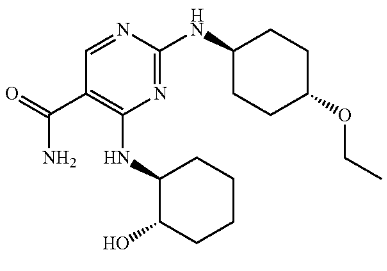 [SMILES: CCO[C@H]1CC[C@H](Nc2ncc(C(N)=O)c(N[C@H]3CCCC[C@@H]3O)n2)CC1] | 2-((1r,4S)-4-ethoxycyclohexylamino)-4-((1S,2S)-2-hydroxycyclohexylamino) pyrimidine-5-carboxamide | 378.3 | D |
| 78 | 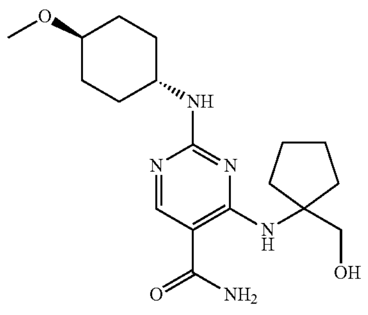 [SMILES: CO[C@H]1CC[C@H](Nc2ncc(C(N)=O)c(NC3(CO)CCCC3)n2)CC1] | 4-(1-(hydroxymethyl) cyclopentylamino)-2-((1r,4r)-4-methoxycyclohexylamino) pyrimidine-5-carboxamide | 364.3 | D |

TABLE 1-continued

| Cmpd. A- | Structure | NAME | MH+ | Act. Level |
|---|---|---|---|---|
| 79 | 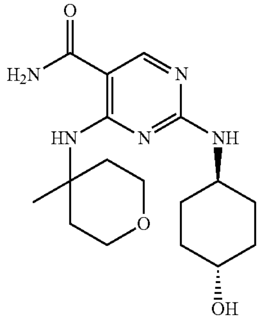 [SMILES: CC1(Nc2nc(N[C@H]3CC[C@H](O)CC3)ncc2C(N)=O)CCOCC1] | 2-((1r,4r)-4-hydroxycyclohexylamino)-4-(4-methyltetrahydro-2H-pyran-4-ylamino)pyrimidine-5-carboxamide | 350.3 | D |
| 80 | 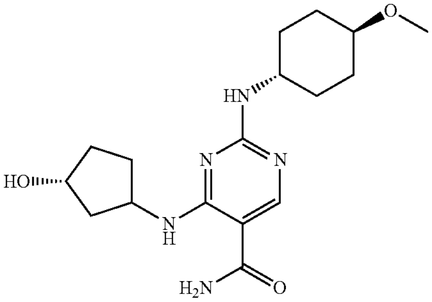 [SMILES: CO[C@H]1CC[C@H](Nc2ncc(C(N)=O)c(NC3CC[C@@H](O)C3)n2)CC1] | 4-((1S,3R)-3-hydroxycyclopentylamino)-2-((1r,4S)-4-methoxycyclohexylamino) pyrimidine-5-carboxamide | 350.3 | D |
| 81 | 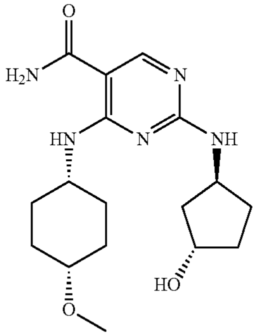 [SMILES: CO[C@H]1CC[C@@H](Nc2nc(N[C@H]3CC[C@H](O)C3)ncc2C(N)=O)CC1] | 2-((1S,3S)-3-hydroxycyclopentylamino)-4-((1s,4R)-4-methoxycyclohexylamino) pyrimidine-5-carboxamide | 350.3 | D |
| 82 | 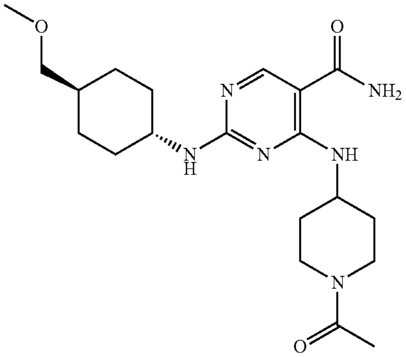 [SMILES: COC[C@H]1CC[C@H](Nc2ncc(C(N)=O)c(NC3CCN(C(C)=O)CC3)n2)CC1] | 4-(1-acetylpiperidin-4-ylamino)-2-((1r,4r)-4-(methoxymethyl) cyclohexylamino) pyrimidine-5-carboxamide | 405.3 | C |

TABLE 1-continued

| Cmpd. A- | Structure | NAME | MH+ | Act. Level |
|---|---|---|---|---|
| 83 | 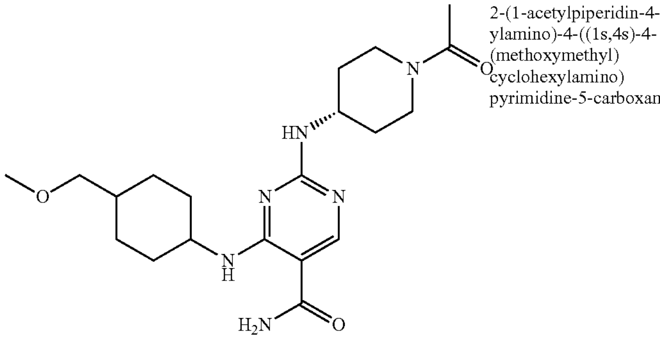 | 2-(1-acetylpiperidin-4-ylamino)-4-((1s,4s)-4-(methoxymethyl) cyclohexylamino) pyrimidine-5-carboxamide | 405.4 | C |
| 84 | 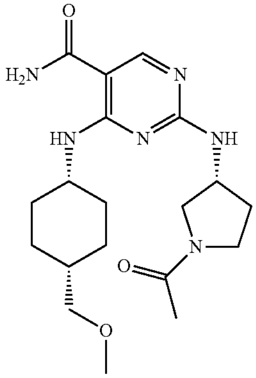 [SMILES: COC[C@H]1CC[C@@H](Nc2nc(N[C@@H]3CCN(C(C)=O)C3)ncc2C(N)=O)CC1] | 2-((R)-1-acetylpyrrolidin-3-ylamino)-4-((1s,4S)-4-(methoxymethyl) cyclohexylamino) pyrimidine-5-carboxamide | 391.4 | C |
| 85 | 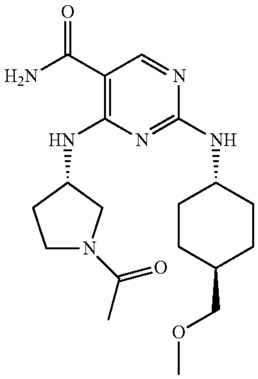 [SMILES: COC[C@H]1CC[C@H](Nc2ncc(C(N)=O)c(N[C@H]3CCN(C(C)=O)C3)n2)CC1] | 4-((S)-1-acetylpyrrolidin-3-ylamino)-2-((1r,4S)-4-(methoxymethyl) cyclohexylamino) pyrimidine-5-carboxamide | 391.3 | C |
| 86 | 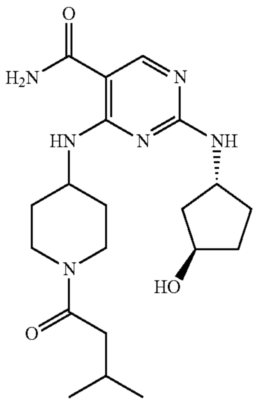 [SMILES: CC(C)CC(=O)N1CCC(Nc2nc(N[C@@H]3CC[C@@H](O)C3)ncc2C(N)=O)CC1] | 2-((1R,3R)-3-hydroxycyclopentylamino)-4-(1-(3-methylbutanoyl)piperidin-4-ylamino)pyrimidine-5-carboxamide | 405.3 | C |

TABLE 1-continued

| Cmpd. A- | Structure | NAME | MH+ | Act. Level |
|---|---|---|---|---|
| 87 | 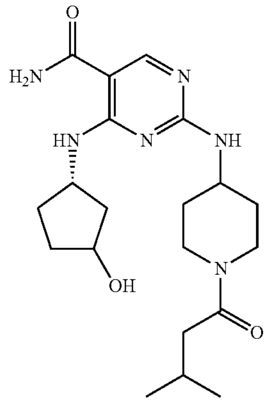 [SMILES: CC(C)CC(=O)N1CCC(Nc2ncc(C(N)=O)c(N[C@H]3CCC(O)C3)n2)CC1] | 4-((1S,3R)-3-hydroxycyclopentylamino)-2-(1-(3-methylbutanoyl)piperidin-4-ylamino)pyrimidine-5-carboxamide | 405.3 | D |
| 88 | 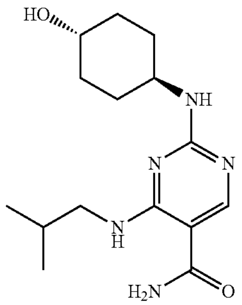 [SMILES: CC(C)CNc1nc(N[C@H]2CC[C@H](O)CC2)ncc1C(N)=O] | 2-((1r,4r)-4-hydroxycyclohexylamino)-4-(isobutylamino)pyrimidine-5-carboxamide | 308.3 | D |
| 89 | 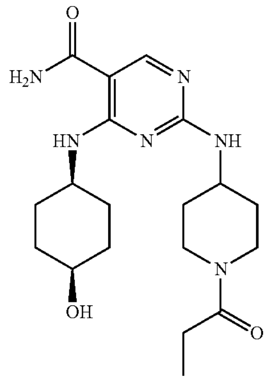 [SMILES: CCC(=O)N1CCC(Nc2ncc(C(N)=O)c(N[C@H]3CC[C@@H](O)CC3)n2)CC1] | 4-((1s,4s)-4-hydroxycyclohexylamino)-2-(1-propionylpiperidin-4-ylamino)pyrimidine-5-carboxamide | 391.3 | D |
| 90 | 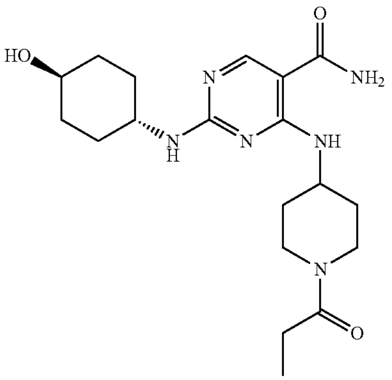 [SMILES: CCC(=O)N1CCC(Nc2nc(N[C@H]3CC[C@H](O)CC3)ncc2C(N)=O)CC1] | 2-((1r,4r)-4-hydroxycyclohexylamino)-4-(1-propionylpiperidin-4-ylamino)pyrimidine-5-carboxamide | 391.3 | D |

TABLE 1-continued
| Cmpd. A- | Structure | NAME | MH+ | Act. Level |
|---|---|---|---|---|
| 91 | 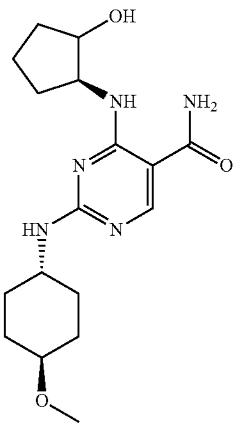 [SMILES: CO[C@H]1CC[C@H](Nc2ncc(C(N)=O)c(N[C@H]3CCCC3O)n2)CC1] | 4-((1S,2S)-2-hydroxycyclopentylamino)-2-((1r,4S)-4-methoxycyclohexylamino) pyrimidine-5-carboxamide | 350.3 | D |
| 92 | 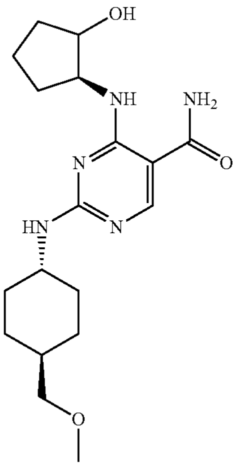 [SMILES: COC[C@H]1CC[C@H](Nc2ncc(C(N)=O)c(N[C@H]3CCCC3O)n2)CC1] | 4-((1S,2S)-2-hydroxycyclopentylamino)-2-((1r,4S)-4-(methoxymethyl) cyclohexylamino) pyrimidine-5-carboxamide | 364.4 | D |
| 93 | 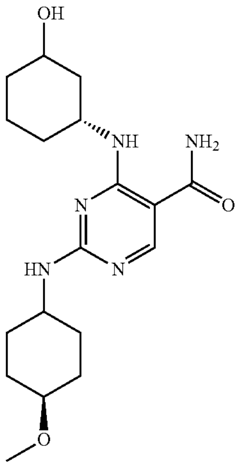 | 4-((1R,3S)-3-hydroxycyclohexylamino)-2-((1r,4R)-4-methoxycyclohexylamino) pyrimidine-5-carboxamide | 364.3 | D |

TABLE 1-continued

| Cmpd. A- | Structure | NAME | MH+ | Act. Level |
|---|---|---|---|---|
| 94 | 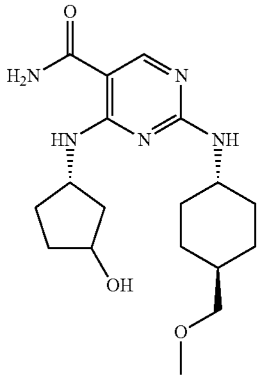 [SMILES: COC[C@H]1CC[C@H](Nc2ncc(C(N)=O)c(N[C@H]3CCC(O)C3)n2)CC1] | 4-((1S,3R)-3-hydroxycyclopentylamino)-2-((1r,4S)-4-(methoxymethyl) cyclohexylamino) pyrimidine-5-carboxamide | 364.3 | D |
| 95 | 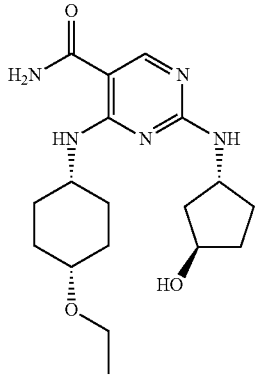 [SMILES: CCO[C@H]1CC[C@@H](Nc2nc(N[C@@H]3CC[C@@H](O)C3)ncc2C(N)=O)CC1] | 4-((1s,4S)-4-ethoxycyclohexylamino)-2-((1R,3R)-3-hydroxycyclopentylamino) pyrimidine-5-carboxamide | 364.3 | D |
| 96 | 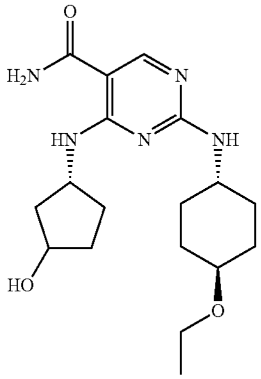 [SMILES: CCO[C@H]1CC[C@H](Nc2ncc(C(N)=O)c(N[C@@H]3CCC(O)C3)n2)CC1] | 4-((1r,4R)-4-ethoxycyclohexylamino)-4-((1R,3S)-3-hydroxycyclopentylamino) pyrimidine-5-carboxamide | 364.3 | D |
| 97 | 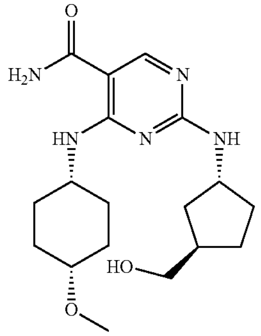 [SMILES: CO[C@H]1CC[C@@H](Nc2nc(N[C@@H]3CC[C@@H](CO)C3)ncc2C(N)=O)CC1] | 2-((1R,3R)-3-(hydroxymethyl) cyclopentylamino)-4-((1s,4S)-4-methoxycyclohexylamino) pyrimidine-5-carboxamide | 364.3 | D |

TABLE 1-continued

| Cmpd. A- | Structure | NAME | MH+ | Act. Level |
|---|---|---|---|---|
| 98 | 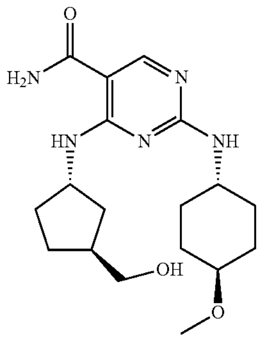 [SMILES: CO[C@H]1CC[C@H](Nc2ncc(C(N)=O)c(N[C@H]3CC[C@H](CO)C3)n2)CC1] | 4-((1S,3S)-3-(hydroxymethyl) cyclopentylamino)-2-((1r,4S)-4-methoxycyclohexylamino) pyrimidine-5-carboxamide | 364.3 | D |
| 99 | 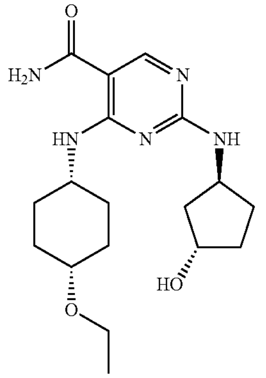 [SMILES: CCO[C@H]1CC[C@@H](Nc2nc(N[C@H]3CC[C@H](O)C3)ncc2C(N)=O)CC1] | 2-((1S,3S)-3-hydroxycyclopentylamino)-4-((1s,4R)-4-(methoxymethyl) cyclohexylamino) pyrimidine-5-carboxamide | 364.3 | D |
| 100 | 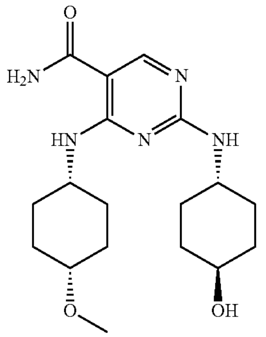 [SMILES: CO[C@H]1CC[C@@H](Nc2nc(N[C@H]3CC[C@H](O)CC3)ncc2C(N)=O)CC1] | 2-((1r,4r)-4-hydroxycyclohexylamino)-4-((1s,4s)-4-methoxycyclohexylamino) pyrimidine-5-carboxamide | 364.3 | D |
| 101 | 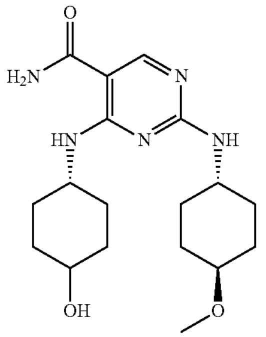 | 4-((1s,4s)-4-hydroxycyclohexylamino)-2-((1r,4r)-4-methoxycyclohexylamino) pyrimidine-5-carboxamide | 364.3 | D |

TABLE 1-continued

| Cmpd. A- | Structure | NAME | MH+ | Act. Level |
|---|---|---|---|---|
| 102 | 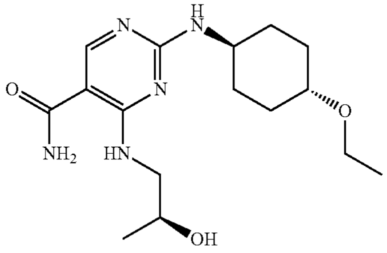 [SMILES: CCO[C@H]1CC[C@H](Nc2ncc(C(N)=O)c(NC[C@H](C)O)n2)CC1] | 2-((1r,4S)-4-ethoxycyclohexylamino)-4-((S)-2-hydroxypropylamino) pyrimidine-5-carboxamide | 338.3 | D |
| 103 | 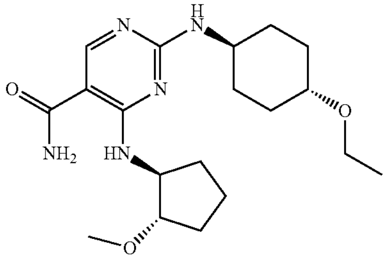 [SMILES: CCO[C@H]1CC[C@H](Nc2ncc(C(N)=O)c(N[C@H]3CCC[C@@H]3OC)n2)CC1] | 2-((1r,4S)-4-ethoxycyclohexylamino)-4-((1S,2S)-2-methoxycyclopentylamino) pyrimidine-5-carboxamide | 378.3 | D |
| 104 | 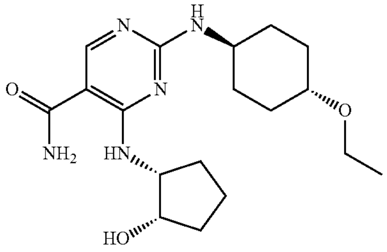 [SMILES: CCO[C@H]1CC[C@H](Nc2ncc(C(N)=O)c(N[C@@H]3CCC[C@@H]3O)n2)CC1] | 2-((1r,4R)-4-ethoxycyclohexylamino)-4-((1R,2S)-2-hydroxycyclopentylamino) pyrimidine-5-carboxamide | 364.3 | D |
| 105 | 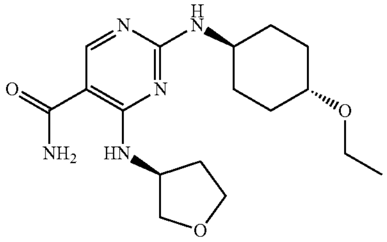 [SMILES: CCO[C@H]1CC[C@H](Nc2ncc(C(N)=O)c(N[C@H]3CCOC3)n2)CC1] | 2-((1r,4S)-4-ethoxycyclohexylamino)-4-((S)-tetrahydrofuran-3-ylamino)pyrimidine-5-carboxamide | 350.3 | D |
| 106 | 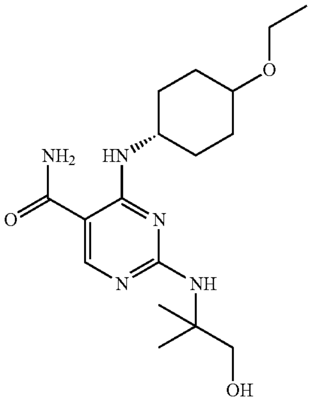 | 4-((1s,4s)-4-ethoxycyclohexylamino)-2-(1-hydroxy-2-methylpropan-2-ylamino)pyrimidine-5-carboxamide | 352.3 | C |

TABLE 1-continued

| Cmpd. A- | Structure | NAME | MH+ | Act. Level |
|---|---|---|---|---|
| 107 | 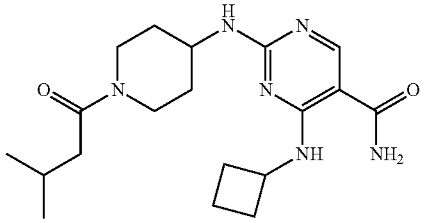 [SMILES: CC(C)CC(=O)N1CCC(Nc2ncc(C(N)=O)c(NC3CCC3)n2)CC1] | 4-(cyclobutylamino)-2-(1-(3-methylbutanoyl)piperidin-4-ylamino)pyrimidine-5-carboxamide | 375.2 | D |
| 108 | 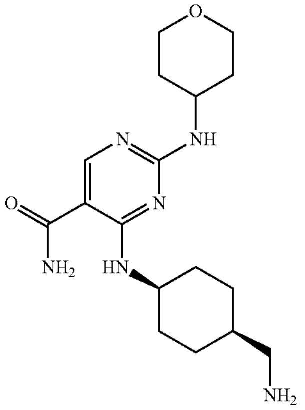 [SMILES: NC[C@H]1CC[C@@H](Nc2nc(NC3CCOCC3)ncc2C(N)=O)CC1] | 4-((1s,4s)-4-(aminomethyl) cyclohexylamino)-2-(tetrahydro-2H-pyran-4-ylamino)pyrimidine-5-carboxamide | 349.3 | D |
| 109 | 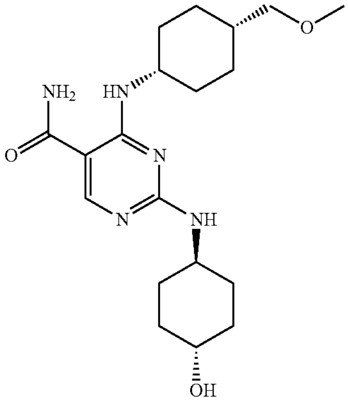 [SMILES: COC[C@H]1CC[C@@H](Nc2nc(N[C@H]3CC[C@H](O)CC3)ncc2C(N)=O)CC1] | 2-((1r,4r)-4-hydroxycyclohexylamino)-4-((1s,4s)-4-(methoxymethyl) cyclohexylamino) pyrimidine-5-carboxamide | 378.1 | D |
| 110 | 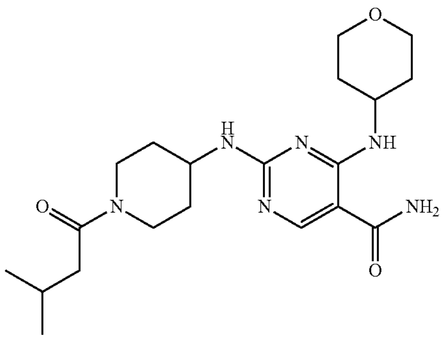 [SMILES: CC(C)CC(=O)N1CCC(Nc2ncc(C(N)=O)c(NC3CCOCC3)n2)CC1] | 2-(1-(3-methylbutanoyl)piperidin-4-ylamino)-4-(tetrahydro-2H-pyran-4-ylamino)pyrimidine-5-carboxamide | 405.2 | C |

TABLE 1-continued

| Cmpd. A- | Structure | NAME | MH+ | Act. Level |
|---|---|---|---|---|
| 111 | 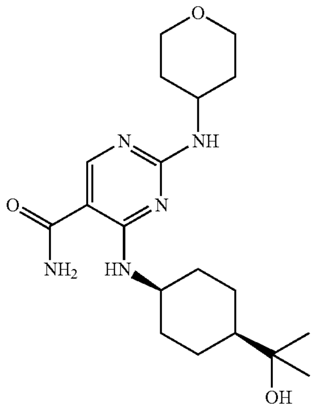 [SMILES: CC(C)(O)[C@H]1CC[C@@H](Nc2nc(NC3CCOCC3)ncc2C(N)=O)CC1] | 4-((1s,4s)-4-(2-hydroxypropan-2-yl)cyclohexylamino)-2-(tetrahydro-2H-pyran-4-ylamino)pyrimidine-5-carboxamide | 378.3 | D |
| 112 | 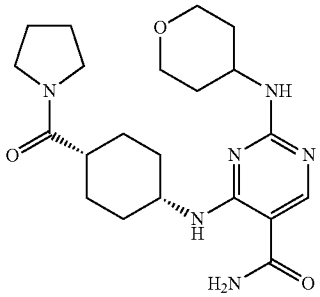 [SMILES: NC(=O)c1cnc(NC2CCOCC2)nc1N[C@H]1CC[C@@H](C(=O)N2CCCC2)CC1] | 4-((1s,4s)-4-(pyrrolidine-1-carbonyl)cyclohexylamino)-2-(tetrahydro-2H-pyran-4-ylamino)pyrimidine-5-carboxamide | 417.3 | B |
| 113 | 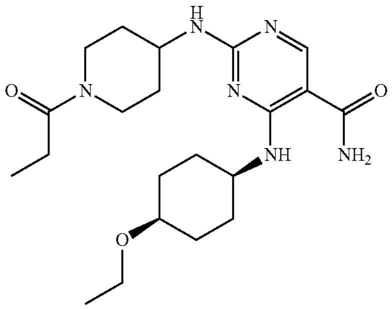 [SMILES: CCO[C@H]1CC[C@@H](Nc2nc(NC3CCN(C(=O)CC)CC3)ncc2C(N)=O)CC1] | 4-((1s,4s)-4-ethoxycyclohexylamino)-2-(1-propionylpiperidin-4-ylamino)pyrimidine-5-carboxamide | 419.4 | D |
| 114 | 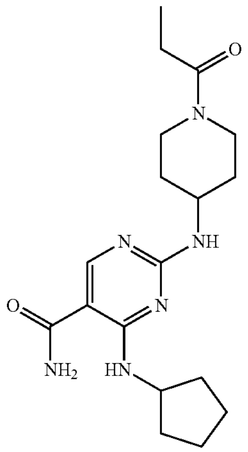 [SMILES: CCC(=O)N1CCC(Nc2ncc(C(N)=O)c(NC3CCCC3)n2)CC1] | 4-(cyclopentylamino)-2-(1-propionylpiperidin-4-ylamino)pyrimidine-5-carboxamide | 361.2 | D |

TABLE 1-continued

| Cmpd. A- | Structure | NAME | MH+ | Act. Level |
|---|---|---|---|---|
| 115 | 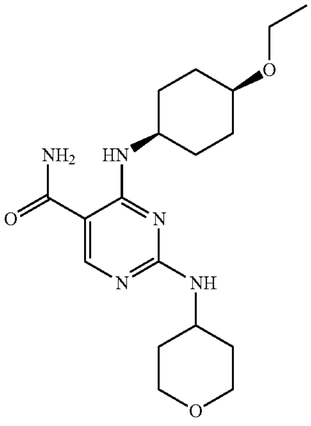 [SMILES: CCO[C@H]1CC[C@@H](Nc2nc(NC3CCOCC3)ncc2C(N)=O)CC1] | 4-((1s,4s)-4-ethoxycyclohexylamino)-2-(tetrahydro-2H-pyran-4-ylamino)pyrimidine-5-carboxamide | 364.3 | D |
| 116 | 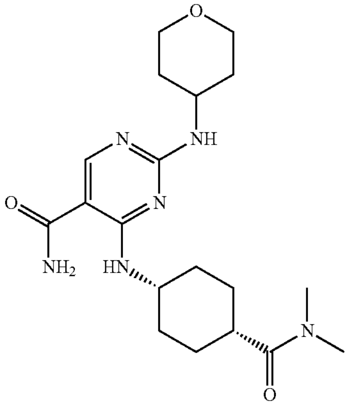 [SMILES: CN(C)C(=O)[C@H]1CC[C@@H](Nc2nc(NC3CCOCC3)ncc2C(N)=O)CC1] | 4-((1s,4s)-4-(dimethylcarbamoyl) cyclohexylamino)-2-(tetrahydro-2H-pyran-4-ylamino)pyrimidine-5-carboxamide | 391.3 | C |
| 117 | 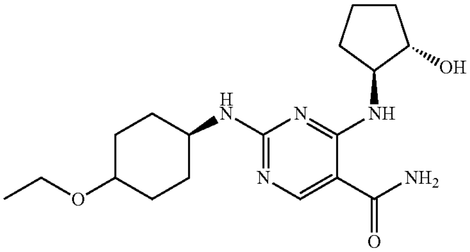 | 2-((1r,4S)-4-ethoxycyclohexylamino)-4-((1S,2S)-2-hydroxycyclopentylamino) pyrimidine-5-carboxamide | 364.3 | D |
| 118 | 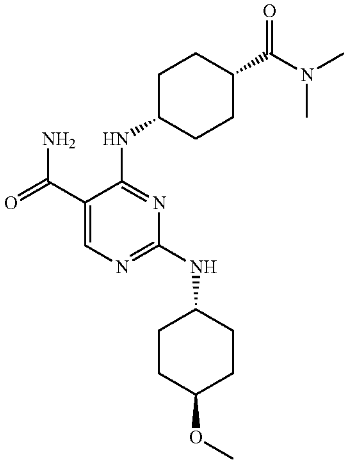 [SMILES: CO[C@H]1CC[C@H](Nc2ncc(C(N)=O)c(N[C@H]3CC[C@@H](C(=O)N(C)C)CC3)n2)CC1] | 4-((1s,4s)-4-(dimethylcarbamoyl) cyclohexylamino)-2-((1r,4r)-4-methoxycyclohexylamino) pyrimidine-5-carboxamide | 419.3 | D |

TABLE 1-continued

| Cmpd. A- | Structure | NAME | MH+ | Act. Level |
|---|---|---|---|---|
| 119 | 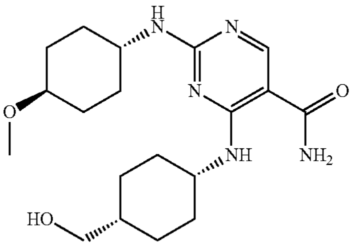 [SMILES: CO[C@H]1CC[C@H](Nc2ncc(C(N)=O)c(N[C@H]3CC[C@@H](CO)CC3)n2)CC1] | 4-((1s,4s)-4-(hydroxymethyl) cyclohexylamino)-2-((1r,4r)-4-methoxycyclohexylamino) pyrimidine-5-carboxamide | 378.3 | D |
| 120 | 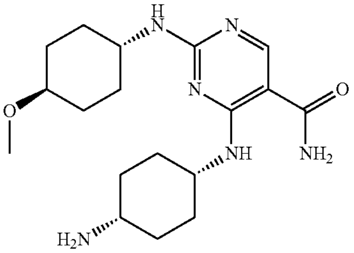 [SMILES: CO[C@H]1CC[C@H](Nc2ncc(C(N)=O)c(N[C@H]3CC[C@@H](N)CC3)n2)CC1] | 4-((1s,4s)-4-aminocyclohexylamino)-2-((1r,4r)-4-methoxycyclohexylamino) pyrimidine-5-carboxamide | 363.3 | D |
| 121 | 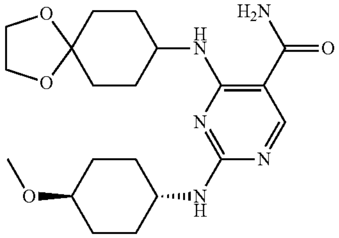 [SMILES: CO[C@H]1CC[C@H](Nc2ncc(C(N)=O)c(NC3CCC4(CC3)OCCO4)n2)CC1] | 4-(1,4-dioxaspiro[4.5]decan-8-ylamino)-2-((1r,4r)-4-methoxycyclohexylamino) pyrimidine-5-carboxamide | 406.3 | D |
| 122 | 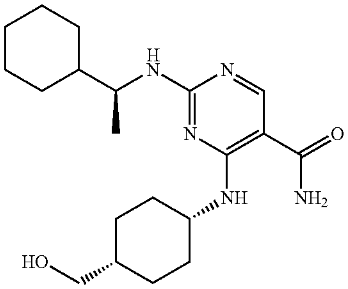 [SMILES: C[C@H](Nc1ncc(C(N)=O)c(N[C@H]2CC[C@@H](CO)CC2)n1)C1CCCCC1] | 2-((S)-1-cyclohexylethylamino)-4-((1s,4R)-4-(hydroxymethyl) cyclohexylamino) pyrimidine-5-carboxamide | 376.3 | D |
| 123 | 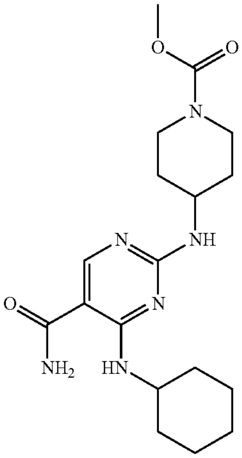 [SMILES: COC(=O)N1CCC(Nc2ncc(C(N)=O)c(NC3CCCCC3)n2)CC1] | methyl 4-(5-carbamoyl-4-(cyclohexylamino) pyrimidin-2-ylamino) piperidine-1-carboxylate | 377.1 | D |

TABLE 1-continued

| Cmpd. A- | Structure | NAME | MH+ | Act. Level |
|---|---|---|---|---|
| 124 | 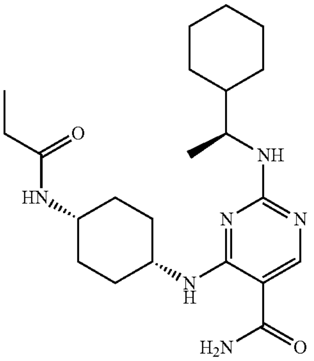 [SMILES: CCC(=O)N[C@H]1CC[C@@H](Nc2nc(N[C@@H](C)C3CCCCC3)ncc2C(N)=O)CC1] | 2-((S)-1-cyclohexylethylamino)-4-((1s,4R)-4-propionamidocyclohexylamino) pyrimidine-5-carboxamide | 417.3 | D |
| 125 | 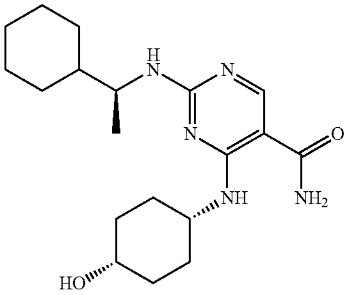 [SMILES: C[C@H](Nc1ncc(C(N)=O)c(N[C@H]2CC[C@@H](O)CC2)n1)C1CCCCC1] | 2-((S)-1-cyclohexylethylamino)-4-((1s,4R)-4-hydroxycyclohexylamino) pyrimidine-5-carboxamide | 362.3 | D |
| 126 | 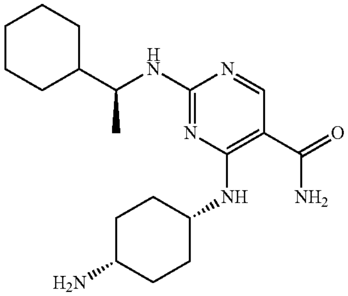 [SMILES: C[C@H](Nc1ncc(C(N)=O)c(N[C@H]2CC[C@@H](N)CC2)n1)C1CCCCC1] | 4-((1s,4R)-4-aminocyclohexylamino)-2-((S)-1-cyclohexylethylamino) pyrimidine-5-carboxamide | 361.3 | D |
| 127 | 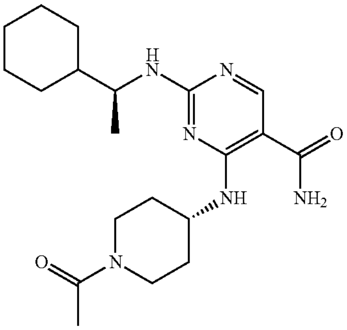 | (S)-4-(1-acetylpiperidin-4-ylamino)-2-(1-cyclohexylethylamino) pyrimidine-5-carboxamide | 389.3 | D |

TABLE 1-continued

| Cmpd. A- | Structure | NAME | MH+ | Act. Level |
|---|---|---|---|---|
| 128 | 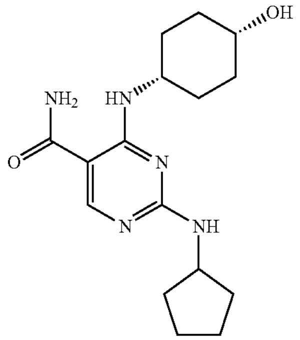 [SMILES: NC(=O)c1cnc(NC2CCCC2)nc1N[C@H]1CC[C@@H](O)CC1] | 2-(cyclopentylamino)-4-((1s,4s)-4-hydroxycyclohexylamino) pyrimidine-5-carboxamide | 320.1 | D |
| 129 | 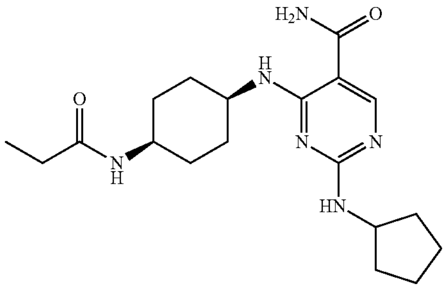 [SMILES: CCC(=O)N[C@H]1CC[C@@H](Nc2nc(NC3CCCC3)ncc2C(N)=O)CC1] | 2-(cyclopentylamino)-4-((1s,4s)-4-propionamidocyclohexylamino) pyrimidine-5-carboxamide | 375.3 | C |
| 130 | 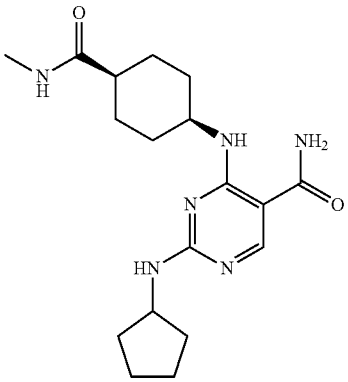 [SMILES: CNC(=O)[C@H]1CC[C@@H](Nc2nc(NC3CCCC3)ncc2C(N)=O)CC1] | 2-(cyclopentylamino)-4-((1s,4s)-4-(methylcarbamoyl) cyclohexylamino) pyrimidine-5-carboxamide | 361.3 | A |
| 131 | 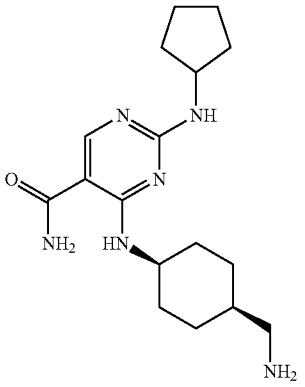 [SMILES: NC[C@H]1CC[C@@H](Nc2nc(NC3CCCC3)ncc2C(N)=O)CC1] | 4-((1s,4s)-4-(aminomethyl) cyclohexylamino)-2-(cyclopentylamino) pyrimidine-5-carboxamide | 333.3 | D |

TABLE 1-continued
| Cmpd. A- | Structure | NAME | MH+ | Act. Level |
|---|---|---|---|---|
| 132 | 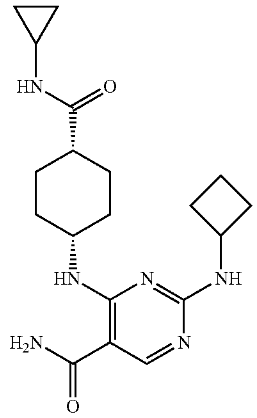 [SMILES: NC(=O)c1cnc(NC2CCC2)nc1N[C@H]1CC[C@@H](C(=O)NC2CC2)CC1] | 2-(cyclobutylamino)-4-((1s,4s)-4-(cyclopropylcarbamoyl)cyclohexylamino)pyrimidine-5-carboxamide | 373.2 | A |
| 133 | 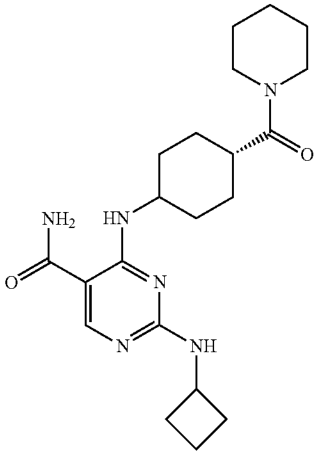 | 2-(cyclobutylamino)-4-((1s,4s)-4-(piperidine-1-carbonyl)cyclohexylamino)pyrimidine-5-carboxamide | 401.2 | B |
| 134 | 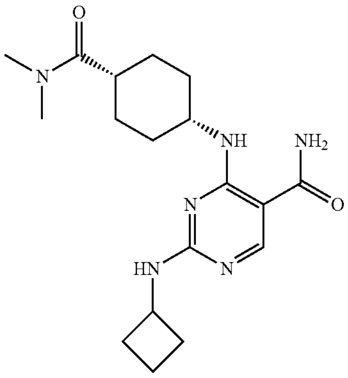 [SMILES: CN(C)C(=O)[C@H]1CC[C@@H](Nc2nc(NC3CCC3)ncc2C(N)=O)CC1] | 2-(cyclobutylamino)-4-((1s,4s)-4-(dimethylcarbamoyl)cyclohexylamino)pyrimidine-5-carboxamide | 361.5 | A |

TABLE 1-continued

| Cmpd. A- | Structure | NAME | MH+ | Act. Level |
|---|---|---|---|---|
| 135 | 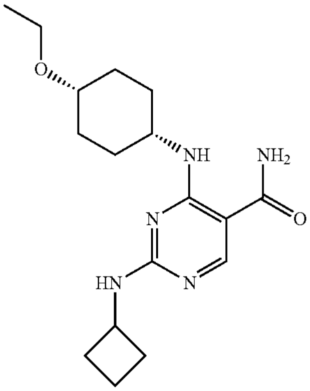 [SMILES: CCO[C@H]1CC[C@@H](Nc2nc(NC3CCC3)ncc2C(N)=O)CC1] | 2-(cyclobutylamino)-4-((1s,4s)-4-ethoxycyclohexylamino) pyrimidine-5-carboxamide | 334.3 | C |
| 136 | 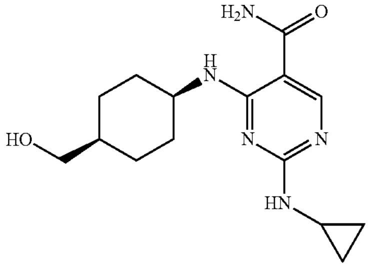 [SMILES: NC(=O)c1cnc(NC2CC2)nc1N[C@H]1CC[C@@H](CO)CC1] | 2-(cyclopropylamino)-4-((1s,4s)-4-(hydroxymethyl) cyclohexylamino) pyrimidine-5-carboxamide | 306.1 | C |
| 137 | 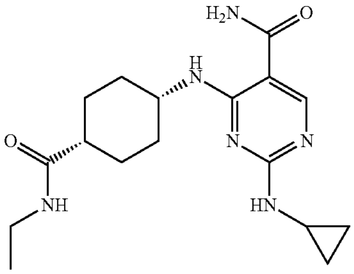 [SMILES: CCNC(=O)[C@H]1CC[C@@H](Nc2nc(NC3CC3)ncc2C(N)=O)CC1] | 2-(cyclopropylamino)-4-((1s,4s)-4-(ethylcarbamoyl) cyclohexylamino) pyrimidine-5-carboxamide | 347.2 | A |
| 138 | 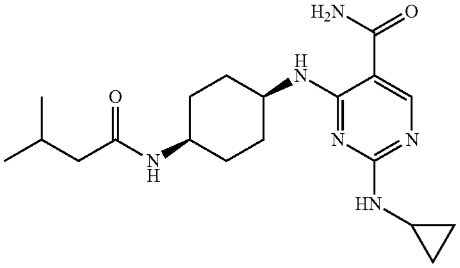 [SMILES: CC(C)CC(=O)N[C@H]1CC[C@@H](Nc2nc(NC3CC3)ncc2C(N)=O)CC1] | 2-(cyclopropylamino)-4-((1s,4s)-4-(3-methylbutanamido) cyclohexylamino) pyrimidine-5-carboxamide | 375.3 | B |
| 139 | 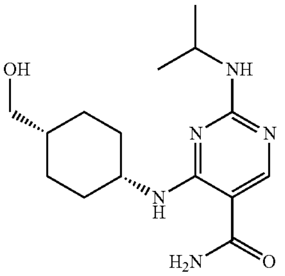 [SMILES: CC(C)Nc1ncc(C(N)=O)c(N[C@H]2CC[C@@H](CO)CC2)n1] | 4-((1s,4s)-4-(hydroxymethyl) cyclohexylamino)-2-(isopropylamino) pyrimidine-5-carboxamide | 308.3 | C |

TABLE 1-continued

| Cmpd. A- | Structure | NAME | MH+ | Act. Level |
|---|---|---|---|---|
| 140 | 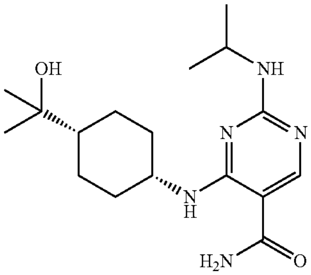 [SMILES: CC(C)Nc1ncc(C(N)=O)c(N[C@H]2CC[C@@H](C(C)(C)O)CC2)n1] | 4-((1s,4s)-4-(2-hydroxypropan-2-yl)cyclohexylamino)-2-(isopropylamino) pyrimidine-5-carboxamide | 336.3 | C |
| 141 | 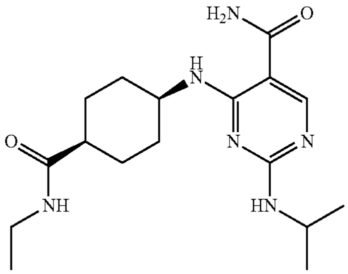 [SMILES: CCNC(=O)[C@H]1CC[C@@H](Nc2nc(NC(C)C)ncc2C(N)=O)CC1] | 4-((1s,4s)-4-(ethylcarbamoyl) cyclohexylamino)-2-(isopropylamino) pyrimidine-5-carboxamide | 349.3 | A |
| 142 | 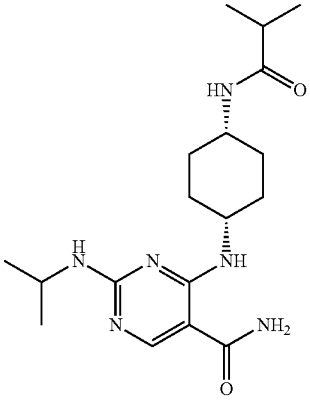 [SMILES: CC(C)Nc1ncc(C(N)=O)c(N[C@H]2CC[C@@H](NC(=O)C(C)C)CC2)n1] | 4-((1s,4s)-4-isobutyramidocyclohexylamino)-2-(isopropylamino) pyrimidine-5-carboxamide | 363.3 | C |
| 143 | 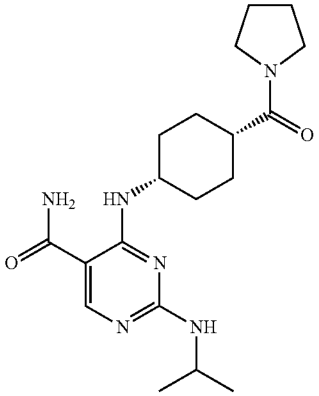 [SMILES: CC(C)Nc1ncc(C(N)=O)c(N[C@H]2CC[C@@H](C(=O)N3CCCC3)CC2)n1] | 2-(isopropylamino)-4-((1s,4s)-4-(pyrrolidine-1-carbonyl)cyclohexylamino) pyrimidine-5-carboxamide | 375.1 | B |

TABLE 1-continued

| Cmpd. A- | Structure | NAME | MH+ | Act. Level |
|---|---|---|---|---|
| 144 | 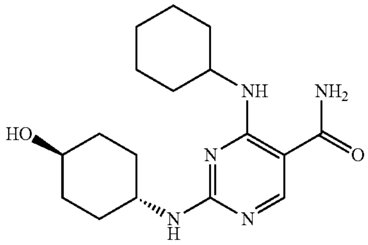 [SMILES: NC(=O)c1cnc(N[C@H]2CC[C@H](O)CC2)nc1NC1CCCCC1] | 4-(cyclohexylamino)-2-((1r,4r)-4-hydroxycyclohexylamino) pyrimidine-5-carboxamide | 334.2 | D |
| 145 | 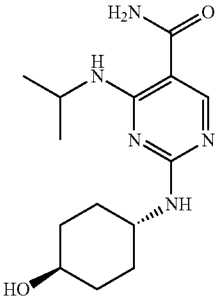 [SMILES: CC(C)Nc1nc(N[C@H]2CC[C@H](O)CC2)ncc1C(N)=O] | 2-((1r,4r)-4-hydroxycyclohexylamino)-4-(isopropylamino) pyrimidine-5-carboxamide | 294.2 | D |
| 146 | 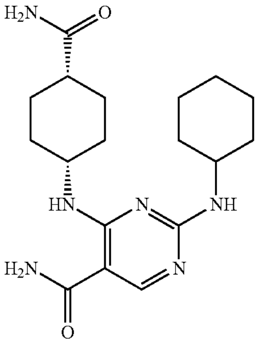 [SMILES: NC(=O)c1cnc(NC2CCCCC2)nc1N[C@H]1CC[C@@H](C(N)=O)CC1] | 4-((1s,4s)-4-carbamoylcyclohexylamino)-2-(cyclohexylamino) pyrimidine-5-carboxamide | 361.2 | D |
| 147 | 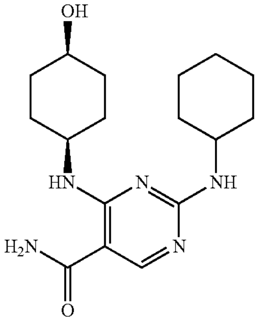 [SMILES: NC(=O)c1cnc(NC2CCCCC2)nc1N[C@H]1CC[C@@H](O)CC1] | 2-(cyclohexylamino)-4-((1s,4s)-4-hydroxycyclohexylamino) pyrimidine-5-carboxamide | 334.2 | D |
| 148 | 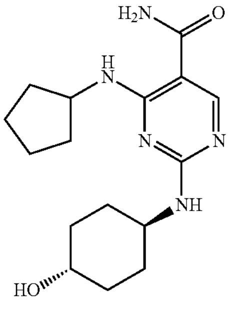 [SMILES: NC(=O)c1cnc(N[C@H]2CC[C@H](O)CC2)nc1NC1CCCC1] | 4-(cyclopentylamino)-2-((1r,4r)-4-hydroxycyclohexylamino) pyrimidine-5-carboxamide | 320.2 | D |

TABLE 1-continued
| Cmpd. A- | Structure | NAME | MH+ | Act. Level |
|---|---|---|---|---|
| 149 | 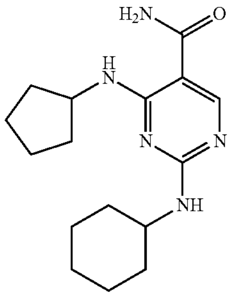 [SMILES: NC(=O)c1cnc(NC2CCCCC2)nc1NC1CCCC1] | 2-(cyclohexylamino)-4-(cyclopentylamino) pyrimidine-5-carboxamide | 304.3 | D |
| 150 | 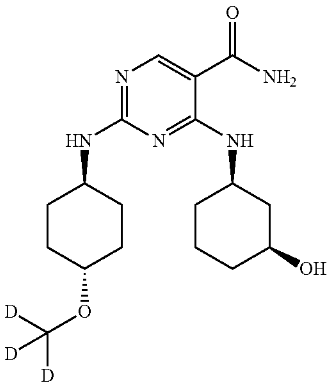 [SMILES: [2H]C([2H])([2H])O[C@H]1CC[C@H](Nc2ncc(C(N)=O)c(N[C@@H]3CCC[C@H](O)C3)n2)CC1] | A name could not be generated for this structure | 367.3 | D |
| 151 | 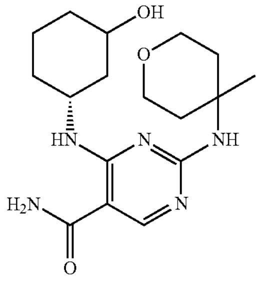 [SMILES: CC1(Nc2ncc(C(N)=O)c(N[C@@H]3CCCC(O)C3)n2)CCOCC1] | 4-((1R,3S)-3-hydroxycyclohexylamino)-2-(4-methyltetrahydro-2H-pyran-4-ylamino)pyrimidine-5-carboxamide | 350.1 | D |
| 152 | 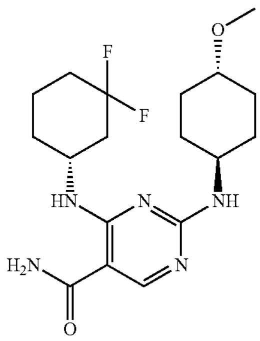 [SMILES: CO[C@H]1CC[C@H](Nc2ncc(C(N)=O)c(N[C@@H]3CCCC(F)(F)C3)n2)CC1] | 4-((R)-3,3-difluorocyclohexylamino)-2-((1r,4R)-4-methoxycyclohexylamino) pyrimidine-5-carboxamide | 384.2 | D |

TABLE 1-continued

| Cmpd. A- | Structure | NAME | MH+ | Act. Level |
|---|---|---|---|---|
| 153 | 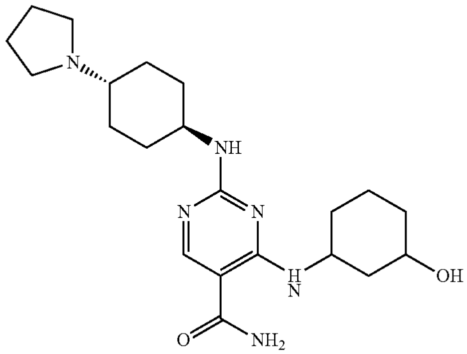 [SMILES: NC(=O)c1cnc(N[C@H]2CC[C@H](N3CCCC3)CC2)nc1NC1CCCC(O)C1] | 4-((1R,3S)-3-hydroxycyclohexylamino)-2-((1r,4R)-4-(pyrrolidin-1-yl)cyclohexylamino) pyrimidine-5-carboxamide | 403.3 | D |
| 154 | 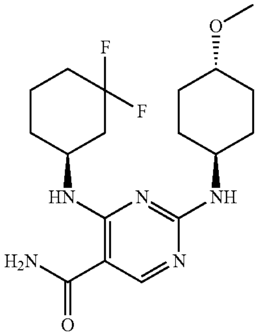 [SMILES: CO[C@H]1CC[C@H](Nc2ncc(C(N)=O)c(N[C@H]3CCCC(F)(F)C3)n2)CC1] | 4-((S)-3,3-difluorocyclohexylamino)-2-((1r,4S)-4-methoxycyclohexylamino) pyrimidine-5-carboxamide | 384.2 | D |
| 155 | 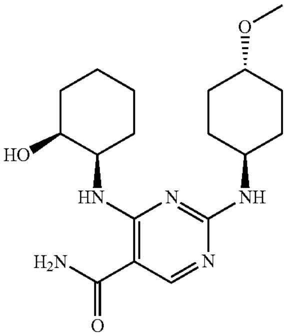 [SMILES: CO[C@H]1CC[C@H](Nc2ncc(C(N)=O)c(N[C@@H]3CCCC[C@@H]3O)n2)CC1] | 4-((1R,2S)-2-hydroxycyclohexylamino)-2-((1r,4R)-4-methoxycyclohexylamino) pyrimidine-5-carboxamide | 364.2 | D |
| 156 | 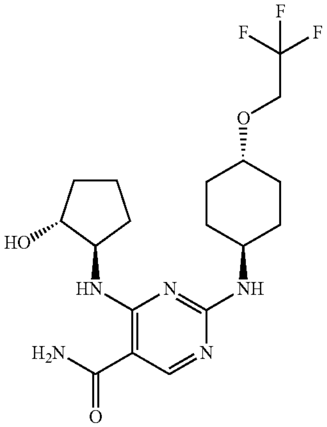 [SMILES: NC(=O)c1cnc(N[C@H]2CC[C@H](OCC(F)(F)F)CC2)nc1N[C@@H]1CCC[C@H]1O] | 4-((1R,2R)-2-hydroxycyclopentylamino)-2-((1r,4R)-4-(2,2,2-trifluoroethoxy) cyclohexylamino) pyrimidine-5-carboxamid | 418.2 | D |

TABLE 1-continued

| Cmpd. A- | Structure | NAME | MH+ | Act. Level |
|---|---|---|---|---|
| 157 | 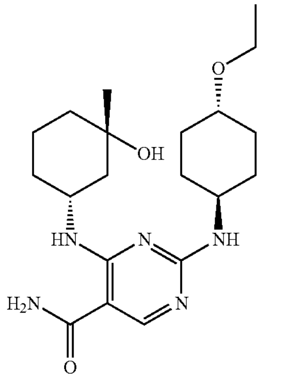 [SMILES: CCO[C@H]1CC[C@H](Nc2ncc(C(N)=O)c(N[C@@H]3CCC[C@](C)(O)C3)n2)CC1] | 2-((1r,4R)-4-ethoxycyclohexylamino)-4-((1R,3S)-3-hydroxy-3-methylcyclohexylamino) pyrimidine-5-carboxamide | 392.3 | D |
| 158 | 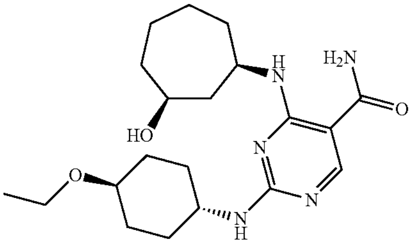 [SMILES: CCO[C@H]1CC[C@H](Nc2ncc(C(N)=O)c(N[C@@H]3CCCC[C@H](O)C3)n2)CC1] | 2-((1r,4R)-4-ethoxycyclohexylamino)-4-((1R,3S)-3-hydroxycycloheptylamino) pyrimidine-5-carboxamide | 392.5 | D |
| 159 | 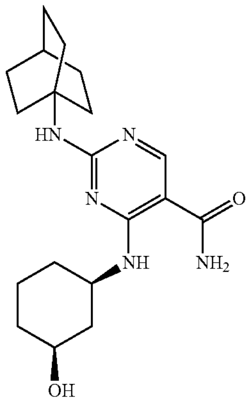 [SMILES: NC(=O)c1cnc(NC23CCC(CC2)CC3)nc1N[C@@H]1CCC[C@H](O)C1] | 2-(bicyclo[2.2.2]octan-1-ylamino)-4-((1R,3S)-3-hydroxycyclohexylamino) pyrimidine-5-carboxamide | 360.1 | D |
| 160 | 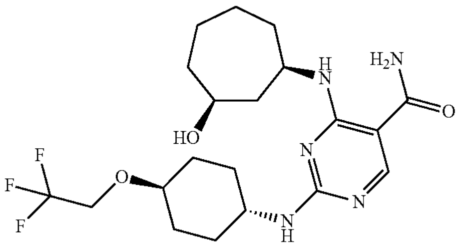 [SMILES: NC(=O)c1cnc(N[C@H]2CC[C@H](OCC(F)(F)F)CC2)nc1N[C@@H]1CCCC[C@H](O)C1] | 4-((1R,3S)-3-hydroxycycloheptylamino)-2-((1r,4R)-4-(2,2,2-trifluoroethoxy) cyclohexylamino) pyrimidine-5-carboxamid | 446.6 | D |

TABLE 1-continued

| Cmpd. A- | Structure | NAME | MH+ | Act. Level |
|---|---|---|---|---|
| 161 | 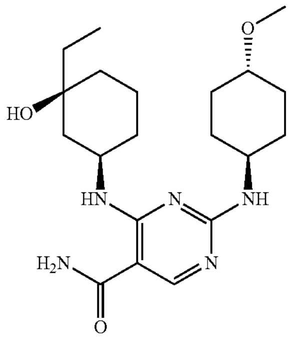 [SMILES: CC[C@]1(O)CCC[C@@H](Nc2nc(N[C@H]3CC[C@H](OC)CC3)ncc2C(N)=O)C1] | 4-((1R,3S)-3-ethyl-3-hydroxycyclohexylamino)-2-((1r,4R)-4-methoxycyclohexylamino) pyrimidine-5-carboxamide | 392.6 | D |
| 162 | 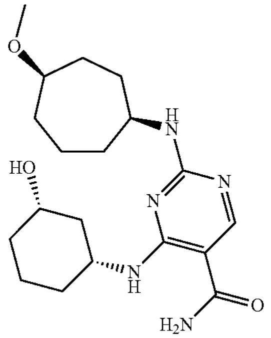 [SMILES: CO[C@@H]1CCC[C@H](Nc2ncc(C(N)=O)c(N[C@@H]3CCC[C@H](O)C3)n2)CC1] | 4-((1R,3S)-3-hydroxycyclohexylamino)-2-((1S,4R)-4-methoxycycloheptylamino) pyrimidine-5-carboxamide | 378.3 | D |
| 163 | 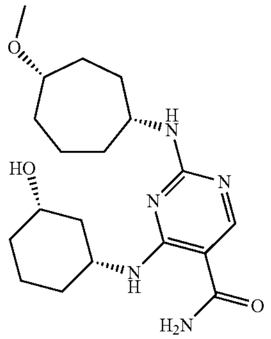 [SMILES: CO[C@H]1CCC[C@@H](Nc2ncc(C(N)=O)c(N[C@@H]3CCC[C@H](O)C3)n2)CC1] | 4-((1R,3S)-3-hydroxycyclohexylamino)-2-((1R,4S)-4-methoxycycloheptylamino) pyrimidine-5-carboxamide | 378.3 | D |
| 164 | 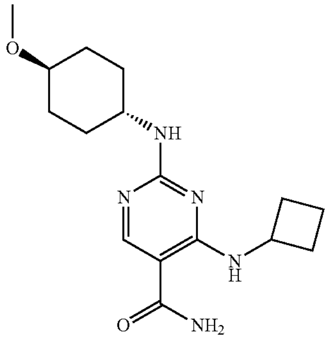 [SMILES: CO[C@H]1CC[C@H](Nc2ncc(C(N)=O)c(NC3CCC3)n2)CC1] | 4-(cyclobutylamino)-2-((1r,4r)-4-methoxycyclohexylamino) pyrimidine-5-carboxamide | 319.9 | D |

TABLE 1-continued

| Cmpd. A- | Structure | NAME | MH+ | Act. Level |
|---|---|---|---|---|
| 165 | 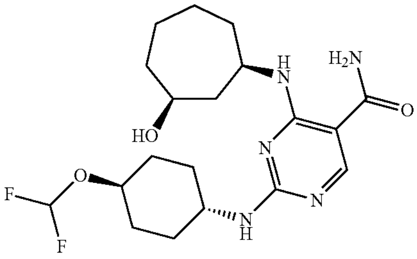 [SMILES: NC(=O)c1cnc(N[C@H]2CC[C@H](OC(F)F)CC2)nc1N[C@@H]1CCCC[C@H](O)C1] | 2-((1r,4R)-4-(difluoromethoxy) cyclohexylamino)-4-((1R,3S)-3-hydroxycycloheptylamino) pyrimidine-5-carboxamide | 414.2 | D |
| 166 | 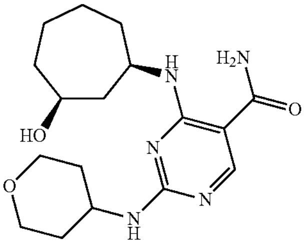 [SMILES: NC(=O)c1cnc(NC2CCOCC2)nc1N[C@@H]1CCCC[C@H](O)C1] | 4-((1R,3S)-3-hydroxycycloheptylamino)-2-(tetrahydro-2H-pyran-4-ylamino)pyrimidine-5-carboxamide | 350.3 | D |
| 167 | 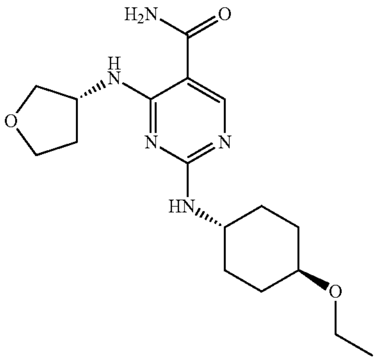 [SMILES: CCO[C@H]1CC[C@H](Nc2ncc(C(N)=O)c(N[C@@H]3CCOC3)n2)CC1] | 2-((1r,4R)-4-ethoxycyclohexylamino)-4-((R)-tetrahydrofuran-3-ylamino)pyrimidine-5-carboxamide | 350 | D |
| 168 | 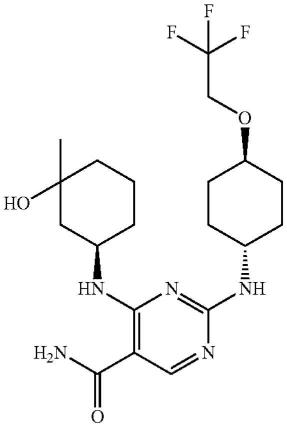 [SMILES: CC1(O)CCC[C@@H](Nc2nc(N[C@H]3CC[C@H](OCC(F)(F)F)CC3)ncc2C(N)=O)C1] | 4-((1R,3S)-3-hydroxy-3-methylcyclohexylamino)-2-((1r,4R)-4-(2,2,2-trifluoroethoxy) cyclohexylamino) pyrimidine-5-carboxamid | 446.2 | D |

TABLE 1-continued

| Cmpd. A- | Structure | NAME | MH+ | Act. Level |
|---|---|---|---|---|
| 169 | 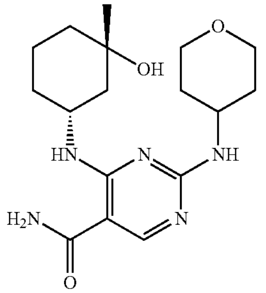 [SMILES: C[C@]1(O)CCC[C@@H](Nc2nc(NC3CCOCC3)ncc2C(N)=O)C1] | 4-((1R,3S)-3-hydroxy-3-methylcyclohexylamino)-2-(tetrahydro-2H-pyran-4-ylamino)pyrimidine-5-carboxamide | 349 8 | D |
| 170 | 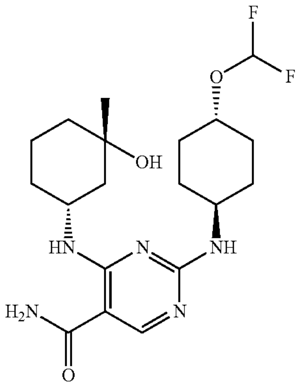 [SMILES: C[C@]1(O)CCC[C@@H](Nc2nc(N[C@H]3CC[C@H](OC(F)F)CC3)ncc2C(N)=O)C1] | 2-((1r,4R)-4-(difluoromethoxy) cyclohexylamino)-4-((1R,3S)-3-hydroxy-3-methylcyclohexylamino) pyrimidine-5-carboxainide | 413.7 | D |
| 171 | 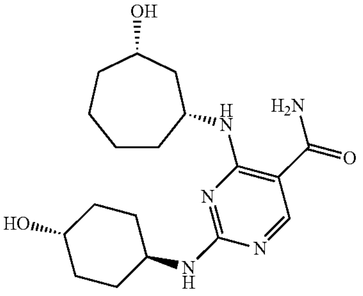 [SMILES: NC(=O)c1cnc(N[C@H]2CC[C@H](O)CC2)nc1N[C@@H]1CCCC[C@H](O)C1] | 4-((1R,3S)-3-hydroxycycloheptylamino)-2-((1r,4R)-4-hydroxycyclohexylamino) pyrimidine-5-carboxamide | 364 | D |
| 172 | 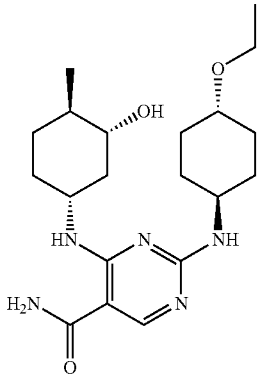 [SMILES: CCO[C@H]1CC[C@H](Nc2ncc(C(N)=O)c(N[C@@H]3CC[C@@H](C)[C@H](O)C3)n2)CC1] | 2-((1r,4R)-4-ethoxycyclohexylamino)-4-((1R,3R,4R)-3-hydroxy-4-methylcyclohexylamino) pyrimidine-5-carboxamide | 391.8 | D |

TABLE 1-continued

| Cmpd. A- | Structure | NAME | MH+ | Act. Level |
|---|---|---|---|---|
| 173 | 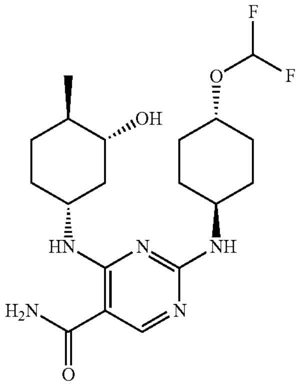 [SMILES: C[C@@H]1CC[C@@H](Nc2nc(N[C@H]3CC[C@H](OC(F)F)CC3)ncc2C(N)=O)C[C@H]1O] | 2-((1r,4R)-4-(difluoromethoxy)cyclohexylamino)-4-((1R,3R,4R)-3-hydroxy-4-methylcyclohexylamino)pyrimidine-5-carboxamide | 413.7 | D |
| 174 | 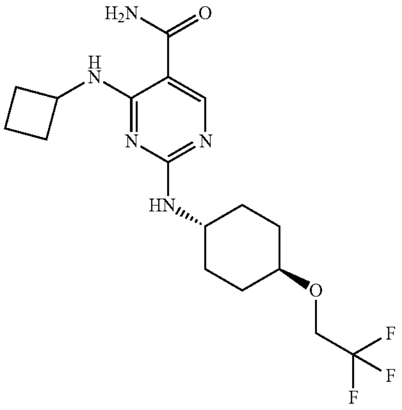 [SMILES: NC(=O)c1cnc(N[C@H]2CC[C@H](OCC(F)(F)F)CC2)nc1NC1CCC1] | 4-(cyclobutylamino)-2-((1r,4r)-4-(2,2,2-trifluoroethoxy)cyclohexylamino)pyrimidine-5-carboxamide | 387.5 | D |
| 175 | 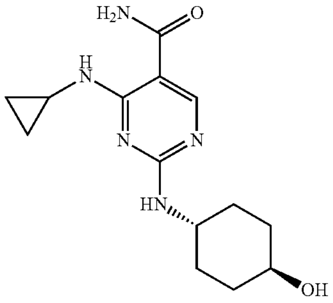 [SMILES: NC(=O)c1cnc(N[C@H]2CC[C@H](O)CC2)nc1NC1CC1] | 4-(cyclopropylamino)-2-((1r,4r)-4-hydroxycyclohexylamino)pyrimidine-5-carboxamide | 292 | D |
| 176 | 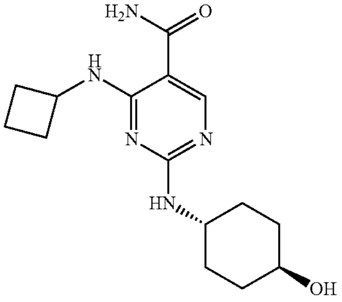 [SMILES: NC(=O)c1cnc(N[C@H]2CC[C@H](O)CC2)nc1NC1CCC1] | 4-(cyclobutylamino)-2-((1r,4r)-4-hydroxycyclohexylamino)pyrimidine-5-carboxamide | 306 | D |

TABLE 1-continued

| Cmpd. A- | Structure | NAME | MH+ | Act. Level |
|---|---|---|---|---|
| 177 | 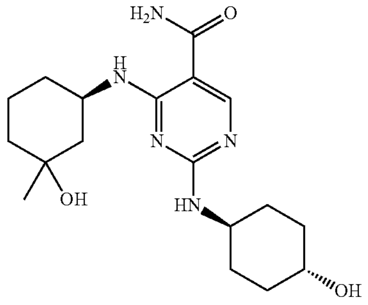 [SMILES: CC1(O)CCC[C@@H](Nc2nc(N[C@H]3CC[C@H](O)CC3)ncc2C(N)=O)C1] | 4-((1R,3S)-3-hydroxy-3-methylcyclohexylamino)-2-((1r,4R)-4-hydroxycyclohexylamino) pyrimidine-5-carboxamide | 364.5 | D |
| 178 | 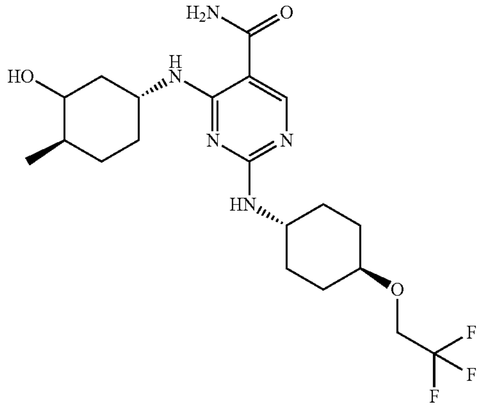 [SMILES: C[C@@H]1CC[C@@H](Nc2nc(N[C@H]3CC[C@H](OCC(F)(F)F)CC3)ncc2C(N)=O)CC1O] | 4-((1R,3R,4R)-3-hydroxy-4-methylcyclohexylamino)-2-((1r,4R)-4-(2,2,2-trifluoroethoxy) cyclohexylamino) pyrimidine-5-carboxamide | 445.9 | D |
| 179 | 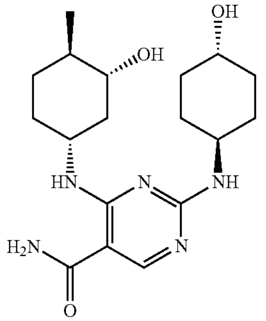 [SMILES: C[C@@H]1CC[C@@H](Nc2nc(N[C@H]3CC[C@H](O)CC3)ncc2C(N)=O)C[C@H]1O] | 4-((1R,3R,4R)-3-hydroxy-4-methylcyclohexylamino)-2-((1r,4R)-4-hydroxycyclohexylamino) pyrimidine-5-carboxamide | 364.7 | D |
| 180 | 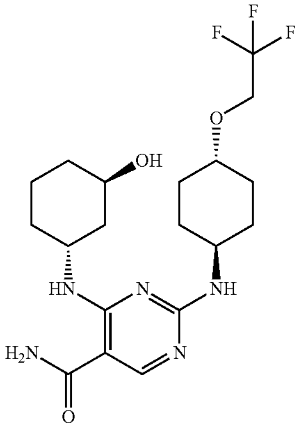 [SMILES: NC(=O)c1cnc(N[C@H]2CC[C@H](OCC(F)(F)F)CC2)nc1N[C@@H]1CCC[C@@H](O)C1] | 4-((1R,3R)-3-hydroxycyclohexylamino)-2-((1r,4R)-4-(2,2,2-trifluoroethoxy) cyclohexylamino) pyrimidine-5-carboxamid | 432.5 | D |

TABLE 1-continued
| Cmpd. A- | Structure | NAME | MH+ | Act. Level |
|---|---|---|---|---|
| 181 | 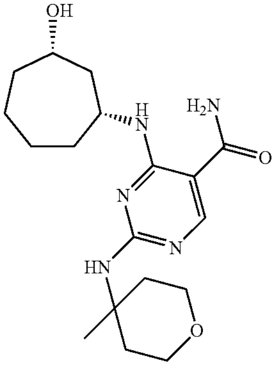 [SMILES: CC1(Nc2ncc(C(N)=O)c(N[C@@H]3CCCC[C@H](O)C3)n2)CCOCC1] | 4-((1R,3S)-3-hydroxycycloheptylamino)-2-(4-methyltetrahydro-2H-pyran-4-ylamino)pyrimidine-5-carboxamide | 364 | D |
| 182 | 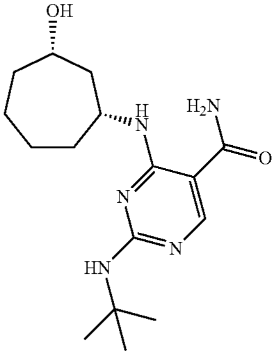 [SMILES: CC(C)(C)Nc1ncc(C(N)=O)c(N[C@@H]2CCCC[C@H](O)C2)n1] | 2-(tert-butylamino)-4-((1R,3S)-3-hydroxycycloheptylamino) pyrimidine-5-carboxamide | 322 | D |
| 183 | 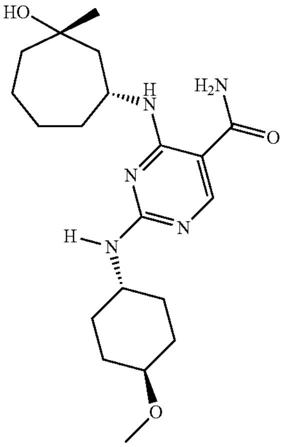 [SMILES: CO[C@H]1CC[C@H](Nc2ncc(C(N)=O)c(N[C@@H]3CCCC[C@](C)(O)C3)n2)CC1] | 4-((1R,3S)-3-hydroxy-3-methylcycloheptylamino)-2-((1r,4R)-4-methoxycyclohexylamino) pyrimidine-5-carboxamide | 392.2 | D |

TABLE 1-continued
| Cmpd. A- | Structure | NAME | MH+ | Act. Level |
|---|---|---|---|---|
| 184 | 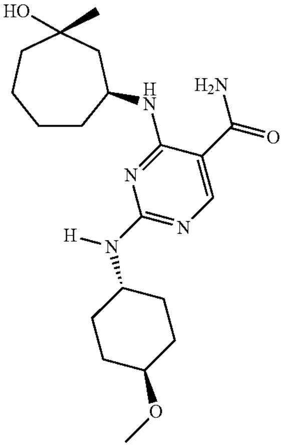 [SMILES: CO[C@H]1CC[C@H](Nc2ncc(C(N)=O)c(N[C@H]3CCCC[C@](C)(O)C3)n2)CC1] | 4-((1S,3S)-3-hydroxy-3-methylcycloheptylamino)-2-((1r,4S)-4-methoxycyclohexylamino) pyrimidine-5-carboxamide | 392.3 | C |
| 185 | 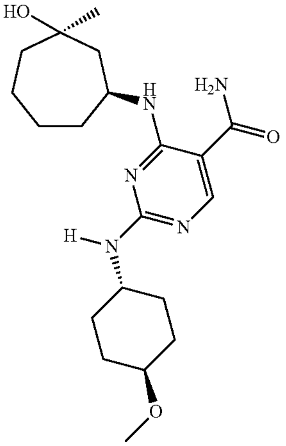 [SMILES: CO[C@H]1CC[C@H](Nc2ncc(C(N)=O)c(N[C@H]3CCCC[C@@](C)(O)C3)n2)CC1] | 4-((1S,3R)-3-hydroxy-3-methylcycloheptylamino)-2-((1r,4S)-4-methoxycyclohexylamino) pyrimidine-5-carboxamide | 392.3 | D |
| 186 | 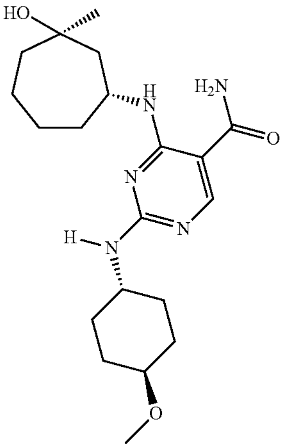 [SMILES: CO[C@H]1CC[C@H](Nc2ncc(C(N)=O)c(N[C@@H]3CCCC[C@@](C)(O)C3)n2)CC1] | 4-((1R,3R)-3-hydroxy-3-methylcycloheptylamino)-2-((1r,4R)-4-methoxycyclohexylamino) pyrimidine-5-carboxamide | 392.2 | D |

TABLE 1-continued

| Cmpd. A- | Structure | NAME | MH+ | Act. Level |
|---|---|---|---|---|
| 187 | 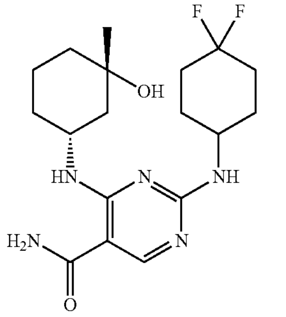 [SMILES: C[C@]1(O)CCC[C@@H](Nc2nc(NC3CCC(F)(F)CC3)ncc2C(N)=O)C1] | 2-(4,4-difluorocyclohexylamino)-4-((1R,3S)-3-hydroxy-3-methylcyclohexylamino) pyrimidine-5-carboxamide | 384.6 | D |
| 188 | 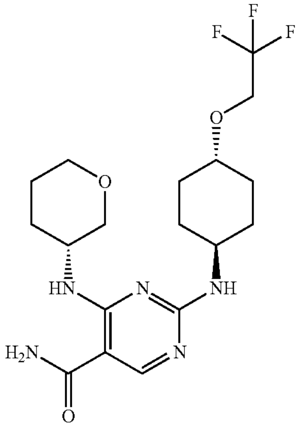 [SMILES: NC(=O)c1cnc(N[C@H]2CC[C@H](OCC(F)(F)F)CC2)nc1N[C@@H]1CCCOC1] | 4-((R)-tetrahydro-2H-pyran-3-ylamino)-2-((1r,4R)-4-(2,2,2-trifluoroethoxy) cyclohexylamino) pyrimidine-5-carboxamide | 418.7 | D |
| 189 | 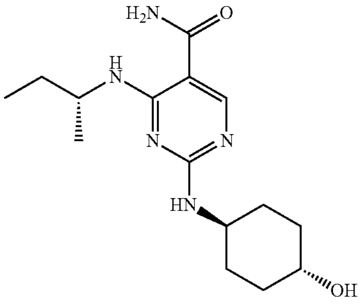 [SMILES: CC[C@@H](C)Nc1nc(N[C@H]2CC[C@H](O)CC2)ncc1C(N)=O] | 4-(sec-butylamino)-2-((1r,4R)-4-hydroxycyclohexylamino) pyrimidine-5-carboxamide | 308.4 | D |
| 190 | 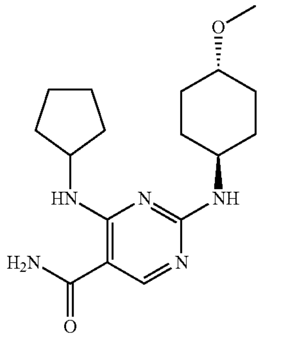 [SMILES: CO[C@H]1CC[C@H](Nc2ncc(C(N)=O)c(NC3CCCC3)n2)CC1] | 4-(cyclopentylamino)-2-((1r,4r)-4-methoxycyclohexylamino) pyrimidine-5-carboxamide | 333.8 | D |

TABLE 1-continued

| Cmpd. A- | Structure | NAME | MH+ | Act. Level |
|---|---|---|---|---|
| 191 | 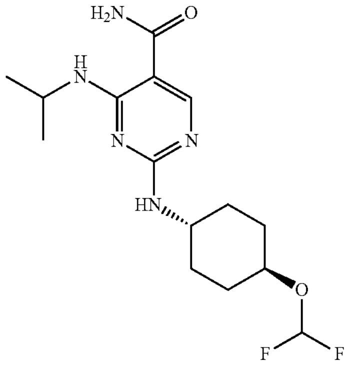 [SMILES: CC(C)Nc1nc(N[C@H]2CC[C@H](OC(F)F)CC2)ncc1C(N)=O] | 2-((1r,4r)-4-(difluoromethoxy)cyclohexylamino)-4-(isopropylamino)pyrimidine-5-carboxamide | 344.2 | D |
| 192 | 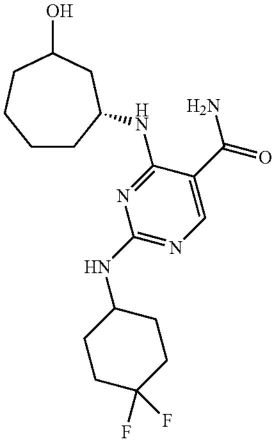 [SMILES: NC(=O)c1cnc(NC2CCC(F)(F)CC2)nc1N[C@@H]1CCCCC(O)C1] | 2-(4,4-difluorocyclohexylamino)-4-((1R,3S)-3-hydroxycycloheptylamino)pyrimidine-5-carboxamide | 384.2 | D |
| 193 | 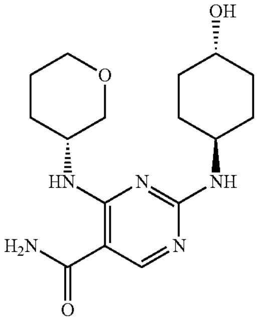 [SMILES: NC(=O)c1cnc(N[C@H]2CC[C@H](O)CC2)nc1N[C@@H]1CCCOC1] | 2-((1r,4R)-4-hydroxycyclohexylamino)-4-((R)-tetrahydro-2H-pyran-3-ylamino)pyrimidine-5-carboxamide | 336.5 | D |
| 194 | 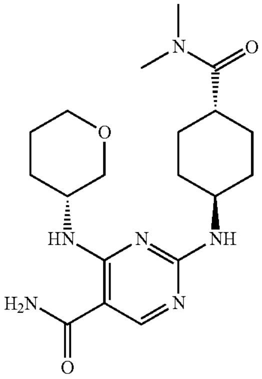 [SMILES: CN(C)C(=O)[C@H]1CC[C@H](Nc2ncc(C(N)=O)c(N[C@@H]3CCCOC3)n2)CC1] | 2-((1r,4R)-4-(dimethylcarbamoyl)cyclohexylamino)-4-((R)-tetrahydro-2H-pyran-3-ylamino)pyrimidine-5-carboxamide | 391.7 | D |

TABLE 1-continued
| Cmpd. A- | Structure | NAME | MH+ | Act. Level |
|---|---|---|---|---|
| 195 | 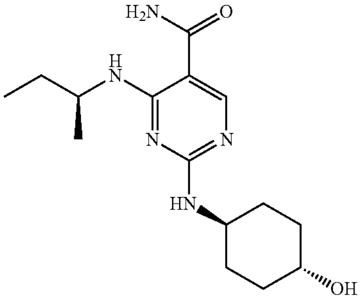 [SMILES: CC[C@H](C)Nc1nc(N[C@H]2CC[C@H](O)CC2)ncc1C(N)=O] | 4-(sec-butylamino)-2-((1r,4S)-4-hydroxycyclohexylamino) pyrimidine-5-carboxamide | 308.3 | D |
| 196 | 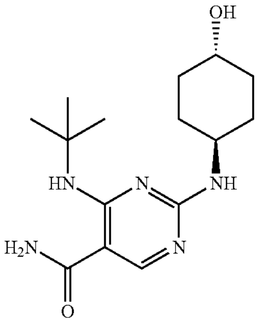 [SMILES: CC(C)(C)Nc1nc(N[C@H]2CC[C@H](O)CC2)ncc1C(N)=O] | 4-(tert-butylamino)-2-((1r,4r)-4-hydroxycyclohexylamino) pyrimidine-5-carboxamide | 307.7 | D |
| 197 | 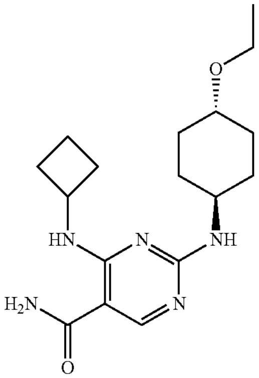 [SMILES: CCO[C@H]1CC[C@H](Nc2ncc(C(N)=O)c(NC3CCC3)n2)CC1] | 4-(cyclobutylamino)-2-((1r,4r)-4-ethoxycyclohexylamino) pyrimidine-5-carboxamide | 333.8 | D |
| 198 | 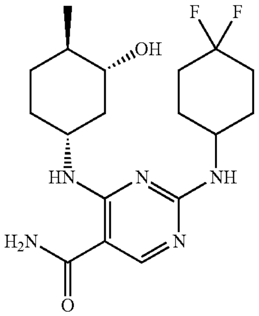 [SMILES: C[C@@H]1CC[C@@H](Nc2nc(NC3CCC(F)(F)CC3)ncc2C(N)=O)C[C@H]1O] | 2-(4,4-difluorocyclohexylamino)-4-((1R,3R,4R)-3-hydroxy-4-methylcyclohexylamino) pyrimidine-5-carboxamide | 384.5 | D |

TABLE 1-continued

| Cmpd. A- | Structure | NAME | MH+ | Act. Level |
|---|---|---|---|---|
| 199 | 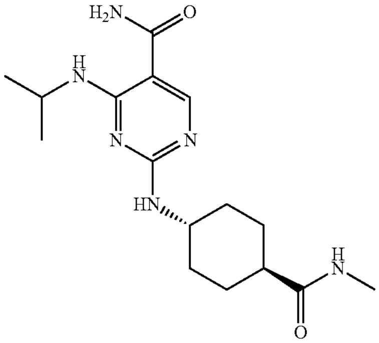 [SMILES: CNC(=O)[C@H]1CC[C@H](Nc2ncc(C(N)=O)c(NC(C)C)n2)CC1] | 4-(isopropylamino)-2-((1r,4r)-4-(methylcarbamoyl)cyclohexylamino)pyrimidine-5-carboxamide | 335.2 | D |
| 200 | 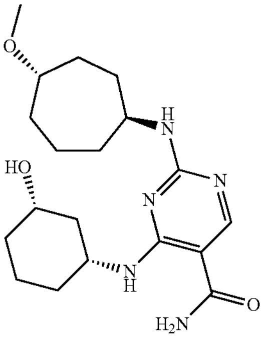 [SMILES: CO[C@H]1CCC[C@H](Nc2ncc(C(N)=O)c(N[C@@H]3CCC[C@H](O)C3)n2)CC1] | 4-((1R,3S)-3-hydroxycyclohexylamino)-2-((1S,4S)-4-methoxycycloheptylamino)pyrimidine-5-carboxamide | 378.5 | D |
| 201 | 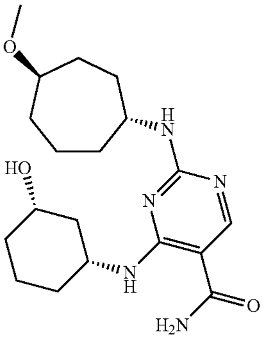 [SMILES: CO[C@@H]1CCC[C@@H](Nc2ncc(C(N)=O)c(N[C@@H]3CCC[C@H](O)C3)n2)CC1] | 4-((1R,3S)-3-hydroxycyclohexylamino)-2-((1R,4R)-4-methoxycycloheptylamino)pyrimidine-5-carboxamide | 378.5 | D |
| 202 | 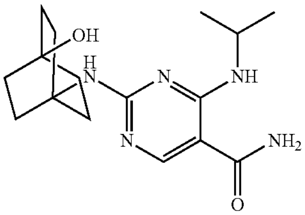 [SMILES: CC(C)Nc1nc(NC23CCC(O)(CC2)CC3)ncc1C(N)=O] | 2-(4-hydroxybicyclo[2.2.2]octan-1-ylamino)-4-(isopropylamino)pyrimidine-5-carboxamide | 320.2 | D |

TABLE 1-continued

| Cmpd. A- | Structure | NAME | MH+ | Act. Level |
|---|---|---|---|---|
| 203 | 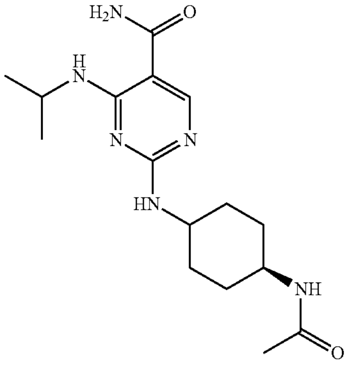 | 2-((1r,4r)-4-acetamidocyclohexylamino)-4-(isopropylamino) pyrimidine-5-carboxamide | 335.2 | D |
| 204 | 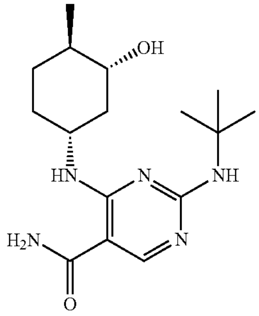 [SMILES: C[C@@H]1CC[C@@H](Nc2nc(NC(C)(C)C)ncc2C(N)=O)C[C@H]1O] | 2-(tert-butylamino)-4-((1R,3R,4R)-3-hydroxy-4-methylcyclohexylamino) pyrimidine-5-carboxamide | 321.7 | D |
| 205 | 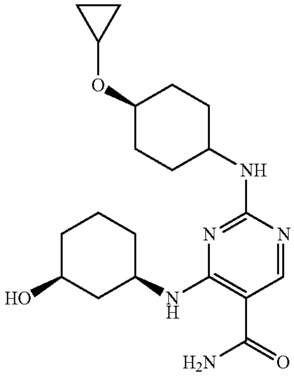 | 2-((1r,4R)-4-cyclopropoxycyclohexylamino)-4-((1R,3S)-3-hydroxycyclohexylamino) pyrimidine-5-carboxamide | 390.1 | D |
| 206 | 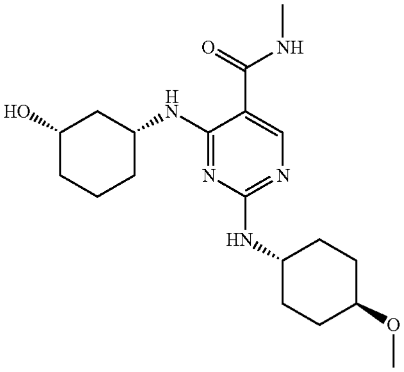 [SMILES: CNC(=O)c1cnc(N[C@H]2CC[C@H](OC)CC2)nc1N[C@@H]1CCC[C@H](O)C1] | 4-((1R,3S)-3-hydroxycyclohexylamino)-2-((1r,4R)-4-methoxycyclohexylamino)-N-methylpyrimidine-5-carboxamide | 378.2 | C |

TABLE 1-continued
| Cmpd. A- | Structure | NAME | MH+ | Act. Level |
|---|---|---|---|---|
| 207 | 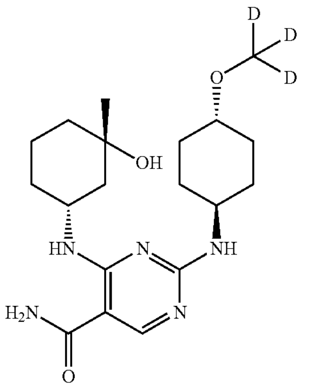 [SMILES: [2H]C([2H])([2H])O[C@H]1CC[C@H](Nc2ncc(C(N)=O)c(N[C@@H]3CCC[C@](C)(O)C3)n2)CC1] | A name could not be generated for this structure | 381.2 | D |
| 208 | 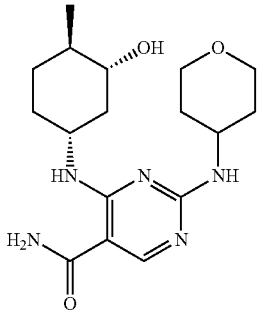 [SMILES: C[C@@H]1CC[C@@H](Nc2nc(NC3CCOCC3)ncc2C(N)=O)C[C@H]1O] | 4-((1R,3R,4R)-3-hydroxy-4-methylcyclohexylamino)-2-(tetrahydro-2H-pyran-4-ylamino)pyrimidine-5-carboxamide | 350.3 | D |
| 209 | 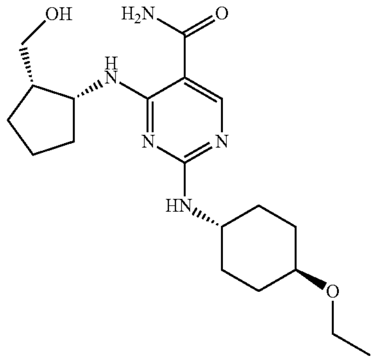 [SMILES: CCO[C@H]1CC[C@H](Nc2ncc(C(N)=O)c(N[C@@H]3CCC[C@@H]3CO)n2)CC1] | 2-((1r,4R)-4-ethoxycyclohexylamino)-4-((1R,2S)-2-(hydroxymethyl) cyclopentylamino) pyrimidine-5-carboxamide | 378.2 | D |
| 210 | 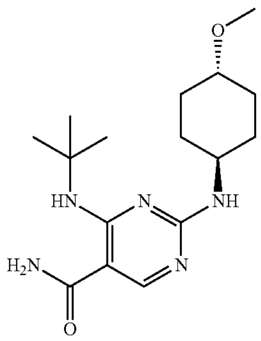 [SMILES: CO[C@H]1CC[C@H](Nc2ncc(C(N)=O)c(NC(C)(C)C)n2)CC1] | 4-(tert-butylamino)-2-((1r,4r)-4-methoxycyclohexylamino) pyrimidine-5-carboxamide | 322.2 | D |

TABLE 1-continued

| Cmpd. A- | Structure | NAME | MH+ | Act. Level |
|---|---|---|---|---|
| 211 | 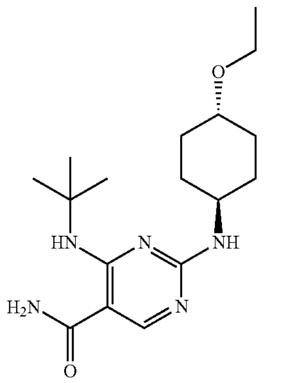 [SMILES: CCO[C@H]1CC[C@H](Nc2ncc(C(N)=O)c(NC(C)(C)C)n2)CC1] | 4-(tert-butylamino)-2-((1r,4r)-4-ethoxycyclohexylamino) pyrimidine-5-carboxamide | 336.4 | D |
| 212 | 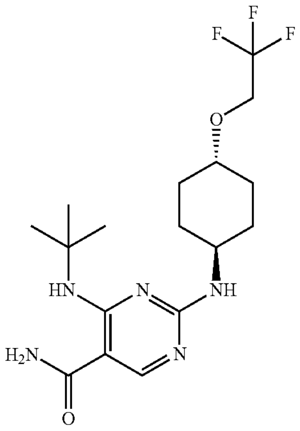 [SMILES: CC(C)(C)Nc1nc(N[C@H]2CC[C@H](OCC(F)(F)F)CC2)ncc1C(N)=O] | 4-(tert-butylamino)-2-((1r,4r)-4-(2,2,2-trifluoroethoxy) cyclohexylamino) pyrimidine-5-carboxamide | 390.3 | D |
| 213 | 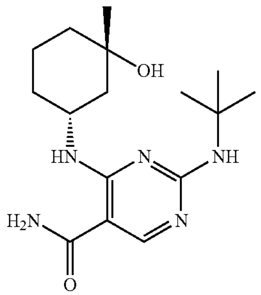 [SMILES: CC(C)(C)Nc1ncc(C(N)=O)c(N[C@@H]2CCC[C@](C)(O)C2)n1] | 2-(tert-butylamino)-4-((1R,3S)-3-hydroxy-3-methylcyclohexylamino) pyrimidine-5-carboxamide | 322.3 | D |
| 214 | 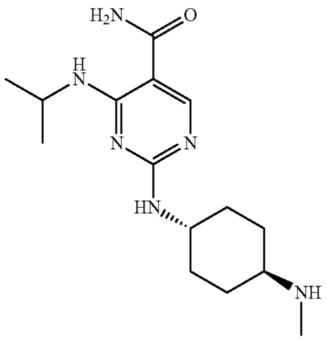 [SMILES: CN[C@H]1CC[C@H](Nc2ncc(C(N)=O)c(NC(C)C)n2)CC1] | 4-(isopropylamino)-2-((1r,4r)-4-(methylamino) cyclohexylamino) pyrimidine-5-carboxamide | 307.2 | D |

TABLE 1-continued

| Cmpd. A- | Structure | NAME | MH+ | Act. Level |
|---|---|---|---|---|
| 215 | 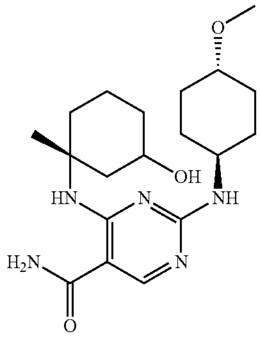 | 4-((1R,3S)-3-hydroxy-1-methylcyclohexylamino)-2-((1r,4R)-4-methoxycyclohexylamino) pyrimidine-5-carboxamide | 378.2 | D |
| 216 | 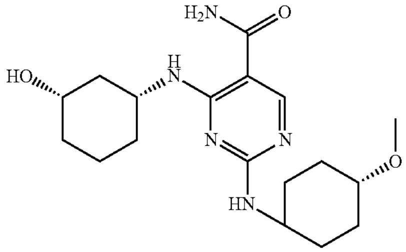 | 4-((1R,3S)-3-hydroxycyclohexylamino)-2-((1r,4R)-4-methoxy-1-methylcyclohexylamino) pyrimidine-5-carboxamide | 378.2 | D |
| 217 | 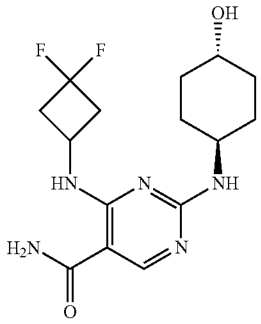 [SMILES: NC(=O)c1cnc(N[C@H]2CC[C@H](O)CC2)nc1NC1CC(F)(F)C1] | 4-(3,3-difluorocyclobutylamino)-2-((1r,4r)-4-hydroxycyclohexylamino) pyrimidine-5-carboxamide | 342 | D |
| 218 | 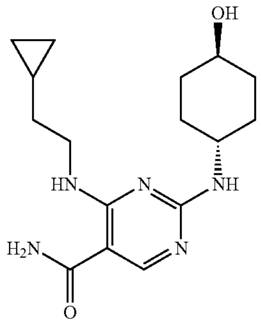 [SMILES: NC(=O)c1cnc(N[C@H]2CC[C@H](O)CC2)nc1NCCC1CC1] | 4-(2-cyclopropylethylamino)-2-((1r,4r)-4-hydroxycyclohexylamino) pyrimidine-5-carboxamide | 320.1 | D |
| 219 | 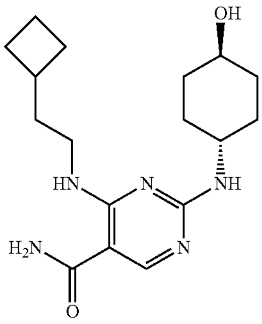 [SMILES: NC(=O)c1cnc(N[C@H]2CC[C@H](O)CC2)nc1NCCC1CCC1] | 4-(2-cyclobutylethylamino)-2-((1r,4r)-4-hydroxycyclohexylamino) pyrimidine-5-carboxamide | 334.1 | D |

TABLE 1-continued
| Cmpd. A- | Structure | NAME | MH+ | Act. Level |
|---|---|---|---|---|
| 220 | 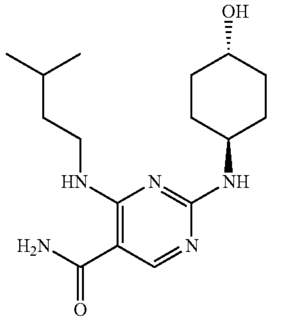 [SMILES: CC(C)CCNc1nc(N[C@H]2CC[C@H](O)CC2)ncc1C(N)=O] | 2-((1r,4r)-4-hydroxycyclohexylamino)-4-(isopentylamino) pyrimidine-5-carboxamide | 322.5 | D |
| 221 | 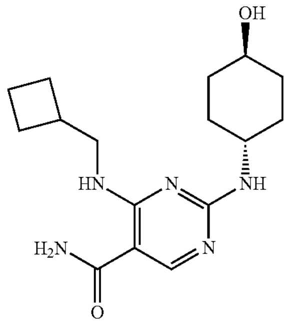 [SMILES: NC(=O)c1cnc(N[C@H]2CC[C@H](O)CC2)nc1NCC1CCC1] | 4-(cyclobutylmethylamino)-2-((1r,4r)-4-hydroxycyclohexylamino) pyrimidine-5-carboxamide | 320.1 | D |
| 222 | 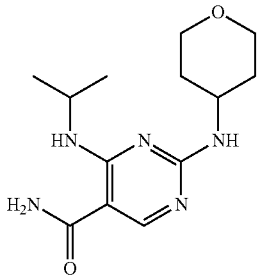 [SMILES: CC(C)Nc1nc(NC2CCOCC2)ncc1C(N)=O] | 4-(isopropylamino)-2-(tetrahydro-2H-pyran-4-ylamino)pyrimidine-5-carboxamide | 280 | C |
| 223 | 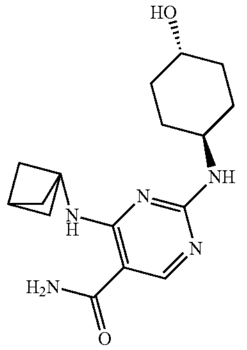 [SMILES: NC(=O)c1cnc(N[C@H]2CC[C@H](O)CC2)nc1NC12CC(C1)C2] | 4-(bicyclo[1.1.1]pentan-1-ylamino)-2-((1r,4r)-4-hydroxycyclohexylamino) pyrimidine-5-carboxamide | 318.6 | D |

TABLE 1-continued
| Cmpd. A- | Structure | NAME | MH+ | Act. Level |
|---|---|---|---|---|
| 224 | 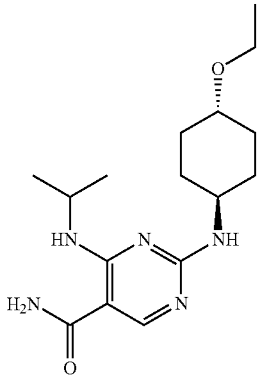 [SMILES: CCO[C@H]1CC[C@H](Nc2ncc(C(N)=O)c(NC(C)C)n2)CC1] | 2-((1r,4r)-4-ethoxycyclohexylamino)-4-(isopropylamino) pyrimidine-5-carboxamide | 322 | D |
| 225 | 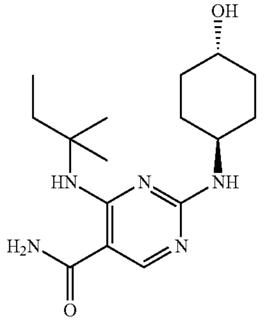 [SMILES: CCC(C)(C)Nc1nc(N[C@H]2CC[C@H](O)CC2)ncc1C(N)=O] | 2-((1r,4r)-4-hydroxycyclohexylamino)-4-(tert-pentylamino)pyrimidine-5-carboxamide | 322 | D |
| 226 | 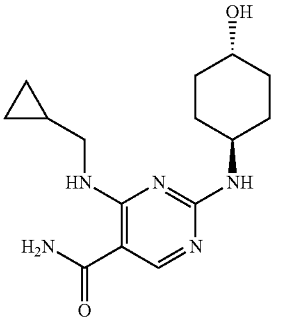 [SMILES: NC(=O)c1cnc(N[C@H]2CC[C@H](O)CC2)nc1NCC1CC1] | 4-(cyclopropylmethylamino)-2-((1r,4r)-4-hydroxycyclohexylamino) pyrimidine-5-carboxamide | 306 | D |
| 227 | 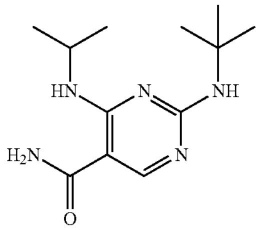 [SMILES: CC(C)Nc1nc(NC(C)(C)C)ncc1C(N)=O] | 2-(tert-butylamino)-4-(isopropylamino) pyrimidine-5-carboxamide | 252.4 | C |

TABLE 1-continued

| Cmpd. A- | Structure | NAME | MH+ | Act. Level |
|---|---|---|---|---|
| 228 | 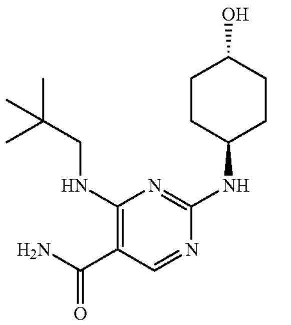 [SMILES: CC(C)(C)CNc1nc(N[C@H]2CC[C@H](O)CC2)ncc1C(N)=O] | 2-((1r,4r)-4-hydroxycyclohexylamino)-4-(neopentylamino) pyrimidine-5-carboxamide | 322.7 | D |
| 229 | 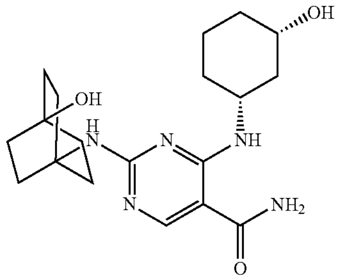 [SMILES: NC(=O)c1cnc(NC23CCC(O)(CC2)CC3)nc1N[C@@H]1CCC[C@H](O)C1] | 2-(4-hydroxybicyclo[2.2.2]octan-1-ylamino)-4-((1R,3S)-3-hydroxycyclohexylamino) pyrimidine-5-carboxamide | 376.2 | D |
| 230 | 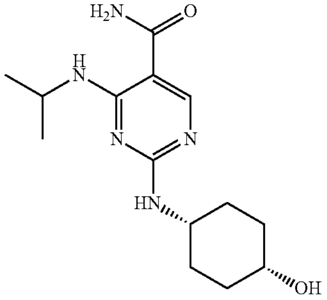 [SMILES: CC(C)Nc1nc(N[C@H]2CC[C@@H](O)CC2)ncc1C(N)=O] | 2-((1s,4s)-4-hydroxycyclohexylamino)-4-(isopropylamino) pyrimidine-5-carboxamide | 294.1 | C |
| 230 | 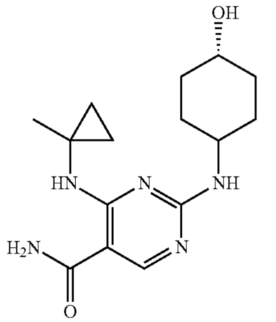 | 2-((1s,4s)-4-hydroxycyclohexylamino)-4-(1-methylcyclopropylamino) pyrimidine-5-carboxamide | 306.4 | D |
| 231 | 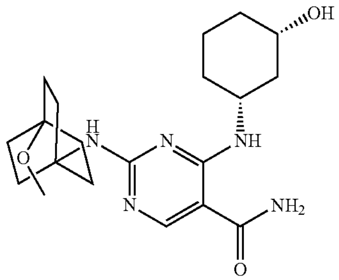 [SMILES: COC12CCC(Nc3ncc(C(N)=O)c(N[C@@H]4CCC[C@H](O)C4)n3)(CC1)CC2] | 4-((1R,3S)-3-hydroxycyclohexylamino)-2-(4-methoxybicyclo[2.2.2]octan-1-ylamino)pyrimidine-5-carboxamide | 390.2 | D |

TABLE 1-continued

| Cmpd. A- | Structure | NAME | MH+ | Act. Level |
|---|---|---|---|---|
| 232 | 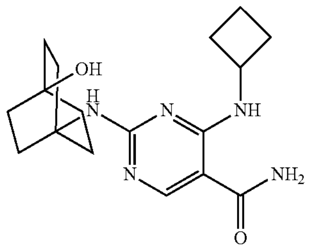 [SMILES: NC(=O)c1cnc(NC23CCC(O)(CC2)CC3)nc1NC1CCC1] | 4-(cyclobutylamino)-2-(4-hydroxybicyclo[2.2.2]octan-1-ylamino)pyrimidine-5-carboxamide | 332.2 | D |
| 233 | 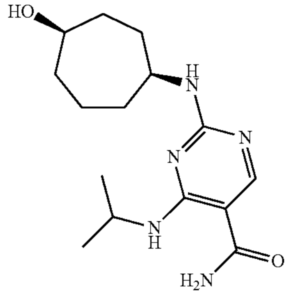 [SMILES: CC(C)Nc1nc(N[C@H]2CCC[C@@H](O)CC2)ncc1C(N)=O] | 2-((1S,4R)-4-hydroxycycloheptylamino)-4-(isopropylamino) pyrimidine-5-carboxamide | 308 | D |
| 234 | 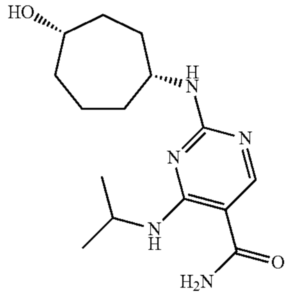 [SMILES: CC(C)Nc1nc(N[C@@H]2CCC[C@H](O)CC2)ncc1C(N)=O] | 2-((1R,4S)-4-hydroxycycloheptylamino)-4-(isopropylamino) pyrimidine-5-carboxamide | 308 | D |
| 235 | 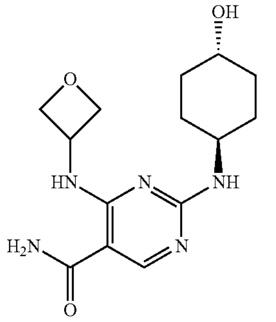 [SMILES: NC(=O)c1cnc(N[C@H]2CC[C@H](O)CC2)nc1NC1COC1] | 2-((1r,4r)-4-hydroxycyclohexylamino)-4-(oxetan-3-ylamino)pyrimidine-5-carboxamide | 308.5 | D |
| 236 | 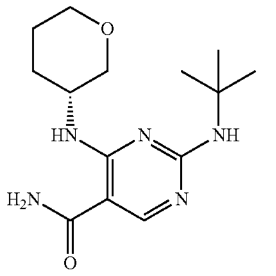 [SMILES: CC(C)(C)Nc1ncc(C(N)=O)c(N[C@@H]2CCCOC2)n1] | (R)-2-(tert-butylamino)-4-(tetrahydro-2H-pyran-3-ylamino)pyrimidine-5-carboxamide | 294 | C |

TABLE 1-continued

| Cmpd. A- | Structure | NAME | MH+ | Act. Level |
|---|---|---|---|---|
| 237 | 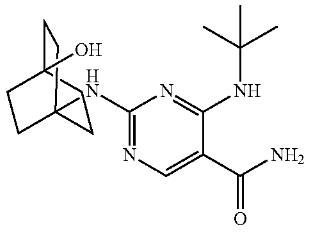 [SMILES: CC(C)(C)Nc1nc(NC23CCC(O)(CC2)CC3)ncc1C(N)=O] | 4-(tert-butylamino)-2-(4-hydroxybicyclo[2.2.2]octan-1-ylamino)pyrimidine-5-carboxamide | 334.2 | D |
| 238 | 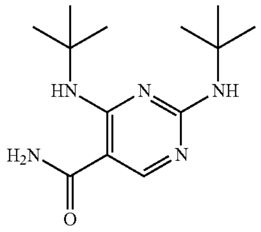 [SMILES: CC(C)(C)Nc1ncc(C(N)=O)c(NC(C)(C)C)n1] | 2,4-bis(tert-butylamino)pyrimidine-5-carboxamide | 266.4 | C |
| 239 | 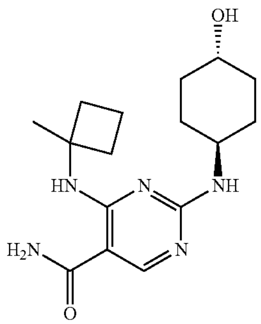 [SMILES: CC1(Nc2nc(N[C@H]3CC[C@H](O)CC3)ncc2C(N)=O)CCC1] | 2-((1r,4r)-4-hydroxycyclohexylamino)-4-(1-methylcyclobutylamino) pyrimidine-5-carboxamide | 320.2 | D |
| 240 | 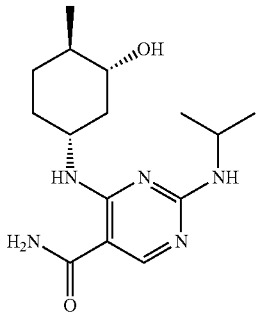 [SMILES: CC(C)Nc1ncc(C(N)=O)c(N[C@@H]2CC[C@@H](C)[C@H](O)C2)n1] | 4-((1R,3R,4R)-3-hydroxy-4-methylcyclohexylamino)-2-(isopropylamino) pyrimidine-5-carboxamide | 308 | D |
| 241 | 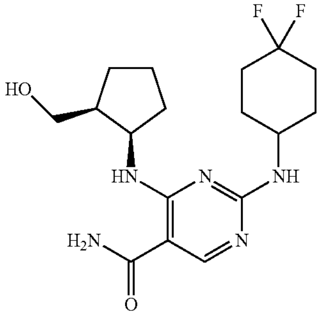 [SMILES: NC(=O)c1cnc(NC2CCC(F)(F)CC2)nc1N[C@@H]1CCC[C@@H]1CO] | 2-(4,4-difluorocyclohexylamino)-4-((1R,2S)-2-(hydroxymethyl) cyclopentylamino) pyrimidine-5-carboxamide | 370.6 | D |

TABLE 1-continued

| Cmpd. A- | Structure | NAME | MH+ | Act. Level |
|---|---|---|---|---|
| 242 | 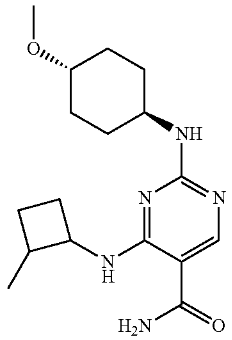 [SMILES: CO[C@H]1CC[C@H](Nc2ncc(C(N)=O)c(NC3CCC3C)n2)CC1] | 2-((1r,4r)-4-methoxycyclohexylamino)-4-(2-methylcyclobutylamino) pyrimidine-5-carboxamide | 334.2 | D |
| 243 | 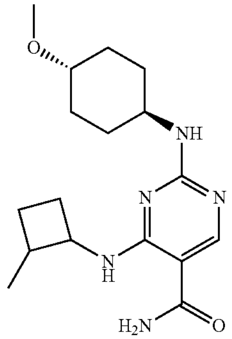 [SMILES: CO[C@H]1CC[C@H](Nc2ncc(C(N)=O)c(NC3CCC3C)n2)CC1] | 2-((1r,4r)-4-methoxycyclohexylamino)-4-(2-methylcyclobutylamino) pyrimidine-5-carboxamide | 334.2 | D |
| 244 | 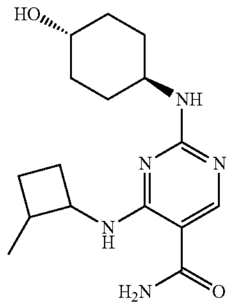 [SMILES: CC1CCC1Nc1nc(N[C@H]2CC[C@H](O)CC2)ncc1C(N)=O] | 2-((1r,4r)-4-hydroxycyclohexylamino)-4-(2-methylcyclobutylamino) pyrimidine-5-carboxamide | 320.2 | D |
| 245 | 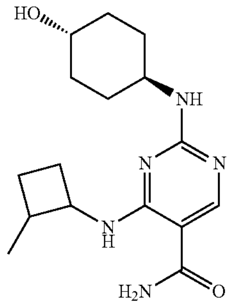 [SMILES: CC1CCC1Nc1nc(N[C@H]2CC[C@H](O)CC2)ncc1C(N)=O] | 2-((1r,4r)-4-hydroxycyclohexylamino)-4-(2-methylcyclobutylamino) pyrimidine-5-carboxamide | 320.2 | D |

TABLE 1-continued

| Cmpd. A- | Structure | NAME | MH+ | Act. Level |
|---|---|---|---|---|
| 246 | 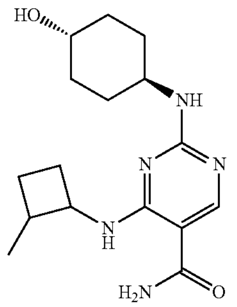 [SMILES: CC1CCC1Nc1nc(N[C@H]2CC[C@H](O)CC2)ncc1C(N)=O] | 2-((1r,4r)-4-hydroxycyclohexylamino)-4-(2-methylcyclobutylamino) pyrimidine-5-carboxamide | 320.2 | D |
| 247 | 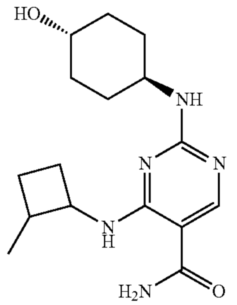 [SMILES: CC1CCC1Nc1nc(N[C@H]2CC[C@H](O)CC2)ncc1C(N)=O] | 2-((1r,4r)-4-hydroxycyclohexylamino)-4-(2-methylcyclobutylamino) pyrimidine-5-carboxamide | 320.2 | D |
| 248 | 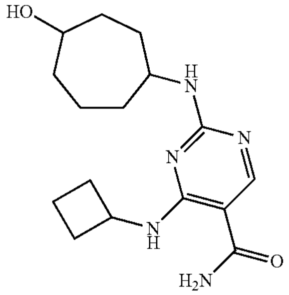 [SMILES: NC(=O)c1cnc(NC2CCCC(O)CC2)nc1NC1CCC1] | 4-(cyclobutylamino)-2-(4-hydroxycycloheptylamino) pyrimidine-5-carboxamide | 320 | D |
| 249 | 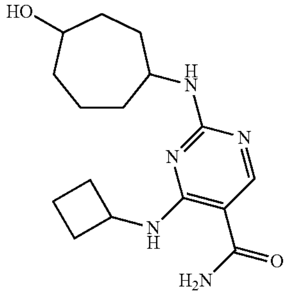 [SMILES: NC(=O)c1cnc(NC2CCCC(O)CC2)nc1NC1CCC1] | 4-(cyclobutylamino)-2-(4-hydroxycycloheptylamino) pyrimidine-5-carboxamide | 320 | D |
| 250 | 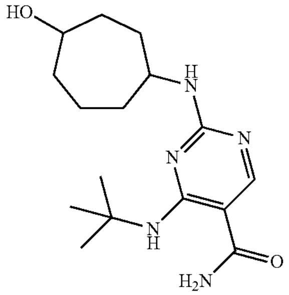 [SMILES: CC(C)(C)Nc1nc(NC2CCCC(O)CC2)ncc1C(N)=O] | 4-(tert-butylamino)-2-(4-hydroxycycloheptylamino) pyrimidine-5-carboxamide | 322 | D |

TABLE 1-continued

| Cmpd. A- | Structure | NAME | MH+ | Act. Level |
|---|---|---|---|---|
| 251 | 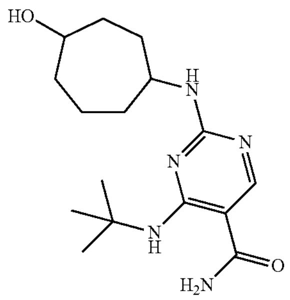 [SMILES: CC(C)(C)Nc1nc(NC2CCCC(O)CC2)ncc1C(N)=O] | 4-(tert-butylamino)-2-(4-hydroxycycloheptylamino) pyrimidine-5-carboxamide | 322.5 | D |
| 252 | 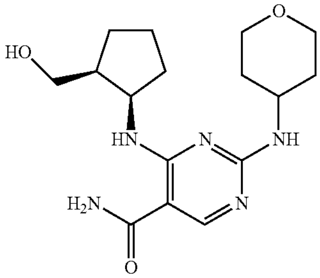 [SMILES: NC(=O)c1cnc(NC2CCOCC2)nc1N[C@@H]1CCC[C@@H]1CO] | 4-((1R,2S)-2-(hydroxymethyl) cyclopentylamino)-2-(tetrahydro-2H-pyran-4-ylamino)pyrimidine-5-carboxamide | 336 | D |
| 253 | 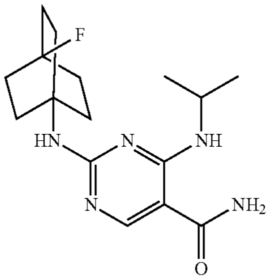 [SMILES: CC(C)Nc1nc(NC23CCC(F)(CC2)CC3)ncc1C(N)=O] | 2-(4-fluorobicyclo[2.2.2]octan-1-ylamino)-4-(isopropylamino) pyrimidine-5-carboxamide | 322.1 | D |
| 254 | 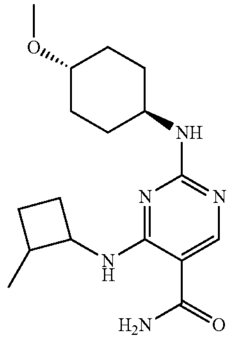 [SMILES: CO[C@H]1CC[C@H](Nc2ncc(C(N)=O)c(NC3CCC3C)n2)CC1] | 2-((1r,4r)-4-methoxycyclohexylamino)-4-(2-methylcyclobutylamino) pyrimidine-5-carboxamide | 334.2 | D |
| 255 | 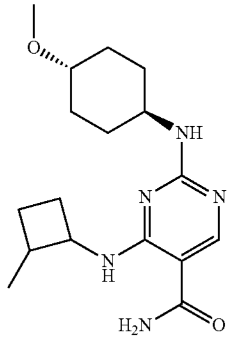 [SMILES: CO[C@H]1CC[C@H](Nc2ncc(C(N)=O)c(NC3CCC3C)n2)CC1] | 2-((1r,4r)-4-methoxycyclohexylamino)-4-(2-methylcyclobutylamino) pyrimidine-5-carboxamide | 334.2 | D |

TABLE 1-continued
| Cmpd. A- | Structure | NAME | MH+ | Act. Level |
|---|---|---|---|---|
| 256 | 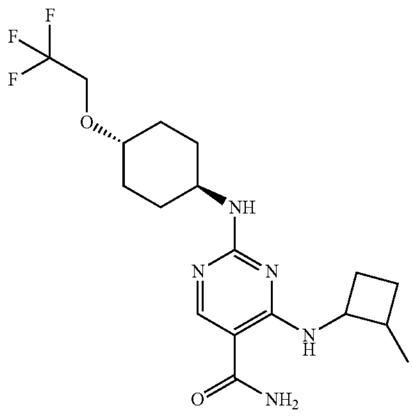 [SMILES: CC1CCC1Nc1nc(N[C@H]2CC[C@H](OCC(F)(F)F)CC2)ncc1C(N)=O] | 4-(2-methylcyclobutylamino)-2-((1r,4r)-4-(2,2,2-trifluoroethoxy) cyclohexylamino) pyrimidine-5-carboxamide | 402.2 | D |
| 257 | 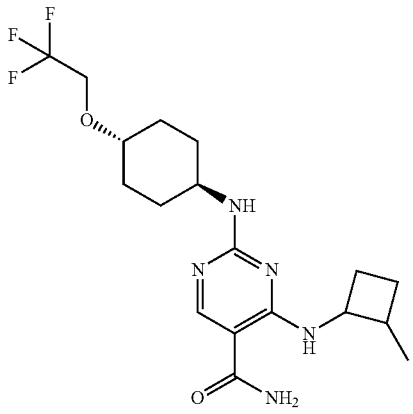 [SMILES: CC1CCC1Nc1nc(N[C@H]2CC[C@H](OCC(F)(F)F)CC2)ncc1C(N)=O] | 4-(2-methylcyclobutylamino)-2-((1r,4r)-4-(2,2,2-trifluoroethoxy) cyclohexylamino) pyrimidine-5-carboxamide | 402.2 | D |
| 258 | 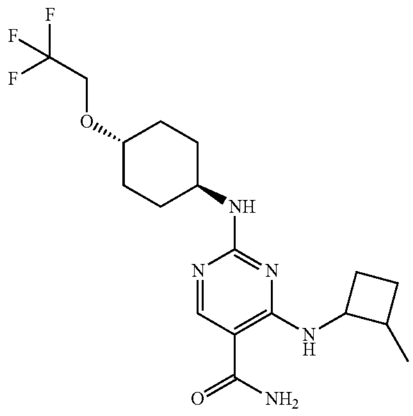 [SMILES: CC1CCC1Nc1nc(N[C@H]2CC[C@H](OCC(F)(F)F)CC2)ncc1C(N)=O] | 4-(2-methylcyclobutylamino)-2-((1r,4r)-4-(2,2,2-trifluoroethoxy) cyclohexylamino) pyrimidine-5-carboxamide | 402.2 | D |

TABLE 1-continued

| Cmpd. A- | Structure | NAME | MH+ | Act. Level |
|---|---|---|---|---|
| 259 | 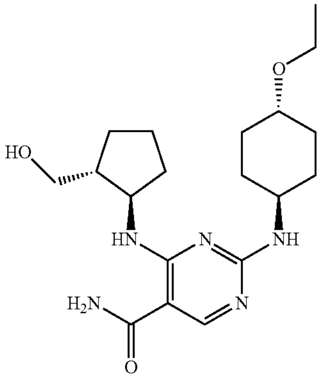 [SMILES: CCO[C@H]1CC[C@H](Nc2ncc(C(N)=O)c(N[C@@H]3CCC[C@H]3CO)n2)CC1] | 2-((1r,4R)-4-ethoxycyclohexylamino)-4-((1R,2R)-2-(hydroxymethyl)cyclopentylamino)pyrimidine-5-carboxamide | 378.2 | D |
| 260 | 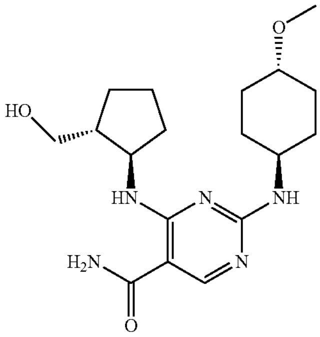 [SMILES: CO[C@H]1CC[C@H](Nc2ncc(C(N)=O)c(N[C@@H]3CCC[C@H]3CO)n2)CC1] | 4-((1R,2R)-2-(hydroxymethyl)cyclopentylamino)-2-((1r,4R)-4-methoxycyclohexylamino)pyrimidine-5-carboxamide | 364.2 | D |
| 261 | 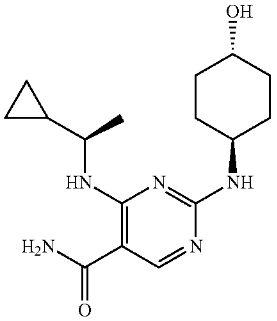 [SMILES: C[C@@H](Nc1nc(N[C@H]2CC[C@H](O)CC2)ncc1C(N)=O)C1CC1] | 4-((R)-1-cyclopropylethylamino)-2-((1r,4R)-4-hydroxycyclohexylamino)pyrimidine-5-carboxamide | 320.2 | D |
| 262 | 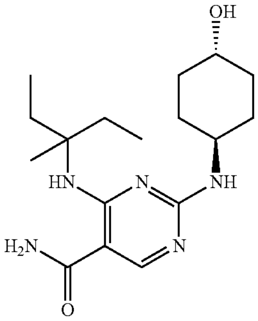 [SMILES: CCC(C)(CC)Nc1nc(N[C@H]2CC[C@H](O)CC2)ncc1C(N)=O] | 2-((1r,4r)-4-hydroxycyclohexylamino)-4-(3-methylpentan-3-ylamino)pyrimidine-5-carboxamide | 336.2 | D |

TABLE 1-continued

| Cmpd. A- | Structure | NAME | MH+ | Act. Level |
|---|---|---|---|---|
| 263 | 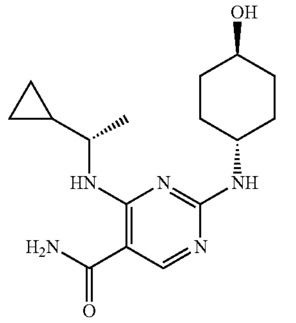 [SMILES: C[C@H](Nc1nc(N[C@H]2CC[C@H](O)CC2)ncc1C(N)=O)C1CC1] | 4-((S)-1-cyclopropylethylamino)-2-((1r,4S)-4-hydroxycyclohexylamino) pyrimidine-5-carboxamide | 320.2 | D |
| 264 | 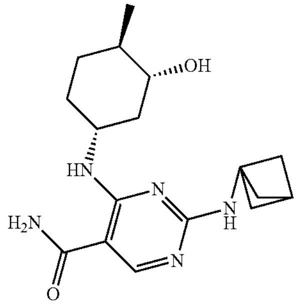 [SMILES: C[C@@H]1CC[C@@H](Nc2nc(NC34CC(C3)C4)ncc2C(N)=O)C[C@H]1O] | 2-(bicyclo[1.1.1]pentan-1-ylamino)-4-((1R,3R,4R)-3-hydroxy-4-methylcyclohexylamino) pyrimidine-5-carboxamide | 332.2 | D |
| 265 | 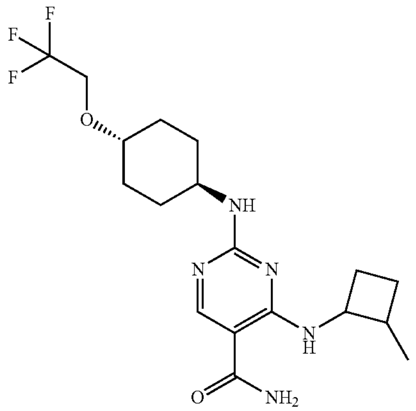 [SMILES: CC1CCC1Nc1nc(N[C@H]2CC[C@H](OCC(F)(F)F)CC2)ncc1C(N)=O] | 4-(2-methylcyclobutylamino)-2-((1r,4r)-4-(2,2,2-trifluoroethoxy) cyclohexylamino) pyrimidine-5-carboxamide | 402.2 | D |
| 266 | 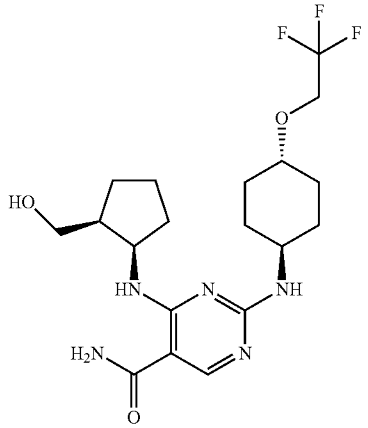 [SMILES: NC(=O)c1cnc(N[C@H]2CC[C@H](OCC(F)(F)F)CC2)nc1N[C@@H]1CCC[C@@H]1CO] | 4-((1R,2S)-2-(hydroxymethyl) cyclopentylamino)-2-((1r,4R)-4-(2,2,2-trifluoroethoxy) cyclohexylamino) pyrimidine-5-carboxamide | 432.2 | D |

TABLE 1-continued

| Cmpd. A- | Structure | NAME | MH+ | Act. Level |
|---|---|---|---|---|
| 267 | 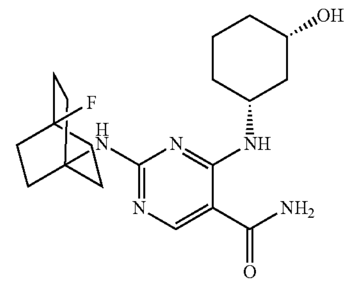 [SMILES: NC(=O)c1cnc(NC23CCC(F)(CC2)CC3)nc1N[C@@H]1CCC[C@H](O)C1] | 2-(4-fluorobicyclo[2.2.2]octan-1-ylamino)-4-((1R,3S)-3-hydroxycyclohexylamino) pyrimidine-5-carboxamide | 378.2 | D |
| 268 | 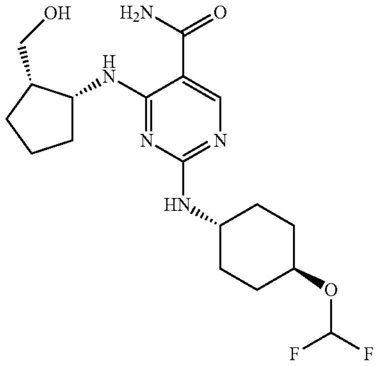 [SMILES: NC(=O)c1cnc(N[C@H]2CC[C@H](OC(F)F)CC2)nc1N[C@@H]1CCC[C@@H]1CO] | 2-((1r,4R)-4-(difluoromethoxy) cyclohexylamino)-4-((1R,2S)-2-(hydroxymethyl) cyclopentylamino) pyrimidine-5-carboxamide | 400.2 | D |
| 269 | 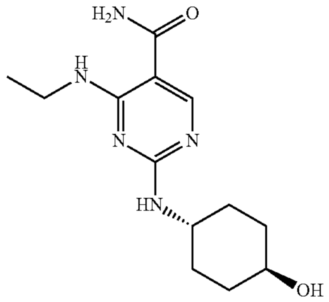 [SMILES: CCNc1nc(N[C@H]2CC[C@H](O)CC2)ncc1C(N)=O] | 4-(ethylamino)-2-((1r,4r)-4-hydroxycyclohexylamino) pyrimidine-5-carboxamide | 280.1 | D |
| 270 | 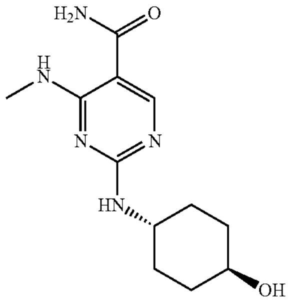 [SMILES: CNc1nc(N[C@H]2CC[C@H](O)CC2)ncc1C(N)=O] | 2-((1r,4r)-4-hydroxycyclohexylamino)-4-(methylamino)pyrimidine-5-carboxamide | 266.1 | C |
| 271 | 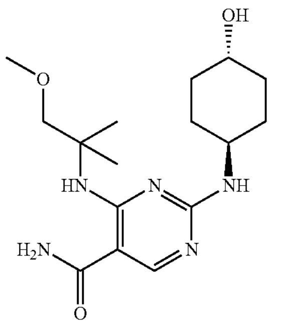 [SMILES: COCC(C)(C)Nc1nc(N[C@H]2CC[C@H](O)CC2)ncc1C(N)=O] | 2-((1r,4r)-4-hydroxycyclohexylamino)-4-(1-methoxy-2-methylpropan-2-ylamino)pyrimidine-5-carboxamide | 338.3 | D |

TABLE 1-continued

| Cmpd. A- | Structure | NAME | MH+ | Act. Level |
|---|---|---|---|---|
| 272 | 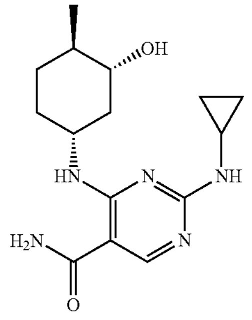 [SMILES: C[C@@H]1CC[C@@H](Nc2nc(NC3CC3)ncc2C(N)=O)C[C@H]1O] | 2-(cyclopropylamino)-4-((1R,3R,4R)-3-hydroxy-4-methylcyclohexylamino) pyrimidine-5-carboxamide | 306.3 | D |
| 273 | 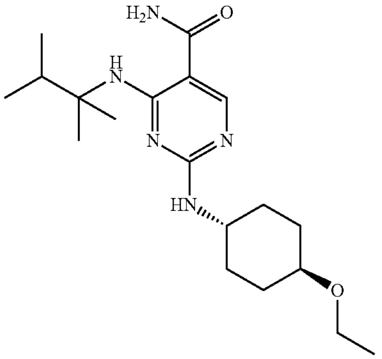 [SMILES: CCO[C@H]1CC[C@H](Nc2ncc(C(N)=O)c(NC(C)(C)C(C)C)n2)CC1] | 4-(2,3-dimethylbutan-2-ylamino)-2-((1r,4r)-4-ethoxycyclohexylamino) pyrimidine-5-carboxamide | 364.2 | D |
| 274 | 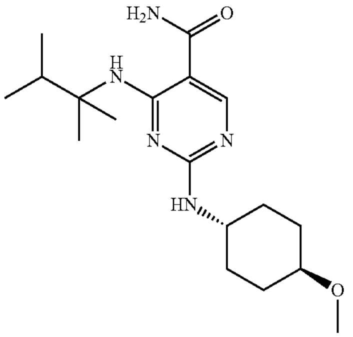 [SMILES: CO[C@H]1CC[C@H](Nc2ncc(C(N)=O)c(NC(C)(C)C(C)C)n2)CC1] | 4-(2,3-dimethylbutan-2-ylamino)-2-((1r,4r)-4-methoxycyclohexylamino) pyrimidine-5-carboxamide | 350.2 | D |
| 275 | 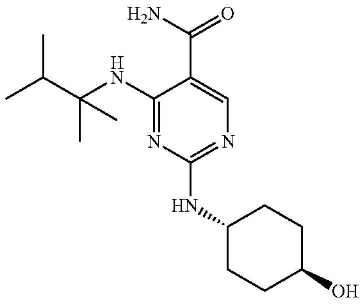 [SMILES: CC(C)C(C)(C)Nc1nc(N[C@H]2CC[C@H](O)CC2)ncc1C(N)=O] | 4-(2,3-dimethylbutan-2-ylamino)-2-((1r,4r)-4-hydroxycyclohexylamino) pyrimidine-5-carboxamide | 336.3 | D |

TABLE 1-continued

| Cmpd. A- | Structure | NAME | MH+ | Act. Level |
|---|---|---|---|---|
| 276 | 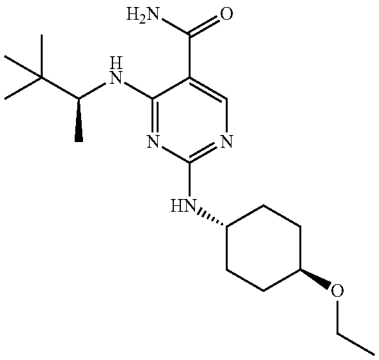 [SMILES: CCO[C@H]1CC[C@H](Nc2ncc(C(N)=O)c(N[C@@H](C)C(C)(C)C)n2)CC1] | 4-((S)-3,3-dimethylbutan-2-ylamino)-2-((1r,4S)-4-ethoxycyclohexylamino) pyrimidine-5-carboxamide | 364.2 | D |
| 277 | 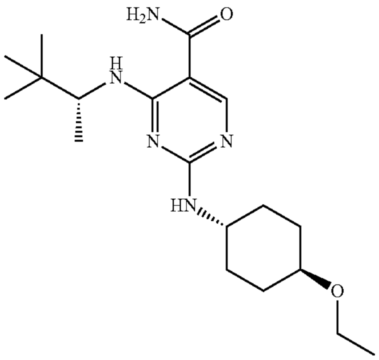 [SMILES: CCO[C@H]1CC[C@H](Nc2ncc(C(N)=O)c(N[C@H](C)C(C)(C)C)n2)CC1] | 4-((R)-3,3-dimethylbutan-2-ylamino)-2-((1r,4R)-4-ethoxycyclohexylamino) pyrimidine-5-carboxamide | 364.2 | D |
| 278 | 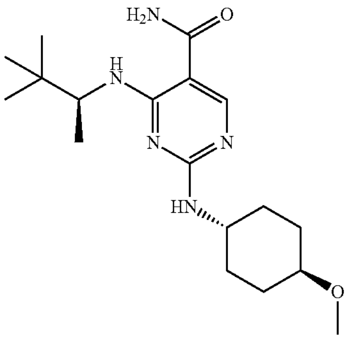 [SMILES: CO[C@H]1CC[C@H](Nc2ncc(C(N)=O)c(N[C@@H](C)C(C)(C)C)n2)CC1] | 4-((S)-3,3-dimethylbutan-2-ylamino)-2-((1r,4S)-4-methoxycyclohexylamino) pyrimidine-5-carboxamide | 350.2 | D |
| 279 | 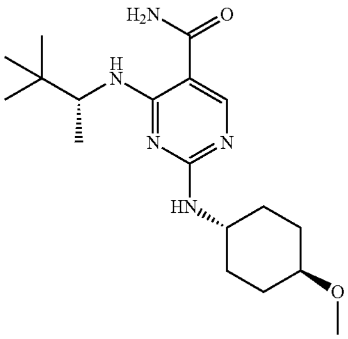 [SMILES: CO[C@H]1CC[C@H](Nc2ncc(C(N)=O)c(N[C@H](C)C(C)(C)C)n2)CC1] | 4-((R)-3,3-dimethylbutan-2-ylamino)-2-((1r,4R)-4-methoxycyclohexylamino) pyrimidine-5-carboxamide | 350.2 | D |

TABLE 1-continued

| Cmpd. A- | Structure | NAME | MH+ | Act. Level |
|---|---|---|---|---|
| 280 | 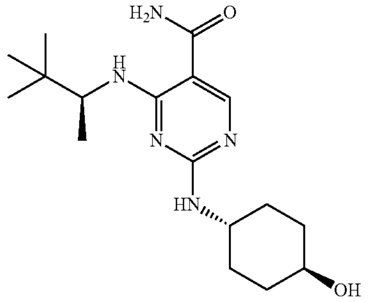 [SMILES: C[C@H](Nc1nc(N[C@H]2CC[C@H](O)CC2)ncc1C(N)=O)C(C)(C)C] | 4-((S)-3,3-dimethylbutan-2-ylamino)-2-((1r,4S)-4-hydroxycyclohexylamino) pyrimidine-5-carboxamide | 336.2 | D |
| 281 | 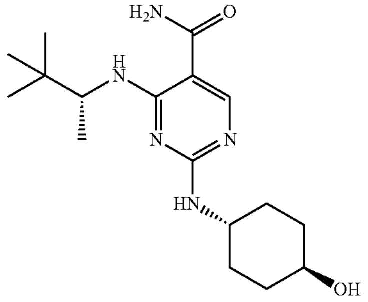 [SMILES: C[C@@H](Nc1nc(N[C@H]2CC[C@H](O)CC2)ncc1C(N)=O)C(C)(C)C] | 4-((R)-3,3-dimethylbutan-2-ylamino)-2-((1r,4R)-4-hydroxycyclohexylamino) pyrimidine-5-carboxamide | 336.2 | D |
| 282 | 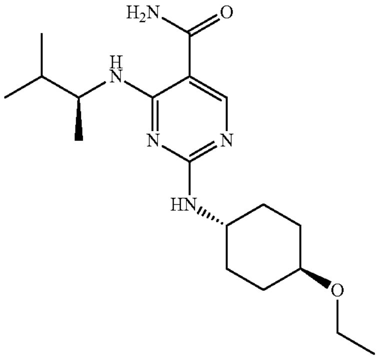 [SMILES: CCO[C@H]1CC[C@H](Nc2ncc(C(N)=O)c(N[C@@H](C)C(C)C)n2)CC1] | 2-((1r,4S)-4-ethoxycyclohexylamino)-4-((S)-3-methylbutan-2-ylamino)pyrimidine-5-carboxamide | 350.2 | D |
| 283 | 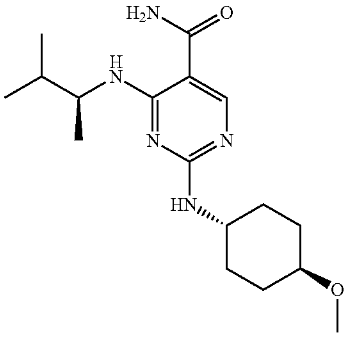 [SMILES: CO[C@H]1CC[C@H](Nc2ncc(C(N)=O)c(N[C@@H](C)C(C)C)n2)CC1] | 2-((1r,4S)-4-methoxycyclohexylamino)-4-((S)-3-methylbutan-2-ylamino)pyrimidine-5-carboxamide | 336.2 | D |

TABLE 1-continued

| Cmpd. A- | Structure | NAME | MH+ | Act. Level |
|---|---|---|---|---|
| 284 | 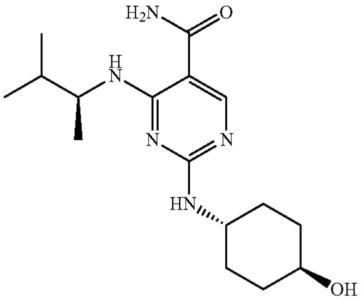 [SMILES: CC(C)[C@H](C)Nc1nc(N[C@H]2CC[C@H](O)CC2)ncc1C(N)=O] | 2-((1r,4S)-4-hydroxycyclohexylamino)-4-((S)-3-methylbutan-2-ylamino)pyrimidine-5-carboxamide | 322.2 | D |
| 285 | 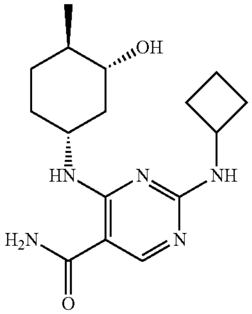 [SMILES: C[C@@H]1CC[C@@H](Nc2nc(NC3CCC3)ncc2C(N)=O)C[C@H]1O] | 2-(cyclobutylamino)-4-((1R,3R,4R)-3-hydroxy-4-methylcyclohexylamino) pyrimidine-5-carboxamide | 320.2 | D |
| 286 | 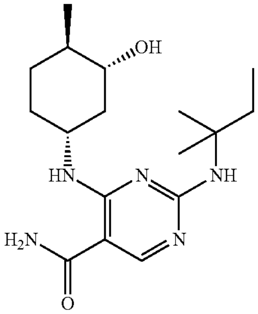 [SMILES: CCC(C)(C)Nc1ncc(C(N)=O)c(N[C@@H]2CC[C@@H](C)[C@H](O)C2)n1] | 4-((1R,3R,4R)-3-hydroxy-4-methylcyclohexylamino)-2-(tert-pentylamino)pyrimidine-5-carboxamide | 336.2 | D |
| 287 | 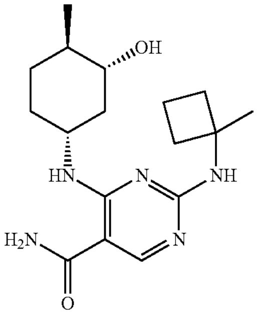 [SMILES: C[C@@H]1CC[C@@H](Nc2nc(NC3(C)CCC3)ncc2C(N)=O)C[C@H]1O] | 4-((1R,3R,4R)-3-hydroxy-4-methylcyclohexylamino)-2-(1-methylcyclobutylamino) pyrimidine-5-carboxamide | 334.1 | D |
| 288 | 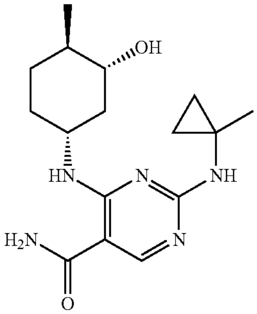 [SMILES: C[C@@H]1CC[C@@H](Nc2nc(NC3(C)CC3)ncc2C(N)=O)C[C@H]1O] | 4-((1R,3R,4R)-3-hydroxy-4-methylcyclohexylamino)-2-(1-methylcyclopropylamino) pyrimidine-5-carboxamide | 320.2 | D |

TABLE 1-continued
| Cmpd. A- | Structure | NAME | MH+ | Act. Level |
|---|---|---|---|---|
| 289 | 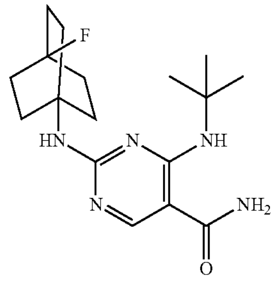 [SMILES: CC(C)(C)Nc1nc(NC23CCC(F)(CC2)CC3)ncc1C(N)=O] | 4-(tert-butylamino)-2-(4-fluorobicyclo[2.2.2]octan-1-ylamino)pyrimidine-5-carboxamide | 336.2 | D |
| 290 | 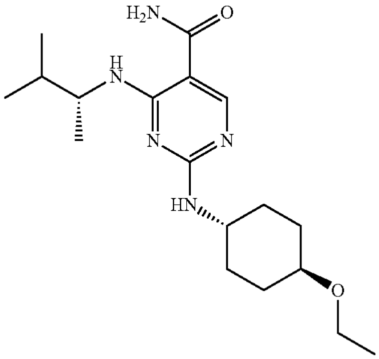 [SMILES: CCO[C@H]1CC[C@H](Nc2ncc(C(N)=O)c(N[C@H](C)C(C)C)n2)CC1] | 2-((1r,4R)-4-ethoxycyclohexylamino)-4-((R)-3-methylbutan-2-ylamino)pyrimidine-5-carboxamide | 350.2 | D |
| 291 | 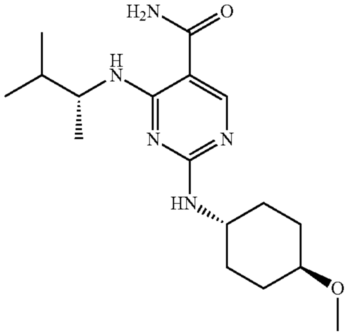 [SMILES: CO[C@H]1CC[C@H](Nc2ncc(C(N)=O)c(N[C@H](C)C(C)C)n2)CC1] | 2-((1r,4R)-4-methoxycyclohexylamino)-4-((R)-3-methylbutan-2-ylamino)pyrimidine-5-carboxamide | 336.2 | D |
| 292 | 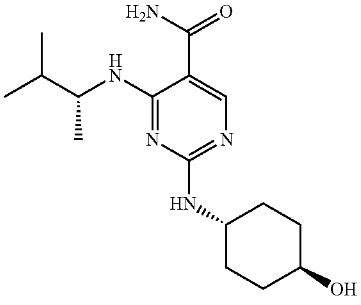 [SMILES: CC(C)[C@@H](C)Nc1nc(N[C@H]2CC[C@H](O)CC2)ncc1C(N)=O] | 2-((1r,4R)-4-hydroxycyclohexylamino)-4-((R)-3-methylbutan-2-ylamino)pyrimidine-5-carboxamide | 322.2 | D |

TABLE 1-continued

| Cmpd. A- | Structure | NAME | MH+ | Act. Level |
|---|---|---|---|---|
| 293 | 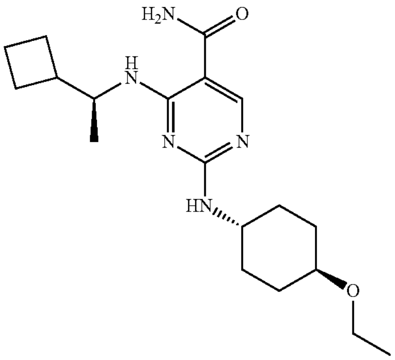 [SMILES: CCO[C@H]1CC[C@H](Nc2ncc(C(N)=O)c(N[C@@H](C)C3CCC3)n2)CC1] | 4-((S)-1-cyclobutylethylamino)-2-((1r,4S)-4-ethoxycyclohexylamino)pyrimidine-5-carboxamide | 362.2 | D |
| 294 | 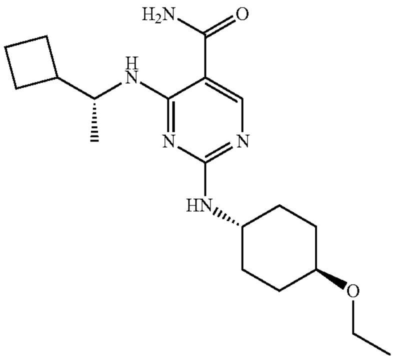 [SMILES: CCO[C@H]1CC[C@H](Nc2ncc(C(N)=O)c(N[C@H](C)C3CCC3)n2)CC1] | 4-((R)-1-cyclobutylethylamino)-2-((1r,4R)-4-ethoxycyclohexylamino)pyrimidine-5-carboxamide | 362.2 | A |
| 295 | 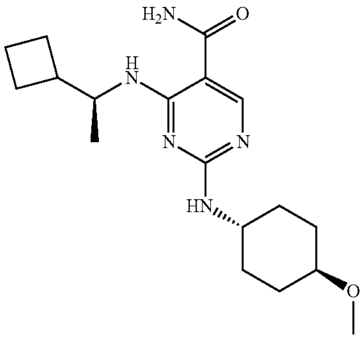 [SMILES: CO[C@H]1CC[C@H](Nc2ncc(C(N)=O)c(N[C@@H](C)C3CCC3)n2)CC1] | 4-((S)-1-cyclobutylethylamino)-2-((1r,4S)-4-methoxycyclohexylamino)pyrimidine-5-carboxamide | 348.2 | D |
| 296 | 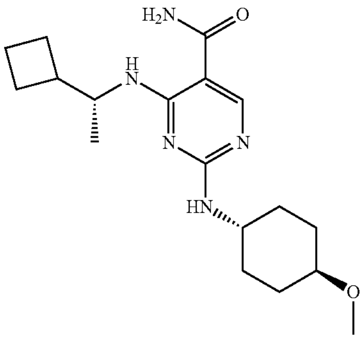 [SMILES: CO[C@H]1CC[C@H](Nc2ncc(C(N)=O)c(N[C@H](C)C3CCC3)n2)CC1] | 4-((R)-1-cyclobutylethylamino)-2-((1r,4R)-4-methoxycyclohexylamino)pyrimidine-5-carboxamide | 348.2 | A |

TABLE 1-continued

| Cmpd. A- | Structure | NAME | MH+ | Act. Level |
|---|---|---|---|---|
| 297 | 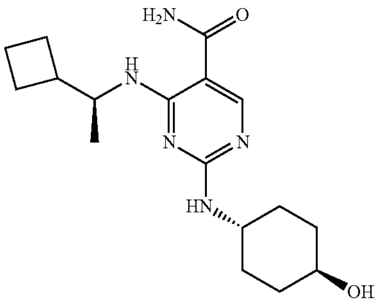 [SMILES: C[C@H](Nc1nc(N[C@H]2CC[C@H](O)CC2)ncc1C(N)=O)C1CCC1] | 4-((S)-1-cyclobutylethylamino)-2-((1r,4S)-4-hydroxycyclohexylamino) pyrimidine-5-carboxamide | 334.2 | D |
| 298 | 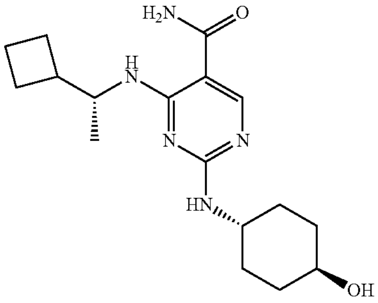 [SMILES: C[C@@H](Nc1nc(N[C@H]2CC[C@H](O)CC2)ncc1C(N)=O)C1CCC1] | 4-((R)-1-cyclobutylethylamino)-2-((1r,4R)-4-hydroxycyclohexylamino) pyrimidine-5-carboxamide | 334.2 | D |
| 299 | 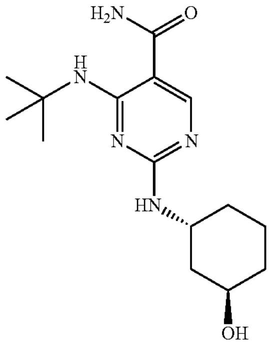 [SMILES: CC(C)(C)Nc1nc(N[C@@H]2CCC[C@@H](O)C2)ncc1C(N)=O] | 4-(tert-butylamino)-2-((1R,3R)-3-hydroxycyclohexylamino) pyrimidine-5-carboxamide | 308.2 | D |
| 300 | 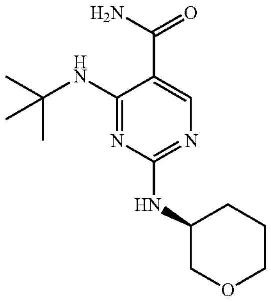 [SMILES: CC(C)(C)Nc1nc(N[C@H]2CCCOC2)ncc1C(N)=O] | (S)-4-(tert-butylamino)-2-(tetrahydro-2H-pyran-3-ylamino)pyrimidine-5-carboxamide | 294.1 | D |
| 301 | 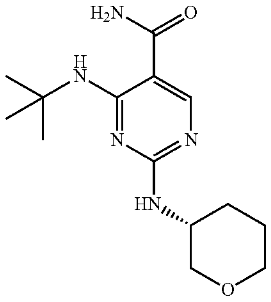 [SMILES: CC(C)(C)Nc1nc(N[C@@H]2CCCOC2)ncc1C(N)=O] | (R)-4-(tert-butylamino)-2-(tetrahydro-2H-pyran-3-ylamino)pyrimidine-5-carboxamide | 294.1 | D |

TABLE 1-continued
| Cmpd. A- | Structure | NAME | MH+ | Act. Level |
|---|---|---|---|---|
| 302 | 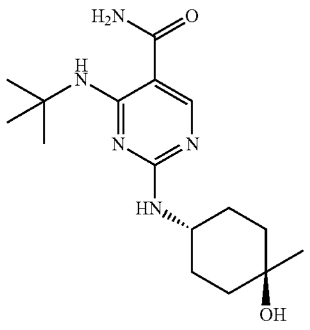 [SMILES: CC(C)(C)Nc1nc(N[C@H]2CC[C@](C)(O)CC2)ncc1C(N)=O] | 4-(tert-butylamino)-2-((1r,4r)-4-hydroxy-4-methylcyclohexylamino) pyrimidine-5-carboxamide | 322.2 | D |
| 303 | 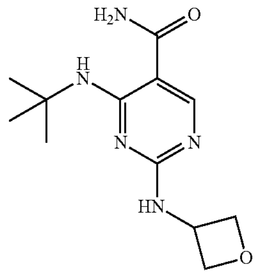 [SMILES: CC(C)(C)Nc1nc(NC2COC2)ncc1C(N)=O] | 4-(tert-butylamino)-2-(oxetan-3-ylamino)pyrimidine-5-carboxamide | 266.1 | C |
| 304 | 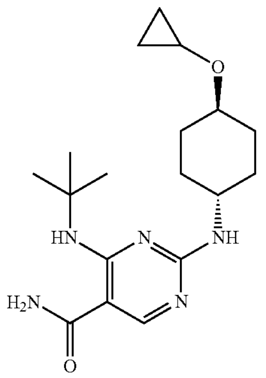 [SMILES: CC(C)(C)Nc1nc(N[C@H]2CC[C@H](OC3CC3)CC2)ncc1C(N)=O] | 4-(tert-butylamino)-2-((1r,4r)-4-cyclopropoxycyclohexylamino) pyrimidine-5-carboxamide | 348.3 | D |
| 305 | 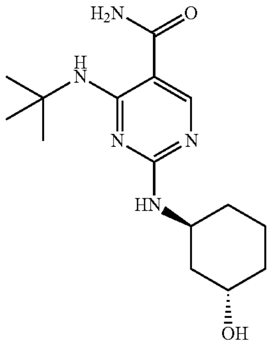 [SMILES: CC(C)(C)Nc1nc(N[C@H]2CCC[C@H](O)C2)ncc1C(N)=O] | 4-(tert-butylamino)-2-((1S,3S)-3-hydroxycyclohexylamino) pyrimidine-5-carboxamide | 308.1 | D |

TABLE 1-continued

| Cmpd. A- | Structure | NAME | MH+ | Act. Level |
|---|---|---|---|---|
| 306 | 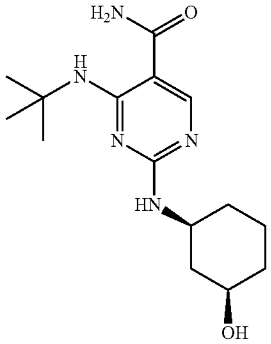 [SMILES: CC(C)(C)Nc1nc(N[C@H]2CCC[C@@H](O)C2)ncc1C(N)=O] | 4-(tert-butylamino)-2-((1S,3R)-3-hydroxycyclohexylamino) pyrimidine-5-carboxamide | 308.2 | D |
| 307 | 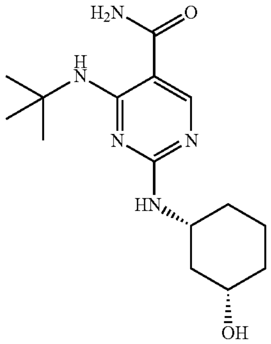 [SMILES: CC(C)(C)Nc1nc(N[C@@H]2CCC[C@H](O)C2)ncc1C(N)=O] | 4-(tert-butylamino)-2-((1R,3S)-3-hydroxycyclohexylamino) pyrimidine-5-carboxamide | 308.2 | D |
| 308 | 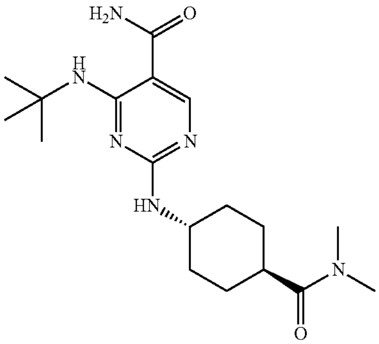 [SMILES: CN(C)C(=O)[C@H]1CC[C@H](Nc2ncc(C(N)=O)c(NC(C)(C)C)n2)CC1] | 4-(tert-butylamino)-2-((1r,4r)-4-(dimethylcarbamoyl) cyclohexylamino) pyrimidine-5-carboxamide | 363.2 | D |
| 309 | 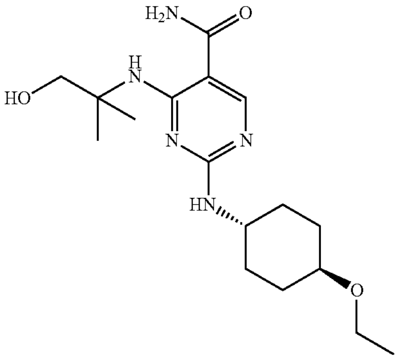 [SMILES: CCO[C@H]1CC[C@H](Nc2ncc(C(N)=O)c(NC(C)(C)CO)n2)CC1] | 2-((1r,4r)-4-ethoxycyclohexylamino)-4-(1-hydroxy-2-methylpropan-2-ylamino)pyrimidine-5-carboxamide | 353.2 | D |

TABLE 1-continued

| Cmpd. A- | Structure | NAME | MH+ | Act. Level |
|---|---|---|---|---|
| 310 | 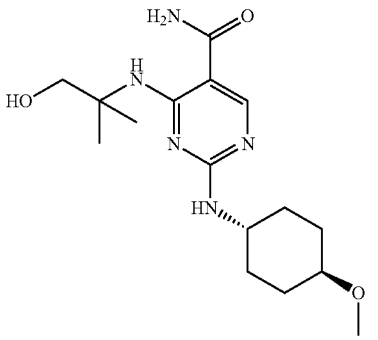 [SMILES: CO[C@H]1CC[C@H](Nc2ncc(C(N)=O)c(NC(C)(C)CO)n2)CC1] | 4-(1-hydroxy-2-methylpropan-2-ylamino)-2-((1r,4r)-4-methoxycyclohexylamino)pyrimidine-5-carboxamide | 338.2 | D |
| 311 | 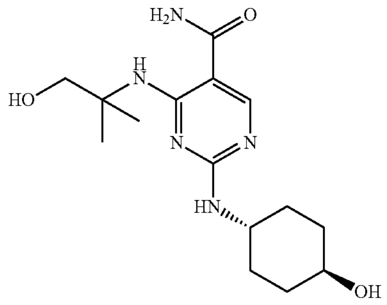 [SMILES: CC(C)(CO)Nc1nc(N[C@H]2CC[C@H](O)CC2)ncc1C(N)=O] | 4-(1-hydroxy-2-methylpropan-2-ylamino)-2-((1r,4r)-4-hydroxycyclohexylamino)pyrimidine-5-carboxamide | 324.2 | D |
| 312 | 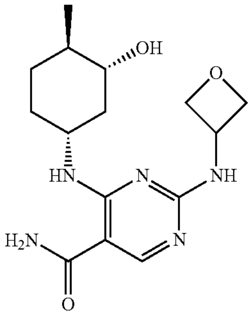 [SMILES: C[C@@H]1CC[C@@H](Nc2nc(NC3COC3)ncc2C(N)=O)C[C@H]1O] | 4-((1R,3R,4R)-3-hydroxy-4-methylcyclohexylamino)-2-(oxetan-3-ylamino)pyrimidine-5-carboxamide | 322.3 | D |
| 313 | 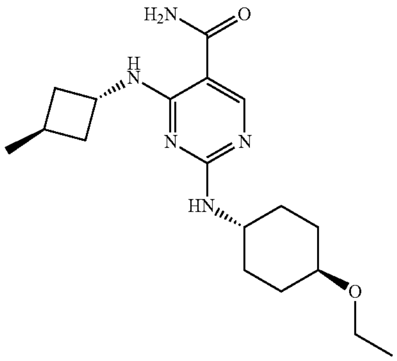 [SMILES: CCO[C@H]1CC[C@H](Nc2ncc(C(N)=O)c(N[C@H]3C[C@H](C)C3)n2)CC1] | 2-((1r,4r)-4-ethoxycyclohexylamino)-4-((1r,3r)-3-methylcyclobutylamino)pyrimidine-5-carboxamide | 348.3 | D |

TABLE 1-continued

| Cmpd. A- | Structure | NAME | MH+ | Act. Level |
|---|---|---|---|---|
| 314 | 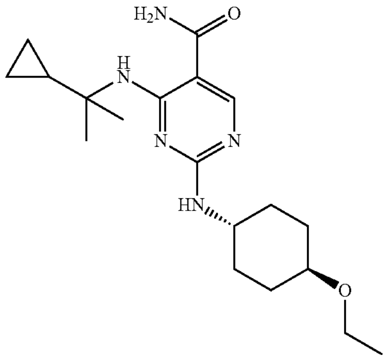 [SMILES: CCO[C@H]1CC[C@H](Nc2ncc(C(N)=O)c(NC(C)(C)C3CC3)n2)CC1] | 4-(2-cyclopropylpropan-2-ylamino)-2-((1r,4r)-4-ethoxycyclohexylamino) pyrimidine-5-carboxamide | 362.2 | D |
| 315 | 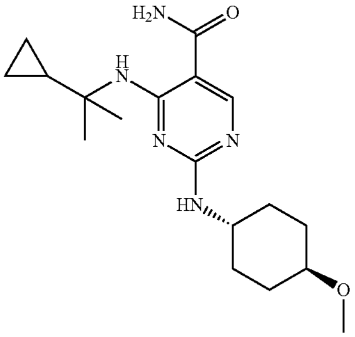 [SMILES: CO[C@H]1CC[C@H](Nc2ncc(C(N)=O)c(NC(C)(C)C3CC3)n2)CC1] | 4-(2-cyclopropylpropan-2-ylamino)-2-((1r,4r)-4-methoxycyclohexylamino) pyrimidine-5-carboxamide | 348.2 | D |
| 316 | 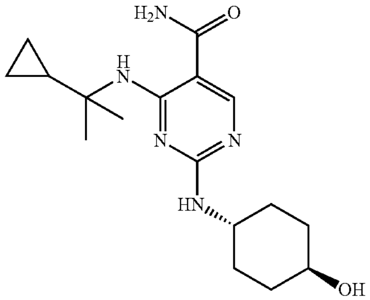 [SMILES: CC(C)(Nc1nc(N[C@H]2CC[C@H](O)CC2)ncc1C(N)=O)C1CC1] | 4-(2-cyclopropylpropan-2-ylamino)-2-((1r,4r)-4-hydroxycyclohexylamino) pyrimidine-5-carboxamide | 334.2 | D |
| 317 | 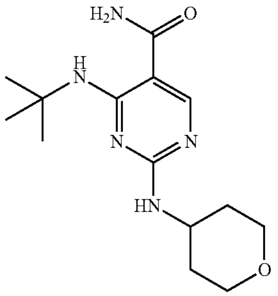 [SMILES: CC(C)(C)Nc1nc(NC2CCOCC2)ncc1C(N)=O] | 4-(tert-butylamino)-2-(tetrahydro-2H-pyran-4-ylamino)pyrimidine-5-carboxamide | 294.1 | D |

TABLE 1-continued

| Cmpd. A- | Structure | NAME | MH+ | Act. Level |
|---|---|---|---|---|
| 318 | 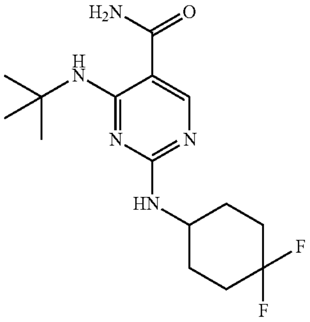 [SMILES: CC(C)(C)Nc1nc(NC2CCC(F)(F)CC2)ncc1C(N)=O] | 4-(tert-butylamino)-2-(4,4-difluorocyclohexylamino) pyrimidine-5-carboxamide | 328.1 | D |
| 319 | 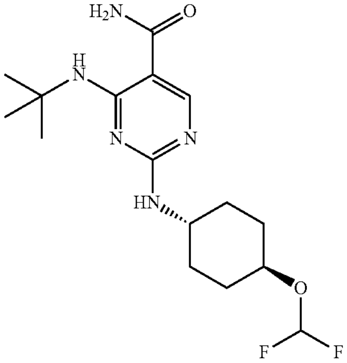 [SMILES: CC(C)(C)Nc1nc(N[C@H]2CC[C@H](OC(F)F)CC2)ncc1C(N)=O] | 4-(tert-butylamino)-2-((1r,4r)-4-(difluoromethoxy) cyclohexylamino) pyrimidine-5-carboxamide | 358.2 | D |
| 320 | 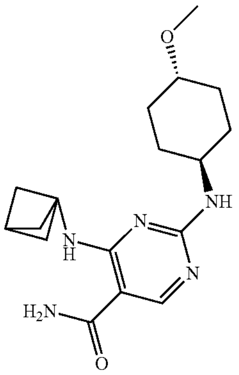 [SMILES: CO[C@H]1CC[C@H](Nc2ncc(C(N)=O)c(NC34CC(C3)C4)n2)CC1] | 4-(bicyclo[1.1.1]pentan-1-ylamino)-2-((1r,4r)-4-methoxycyclohexylamino) pyrimidine-5-carboxamide | 332.1 | D |
| 321 | 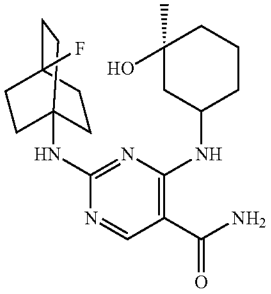 [SMILES: C[C@]1(O)CCCC(Nc2nc(NC34CCC(F)(CC3)CC4)ncc2C(N)=O)C1] | 2-(4-fluorobicyclo[2.2.2]octan-1-ylamino)-4-((3S)-3-hydroxy-3-methylcyclohexylamino) pyrimidine-5-carboxamide | 392.4 | D |

TABLE 1-continued

| Cmpd. A- | Structure | NAME | MH+ | Act. Level |
|---|---|---|---|---|
| 322 | 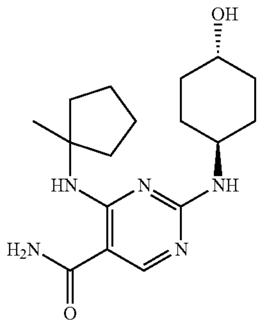 [SMILES: CC1(Nc2nc(N[C@H]3CC[C@H](O)CC3)ncc2C(N)=O)CCCC1] | 2-((1r,4r)-4-hydroxycyclohexylamino)-4-(1-methylcyclopentylamino) pyrimidine-5-carboxamide | 334.2 | D |
| 323 | 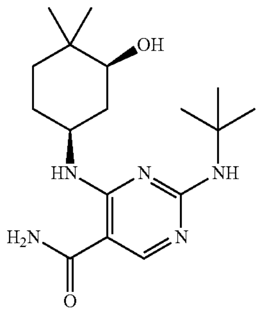 [SMILES: CC(C)(C)Nc1ncc(C(N)=O)c(N[C@H]2CCC(C)(C)[C@@H](O)C2)n1] | 2-(tert-butylamino)-4-((1S,3S)-3-hydroxy-4,4-dimethylcyclohexylamino) pyrimidine-5-carboxamide | 336.2 | C |
| 324 | 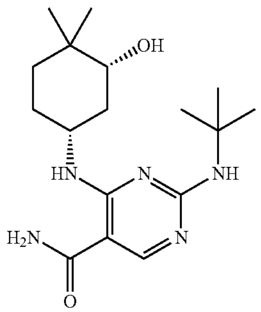 [SMILES: CC(C)(C)Nc1ncc(C(N)=O)c(N[C@@H]2CCC(C)(C)[C@H](O)C2)n1] | 2-(tert-butylamino)-4-((1R,3R)-3-hydroxy-4,4-dimethylcyclohexylamino) pyrimidine-5-carboxamide | 336.2 | D |
| 325 | 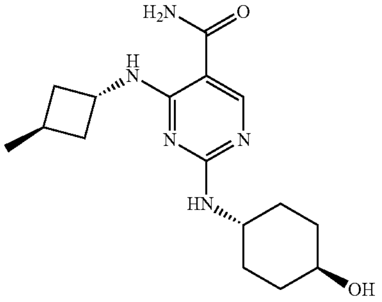 [SMILES: C[C@H]1C[C@H](Nc2nc(N[C@H]3CC[C@H](O)CC3)ncc2C(N)=O)C1] | 2-((1r,4r)-4-hydroxycyclohexylamino)-4-((1r,3r)-3-methylcyclobutylamino) pyrimidine-5-carboxamide | 320.2 | D |

TABLE 1-continued

| Cmpd. A- | Structure | NAME | MH+ | Act. Level |
|---|---|---|---|---|
| 326 | 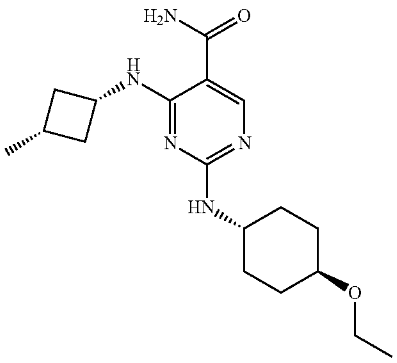 [SMILES: CCO[C@H]1CC[C@H](Nc2ncc(C(N)=O)c(N[C@H]3C[C@@H](C)C3)n2)CC1] | 2-((1r,4r)-4-ethoxycyclohexylamino)-4-((1s,3s)-3-methylcyclobutylamino) pyrimidine-5-carboxamide | 348.2 | D |
| 327 | 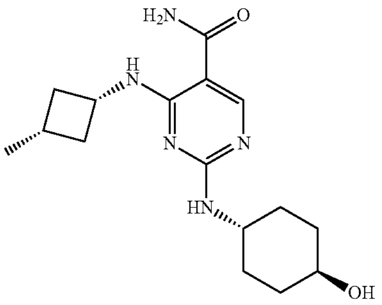 [SMILES: C[C@H]1C[C@@H](Nc2nc(N[C@H]3CC[C@H](O)CC3)ncc2C(N)=O)C1] | 2-((1r,4r)-4-hydroxycyclohexylamino)-4-((1s,3s)-3-methylcyclobutylamino) pyrimidine-5-carboxamide | 320.2 | D |
| 328 | 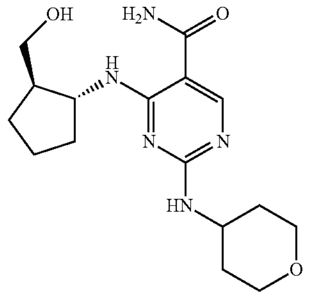 [SMILES: NC(=O)c1cnc(NC2CCOCC2)nc1N[C@@H]1CCC[C@H]1CO] | 4-((1R,2R)-2-(hydroxymethyl) cyclopentylamino)-2-(tetrahydro-2H-pyran-4-ylamino)pyrimidine-5-carboxamide | 336.1 | D |
| 329 | 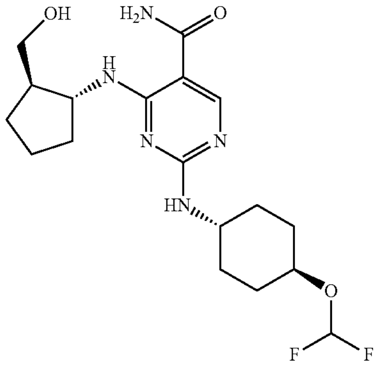 [SMILES: NC(=O)c1cnc(N[C@H]2CC[C@H](OC(F)F)CC2)nc1N[C@@H]1CCC[C@H]1CO] | 2-((1r,4R)-4-(difluoromethoxy) cyclohexylamino)-4-((1R,2R)-2-(hydroxymethyl) cyclopentylamino) pyrimidine-5-carboxamide | 400.2 | D |

TABLE 1-continued

| Cmpd. A- | Structure | NAME | MH+ | Act. Level |
|---|---|---|---|---|
| 330 | 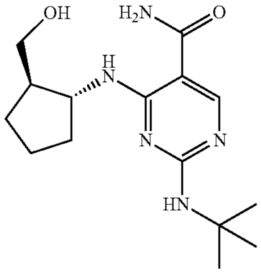 [SMILES: CC(C)(C)Nc1ncc(C(N)=O)c(N[C@@H]2CCC[C@H]2CO)n1] | 2-(tert-butylamino)-4-((1R,2R)-2-(hydroxymethyl) cyclopentylamino) pyrimidine-5-carboxamide | 308 2 | D |
| 331 | 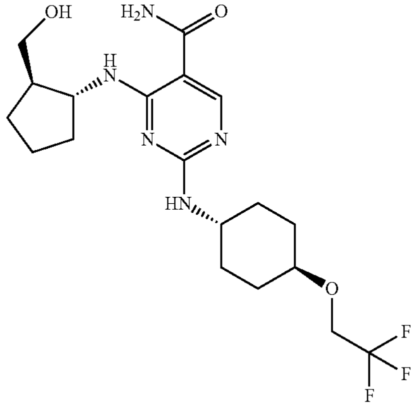 [SMILES: NC(=O)c1cnc(N[C@H]2CC[C@H](OCC(F)(F)F)CC2)nc1N[C@@H]1CCC[C@H]1CO] | 4-((1R,2R)-2-(hydroxymethyl) cyclopentylamino)-2-((1r,4R)-4-(2,2,2-trifluoroethoxy) cyclohexylamino) pyrimidine-5-carboxamide | 432.2 | D |
| 332 | 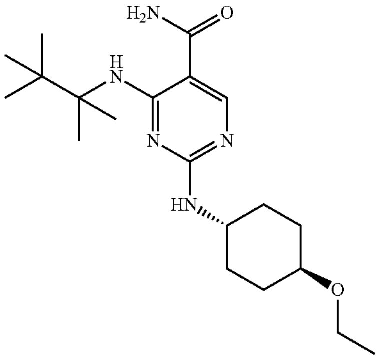 [SMILES: CCO[C@H]1CC[C@H](Nc2ncc(C(N)=O)c(NC(C)(C)C(C)(C)C)n2)CC1] | 2-((1r,4r)-4-ethoxycyclohexylamino)-4-(2,3,3-trimethylbutan-2-ylamino)pyrimidine-5-carboxamide | 378.2 | D |
| 333 | 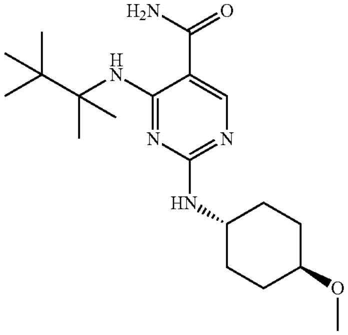 [SMILES: CO[C@H]1CC[C@H](Nc2ncc(C(N)=O)c(NC(C)(C)C(C)(C)C)n2)CC1] | 2-((1r,4r)-4-methoxycyclohexylamino)-4-(2,3,3-trimethylbutan-2-ylamino)pyrimidine-5-carboxamide | 364.2 | D |

TABLE 1-continued

| Cmpd. A- | Structure | NAME | MH+ | Act. Level |
|---|---|---|---|---|
| 334 | 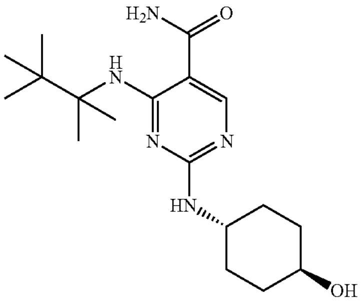 [SMILES: CC(C)(C)C(C)(C)Nc1nc(N[C@H]2CC[C@H](O)CC2)ncc1C(N)=O] | 2-((1r,4r)-4-hydroxycyclohexylamino)-4-(2,3,3-trimethylbutan-2-ylamino)pyrimidine-5-carboxamide | 350.2 | D |
| 335 | 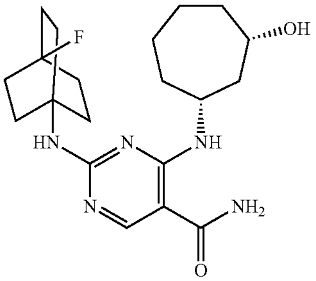 [SMILES: NC(=O)c1cnc(NC23CCC(F)(CC2)CC3)nc1N[C@@H]1CCCC[C@H](O)C1] | 2-(4-fluorobicyclo[2.2.2]octan-1-ylamino)-4-((1R,3S)-3-hydroxycycloheptylamino) pyrimidine-5-carboxamide | 392.4 | D |
| 336 | 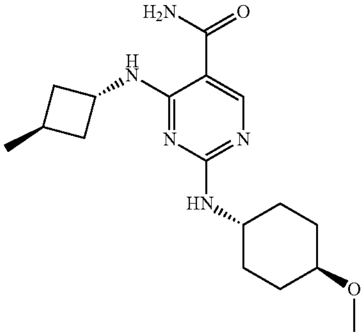 | 2-((1r,4r)-4-methoxycyclohexylamino)-4-((1r,3r)-3-methylcyclobutylamino) pyrimidine-5-carboxamide | 334.2 | D |
| 337 | 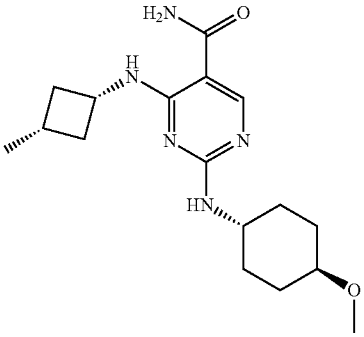 | 2-((1r,4r)-4-methoxycyclohexylamino)-4-((1s,3s)-3-methylcyclobutylamino) pyrimidine-5-carboxamide | 334.2 | D |
| 338 | 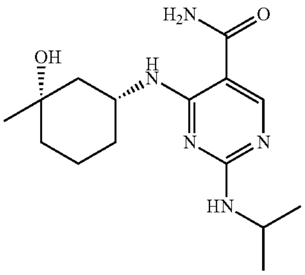 [SMILES: CC(C)Nc1ncc(C(N)=O)c(N[C@@H]2CCC[C@](C)(O)C2)n1] | 4-((1R,3S)-3-hydroxy-3-methylcyclohexylamino)-2-(isopropylamino) pyrimidine-5-carboxamide | 308.2 | D |

TABLE 1-continued

| Cmpd. A- | Structure | NAME | MH+ | Act. Level |
|---|---|---|---|---|
| 339 | 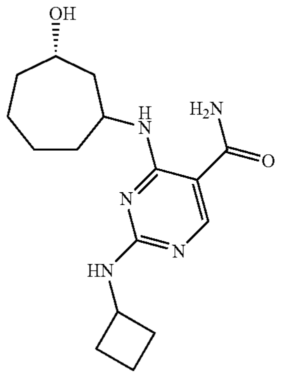 [SMILES: NC(=O)c1cnc(NC2CCC2)nc1NC1CCCC[C@H](O)C1] | 2-(cyclobutylamino)-4-((1R,3S)-3-hydroxycycloheptylamino) pyrimidine-5-carboxamide | 320.2 | D |
| 340 | 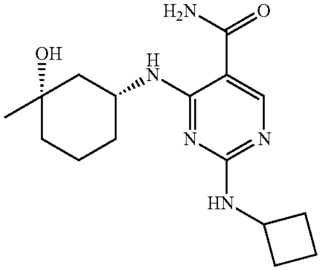 [SMILES: C[C@]1(O)CCC[C@@H](Nc2nc(NC3CCC3)ncc2C(N)=O)C1] | 2-(cyclobutylamino)-4-((1R,3S)-3-hydroxy-3-methylcyclohexylamino) pyrimidine-5-carboxamide | 320.2 | D |
| 341 | 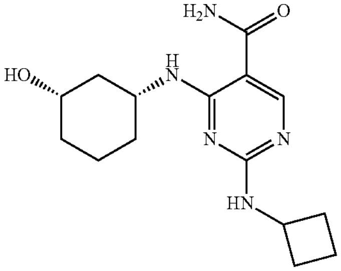 [SMILES: NC(=O)c1cnc(NC2CCC2)nc1N[C@@H]1CCC[C@H](O)C1] | 2-(cyclobutylamino)-4-((1R,3S)-3-hydroxycyclohexylamino) pyrimidine-5-carboxamide | 306.2 | D |
| 342 | 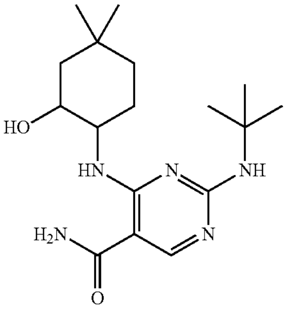 [SMILES: CC1(C)CCC(Nc2nc(NC(C)(C)C)ncc2C(N)=O)C(O)C1] | 2-(tert-butylamino)-4-(2-hydroxy-4,4-dimethylcyclohexylamino) pyrimidine-5-carboxamide | 336.2 | C |
| 343 | 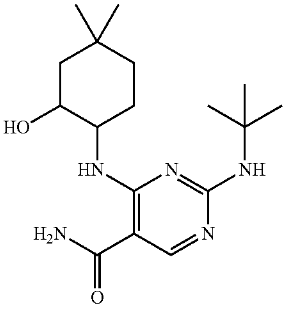 [SMILES: CC1(C)CCC(Nc2nc(NC(C)(C)C)ncc2C(N)=O)C(O)C1] | 2-(tert-butylamino)-4-(2-hydroxy-4,4-dimethylcyclohexylamino) pyrimidine-5-carboxamide | 336.2 | D |

TABLE 1-continued

| Cmpd. A- | Structure | NAME | MH+ | Act. Level |
|---|---|---|---|---|
| 344 | 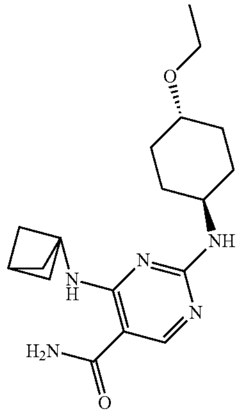 [SMILES: CCO[C@H]1CC[C@H](Nc2ncc(C(N)=O)c(NC34CC(C3)C4)n2)CC1] | 4-(bicyclo[1.1.1]pentan-1-ylamino)-2-((1r,4r)-4-ethoxycyclohexylamino)pyrimidine-5-carboxamide | 346.4 | D |
| 345 | 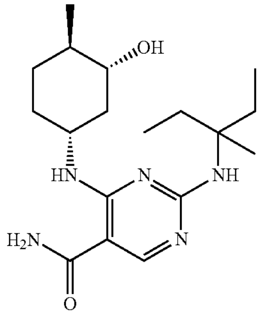 [SMILES: CCC(C)(CC)Nc1ncc(C(N)=O)c(N[C@@H]2CC[C@@H](C)[C@H](O)C2)n1] | 4-((1R,3R,4R)-3-hydroxy-4-methylcyclohexylamino)-2-(3-methylpentan-3-ylamino)pyrimidine-5-carboxamide | 350.5 | D |
| 346 | 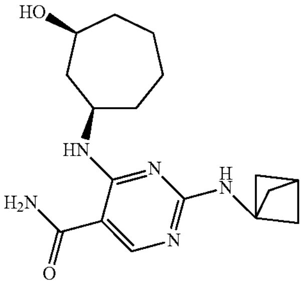 [SMILES: NC(=O)c1cnc(NC23CC(C2)C3)nc1N[C@@H]1CCCC[C@H](O)C1] | 2-(bicyclo[1.1.1]pentan-1-ylamino)-4-((1R,3S)-3-hydroxycycloheptylamino)pyrimidine-5-carboxamide | 332.2 | D |
| 347 | 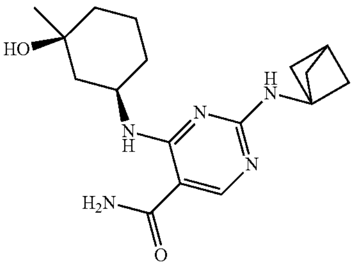 [SMILES: C[C@]1(O)CCC[C@@H](Nc2nc(NC34CC(C3)C4)ncc2C(N)=O)C1] | 2-(bicyclo[1.1.1]pentan-1-ylamino)-4-((1R,3S)-3-hydroxy-3-methylcyclohexylamino)pyrimidine-5-carboxamide | 332.2 | D |
| 348 | 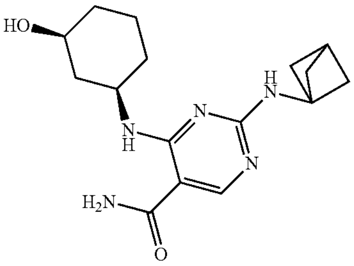 [SMILES: NC(=O)c1cnc(NC23CC(C2)C3)nc1N[C@@H]1CCC[C@H](O)C1] | 2-(bicyclo[1.1.1]pentan-1-ylamino)-4-((1R,3S)-3-hydroxycyclohexylamino)pyrimidine-5-carboxamide | 318.1 | D |

TABLE 1-continued

| Cmpd. A- | Structure | NAME | MH+ | Act. Level |
|---|---|---|---|---|
| 349 | 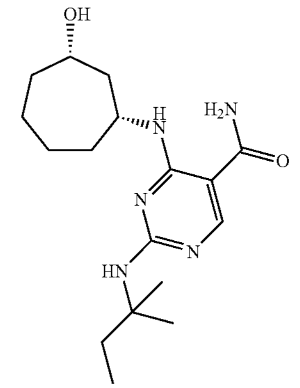 [SMILES: CCC(C)(C)Nc1ncc(C(N)=O)c(N[C@@H]2CCCC[C@H](O)C2)n1] | 4-((1R,3S)-3-hydroxycycloheptylamino)-2-(tert-pentylamino) pyrimidine-5-carboxamide | 336.2 | D |
| 350 | 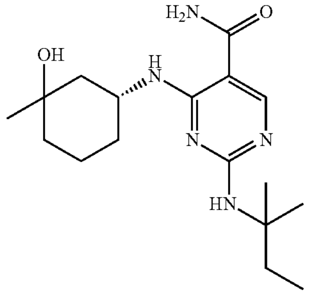 [SMILES: CCC(C)(C)Nc1ncc(C(N)=O)c(N[C@@H]2CCCC(C)(O)C2)n1] | 4-((1R,3S)-3-hydroxy-3-methylcyclohexylamino)-2-(tert-pentylamino) pyrimidine-5-carboxamide | 336.2 | D |
| 351 | 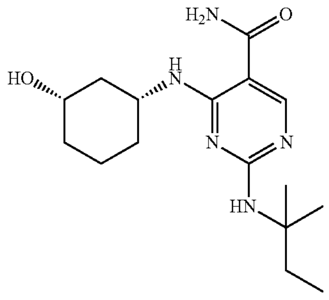 [SMILES: CCC(C)(C)Nc1ncc(C(N)=O)c(N[C@@H]2CCC[C@H](O)C2)n1] | 4-((1R,3S)-3-hydroxycyclohexylamino)-2-(tert-pentylamino) pyrimidine-5-carboxamide | 332.2 | D |
| 352 | 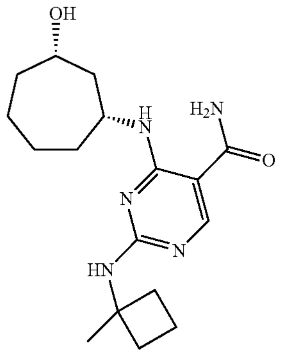 [SMILES: CC1(Nc2ncc(C(N)=O)c(N[C@@H]3CCCC[C@H](O)C3)n2)CCC1] | 4-((1R,3S)-3-hydroxycycloheptylamino)-2-(1-methylcyclobutylamino) pyrimidine-5-carboxamide | 334.2 | D |

TABLE 1-continued

| Cmpd. A- | Structure | NAME | MH⁺ | Act. Level |
|---|---|---|---|---|
| 353 | 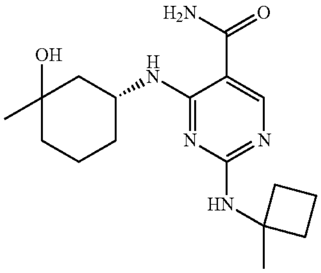 [SMILES: CC1(O)CCC[C@@H](Nc2nc(NC3(C)CCC3)ncc2C(N)=O)C1] | 4-((1R,3S)-3-hydroxy-3-methylcyclohexylamino)-2-(1-methylcyclobutylamino) pyrimidine-5-carboxamide | 334.2 | D |
| 354 | 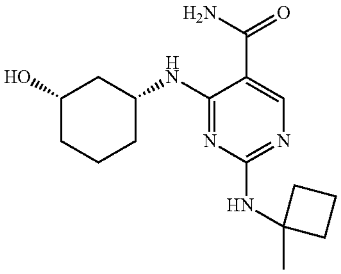 [SMILES: CC1(Nc2ncc(C(N)=O)c(N[C@@H]3CCC[C@H](O)C3)n2)CCC1] | 4-((1R,3S)-3-hydroxycyclohexylamino)-2-(1-methylcyclobutylamino) pyrimidine-5-carboxamide | 320.2 | D |
| 355 | 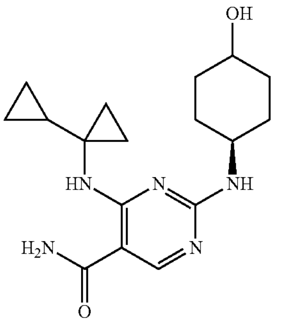 | 4-(bi(cycloprop)ylamino)-2-((1r,4r)-4-hydroxycyclohexylamino) pyrimidine-5-carboxamide | 332.4 | D |
| 356 | 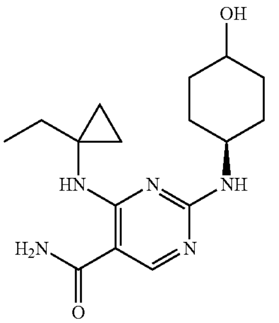 | 4-(1-ethylcyclopropylamino)-2-((1r,4r)-4-hydroxycyclohexylamino) pyrimidine-5-carboxamide | 320.3 | D |
| 357 | 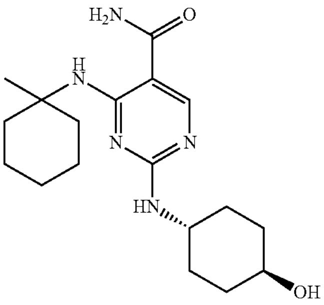 [SMILES: CC1(Nc2nc(N[C@H]3CC[C@H](O)CC3)ncc2C(N)=O)CCCCC1] | 2-((1r,4r)-4-hydroxycyclohexylamino)-4-(1-methylcyclohexylamino) pyrimidine-5-carboxamide | 348.2 | D |

TABLE 1-continued

| Cmpd. A- | Structure | NAME | MH+ | Act. Level |
|---|---|---|---|---|
| 358 | 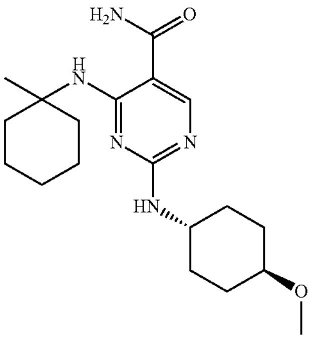 | 2-((1r,4r)-4-methoxycyclohexylamino)-4-(1-methylcyclohexylamino) pyrimidine-5-carboxamide | 362.2 | D |
| 359 | 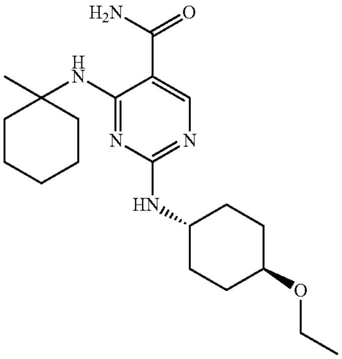 [SMILES: CCO[C@H]1CC[C@H](Nc2ncc(C(N)=O)c(NC3(C)CCCCC3)n2)CC1] | 2-((1r,4r)-4-ethoxycyclohexylamino)-4-(1-methylcyclohexylamino) pyrimidine-5-carboxamide | 376.3 | D |
| 360 | 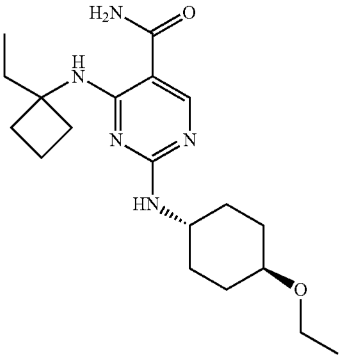 [SMILES: CCO[C@H]1CC[C@H](Nc2ncc(C(N)=O)c(NC3(CC)CCC3)n2)CC1] | 2-((1r,4r)-4-ethoxycyclohexylamino)-4-(1-ethylcyclobutylamino) pyrimidine-5-carboxamide | 362.2 | D |
| 361 | 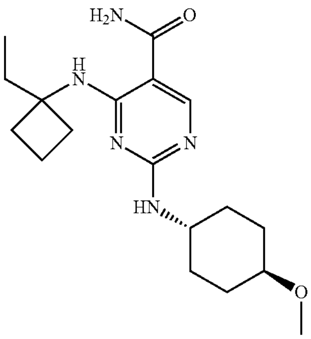 [SMILES: CCC1(Nc2nc(N[C@H]3CC[C@H](OC)CC3)ncc2C(N)=O)CCC1] | 4-(1-ethylcyclobutylamino)-2-((1r,4r)-4-methoxycyclohexylamino) pyrimidine-5-carboxamide | 348.2 | D |

TABLE 1-continued

| Cmpd. A- | Structure | NAME | MH⁺ | Act. Level |
|---|---|---|---|---|
| 362 | 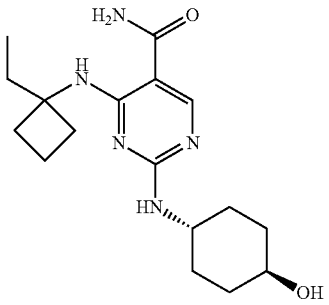 [SMILES: CCC1(Nc2nc(N[C@H]3CC[C@H](O)CC3)ncc2C(N)=O)CCC1] | 4-(1-ethylcyclobutylamino)-2-((1r,4r)-4-hydroxycyclohexylamino) pyrimidine-5-carboxamide | 334.2 | D |
| 363 | 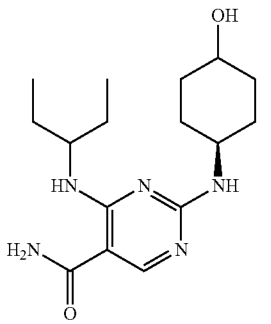 | 2-((1r,4r)-4-hydroxycyclohexylamino)-4-(pentan-3-ylamino)pyrimidine-5-carboxamide | 322.4 | D |
| 364 | 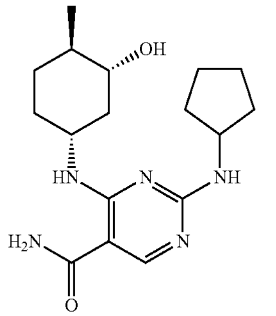 [SMILES: C[C@@H]1CC[C@@H](Nc2nc(NC3CCCC3)ncc2C(N)=O)C[C@H]1O] | 2-(cyclopentylamino)-4-((1R,3R,4R)-3-hydroxy-4-methylcyclohexylamino) pyrimidine-5-carboxamide | 334.2 | D |
| 365 | 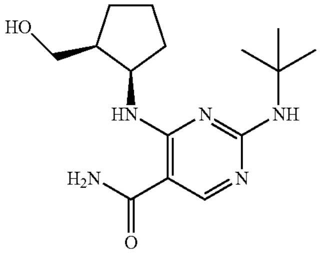 [SMILES: CC(C)(C)Nc1ncc(C(N)=O)c(N[C@@H]2CCC[C@@H]2CO)n1] | 2-(tert-butylamino)-4-((1R,2S)-2-(hydroxymethyl) cyclopentylamino) pyrimidine-5-carboxamide | 308.3 | D |
| 366 | 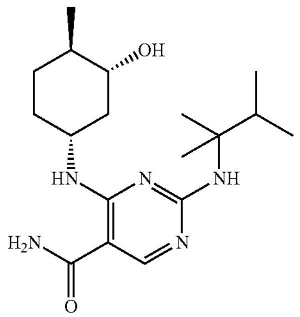 [SMILES: CC(C)C(C)(C)Nc1ncc(C(N)=O)c(N[C@@H]2CC[C@@H](C)[C@H](O)C2)n1] | 2-(2,3-dimethylbutan-2-ylamino)-4-((1R,3R,4R)-3-hydroxy-4-methylcyclohexylamino) pyrimidine-5-carboxamide | 350.4 | D |

TABLE 1-continued

| Cmpd. A- | Structure | NAME | MH+ | Act. Level |
|---|---|---|---|---|
| 367 | 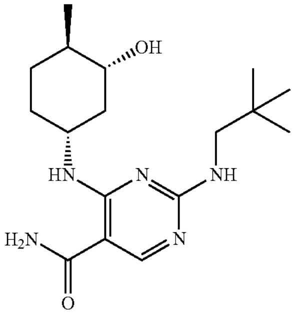 [SMILES: C[C@@H]1CC[C@@H](Nc2nc(NCC(C)(C)C)ncc2C(N)=O)C[C@H]1O] | 4-((1R,3R,4R)-3-hydroxy-4-methylcyclohexylamino)-2-(neopentylamino) pyrimidine-5-carboxamide | 336.2 | D |
| 368 | 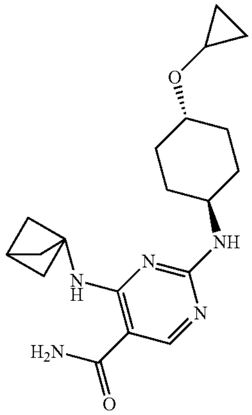 [SMILES: NC(=O)c1cnc(N[C@H]2CC[C@H](OC3CC3)CC2)nc1NC12CC(C1)C2] | 4-(bicyclo[1.1.1]pentan-1-ylamino)-2-((1r,4r)-4-cyclopropoxycyclohexylamino) pyrimidine-5-carboxamide | 358.3 | D |
| 369 | 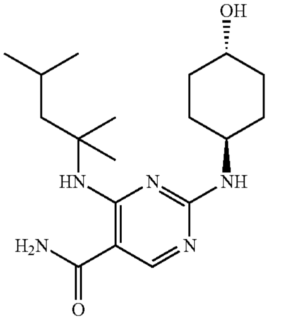 [SMILES: CC(C)CC(C)(C)Nc1nc(N[C@H]2CC[C@H](O)CC2)ncc1C(N)=O] | 4-(2,4-dimethylpentan-2-ylamino)-2-((1r,4r)-4-hydroxycyclohexylamino) pyrimidine-5-carboxamide | 350.3 | D |
| 370 | 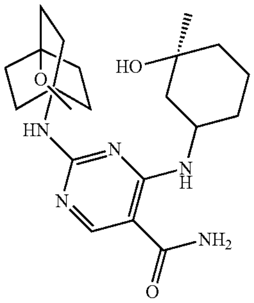 [SMILES: COC12CCC(Nc3ncc(C(N)=O)c(NC4CCC[C@](C)(O)C4)n3)(CC1)CC2] | 4-((3S)-3-hydroxy-3-methylcyclohexylamino)-2-(4-methoxybicyclo[2.2.2]octan-1-ylamino)pyrimidine-5-carboxamide | 404.4 | D |

TABLE 1-continued

| Cmpd. A- | Structure | NAME | MH+ | Act. Level |
|---|---|---|---|---|
| 371 | 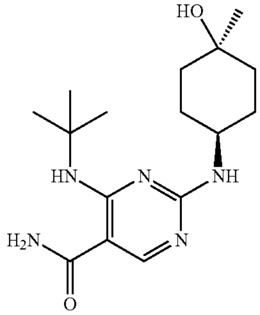 [SMILES: CC(C)(C)Nc1nc(N[C@H]2CC[C@@](C)(O)CC2)ncc1C(N)=O] | 4-(tert-butylamino)-2-((1s,4s)-4-hydroxy-4-methylcyclohexylamino) pyrimidine-5-carboxamide | 322.2 | D |
| 372 | 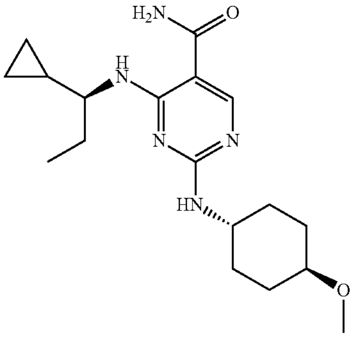 [SMILES: CC[C@H](Nc1nc(N[C@H]2CC[C@H](OC)CC2)ncc1C(N)=O)C1CC1] | 4-((S)-1-cyclopropylpropylamino)-2-((1r,4S)-4-methoxycyclohexylamino) pyrimidine-5-carboxamide | 348.2 | D |
| 373 | 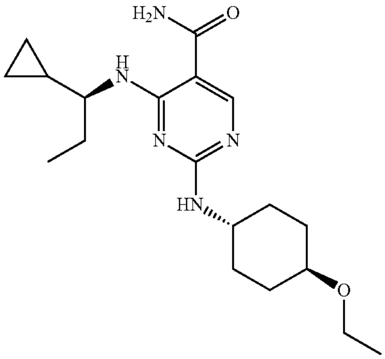 [SMILES: CCO[C@H]1CC[C@H](Nc2ncc(C(N)=O)c(N[C@@H](CC)C3CC3)n2)CC1] | 4-((S)-1-cyclopropylpropylamino)-2-((1r,4S)-4-ethoxycyclohexylamino) pyrimidine-5-carboxamide | 362.2 | D |
| 374 | 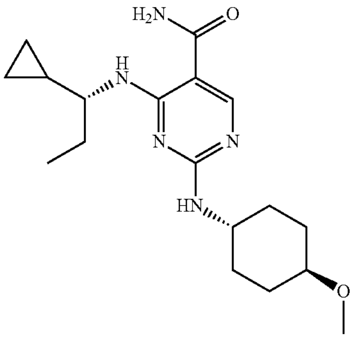 [SMILES: CC[C@@H](Nc1nc(N[C@H]2CC[C@H](OC)CC2)ncc1C(N)=O)C1CC1] | 4-((R)-1-cyclopropylpropylamino)-2-((1r,4R)-4-methoxycyclohexylamino) pyrimidine-5-carboxamide | 348.2 | D |

TABLE 1-continued

| Cmpd. A- | Structure | NAME | MH+ | Act. Level |
|---|---|---|---|---|
| 375 | 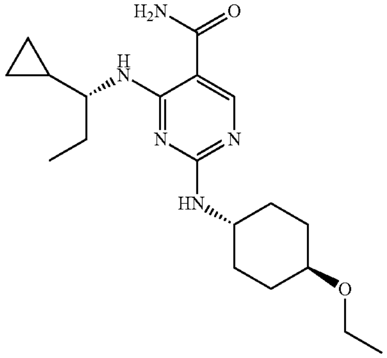 [SMILES: CCO[C@H]1CC[C@H](Nc2ncc(C(N)=O)c(N[C@H](CC)C3CC3)n2)CC1] | 4-((R)-1-cyclopropylpropylamino)-2-((1r,4R)-4-ethoxycyclohexylamino) pyrimidine-5-carboxamide | 362.3 | D |
| 376 | 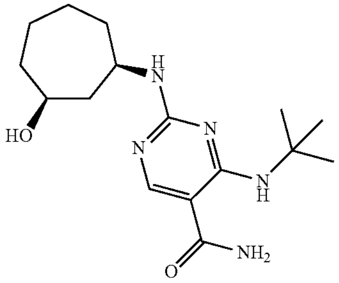 [SMILES: CC(C)(C)Nc1nc(N[C@@H]2CCCC[C@H](O)C2)ncc1C(N)=O] | 4-(tert-butylamino)-2-((1R,3S)-3-hydroxycycloheptylamino) pyrimidine-5-carboxamide | 322.2 | D |
| 377 | 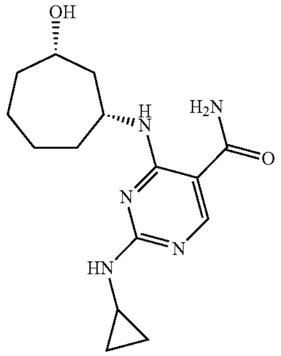 [SMILES: NC(=O)c1cnc(NC2CC2)nc1N[C@@H]1CCCC[C@H](O)C1] | 2-(cyclopropylamino)-4-((1R,3S)-3-hydroxycycloheptylamino) pyrimidine-5-carboxamide | 306.2 | D |
| 378 | 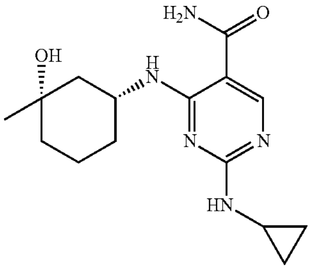 [SMILES: C[C@]1(O)CCC[C@@H](Nc2nc(NC3CC3)ncc2C(N)=O)C1] | 2-(cyclopropylamino)-4-((1R,3S)-3-hydroxy-3-methylcyclohexylamino) pyrimidine-5-carboxamide | 306.2 | D |
| 379 | 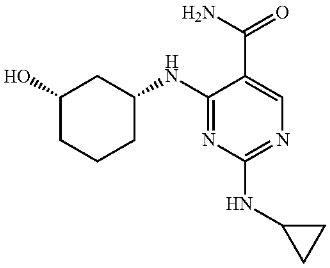 [SMILES: NC(=O)c1cnc(NC2CC2)nc1N[C@@H]1CCC[C@H](O)C1] | 2-(cyclopropylamino)-4-((1R,3S)-3-hydroxycyclohexylamino) pyrimidine-5-carboxamide | 292.1 | D |

TABLE 1-continued

| Cmpd. A- | Structure | NAME | MH+ | Act. Level |
|---|---|---|---|---|
| 380 | 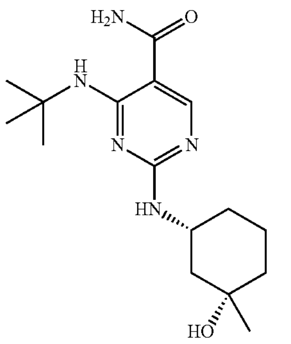 [SMILES: CC(C)(C)Nc1nc(N[C@@H]2CCC[C@](C)(O)C2)ncc1C(N)=O] | 4-(tert-butylamino)-2-((1R,3S)-3-hydroxy-3-methylcyclohexylamino) pyrimidine-5-carboxamide | 322.2 | D |
| 381 | 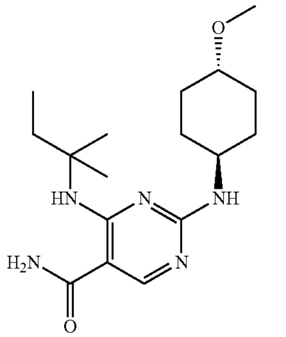 [SMILES: CCC(C)(C)Nc1nc(N[C@H]2CC[C@H](OC)CC2)ncc1C(N)=O] | 2-((1r,4r)-4-methoxycyclohexylamino)-4-(tert-pentylamino)pyrimidine-5-carboxamide | 336.2 | D |
| 382 | 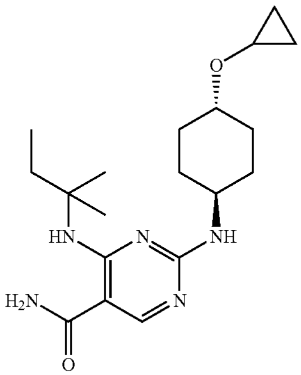 [SMILES: CCC(C)(C)Nc1nc(N[C@H]2CC[C@H](OC3CC3)CC2)ncc1C(N)=O] | 2-((1r,4r)-4-cyclopropoxycyclohexylamino)-4-(tert-pentylamino)pyrimidine-5-carboxamide | 362.3 | D |
| 383 | 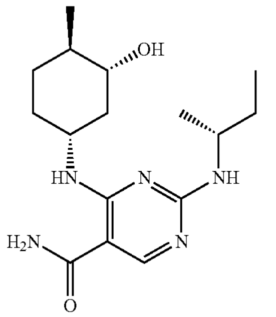 [SMILES: CC[C@@H](C)Nc1ncc(C(N)=O)c(N[C@@H]2CC[C@@H](C)[C@H](O)C2)n1] | 2-(sec-butylamino)-4-((1R,3R,4R)-3-hydroxy-4-methylcyclohexylamino) pyrimidine-5-carboxamide | 322.3 | D |

TABLE 1-continued

| Cmpd. A- | Structure | NAME | MH+ | Act. Level |
|---|---|---|---|---|
| 384 | 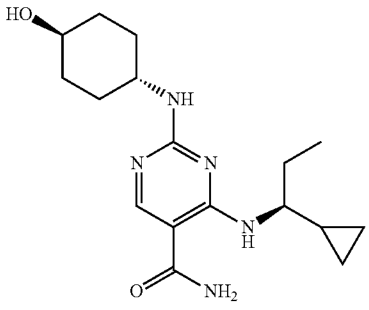 [SMILES: CC[C@H](Nc1nc(N[C@H]2CC[C@H](O)CC2)ncc1C(N)=O)C1CC1] | 4-((S)-1-cyclopropylpropylamino)-2-((1r,4S)-4-hydroxycyclohexylamino) pyrimidine-5-carboxamide | 334.2 | D |
| 385 | 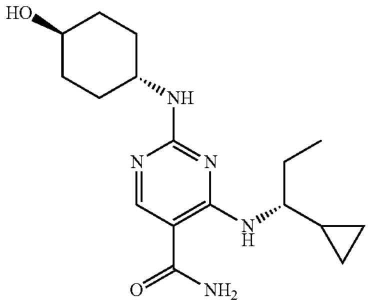 [SMILES: CC[C@@H](Nc1nc(N[C@H]2CC[C@H](O)CC2)ncc1C(N)=O)C1CC1] | 4-((R)-1-cyclopropylpropylamino)-2-((1r,4R)-4-hydroxycyclohexylamino) pyrimidine-5-carboxamide | 334.2 | D |
| 386 | 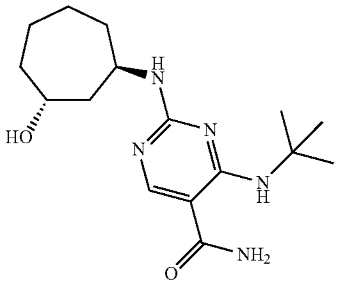 [SMILES: CC(C)(C)Nc1nc(N[C@@H]2CCCC[C@@H](O)C2)ncc1C(N)=O] | 4-(tert-butylamino)-2-((1R,3R)-3-hydroxycycloheptylamino) pyrimidine-5-carboxamide | 322.2 | D |
| 387 | 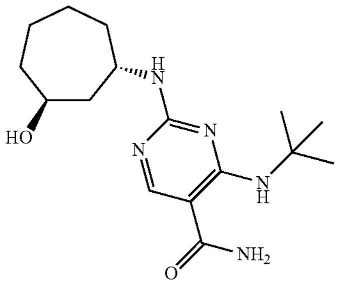 [SMILES: CC(C)(C)Nc1nc(N[C@H]2CCCC[C@H](O)C2)ncc1C(N)=O] | 4-(tert-butylamino)-2-((1S,3S)-3-hydroxycycloheptylamino) pyrimidine-5-carboxamide | 322.2 | D |
| 388 | 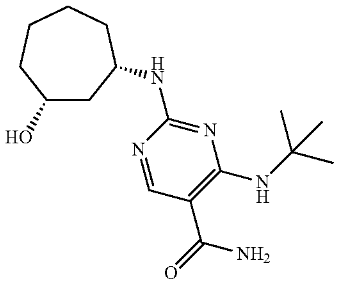 [SMILES: CC(C)(C)Nc1nc(N[C@H]2CCCC[C@@H](O)C2)ncc1C(N)=O] | 4-(tert-butylamino)-2-((1S,3R)-3-hydroxycycloheptylamino) pyrimidine-5-carboxamide | 322.2 | D |

TABLE 1-continued

| Cmpd. A- | Structure | NAME | MH+ | Act. Level |
|---|---|---|---|---|
| 389 | 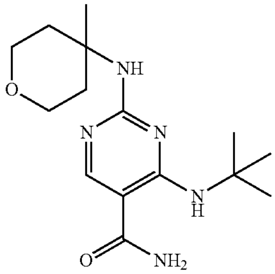 [SMILES: CC(C)(C)Nc1nc(NC2(C)CCOCC2)ncc1C(N)=O] | 4-(tert-butylamino)-2-(4-methyltetrahydro-2H-pyran-4-ylamino)pyrimidine-5-carboxamide | 308.2 | D |
| 390 | 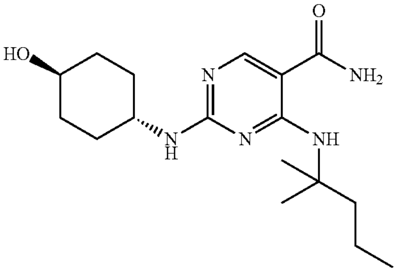 [SMILES: CCCC(C)(C)Nc1nc(N[C@H]2CC[C@H](O)CC2)ncc1C(N)=O] | 2-((1r,4r)-4-hydroxycyclohexylamino)-4-(2-methylpentan-2-ylamino)pyrimidine-5-carboxamide | 336.2 | D |
| 391 | 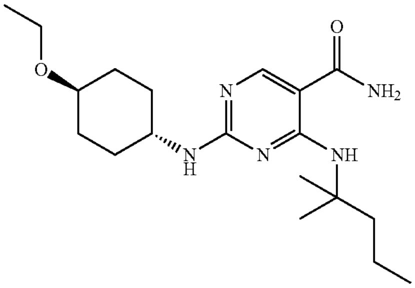 [SMILES: CCCC(C)(C)Nc1nc(N[C@H]2CC[C@H](OCC)CC2)ncc1C(N)=O] | 2-((1r,4r)-4-ethoxycyclohexylamino)-4-(2-methylpentan-2-ylamino)pyrimidine-5-carboxamide | 364.3 | D |
| 392 | 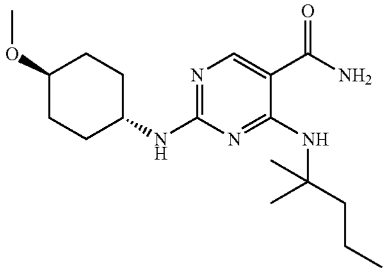 [SMILES: CCCC(C)(C)Nc1nc(N[C@H]2CC[C@H](OC)CC2)ncc1C(N)=O] | 2-((1r,4r)-4-methoxycyclohexylamino)-4-(2-methylpentan-2-ylamino)pyrimidine-5-carboxamide | 350.2 | D |
| 393 | 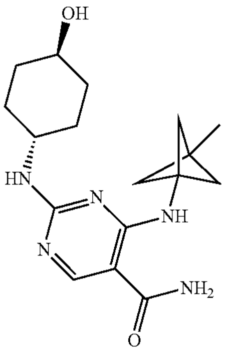 [SMILES: CC12CC(Nc3nc(N[C@H]4CC[C@H](O)CC4)ncc3C(N)=O)(C1)C2] | 2-((1r,4r)-4-hydroxycyclohexylamino)-4-(3-methylbicyclo[1.1.1]pentan-1-ylamino)pyrimidine-5-carboxamide | 332.3 | D |

TABLE 1-continued

| Cmpd. A- | Structure | NAME | MH+ | Act. Level |
|---|---|---|---|---|
| 394 | 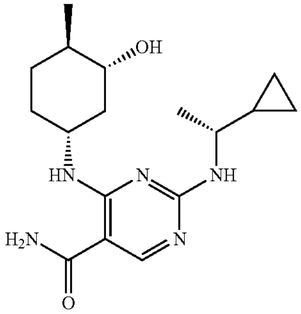 [SMILES: C[C@@H]1CC[C@@H](Nc2nc(N[C@H](C)C3CC3)ncc2C(N)=O)C[C@H]1O] | 2-((R)-1-cyclopropylethylamino)-4-((1R,3R,4R)-3-hydroxy-4-methylcyclohexylamino) pyrimidine-5-carboxamide | 334.4 | D |
| 395 | 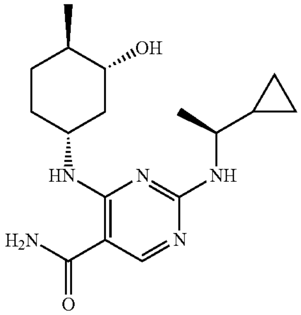 [SMILES: C[C@H](Nc1ncc(C(N)=O)c(N[C@@H]2CC[C@@H](C)[C@H](O)C2)n1)C1CC1] | 2-((S)-1-cyclopropylethylamino)-4-((1R,3R,4R)-3-hydroxy-4-methylcyclohexylamino) pyrimidine-5-carboxamide | 334.2 | D |
| 396 | 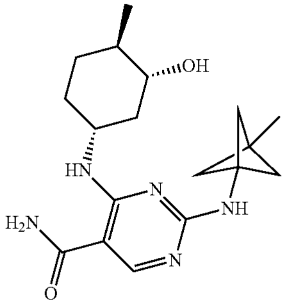 [SMILES: C[C@@H]1CC[C@@H](Nc2nc(NC34CC(C)(C3)C4)ncc2C(N)=O)C[C@H]1O] | 4-((1R,3R,4R)-3-hydroxy-4-methylcyclohexylamino)-2-(3-methylbicyclo[1.1.1] pentan-1-ylamino) pyrimidine-5-carboxamide | 346.3 | D |
| 397 | 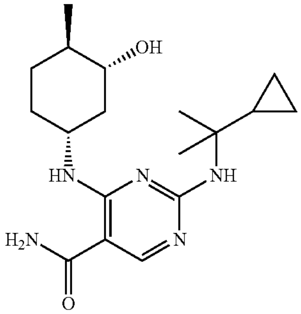 [SMILES: C[C@@H]1CC[C@@H](Nc2nc(NC(C)(C)C3CC3)ncc2C(N)=O)C[C@H]1O] | 2-(2-cyclopropylpropan-2-ylamino)-4-((1R,3R,4R)-3-hydroxy-4-methylcyclohexylamino) pyrimidine-5-carboxamide | 348.3 | D |
| 398 | 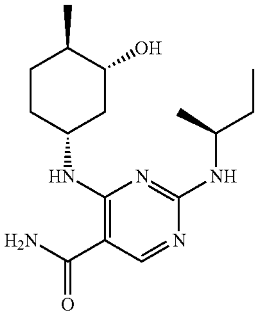 [SMILES: CC[C@H](C)Nc1ncc(C(N)=O)c(N[C@@H]2CC[C@@H](C)[C@H](O)C2)n1] | 2-(sec-butylamino)-4-((1R,3R,4R)-3-hydroxy-4-methylcyclohexylamino) pyrimidine-5-carboxamide | 322.3 | D |

TABLE 1-continued

| Cmpd. A- | Structure | NAME | MH+ | Act. Level |
|---|---|---|---|---|
| 399 | 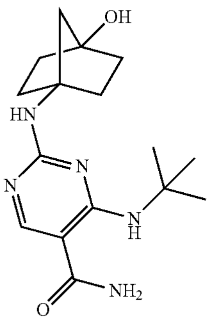 [SMILES: CC(C)(C)Nc1nc(NC23CCC(O)(CC2)C3)ncc1C(N)=O] | 4-(tert-butylamino)-2-(4-hydroxybicyclo[2.2.1]heptan-1-ylamino)pyrimidine-5-carboxamide | 320.2 | D |
| 400 | 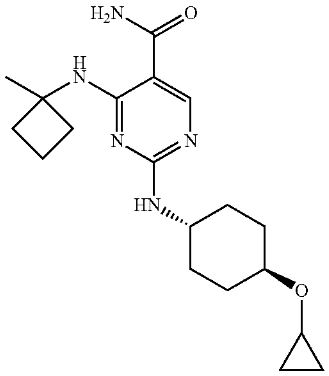 [SMILES: CC1(Nc2nc(N[C@H]3CC[C@H](OC4CC4)CC3)ncc2C(N)=O)CCC1] | 2-((1r,4r)-4-cyclopropoxycyclohexylamino)-4-(1-methylcyclobutylamino)pyrimidine-5-carboxamide | 360.2 | D |
| 401 | 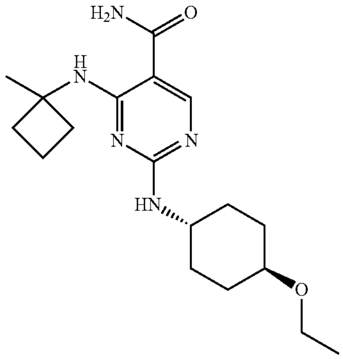 | 2-((1r,4r)-4-ethoxycyclohexylamino)-4-(1-methylcyclobutylamino)pyrimidine-5-carboxamide | 348.2 | D |
| 402 | 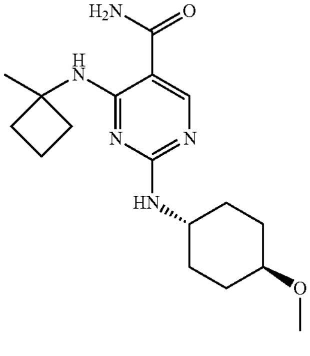 | 2-((1r,4r)-4-methoxycyclohexylamino)-4-(1-methylcyclobutylamino)pyrimidine-5-carboxamide | 334.2 | D |

TABLE 1-continued

| Cmpd. A- | Structure | NAME | MH+ | Act. Level |
|---|---|---|---|---|
| 403 | 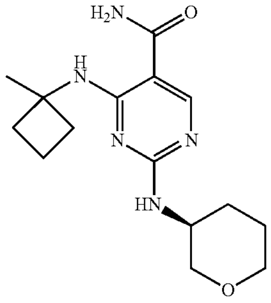 [SMILES: CC1(Nc2nc(N[C@H]3CCCOC3)ncc2C(N)=O)CCC1] | (S)-4-(1-methylcyclobutylamino)-2-(tetrahydro-2H-pyran-3-ylamino)pyrimidine-5-carboxamide | 306.2 | D |
| 404 | 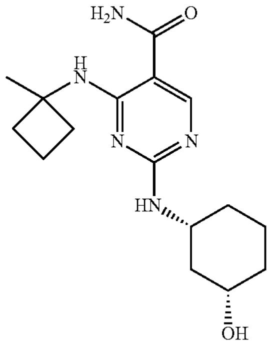 [SMILES: CC1(Nc2nc(N[C@@H]3CCC[C@H](O)C3)ncc2C(N)=O)CCC1] | 2-((1R,3S)-3-hydroxycyclohexylamino)-4-(1-methylcyclobutylamino) pyrimidine-5-carboxamide | 320.2 | D |
| 405 | 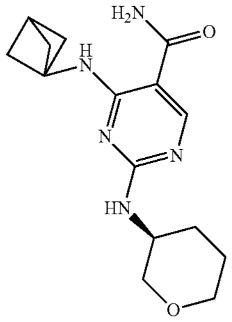 [SMILES: NC(=O)c1cnc(N[C@H]2CCCOC2)nc1NC12CC(C1)C2] | (S)-4-(bicyclo[1.1.1]pentan-1-ylamino)-2-(tetrahydro-2H-pyran-3-ylamino)pyrimidine-5-carboxamide | 304.2 | D |
| 406 | 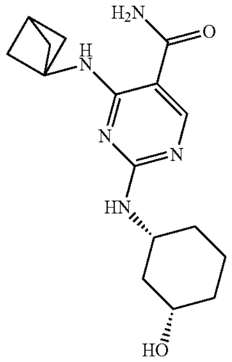 [SMILES: NC(=O)c1cnc(N[C@@H]2CCC[C@H](O)C2)nc1NC12CC(C1)C2] | 4-(bicyclo[1.1.1]pentan-1-ylamino)-2-((1R,3S)-3-hydroxycyclohexylamino) pyrimidine-5-carboxamide | 318.2 | D |

TABLE 1-continued

| Cmpd. A- | Structure | NAME | MH+ | Act. Level |
|---|---|---|---|---|
| 407 | 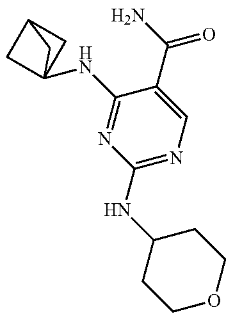 [SMILES: NC(=O)c1cnc(NC2CCOCC2)nc1NC12CC(C1)C2] | 4-(bicyclo[1.1.1]pentan-1-ylamino)-2-(tetrahydro-2H-pyran-4-ylamino)pyrimidine-5-carboxamide | 304.2 | D |
| 408 | 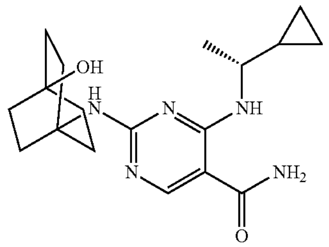 [SMILES: C[C@@H](Nc1nc(NC23CCC(O)(CC2)CC3)ncc1C(N)=O)C1CC1] | (R)-4-(1-cyclopropylethylamino)-2-(4-hydroxybicyclo[2.2.2]octan-1-ylamino)pyrimidine-5-carboxamide | 346.2 | D |
| 409 | 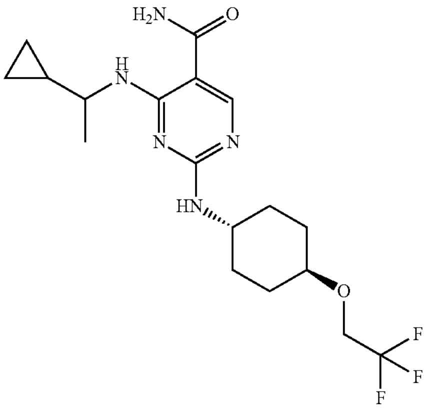 [SMILES: CC(Nc1nc(N[C@H]2CC[C@H](OCC(F)(F)F)CC2)ncc1C(N)=O)C1CC1] | 4-((R)-1-cyclopropylethylamino)-2-((1r,4R)-4-(2,2,2-trifluoroethoxy)cyclohexylamino)pyrimidine-5-carboxamide | 402.2 | D |
| 410 | 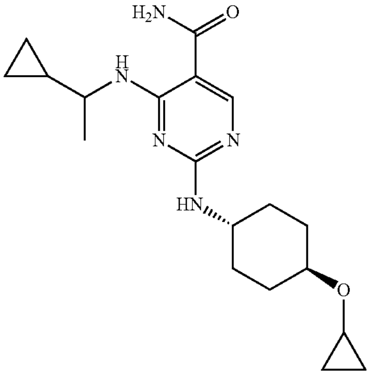 [SMILES: CC(Nc1nc(N[C@H]2CC[C@H](OC3CC3)CC2)ncc1C(N)=O)C1CC1] | 2-((1r,4R)-4-cyclopropoxycyclohexylamino)-4-((R)-1-cyclopropylethylamino)pyrimidine-5-carboxamide | 360.2 | D |

TABLE 1-continued

| Cmpd. A- | Structure | NAME | MH+ | Act. Level |
|---|---|---|---|---|
| 411 | 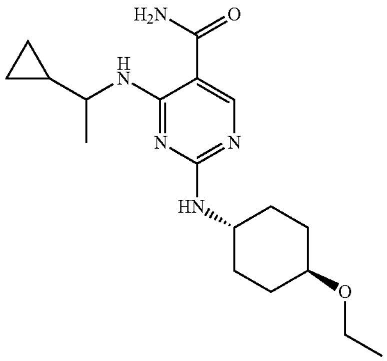 [SMILES: CCO[C@H]1CC[C@H](Nc2ncc(C(N)=O)c(NC(C)C3CC3)n2)CC1] | 4-((R)-1-cyclopropylethylamino)-2-((1r,4R)-4-ethoxycyclohexylamino)pyrimidine-5-carboxamide | 348.2 | D |
| 412 | 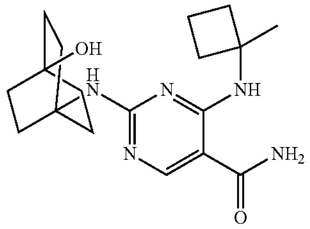 [SMILES: CC1(Nc2nc(NC34CCC(O)(CC3)CC4)ncc2C(N)=O)CCC1] | 2-(4-hydroxybicyclo[2.2.2]octan-1-ylamino)-4-(1-methylcyclobutylamino)pyrimidine-5-carboxamide | 346.2 | D |
| 413 | 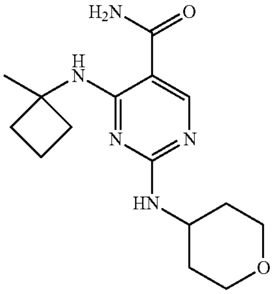 [SMILES: CC1(Nc2nc(NC3CCOCC3)ncc2C(N)=O)CCC1] | 4-(1-methylcyclobutylamino)-2-(tetrahydro-2H-pyran-4-ylamino)pyrimidine-5-carboxamide | 306.2 | D |
| 414 | 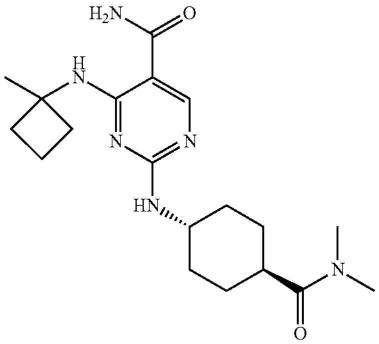 | 2-((1r,4r)-4-(dimethylcarbamoyl)cyclohexylamino)-4-(1-methylcyclobutylamino)pyrimidine-5-carboxamide | 375.2 | D |

TABLE 1-continued

| Cmpd. A- | Structure | NAME | MH+ | Act. Level |
|---|---|---|---|---|
| 415 | 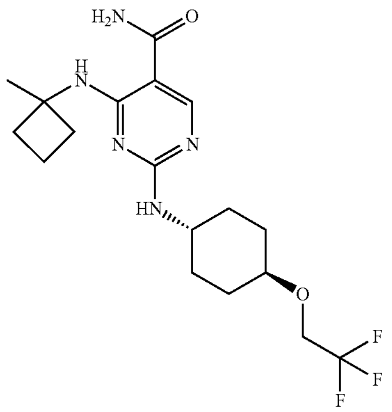 [SMILES: CC1(Nc2nc(N[C@H]3CC[C@H](OCC(F)(F)F)CC3)ncc2C(N)=O)CCC1] | 4-(1-methylcyclobutylamino)-2-((1r,4r)-4-(2,2,2-trifluoroethoxy) cyclohexylamino)pyrimidine-5-carboxamide | 402.2 | D |
| 416 | 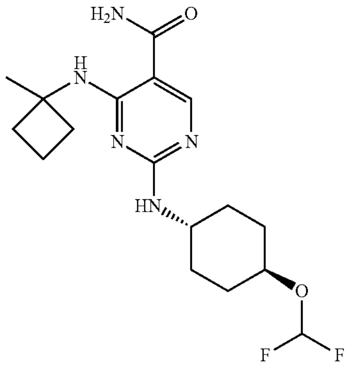 [SMILES: CC1(Nc2nc(N[C@H]3CC[C@H](OC(F)F)CC3)ncc2C(N)=O)CCC1] | 2-((1r,4r)-4-(difluoromethoxy) cyclohexylamino)-4-(1-methylcyclobutylamino) pyrimidine-5-carboxamide | 370.2 | D |
| 417 | 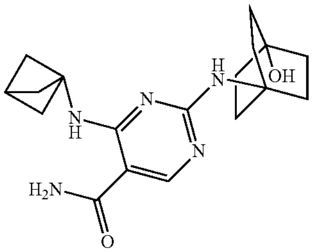 [SMILES: NC(=O)c1cnc(NC23CCC(O)(CC2)CC3)nc1NC12CC(C1)C2] | 4-(bicyclo[1.1.1]pentan-1-ylamino)-2-(4-hydroxybicyclo[2.2.2]octan-1-ylamino)pyrimidine-5-carboxamide | 344.2 | D |
| 418 | 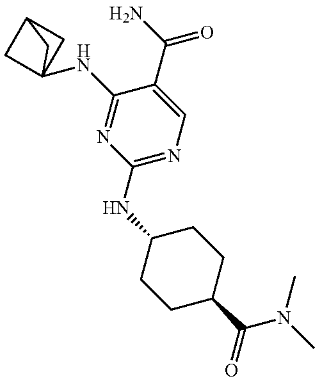 [SMILES: CN(C)C(=O)[C@H]1CC[C@H](Nc2ncc(C(N)=O)c(NC34CC(C3)C4)n2)CC1] | 4-(bicyclo[1.1.1]pentan-1-ylamino)-2-((1r,4r)-4-(dimethylcarbamoyl) cyclohexylamino)pyrimidine-5-carboxamide | 373.3 | D |

TABLE 1-continued

| Cmpd. A- | Structure | NAME | MH+ | Act. Level |
|---|---|---|---|---|
| 419 | 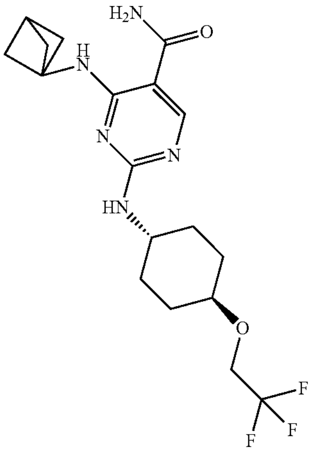 [SMILES: NC(=O)c1cnc(N[C@H]2CC[C@H](OCC(F)(F)F)CC2)nc1NC12CC(C1)C2] | 4-(bicyclo[1.1.1]pentan-1-ylamino)-2-((1r,4r)-4-(2,2,2-trifluoroethoxy) cyclohexylamino)pyrimidine-5-carboxamide | 400.2 | D |
| 420 | 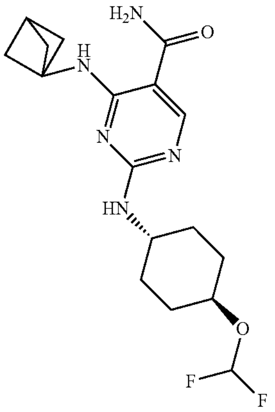 [SMILES: NC(=O)c1cnc(N[C@H]2CC[C@H](OC(F)F)CC2)nc1NC12CC(C1)C2] | 4-(bicyclo[1.1.1]pentan-1-ylamino)-2-((1r,4r)-4-(difluoromethoxy) cyclohexylamino)pyrimidine-5-carboxamide | 368.2 | D |
| 421 | 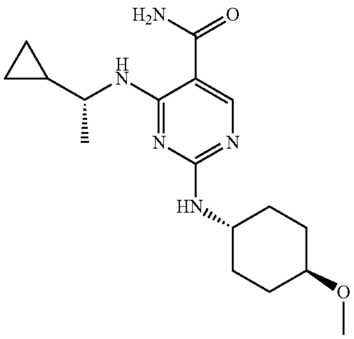 [SMILES: CO[C@H]1CC[C@H](Nc2ncc(C(N)=O)c(N[C@H](C)C3CC3)n2)CC1] | 4-((R)-1-cyclopropylethylamino)-2-((1r,4R)-4-methoxycyclohexylamino) pyrimidine-5-carboxamide | 334.2 | D |
| 422 | 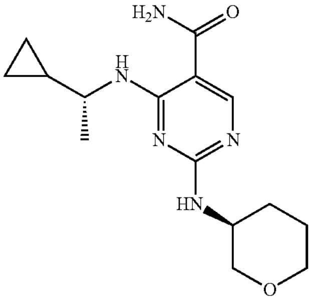 [SMILES: C[C@@H](Nc1nc(N[C@H]2CCCOC2)ncc1C(N)=O)C1CC1] | 4-((R)-1-cyclopropylethylamino)-2-((S)-tetrahydro-2H-pyran-3-ylamino)pyrimidine-5-carboxamide | 306.2 | D |

TABLE 1-continued

| Cmpd. A- | Structure | NAME | MH+ | Act. Level |
|---|---|---|---|---|
| 423 | 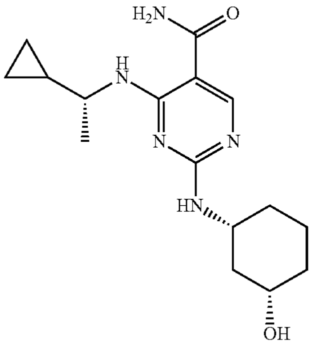 [SMILES: C[C@@H](Nc1nc(N[C@@H]2CCC[C@H](O)C2)ncc1C(N)=O)C1CC1] | 4-((R)-1-cyclopropylethylamino)-2-((1R,3S)-3-hydroxycyclohexylamino) pyrimidine-5-carboxamide | 320.2 | D |
| 424 | 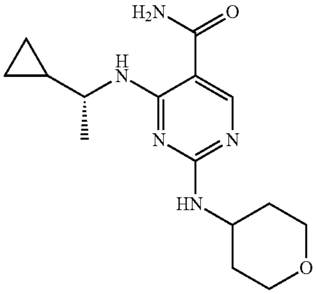 [SMILES: C[C@@H](Nc1nc(NC2CCOCC2)ncc1C(N)=O)C1CC1] | (R)-4-(1-cyclopropylethylamino)-2-(tetrahydro-2H-pyran-4-ylamino)pyrimidine-5-carboxamide | 306.2 | D |
| 425 | 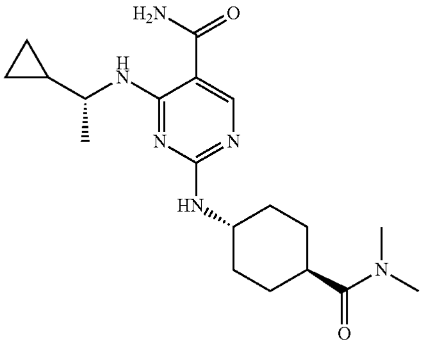 [SMILES: C[C@@H](Nc1nc(N[C@H]2CC[C@H](C(=O)N(C)C)CC2)ncc1C(N)=O)C1CC1] | 4-((R)-1-cyclopropylethylamino)-2-((1r,4R)-4-(dimethylcarbamoyl) cyclohexylamino)pyrimidine-5-carboxamide | 375.2 | D |
| 426 | 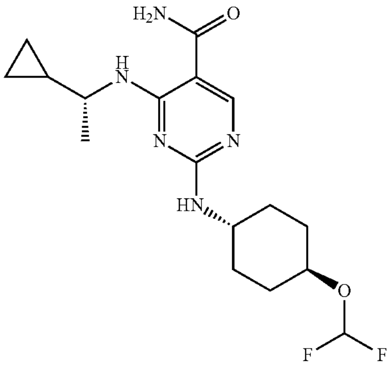 [SMILES: C[C@@H](Nc1nc(N[C@H]2CC[C@H](OC(F)F)CC2)ncc1C(N)=O)C1CC1] | 4-((R)-1-cyclopropylethylamino)-2-((1r,4R)-4-(difluoromethoxy) cyclohexylamino)pyrimidine-5-carboxamide | 370.2 | D |

TABLE 1-continued

| Cmpd. A- | Structure | NAME | MH+ | Act. Level |
|---|---|---|---|---|
| 427 | 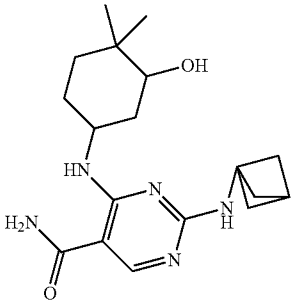 [SMILES: CC1(C)CCC(Nc2nc(NC34CC(C3)C4)ncc2C(N)=O)CC1O] | 2-(bicyclo[1.1.1]pentan-1-ylamino)-4-(3-hydroxy-4,4-dimethylcyclohexylamino) pyrimidine-5-carboxamide | 346.3 | C |
| 428 | 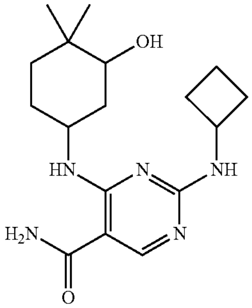 [SMILES: CC1(C)CCC(Nc2nc(NC3CCC3)ncc2C(N)=O)CC1O] | 2-(cyclobutylamino)-4-(3-hydroxy-4,4-dimethylcyclohexylamino) pyrimidine-5-carboxamide | 334.2 | D |
| 429 | 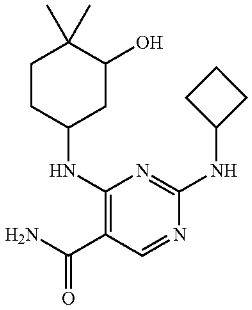 [SMILES: CC1(C)CCC(Nc2nc(NC3CCC3)ncc2C(N)=O)CC1O] | 2-(cyclobutylamino)-4-(3-hydroxy-4,4-dimethylcyclohexylamino) pyrimidine-5-carboxamide | 334.2 | D |
| 430 | 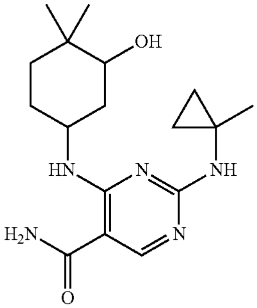 [SMILES: CC1(Nc2ncc(C(N)=O)c(NC3CCC(C)(C)C(O)C3)n2)CC1] | 4-(3-hydroxy-4,4-dimethylcyclohexylamino)-2-(1-methylcyclopropylamino) pyrimidine-5-carboxamide | 334.2 | D |
| 431 | 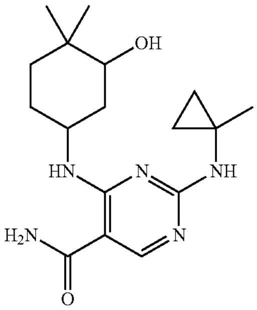 [SMILES: CC1(Nc2ncc(C(N)=O)c(NC3CCC(C)(C)C(O)C3)n2)CC1] | 4-(3-hydroxy-4,4-dimethylcyclohexylamino)-2-(1-methylcyclopropylamino) pyrimidine-5-carboxamide | 334.2 | D |

TABLE 1-continued

| Cmpd. A- | Structure | NAME | MH+ | Act. Level |
|---|---|---|---|---|
| 432 | 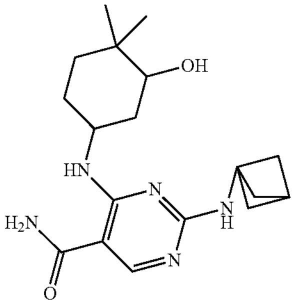 [SMILES: CC1(C)CCC(Nc2nc(NC34CC(C3)C4)ncc2C(N)=O)CC1O] | 2-(bicyclo[1.1.1]pentan-1-ylamino)-4-(3-hydroxy-4,4-dimethylcyclohexylamino) pyrimidine-5-carboxamide | 346.3 | D |
| 433 | 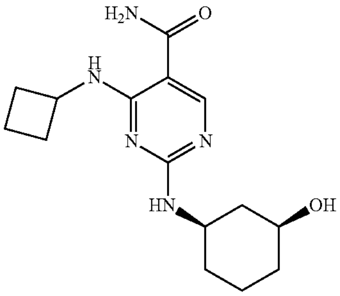 [SMILES: NC(=O)c1cnc(N[C@@H]2CCC[C@H](O)C2)nc1NC1CCC1] | 4-(cyclobutylamino)-2-((1R,3S)-3-hydroxycyclohexylamino) pyrimidine-5-carboxamide | 306.2 | D |
| 434 | 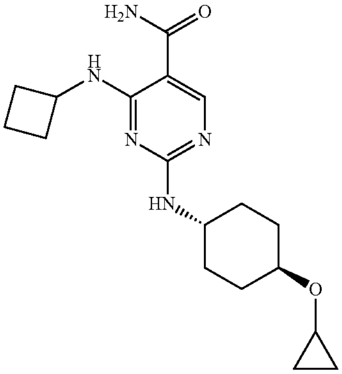 [SMILES: NC(=O)c1cnc(N[C@H]2CC[C@H](OC3CC3)CC2)nc1NC1CCC1] | 4-(cyclobutylamino)-2-((1r,4r)-4-cyclopropoxycyclohexylamino) pyrimidine-5-carboxamide | 346.2 | D |
| 435 | 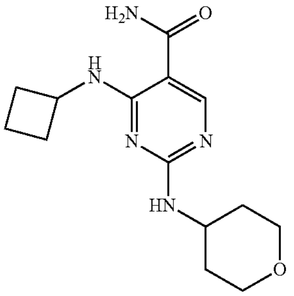 [SMILES: NC(=O)c1cnc(NC2CCOCC2)nc1NC1CCC1] | 4-(cyclobutylamino)-2-(tetrahydro-2H-pyran-4-ylamino)pyrimidine-5-carboxamide | 292.2 | D |

TABLE 1-continued

| Cmpd. A- | Structure | NAME | MH+ | Act. Level |
|---|---|---|---|---|
| 436 | 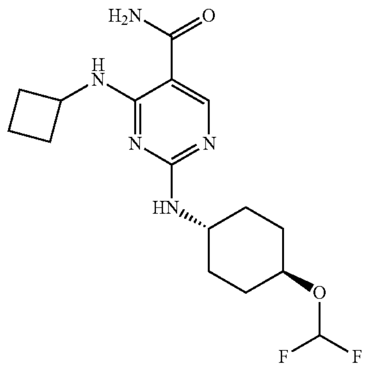 [SMILES: NC(=O)c1cnc(N[C@H]2CC[C@H](OC(F)F)CC2)nc1NC1CCC1] | 4-(cyclobutylamino)-2-((1r,4r)-4-(difluoromethoxy) cyclohexylamino) pyrimidine-5-carboxamide | 356.2 | D |
| 437 | 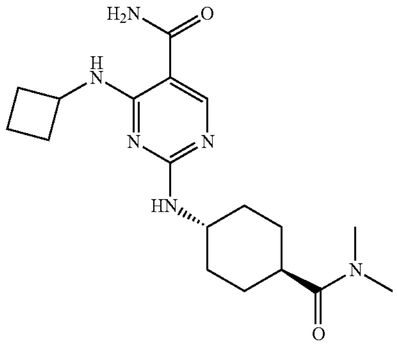 [SMILES: CN(C)C(=O)[C@H]1CC[C@H](Nc2ncc(C(N)=O)c(NC3CCC3)n2)CC1] | 4-(cyclobutylamino)-2-((1r,4r)-4-(dimethylcarbamoyl) cyclohexylamino) pyrimidine-5-carboxamide | 361.2 | D |
| 438 | 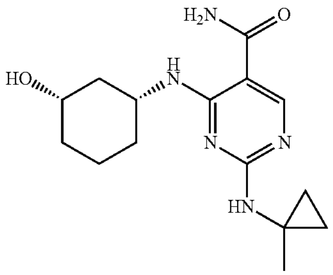 [SMILES: CC1(Nc2ncc(C(N)=O)c(N[C@@H]3CCC[C@H](O)C3)n2)CC1] | 4-((1R,3S)-3-hydroxycyclohexylamino)-2-(1-methylcyclopropylamino) pyrimidine-5-carboxamide | 306.2 | D |
| 439 | 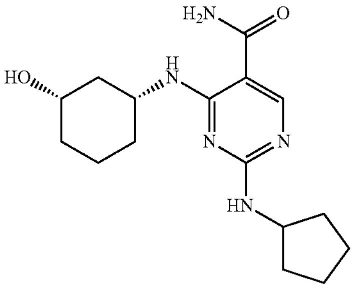 [SMILES: NC(=O)c1cnc(NC2CCCC2)nc1N[C@@H]1CCC[C@H](O)C1] | 2-(cyclopentylamino)-4-((1R,3S)-3-hydroxycyclohexylamino) pyrimidine-5-carboxamide | 320.2 | D |

TABLE 1-continued

| Cmpd. A- | Structure | NAME | MH+ | Act. Level |
|---|---|---|---|---|
| 440 | 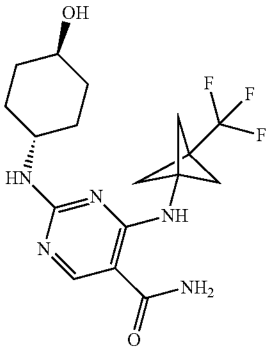 [SMILES: NC(=O)c1cnc(N[C@H]2CC[C@H](O)CC2)nc1NC12CC(C(F)(F)F)(C1)C2] | 2-((1r,4r)-4-hydroxycyclohexylamino)-4-(3-(trifluoromethyl)bicyclo[1.1.1]pentan-1-ylamino)pyrimidine-5-carboxamide | 386 | D |
| 441 | 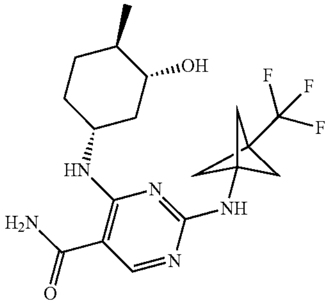 [SMILES: C[C@@H]1CC[C@@H](Nc2nc(NC34CC(C(F)(F)F)(C3)C4)ncc2C(N)=O)C[C@H]1O] | 4-((1R,3R,4R)-3-hydroxy-4-methylcyclohexylamino)-2-(3-(trifluoromethyl)bicyclo[1.1.1]pentan-1-ylamino)pyrimidine-5-carboxamide | 400 | D |
| 442 | 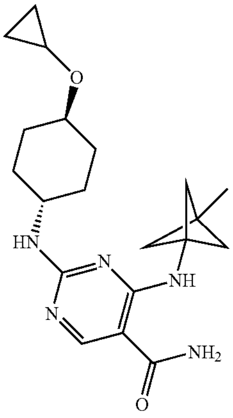 [SMILES: CC12CC(Nc3nc(N[C@H]4CC[C@H](OC5CC5)CC4)ncc3C(N)=O)(C1)C2] | 2-((1r,4r)-4-cyclopropoxycyclohexylamino)-4-(3-methylbicyclo[1.1.1]pentan-1-ylamino)pyrimidine-5-carboxamide | 372.3 | D |
| 443 | 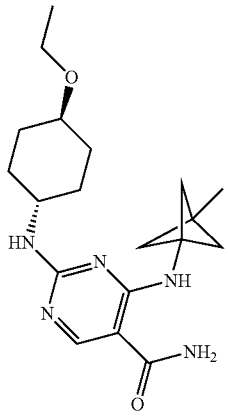 [SMILES: CCO[C@H]1CC[C@H](Nc2ncc(C(N)=O)c(NC34CC(C)(C3)C4)n2)CC1] | 2-((1r,4r)-4-ethoxycyclohexylamino)-4-(3-methylbicyclo[1.1.1]pentan-1-ylamino)pyrimidine-5-carboxamide | 360.3 | D |

TABLE 1-continued

| Cmpd. A- | Structure | NAME | MH+ | Act. Level |
|---|---|---|---|---|
| 444 | 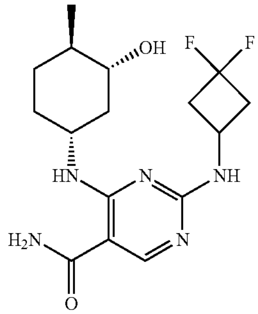 [SMILES: C[C@@H]1CC[C@@H](Nc2nc(NC3CC(F)(F)C3)ncc2C(N)=O)C[C@H]1O] | 2-(3,3-difluorocyclobutylamino)-4-((1R,3R,4R)-3-hydroxy-4-methylcyclohexylamino) pyrimidine-5-carboxamide | 356.1 | D |
| 445 | 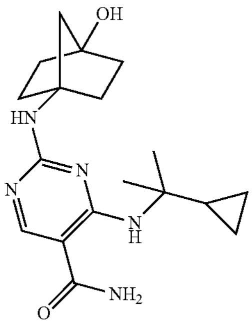 [SMILES: CC(C)(Nc1nc(NC23CCC(O)(CC2)C3)ncc1C(N)=O)C1CC1] | 4-(2-cyclopropylpropan-2-ylamino)-2-(4-hydroxybicyclo[2.2.1]heptan-1-ylamino)pyrimidine-5-carboxamide | 346.3 | D |
| 446 | 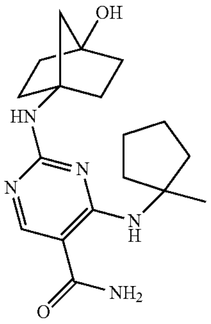 [SMILES: CC1(Nc2nc(NC34CCC(O)(CC3)C4)ncc2C(N)=O)CCCC1] | 2-(4-hydroxybicyclo[2.2.1]heptan-1-ylamino)-4-(1-methylcyclopentylamino) pyrimidine-5-carboxamide | 346.3 | D |
| 447 | 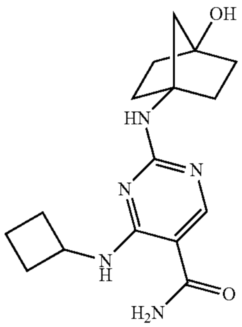 [SMILES: NC(=O)c1cnc(NC23CCC(O)(CC2)C3)nc1NC1CCC1] | 4-(cyclobutylamino)-2-(4-hydroxybicyclo[2.2.1]heptan-1-ylamino)pyrimidine-5-carboxamide | 318.2 | D |

TABLE 1-continued

| Cmpd. A- | Structure | NAME | MH+ | Act. Level |
|---|---|---|---|---|
| 448 | 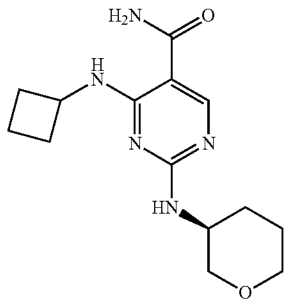 [SMILES: NC(=O)c1cnc(N[C@H]2CCCOC2)nc1NC1CCC1] | (S)-4-(cyclobutylamino)-2-(tetrahydro-2H-pyran-3-ylamino)pyrimidine-5-carboxamide | 292.1 | D |
| 449 | 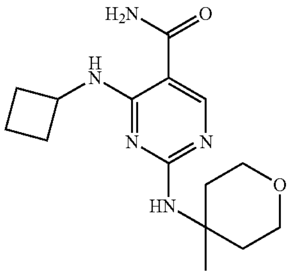 [SMILES: CC1(Nc2ncc(C(N)=O)c(NC3CCC3)n2)CCOCC1] | 4-(cyclobutylamino)-2-(4-methyltetrahydro-2H-pyran-4-ylamino)pyrimidine-5-carboxamide | 306.2 | D |
| 450 | 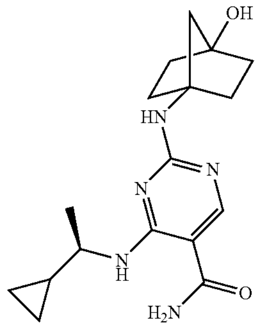 [SMILES: C[C@@H](Nc1nc(NC23CCC(O)(CC2)C3)ncc1C(N)=O)C1CC1] | (R)-4-(1-cyclopropylethylamino)-2-(4-hydroxybicyclo[2.2.1]heptan-1-ylamino)pyrimidine-5-carboxamide | 332.2 | D |
| 451 | 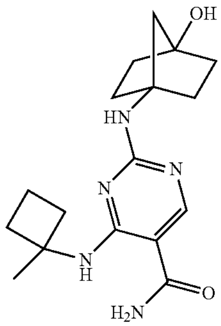 [SMILES: CC1(Nc2nc(NC34CCC(O)(CC3)C4)ncc2C(N)=O)CCC1] | 2-(4-hydroxybicyclo[2.2.1]heptan-1-ylamino)-4-(1-methylcyclobutylamino) pyrimidine-5-carboxamide | 332.2 | D |
| 452 | 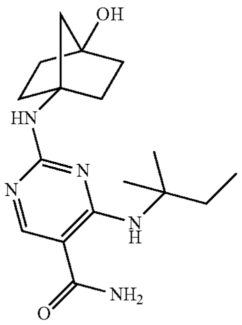 [SMILES: CCC(C)(C)Nc1nc(NC23CCC(O)(CC2)C3)ncc1C(N)=O] | 2-(4-hydroxybicyclo[2.2.1]heptan-1-ylamino)-4-(tert-pentylamino)pyrimidine-5-carboxamide | 334.2 | D |

TABLE 1-continued

| Cmpd. A- | Structure | NAME | MH+ | Act. Level |
|---|---|---|---|---|
| 453 | 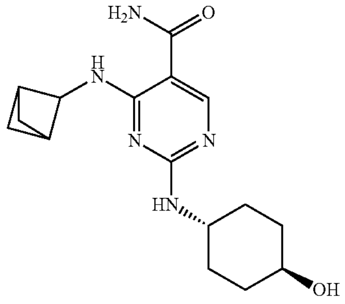 [SMILES: NC(=O)c1cnc(N[C@H]2CC[C@H](O)CC2)nc1NC1C2CC1C2] | 4-(bicyclo[1.1.1]pentan-2-ylamino)-2-((1r,4r)-4-hydroxycyclohexylamino) pyrimidine-5-carboxamide | 318.1 | D |
| 454 | 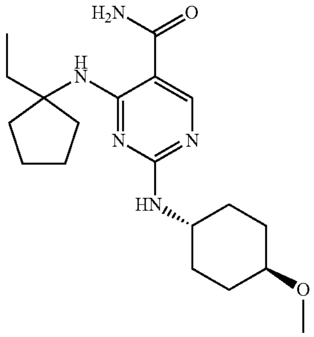 [SMILES: CCC1(Nc2nc(N[C@H]3CC[C@H](OC)CC3)ncc2C(N)=O)CCCC1] | 4-(1-ethylcyclopentylamino)-2-((1r,4r)-4-methoxycyclohexylamino) pyrimidine-5-carboxamide | 362.2 | D |
| 455 | 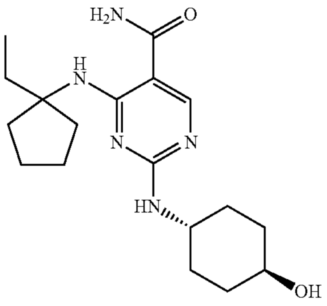 [SMILES: CCC1(Nc2nc(N[C@H]3CC[C@H](O)CC3)ncc2C(N)=O)CCCC1] | 4-(1-ethylcyclopentylamino)-2-((1r,4r)-4-hydroxycyclohexylamino) pyrimidine-5-carboxamide | 348.2 | D |
| 456 | 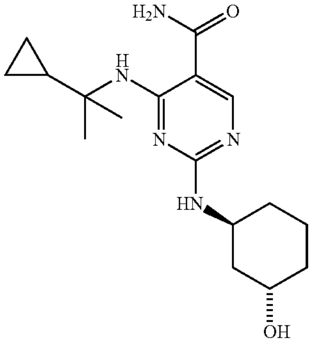 [SMILES: CC(C)(Nc1nc(N[C@H]2CCC[C@H](O)C2)ncc1C(N)=O)C1CC1] | 4-(2-cyclopropylpropan-2-ylamino)-2-((1S,3S)-3-hydroxycyclohexylamino) pyrimidine-5-carboxamide | 334.2 | D |

TABLE 1-continued

| Cmpd. A- | Structure | NAME | MH+ | Act. Level |
|---|---|---|---|---|
| 457 | 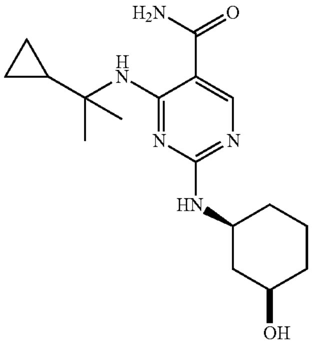 [SMILES: CC(C)(Nc1nc(N[C@H]2CCC[C@@H](O)C2)ncc1C(N)=O)C1CC1] | 4-(2-cyclopropylpropan-2-ylamino)-2-((1S,3R)-3-hydroxycyclohexylamino) pyrimidine-5-carboxamide | 334.2 | D |
| 458 | 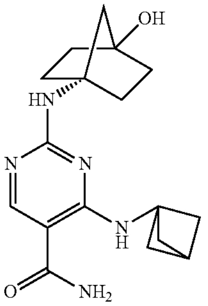 | 4-(bicyclo[1.1.1]pentan-1-ylamino)-2-((1r,4r)-4-hydroxybicyclo[2.2.1]heptan-1-ylamino)pyrimidine-5-carboxamide | 330 | D |
| 459 | 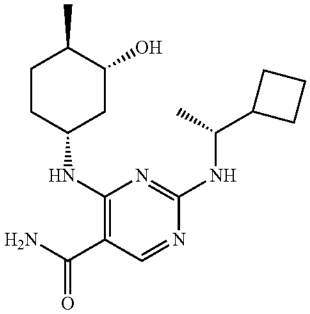 [SMILES: C[C@@H]1CC[C@@H](Nc2nc(N[C@H](C)C3CCC3)ncc2C(N)=O)C[C@H]1O] | 2-((R)-1-cyclobutylethylamino)-4-((1R,3R,4R)-3-hydroxy-4-methylcyclohexylamino) pyrimidine-5-carboxamide | 348.3 | D |
| 460 | 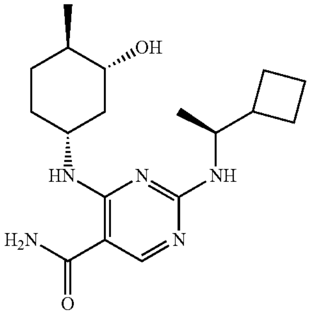 [SMILES: C[C@H](Nc1ncc(C(N)=O)c(N[C@@H]2CC[C@@H](C)[C@H](O)C2)n1)C1CCC1] | 2-((S)-1-cyclobutylethylamino)-4-((1R,3R,4R)-3-hydroxy-4-methylcyclohexylamino) pyrimidine-5-carboxamide | 348.3 | D |

TABLE 1-continued

| Cmpd. A- | Structure | NAME | MH+ | Act. Level |
|---|---|---|---|---|
| 461 | 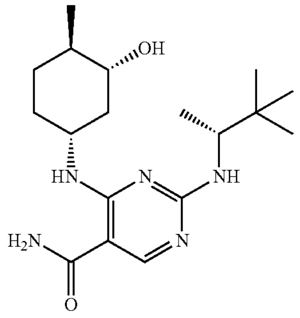 [SMILES: C[C@@H]1CC[C@@H](Nc2nc(N[C@H](C)C(C)(C)C)ncc2C(N)=O)C[C@H]1O] | 2-((R)-3,3-dimethylbutan-2-ylamino)-4-((1R,3R,4R)-3-hydroxy-4-methylcyclohexylamino) pyrimidine-5-carboxamide | 350.2 | D |
| 462 | 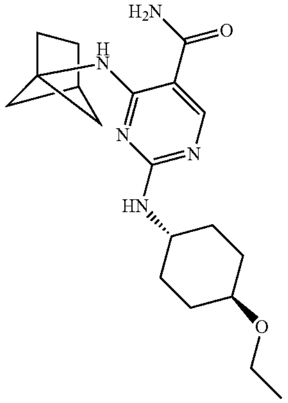 [SMILES: CCO[C@H]1CC[C@H](Nc2ncc(C(N)=O)c(NC34CCC(C3)C4)n2)CC1] | 4-(bicyclo[2.1.1]hexan-1-ylamino)-2-((1r,4r)-4-ethoxycyclohexylamino) pyrimidine-5-carboxamide | 360.2 | D |
| 463 | 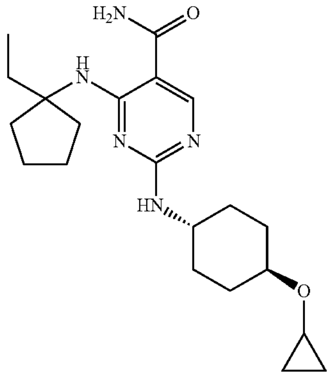 [SMILES: CCC1(Nc2nc(N[C@H]3CC[C@H](OC4CC4)CC3)ncc2C(N)=O)CCCC1] | 2-((1r,4r)-4-cyclopropoxycyclohexylamino)-4-(1-ethylcyclopentylamino) pyrimidine-5-carboxamide | 388.2 | D |
| 464 | 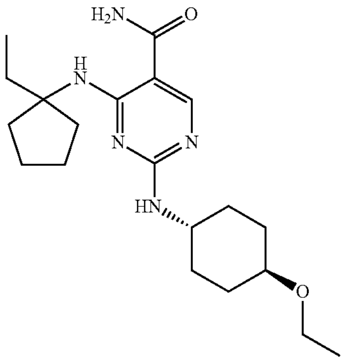 [SMILES: CCO[C@H]1CC[C@H](Nc2ncc(C(N)=O)c(NC3(CC)CCCC3)n2)CC1] | 2-((1r,4r)-4-ethoxycyclohexylamino)-4-(1-ethylcyclopentylamino) pyrimidine-5-carboxamide | 376.2 | D |

TABLE 1-continued

| Cmpd. A- | Structure | NAME | MH+ | Act. Level |
|---|---|---|---|---|
| 465 | 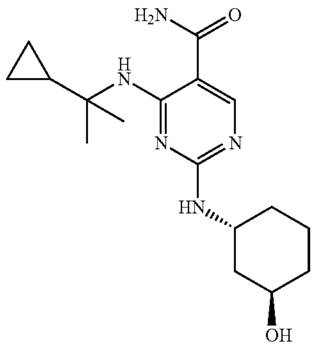 [SMILES: CC(C)(Nc1nc(N[C@@H]2CCC[C@@H](O)C2)ncc1C(N)=O)C1CC1] | 4-(2-cyclopropylpropan-2-ylamino)-2-((1R,3R)-3-hydroxycyclohexylamino) pyrimidine-5-carboxamide | 334.2 | D |
| 466 | 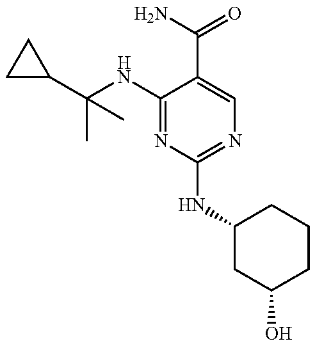 [SMILES: CC(C)(Nc1nc(N[C@@H]2CCC[C@H](O)C2)ncc1C(N)=O)C1CC1] | 4-(2-cyclopropylpropan-2-ylamino)-2-((1R,3S)-3-hydroxycyclohexylamino) pyrimidine-5-carboxamide | 334.2 | D |
| 467 | 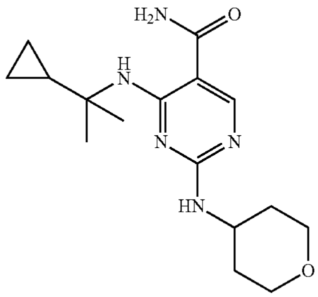 [SMILES: CC(C)(Nc1nc(NC2CCOCC2)ncc1C(N)=O)C1CC1] | 4-(2-cyclopropylpropan-2-ylamino)-2-(tetrahydro-2H-pyran-4-ylamino)pyrimidine-5-carboxamide | 320.2 | D |
| 468 | 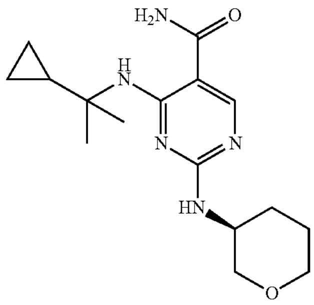 [SMILES: CC(C)(Nc1nc(N[C@H]2CCCOC2)ncc1C(N)=O)C1CC1] | (S)-4-(2-cyclopropylpropan-2-ylamino)-2-(tetrahydro-2H-pyran-3-ylamino)pyrimidine-5-carboxamide | 320.2 | D |

TABLE 1-continued

| Cmpd. A- | Structure | NAME | MH+ | Act. Level |
|---|---|---|---|---|
| 469 | 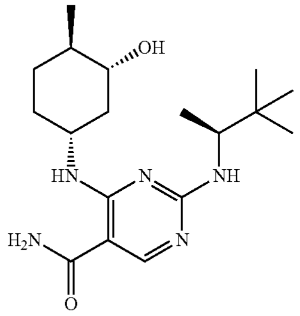 [SMILES: C[C@@H]1CC[C@@H](Nc2nc(N[C@@H](C)C(C)(C)C)ncc2C(N)=O)C[C@H]1O] | 2-((S)-3,3-dimethylbutan-2-ylamino)-4-((1R,3R,4R)-3-hydroxy-4-methylcyclohexylamino) pyrimidine-5-carboxamide | 350.3 | D |
| 470 | 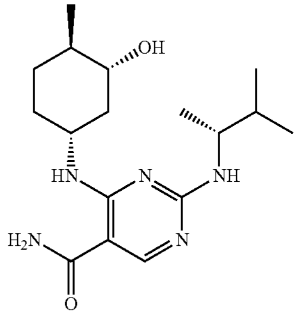 [SMILES: CC(C)[C@@H](C)Nc1ncc(C(N)=O)c(N[C@@H]2CC[C@@H](C)[C@H](O)C2)n1] | 4-((1R,3R,4R)-3-hydroxy-4-methylcyclohexylamino)-2-((R)-3-methylbutan-2-ylamino)pyrimidine-5-carboxamide | 336.2 | D |
| 471 | 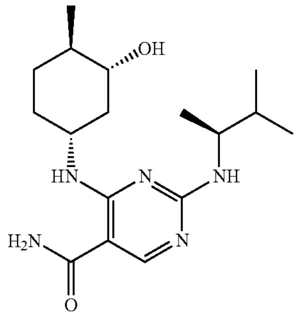 [SMILES: CC(C)[C@H](C)Nc1ncc(C(N)=O)c(N[C@@H]2CC[C@@H](C)[C@H](O)C2)n1] | 4-((1R,3R,4R)-3-hydroxy-4-methylcyclohexylamino)-2-((S)-3-methylbutan-2-ylamino)pyrimidine-5-carboxamide | 336.3 | D |
| 472 | 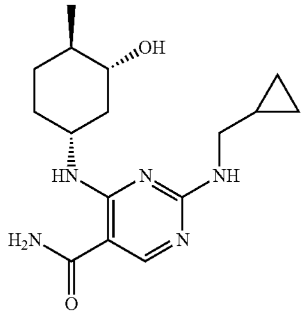 [SMILES: C[C@@H]1CC[C@@H](Nc2nc(NCC3CC3)ncc2C(N)=O)C[C@H]1O] | 2-(cyclopropylmethylamino)-4-((1R,3R,4R)-3-hydroxy-4-methylcyclohexylamino) pyrimidine-5-carboxamide | 320.1 | D |

TABLE 1-continued

| Cmpd. A- | Structure | NAME | MH+ | Act. Level |
|---|---|---|---|---|
| 473 | 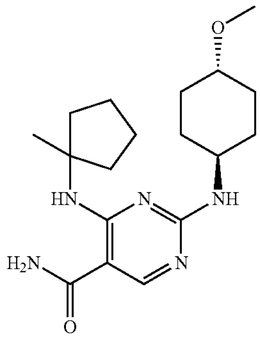 [SMILES: CO[C@H]1CC[C@H](Nc2ncc(C(N)=O)c(NC3(C)CCCC3)n2)CC1] | 2-((1r,4r)-4-methoxycyclohexylamino)-4-(1-methylcyclopentylamino) pyrimidine-5-carboxamide | 348.3 | D |
| 474 | 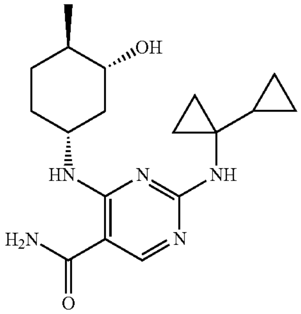 [SMILES: C[C@@H]1CC[C@@H](Nc2nc(NC3(C4CC4)CC3)ncc2C(N)=O)C[C@H]1O] | 2-(bi(cycloprop)ylamino)-4-((1R,3R,4R)-3-hydroxy-4-methylcyclohexylamino) pyrimidine-5-carboxamide | 346.2 | D |
| 475 | 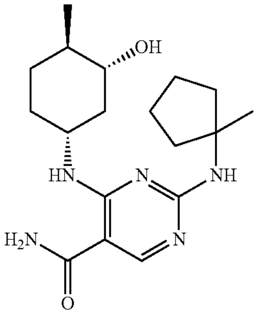 [SMILES: C[C@@H]1CC[C@@H](Nc2nc(NC3(C)CCCC3)ncc2C(N)=O)C[C@H]1O] | 4-((1R,3R,4R)-3-hydroxy-4-methylcyclohexylamino)-2-(1-methylcyclopentylamino) pyrimidine-5-carboxamide | 348.2 | D |
| 476 | 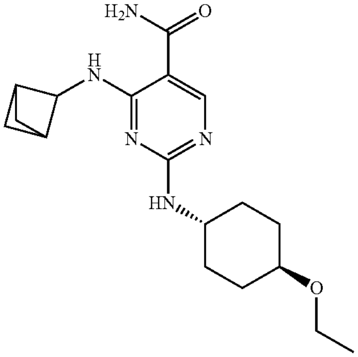 [SMILES: CCO[C@H]1CC[C@H](Nc2ncc(C(N)=O)c(NC3C4CC3C4)n2)CC1] | 4-(bicyclo[1.1.1]pentan-2-ylamino)-2-((1r,4r)-4-ethoxycyclohexylamino) pyrimidine-5-carboxamide | 346.2 | D |

TABLE 1-continued

| Cmpd. A- | Structure | NAME | MH+ | Act. Level |
|---|---|---|---|---|
| 477 | 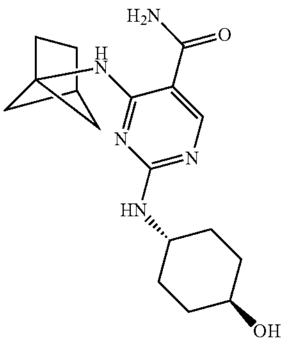 [SMILES: NC(=O)c1cnc(N[C@H]2CC[C@H](O)CC2)nc1NC12CCC(C1)C2] | 4-(bicyclo[2.1.1]hexan-1-ylamino)-2-((1r,4r)-4-hydroxycyclohexylamino) pyrimidine-5-carboxamide | 332.2 | D |
| 478 | 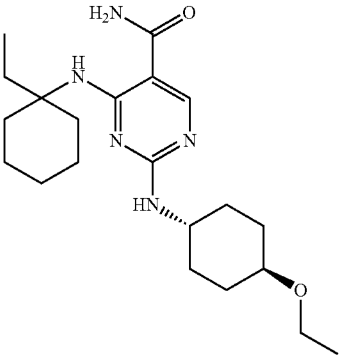 [SMILES: CCO[C@H]1CC[C@H](Nc2ncc(C(N)=O)c(NC3(CC)CCCCC3)n2)CC1] | 2-((1r,4r)-4-ethoxycyclohexylamino)-4-(1-ethylcyclohexylamino) pyrimidine-5-carboxamide | 390.2 | D |
| 479 | 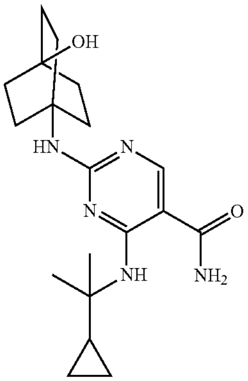 [SMILES: CC(C)(Nc1nc(NC23CCC(O)(CC2)CC3)ncc1C(N)=O)C1CC1] | 4-(2-cyclopropylpropan-2-ylamino)-2-(4-hydroxybicyclo[2.2.2]octan-1-ylamino)pyrimidine-5-carboxamide | 360.2 | D |
| 480 | 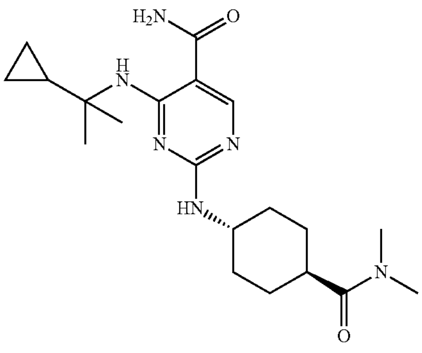 [SMILES: CN(C)C(=O)[C@H]1CC[C@H](Nc2ncc(C(N)=O)c(NC(C)(C)C3CC3)n2)CC1] | 4-(2-cyclopropylpropan-2-ylamino)-2-((1r,4r)-4-(dimethylcarbamoyl) cyclohexylamino)pyrimidine-5-carboxamide | 389.2 | D |

TABLE 1-continued

| Cmpd. A- | Structure | NAME | MH+ | Act. Level |
|---|---|---|---|---|
| 481 | 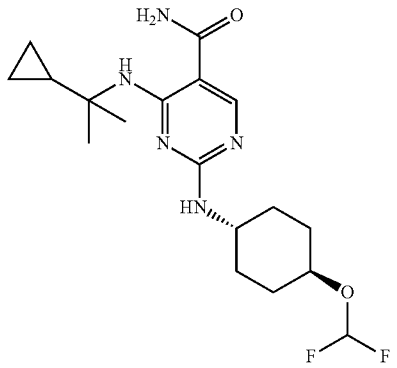 [SMILES: CC(C)(Nc1nc(N[C@H]2CC[C@H](OC(F)F)CC2)ncc1C(N)=O)C1CC1] | 4-(2-cyclopropylpropan-2-ylamino)-2-((1r,4r)-4-(difluoromethoxy) cyclohexylamino)pyrimidine-5-carboxamide | 384.2 | D |
| 482 | 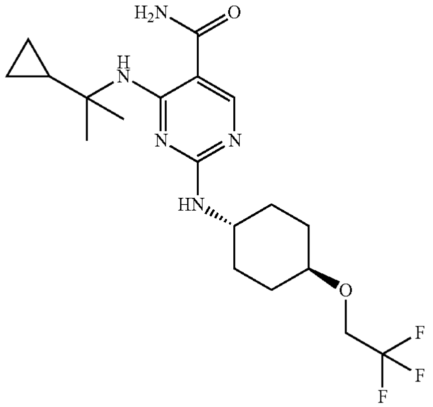 [SMILES: CC(C)(Nc1nc(N[C@H]2CC[C@H](OCC(F)(F)F)CC2)ncc1C(N)=O)C1CC1] | 4-(2-cyclopropylpropan-2-ylamino)-2-((1r,4r)-4-(2,2,2-trifluoroethoxy) cyclohexylamino)pyrimidine-5-carboxamide | 416.2 | D |
| 483 | 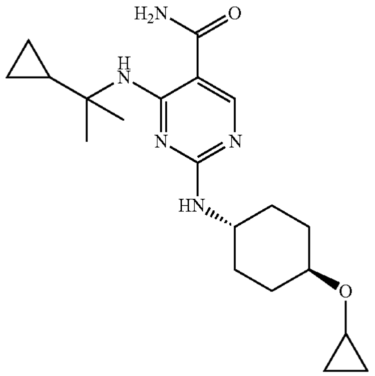 [SMILES: CC(C)(Nc1nc(N[C@H]2CC[C@H](OC3CC3)CC2)ncc1C(N)=O)C1CC1] | 2-((1r,4r)-4-cyclopropoxycyclohexylamino)-4-(2-cyclopropylpropan-2-ylamino)pyrimidine-5-carboxamide | 374.2 | D |
| 484 | 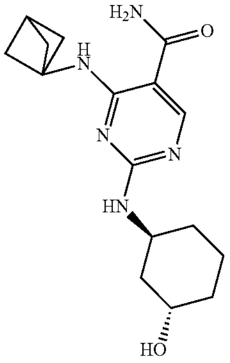 [SMILES: NC(=O)c1cnc(N[C@H]2CCC[C@H](O)C2)nc1NC12CC(C1)C2] | 4-(bicyclo[1.1.1]pentan-1-ylamino)-2-((1S,3S)-3-hydroxycyclohexylamino) pyrimidine-5-carboxamide | 318.1 | D |

TABLE 1-continued

| Cmpd. A- | Structure | NAME | MH+ | Act. Level |
|---|---|---|---|---|
| 485 | 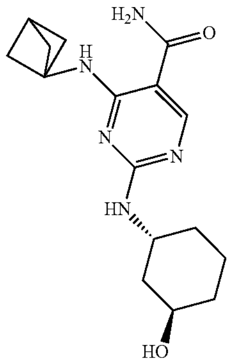 [SMILES: NC(=O)c1cnc(N[C@@H]2CCC[C@@H](O)C2)nc1NC12CC(C1)C2] | 4-(bicyclo[1.1.1]pentan-1-ylamino)-2-((1R,3R)-3-hydroxycyclohexylamino) pyrimidine-5-carboxamide | 318.2 | D |
| 486 | 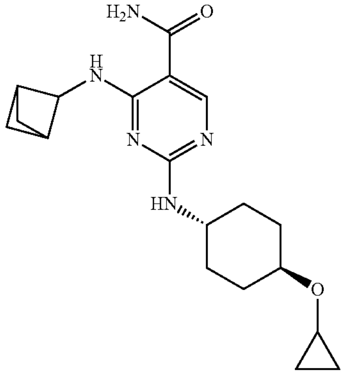 [SMILES: NC(=O)c1cnc(N[C@H]2CC[C@H](OC3CC3)CC2)nc1NC1C2CC1C2] | 4-(bicyclo[1.1.1]pentan-2-ylamino)-2-((1r,4r)-4-cyclopropoxycyclohexylamino) pyrimidine-5-carboxamide | 358.2 | D |
| 487 | 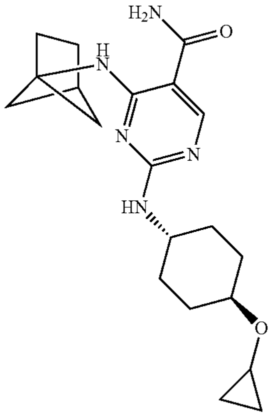 [SMILES: NC(=O)c1cnc(N[C@H]2CC[C@H](OC3CC3)CC2)nc1NC12CCC(C1)C2] | 4-(bicyclo[2.1.1]hexan-1-ylamino)-2-((1r,4r)-4-cyclopropoxycyclohexylamino) pyrimidine-5-carboxamide | 372.2 | D |
| 488 | 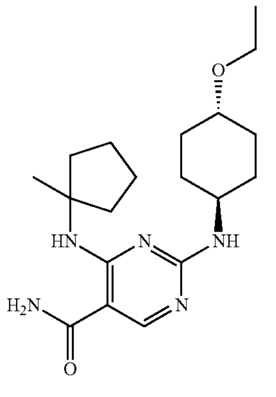 [SMILES: CCO[C@H]1CC[C@H](Nc2ncc(C(N)=O)c(NC3(C)CCCC3)n2)CC1] | 2-((1r,4r)-4-ethoxycyclohexylamino)-4-(1-methylcyclopentylamino) pyrimidine-5-carboxamide | 362.3 | D |

TABLE 1-continued

| Cmpd. A- | Structure | NAME | MH+ | Act. Level |
|---|---|---|---|---|
| 489 | 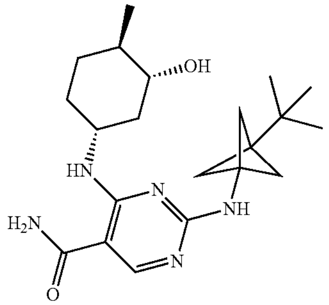 [SMILES: C[C@@H]1CC[C@@H](Nc2nc(NC34CC(C(C)(C)C)(C3)C4)ncc2C(N)=O)C[C@H]1O] | 2-(3-tert-butylbicyclo[1.1.1]pentan-1-ylamino)-4-((1R,3R,4R)-3-hydroxy-4-methylcyclohexylamino)pyrimidine-5-carboxamide | 388.4 | D |
| 490 | 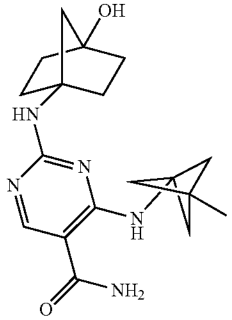 [SMILES: CC12CC(Nc3nc(NC45CCC(O)(CC4)C5)ncc3C(N)=O)(C1)C2] | 2-(4-hydroxybicyclo[2.2.1]heptan-1-ylamino)-4-(3-methylbicyclo[1.1.1]pentan-1-ylamino)pyrimidine-5-carboxamide | 344 | D |
| 491 | 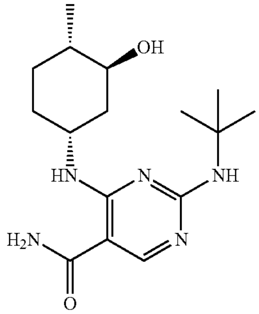 [SMILES: C[C@H]1CC[C@@H](Nc2nc(NC(C)(C)C)ncc2C(N)=O)C[C@@H]1O] | 2-(tert-butylamino)-4-((1R,3S,4S)-3-hydroxy-4-methylcyclohexylamino)pyrimidine-5-carboxamide | 322.3 | D |
| 492 | 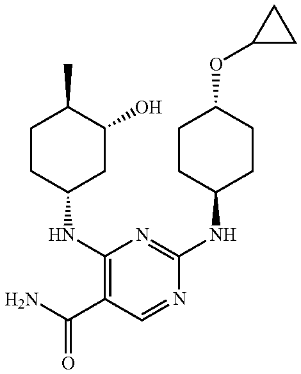 [SMILES: C[C@@H]1CC[C@@H](Nc2nc(N[C@H]3CC[C@H](OC4CC4)CC3)ncc2C(N)=O)C[C@H]1O] | 2-((1r,4R)-4-cyclopropoxycyclohexylamino)-4-((1R,3R,4R)-3-hydroxy-4-methylcyclohexylamino)pyrimidine-5-carboxamide | 404.2 | D |

TABLE 1-continued

| Cmpd. A- | Structure | NAME | MH+ | Act. Level |
|---|---|---|---|---|
| 493 | 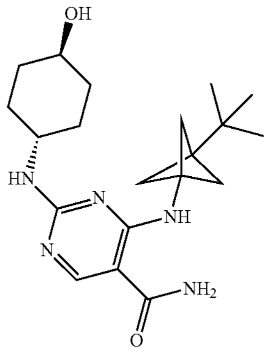 [SMILES: CC(C)(C)C12CC(Nc3nc(N[C@H]4CC[C@H](O)CC4)ncc3C(N)=O)(C1)C2] | 4-(3-tert-butylbicyclo[1.1.1]pentan-1-ylamino)-2-((1r,4r)-4-hydroxycyclohexylamino) pyrimidine-5-carboxamide | 374.4 | D |
| 494 | 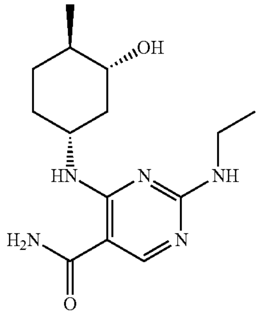 [SMILES: CCNc1ncc(C(N)=O)c(N[C@@H]2CC[C@@H](C)[C@H](O)C2)n1] | 2-(ethylamino)-4-((1R,3R,4R)-3-hydroxy-4-methylcyclohexylamino) pyrimidine-5-carboxamide | 294 | D |
| 495 | 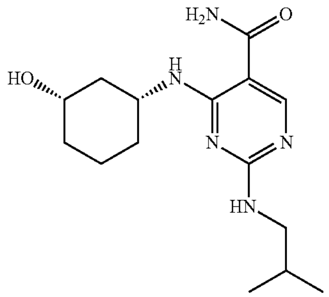 [SMILES: CC(C)CNc1ncc(C(N)=O)c(N[C@@H]2CCC[C@H](O)C2)n1] | 4-((1R,3S)-3-hydroxycyclohexylamino)-2-(isobutylamino)pyrimidine-5-carboxamide | 308.2 | D |
| 496 | 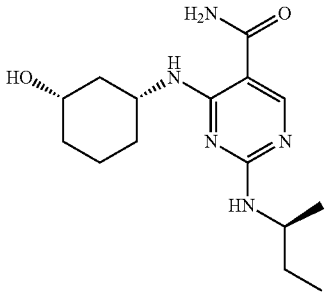 [SMILES: CC[C@H](C)Nc1ncc(C(N)=O)c(N[C@@H]2CCC[C@H](O)C2)n1] | 2-(sec-butylamino)-4-((1R,3S)-3-hydroxycyclohexylamino) pyrimidine-5-carboxamide | 308.2 | D |
| 497 | 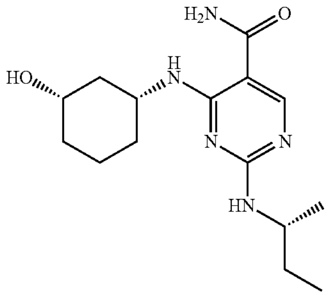 [SMILES: CC[C@@H](C)Nc1ncc(C(N)=O)c(N[C@@H]2CCC[C@H](O)C2)n1] | 2-(sec-butylamino)-4-((1R,3S)-3-hydroxycyclohexylamino) pyrimidine-5-carboxamide | 308.2 | D |

TABLE 1-continued

| Cmpd. A- | Structure | NAME | MH+ | Act. Level |
|---|---|---|---|---|
| 498 | 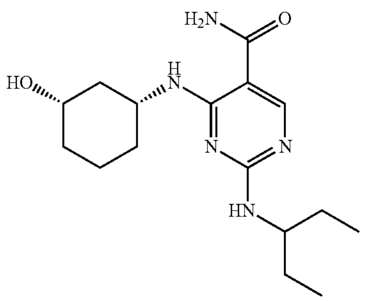 [SMILES: CCC(CC)Nc1ncc(C(N)=O)c(N[C@@H]2CCC[C@H](O)C2)n1] | 4-((1R,3S)-3-hydroxycyclohexylamino)-2-(pentan-3-ylamino)pyrimidine-5-carboxamide | 322.2 | D |

TABLE 2

| Cmpd. B- | Structure | Name | MH+ | Act. Level |
|---|---|---|---|---|
| 1 | 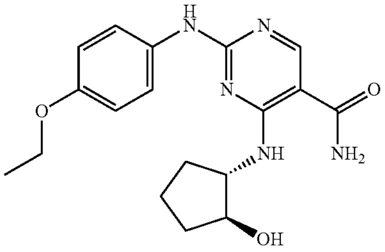 [SMILES: CCOc1ccc(Nc2ncc(C(N)=O)c(N[C@H]3CCC[C@@H]3O)n2)cc1] | 2-(4-ethoxyphenylamino)-4-((1S,2S)-2-hydroxycyclopentylamino)pyrimidine-5-carboxamide | 376.2 | D |
| 2 | 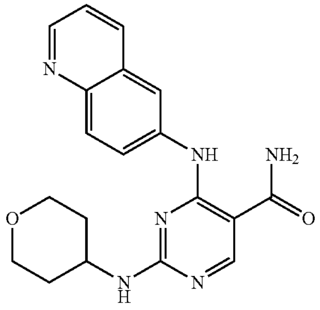 [SMILES: NC(=O)c1cnc(NC2CCOCC2)nc1Nc1ccc2ncccc2c1] | 4-(quinolin-6-ylamino)-2-(tetrahydro-2H-pyran-4-ylamino)pyrimidine-5-carboxamide | 365.2 | D |
| 3 | 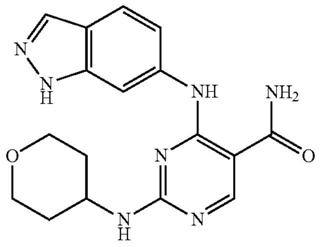 [SMILES: NC(=O)c1cnc(NC2CCOCC2)nc1Nc1ccc2cn[nH]c2c1] | 4-(1H-indazol-6-ylamino)-2-(tetrahydro-2H-pyran-4-ylamino)pyrimidine-5-carboxamide | 354.2 | D |

TABLE 2-continued

| Cmpd. B- | Structure | Name | MH+ | Act. Level |
|---|---|---|---|---|
| 4 | 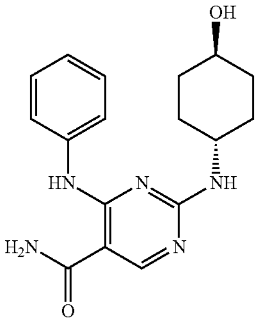 [SMILES: NC(=O)c1cnc(N[C@H]2CC[C@H](O)CC2)nc1Nc1ccccc1] | 2-((1r,4r)-4-hydroxycyclohexylamino)-4-(phenylamino)pyrimidine-5-carboxamide | 328 | D |
| 5 | 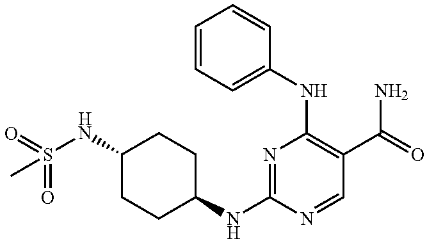 [SMILES: CS(=O)(=O)N[C@H]1CC[C@H](Nc2ncc(C(N)=O)c(Nc3ccccc3)n2)CC1] | 2-((1r,4r)-4-(methylsulfonamido) cyclohexylamino)-4-(phenylamino)pyrimidine-5-carboxamide | 405 | D |
| 6 | 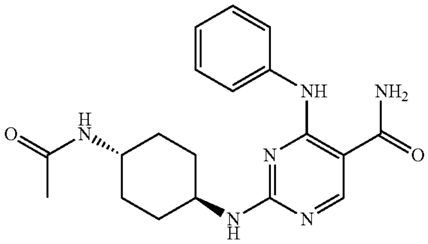 [SMILES: CC(=O)N[C@H]1CC[C@H](Nc2ncc(C(N)=O)c(Nc3ccccc3)n2)CC1] | 2-((1r,4r)-4-acetamidocyclohexyl-amino)-4-(phenylamino)pyrimidine-5-carboxamide | 369 | D |
| 7 | 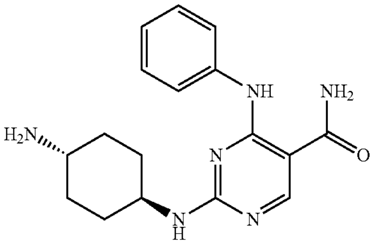 [SMILES: NC(=O)c1cnc(N[C@H]2CC[C@H](N)CC2)nc1Nc1ccccc1] | 2-((1r,4r)-4-aminocyclohexylamino)-4-(phenylamino)pyrimidine-5-carboxamide | 327.2 | D |
| 8 | 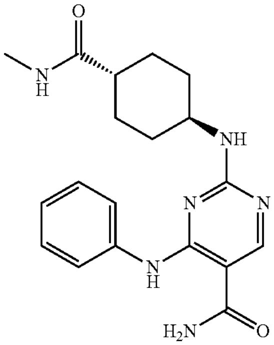 [SMILES: CNC(=O)[C@H]1CC[C@H](Nc2ncc(C(N)=O)c(Nc3ccccc3)n2)CC1] | 2-((1r,4r)-4-(methylcarbamoyl) cyclohexylamino)-4-(phenylamino)pyrimidine-5-carboxamide | 369.3 | D |

TABLE 2-continued

| Cmpd. B- | Structure | Name | MH+ | Act. Level |
|---|---|---|---|---|
| 9 | 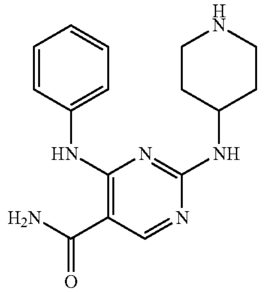 [SMILES: NC(=O)c1cnc(NC2CCNCC2)nc1Nc1ccccc1] | 4-(phenylamino)-2-(piperidin-4-ylamino)pyrimidine-5-carboxamide | 313 | A |
| 10 | 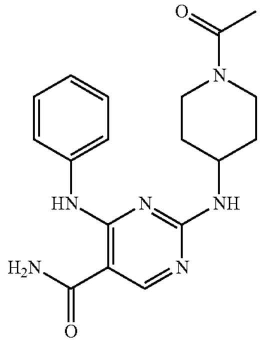 [SMILES: CC(=O)N1CCC(Nc2ncc(C(N)=O)c(Nc3ccccc3)n2)CC1] | 2-(1-acetylpiperidin-4-ylamino)-4-(phenylamino)pyrimidine-5-carboxamide | 355 | A |
| 11 | 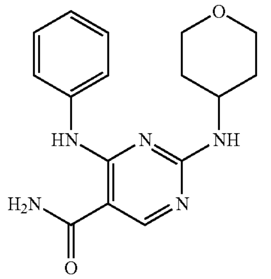 [SMILES: NC(=O)c1cnc(NC2CCOCC2)nc1Nc1ccccc1] | 4-(phenylamino)-2-(tetrahydro-2H-pyran-4-ylamino)pyrimidine-5-carboxamide | 314.3 | D |
| 12 | 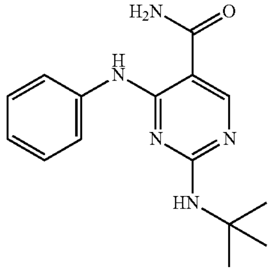 [SMILES: CC(C)(C)Nc1ncc(C(N)=O)c(Nc2ccccc2)n1] | 2-(tert-butylamino)-4-(phenylamino)pyrimidine-5-carboxamide | 286.2 | D |
| 13 | 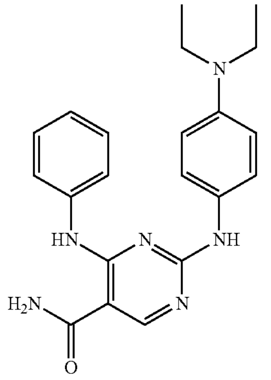 [SMILES: CCN(CC)c1ccc(Nc2ncc(C(N)=O)c(Nc3ccccc3)n2)cc1] | 2-(4-(diethylamino)phenylamino)-4-(phenylamino)pyrimidine-5-carboxamide | 377.5 | D |

TABLE 2-continued

| Cmpd. B- | Structure | Name | MH+ | Act. Level |
|---|---|---|---|---|
| 14 | 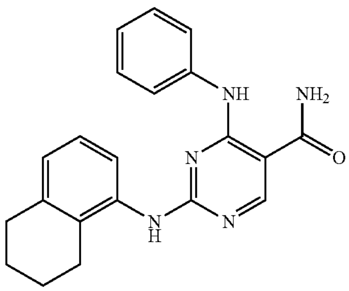 [SMILES: NC(=O)c1cnc(Nc2cccc3c2CCCC3)nc1Nc1ccccc1] | 4-(phenylamino)-2-(5,6,7,8-tetrahydronaphthalen-1-ylamino)pyrimidine-5-carboxamide | 360.4 | C |
| 15 | 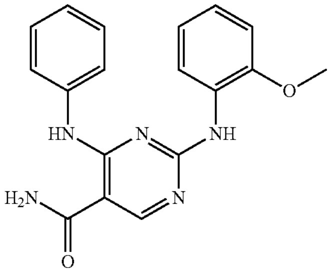 [SMILES: COc1ccccc1Nc1ncc(C(N)=O)c(Nc2ccccc2)n1] | 2-(2-methoxyphenylamino)-4-(phenylamino)pyrimidine-5-carboxamide | 336.4 | D |
| 16 | 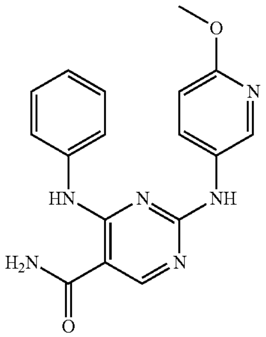 [SMILES: COc1ccc(Nc2ncc(C(N)=O)c(Nc3ccccc3)n2)cn1] | 2-(6-methoxypyridin-3-ylamino)-4-(phenylamino)pyrimidine-5-carboxamide | 337.4 | D |
| 17 | 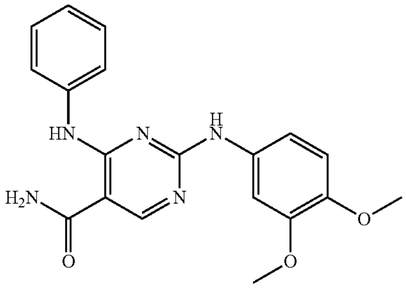 [SMILES: COc1ccc(Nc2ncc(C(N)=O)c(Nc3ccccc3)n2)cc1OC] | 2-(3,4-dimethoxyphenylamino)-4-(phenylamino)pyrimidine-5-carboxamide | 366.4 | D |
| 18 | 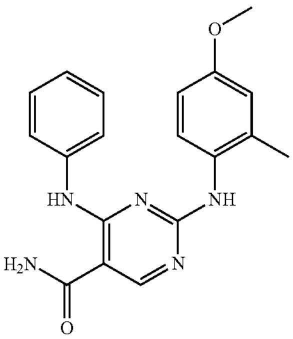 [SMILES: COc1ccc(Nc2ncc(C(N)=O)c(Nc3ccccc3)n2)c(C)c1] | 2-(4-methoxy-2-methylphenylamino)-4-(phenylamino)pyrimidine-5-carboxamide | 350.4 | D |

TABLE 2-continued

| Cmpd. B- | Structure | Name | MH+ | Act. Level |
|---|---|---|---|---|
| 19 | 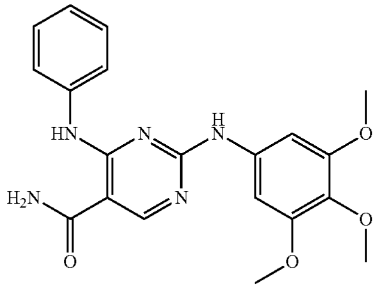 [SMILES: COc1cc(Nc2ncc(C(N)=O)c(Nc3ccccc3)n2)cc(OC)c1OC] | 4-(phenylamino)-2-(3,4,5-trimethoxyphenylamino) pyrimidine-5-carboxamide | 395.9 | D |
| 20 | 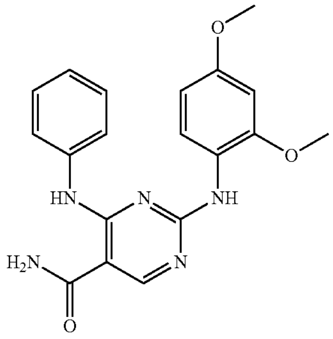 [SMILES: COc1ccc(Nc2ncc(C(N)=O)c(Nc3ccccc3)n2)c(OC)c1] | 2-(2,4-dimethoxyphenylamino)-4-(phenylamino)pyrimidine-5-carboxamide | 365.9 | D |
| 21 | 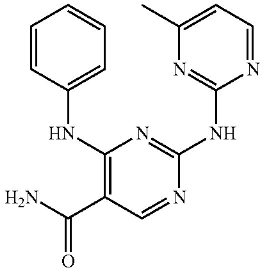 [SMILES: Cc1ccnc(Nc2ncc(C(N)=O)c(Nc3ccccc3)n2)n1] | 2-(4-methylpyrimidin-2-ylamino)-4-(phenylamino)pyrimidine-5-carboxamide | 321.9 | A |
| 22 | 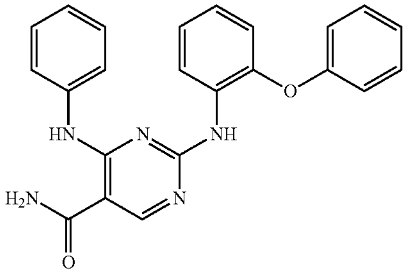 [SMILES: NC(=O)c1cnc(Nc2ccccc2Oc2ccccc2)nc1Nc1ccccc1] | 2-(2-phenoxyphenylamino)-4-(phenylamino)pyrimidine-5-carboxamide | 397.9 | C |
| 23 | 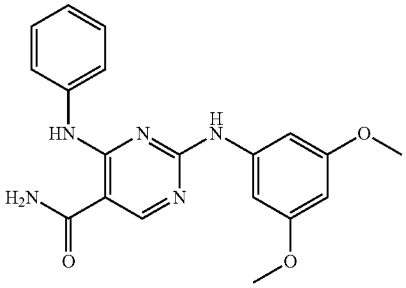 [SMILES: COc1cc(Nc2ncc(C(N)=O)c(Nc3ccccc3)n2)cc(OC)c1] | 2-(3,5-dimethoxyphenylamino)-4-(phenylamino)pyrimidine-5-carboxamide | 365.9 | D |

TABLE 2-continued
| Cmpd. B- | Structure | Name | MH+ | Act. Level |
|---|---|---|---|---|
| 24 | 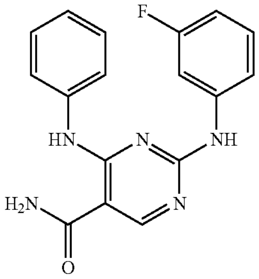 [SMILES: NC(=O)c1cnc(Nc2cccc(F)c2)nc1Nc1ccccc1] | 2-(3-fluorophenylamino)-4-(phenylamino)pyrimidine-5-carboxamide | 324.4 | D |
| 25 | 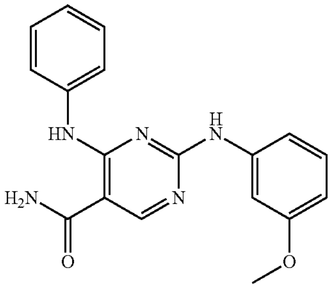 [SMILES: COc1cccc(Nc2ncc(C(N)=O)c(Nc3ccccc3)n2)c1] | 2-(3-methoxyphenylamino)-4-(phenylamino)pyrimidine-5-carboxamide | 336.4 | D |
| 26 | 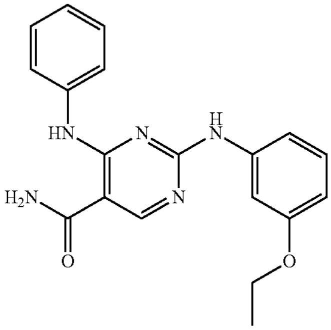 [SMILES: CCOc1cccc(Nc2ncc(C(N)=O)c(Nc3ccccc3)n2)c1] | 2-(3-ethoxyphenylamino)-4-(phenylamino) pyrimidine-5-carboxamide | 349.9 | D |
| 27 | 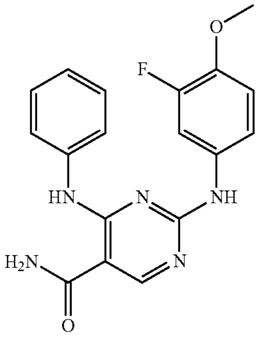 [SMILES: COc1ccc(Nc2ncc(C(N)=O)c(Nc3ccccc3)n2)cc1F] | 2-(3-fluoro-4-methoxyphenylamino)-4-(phenylamino)pyrimidine-5-carboxamide | 353.9 | D |
| 28 | 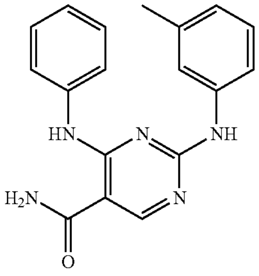 [SMILES: Cc1cccc(Nc2ncc(C(N)=O)c(Nc3ccccc3)n2)c1] | 4-(phenylamino)-2-(m-tolylamino)pyrimidine-5-carboxamide | 320 | D |

TABLE 2-continued

| Cmpd. B- | Structure | Name | MH+ | Act. Level |
|---|---|---|---|---|
| 29 | 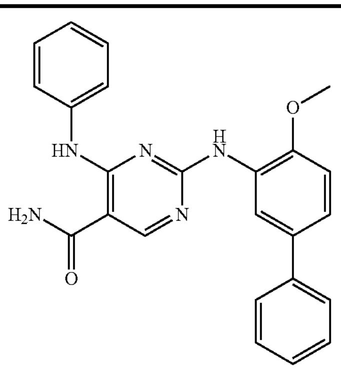 | 2-(4-methoxybiphenyl-3-ylamino)-4-(phenylamino)pyrimidine-5-carboxamide | 412.4 | A |
| 30 | 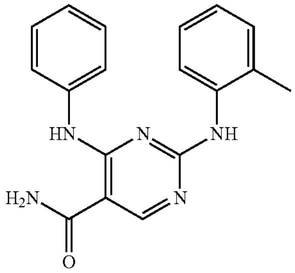 [SMILES: Cc1ccccc1Nc1ncc(C(N)=O)c(Nc2ccccc2)n1] | 4-(phenylamino)-2-(o-tolylamino)pyrimidine-5-carboxamide | 320.4 | D |
| 31 | 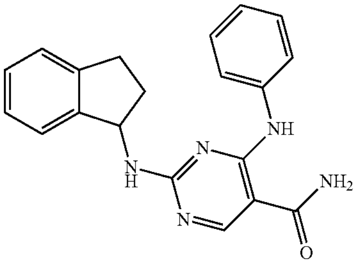 [SMILES: NC(=O)c1cnc(NC2CCc3ccccc32)nc1Nc1ccccc1] | 2-(2,3-dihydro-1H-inden-1-ylamino)-4-(phenylamino)pyrimidine-5-carboxamide | 345.9 | C |
| 32 | 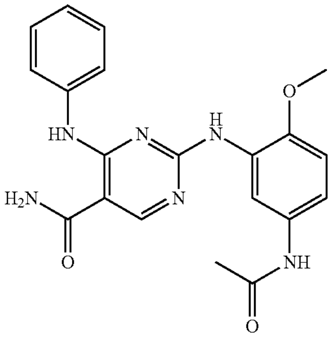 [SMILES: COc1ccc(NC(C)=O)cc1Nc1ncc(C(N)=O)c(Nc2ccccc2)n1] | 2-(5-acetamido-2-methoxyphenylamino)-4-(phenylamino)pyrimidine-5-carboxamide | 393.4 | C |
| 33 | 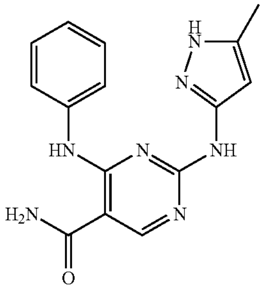 [SMILES: Cc1cc(Nc2ncc(C(N)=O)c(Nc3ccccc3)n2)n[nH]1] | 2-(5-methyl-1H-pyrazol-3-ylamino)-4-(phenylamino)pyrimidine-5-carboxamide | 310.4 | C |

TABLE 2-continued
| Cmpd. B- | Structure | Name | MH+ | Act. Level |
|---|---|---|---|---|
| 34 | 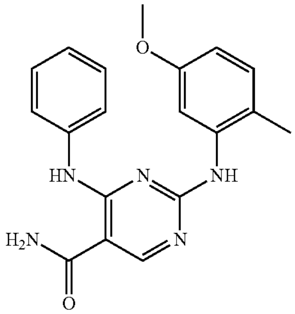 [SMILES: COc1ccc(C)c(Nc2ncc(C(N)=O)c(Nc3ccccc3)n2)c1] | 2-(5-methoxy-2-methylphenylamino)-4-(phenylamino)pyrimidine-5-carboxamide | 349.9 | D |
| 35 | 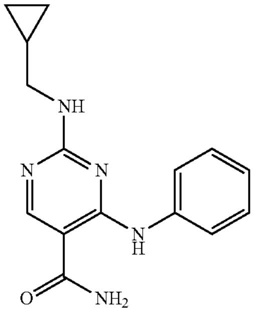 [SMILES: NC(=O)c1cnc(NCC2CC2)nc1Nc1ccccc1] | 2-(cyclopropylmethylamino)-4-(phenylamino)pyrimidine-5-carboxamide | 283.9 | C |
| 36 | 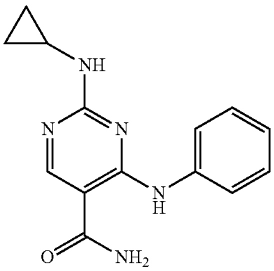 [SMILES: NC(=O)c1cnc(NC2CC2)nc1Nc1ccccc1] | 2-(cyclopropylamino)-4-(phenylamino)pyrimidine-5-carboxamide | 270 | D |
| 37 | 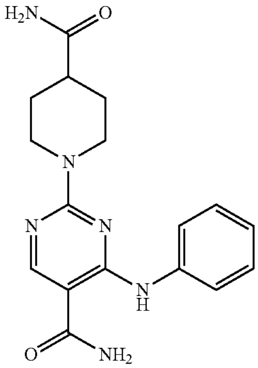 [SMILES: NC(=O)c1cnc(N2CCC(C(N)=O)CC2)nc1Nc1ccccc1] | 2-(4-carbamoylpiperidin-1-yl)-4-(phenylamino)pyrimidine-5-carboxamide | 340.9 | A |

TABLE 2-continued
| Cmpd. B- | Structure | Name | MH+ | Act. Level |
|---|---|---|---|---|
| 38 | 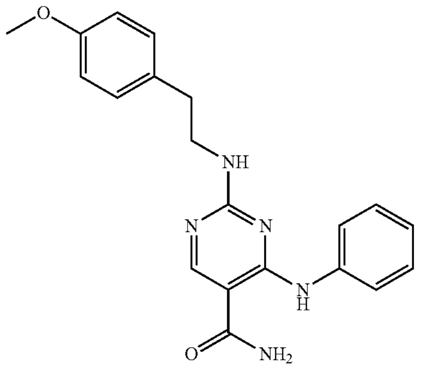 [SMILES: COc1ccc(CCNc2ncc(C(N)=O)c(Nc3ccccc3)n2)cc1] | 2-(4-methoxyphenethylamino)-4-(phenylamino)pyrimidine-5-carboxamide | 363.9 | C |
| 39 | 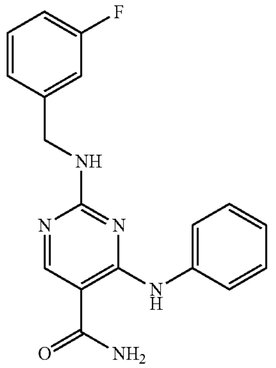 [SMILES: NC(=O)c1cnc(NCc2cccc(F)c2)nc1Nc1ccccc1] | 2-(3-fluorobenzylamino)-4-(phenylamino)pyrimidine-5-carboxamide | 337.9 | C |
| 40 | 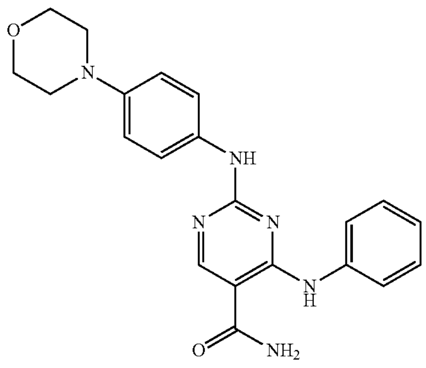 [SMILES: NC(=O)c1cnc(Nc2ccc(N3CCOCC3)cc2)nc1Nc1ccccc1] | 2-(4-morpholinophenylamino)-4-(phenylamino)pyrimidine-5-carboxamide | 391.4 | D |
| 41 | 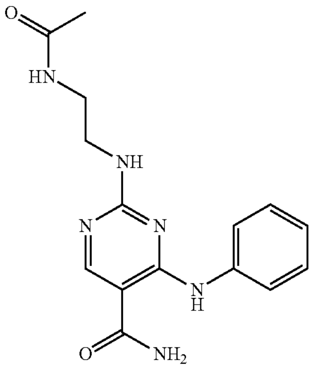 [SMILES: CC(=O)NCCNc1ncc(C(N)=O)c(Nc2ccccc2)n1] | 2-(2-acetamidoethylamino)-4-(phenylamino)pyrimidine-5-carboxamide | 315.4 | A |

TABLE 2-continued
| Cmpd. B- | Structure | Name | MH+ | Act. Level |
|---|---|---|---|---|
| 42 | 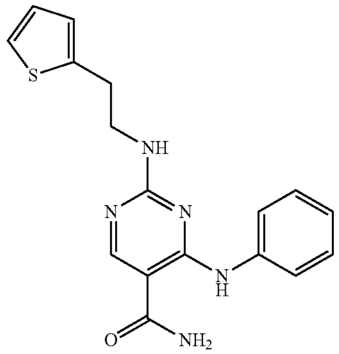 [SMILES: NC(=O)c1cnc(NCCc2cccs2)nc1Nc1ccccc1] | 4-(phenylamino)-2-(2-(thiophen-2-yl)ethylamino)pyrimidine-5-carboxamide | 340.4 | C |
| 43 | 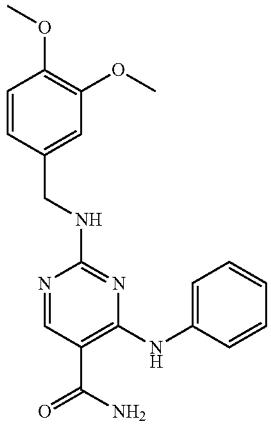 [SMILES: COc1ccc(CNc2ncc(C(N)=O)c(Nc3ccccc3)n2)cc1OC] | 2-(3,4-dimethoxybenzylamino)-4-(phenylamino)pyrimidine-5-carboxamide | 380.5 | C |
| 44 | 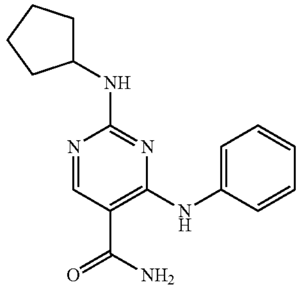 [SMILES: NC(=O)c1cnc(NC2CCCC2)nc1Nc1ccccc1] | 2-(cyclopentylamino)-4-(phenylamino)pyrimidine-5-carboxamide | 298 | D |
| 45 | 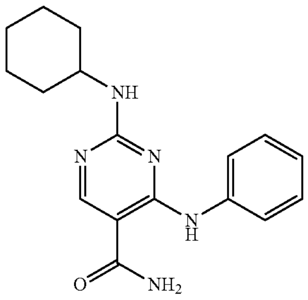 [SMILES: NC(=O)c1cnc(NC2CCCCC2)nc1Nc1ccccc1] | 2-(cyclohexylamino)-4-(phenylamino)pyrimidine-5-carboxamide | 312 | D |

TABLE 2-continued
| Cmpd. B- | Structure | Name | MH+ | Act. Level |
|---|---|---|---|---|
| 46 | 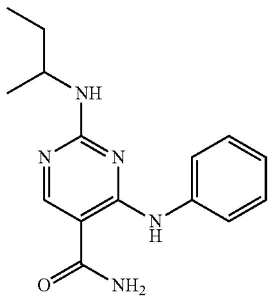 [SMILES: CCC(C)Nc1ncc(C(N)=O)c(Nc2ccccc2)n1] | 2-(sec-butylamino)-4-(phenylamino)pyrimidine-5-carboxamide | 286 | D |
| 47 | 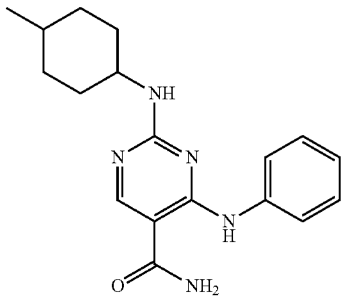 [SMILES: CC1CCC(Nc2ncc(C(N)=O)c(Nc3ccccc3)n2)CC1] | 2-(4-methylcyclohexylamino)-4-(phenylamino)pyrimidine-5-carboxamide | 326 | D |
| 48 | 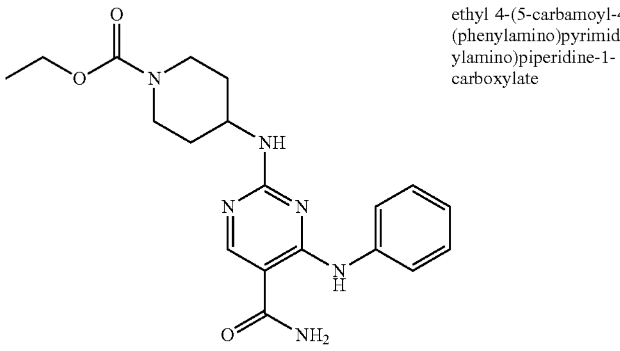 | ethyl 4-(5-carbamoyl-4-(phenylamino)pyrimidin-2-ylamino)piperidine-1-carboxylate | 384.9 | D |
| 49 | 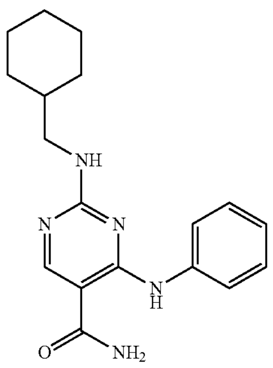 [SMILES: NC(=O)c1cnc(NCC2CCCCC2)nc1Nc1ccccc1] | 2-(cyclohexylmethylamino)-4-(phenylamino)pyrimidine-5-carboxamide | 326 | C |

TABLE 2-continued
| Cmpd. B- | Structure | Name | MH+ | Act. Level |
|---|---|---|---|---|
| 50 | 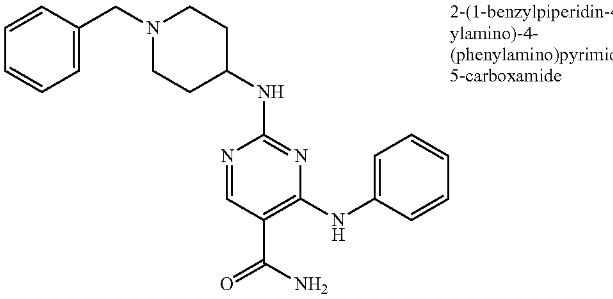 | 2-(1-benzylpiperidin-4-ylamino)-4-(phenylamino)pyrimidine-5-carboxamide | 402.9 | C |
| 51 | 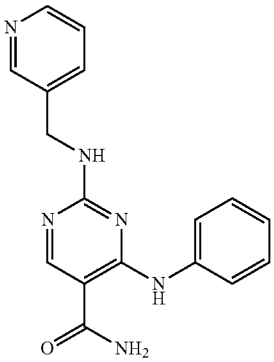 [SMILES: NC(=O)c1cnc(NCc2cccnc2)nc1Nc1ccccc1] | 4-(phenylamino)-2-(pyridin-3-ylmethylamino)pyrimidine-5-carboxamide | 320.9 | C |
| 52 | 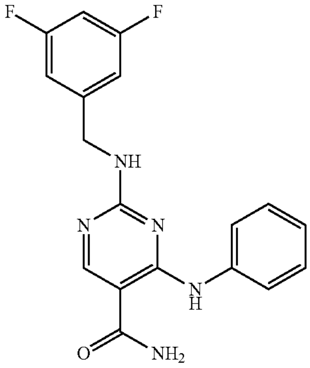 [SMILES: NC(=O)c1cnc(NCc2cc(F)cc(F)c2)nc1Nc1ccccc1] | 2-(3,5-difluorobenzylamino)-4-(phenylamino)pyrimidine-5-carboxamide | 355.9 | B |
| 53 | 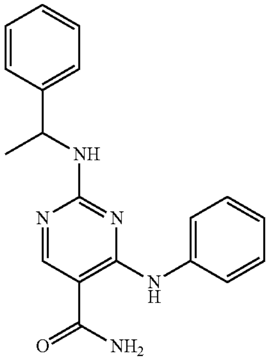 [SMILES: CC(Nc1ncc(C(N)=O)c(Nc2ccccc2)n1)c1ccccc1] | 4-(phenylamino)-2-(1-phenylethylamino) pyrimidine-5-carboxamide | 333.9 | C |

TABLE 2-continued
| Cmpd. B- | Structure | Name | MH+ | Act. Level |
|---|---|---|---|---|
| 54 | 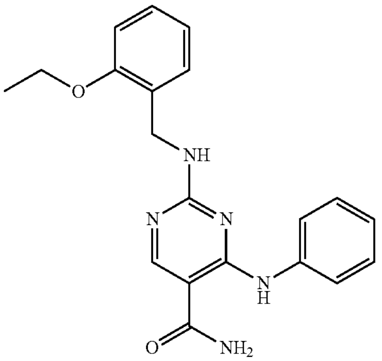 [SMILES: CCOc1ccccc1CNc1ncc(C(N)=O)c(Nc2ccccc2)n1] | 2-(2-ethoxybenzylamino)-4-(phenylamino) pyrimidine-5-carboxamide | 363.9 | B |
| 55 | 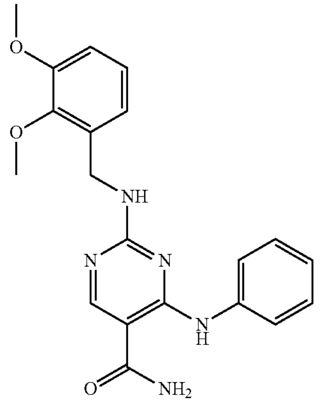 [SMILES: COc1cccc(CNc2ncc(C(N)=O)c(Nc3ccccc3)n2)c1OC] | 2-(2,3-dimethoxybenzylamino)-4-(phenylamino)pyrimidine-5-carboxamide | 379.9 | C |
| 56 | 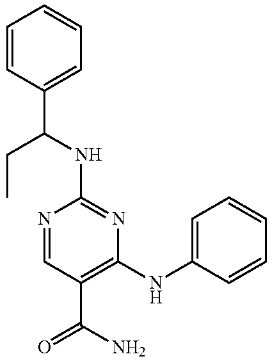 [SMILES: CCC(Nc1ncc(C(N)=O)c(Nc2ccccc2)n1)c1ccccc1] | 4-(phenylamino)-2-(1-phenylpropylamino) pyrimidine-5-carboxamide | 347.9 | C |
| 57 | 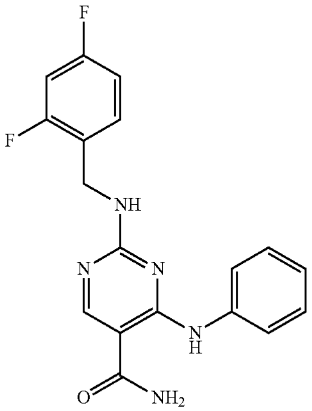 [SMILES: NC(=O)c1cnc(NCc2ccc(F)cc2F)nc1Nc1ccccc1] | 2-(2,4-difluorobenzylamino)-4-(phenylamino)pyrimidine-5-carboxamide | 355.9 | C |

TABLE 2-continued
| Cmpd. B- | Structure | Name | MH+ | Act. Level |
|---|---|---|---|---|
| 58 | 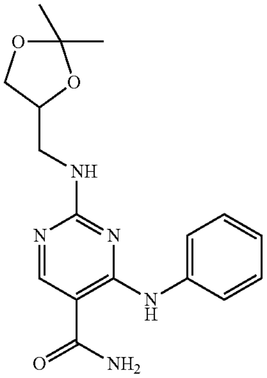 [SMILES: CC1(C)OCC(CNc2ncc(C(N)=O)c(Nc3ccccc3)n2)O1] | 2-((2,2-dimethyl-1,3-dioxolan-4-yl)methylamino)-4-(phenylamino)pyrimidine-5-carboxamide | 343.9 | C |
| 59 | 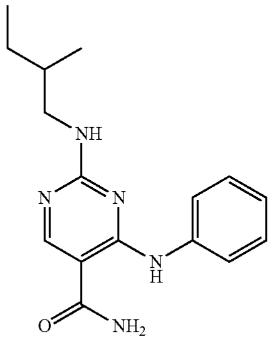 [SMILES: CCC(C)CNc1ncc(C(N)=O)c(Nc2ccccc2)n1] | 2-(2-methylbutylamino)-4-(phenylamino)pyrimidine-5-carboxamide | 300 | D |
| 60 | 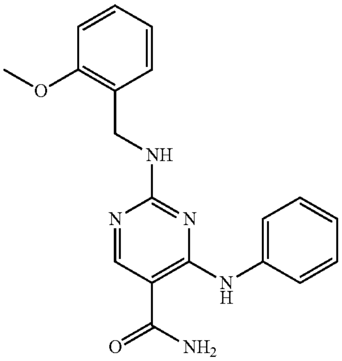 [SMILES: COc1ccccc1CNc1ncc(C(N)=O)c(Nc2ccccc2)n1] | 2-(2-methoxybenzylamino)-4-(phenylamino)pyrimidine-5-carboxamide | 349.9 | C |
| 61 | 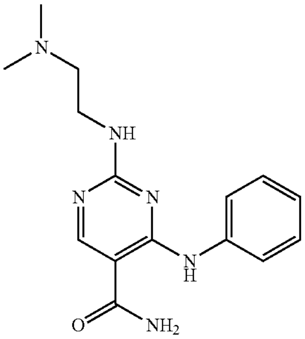 [SMILES: CN(C)CCNc1ncc(C(N)=O)c(Nc2ccccc2)n1] | 2-(2-(dimethylamino) ethylamino)-4-(phenylamino)pyrimidine-5-carboxamide | 301.4 | A |

TABLE 2-continued
| Cmpd. B- | Structure | Name | MH+ | Act. Level |
|---|---|---|---|---|
| 62 | 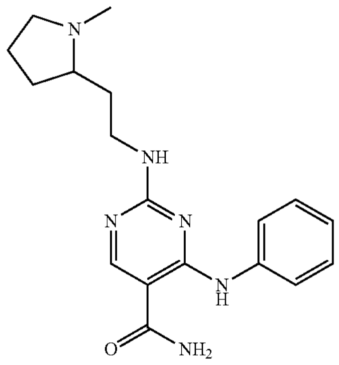 [SMILES: CN1CCCC1CCNc1ncc(C(N)=O)c(Nc2ccccc2)n1] | 2-(2-(1-methylpyrrolidin-2-yl)ethylamino)-4-(phenylamino)pyrimidine-5-carboxamide | 341.5 | A |
| 63 | 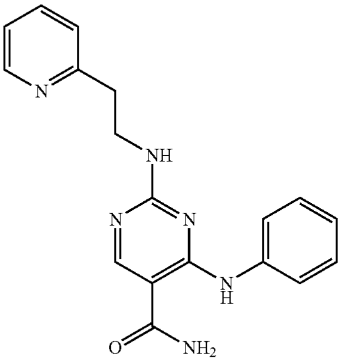 [SMILES: NC(=O)c1cnc(NCCc2ccccn2)nc1Nc1ccccc1] | 4-(phenylamino)-2-(2-(pyridin-2-yl)ethylamino)pyrimidine-5-carboxamide | 335.5 | C |
| 64 | 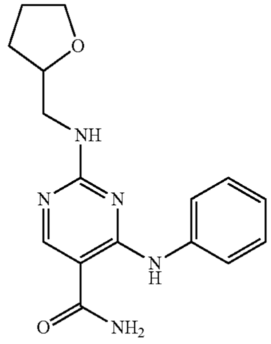 [SMILES: NC(=O)c1cnc(NCC2CCCO2)nc1Nc1ccccc1] | 4-(phenylamino)-2-((tetrahydrofuran-2-yl)methylamino)pyrimidine-5-carboxamide | 314.5 | C |
| 65 | 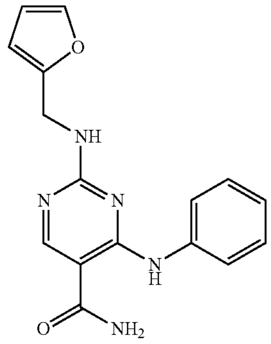 [SMILES: NC(=O)c1cnc(NCc2ccco2)nc1Nc1ccccc1] | 2-(furan-2-ylmethylamino)-4-(phenylamino)pyrimidine-5-carboxamide | 310.4 | A |

TABLE 2-continued
| Cmpd. B- | Structure | Name | MH+ | Act. Level |
|---|---|---|---|---|
| 66 | 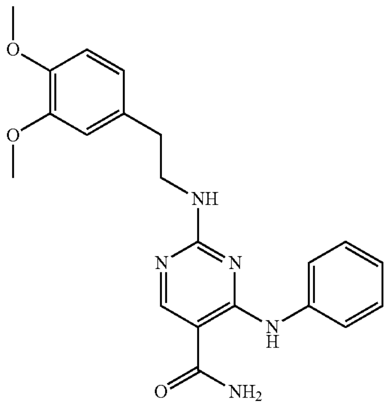 [SMILES: COc1ccc(CCNc2ncc(C(N)=O)c(Nc3ccccc3)n2)cc1OC] | 2-(3,4-dimethoxyphenethylamino)-4-(phenylamino)pyrimidine-5-carboxamide | 394.4 | C |
| 67 | 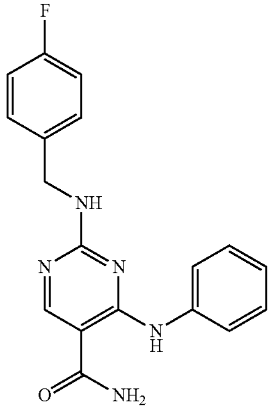 [SMILES: NC(=O)c1cnc(NCc2ccc(F)cc2)nc1Nc1ccccc1] | 2-(4-fluorobenzylamino)-4-(phenylamino)pyrimidine-5-carboxamide | 338.3 | C |
| 68 | 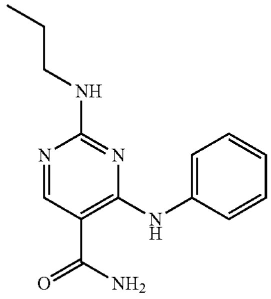 [SMILES: CCCNc1ncc(C(N)=O)c(Nc2ccccc2)n1] | 4-(phenylamino)-2-(propylamino)pyrimidine-5-carboxamide | 272.4 | C |
| 69 | 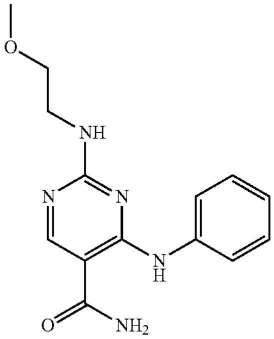 [SMILES: COCCNc1ncc(C(N)=O)c(Nc2ccccc2)n1] | 2-(2-methoxyethylamino)-4-(phenylamino)pyrimidine-5-carboxamide | 288.4 | B |

TABLE 2-continued
| Cmpd. B- | Structure | Name | MH+ | Act. Level |
|---|---|---|---|---|
| 70 | 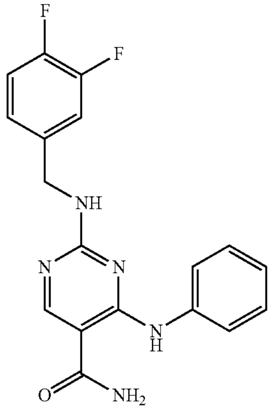 [SMILES: NC(=O)c1cnc(NCc2ccc(F)c(F)c2)nc1Nc1ccccc1] | 2-(3,4-difluorobenzylamino)-4-(phenylamino)pyrimidine-5-carboxamide | 356.3 | C |
| 71 | 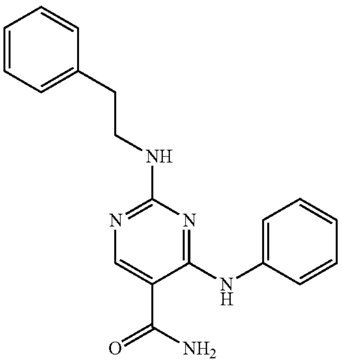 [SMILES: NC(=O)c1cnc(NCCc2ccccc2)nc1Nc1ccccc1] | 2-(phenethylamino)-4-(phenylamino)pyrimidine-5-carboxamide | 334.9 | C |
| 72 | 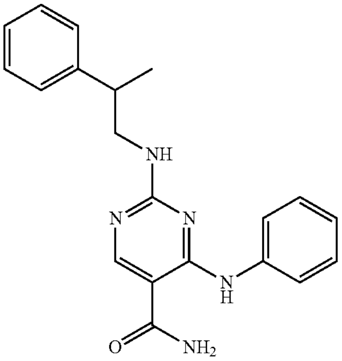 [SMILES: CC(CNc1ncc(C(N)=O)c(Nc2ccccc2)n1)c1ccccc1] | 4-(phenylamino)-2-(2-phenylpropylamino) pyrimidine-5-carboxamide | 348.9 | C |
| 73 | 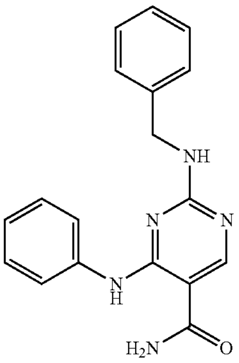 [SMILES: NC(=O)c1cnc(NCc2ccccc2)nc1Nc1ccccc1] | 2-(benzylamino)-4-(phenylamino)pyrimidine-5-carboxamide | 320.3 | B |

TABLE 2-continued

| Cmpd. B- | Structure | Name | MH+ | Act. Level |
|---|---|---|---|---|
| 74 | 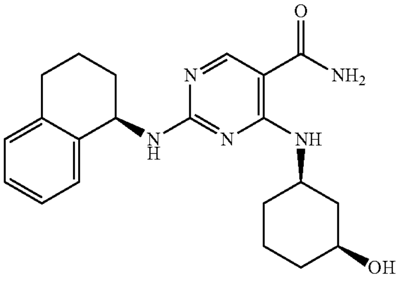 [SMILES: NC(=O)c1cnc(N[C@@H]2CCCc3ccccc32)nc1N[C@@H]1CCC[C@H](O)C1] | 4-((1R,3S)-3-hydroxycyclohexylamino)-2-((R)-1,2,3,4-tetrahydronaphthalen-1-ylamino)pyrimidine-5-carboxamid | 382.2 | D |
| 75 | 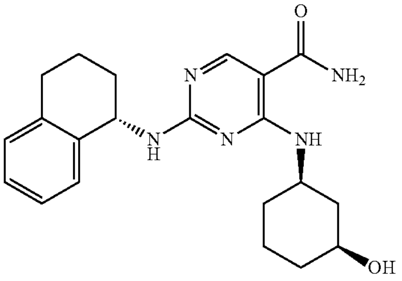 [SMILES: NC(=O)c1cnc(N[C@H]2CCCc3ccccc32)nc1N[C@@H]1CCC[C@H](O)C1] | 4-((1R,3S)-3-hydroxycyclohexylamino)-2-((S)-1,2,3,4-tetrahydronaphthalen-1-ylamino)pyrimidine-5-carboxamid | 382.2 | D |
| 76 | 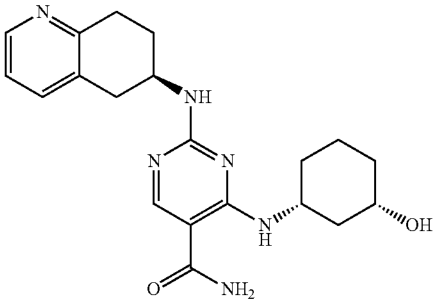 [SMILES: NC(=O)c1cnc(N[C@@H]2CCc3ncccc3C2)nc1N[C@@H]1CCC[C@H](O)C1] | 4-((1R,3S)-3-hydroxycyclohexylamino)-2-((R)-5,6,7,8-tetrahydroquinolin-6-ylamino)pyrimidine-5-carboxamid | 383.2 | D |
| 77 | 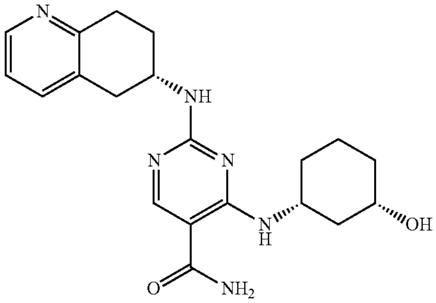 [SMILES: NC(=O)c1cnc(N[C@H]2CCc3ncccc3C2)nc1N[C@@H]1CCC[C@H](O)C1] | 4-((1R,3S)-3-hydroxycyclohexylamino)-2-((S)-5,6,7,8-tetrahydroquinolin-6-ylamino)pyrimidine-5-carboxamid | 383.2 | D |
| 78 | 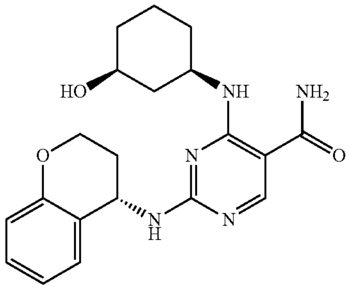 [SMILES: NC(=O)c1cnc(N[C@H]2CCOc3ccccc32)nc1N[C@@H]1CCC[C@H](O)C1] | 2-((S)-chroman-4-ylamino)-4-((1R,3S)-3-hydroxycyclohexylamino) pyrimidine-5-carboxamide | 384.4 | B |

TABLE 2-continued
| Cmpd. B- | Structure | Name | MH+ | Act. Level |
|---|---|---|---|---|
| 79 | 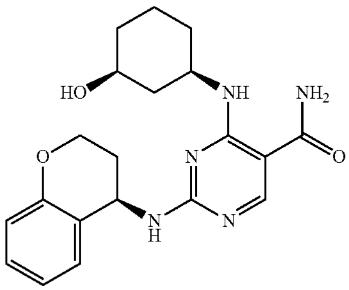 [SMILES: NC(=O)c1cnc(N[C@@H]2CCOc3ccccc32)nc1N[C@@H]1CCC[C@H](O)C1] | 2-((R)-chroman-4-ylamino)-4-((1R,3S)-3-hydroxycyclohexylamino) pyrimidine-5-carboxamide | 383.7 | D |
| 80 | 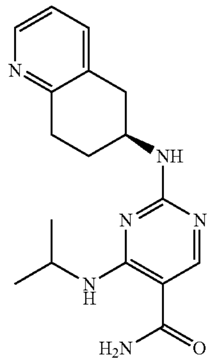 [SMILES: CC(C)Nc1nc(N[C@H]2CCc3ncccc3C2)ncc1C(N)=O] | (S)-4-(isopropylamino)-2-(5,6,7,8-tetrahydroquinolin-6-ylamino)pyrimidine-5-carboxamide | 327.1 | D |
| 81 | 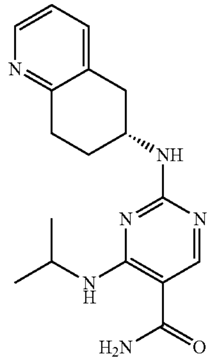 [SMILES: CC(C)Nc1nc(N[C@@H]2CCc3ncccc3C2)ncc1C(N)=O] | (R)-4-(isopropylamino)-2-(5,6,7,8-tetrahydroquinolin-6-ylamino)pyrimidine-5-carboxamide | 327.1 | C |
| 82 | 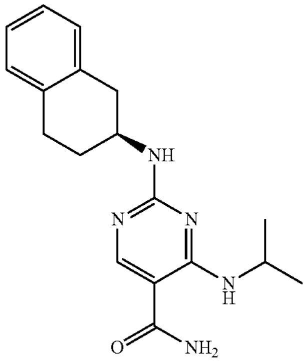 [SMILES: CC(C)Nc1nc(N[C@H]2CCc3ccccc3C2)ncc1C(N)=O] | (S)-4-(isopropylamino)-2-(1,2,3,4-tetrahydronaphthalen-2-ylamino)pyrimidine-5-carboxamide | 326.1 | C |

TABLE 2-continued

| Cmpd. B- | Structure | Name | MH+ | Act. Level |
|---|---|---|---|---|
| 83 | 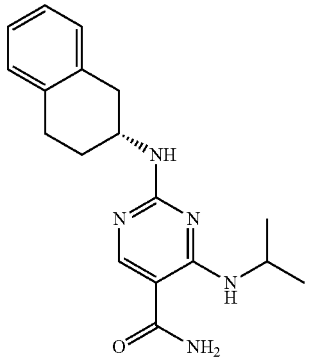 [SMILES: CC(C)Nc1nc(N[C@@H]2CCc3ccccc3C2)ncc1C(N)=O] | (R)-4-(isopropylamino)-2-(1,2,3,4-tetrahydronaphthalen-2-ylamino)pyrimidine-5-carboxamide | 326.1 | D |
| 84 | 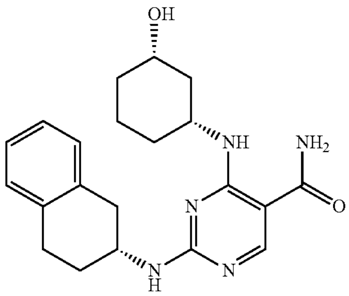 [SMILES: NC(=O)c1cnc(N[C@@H]2CCc3ccccc3C2)nc1N[C@@H]1CCC[C@H](O)C1] | 4-((1R,3S)-3-hydroxycyclohexylamino)-2-((R)-1,2,3,4-tetrahydronaphthalen-2-ylamino)pyrimidine-5-carboxamide | 382 | D |
| 85 | 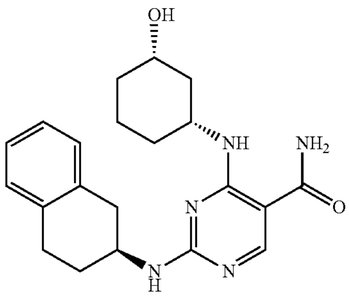 [SMILES: NC(=O)c1cnc(N[C@H]2CCc3ccccc3C2)nc1N[C@@H]1CCC[C@H](O)C1] | 4-((1R,3S)-3-hydroxycyclohexylamino)-2-((S)-1,2,3,4-tetrahydronaphthalen-2-ylamino)pyrimidine-5-carboxamide | 382 | B |
| 86 | 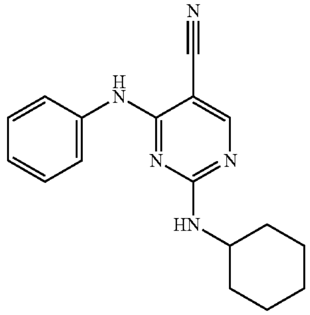 [SMILES: N#Cc1cnc(NC2CCCCC2)nc1Nc1ccccc1] | 2-(cyclohexylamino)-4-(phenylamino)pyrimidine-5-carbonitrile | 294.1 | A |

TABLE 2-continued

| Cmpd. B- | Structure | Name | MH+ | Act. Level |
|---|---|---|---|---|
| 87 | 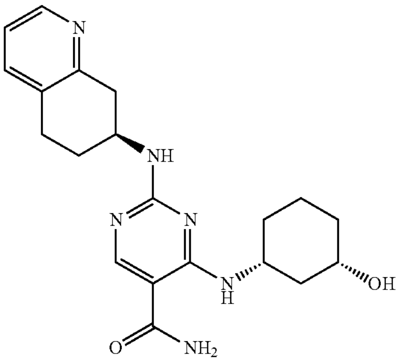 [SMILES: NC(=O)c1cnc(N[C@H]2CCc3cccnc3C2)nc1N[C@@H]1CCC[C@H](O)C1] | 4-((1R,3S)-3-hydroxycyclohexylamino)-2-((S)-5,6,7,8-tetrahydroquinolin-7-ylamino)pyrimidine-5-carboxamide | 383.2 | D |
| 88 | 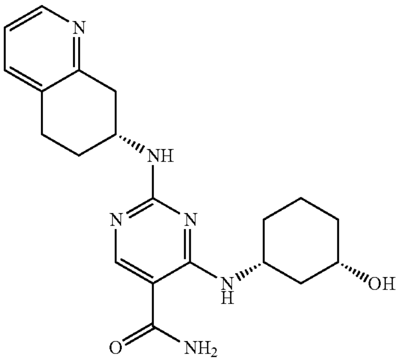 [SMILES: NC(=O)c1cnc(N[C@@H]2CCc3cccnc3C2)nc1N[C@@H]1CCC[C@H](O)C1] | 4-((1R,3S)-3-hydroxycyclohexylamino)-2-((R)-5,6,7,8-tetrahydroquinolin-7-ylamino)pyrimidine-5-carboxamide | 383.2 | D |
| 89 | 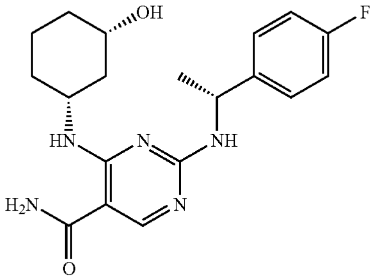 [SMILES: C[C@@H](Nc1ncc(C(N)=O)c(N[C@@H]2CCC[C@H](O)C2)n1)c1ccc(F)cc1] | 2-((R)-1-(4-fluorophenyl)ethylamino)-4-((1R,3S)-3-hydroxycyclohexylamino)pyrimidine-5-carboxamide | 374.2 | D |
| 90 | 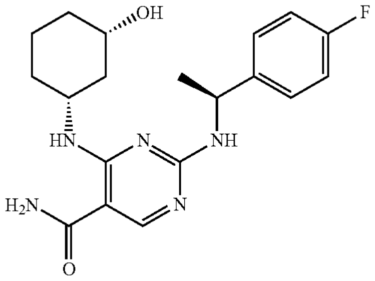 [SMILES: C[C@H](Nc1ncc(C(N)=O)c(N[C@@H]2CCC[C@H](O)C2)n1)c1ccc(F)cc1] | 2-((S)-1-(4-fluorophenyl)ethylamino)-4-((1R,3S)-3-hydroxycyclohexylamino)pyrimidine-5-carboxamide | 374.1 | A |

TABLE 2-continued

| Cmpd. B- | Structure | Name | MH+ | Act. Level |
|---|---|---|---|---|
| 91 | 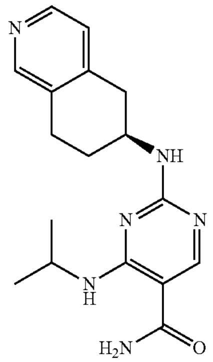 [SMILES: CC(C)Nc1nc(N[C@H]2CCc3cnccc3C2)ncc1C(N)=O] | (S)-4-(isopropylamino)-2-(5,6,7,8-tetrahydroisoquinolin-6-ylamino)pyrimidine-5-carboxamide | 327.1 | C |
| 92 | 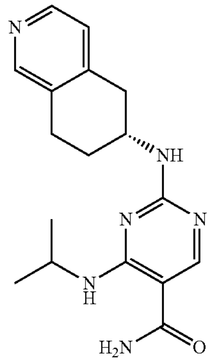 [SMILES: CC(C)Nc1nc(N[C@@H]2CCc3cnccc3C2)ncc1C(N)=O] | (R)-4-(isopropylamino)-2-(5,6,7,8-tetrahydroisoquinolin-6-ylamino)pyrimidine-5-carboxamide | 327.1 | D |
| 93 | 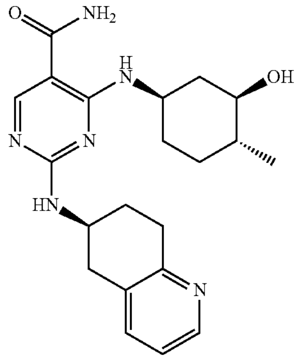 [SMILES: C[C@@H]1CC[C@@H](Nc2nc(N[C@H]3CCc4ncccc4C3)ncc2C(N)=O)C[C@H]1O] | 4-((1R,3R,4R)-3-hydroxy-4-methylcyclohexylamino)-2-((S)-5,6,7,8-tetrahydroquinolin-6-ylamino)pyrimidine-5-carboxamide | 397.2 | D |
| 94 | 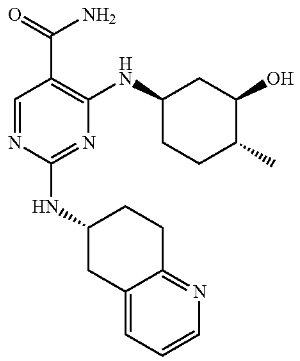 [SMILES: C[C@@H]1CC[C@@H](Nc2nc(N[C@@H]3CCc4ncccc4C3)ncc2C(N)=O)C[C@H]1O] | 4-((1R,3R,4R)-3-hydroxy-4-methylcyclohexylamino)-2-((R)-5,6,7,8-tetrahydroquinolin-6-ylamino)pyrimidine-5-carboxamide | 397.2 | D |

TABLE 2-continued

| Cmpd. B- | Structure | Name | MH+ | Act. Level |
|---|---|---|---|---|
| 95 | 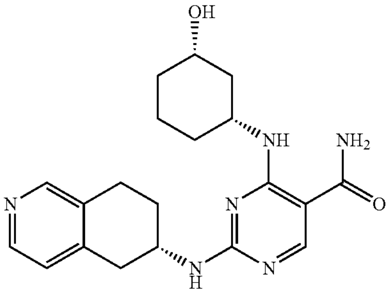 [SMILES: NC(=O)c1cnc(N[C@H]2CCc3cnccc3C2)nc1N[C@@H]1CCC[C@H](O)C1] | 4-((1R,3S)-3-hydroxycyclohexylamino)-2-((S)-5,6,7,8-tetrahydroisoquinolin-6-ylamino)pyrimidine-5-carboxamide | 383.2 | D |
| 96 | 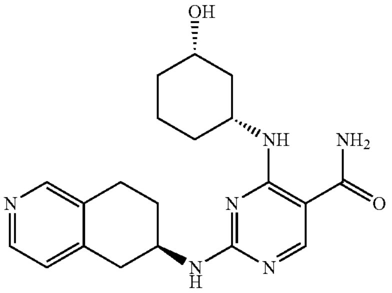 [SMILES: NC(=O)c1cnc(N[C@@H]2CCc3cnccc3C2)nc1N[C@@H]1CCC[C@H](O)C1] | 4-((1R,3S)-3-hydroxycyclohexylamino)-2-((R)-5,6,7,8-tetrahydroisoquinolin-6-ylamino)pyrimidine-5-carboxamide | 383.2 | D |
| 97 | 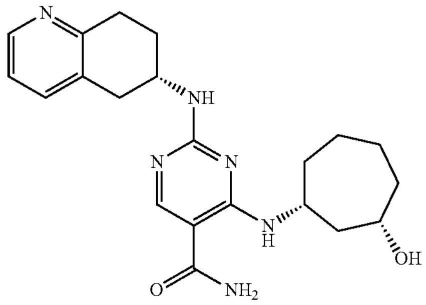 [SMILES: NC(=O)c1cnc(N[C@H]2CCc3ncccc3C2)nc1N[C@@H]1CCCC[C@H](O)C1] | 4-((1R,3S)-3-hydroxycycloheptylamino)-2-((S)-5,6,7,8-tetrahydroquinolin-6-ylamino)pyrimidine-5-carboxamide | 397.2 | D |
| 98 | 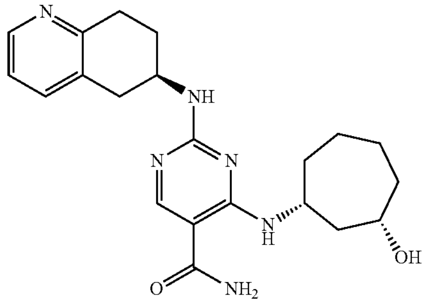 [SMILES: NC(=O)c1cnc(N[C@@H]2CCc3ncccc3C2)nc1N[C@@H]1CCCC[C@H](O)C1] | 4-((1R,3S)-3-hydroxycycloheptylamino)-2-((R)-5,6,7,8-tetrahydroquinolin-6-ylamino)pyrimidine-5-carboxamide | 397.2 | D |
| 99 | 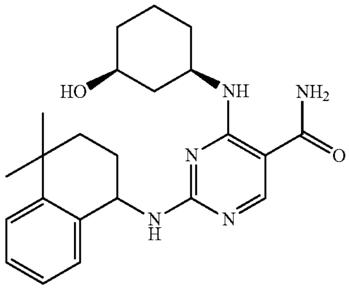 [SMILES: CC1(C)CCC(Nc2ncc(C(N)=O)c(N[C@@H]3CCC[C@H](O)C3)n2)c2ccccc21] | 2-(4,4-dimethyl-1,2,3,4-tetrahydronaphthalen-1-ylamino)-4-((1R,3S)-3-hydroxycyclohexylamino) pyrimidine-5-carboxamide | 410.2 | C |

TABLE 2-continued

| Cmpd. B- | Structure | Name | MH+ | Act. Level |
|---|---|---|---|---|
| 100 | 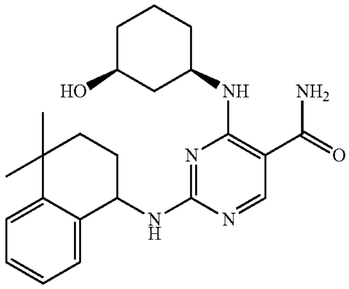 [SMILES: CC1(C)CCC(Nc2ncc(C(N)=O)c(N[C@@H]3CCC[C@H](O)C3)n2)c2ccccc21] | 2-(4,4-dimethyl-1,2,3,4-tetrahydronaphthalen-1-ylamino)-4-((1R,3S)-3-hydroxycyclohexylamino) pyrimidine-5-carboxamide | 410.2 | D |
| 101 | 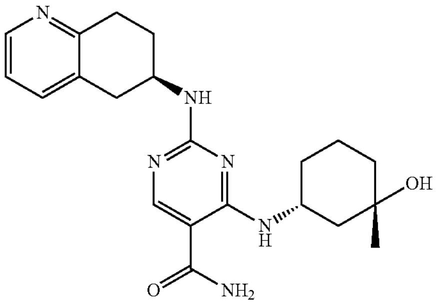 [SMILES: C[C@]1(O)CCC[C@@H](Nc2nc(N[C@@H]3CCc4ncccc4C3)ncc2C(N)=O)C1] | 4-((1R,3S)-3-hydroxy-3-methylcyclohexylamino)-2-((R)-5,6,7,8-tetrahydroquinolin-6-ylamino)pyrimidine-5-carboxamide | 397.2 | D |
| 102 | 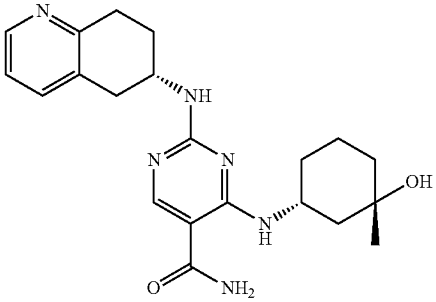 [SMILES: C[C@]1(O)CCC[C@@H](Nc2nc(N[C@H]3CCc4ncccc4C3)ncc2C(N)=O)C1] | 4-((1R,3S)-3-hydroxy-3-methylcyclohexylamino)-2-((S)-5,6,7,8-tetrahydroquinolin-6-ylamino)pyrimidine-5-carboxamide | 397.2 | D |

TABLE 3

| Cmpd. C- | Structure | Name | MH+ | Act. Level |
|---|---|---|---|---|
| 1 | 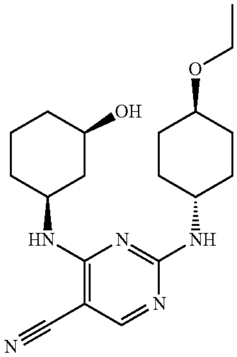 [SMILES: CCO[C@H]1CC[C@H](Nc2ncc(C#N)c(N[C@H]3CCC[C@@H](O)C3)n2)CC1] | 2-((1r,4S)-4-ethoxycyclohexylamino)-4-((1S,3R)-3-hydroxycyclohexylamino) pyrimidine-5-carbonitrile | 359.8 | C |

TABLE 3-continued

| Cmpd. C- | Structure | Name | MH+ | Act. Level |
|---|---|---|---|---|
| 2 | 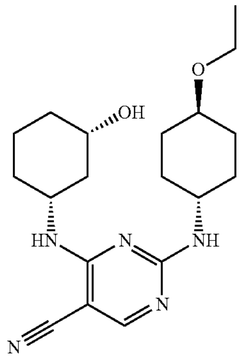 [SMILES: CCO[C@H]1CC[C@H](Nc2ncc(C#N)c(N[C@@H]3CCC[C@H](O)C3)n2)CC1] | 2-((1r,4R)-4-ethoxycyclohexylamino)-4-((1R,3S)-3-hydroxycyclohexylamino)pyrimidine-5-carbonitrile | 360.3 | D |
| 3 | 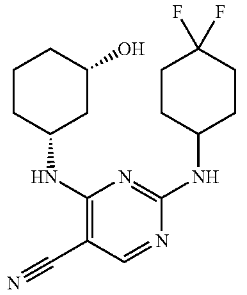 [SMILES: N#Cc1cnc(NC2CCC(F)(F)CC2)nc1N[C@@H]1CCC[C@H](O)C1] | 2-(4,4-difluorocyclohexylamino)-4-((1R,3S)-3-hydroxycyclohexylamino)pyrimidine-5-carbonitrile | 352.3 | C |
| 4 | 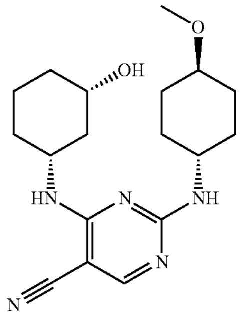 [SMILES: CO[C@H]1CC[C@H](Nc2ncc(C#N)c(N[C@@H]3CCC[C@H](O)C3)n2)CC1] | 4-((1R,3S)-3-hydroxycyclohexylamino)-2-((1r,4R)-4-methoxycyclohexylamino)pyrimidine-5-carbonitrile | 346.2 | D |
| 5 | 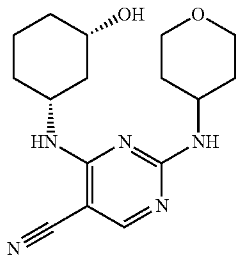 [SMILES: N#Cc1cnc(NC2CCOCC2)nc1N[C@@H]1CCC[C@H](O)C1] | 4-((1R,3S)-3-hydroxycyclohexylamino)-2-(tetrahydro-2H-pyran-4-ylamino)pyrimidine-5-carbonitrile | 318.2 | C |

TABLE 3-continued

| Cmpd. C- | Structure | Name | MH+ | Act. Level |
|---|---|---|---|---|
| 6 | 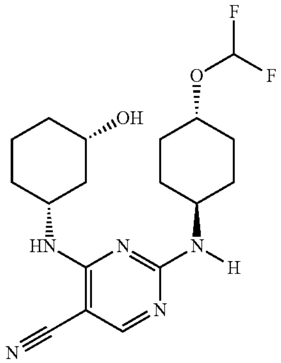 [SMILES: N#Cc1cnc(N[C@H]2CC[C@H](OC(F)F)CC2)nc1N[C@@H]1CCC[C@H](O)C1] | 2-((1r,4R)-4-(difluoromethoxy)cyclohexyl-amino)-4-((1R,3S)-3-hydroxycyclohexylamino) pyrimidine-5-carbonitrile | 382.3 | D |
| 7 | 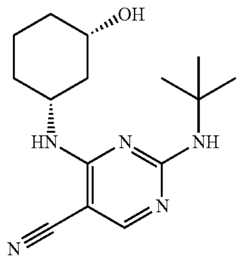 [SMILES: CC(C)(C)Nc1ncc(C#N)c(N[C@@H]2CCC[C@H](O)C2)n1] | 2-(tert-butylamino)-4-((1R,3S)-3-hydroxycyclohexylamino) pyrimidine-5-carbonitrile | 290.1 | C |
| 8 | 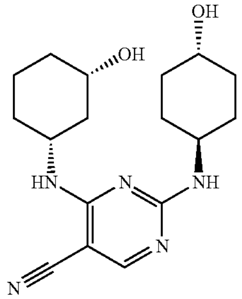 [SMILES: N#Cc1cnc(N[C@H]2CC[C@H](O)CC2)nc1N[C@@H]1CCC[C@H](O)C1] | 4-((1R,3S)-3-hydroxycyclohexylamino)-2-((1r,4R)-4-hydroxycyclohexylamino) pyrimidine-5-carbonitrile | 332.1 | D |
| 9 | 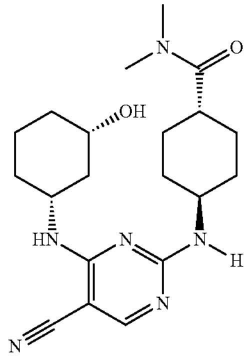 [SMILES: CN(C)C(=O)[C@H]1CC[C@H](Nc2ncc(C#N)c(N[C@@H]3CCC[C@H](O)C3)n2)CC1] | (1R,4r)-4-(5-cyano-4-((1R,3S)-3-hydroxycyclohexylamino) pyrimidin-2-ylamino)-N,N-dimethylcyclohexanecarboxamide | 387.1 | D |
| 10 | 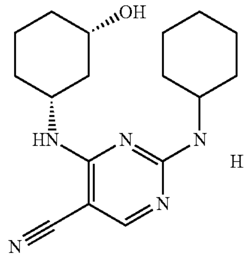 | 2-(cyclohexylamino)-4-((1R,3S)-3-hydroxycyclohexylamino) pyrimidine-5-carbonitrile | 316.1 | D |

TABLE 3-continued

| Cmpd. C- | Structure | Name | MH+ | Act. Level |
|---|---|---|---|---|
| 11 | 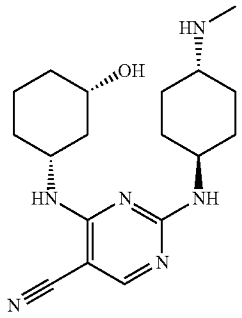 [SMILES: CN[C@H]1CC[C@H](Nc2ncc(C#N)c(N[C@@H]3CCC[C@H](O)C3)n2)CC1] | 4-((1R,3S)-3-hydroxycyclohexylamino)-2-((1r,4R)-4-(methylamino)cyclohexyl-amino)pyrimidine-5-carbonitrile | 345.2 | D |
| 12 | 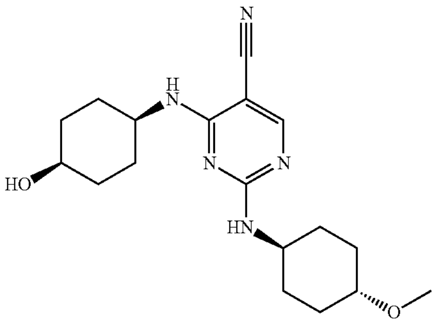 [SMILES: CO[C@H]1CC[C@H](Nc2ncc(C#N)c(N[C@H]3CC[C@@H](O)CC3)n2)CC1] | 4-((1s,4s)-4-hydroxycyclohexylamino)-2-((1r,4r)-4-methoxycyclohexylamino) pyrimidine-5-carbonitrile | 346.2 | C |
| 13 | 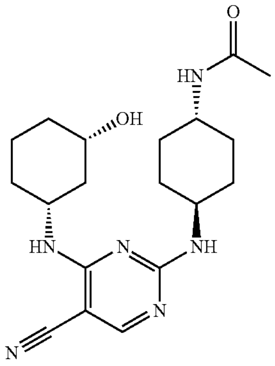 [SMILES: CC(=O)N[C@H]1CC[C@H](Nc2ncc(C#N)c(N[C@@H]3CCC[C@H](O)C3)n2)CC1] | N-((1R,4r)-4-(5-cyano-4-((1R,3S)-3-hydroxycyclohexylamino) pyrimidin-2-ylamino)cyclohexyl)acetamide | 373.3 | D |
| 14 | 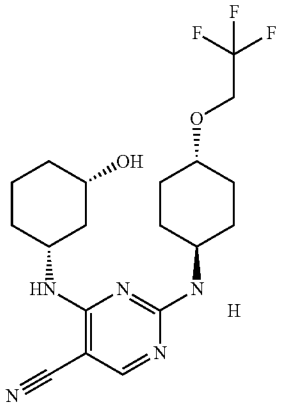 | 4-((1R,3S)-3-hydroxycyclohexylamino)-2-((1r,4R)-4-(2,2,2-trifluoroethoxy)cyclohexyl-amino)pyrimidine-5-carbonitril | 414.2 | D |

TABLE 3-continued

| Cmpd. C- | Structure | Name | MH+ | Act. Level |
|---|---|---|---|---|
| 15 | 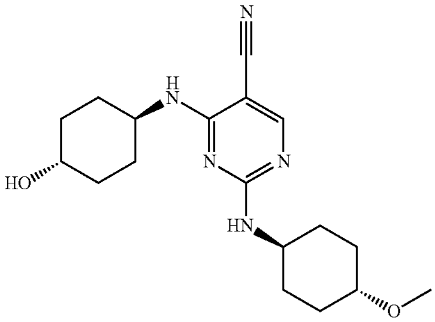 [SMILES: CO[C@H]1CC[C@H](Nc2ncc(C#N)c(N[C@H]3CC[C@H](O)CC3)n2)CC1] | 4-((1r,4r)-4-hydroxycyclohexylamino)-2-((1r,4r)-4-methoxycyclohexylamino) pyrimidine-5-carbonitrile | 346.2 | B |
| 16 | 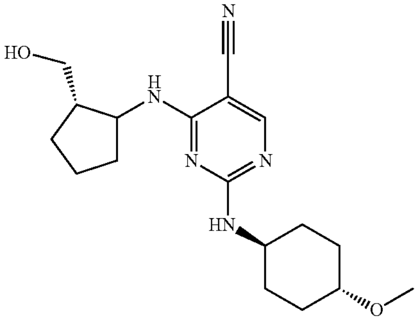 [SMILES: CO[C@H]1CC[C@H](Nc2ncc(C#N)c(NC3CCC[C@@H]3CO)n2)CC1] | 4-((1R,2S)-2-(hydroxymethyl)cyclopentyl-amino)-2-((1r,4R)-4-methoxycyclohexylamino) pyrimidine-5-carbonitrile | 346.1 | D |
| 17 | 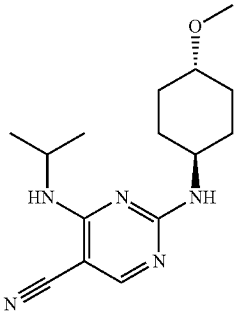 [SMILES: CO[C@H]1CC[C@H](Nc2ncc(C#N)c(NC(C)C)n2)CC1] | 4-(isopropylamino)-2-((1r,4r)-4-methoxycyclohexylamino) pyrimidine-5-carbonitrile | 290.1 | B |
| 18 | 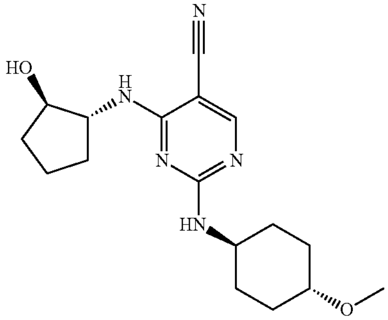 [SMILES: CO[C@H]1CC[C@H](Nc2ncc(C#N)c(N[C@@H]3CCC[C@H]3O)n2)CC1] | 4-((1R,2R)-2-hydroxycyclopentylamino)-2-((1r,4R)-4-methoxycyclohexylamino) pyrimidine-5-carbonitrile | 332.2 | D |

TABLE 3-continued

| Cmpd. C- | Structure | Name | MH+ | Act. Level |
|---|---|---|---|---|
| 19 | 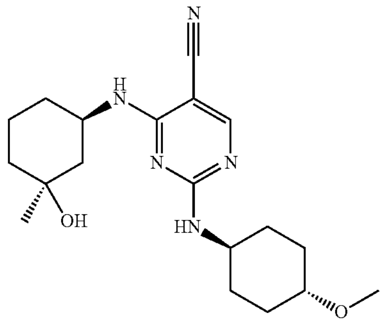 [SMILES: CO[C@H]1CC[C@H](Nc2ncc(C#N)c(N[C@@H]3CCC[C@](C)(O)C3)n2)CC1] | 4-((1R,3S)-3-hydroxy-3-methylcyclohexylamino)-2-((1r,4R)-4-methoxycyclohexylamino) pyrimidine-5-carbonitrile | 360.2 | D |
| 20 | 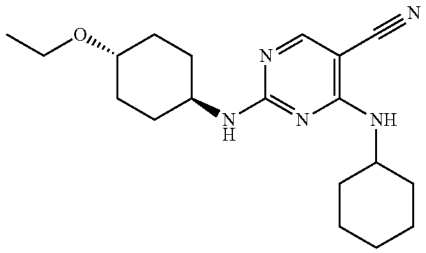 [SMILES: CCO[C@H]1CC[C@H](Nc2ncc(C#N)c(NC3CCCCC3)n2)CC1] | 4-(cyclohexylamino)-2-((1r,4r)-4-ethoxycyclohexylamino) pyrimidine-5-carbonitrile | 344.2 | C |
| 21 | 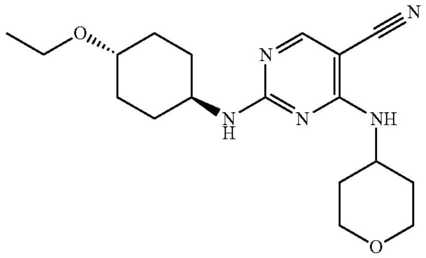 [SMILES: CCO[C@H]1CC[C@H](Nc2ncc(C#N)c(NC3CCOCC3)n2)CC1] | 2-((1r,4r)-4-ethoxycyclohexylamino)-4-(tetrahydro-2H-pyran-4-ylamino)pyrimidine-5-carbonitrile | 346.2 | A |
| 22 | 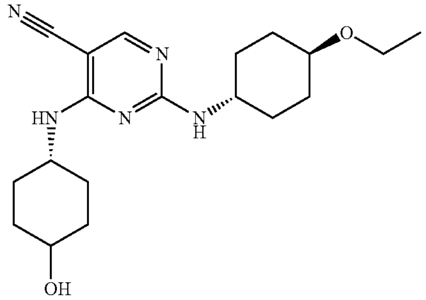 | 2-((1r,4r)-4-ethoxycyclohexylamino)-4-((1s,4s)-4-hydroxycyclohexylamino) pyrimidine-5-carbonitrile | 360.1 | C |
| 23 | 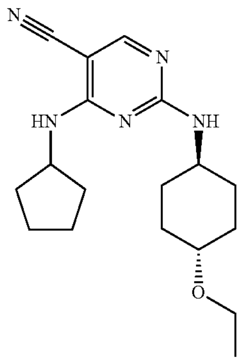 [SMILES: CCO[C@H]1CC[C@H](Nc2ncc(C#N)c(NC3CCCC3)n2)CC1] | 4-(cyclopentylamino)-2-((1r,4r)-4-ethoxycyclohexylamino) pyrimidine-5-carbonitrile | 330.1 | C |

TABLE 3-continued

| Cmpd. C- | Structure | Name | MH+ | Act. Level |
|---|---|---|---|---|
| 24 | 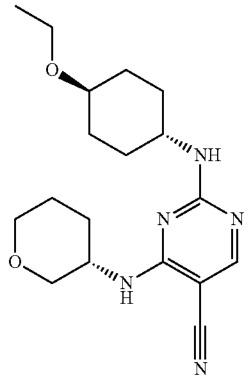 [SMILES: CCO[C@H]1CC[C@H](Nc2ncc(C#N)c(N[C@H]3CCCOC3)n2)CC1] | 2-((1r,4S)-4-ethoxycyclohexylamino)-4-((S)-tetrahydro-2H-pyran-3-ylamino)pyrimidine-5-carbonitrile | 346.1 | A |
| 25 | 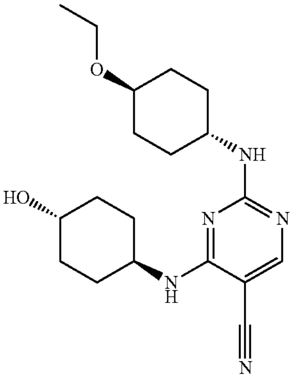 [SMILES: CCO[C@H]1CC[C@H](Nc2ncc(C#N)c(N[C@H]3CC[C@H](O)CC3)n2)CC1] | 2-((1r,4r)-4-ethoxycyclohexylamino)-4-((1r,4r)-4-hydroxycyclohexylamino) pyrimidine-5-carbonitrile | 360.1 | B |
| 26 | 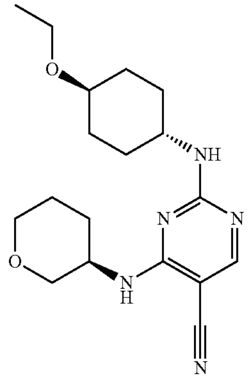 [SMILES: CCO[C@H]1CC[C@H](Nc2ncc(C#N)c(N[C@@H]3CCCOC3)n2)CC1] | 2-((1r,4R)-4-ethoxycyclohexylamino)-4-((R)-tetrahydro-2H-pyran-3-ylamino)pyrimidine-5-carbonitrile | 346.1 | C |
| 27 | 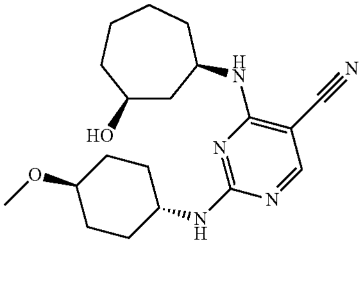 [SMILES: CO[C@H]1CC[C@H](Nc2ncc(C#N)c(N[C@@H]3CCCC[C@H](O)C3)n2)CC1] | 4-((1R,3S)-3-hydroxycycloheptylamino)-2-((1r,4R)-4-methoxycyclohexylamino) pyrimidine-5-carbonitrile | 360.5 | D |

TABLE 3-continued

| Cmpd. C- | Structure | Name | MH+ | Act. Level |
|---|---|---|---|---|
| 28 | 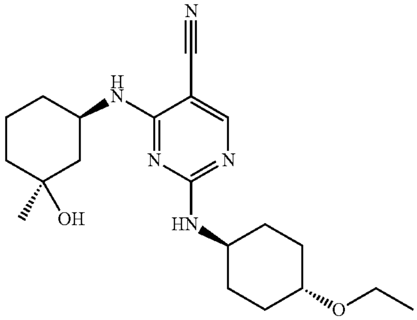 [SMILES: CCO[C@H]1CC[C@H](Nc2ncc(C#N)c(N[C@@H]3CCC[C@](C)(O)C3)n2)CC1] | 2-((1r,4R)-4-ethoxycyclohexylamino)-4-((1R,3S)-3-hydroxy-3-methylcyclohexylamino) pyrimidine-5-carbonitrile | 374.3 | D |
| 29 | 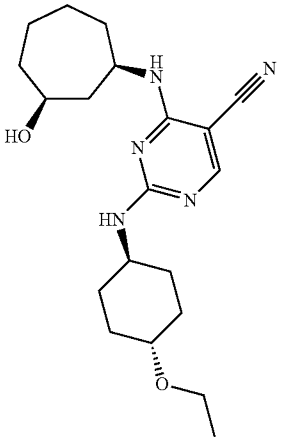 [SMILES: CCO[C@H]1CC[C@H](Nc2ncc(C#N)c(N[C@@H]3CCCC[C@H](O)C3)n2)CC1] | 2-((1r,4R)-4-ethoxycyclohexylamino)-4-((1R,3S)-3-hydroxycycloheptylamino) pyrimidine-5-carbonitrile | 374.2 | D |
| 30 | 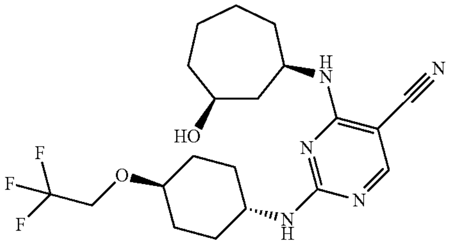 [SMILES: N#Cc1cnc(N[C@H]2CC[C@H](OCC(F)(F)F)CC2)nc1N[C@@H]1CCCC[C@H](O)C1] | 4-((1R,3S)-3-hydroxycycloheptylamino)-2-((1r,4R)-4-(2,2,2-trifluoroethoxy)cyclohexyl-amino)pyrimidine-5-carbonitril | 428.3 | D |
| 31 | 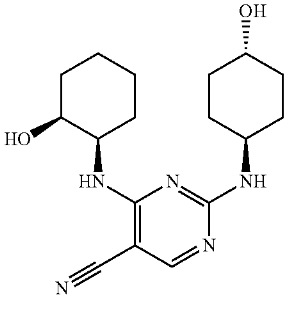 [SMILES: N#Cc1cnc(N[C@H]2CC[C@H](O)CC2)nc1N[C@@H]1CCCC[C@@H]1O] | 4-((1R,2S)-2-hydroxycyclohexylamino)-2-((1r,4R)-4-hydroxycyclohexylamino) pyrimidine-5-carbonitrile | 346.2 | C |
| 32 | 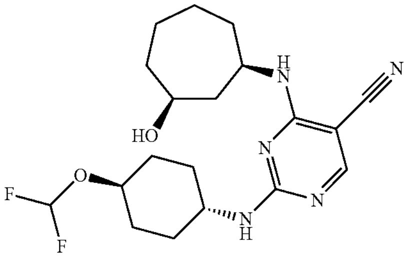 [SMILES: N#Cc1cnc(N[C@H]2CC[C@H](OC(F)F)CC2)nc1N[C@@H]1CCCC[C@H](O)C1] | 2-((1r,4R)-4-(difluoromethoxy)cyclohexyl-amino)-4-((1R,3S)-3-hydroxycycloheptylamino) pyrimidine-5-carbonitrile | 396.1 | D |

TABLE 3-continued

| Cmpd. C- | Structure | Name | MH+ | Act. Level |
|---|---|---|---|---|
| 33 | 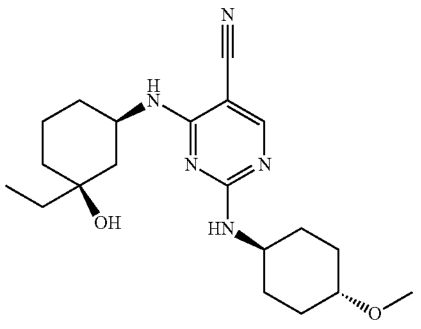 [SMILES: CC[C@]1(O)CCC[C@@H](Nc2nc(N[C@H]3CC[C@H](OC)CC3)ncc2C#N)C1] | 4-((1R,3S)-3-ethyl-3-hydroxycyclohexylamino)-2-((1r,4R)-4-methoxycyclohexylamino) pyrimidine-5-carbonitrile | 374.2 | D |
| 34 | 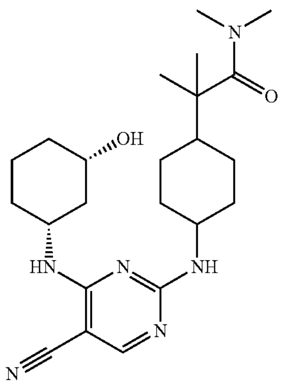 [SMILES: CN(C)C(=O)C(C)(C)C1CCC(Nc2ncc(C#N)c(N[C@@H]3CCC[C@H](O)C3)n2)CC1] | 2-(4-(5-cyano-4-((1R,3S)-3-hydroxycyclohexylamino) pyrimidin-2-ylamino) cyclohexyl)-N,N,2-trimethylpropanamide | 429.2 | D |
| 35 | 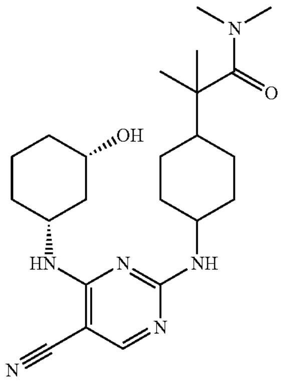 [SMILES: CN(C)C(=O)C(C)(C)C1CCC(Nc2ncc(C#N)c(N[C@@H]3CCC[C@H](O)C3)n2)CC1] | 2-(4-(5-cyano-4-((1R,3S)-3-hydroxycyclohexylamino) pyrimidin-2-ylamino) cyclohexyl)-N,N,2-trimethylpropanamide | 429.2 | C |
| 36 | 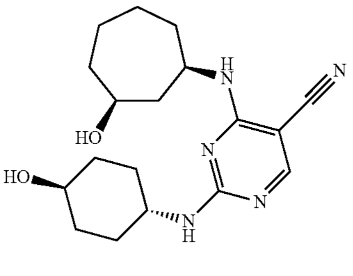 [SMILES: N#Cc1cnc(N[C@H]2CC[C@H](O)CC2)nc1N[C@@H]1CCCC[C@H](O)C1] | 4-((1R,3S)-3-hydroxycycloheptylamino)-2-((1r,4R)-4-hydroxycyclohexylamino) pyrimidine-5-carbonitrile | 346.3 | D |

TABLE 3-continued

| Cmpd. C- | Structure | Name | MH+ | Act. Level |
|---|---|---|---|---|
| 37 | 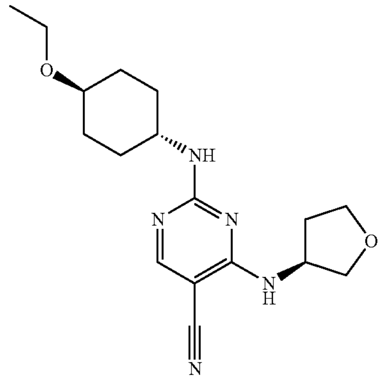 [SMILES: CCO[C@H]1CC[C@H](Nc2ncc(C#N)c(N[C@H]3CCOC3)n2)CC1] | 2-((1r,4S)-4-ethoxycyclohexylamino)-4-((S)-tetrahydrofuran-3-ylamino)pyrimidine-5-carbonitrile | 332.9 | C |
| 38 | 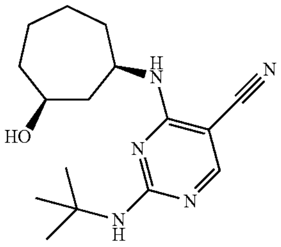 [SMILES: CC(C)(C)Nc1ncc(C#N)c(N[C@@H]2CCCC[C@H](O)C2)n1] | 2-(tert-butylamino)-4-((1R,3S)-3-hydroxycycloheptylamino)pyrimidine-5-carbonitrile | 304.5 | D |
| 39 | 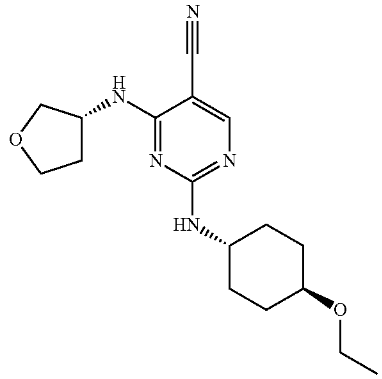 [SMILES: CCO[C@H]1CC[C@H](Nc2ncc(C#N)c(N[C@@H]3CCOC3)n2)CC1] | 2-((1r,4R)-4-ethoxycyclohexylamino)-4-((R)-tetrahydrofuran-3-ylamino)pyrimidine-5-carbonitrile | 331.9 | A |
| 40 | 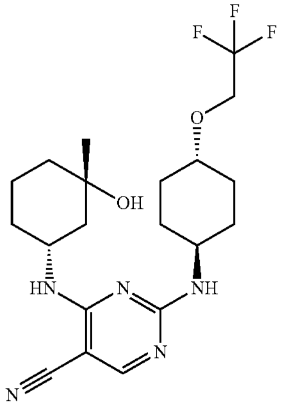 [SMILES: C[C@]1(O)CCC[C@@H](Nc2nc(N[C@H]3CC[C@H](OCC(F)(F)F)CC3)ncc2C#N)C1] | 4-((1R,3S)-3-hydroxy-3-methylcyclohexylamino)-2-((1r,4R)-4-(2,2,2-trifluoroethoxy)cyclohexyl-amino)pyrimidine-5-carbonitril | 428.6 | D |

TABLE 3-continued

| Cmpd. C- | Structure | Name | MH+ | Act. Level |
|---|---|---|---|---|
| 41 | 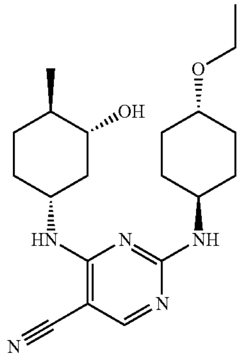 [SMILES: CCO[C@H]1CC[C@H](Nc2ncc(C#N)c(N[C@@H]3CC[C@@H](C)[C@H](O)C3)n2)CC1] | 2-((1r,4R)-4-ethoxycyclohexylamino)-4-((1R,3R,4R)-3-hydroxy-4-methylcyclohexylamino) pyrimidine-5-carbonitrile | 373.8 | D |
| 42 | 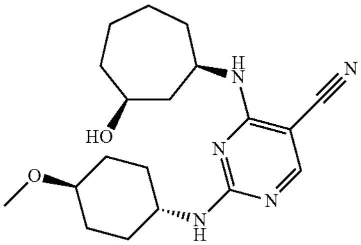 [SMILES: CO[C@H]1CC[C@H](Nc2ncc(C#N)c(N[C@@H]3CCCC[C@H](O)C3)n2)CC1] | 4-((1R,3R)-3-hydroxycycloheptylamino)-2-((1r,4R)-4-methoxycyclohexylamino) pyrimidine-5-carbonitrile | 360.3 | D |
| 43 | 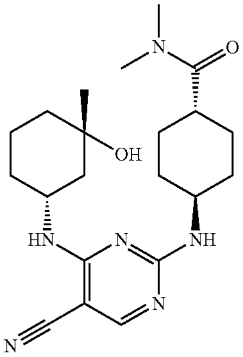 [SMILES: CN(C)C(=O)[C@H]1CC[C@H](Nc2ncc(C#N)c(N[C@@H]3CCC[C@](C)(O)C3)n2)CC1] | (1R,4r)-4-(5-cyano-4-((1R,3S)-3-hydroxy-3-methylcyclohexylamino) pyrimidin-2-ylamino)-N,N-dimethylcyclohexanecarboxamide | 401.5 | D |
| 44 | 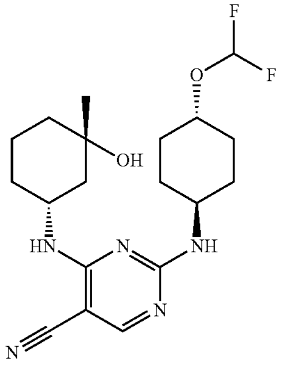 [SMILES: C[C@]1(O)CCC[C@@H](Nc2nc(N[C@H]3CC[C@H](OC(F)F)CC3)ncc2C#N)C1] | 2-((1r,4R)-4-(difluoromethoxy)cyclohexyl-amino)-4-((1R,3S)-3-hydroxy-3-methylcyclohexylamino) pyrimidine-5-carbonitrile | 395.7 | D |

TABLE 3-continued

| Cmpd. C- | Structure | Name | MH+ | Act. Level |
| --- | --- | --- | --- | --- |
| 45 | 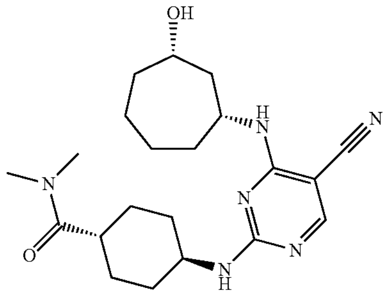 [SMILES: CN(C)C(=O)[C@H]1CC[C@H](Nc2ncc(C#N)c(N[C@@H]3CCCC[C@H](O)C3)n2)CC1] | (1R,4r)-4-(5-cyano-4-((1R,3S)-3-hydroxycycloheptylamino)pyrimidin-2-ylamino)-N,N-dimethylcyclohexanecarboxamide | 401 | D |
| 46 | 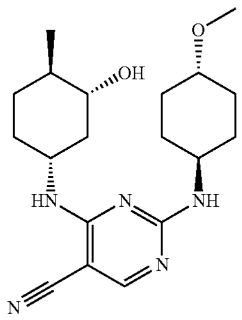 [SMILES: CO[C@H]1CC[C@H](Nc2ncc(C#N)c(N[C@@H]3CC[C@@H](C)[C@H](O)C3)n2)CC1] | 4-((1R,3R,4R)-3-hydroxy-4-methylcyclohexylamino)-2-((1r,4R)-4-methoxycyclohexylamino)pyrimidine-5-carbonitrile | 359.9 | D |
| 47 | 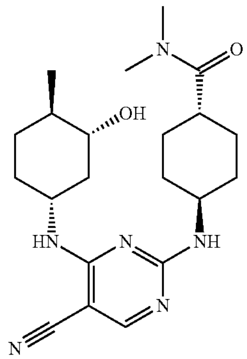 [SMILES: C[C@@H]1CC[C@@H](Nc2nc(N[C@H]3CC[C@H](C(=O)N(C)C)CC3)ncc2C#N)C[C@H]1O] | (1R,4r)-4-(5-cyano-4-((1R,3R,4R)-3-hydroxy-4-methylcyclohexylamino)pyrimidin-2-ylamino)-N,N-dimethylcyclohexanecarboxamide | 400.8 | D |
| 48 | 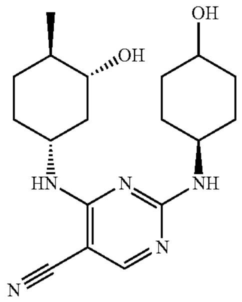 | 4-((1R,3R,4R)-3-hydroxy-4-methylcyclohexylamino)-2-((1r,4R)-4-hydroxycyclohexylamino)pyrimidine-5-carbonitrile | 346.7 | D |

TABLE 3-continued
| Cmpd. C- | Structure | Name | MH+ | Act. Level |
|---|---|---|---|---|
| 49 | 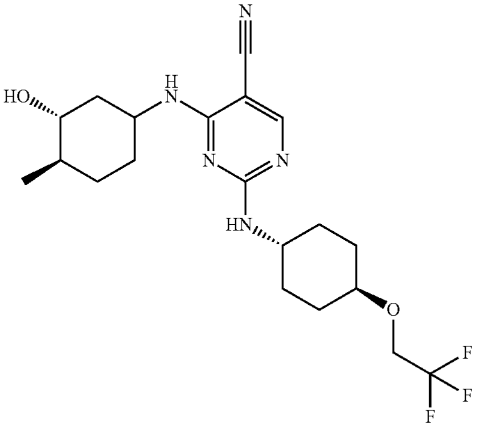 [SMILES: C[C@@H]1CCC(Nc2nc(N[C@H]3CC[C@H](OCC(F)(F)F)CC3)ncc2C#N)C[C@H]1O] | 4-((1R,3R,4R)-3-hydroxy-4-methylcyclohexylamino)-2-((1r,4R)-4-(2,2,2-trifluoroethoxy)cyclohexyl-amino)pyrimidine-5-carbonitrile | 427.9 | D |
| 50 | 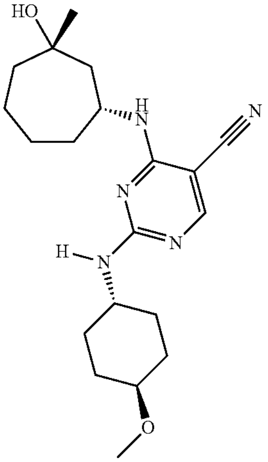 [SMILES: CO[C@H]1CC[C@H](Nc2ncc(C#N)c(N[C@@H]3CCCC[C@](C)(O)C3)n2)CC1] | 4-((1R,3S)-3-hydroxy-3-methylcycloheptylamino)-2-((1r,4R)-4-methoxycyclohexylamino) pyrimidine-5-carbonitrile | 374 | C |
| 51 | 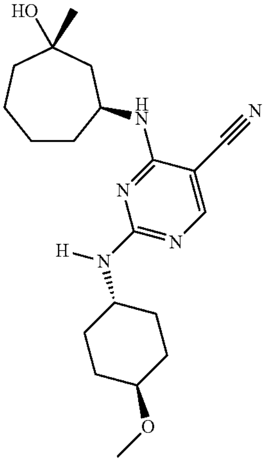 [SMILES: CO[C@H]1CC[C@H](Nc2ncc(C#N)c(N[C@H]3CCCC[C@](C)(O)C3)n2)CC1] | 4-((1S,3S)-3-hydroxy-3-methylcycloheptylamino)-2-((1r,4S)-4-methoxycyclohexylamino) pyrimidine-5-carbonitrile | 374 | A |

TABLE 3-continued

| Cmpd. C- | Structure | Name | MH+ | Act. Level |
|---|---|---|---|---|
| 52 | 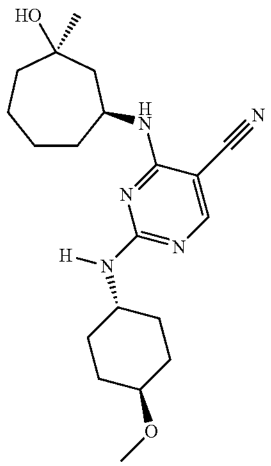 [SMILES: CO[C@H]1CC[C@H](Nc2ncc(C#N)c(N[C@H]3CCCC[C@@](C)(O)C3)n2)CC1] | 4-((1S,3R)-3-hydroxy-3-methylcycloheptylamino)-2-((1r,4S)-4-methoxycyclohexylamino) pyrimidine-5-carbonitrile | 374 | D |
| 53 | 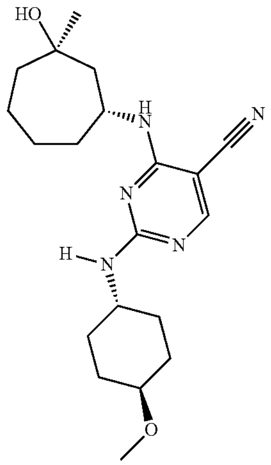 [SMILES: CO[C@H]1CC[C@H](Nc2ncc(C#N)c(N[C@@H]3CCCC[C@@](C)(O)C3)n2)CC1] | 4-((1R,3R)-3-hydroxy-3-methylcycloheptylamino)-2-((1r,4R)-4-methoxycyclohexylamino) pyrimidine-5-carbonitrile | 374 | D |
| 54 | 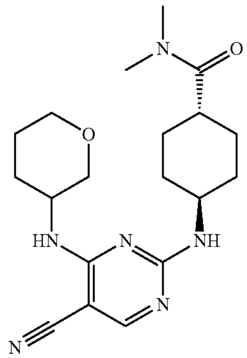 [SMILES: CN(C)C(=O)[C@H]1CC[C@H](Nc2ncc(C#N)c(NC3CCCOC3)n2)CC1] | (1R,4r)-4-(5-cyano-4-((R)-tetrahydro-2H-pyran-3-ylamino)pyrimidin-2-ylamino)-N,N-dimethyl-cyclohexanecarboxamide | 373.7 | C |
| 55 | 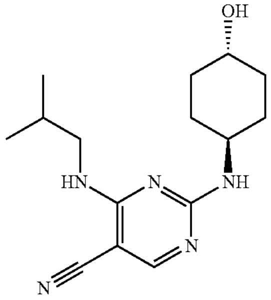 [SMILES: CC(C)CNc1nc(N[C@H]2CC[C@H](O)CC2)ncc1C#N] | 2-((1r,4r)-4-hydroxycyclohexylamino)-4-(isobutylamino)pyrimidine-5-carbonitrile | 290.5 | A |

TABLE 3-continued

| Cmpd. C- | Structure | Name | MH+ | Act. Level |
|---|---|---|---|---|
| 56 | 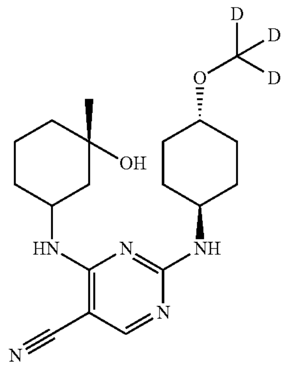 [SMILES: [2H]C([2H])([2H])O[C@H]1CC[C@H](Nc2ncc(C#N)c(NC3CCC[C@](C)(O)C3)n2)CC1] | A name could not be generated for this structure | 362.8 | D |
| 57 | 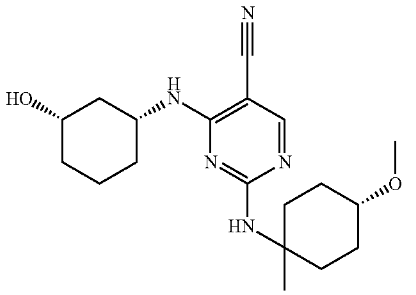 | 4-((1R,3S)-3-hydroxycyclohexylamino)-2-((1r,4R)-4-methoxy-1-methylcyclohexylamino) pyrimidine-5-carbonitrile | 360.2 | C |
| 58 | 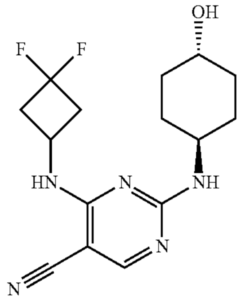 [SMILES: N#Cc1cnc(N[C@H]2CC[C@H](O)CC2)nc1NC1CC(F)(F)C1] | 4-(3,3-difluorocyclobutylamino)-2-((1r,4r)-4-hydroxycyclohexylamino) pyrimidine-5-carbonitrile | 324.5 | A |
| 59 | 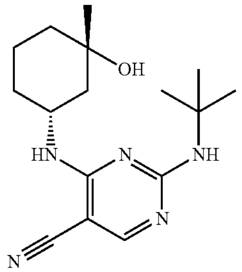 [SMILES: CC(C)(C)Nc1ncc(C#N)c(N[C@@H]2CCC[C@](C)(O)C2)n1] | 2-(tert-butylamino)-4-((1R,3S)-3-hydroxy-3-methylcyclohexylamino) pyrimidine-5-carbonitrile | 304.3 | C |
| 60 | 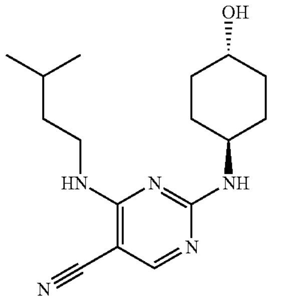 [SMILES: CC(C)CCNc1nc(N[C@H]2CC[C@H](O)CC2)ncc1C#N] | 2-((1r,4r)-4-hydroxycyclohexylamino)-4-(isopentylamino)pyrimidine-5-carbonitrile | 304.7 | A |

TABLE 3-continued
| Cmpd. C- | Structure | Name | MH+ | Act. Level |
|---|---|---|---|---|
| 61 | 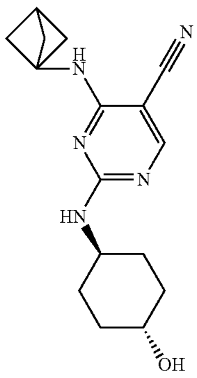 [SMILES: N#Cc1cnc(N[C@H]2CC[C@H](O)CC2)nc1NC12CC(C1)C2] | 4-(bicyclo[1.1.1]pentan-1-ylamino)-2-((1r,4r)-4-hydroxycyclohexylamino) pyrimidine-5-carbonitrile | 300.6 | C |
| 62 | 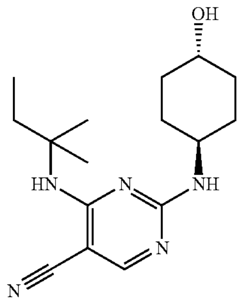 [SMILES: CCC(C)(C)Nc1nc(N[C@H]2CC[C@H](O)CC2)ncc1C#N] | 2-((1r,4r)-4-hydroxycyclohexylamino)-4-(tert-pentylamino)pyrimdine-5-carbonitrile | 304.1 | D |
| 63 | 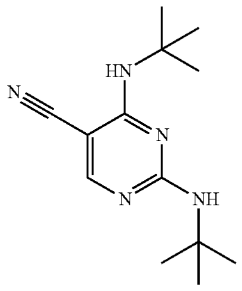 [SMILES: CC(C)(C)Nc1ncc(C#N)c(NC(C)(C)C)n1] | 2,4-bis(tert-butylamino)pyrimidine-5-carbonitrile | 248.5 | C |
| 64 | 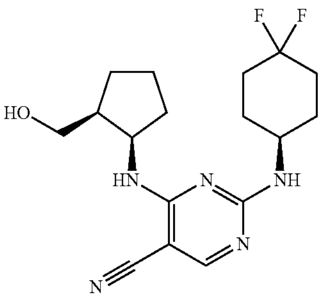 | 2-(4,4-difluorocyclohexylamino)-4-((1R,2S)-2-(hydroxymethyl)cyclopentyl-amino)pyrimidine-5-carbonitrile | 352.6 | C |

TABLE 3-continued

| Cmpd. C- | Structure | Name | MH+ | Act. Level |
|---|---|---|---|---|
| 65 | 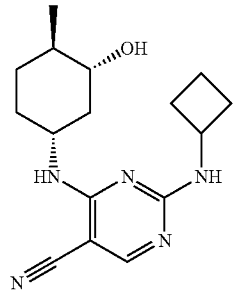 [SMILES: C[C@@H]1CC[C@@H](Nc2nc(NC3CCC3)ncc2C#N)C[C@H]1O] | 2-(cyclobutylamino)-4-((1R,3R,4R)-3-hydroxy-4-methylcyclohexylamino) pyrimidine-5-carbonitrile | 302.3 | D |

A number of references have been cited, the disclosures of which are incorporated herein by reference in their entirety.

What is claimed is:

1. A compound of formula (I):

(I)

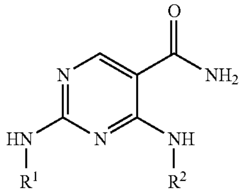

or a pharmaceutically acceptable salt, tautomer, or stereoisomer thereof, wherein:

$R^1$ is substituted or unsubstituted branched $C_{3-8}$ alkyl; and $R^2$ is substituted or unsubstituted cyclohexyl, wherein the compound at a concentration of 10 μM inhibits JNK1 by at least about 50%.

2. The compound of claim 1, wherein $R^1$ is an unsubstituted branched $C_{3-8}$ alkyl.

3. The compound of claim 1, wherein $R^2$ is a substituted cyclohexyl.

4. A compound of formula (TB):

(IB)

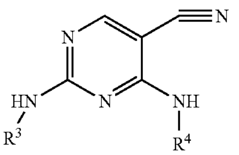

or a pharmaceutically acceptable salt, tautomer, or stereoisomer thereof, wherein:

$R^3$ is substituted or unsubstituted branched $C_{3-8}$ alkyl; and $R^4$ is substituted or unsubstituted cyclohexyl.

5. The compound of claim 4, wherein $R^4$ is a substituted cyclohexyl.

6. A pharmaceutical composition comprising an effective amount of a compound of claim 1, or a pharmaceutically acceptable salt, tautomer or stereoisomer thereof, and a pharmaceutically acceptable carrier, excipient or vehicle.

7. The compound of claim 1, wherein the compound is 4-((1R,3S)-3-hydroxycyclohexylamino)-2-(isopropylamino)pyrimidine-5-carboxamide.

8. The compound of claim 1, wherein the compound is 4-((1R,3S)-3-hydroxy-3-methylcyclohexylamino)-2-(isopropylamino)pyrimidine-5-carboxamide.

9. The compound of claim 1, wherein the compound is 4-((1R,3R,4R)-3-hydroxy-4-methylcyclohexylamino)-2-(isopropylamino)pyrimidine-5-carboxamide.

10. The compound of claim 1, wherein the compound is 4-((1R,3R,4R)-3-hydroxy-4-methylcyclohexylamino)-2-(tert-pentylamino)pyrimidine-5-carboxamide.

11. The compound of claim 1, wherein the compound is 2-(tert-Butylamino)-4-((1R,3R,4R)-3-hydroxy-4-methylcyclohexylamino)-pyrimidine-5-carboxamide.

12. The compound of claim 1, wherein the compound is 4-((1R,3R,4R)-3-hydroxy-4-methylcyclohexylamino)-2-(3-methylpentan-3-ylamino)pyrimidine-5-carboxamide.

13. The compound of claim 1, wherein the compound is 4-((1R,3S)-3-hydroxycyclohexylamino)-2-(tert-pentylamino)pyrimidine-5-carboxamide.

14. The compound of claim 1, wherein the compound is 2-(2,3-dimethylbutan-2-ylamino)-4-((1R,3R,4R)-3-hydroxy-4-methylcyclohexylamino)pyrimidine-5-carboxamide.

15. The compound of claim 1, wherein the compound is 2-(sec-butylamino)-4-((1R,3R,4R)-3-hydroxy-4-methylcyclohexylamino)pyrimidine-5-carboxamide.

16. The compound of claim 1, wherein the compound is 2-((R)-3,3-dimethylbutan-2-ylamino)-4-((1R,3R,4R)-3-hydroxy-4-methylcyclohexylamino)pyrimidine-5-carboxamide.

17. The compound of claim 4, wherein the compound at a concentration of 10 μM inhibits JNK1 by at least about 50%.

18. A pharmaceutical composition comprising an effective amount of a compound of claim 4, or a pharmaceutically acceptable salt, tautomer or stereoisomer thereof, and a pharmaceutically acceptable carrier, excipient or vehicle.

* * * * *